(12) United States Patent
Jorand-Lebrun et al.

(10) Patent No.: US 9,790,221 B2
(45) Date of Patent: Oct. 17, 2017

(54) HETEROARYL COMPOUNDS AS IRAK INHIBITORS AND USES THEREOF

(71) Applicant: Merck Patent GmbH, Darmstadt (DE)

(72) Inventors: Catherine Jorand-Lebrun, Arlington, MA (US); Reinaldo Jones, Lowell, MA (US); Annie Cho Won, Somerville, MA (US); Ngan Nguyen, Arlington, MA (US); Theresa L. Johnson, Salem, MA (US); Lizbeth Celeste Deselm, Melrose, MA (US); Kausik Panda, Bangalore-Karnataka (IN)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/945,610

(22) Filed: Nov. 19, 2015

(65) Prior Publication Data

US 2016/0145252 A1 May 26, 2016

Related U.S. Application Data

(60) Provisional application No. 62/082,231, filed on Nov. 20, 2014.

(51) Int. Cl.

| | | |
|---|---|---|
| C07D 451/04 | (2006.01) | |
| C07D 401/12 | (2006.01) | |
| C07D 403/14 | (2006.01) | |
| C07D 405/14 | (2006.01) | |
| C07D 413/14 | (2006.01) | |
| C07D 417/14 | (2006.01) | |
| C07D 401/14 | (2006.01) | |
| C07D 451/14 | (2006.01) | |
| C07D 487/04 | (2006.01) | |

(52) U.S. Cl.
CPC ......... *C07D 451/04* (2013.01); *C07D 401/12* (2013.01); *C07D 401/14* (2013.01); *C07D 403/14* (2013.01); *C07D 405/14* (2013.01); *C07D 413/14* (2013.01); *C07D 417/14* (2013.01); *C07D 451/14* (2013.01); *C07D 487/04* (2013.01)

(58) Field of Classification Search
CPC .......................... C07D 401/14; C07D 403/14
See application file for complete search history.

(56) References Cited

FOREIGN PATENT DOCUMENTS

| JP | WO 2009054253 A1 * | 4/2009 | ........... C07D 213/36 |
|---|---|---|---|
| WO | 2009054253 A1 | 4/2009 | |
| WO | 2010017051 A1 | 2/2010 | |
| WO | WO 2013134415 A1 * | 9/2013 | ............... C07H 3/04 |
| WO | 2014008992 A1 | 1/2014 | |
| WO | 2015106058 A1 | 7/2015 | |

OTHER PUBLICATIONS

G.W. Rhyasen et al., 112 British Journal of Cancer, 232-237 (2015).*
K. Kobayashi et al., 110 Cell, 191-202 (2002).*
J. Su et al., 19 Cellular Signalling, 1596-1601 (2007).*
W.R. Balasubramanian et al., 75 Cancer Research Supplement, 3646-3646 (2015).*
R. Srivastava et al., 72 Cancer Research, 6209-6216 (2012).*
J.P. Powers et al., 16 Bioorganic & Medicinal Chemistry Letters, 2842-2845 (2006).*
E-H Joh et al., 82 Biochemical Pharmacology, 278-286 (2011).*
Z. Wang et al., 9 Current Topics in Medicinal Chemistry, 724-737 (2009).*
K Kanakaraj et al., Journal of Experimental Medicine, 2073-2079 (1998).*
C. Wietek et al., IRAK-4: A New Drug Target in Inflammation, Sepsis, and Autoimmunity, 2 Molecular interventions, 212 (2002).*
CAS Registry Nos. (2009).*
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013).*
H. Girouard et al., 100 Journal of Applied Physiology, 328-335, 332 (2006).*
R. S. Shah et al., 52 Biomedicine & Pharmacotherapy, 199-207 (2008).*
P.A. LeWitt, 359 New England Journal of Medicine, 2468-2473 (2008).*
J. Luo et al., 36 Cell, 823-837 (2009).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
S. Judge et al., 111 Pharmacology & Therapeutics, 224-259 (2006).*
V. Brinkmann et al., 9 Nature Reviews | Drug Discovery, 883-897 (2010).*
Z. Wang et al., 19 Drug Discovery Today, 145-150 (2014).*
R.D. Prasasya et al., 21 Seminars in Cancer Biology, 200-206 (2011).*
Kinase Inhibitors, Methods in Molecular Biology 795 (B. Kuster ed., 2012).*
Berge et al., J. Pharmaceutical Sciences, 1977, 66: 1-19.
Buckley et al., Bioorg. Med Chem Lett., 2008, 18(12): 3656-3660.
Cao et al., Science, 1996, 271(5252): 1128-1131.
Cohen P., Current Opinion in Cell Biology, 2009, 21(2): 317-324.
Foster, Adv. Drug Res., 1985, 14:1-40.
Gillette, Biochemistry, 1994, 33(10): 2927-2937.
Greene and Wuts, "Protective Groups in Organic Synthesis", Wiley Interscience, 3rd Edition, 1999.
Hanzlik, J. Org. Chem., 1990, 55: 3992-3997.
Jarman, Carcinogenesis, 1993, 16(4): 683-688.
Kocienski Philip J., "Protecting Groups", Georg Thieme Verlag Stuttgart, New York, 1994.
Li et al., Proc. Natl. Acad. Sci. USA, 2002, 99(8): 5567-5572.

(Continued)

*Primary Examiner* — Alexander R Pagano
(74) *Attorney, Agent, or Firm* — Dwight D. Kim; EMD Serono Research and Development Institute

(57) ABSTRACT

The present invention relates to compounds of Formula I and pharmaceutically acceptable compositions thereof, useful as IRAK inhibitors.

17 Claims, No Drawings

(56) References Cited

OTHER PUBLICATIONS

March's Advanced Organic Chemistry, 5th Ed., Ed.: Smith, M.B. and March, J., John Wiley & Sons, New York: 2001.
Muzio et al., Science, 1997, 278(5343): 1612-1615.
"Organic Chemistry", Thomas Sorrell, University Science Books, Sausalito: 1999.
Periodic Table of the Elements, CAS version, Handbook of Chemistry and Physics, 75th Ed.
Reider et al., J. Org. Chem., 1987, 52: 3326-3334.
Ringwood and Li, Cytokine, 2008, 42(1): 1-7.
Wesche et al., J. Biol. Chem., 1999, 274(27): 19403-19410.

* cited by examiner

HETEROARYL COMPOUNDS AS IRAK INHIBITORS AND USES THEREOF

RELATED APPLICATIONS

This application claims the benefit of U.S. Provisional Application 62/082,231, filed on Nov. 20, 2014, the contents of which are incorporated in its entirety by reference.

TECHNICAL FIELD OF THE INVENTION

The present invention provides for compounds of Formula (I) as IRAK inhibitors and their use in the treatment of cancer, and other diseases related to IRAK overexpression, including rheumatoid arthritis, systemic lupus erythematosus or lupus nephritis.

BACKGROUND OF THE INVENTION

Kinases catalyze the phosphorylation of proteins, lipids, sugars, nucleosides and other cellular metabolites and play key roles in all aspects of eukaryotic cell physiology. Especially, protein kinases and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues.

Kinases are important therapeutic targets for the development of anti-inflammatory drugs (Cohen, 2009. Current Opinion in Cell Biology 21, 1-8), for example kinases that are involved in the orchestration of adaptive and innate immune responses. Kinase targets of particular interest are members of the IRAK family.

The interleukin-1 receptor-associated kinases (IRAKs) are critically involved in the regulation of intracellular signaling networks controlling inflammation (Ringwood and Li, 2008. Cytokine 42, 1-7). IRAKs are expressed in many cell types and can mediate signals from various cell receptors including toll-like receptors (TLRs). IRAK4 is thought to be the initial protein kinase activated downstream of the interleukin-1 (IL-1) receptor and all toll-like-receptors (TLRs) except TLR3, and initiates signaling in the innate immune system via the rapid activation of IRAK1 and slower activation of IRAK2. IRAK1 was first identified through biochemical purification of the IL-1 dependent kinase activity that co-immunoprecipitates with the IL-1 type 1 receptor (Cao et al., 1996. Science 271(5252): 1128-31). IRAK2 was identified by the search of the human expressed sequence tag (EST) database for sequences homologous to IRAK1 (Muzio et al., 1997. Science 278 (5343): 1612-5). IRAK3 (also called IRAKM) was identified using a murine EST sequence encoding a polypeptide with significant homology to IRAK1 to screen a human phytohemagglutinin-activated peripheral blood leukocyte (PBL) cDNA library (Wesche et al., 1999. J. Biol. Chem. 274(27): 19403-10). IRAK4 was identified by database searching for IRAK-like sequences and PCR of a universal cDNA library (Li et al., 2002. Proc. Natl. Acad. Sci. USA 99(8):5567-5572).

Mice that express a catalytically inactive mutant of IRAK4 instead of the wild-type kinase are completely resistant to septic shock triggered by several TLR agonists and are impaired in their response to IL-1. Children who lack IRAK4 activity due to a genetic defect suffer from recurring infection by pyogenic bacteria. It appears that IRAK-dependent TLRs and IL-1Rs are vital for childhood immunity against some pyogenic bacteria but play a redundant role in protective immunity to most infections in adults. Therefore IRAK4 inhibitors may be useful for the treatment of chronic inflammatory diseases in adults without making them too susceptible to bacterial and viral infections (Cohen, 2009. Current Opinion in Cell Biology 21, 1-8). Potent IRAK4 inhibitors have been developed (Buckley et al., 2008. Bioorg Med Chem Lett. 18(12):3656-60). IRAK1 is essential for the TLR7-mediated and TLR9-mediated activation of IRF7 and the production of interferon-alpha (IFN-α) suggesting that IRAK1 inhibitors may be useful for the treatment of Systemic lupus erythematosus (SLE). IRAK2 is activated downstream of IRAK4 and plays a role in proinflammatory cytokine production. Therefore IRAK2 inhibitors may be useful for inflammatory diseases.

SUMMARY OF THE INVENTION

In one aspect, the invention provides compounds of Formula (I):

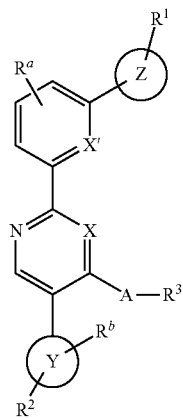

and pharmaceutically acceptable derivatives, solvates, salts, hydrates and stereoisomers thereof.

In another aspect, the invention provides compounds of Formula (I) which are suitable for the treatment and/or prevention of disorders related to IRAK. In another aspect, the invention provides compounds which are able to modulate, especially inhibit the activity or function of IRAK in disease states in mammals, especially in humans.

According to another aspect of the invention are provided methods for the treatment and/or prevention of disorders selected from auto-immune, inflammatory disorders, cardiovascular diseases, neurodegenerative disorders, bacterial and viral infections, allergy, asthma, pancreatitis, multi-organ failure, kidney diseases, platelet aggregation, cancer, transplantation, sperm motility, erythrocyte deficiency, graft rejection, lung injuries, respiratory diseases and ischemic conditions.

According to another aspect, the present invention provides compounds of Formula (I) which are selective for IRAK-4 and/or IRAK-1.

According to another aspect, the present invention provides compounds of Formula (I) which are selective for IRAK-4 and IRAK-1.

According to another aspect the invention provides a kit or a set comprising at least one compound of Formula (I), preferably in combination with immunomodulating agents.

Preferably, the kit consists of separate packs of:
(a) an effective amount of a compound of the formula (I) and/or pharmaceutically usable derivatives, solvates, salts, hydrates and stereoisomers thereof, including mixtures thereof in all ratios, and
(b) an effective amount of a further medicament active ingredient.

According to another aspect the invention provides a process for the synthesis of compounds of Formulae (I).

DETAILED DESCRIPTION OF CERTAIN EMBODIMENTS

1. General Description of Compounds of the Invention

In certain aspects, the present invention provides for inhibitors of IRAK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

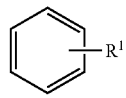

refers to at least

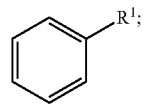

and

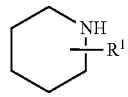

refers to at least

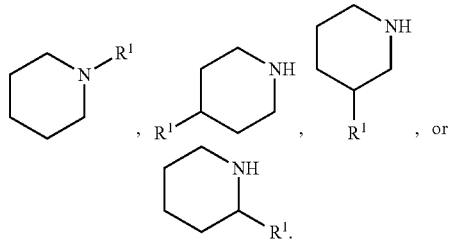

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH═CHPh, which is optionally substituted with R°; —(CH$_2$)$_{0-4}$(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —$(CH_2)_{0-2}R^•$, -(haloR$^•$), —$(CH_2)_{0-2}$OH, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)$C(O)OR^•$, or —$SSR^•$ wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^•$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, Cl 6 aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^•$, -(haloR$^•$), —OH, —$OR^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, -(haloR$^•$), —OH, —$OR^•$, —O(haloR$^•$), —CN, —C(O)OH, —C(O)OR$^•$, —$NH_2$, —NHR$^•$, —$NR^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-carbocyclyl, —C(O)-aryl, —C(O)-heteroaryl, —C(O)-heterocyclyl, —$CONH_2$, —CONH-alkyl, —CONH-alkenyl, —CONH-alkynyl, —CONH-carbocyclyl, —CONH-aryl, —CONH-heteroaryl, —CONH-heterocyclyl, —$OCO_2$-alkyl, —$OCO_2$-alkenyl, —$OCO_2$-alkynyl, —$OCO_2$-carbocyclyl, —$OCO_2$-aryl, —$OCO_2$-heteroaryl, —$OCO_2$-heterocyclyl, —$OCONH_2$, —OCONH-alkyl, —OCONH-alkenyl, —OCONH-alkynyl, —OCONH-carbocyclyl, —OCONH-aryl, —OCONH-heteroaryl, —OCONH-heterocyclyl, —NHC(O)-alkyl, —NHC(O)-alkenyl, —NHC(O)-alkynyl, —NHC(O)-carbocyclyl, —NHC(O)-aryl, —NHC(O)-heteroaryl, —NHC(O)-heterocyclyl, —$NHCO_2$-alkyl, —$NHCO_2$-alkenyl, —$NHCO_2$-alkynyl, —$NHCO_2$-carbocyclyl, —$NHCO_2$-aryl, —$NHCO_2$-heteroaryl, —$NHCO_2$-heterocyclyl, —$NHC(O)NH_2$, —NHC(O)NH-alkyl, —NHC(O)NH-alkenyl, —NHC(O)NH-alkenyl, —NHC(O)NH-carbocyclyl, —NHC(O)NH-aryl, —NHC(O)NH-heteroaryl, —NHC(O)NH-heterocyclyl, $NHC(S)NH_2$, —NHC(S)NH-alkyl, —NHC(S)NH-alkenyl, —NHC(S)NH-alkynyl, —NHC(S)NH-carbocyclyl, —NHC(S)NH-aryl, —NHC(S)NH-heteroaryl, —NHC(S)NH-heterocyclyl, —$NHC(NH)NH_2$, —NHC(NH)NH-alkyl, —NHC(NH)NH-alkenyl, —NHC(NH)NH-alkenyl, —NHC(NH)NH-carbocyclyl, —NHC(NH)NH-aryl, —NHC(NH)NH-heteroaryl, —NHC(NH)NH-heterocyclyl, —NHC(NH)-alkyl, —NHC(NH)-alkenyl, —NHC(NH)-alkenyl, —NHC(NH)-carbocyclyl, —NHC(NH)-aryl, —NHC(NH)-heteroaryl, —NHC(NH)-heterocyclyl, —C(NH)NH-alkyl, —C(NH)NH-alkenyl, —C(NH)NH-alkynyl, —C(NH)NH-carbocyclyl, —C(NH)NH-aryl, —C(NH)NH-heteroaryl, —C(NH)NH-heterocyclyl, —S(O)-alkyl, —S(O)-alkenyl, —S(O)-alkynyl, —S(O)-carbocyclyl, —S(O)-aryl, —S(O)-heteroaryl, —S(O)-heterocyclyl —SO$_2$NH$_2$, —SO$_2$NH-alkyl, —SO$_2$NH-alkenyl, —SO$_2$NH-alkynyl, —SO$_2$NH-carbocyclyl, —SO$_2$NH-aryl, —SO$_2$NH-heteroaryl, —SO$_2$NH-heterocyclyl, —NHSO$_2$-alkyl, —NHSO$_2$-alkenyl, —NHSO$_2$-alkynyl, —NHSO$_2$-carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^2$H, $^3$H, $^{13}$C, $^{14}$C, $^{15}$N, $^{18}$O, $^{17}$O, $^{31}$P, $^{32}$P, $^{35}$S, $^{18}$F and $^{36}$Cl, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^3$H or $^{14}$C, has been incorporated, is suitable for medicament and/or substrate tissue distribution assays. These radioisotopes, i.e. tritium ($^3$H) and carbon-14 ($^{14}$C), are particularly preferred owing to simple preparation and excellent detectability. Incorporation of heavier isotopes, for example deuterium ($^2$H), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^2$H) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in IRAK activity between a sample comprising a compound of the present invention, or composition thereof, and IRAK, and an equivalent sample comprising IRAK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

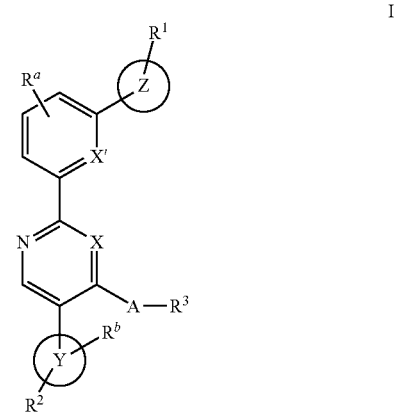

or a pharmaceutically acceptable salt thereof, wherein:

X is CR or N;

A is O, S, $SO_2$, SO, —NRC(O), —$NRSO_2$, or N(R); or A is absent;

$R^3$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$; or when A is —NRC(O), —$NRSO_2$, or N(R); then R and $R^3$, together with the atoms to which each is attached, may form a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

X' is CR or N;

Ring Z is a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

$R^1$ is —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

$R^a$ is absent, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;

Ring Y is an optionally substituted 5-6 membered monocyclic heteroaryl ring having 2-4 heteroatoms independently selected from nitrogen, oxygen, or sulfur;

R² is —R, halogen, -haloalkyl, —OR, —SR, —CN, —NO₂, —SO₂R, —SOR, —C(O)R, —CO₂R, —C(O)N(R)₂, —NRC(O)R, —NRC(O)N(R)₂, —NRSO₂R, or —N(R)₂;

R^b is absent, —R, halogen, -haloalkyl, —OR, —SR, —CN, —NO₂, —SO₂R, —SOR, —C(O)R, —CO₂R, —C(O)N (R)₂, —NRC(O)R, —NRC(O)N(R)₂, —NRSO₂R, or —N(R)₂;

each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

wherein when X is N and A is absent, then R³ is not H.

In certain embodiments, X is CR. In certain embodiments, X is CH. In certain embodiments, X is N.

In certain embodiments, A is O or N(R). In certain embodiments, A is O. In certain embodiments, A is N(R). In a further embodiment, A is NH or N-Me.

In certain embodiments, A is absent.

In certain embodiments, A is absent when R³ is alkyl or substituted alkyl.

In certain embodiments, A is N(R), and the ring formed by R and R³ is a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R³ is —R, -haloalkyl, —C(O)R, —CO₂R, or —C(O)N(R)₂.

In certain embodiments, R³ is —H.

In certain embodiments, R³ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R³ is methyl, ethyl, ethyl, propyl, i-propyl, butyl, s-butyl, t-butyl, straight or branched pentyl, or straight or branched hexyl; each of which is optionally substituted.

In certain embodiments, R³ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl;-1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, R³ is cyclopropyl, cyclobutyl, cyclopentyl, cyclohexyl, tetrahydrofuran, piperidine, piperidin-one, spiroheptane, or bicyclohexane; each of which is optionally substituted.

In certain embodiments, -A-R³ is —H, —CH₃, —CF₃,

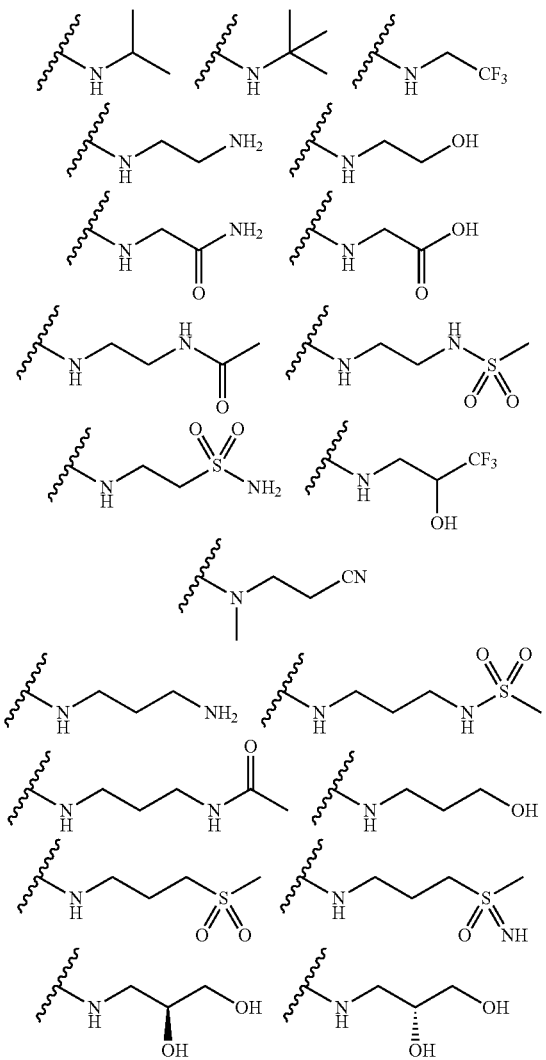

-continued
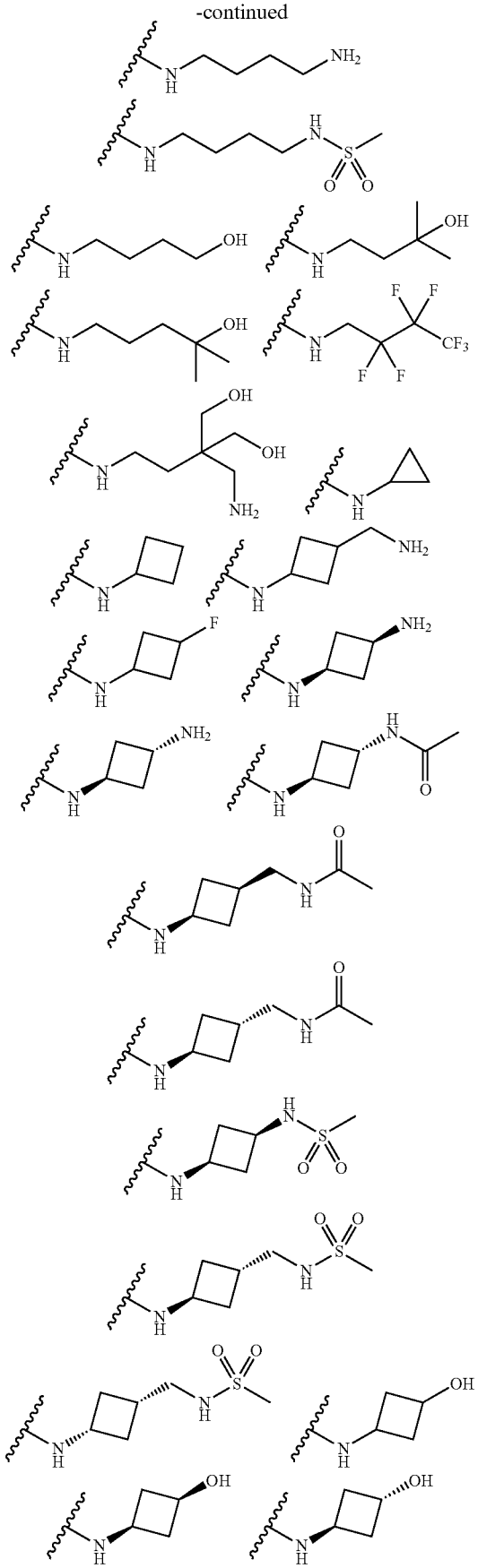
-continued
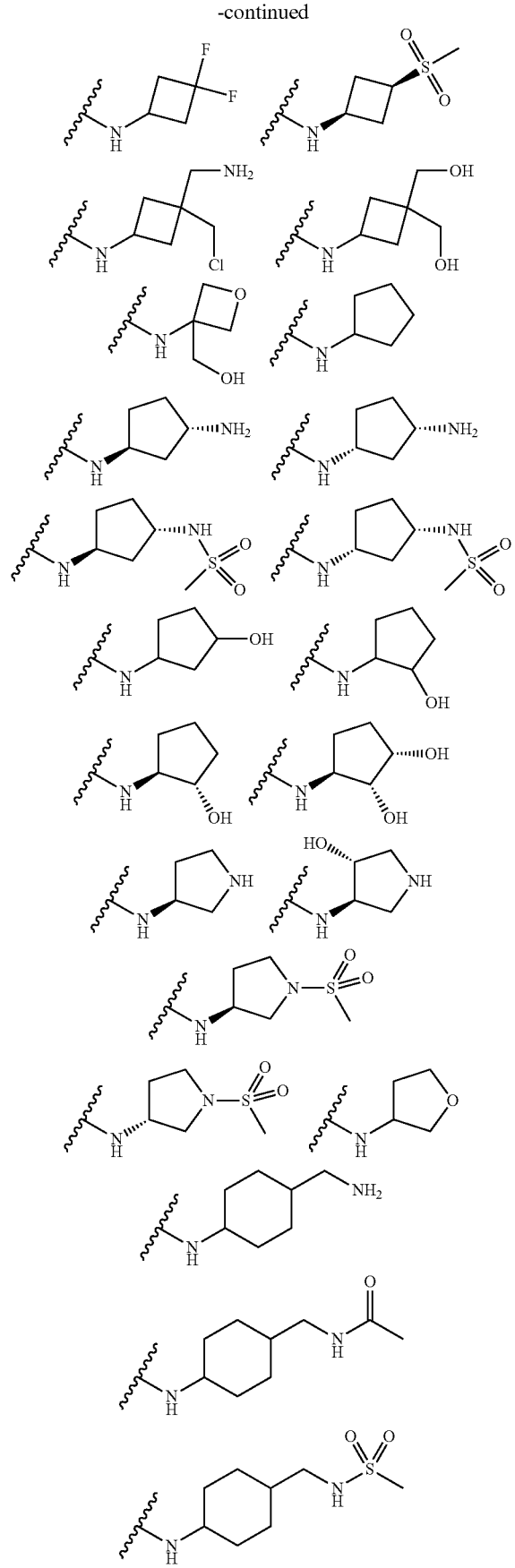

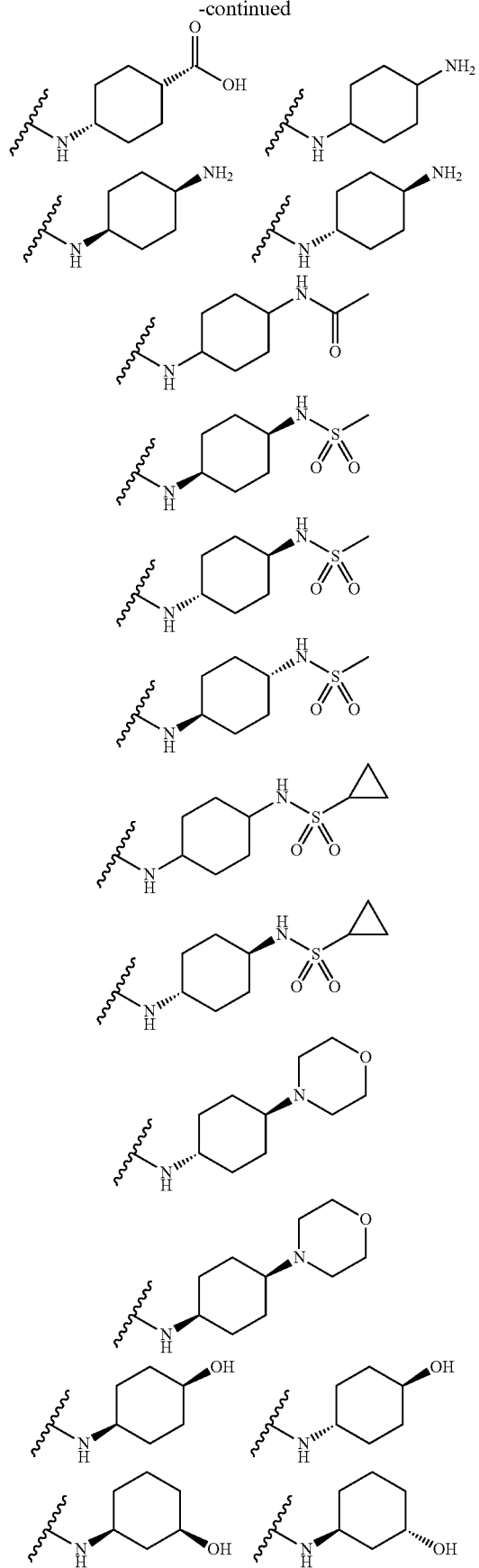
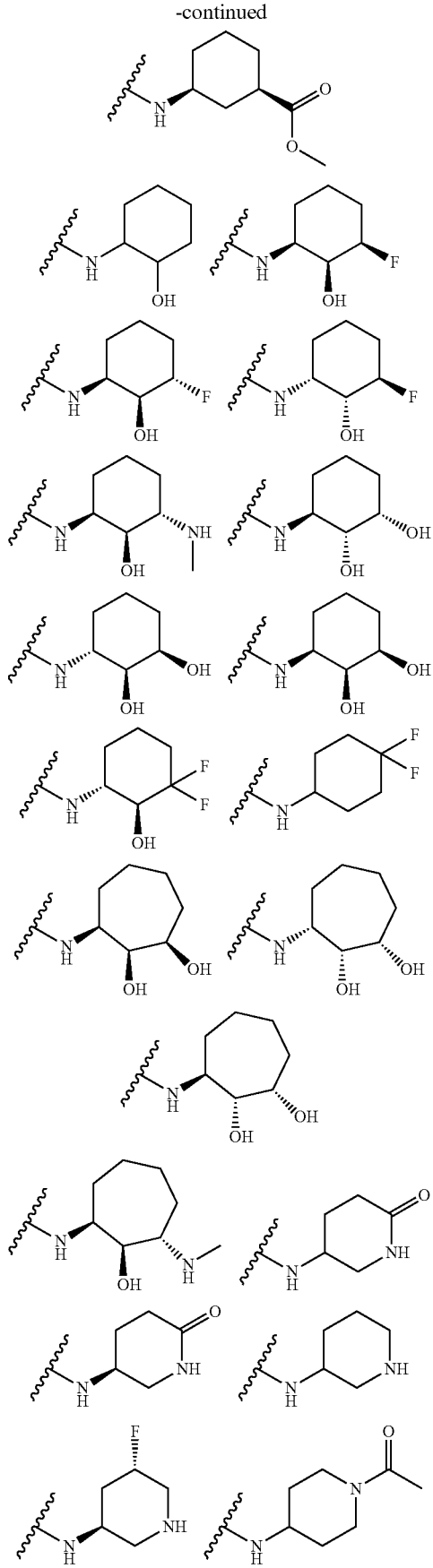

-continued
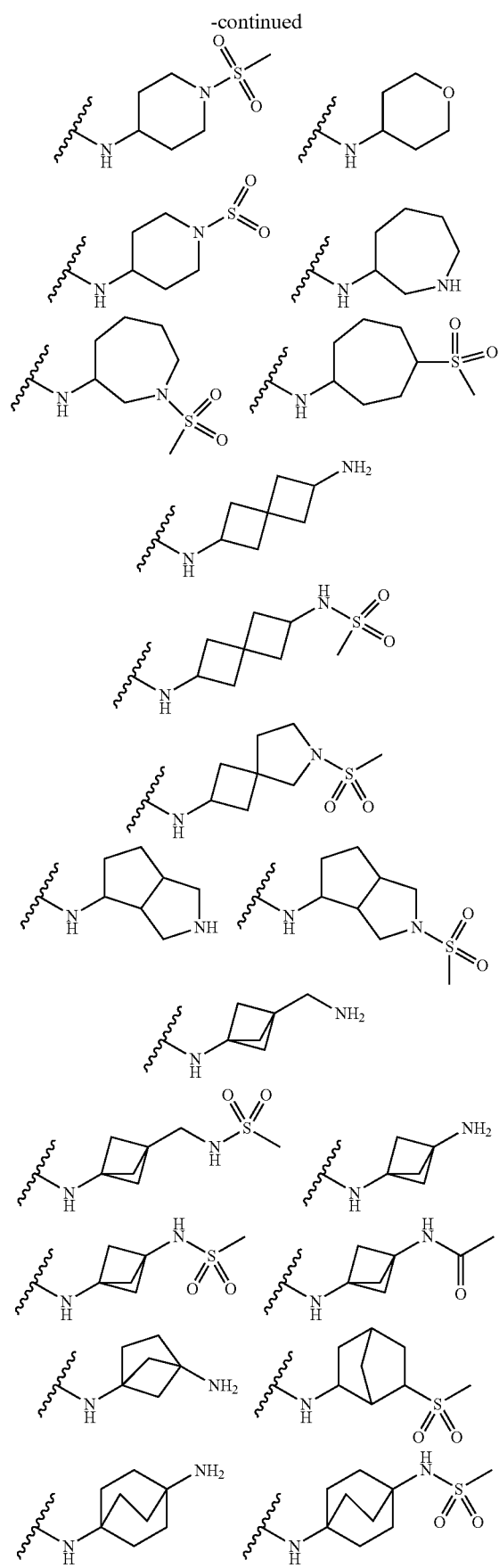
-continued
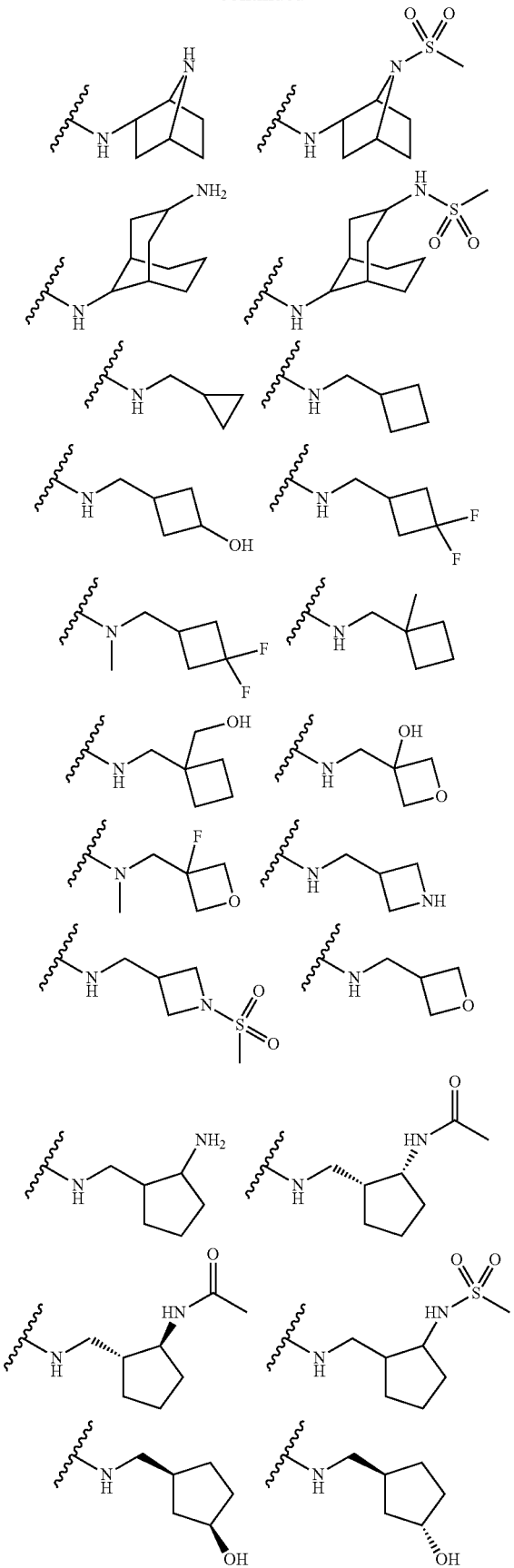

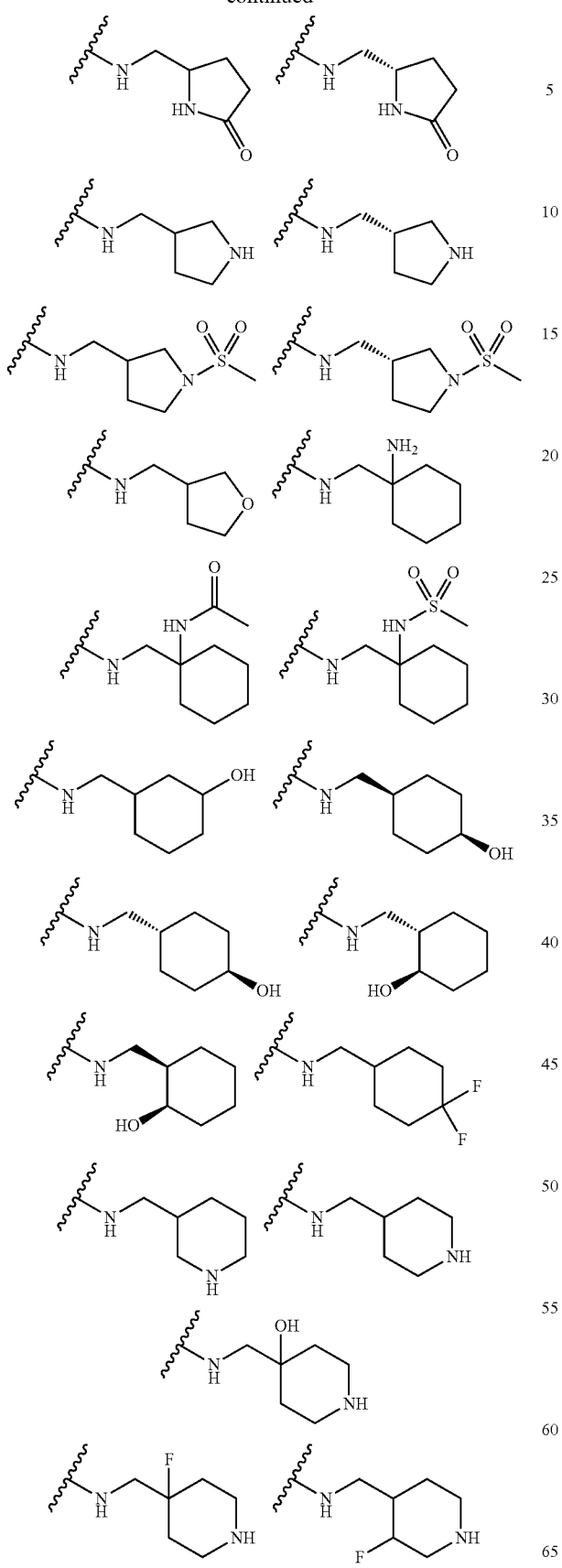
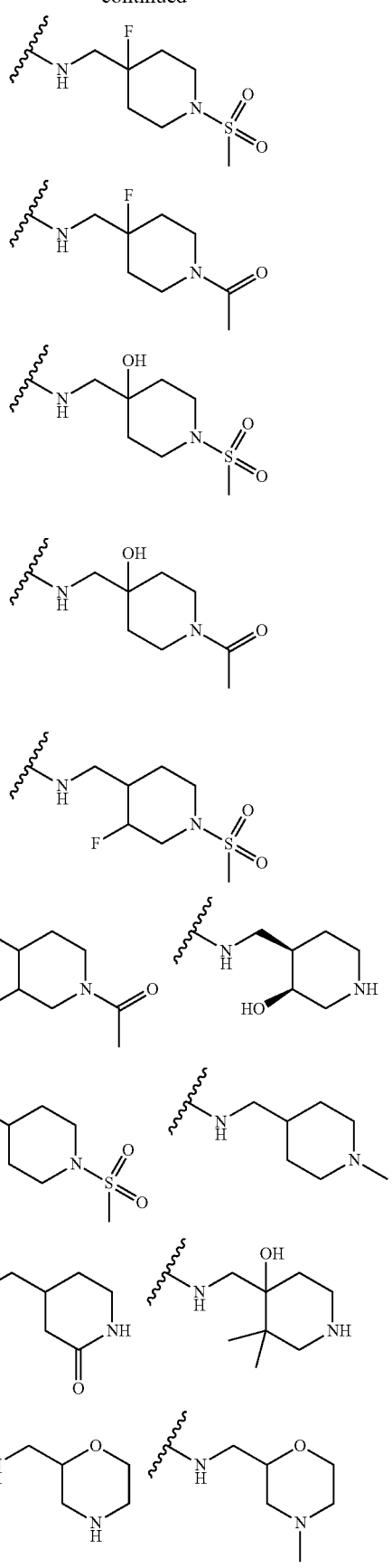

23
-continued
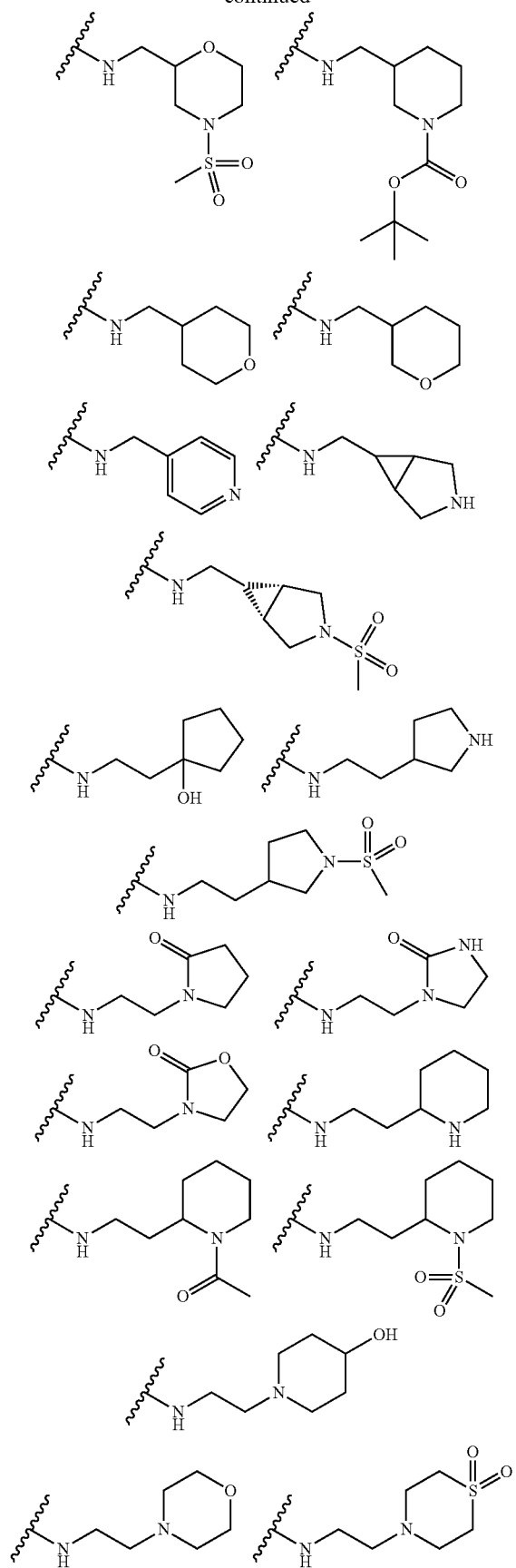
24
-continued
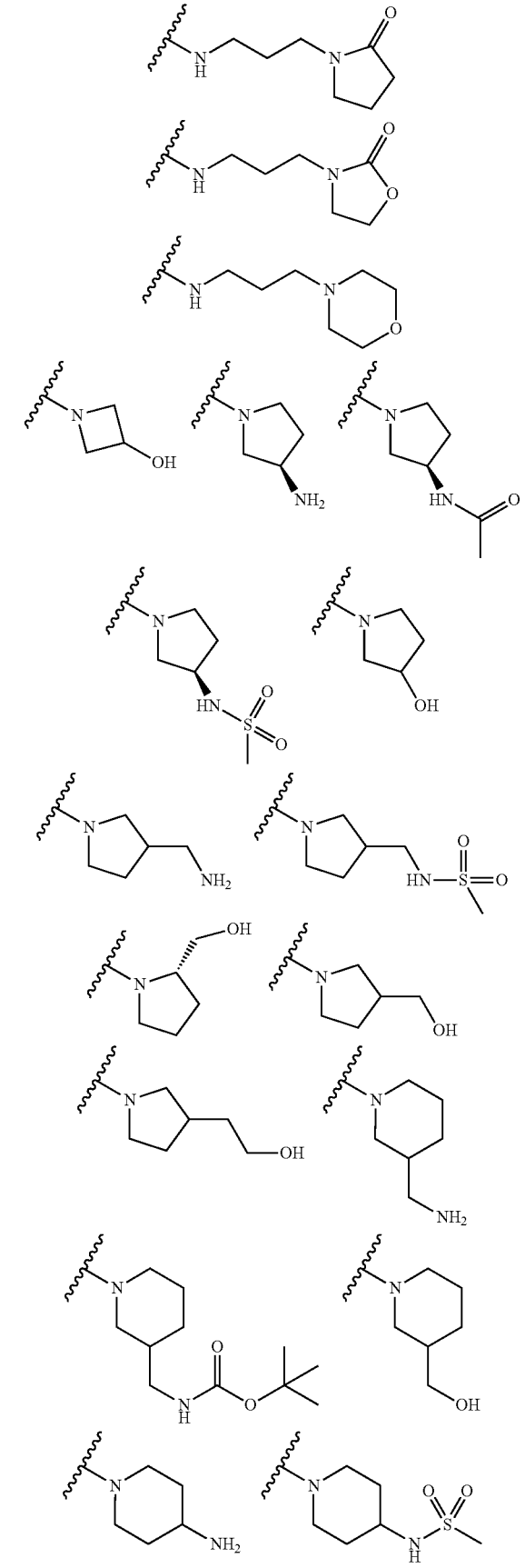

-continued

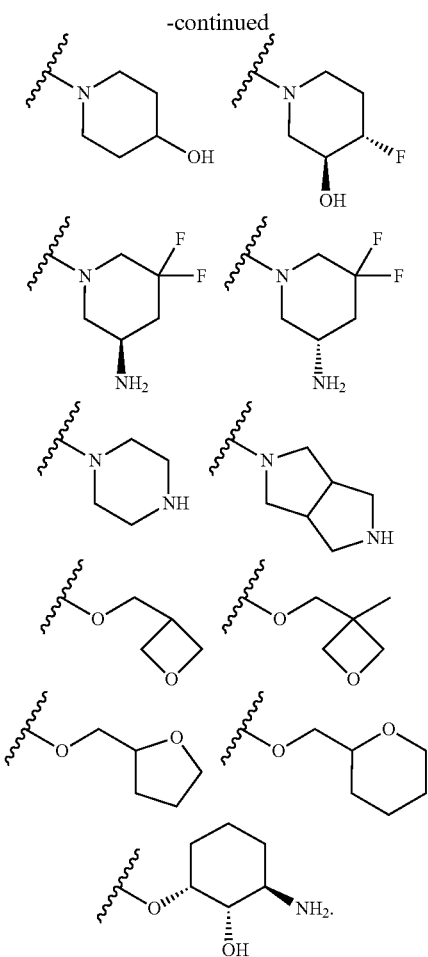

In certain embodiments, X' is CR. In certain embodiments, X' is CH. In certain embodiments, X' is N.

In certain embodiments, Ring Z is a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

In certain embodiments, Ring Z is:

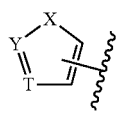

wherein X is O, S or NR$^1$; Y is C or N; and T is C or N.

In certain embodiments, Ring Z is tetrahydrofuran, furanyl, furazanyl, imidazolidinyl, imidazolinyl, imidazolyl, 1H-indazolyl, isothiazolyl, isoxazolyl, morpholinyl, oxadiazolyl, 1,2,3-oxadiazolyl, 1,2,4-oxadiazolyl;- 1,2,5oxadiazolyl, 1,3,4-oxadiazolyl, oxazolidinyl, oxazolyl, oxazolidinyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, thiazolyl, thienyl, triazinyl, thiadiazole, 1,2,3-triazolyl, 1,2,4-triazolyl, 1,2,5-triazolyl, or 1,3,4-triazolyl; each of which is optionally substituted.

In certain embodiments, Ring Z is a pyrazole ring.

In certain embodiments, R$^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, R$^1$ is —R.

In certain embodiments, Ring Z is

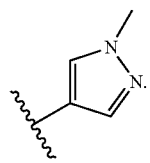 [SMILES: *c1cnn(C)c1]

In certain embodiments, R$^a$ is absent.

In certain embodiments, R$^a$ is OR, CF$_3$, Hal, or NO$_2$.

In certain embodiments, Ring Y is an optionally substituted 5-6 membered monocyclic heteroaryl ring having 2-4 heteroatoms independently selected from nitrogen, oxygen, or sulfur.

In certain embodiments, Ring Y is tetrahydrofuran, furanyl, furazanyl, imidazolidinyl, imidazolinyl, imidazolyl, 1H-indazolyl, isothiazolyl, isoxazolyl, morpholinyl, oxadiazolyl, 1,2,3-oxadiazolyl, 1,2,4-oxadiazolyl;- 1,2,5oxadiazolyl, 1,3,4-oxadiazolyl, oxazolidinyl, oxazolyl, oxazolidinyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, thiazolyl, thienyl, triazinyl, thiadiazole, 1,2,3-triazolyl, 1,2,4-triazolyl, 1,2,5-triazolyl, or 1,3,4-triazolyl; each of which is optionally substituted.

In certain embodiments, Ring Y is an optionally substituted pyridyl, pyrazole or thiadiazole.

In certain embodiments, Ring Y is an optionally substituted pyrazole.

In certain embodiments, Ring Y is an optionally substituted thiadiazole.

In certain embodiments, Ring Y is an optionally substituted pyridyl.

In certain embodiments, R$^2$ is —R, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, R$^2$ is —R, —C(O)R, —CO$_2$R, —C(O)N(R)$_2$, or —N(R)$_2$.

In certain embodiments, R$^b$ is absent. In certain embodiments, R$^b$ is an optionally substituted C$_{1-6}$ aliphatic, C(O)NR$_2$, or COR.

In certain embodiments, Ring Y is

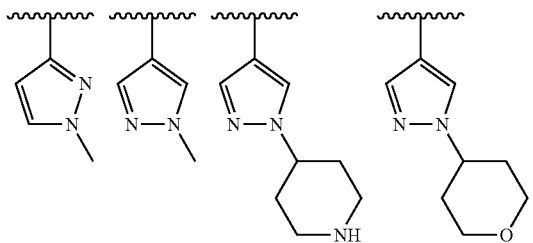

-continued

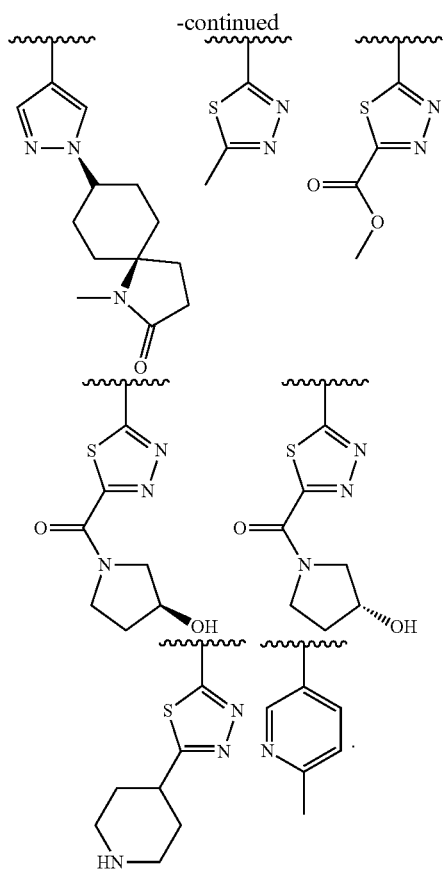

In certain embodiments, each of Ring Z, Ring Y, $R^1$, $R^2$, $R^3$, $R^a$, $R^b$, A, X, and X', is as defined above and described in embodiments, classes and subclasses above and herein, singly or in combination.

In certain embodiments, the present invention provides a compound of formula I-a,

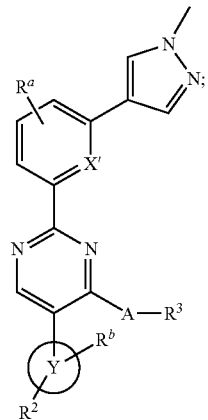

I-a or a pharmaceutically acceptable salt thereof, wherein each of Ring Y, $R^2$, $R^3$, $R^a$, $R^b$, A, X, and X', is as defined above and described in embodiments, classes and subclasses above and herein, singly or in combination.

In certain embodiments, the present invention provides a compound of formula I-b,

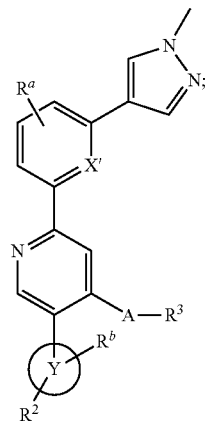

I-b or a pharmaceutically acceptable salt thereof, wherein each of Ring Y, $R^2$, $R^3$, $R^a$, $R^b$, A, and X', is as defined above and described in embodiments, classes and subclasses above and herein, singly or in combination.

In certain embodiments, the present invention provides a compound of formula I-c,

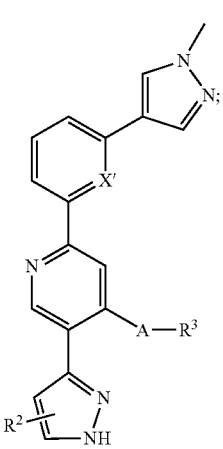

I-c or a pharmaceutically acceptable salt thereof, wherein each of Ring Y, $R^2$, $R^3$, $R^a$, $R^b$, A, and X', and m is as defined above and described in embodiments, classes and subclasses above and herein, singly or in combination.

In certain embodiments, the present invention provides a compound of formula I-d, I-d or a pharmaceutically acceptable salt thereof, wherein each of $R^2$, $R^3$, A, and X', is as defined above and described in embodiments, classes and subclasses above and herein, singly or in combination.

In certain embodiments, the present invention provides a compound of formula I-e,

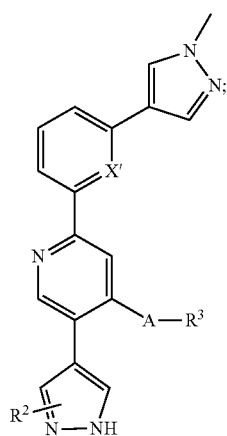

I-e or a pharmaceutically acceptable salt thereof, wherein each of $R^2$, $R^3$, A, and X', is as defined above and described in embodiments, classes and subclasses above and herein, singly or in combination.

In certain embodiments, the present invention provides a compound of formula I-f,

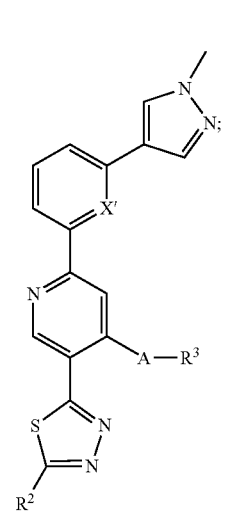

I-f or a pharmaceutically acceptable salt thereof, wherein each of $R^2$, $R^3$, A, and X', is as defined above and described in embodiments, classes and subclasses above and herein, singly or in combination.

In certain embodiments, the invention provides a compound selected from Table 1:

TABLE 1

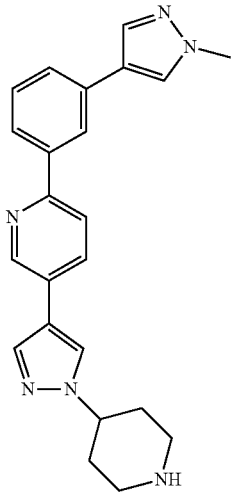

1

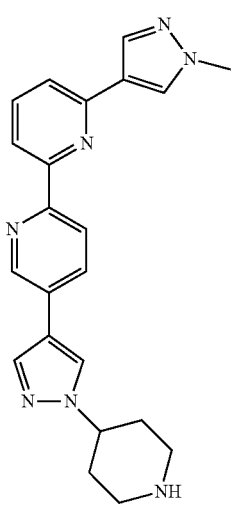 [SMILES: Cn1cc(-c2cccc(-c3ccc(-c4cnn(C5CCNCC5)c4)cn3)n2)cn1]

2

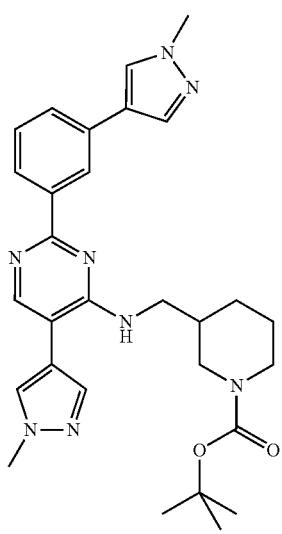 [SMILES: Cn1cc(-c2cccc(-c3ncc(-c4cnn(C)c4)c(NCC4CCCN(C(=O)OC(C)(C)C)C4)n3)c2)cn1]

3

TABLE 1-continued
4
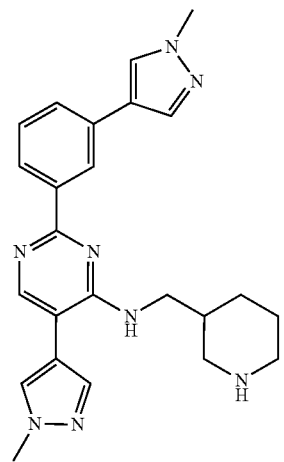 [SMILES: Cn1cc(-c2cccc(-c3ncc(-c4cnn(C)c4)c(NCC4CCCNC4)n3)c2)cn1]
5
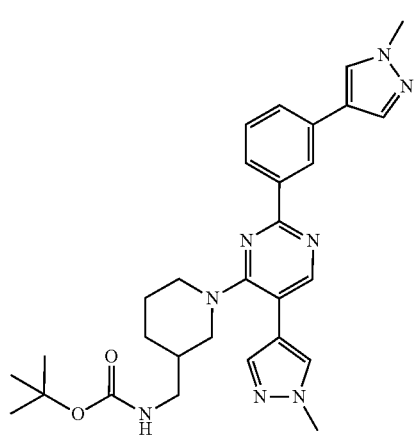 [SMILES: Cn1cc(-c2cccc(-c3ncc(-c4cnn(C)c4)c(N4CCCC(CNC(=O)OC(C)(C)C)C4)n3)c2)cn1]
6
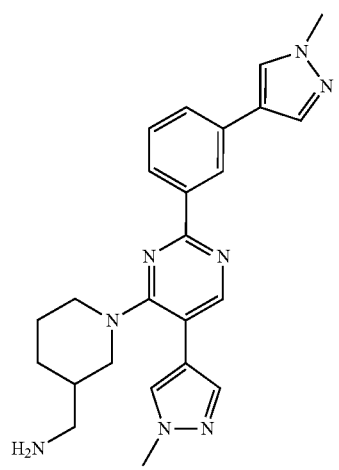 [SMILES: Cn1cc(-c2cccc(-c3ncc(-c4cnn(C)c4)c(N4CCCC(CN)C4)n3)c2)cn1]
TABLE 1-continued
7
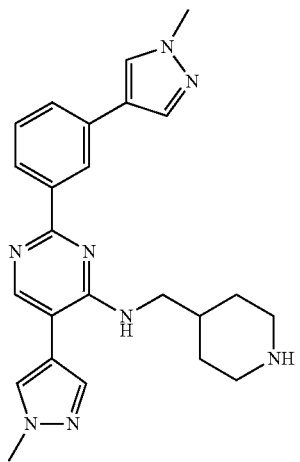 [SMILES: Cn1cc(-c2cccc(-c3ncc(-c4cnn(C)c4)c(NCC4CCNCC4)n3)c2)cn1]
8
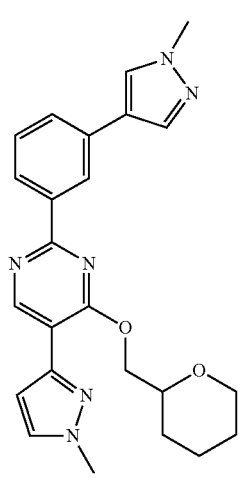 [SMILES: Cn1cc(-c2cccc(-c3ncc(-c4ccn(C)n4)c(OCC4CCCCO4)n3)c2)cn1]
9
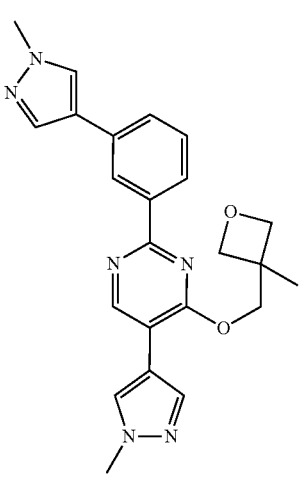 [SMILES: Cn1cc(-c2cccc(-c3ncc(-c4cnn(C)c4)c(OCC4(C)COC4)n3)c2)cn1]

TABLE 1-continued
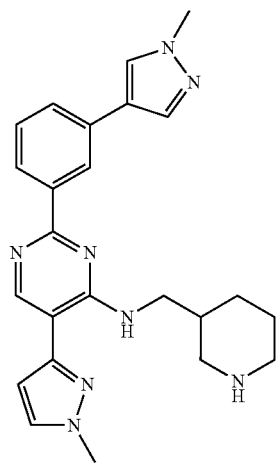 [SMILES: Cn1cc(-c2cccc(-c3ncc(-c4ccn(C)n4)c(NCC4CCCNC4)n3)c2)cn1]
10
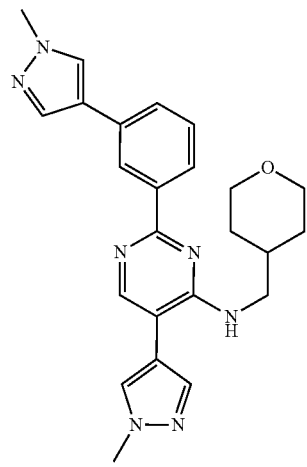
13
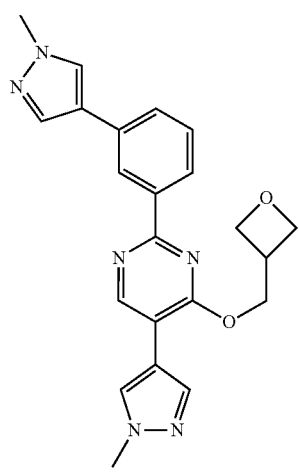 [SMILES: Cn1cc(-c2cccc(-c3ncc(-c4cnn(C)c4)c(OCC4COC4)n3)c2)cn1]
11
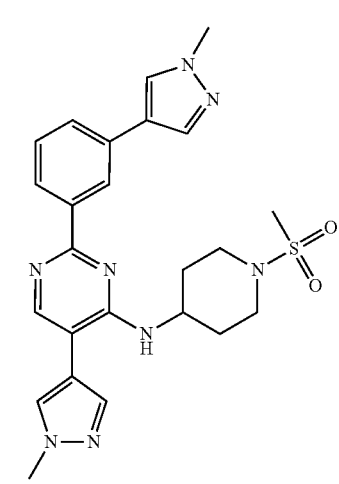
14
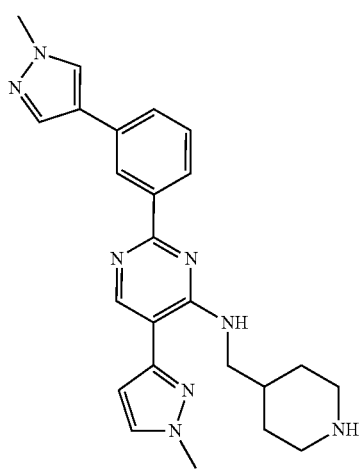 [SMILES: Cn1cc(-c2cccc(-c3ncc(-c4ccn(C)n4)c(NCC4CCNCC4)n3)c2)cn1]
12
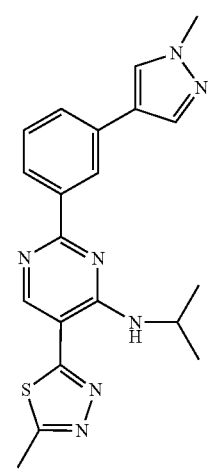 [SMILES: Cc1nnc(-c2cnc(-c3cccc(-c4cnn(C)c4)c3)nc2NC(C)C)s1]
15

TABLE 1-continued
| | |
|---|---|
| 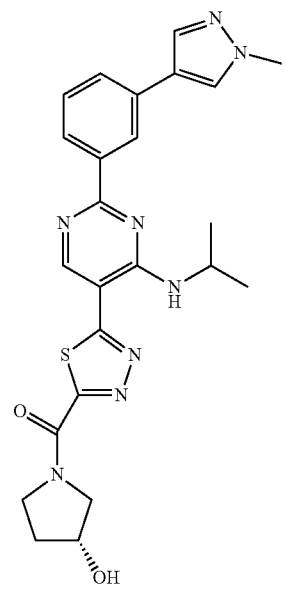 [SMILES: CC(C)Nc1nc(-c2cccc(-c3cnn(C)c3)c2)ncc1-c1nnc(C(=O)N2CC[C@@H](O)C2)s1] 16 | 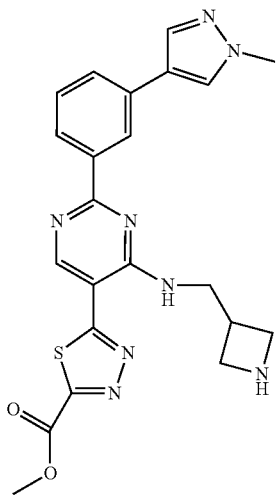 19 |
| 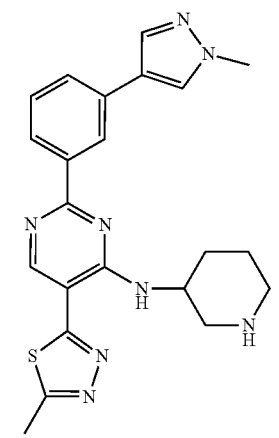 [SMILES: Cc1nnc(-c2cnc(-c3cccc(-c4cnn(C)c4)c3)nc2NC2CCCNC2)s1] 17 | |
| 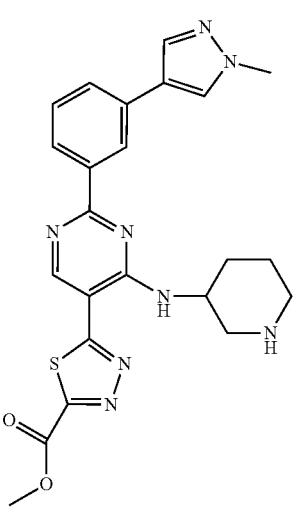 [SMILES: COC(=O)c1nnc(-c2cnc(-c3cccc(-c4cnn(C)c4)c3)nc2NC2CCCNC2)s1] 18 | 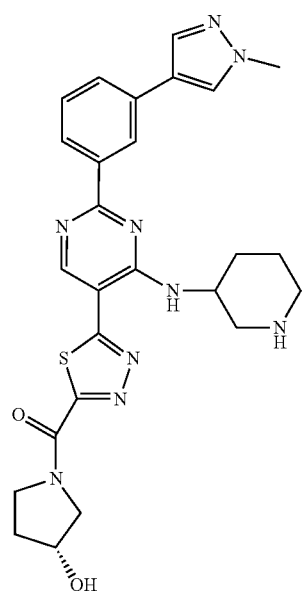 [SMILES: Cn1cc(-c2cccc(-c3ncc(-c4nnc(C(=O)N5CC[C@@H](O)C5)s4)c(NC4CCCNC4)n3)c2)cn1] 20 |

TABLE 1-continued
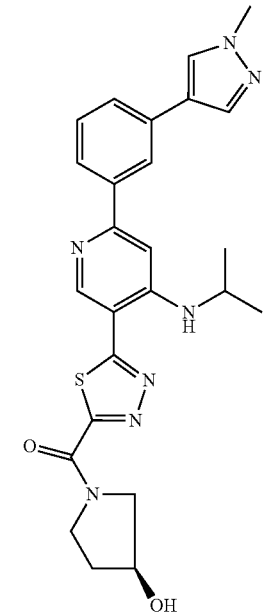 [SMILES: CC(C)Nc1cc(-c2cccc(-c3cnn(C)c3)c2)ncc1-c1nnc(C(=O)N2CC[C@H](O)C2)s1]
21
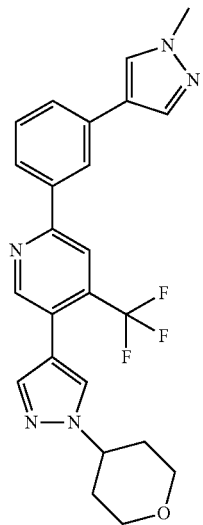 [SMILES: Cn1cc(-c2cccc(-c3cc(C(F)(F)F)c(-c4cnn(C5CCOCC5)c4)cn3)c2)cn1]
23
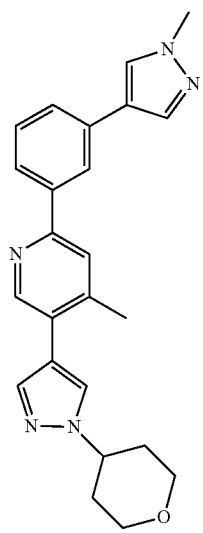 [SMILES: Cc1cc(-c2cccc(-c3cnn(C)c3)c2)ncc1-c1cnn(C2CCOCC2)c1]
24
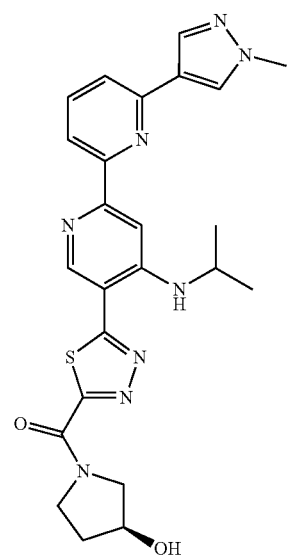
22
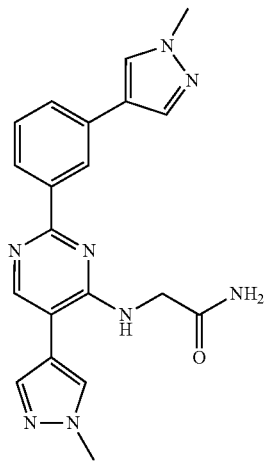 [SMILES: Cn1cc(-c2cccc(-c3ncc(-c4cnn(C)c4)c(NCC(N)=O)n3)c2)cn1]
25

TABLE 1-continued
26
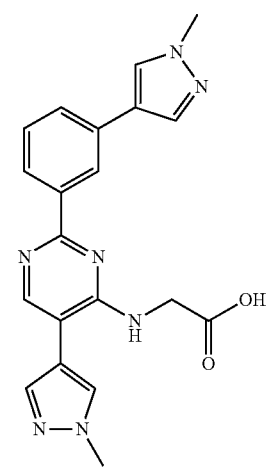 [SMILES: Cn1cc(-c2cccc(-c3ncc(-c4cnn(C)c4)c(NCC(=O)O)n3)c2)cn1]
29
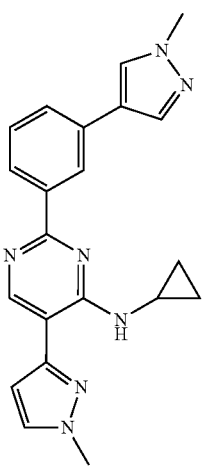
27
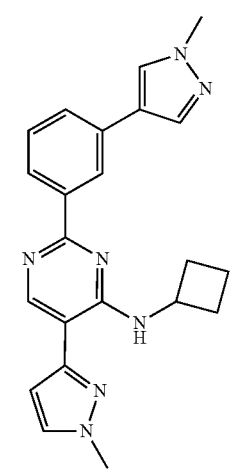 [SMILES: Cn1cc(-c2cccc(-c3ncc(-c4ccn(C)n4)c(NC4CCC4)n3)c2)cn1]
30
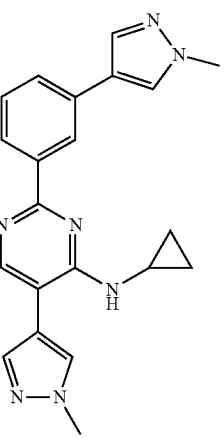
28
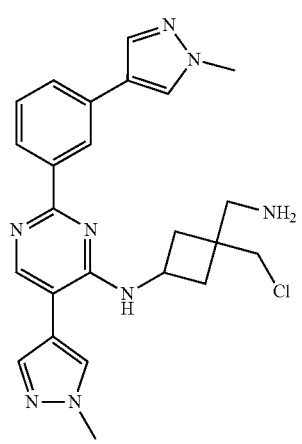 [SMILES: Cn1cc(-c2cccc(-c3ncc(-c4cnn(C)c4)c(NC4CC(CN)(CCl)C4)n3)c2)cn1]
31
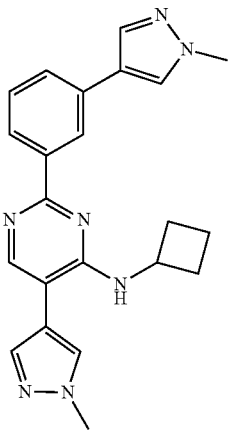 [SMILES: Cn1cc(-c2cccc(-c3ncc(-c4cnn(C)c4)c(NC4CCC4)n3)c2)cn1]

TABLE 1-continued
32
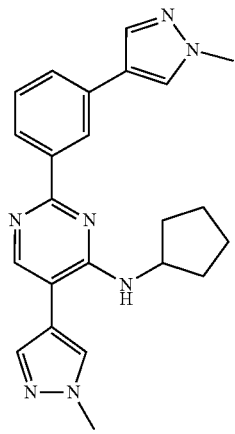 [SMILES: Cn1cc(-c2cccc(-c3ncc(-c4cnn(C)c4)c(NC4CCCC4)n3)c2)cn1]
33
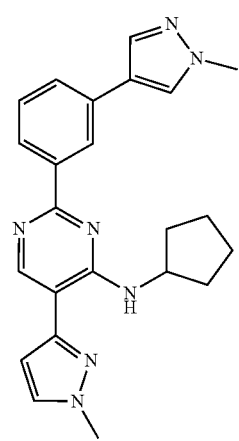
34
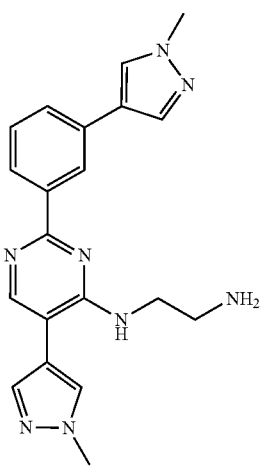 [SMILES: Cn1cc(-c2cccc(-c3ncc(-c4cnn(C)c4)c(NCCN)n3)c2)cn1]
TABLE 1-continued
35
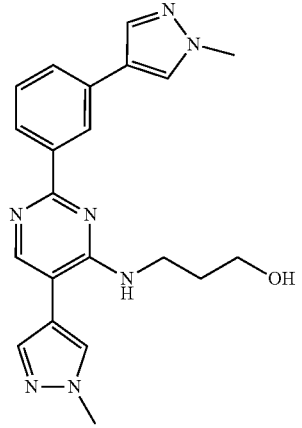 [SMILES: Cn1cc(-c2cccc(-c3ncc(-c4cnn(C)c4)c(NCCCO)n3)c2)cn1]
36
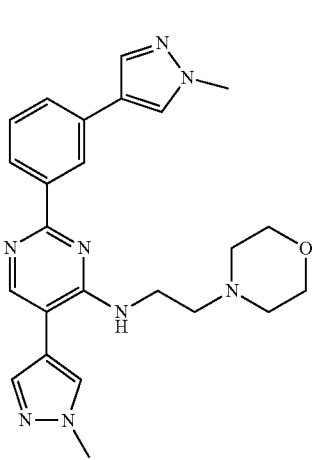 [SMILES: Cn1cc(-c2cccc(-c3ncc(-c4cnn(C)c4)c(NCCN4CCOCC4)n3)c2)cn1]
37
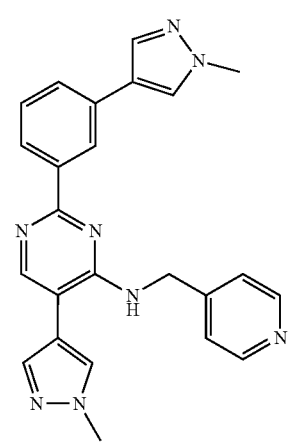 [SMILES: Cn1cc(-c2cccc(-c3ncc(-c4cnn(C)c4)c(NCc4ccncc4)n3)c2)cn1]

TABLE 1-continued
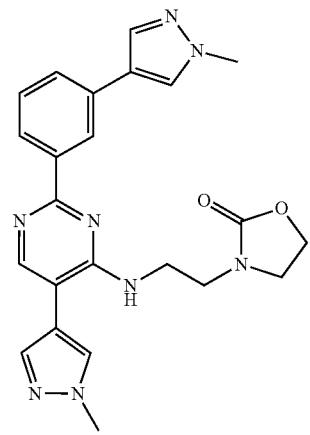 [SMILES: Cn1cc(-c2cccc(-c3ncc(-c4cnn(C)c4)c(NCCN4CCOC4=O)n3)c2)cn1]
38
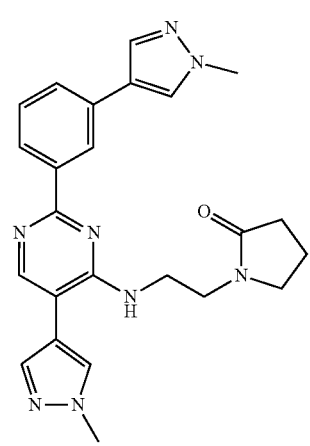 [SMILES: Cn1cc(-c2cccc(-c3ncc(-c4cnn(C)c4)c(NCCN4CCCC4=O)n3)c2)cn1]
39
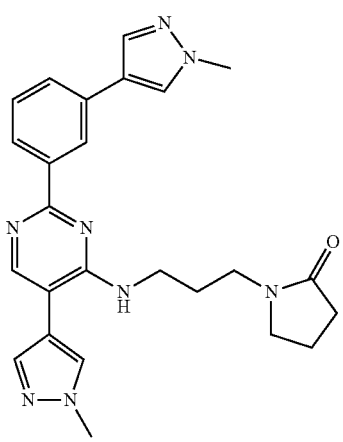 [SMILES: Cn1cc(-c2cccc(-c3ncc(-c4cnn(C)c4)c(NCCCN4CCCC4=O)n3)c2)cn1]
40
TABLE 1-continued
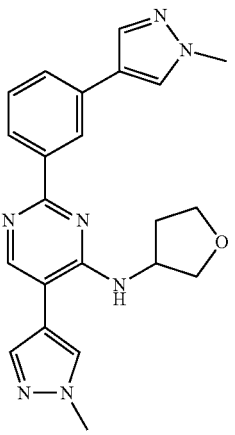
41
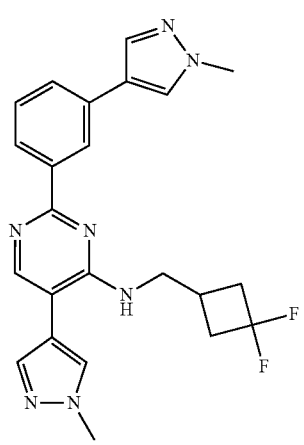 [SMILES: Cn1cc(-c2cccc(-c3ncc(-c4cnn(C)c4)c(NCC4CC(F)(F)C4)n3)c2)cn1]
42
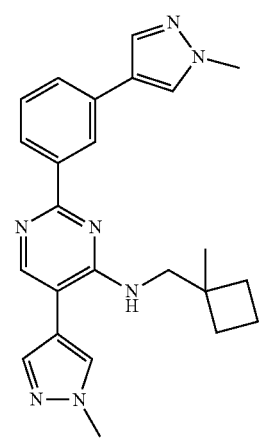 [SMILES: Cn1cc(-c2cccc(-c3ncc(-c4cnn(C)c4)c(NCC4(C)CCC4)n3)c2)cn1]
43

TABLE 1-continued
| 44 | 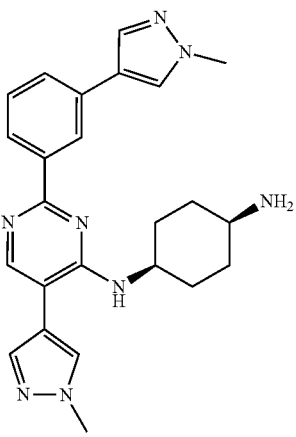 [SMILES: Cn1cc(-c2cccc(-c3ncc(-c4cnn(C)c4)c(N[C@H]4CC[C@@H](N)CC4)n3)c2)cn1] |
| 45 | 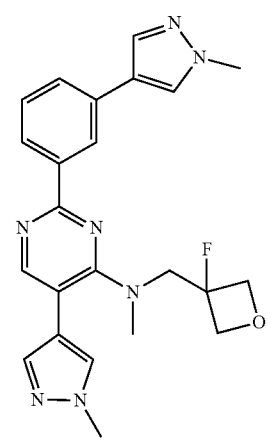 [SMILES: CN(CC1(F)COC1)c1nc(-c2cccc(-c3cnn(C)c3)c2)ncc1-c1cnn(C)c1] |
| 46 | 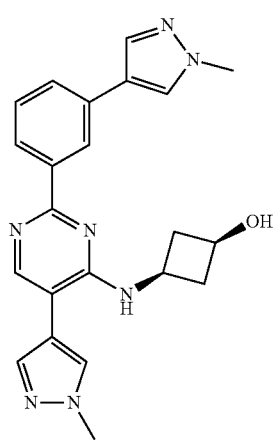 [SMILES: Cn1cc(-c2cccc(-c3ncc(-c4cnn(C)c4)c(N[C@H]4C[C@@H](O)C4)n3)c2)cn1] |
| 47 | 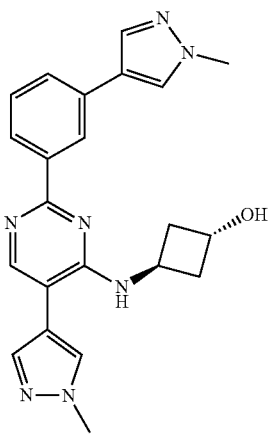 [SMILES: Cn1cc(-c2cccc(-c3ncc(-c4cnn(C)c4)c(N[C@H]4C[C@H](O)C4)n3)c2)cn1] |
| 48 | 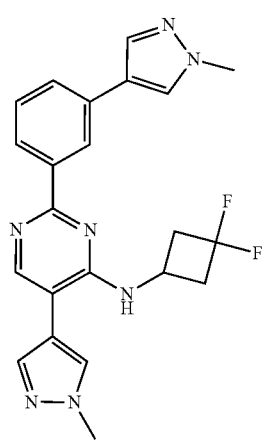 [SMILES: Cn1cc(-c2cccc(-c3ncc(-c4cnn(C)c4)c(NC4CC(F)(F)C4)n3)c2)cn1] |
| 49 | 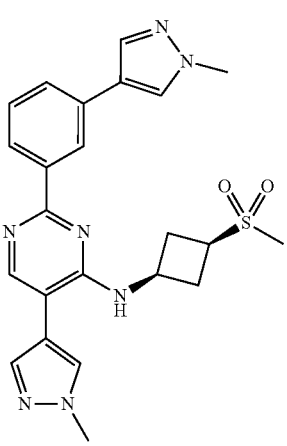 [SMILES: Cn1cc(-c2cccc(-c3ncc(-c4cnn(C)c4)c(N[C@H]4C[C@@H](S(C)(=O)=O)C4)n3)c2)cn1] |

TABLE 1-continued
| 50 | 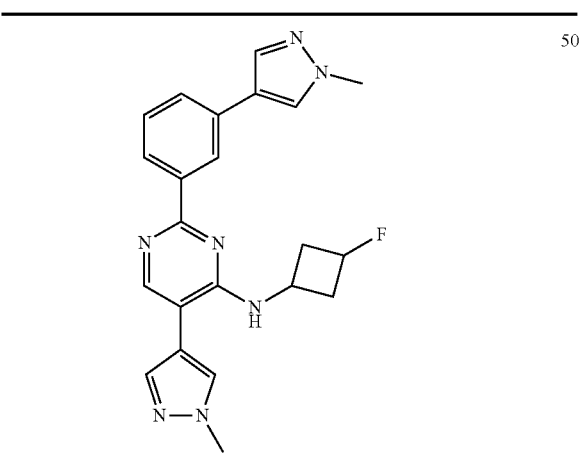 |
| --- | --- |
| 51 | 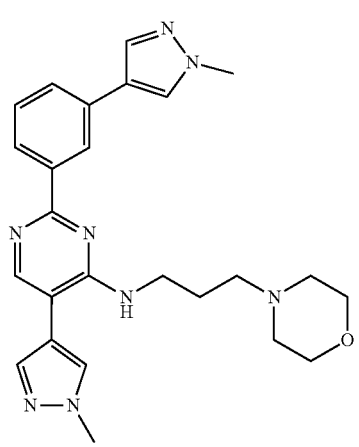 [SMILES: Cn1cc(-c2cccc(-c3ncc(-c4cnn(C)c4)c(NCCCN4CCOCC4)n3)c2)cn1] |
| 52 | 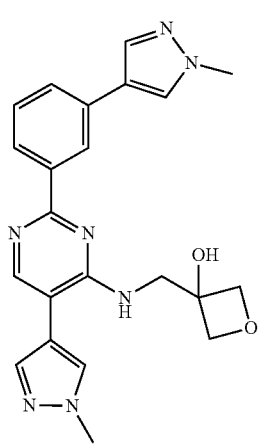 [SMILES: Cn1cc(-c2cccc(-c3ncc(-c4cnn(C)c4)c(NCC4(O)COC4)n3)c2)cn1] |
TABLE 1-continued
| 53 | 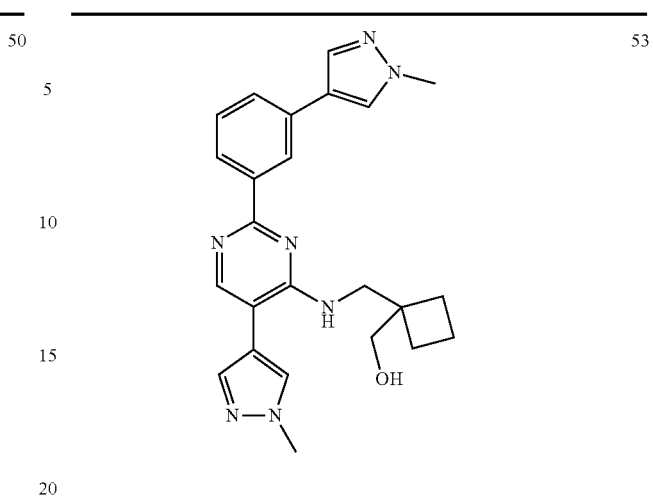 |
| --- | --- |
| 54 | |
| 55 | 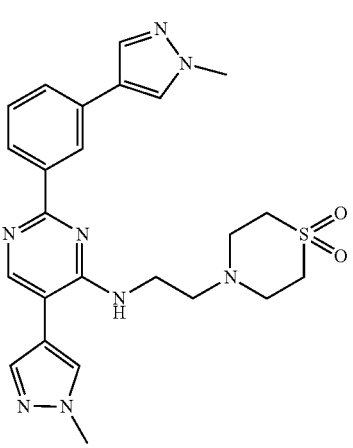 [SMILES: Cn1cc(-c2cccc(-c3ncc(-c4cnn(C)c4)c(NCCN4CCS(=O)(=O)CC4)n3)c2)cn1] |

TABLE 1-continued
56 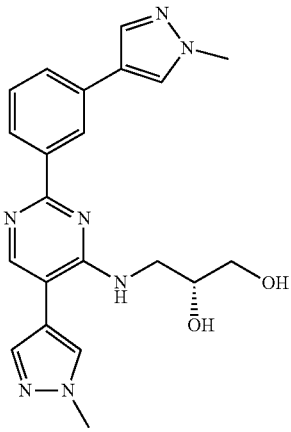
57 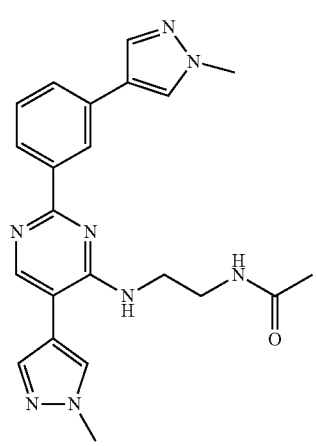 [SMILES: CC(=O)NCCNc1nc(-c2cccc(-c3cnn(C)c3)c2)ncc1-c1cnn(C)c1]
58 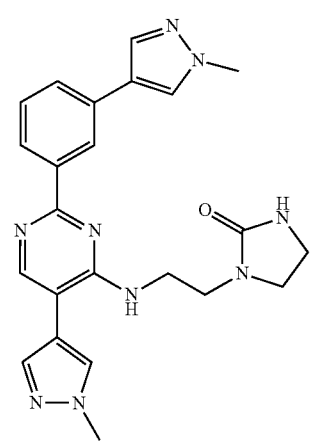
TABLE 1-continued
59 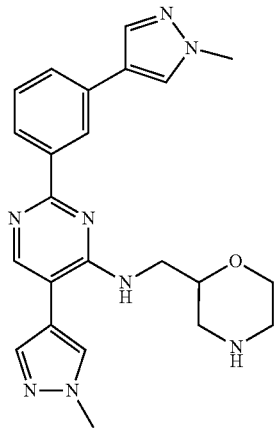
60 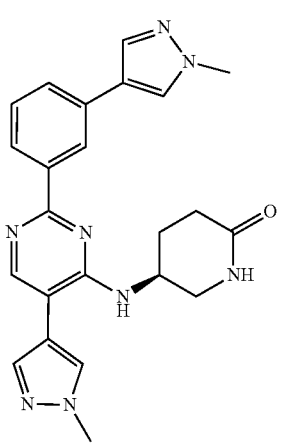 [SMILES: Cn1cc(-c2cccc(-c3ncc(-c4cnn(C)c4)c(N[C@H]4CCC(=O)NC4)n3)c2)cn1]
61 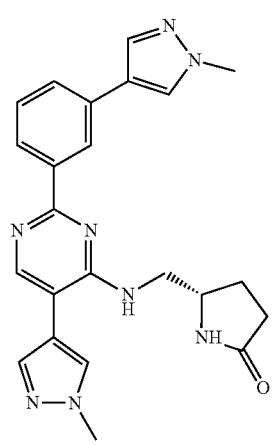 [SMILES: Cn1cc(-c2cccc(-c3ncc(-c4cnn(C)c4)c(NC[C@@H]4CCC(=O)N4)n3)c2)cn1]

TABLE 1-continued
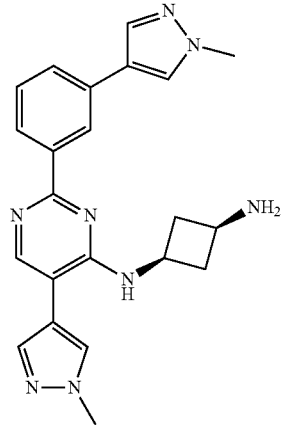 [SMILES: Cn1cc(-c2cccc(-c3ncc(-c4cnn(C)c4)c(N[C@H]4C[C@@H](N)C4)n3)c2)cn1]
62
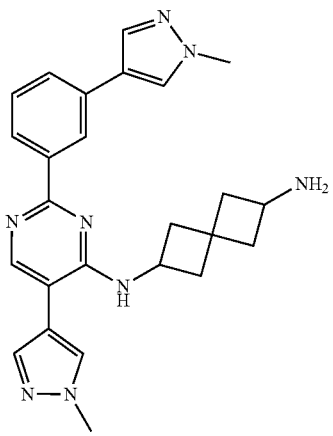
65
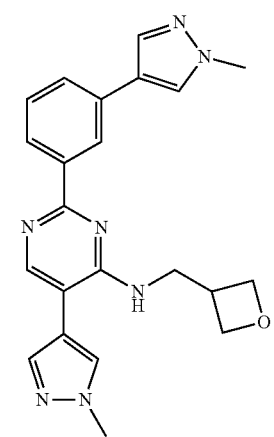 [SMILES: Cn1cc(-c2cccc(-c3ncc(-c4cnn(C)c4)c(NCC4COC4)n3)c2)cn1]
63
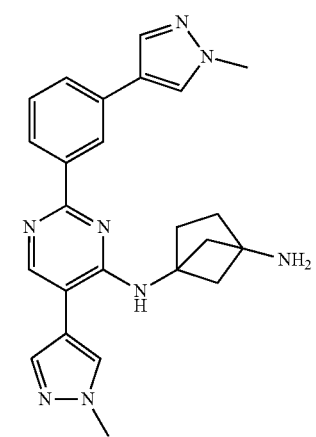
66
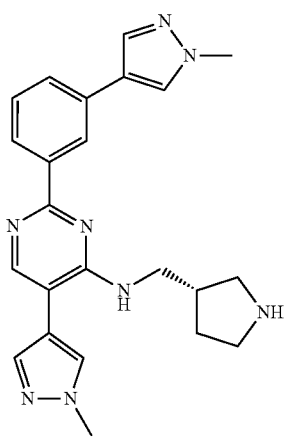 [SMILES: Cn1cc(-c2cccc(-c3ncc(-c4cnn(C)c4)c(NC[C@H]4CCNC4)n3)c2)cn1]
64
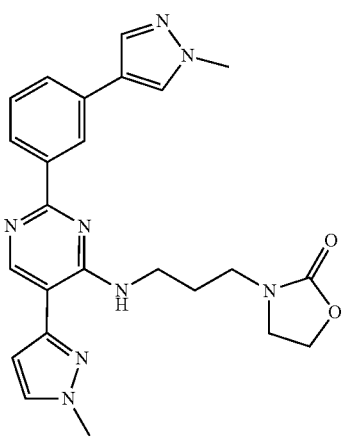 [SMILES: Cn1cc(-c2cccc(-c3ncc(-c4ccn(C)n4)c(NCCCN4CCOC4=O)n3)c2)cn1]
67

TABLE 1-continued
| | |
|---|---|
| 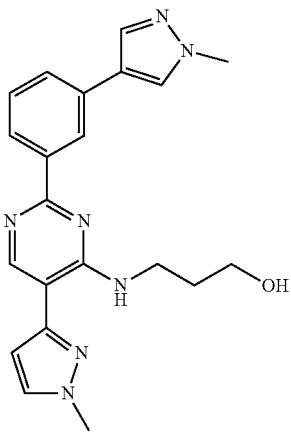 [SMILES: Cn1cc(-c2cccc(-c3ncc(-c4ccn(C)n4)c(NCCCO)n3)c2)cn1] 68 | 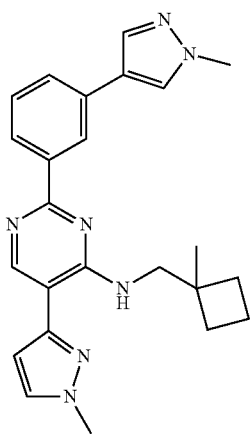 71 |
| 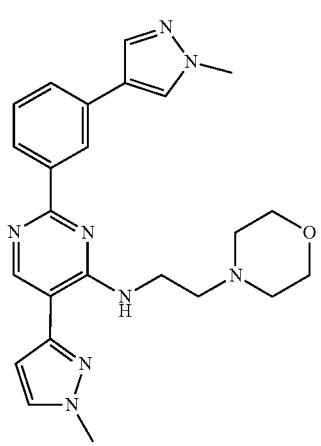 [SMILES: Cn1cc(-c2cccc(-c3ncc(-c4ccn(C)n4)c(NCCN4CCOCC4)n3)c2)cn1] 69 | 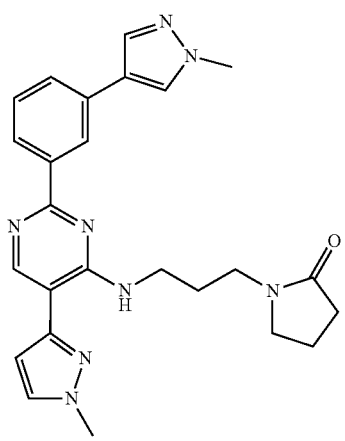 72 |
| 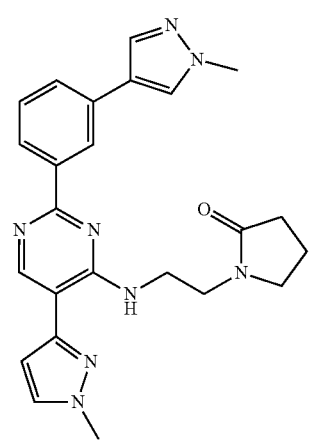 [SMILES: Cn1cc(-c2cccc(-c3ncc(-c4ccn(C)n4)c(NCCN4CCCC4=O)n3)c2)cn1] 70 | 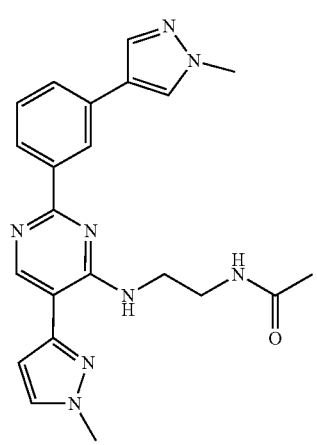 [SMILES: CC(=O)NCCNc1nc(-c2cccc(-c3cnn(C)c3)c2)ncc1-c1ccn(C)n1] 73 |

TABLE 1-continued
74
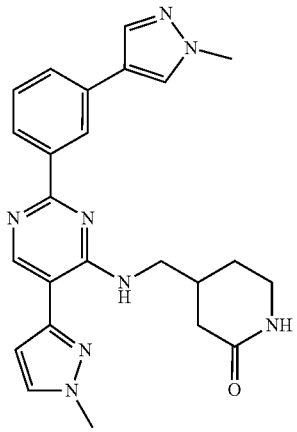 [SMILES: Cn1cc(-c2cccc(-c3ncc(-c4ccn(C)n4)c(NCC4CCNC(=O)C4)n3)c2)cn1]
75
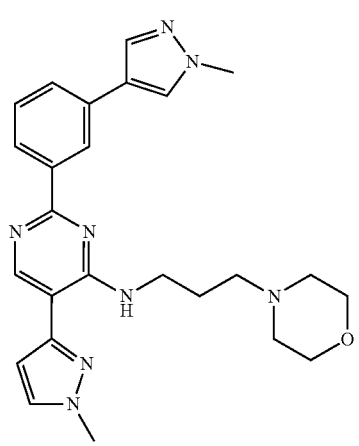 [SMILES: Cn1cc(-c2cccc(-c3ncc(-c4ccn(C)n4)c(NCCCN4CCOCC4)n3)c2)cn1]
76
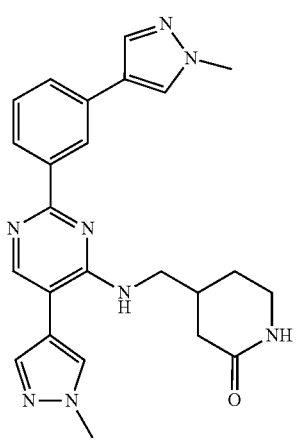 [SMILES: Cn1cc(-c2cccc(-c3ncc(-c4cnn(C)c4)c(NCC4CCNC(=O)C4)n3)c2)cn1]
TABLE 1-continued
77
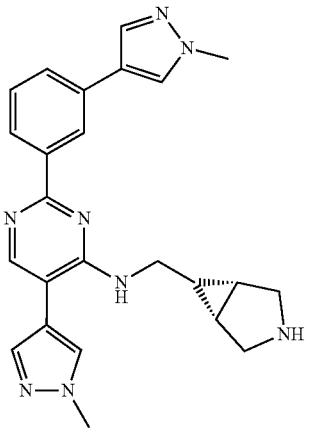
78
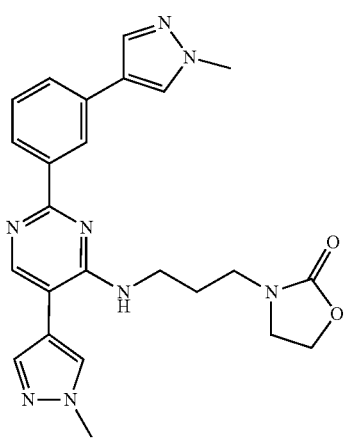 [SMILES: Cn1cc(-c2cccc(-c3ncc(-c4cnn(C)c4)c(NCCCN4CCOC4=O)n3)c2)cn1]
79
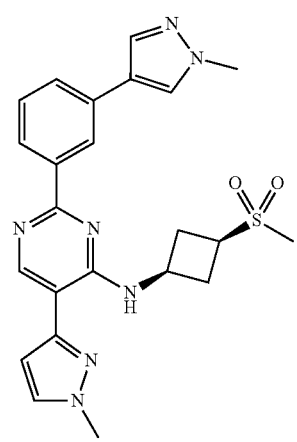 [SMILES: Cn1cc(-c2cccc(-c3ncc(-c4ccn(C)n4)c(N[C@H]4C[C@@H](S(C)(=O)=O)C4)n3)c2)cn1]

TABLE 1-continued
80
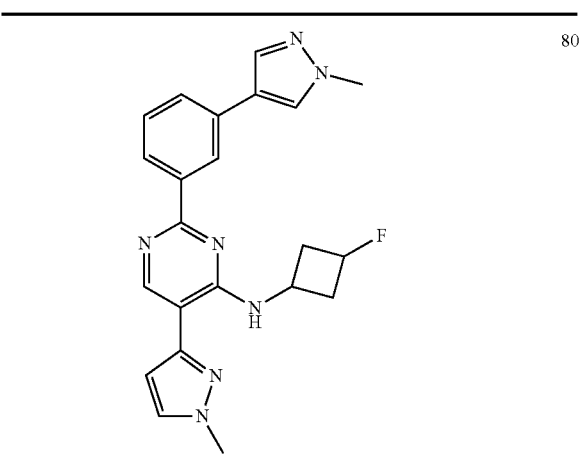
81
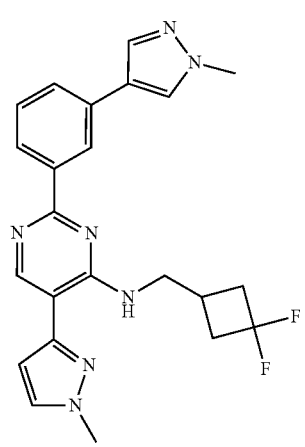 [SMILES: Cn1cc(-c2cccc(-c3ncc(-c4ccn(C)n4)c(NCC4CC(F)(F)C4)n3)c2)cn1]
82
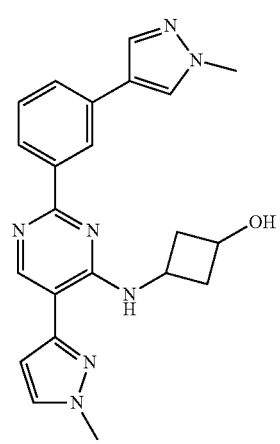
TABLE 1-continued
83
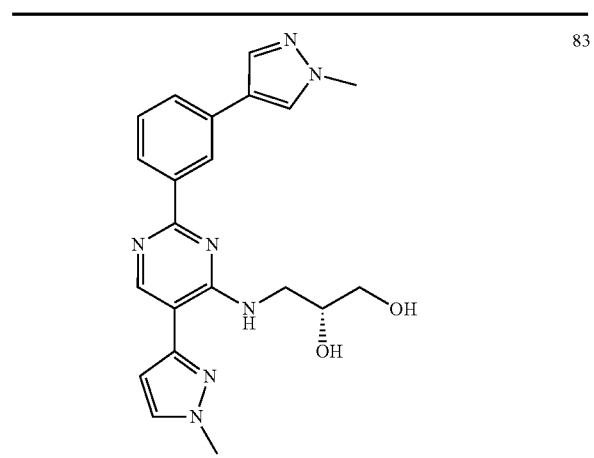
84
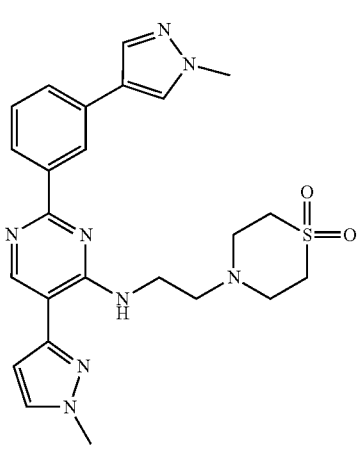 [SMILES: Cn1cc(-c2cccc(-c3ncc(-c4ccn(C)n4)c(NCCN4CCS(=O)(=O)CC4)n3)c2)cn1]
85
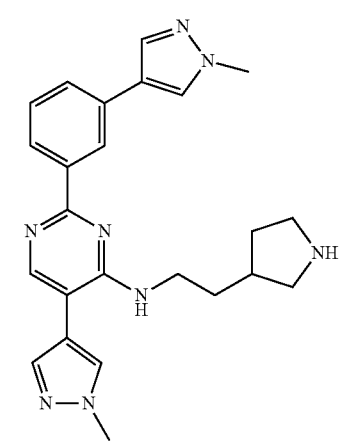 [SMILES: Cn1cc(-c2cccc(-c3ncc(-c4cnn(C)c4)c(NCCC4CCNC4)n3)c2)cn1]

TABLE 1-continued
| 86 | 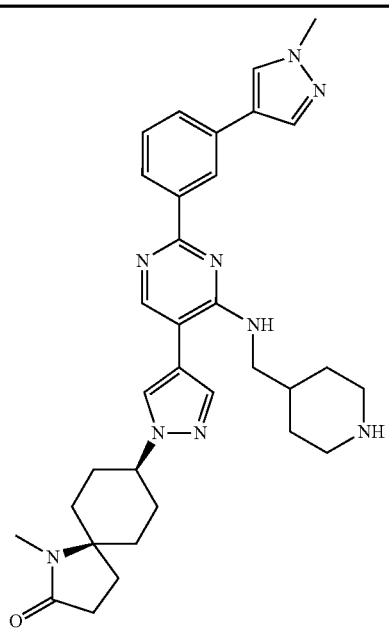 |
| --- | --- |
| 87 | 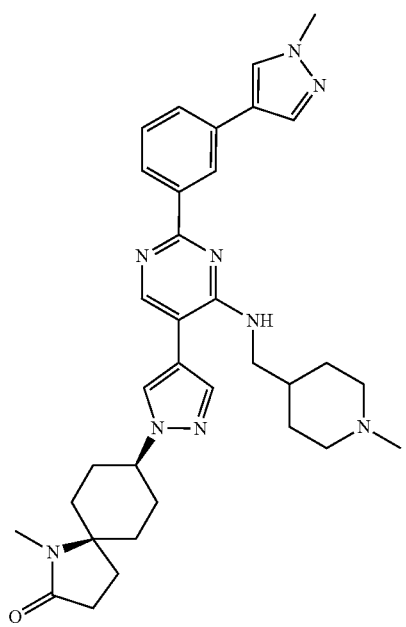 |
| 88 | 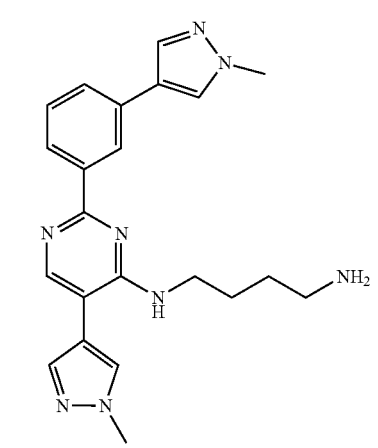 [SMILES: Cn1cc(-c2cccc(-c3ncc(-c4cnn(C)c4)c(NCCCCN)n3)c2)cn1] |
TABLE 1-continued
| 89 | 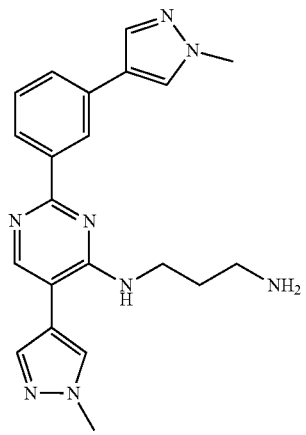 [SMILES: Cn1cc(-c2cccc(-c3ncc(-c4cnn(C)c4)c(NCCCN)n3)c2)cn1] |
| --- | --- |
| 90 | 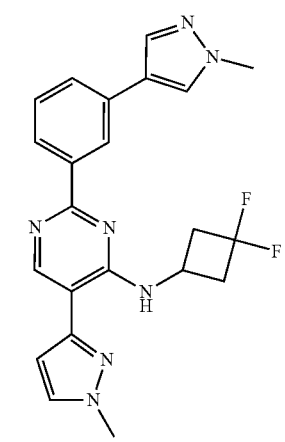 [SMILES: Cn1cc(-c2cccc(-c3ncc(-c4ccn(C)n4)c(NC4CC(F)(F)C4)n3)c2)cn1] |
| 91 | 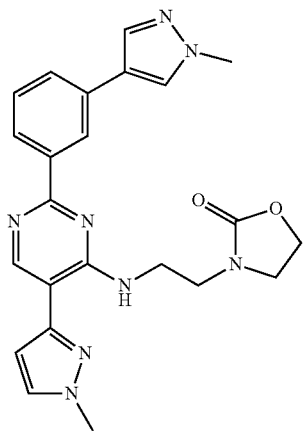 |

TABLE 1-continued
| | |
|---|---|
| 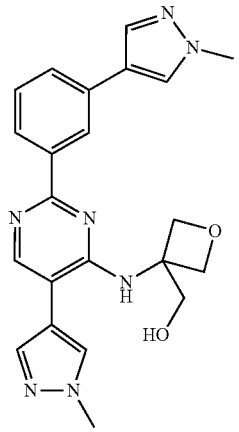 [SMILES: Cn1cc(-c2cccc(-c3ncc(-c4cnn(C)c4)c(NC4(CO)COC4)n3)c2)cn1] 92 | 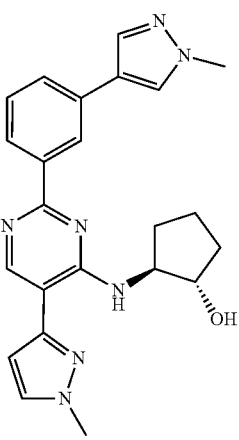 95 |
| 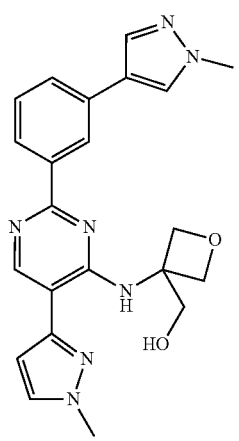 [SMILES: Cn1cc(-c2cccc(-c3ncc(-c4ccn(C)n4)c(NC4(CO)COC4)n3)c2)cn1] 93 | 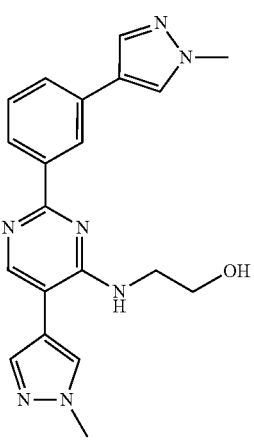 96 |
| 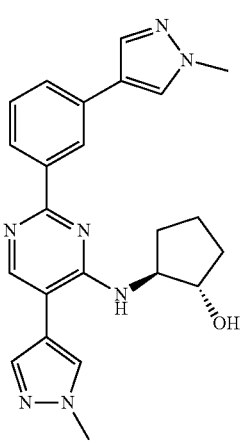 [SMILES: Cn1cc(-c2cccc(-c3ncc(-c4cnn(C)c4)c(N[C@H]4CCC[C@@H]4O)n3)c2)cn1] 94 | 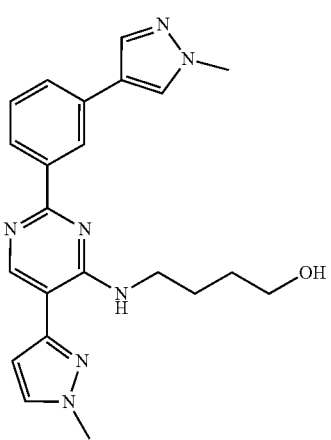 97 |

TABLE 1-continued
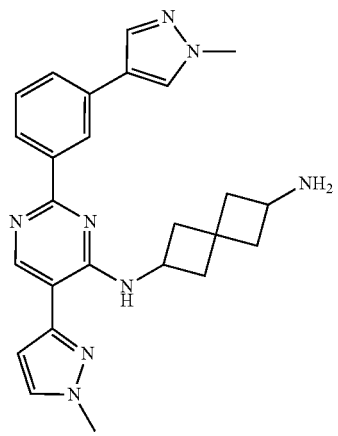 [SMILES: Cn1cc(-c2cccc(-c3ncc(-c4ccn(C)n4)c(NC4CC5(CC(N)C5)C4)n3)c2)cn1] 98
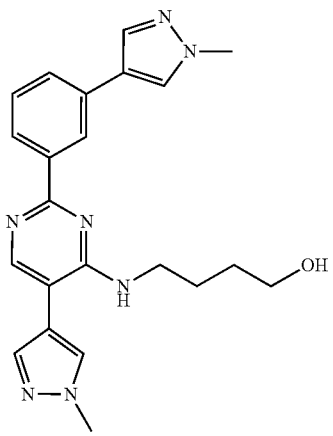 101
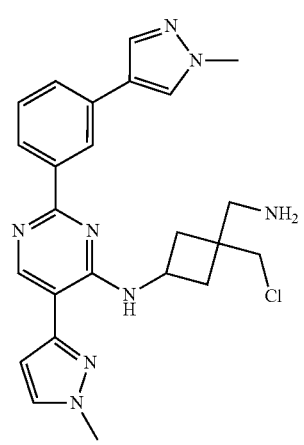 [SMILES: Cn1cc(-c2cccc(-c3ncc(-c4ccn(C)n4)c(NC4CC(CN)(CCl)C4)n3)c2)cn1] 99
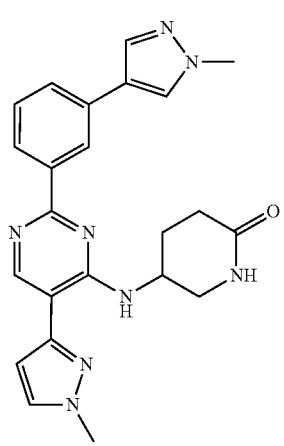 102
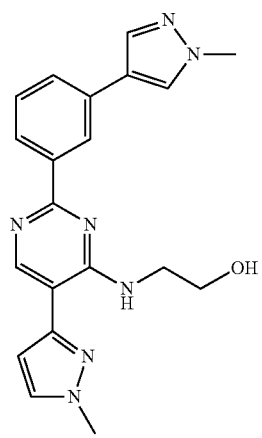 [SMILES: Cn1cc(-c2cccc(-c3ncc(-c4ccn(C)n4)c(NCCO)n3)c2)cn1] 100
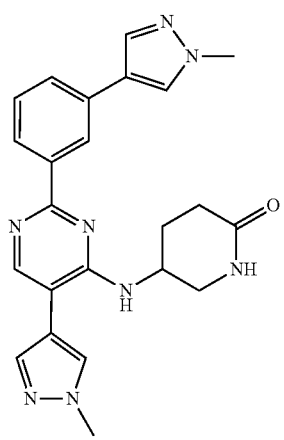 [SMILES: Cn1cc(-c2cccc(-c3ncc(-c4cnn(C)c4)c(NC4CCC(=O)NC4)n3)c2)cn1] 103

TABLE 1-continued
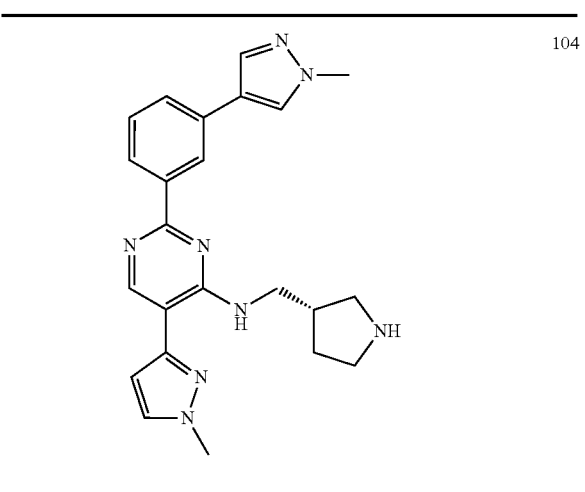
104
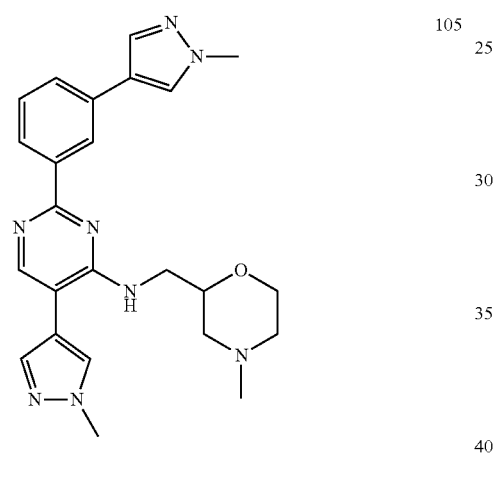
105
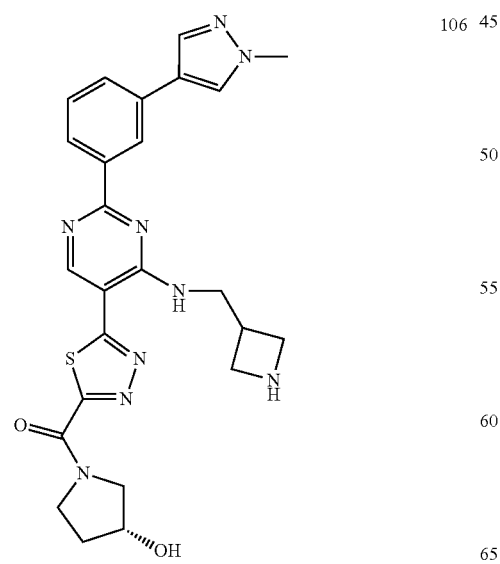
106
TABLE 1-continued
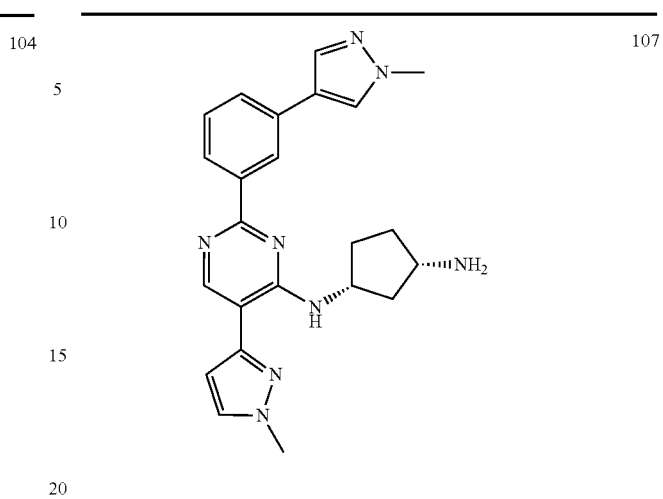
107
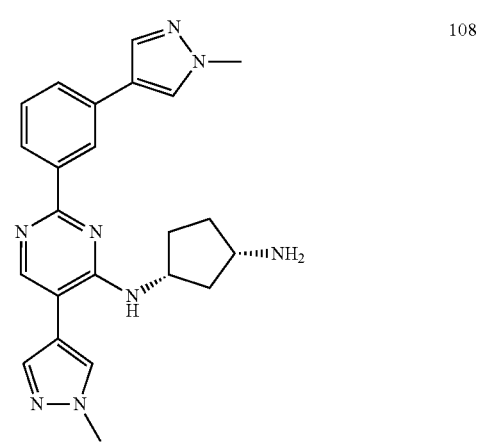
108
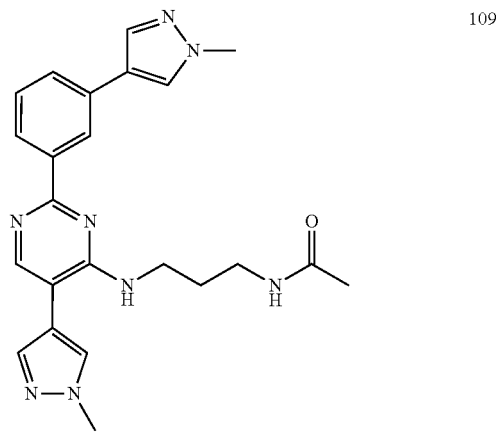
109

TABLE 1-continued
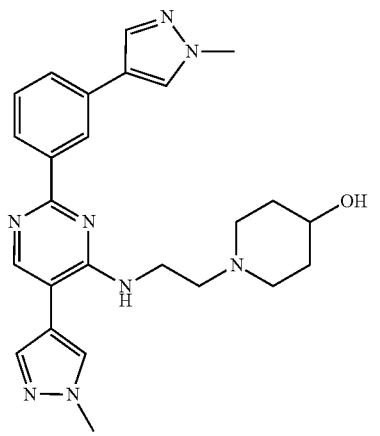 [SMILES: Cn1cc(-c2cccc(-c3ncc(-c4cnn(C)c4)c(NCCN4CCC(O)CC4)n3)c2)cn1]
110
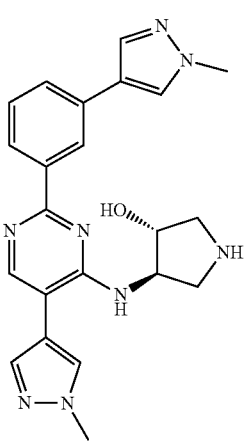
113
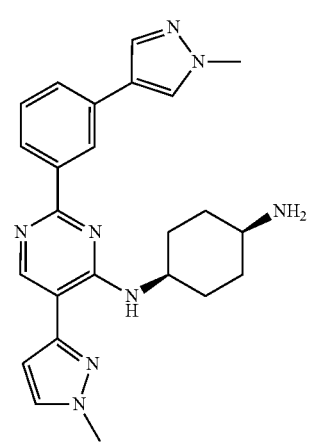 [SMILES: Cn1cc(-c2cccc(-c3ncc(-c4ccn(C)n4)c(N[C@H]4CC[C@@H](N)CC4)n3)c2)cn1]
111
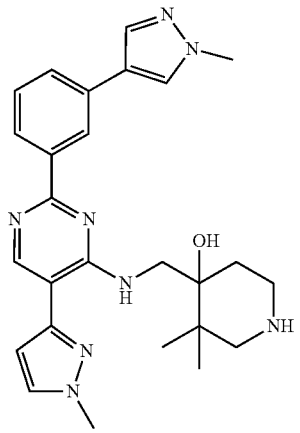
114
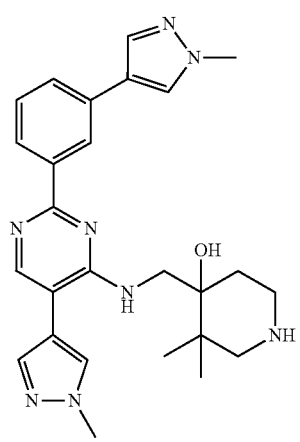 [SMILES: Cn1cc(-c2cccc(-c3ncc(-c4cnn(C)c4)c(NCC4(O)CCNCC4(C)C)n3)c2)cn1]
112
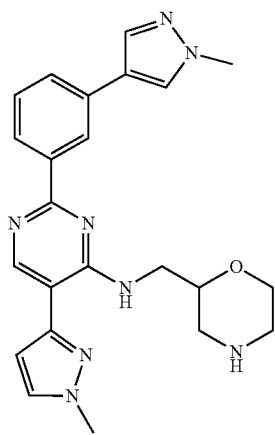 [SMILES: Cn1cc(-c2cccc(-c3ncc(-c4ccn(C)n4)c(NCC4CNCCO4)n3)c2)cn1]
115

TABLE 1-continued
| | |
|---|---|
| 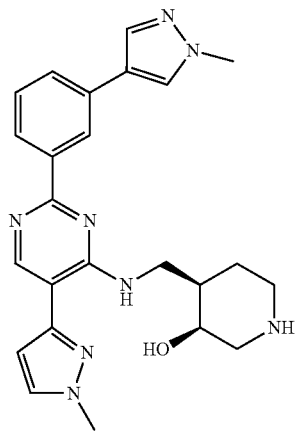 [SMILES: Cn1cc(-c2cccc(-c3ncc(-c4ccn(C)n4)c(NC[C@H]4CCNC[C@H]4O)n3)c2)cn1] | 116 |
| 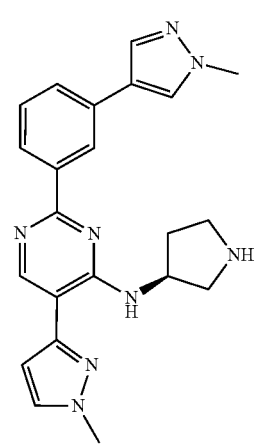 | 117 |
| 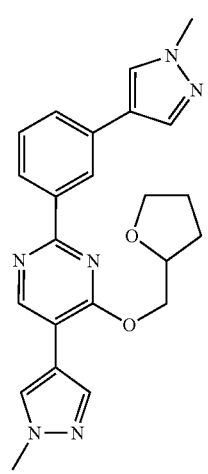 [SMILES: Cn1cc(-c2cccc(-c3ncc(-c4cnn(C)c4)c(OCC4CCCO4)n3)c2)cn1] | 118 |
TABLE 1-continued
| | |
|---|---|
| 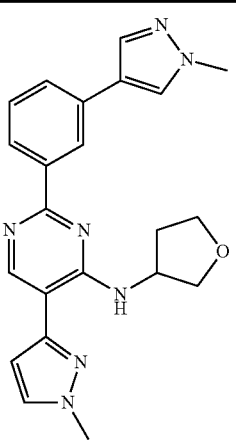 | 119 |
| 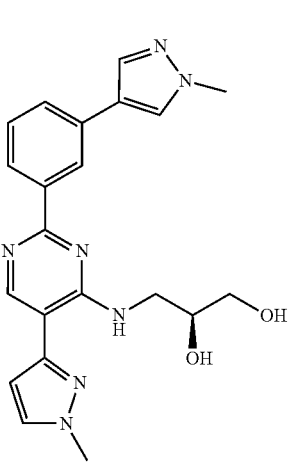 [SMILES: Cn1cc(-c2cccc(-c3ncc(-c4ccn(C)n4)c(NC[C@H](O)CO)n3)c2)cn1] | 120 |
| 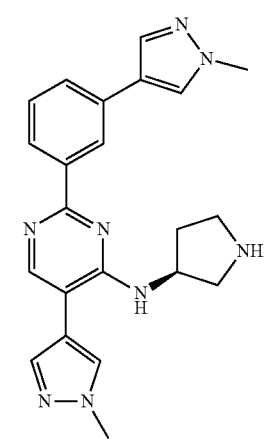 [SMILES: Cn1cc(-c2cccc(-c3ncc(-c4cnn(C)c4)c(N[C@H]4CCNC4)n3)c2)cn1] | 121 |

TABLE 1-continued
122
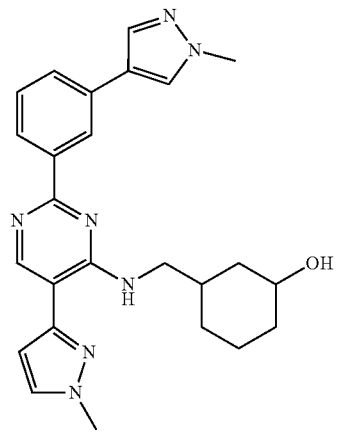
123
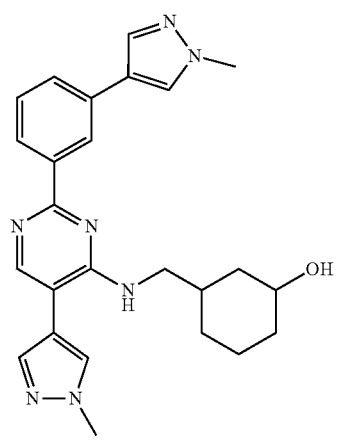
124
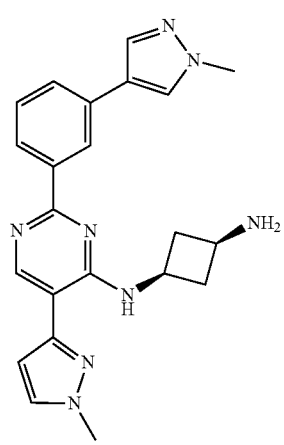 [SMILES: Cn1cc(-c2cccc(-c3ncc(-c4ccn(C)n4)c(N[C@H]4C[C@@H](N)C4)n3)c2)cn1]
TABLE 1-continued
125
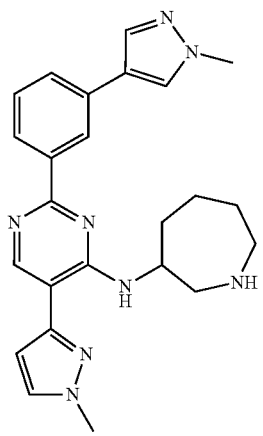
126
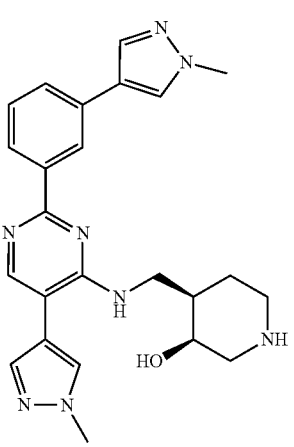 [SMILES: Cn1cc(-c2cccc(-c3ncc(-c4cnn(C)c4)c(NC[C@H]4CCNC[C@H]4O)n3)c2)cn1]
127
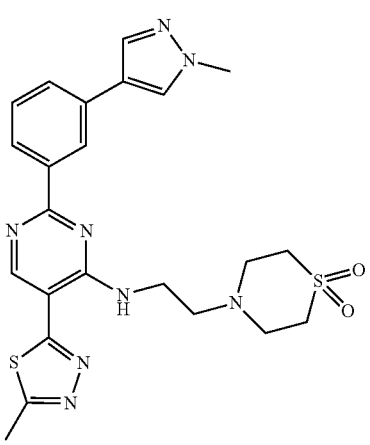 [SMILES: Cc1nnc(-c2cnc(-c3cccc(-c4cnn(C)c4)c3)nc2NCCN2CCS(=O)(=O)CC2)s1]

TABLE 1-continued
128 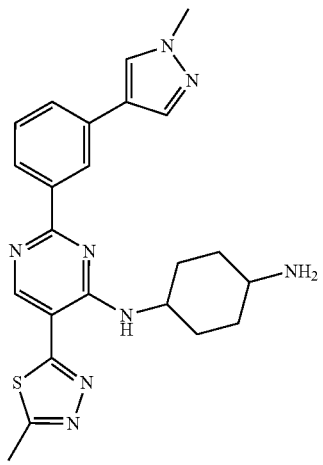 [SMILES: Cc1nnc(-c2cnc(-c3cccc(-c4cnn(C)c4)c3)nc2NC2CCC(N)CC2)s1]
129 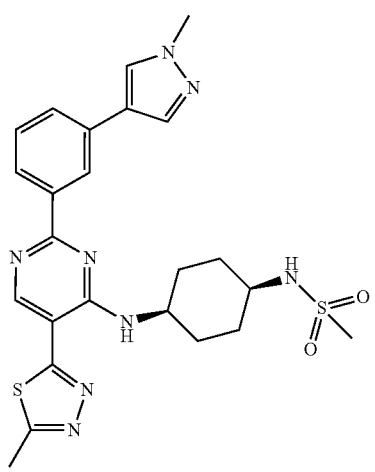 [SMILES: Cc1nnc(-c2cnc(-c3cccc(-c4cnn(C)c4)c3)nc2N[C@H]2CC[C@@H](NS(C)(=O)=O)CC2)s1]
130 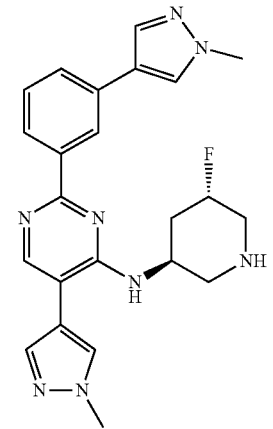 [SMILES: Cn1cc(-c2cccc(-c3ncc(-c4cnn(C)c4)c(N[C@@H]4CNC[C@@H](F)C4)n3)c2)cn1]
TABLE 1-continued
131 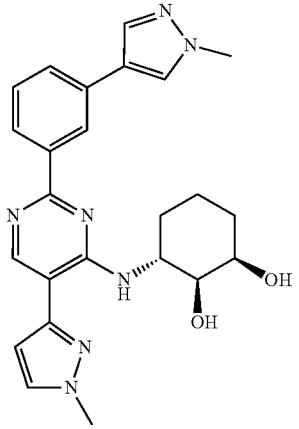 [SMILES: Cn1cc(-c2cccc(-c3ncc(-c4ccn(C)n4)c(N[C@@H]4CCC[C@@H](O)[C@H]4O)n3)c2)cn1]
132 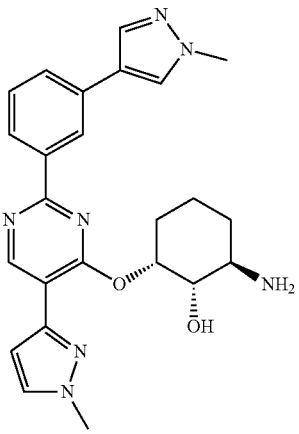 [SMILES: Cn1cc(-c2cccc(-c3ncc(-c4ccn(C)n4)c(O[C@@H]4CCC[C@@H](N)[C@@H]4O)n3)c2)cn1]
133

TABLE 1-continued
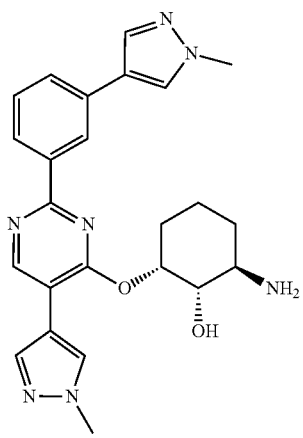 [SMILES: Cn1cc(-c2cccc(-c3ncc(-c4cnn(C)c4)c(O[C@@H]4CCC[C@@H](N)[C@@H]4O)n3)c2)cn1]
134
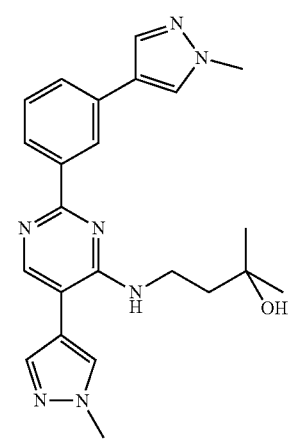 [SMILES: Cn1cc(-c2cccc(-c3ncc(-c4cnn(C)c4)c(NCCC(C)(C)O)n3)c2)cn1]
135
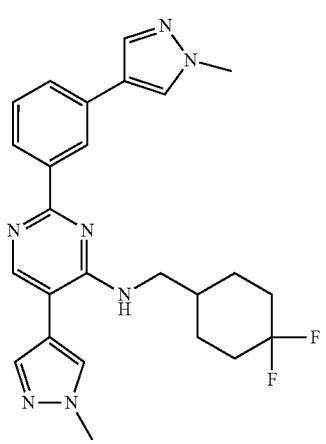
136
TABLE 1-continued
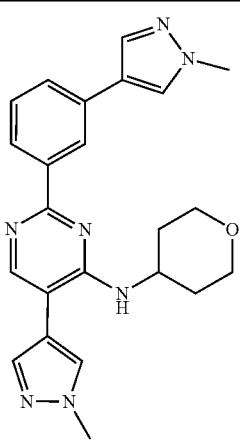
137
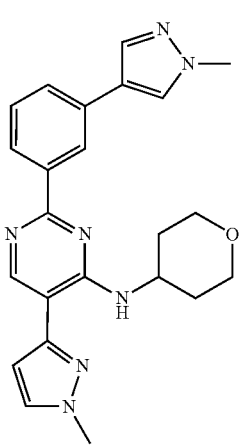
138
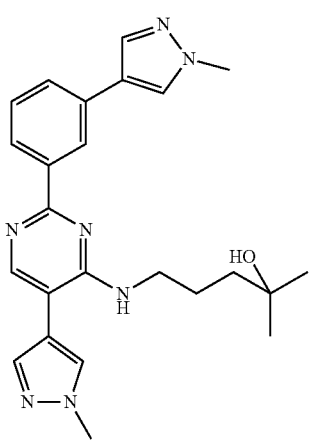 [SMILES: Cn1cc(-c2cccc(-c3ncc(-c4cnn(C)c4)c(NCCCC(C)(C)O)n3)c2)cn1]
139

TABLE 1-continued
140 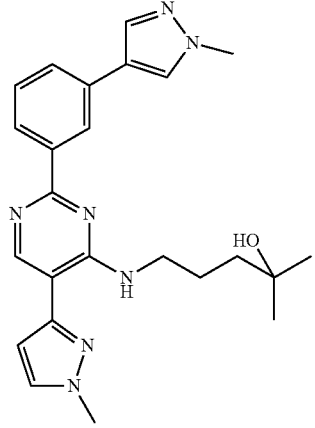 [SMILES: Cn1cc(-c2cccc(-c3ncc(-c4ccn(C)n4)c(NCCCC(C)(C)O)n3)c2)cn1]
141 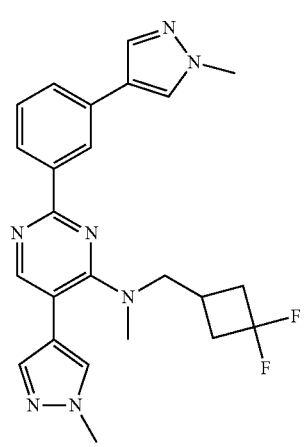 [SMILES: CN(CC1CC(F)(F)C1)c1nc(-c2cccc(-c3cnn(C)c3)c2)ncc1-c1cnn(C)c1]
142 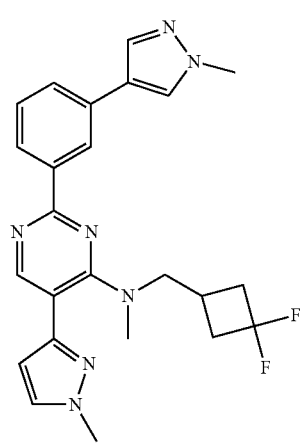 [SMILES: CN(CC1CC(F)(F)C1)c1nc(-c2cccc(-c3cnn(C)c3)c2)ncc1-c1ccn(C)n1]
TABLE 1-continued
143 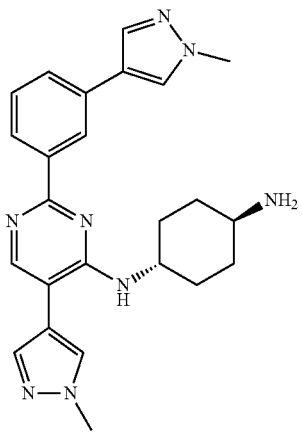 [SMILES: Cn1cc(-c2cccc(-c3ncc(-c4cnn(C)c4)c(N[C@H]4CC[C@H](N)CC4)n3)c2)cn1]
144 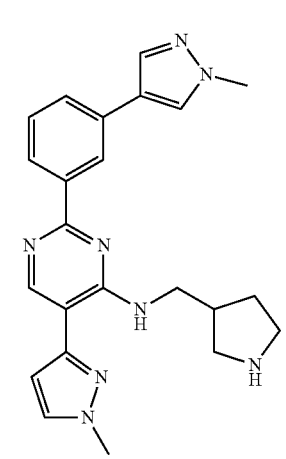 [SMILES: Cn1cc(-c2cccc(-c3ncc(-c4ccn(C)n4)c(NCC4CCNC4)n3)c2)cn1]
145 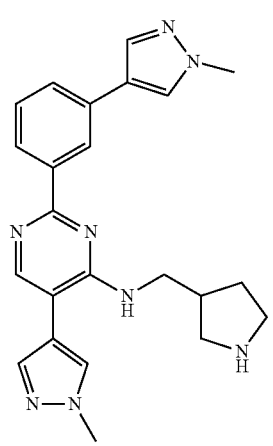 [SMILES: Cn1cc(-c2cccc(-c3ncc(-c4cnn(C)c4)c(NCC4CCNC4)n3)c2)cn1]

TABLE 1-continued
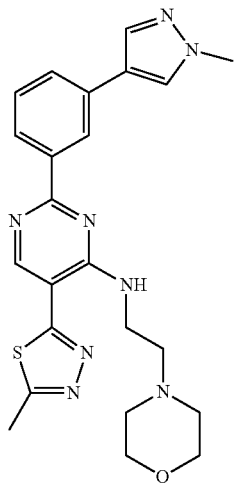
146
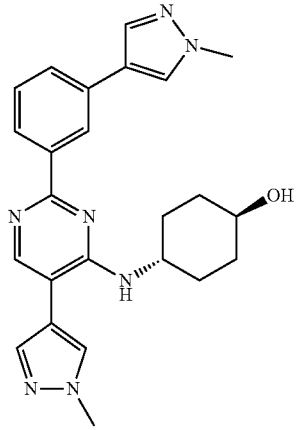
149
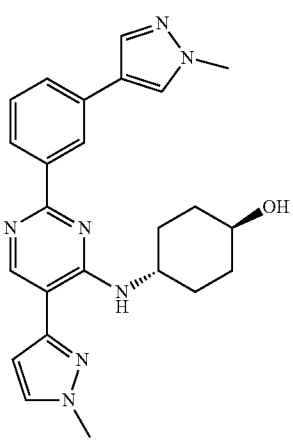 [SMILES: Cn1cc(-c2cccc(-c3ncc(-c4ccn(C)n4)c(N[C@H]4CC[C@H](O)CC4)n3)c2)cn1]
147
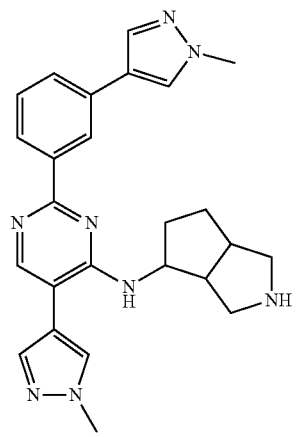
150
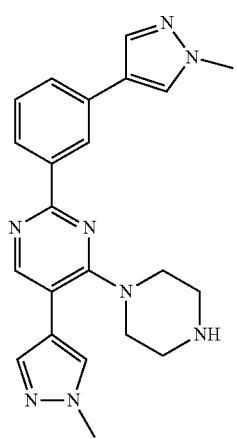 [SMILES: Cn1cc(-c2cccc(-c3ncc(-c4cnn(C)c4)c(N4CCNCC4)n3)c2)cn1]
148
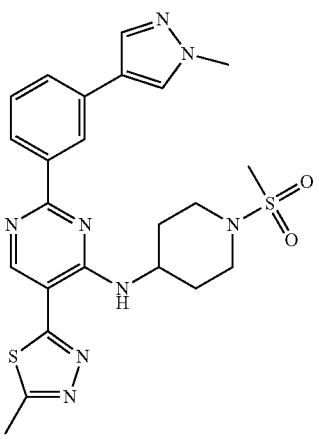 [SMILES: Cc1nnc(-c2cnc(-c3cccc(-c4cnn(C)c4)c3)nc2NC2CCN(S(C)(=O)=O)CC2)s1]
151

TABLE 1-continued
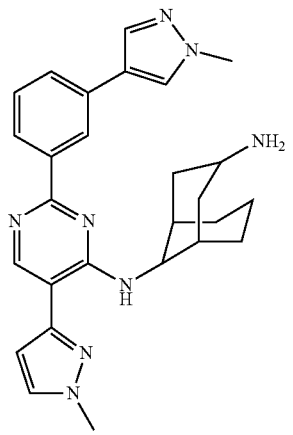 [SMILES: Cn1cc(-c2cccc(-c3ncc(-c4ccn(C)n4)c(NC4C5CCCC4CC(N)C5)n3)c2)cn1]
152
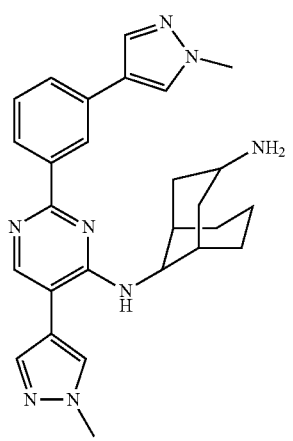 [SMILES: Cn1cc(-c2cccc(-c3ncc(-c4cnn(C)c4)c(NC4C5CCCC4CC(N)C5)n3)c2)cn1]
153
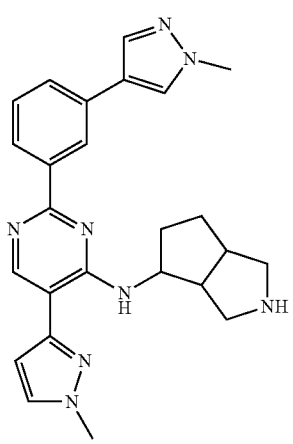
154
TABLE 1-continued
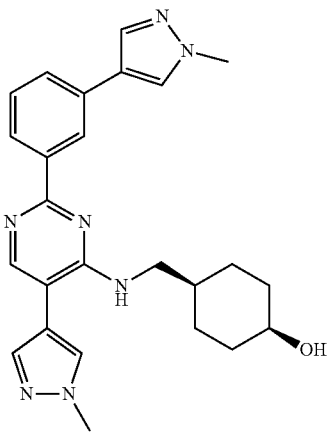 [SMILES: Cn1cc(-c2cccc(-c3ncc(-c4cnn(C)c4)c(NC[C@H]4CC[C@@H](O)CC4)n3)c2)cn1]
155
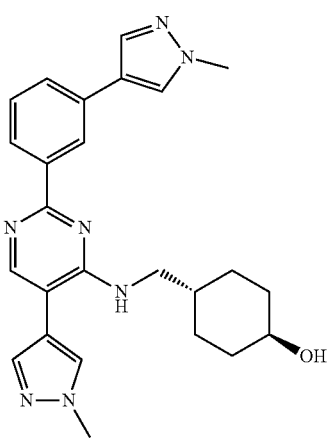 [SMILES: Cn1cc(-c2cccc(-c3ncc(-c4cnn(C)c4)c(NC[C@H]4CC[C@H](O)CC4)n3)c2)cn1]
156
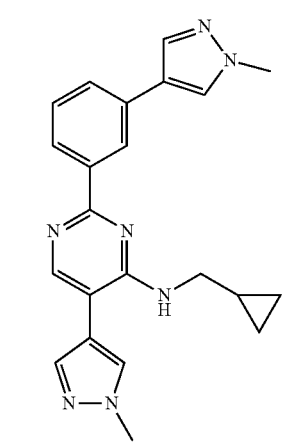 [SMILES: Cn1cc(-c2cccc(-c3ncc(-c4cnn(C)c4)c(NCC4CC4)n3)c2)cn1]
157

TABLE 1-continued
158
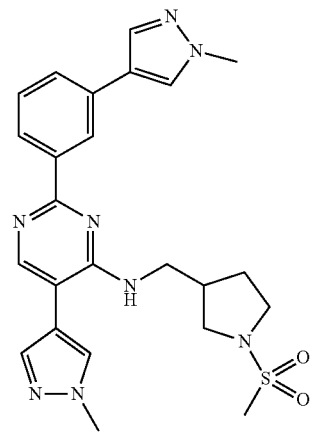 [SMILES: Cn1cc(-c2cccc(-c3ncc(-c4cnn(C)c4)c(NCC4CCN(S(C)(=O)=O)C4)n3)c2)cn1]
159
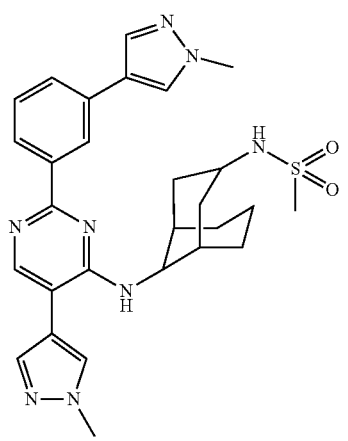 [SMILES: Cn1cc(-c2cccc(-c3ncc(-c4cnn(C)c4)c(NC4C5CCCC4CC(NS(C)(=O)=O)C5)n3)c2)cn1]
160
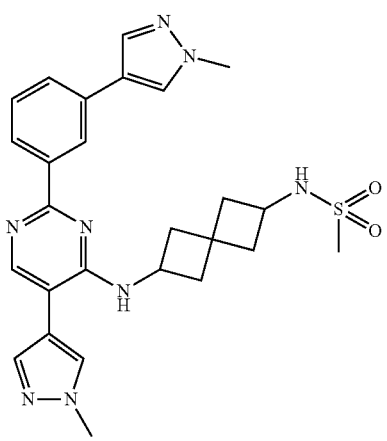 [SMILES: Cn1cc(-c2cccc(-c3ncc(-c4cnn(C)c4)c(NC4CC5(C4)CC(NS(C)(=O)=O)C5)n3)c2)cn1]
TABLE 1-continued
161
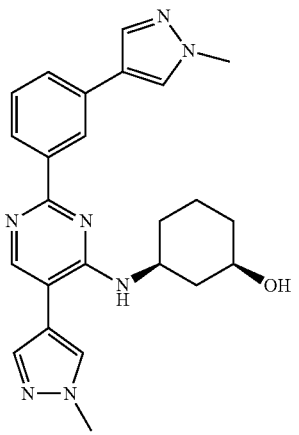 [SMILES: Cn1cc(-c2cccc(-c3ncc(-c4cnn(C)c4)c(N[C@H]4CCC[C@@H](O)C4)n3)c2)cn1]
162
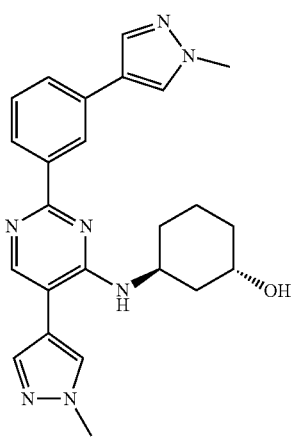 [SMILES: Cn1cc(-c2cccc(-c3ncc(-c4cnn(C)c4)c(N[C@H]4CCC[C@H](O)C4)n3)c2)cn1]
163
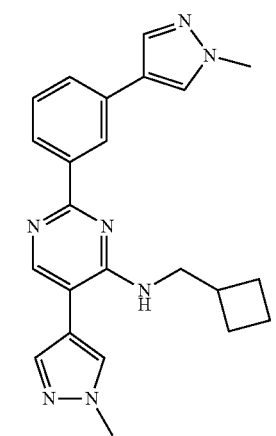

TABLE 1-continued
| | |
|---|---|
| 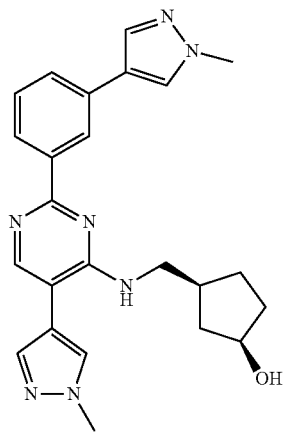 [SMILES: Cn1cc(-c2cccc(-c3ncc(-c4cnn(C)c4)c(NC[C@H]4CC[C@@H](O)C4)n3)c2)cn1] 164 | 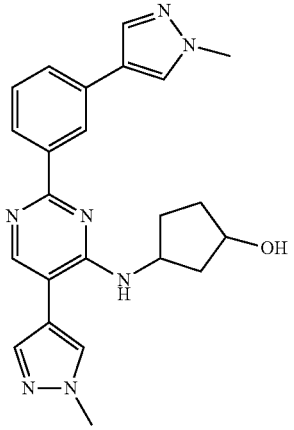 167 |
| 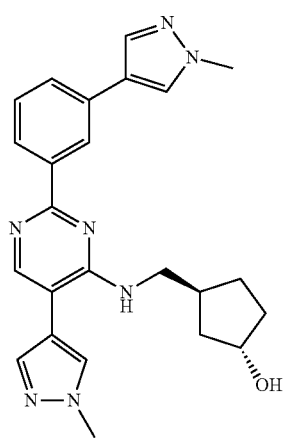 [SMILES: Cn1cc(-c2cccc(-c3ncc(-c4cnn(C)c4)c(NC[C@H]4CC[C@H](O)C4)n3)c2)cn1] 165 | 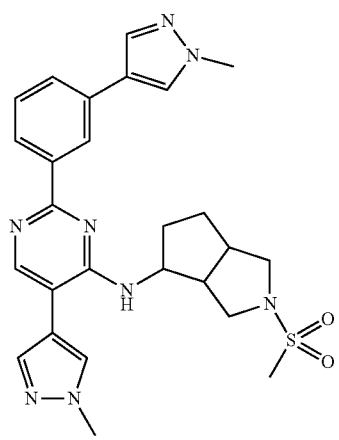 168 |
| 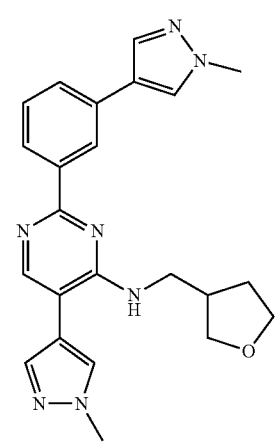 [SMILES: Cn1cc(-c2cccc(-c3ncc(-c4cnn(C)c4)c(NCC4CCOC4)n3)c2)cn1] 166 | 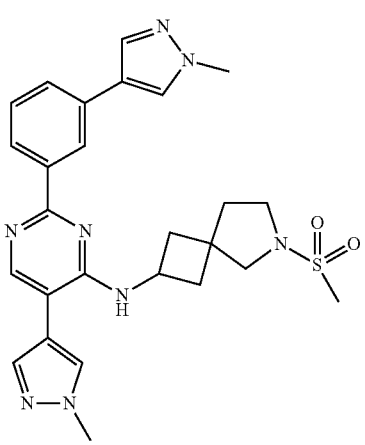 [SMILES: Cn1cc(-c2cccc(-c3ncc(-c4cnn(C)c4)c(NC4CC5(CCN(S(C)(=O)=O)C5)C4)n3)c2)cn1] 169 |

TABLE 1-continued
170 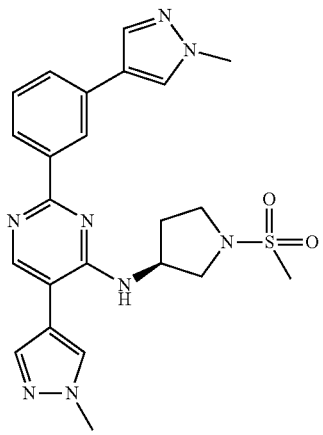 [SMILES: Cn1cc(-c2cccc(-c3ncc(-c4cnn(C)c4)c(N[C@H]4CCN(S(C)(=O)=O)C4)n3)c2)cn1]
171 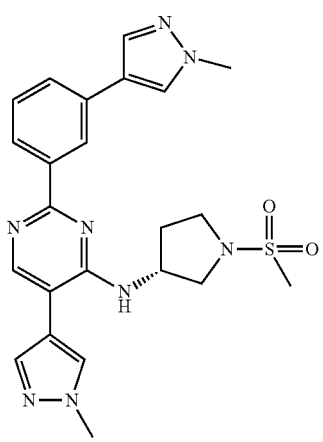 [SMILES: Cn1cc(-c2cccc(-c3ncc(-c4cnn(C)c4)c(N[C@@H]4CCN(S(C)(=O)=O)C4)n3)c2)cn1]
172 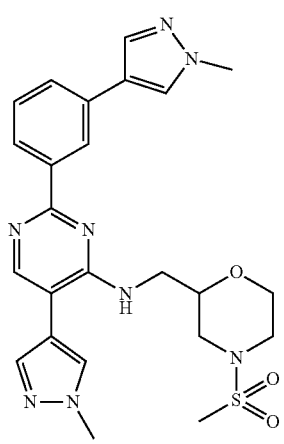 [SMILES: Cn1cc(-c2cccc(-c3ncc(-c4cnn(C)c4)c(NCC4CN(S(C)(=O)=O)CCO4)n3)c2)cn1]
TABLE 1-continued
173 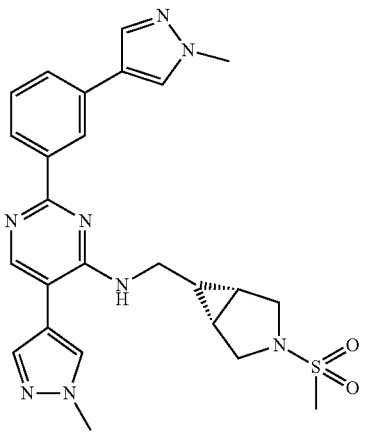
174 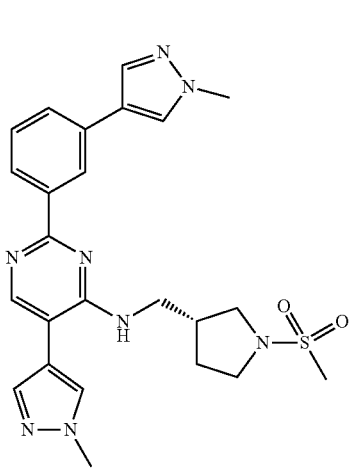 [SMILES: Cn1cc(-c2cccc(-c3ncc(-c4cnn(C)c4)c(NC[C@H]4CCN(S(C)(=O)=O)C4)n3)c2)cn1]
175 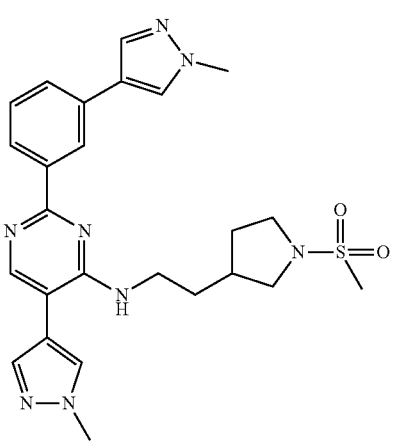 [SMILES: Cn1cc(-c2cccc(-c3ncc(-c4cnn(C)c4)c(NCCC4CCN(S(C)(=O)=O)C4)n3)c2)cn1]

TABLE 1-continued
176 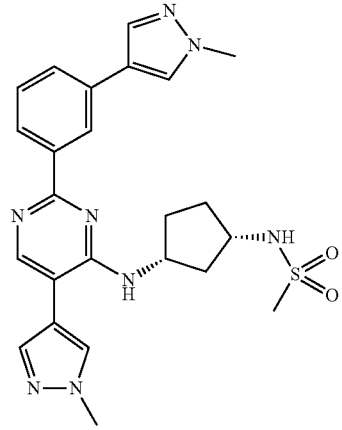 [SMILES: Cn1cc(-c2cccc(-c3ncc(-c4cnn(C)c4)c(N[C@@H]4CC[C@H](NS(C)(=O)=O)C4)n3)c2)cn1]
177 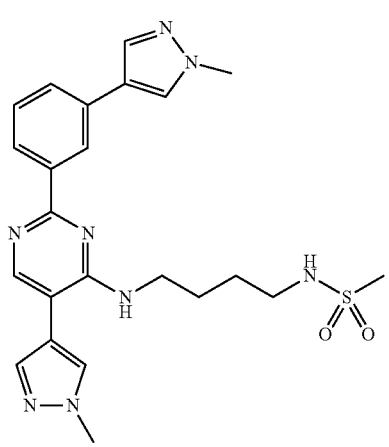 [SMILES: Cn1cc(-c2cccc(-c3ncc(-c4cnn(C)c4)c(NCCCCNS(C)(=O)=O)n3)c2)cn1]
178 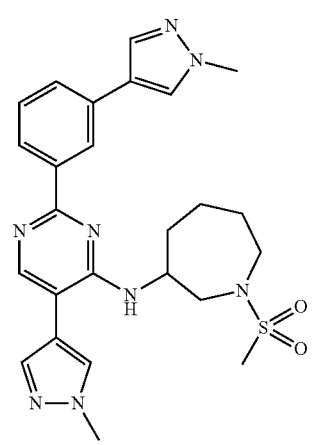 [SMILES: Cn1cc(-c2cccc(-c3ncc(-c4cnn(C)c4)c(NC4CCCCN(S(C)(=O)=O)C4)n3)c2)cn1]
TABLE 1-continued
179 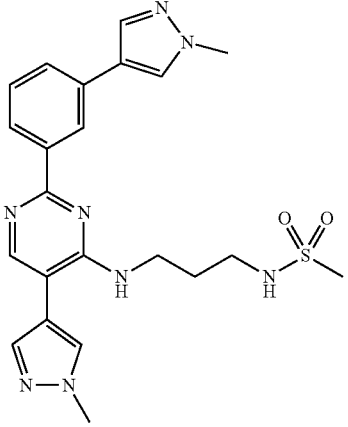 [SMILES: Cn1cc(-c2cccc(-c3ncc(-c4cnn(C)c4)c(NCCCNS(C)(=O)=O)n3)c2)cn1]
180 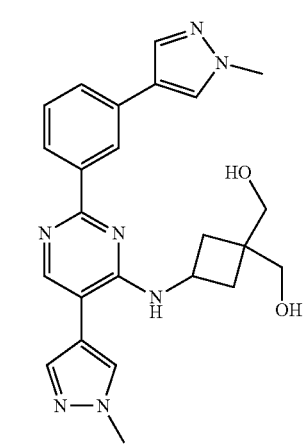 [SMILES: Cn1cc(-c2cccc(-c3ncc(-c4cnn(C)c4)c(NC4CC(CO)(CO)C4)n3)c2)cn1]
181 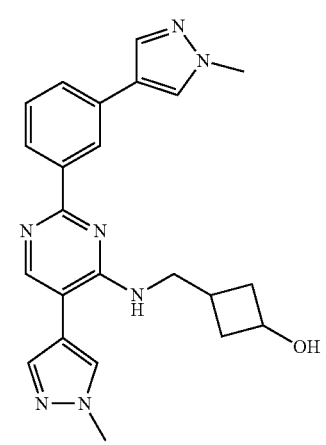 [SMILES: Cn1cc(-c2cccc(-c3ncc(-c4cnn(C)c4)c(NCC4CC(O)C4)n3)c2)cn1]

| | | | |
|---|---|---|---|
| 182 | 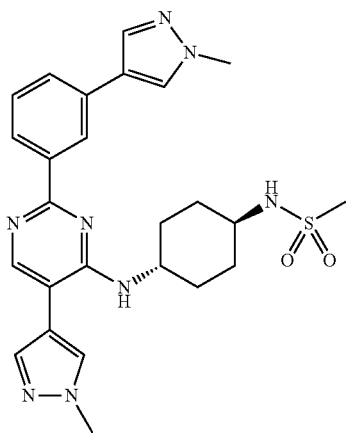 [SMILES: Cn1cc(-c2cccc(-c3ncc(-c4cnn(C)c4)c(N[C@H]4CC[C@H](NS(C)(=O)=O)CC4)n3)c2)cn1] | 185 | 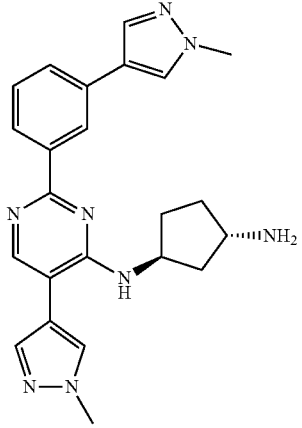 [SMILES: Cn1cc(-c2cccc(-c3ncc(-c4cnn(C)c4)c(N[C@H]4CC[C@H](N)C4)n3)c2)cn1] |
| 183 | | 186 | 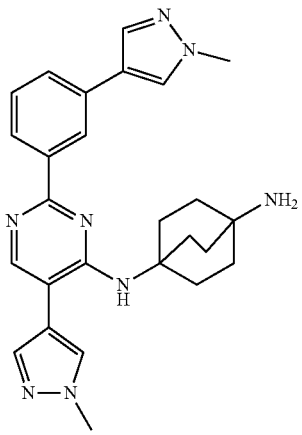 [SMILES: Cn1cc(-c2cccc(-c3ncc(-c4cnn(C)c4)c(NC45CCC(N)(CC4)CC5)n3)c2)cn1] |
| 184 | 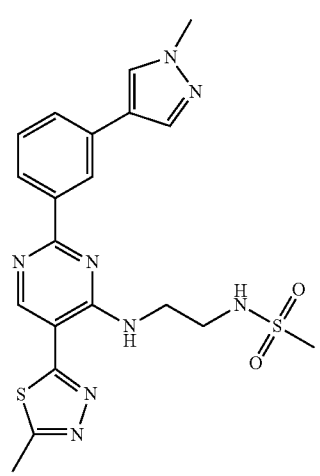 | 187 | 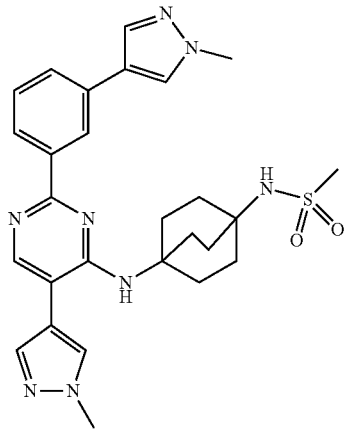 [SMILES: Cn1cc(-c2cccc(-c3ncc(-c4cnn(C)c4)c(NC45CCC(NS(C)(=O)=O)(CC4)CC5)n3)c2)cn1] |

TABLE 1-continued
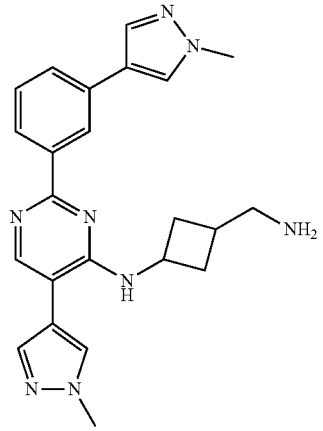 [SMILES: Cn1cc(-c2cccc(-c3ncc(-c4cnn(C)c4)c(NC4CC(CN)C4)n3)c2)cn1] 188
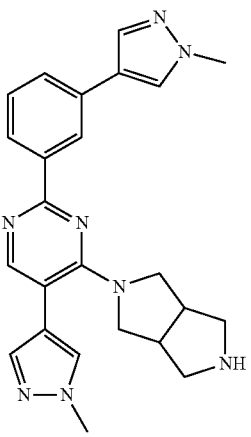 191
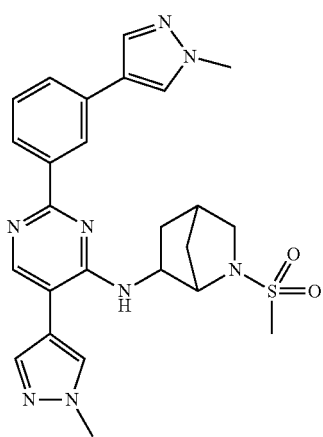 [SMILES: Cn1cc(-c2cccc(-c3ncc(-c4cnn(C)c4)c(NC4CC5CC4N(S(C)(=O)=O)C5)n3)c2)cn1] 189
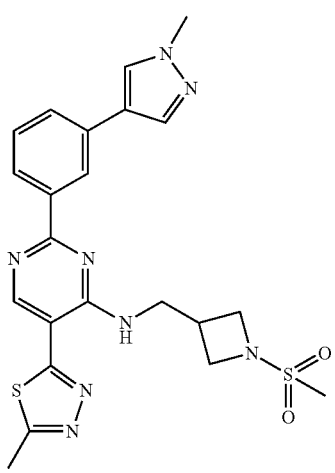 192
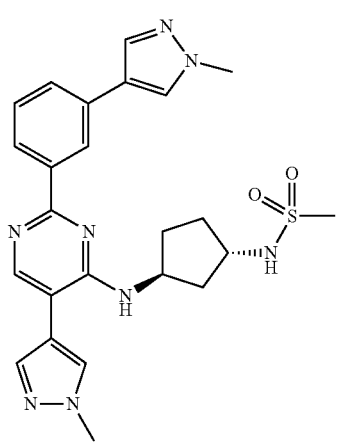 [SMILES: Cn1cc(-c2cccc(-c3ncc(-c4cnn(C)c4)c(N[C@H]4CC[C@H](NS(C)(=O)=O)C4)n3)c2)cn1] 190
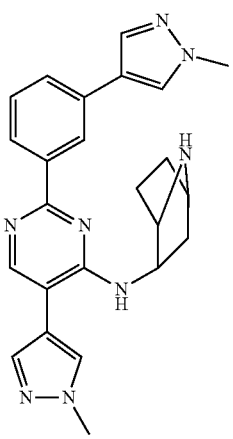 [SMILES: Cn1cc(-c2cccc(-c3ncc(-c4cnn(C)c4)c(NC4CC5CCC4N5)n3)c2)cn1] 193

TABLE 1-continued
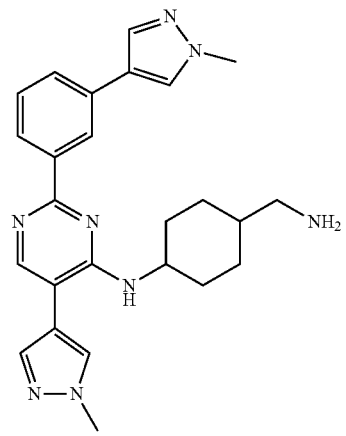 [SMILES: Cn1cc(-c2cccc(-c3ncc(-c4cnn(C)c4)c(NC4CCC(CN)CC4)n3)c2)cn1] 194
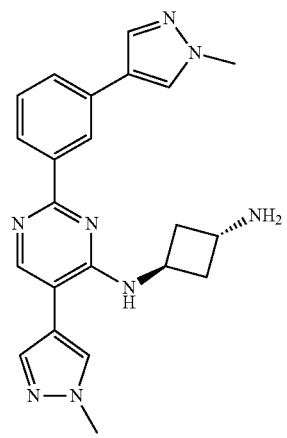 197
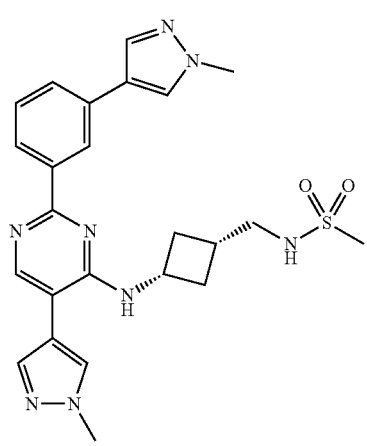 [SMILES: Cn1cc(-c2cccc(-c3ncc(-c4cnn(C)c4)c(N[C@H]4C[C@@H](CNS(C)(=O)=O)C4)n3)c2)cn1] 195
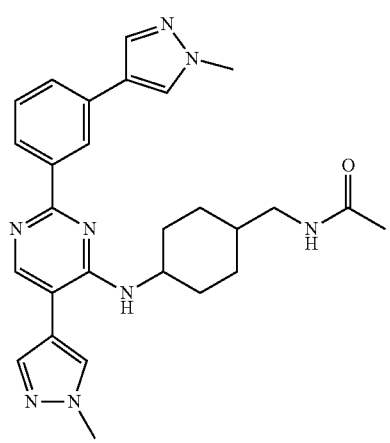 198
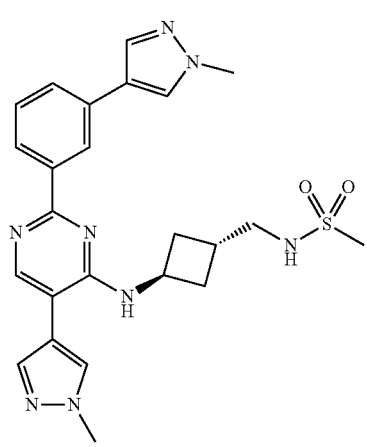 [SMILES: Cn1cc(-c2cccc(-c3ncc(-c4cnn(C)c4)c(N[C@H]4C[C@H](CNS(C)(=O)=O)C4)n3)c2)cn1] 196
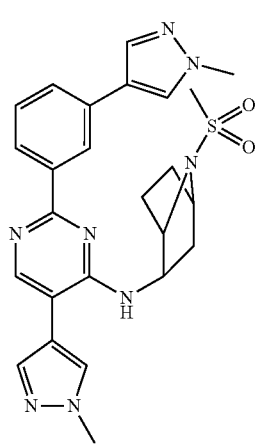 [SMILES: Cn1cc(-c2cccc(-c3ncc(-c4cnn(C)c4)c(NC4CC5CCC4N5S(C)(=O)=O)n3)c2)cn1] 199

TABLE 1-continued
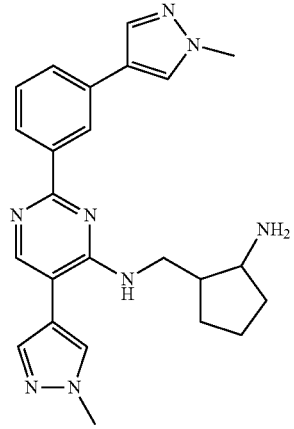 [SMILES: Cn1cc(-c2cccc(-c3ncc(-c4cnn(C)c4)c(NCC4CCCC4N)n3)c2)cn1]
200
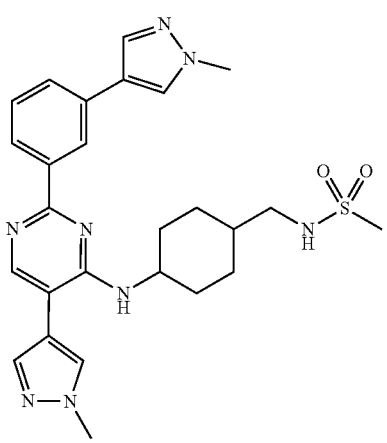 [SMILES: Cn1cc(-c2cccc(-c3ncc(-c4cnn(C)c4)c(NC4CCC(CNS(C)(=O)=O)CC4)n3)c2)cn1]
201
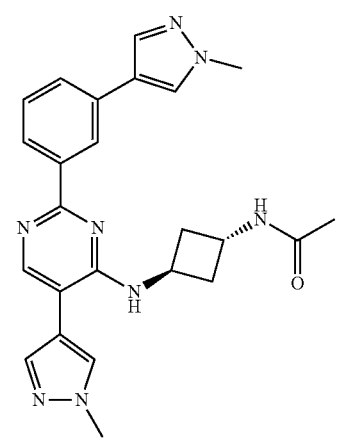 [SMILES: CC(=O)N[C@H]1C[C@H](Nc2nc(-c3cccc(-c4cnn(C)c4)c3)ncc2-c2cnn(C)c2)C1]
202
TABLE 1-continued
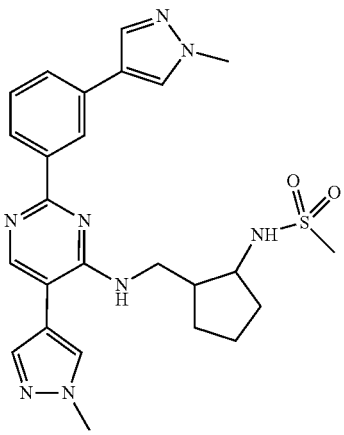 [SMILES: Cn1cc(-c2cccc(-c3ncc(-c4cnn(C)c4)c(NCC4CCCC4NS(C)(=O)=O)n3)c2)cn1]
203
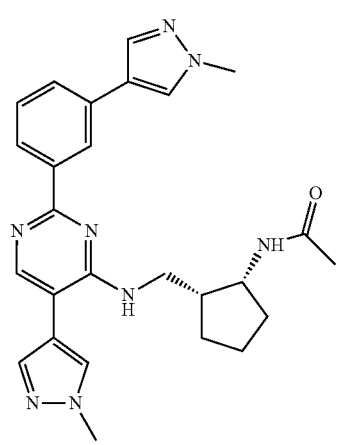 [SMILES: CC(=O)N[C@@H]1CCC[C@@H]1CNc1nc(-c2cccc(-c3cnn(C)c3)c2)ncc1-c1cnn(C)c1]
205
206

TABLE 1-continued
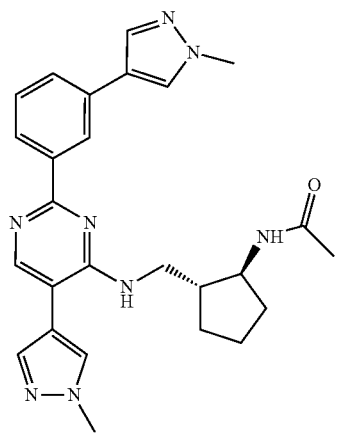 [SMILES: CC(=O)N[C@H]1CCC[C@@H]1CNc1nc(-c2cccc(-c3cnn(C)c3)c2)ncc1-c1cnn(C)c1]
207
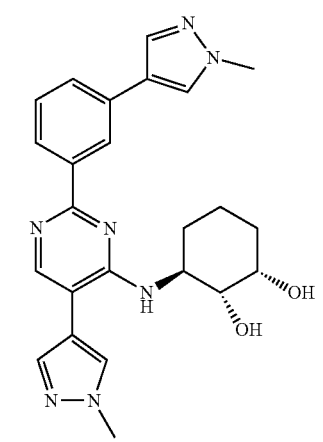 [SMILES: Cn1cc(-c2cccc(-c3ncc(-c4cnn(C)c4)c(N[C@H]4CCC[C@H](O)[C@@H]4O)n3)c2)cn1]
208
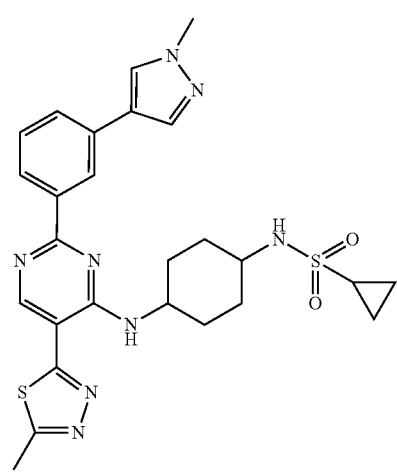 [SMILES: Cc1nnc(-c2cnc(-c3cccc(-c4cnn(C)c4)c3)nc2NC2CCC(NS(=O)(=O)C3CC3)CC2)s1]
209
TABLE 1-continued
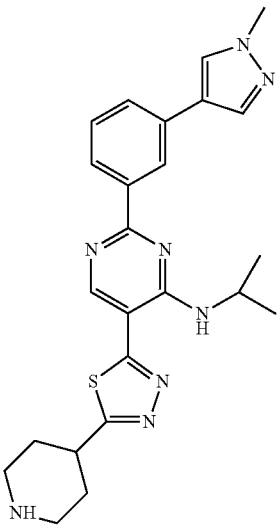 [SMILES: CC(C)Nc1nc(-c2cccc(-c3cnn(C)c3)c2)ncc1-c1nnc(C2CCNCC2)s1]
210
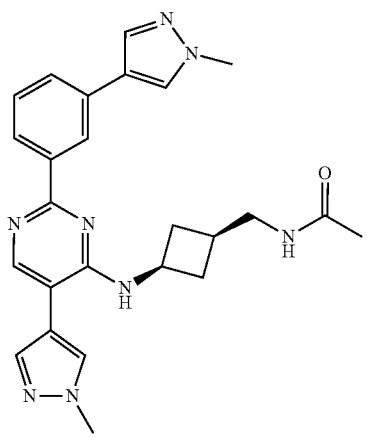 [SMILES: CC(=O)NC[C@H]1C[C@@H](Nc2nc(-c3cccc(-c4cnn(C)c4)c3)ncc2-c2cnn(C)c2)C1]
211
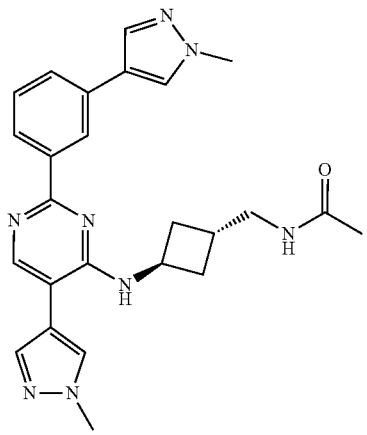 [SMILES: CC(=O)NC[C@H]1C[C@H](Nc2nc(-c3cccc(-c4cnn(C)c4)c3)ncc2-c2cnn(C)c2)C1]
212

TABLE 1-continued
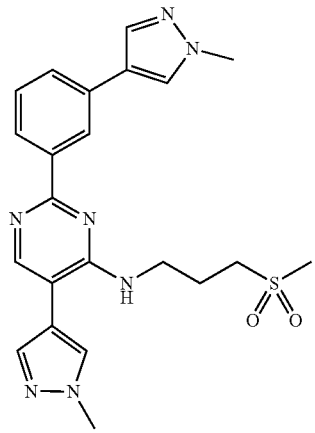 [SMILES: Cn1cc(-c2cccc(-c3ncc(-c4cnn(C)c4)c(NCCCS(C)(=O)=O)n3)c2)cn1]
213
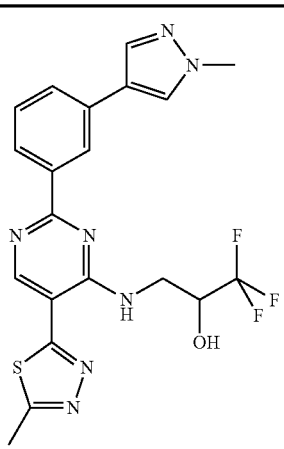
216
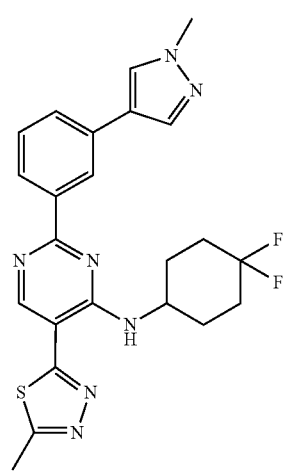 [SMILES: Cc1nnc(-c2cnc(-c3cccc(-c4cnn(C)c4)c3)nc2NC2CCC(F)(F)CC2)s1]
214
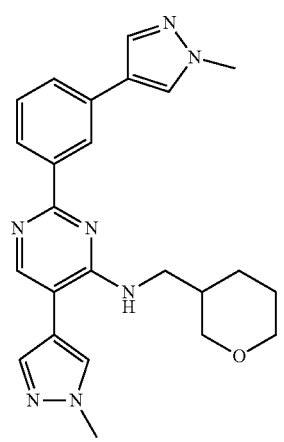
217
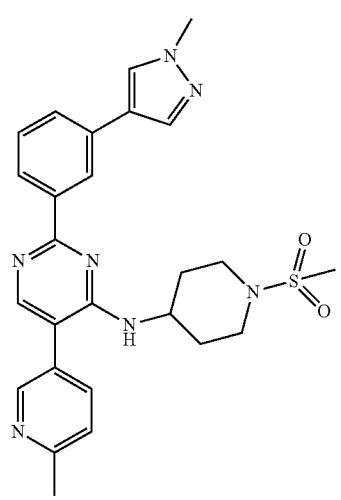 [SMILES: Cc1ccc(-c2cnc(-c3cccc(-c4cnn(C)c4)c3)nc2NC2CCN(S(C)(=O)=O)CC2)cn1]
215
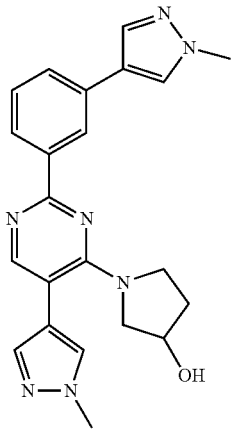 [SMILES: Cn1cc(-c2cccc(-c3ncc(-c4cnn(C)c4)c(N4CCC(O)C4)n3)c2)cn1]
218

TABLE 1-continued
219
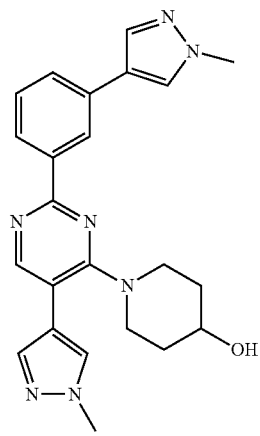 [SMILES: Cn1cc(-c2cccc(-c3ncc(-c4cnn(C)c4)c(N4CCC(O)CC4)n3)c2)cn1]
220
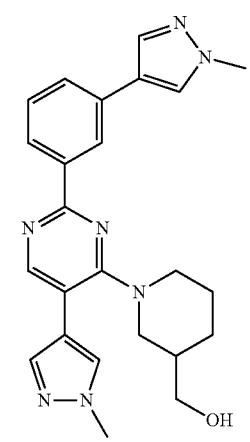 [SMILES: Cn1cc(-c2cccc(-c3ncc(-c4cnn(C)c4)c(N4CCCC(CO)C4)n3)c2)cn1]
221
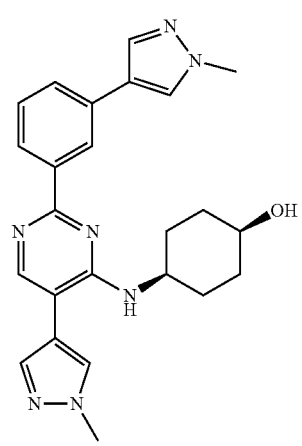 [SMILES: Cn1cc(-c2cccc(-c3ncc(-c4cnn(C)c4)c(N[C@H]4CC[C@@H](O)CC4)n3)c2)cn1]
TABLE 1-continued
222
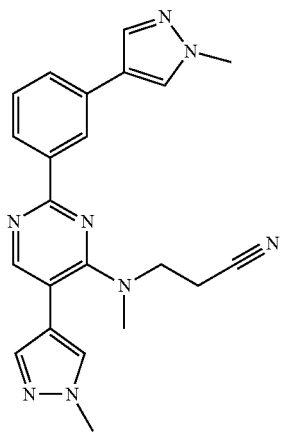 [SMILES: CN(CCC#N)c1nc(-c2cccc(-c3cnn(C)c3)c2)ncc1-c1cnn(C)c1]
223
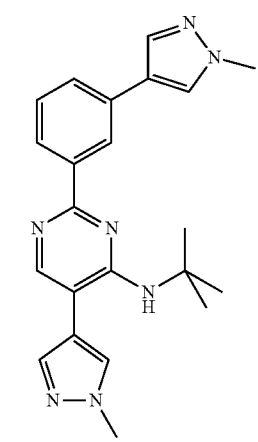
224
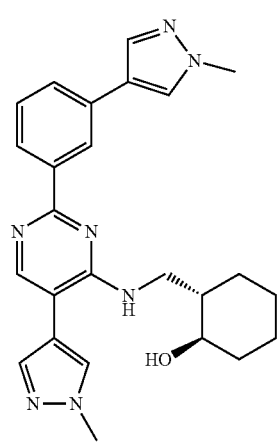 [SMILES: Cn1cc(-c2cccc(-c3ncc(-c4cnn(C)c4)c(NC[C@@H]4CCCC[C@H]4O)n3)c2)cn1]

TABLE 1-continued
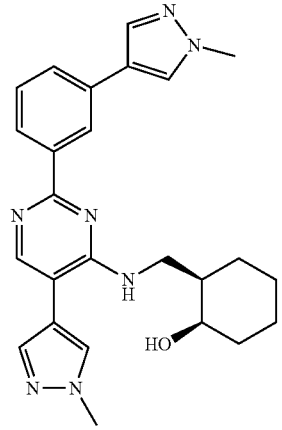 [SMILES: Cn1cc(-c2cccc(-c3ncc(-c4cnn(C)c4)c(NC[C@H]4CCCC[C@H]4O)n3)c2)cn1]
225
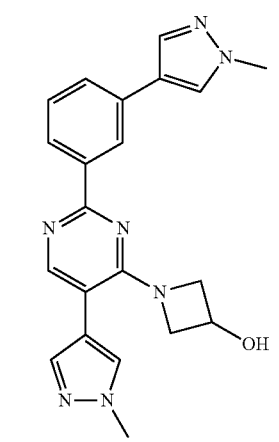 [SMILES: Cn1cc(-c2cccc(-c3ncc(-c4cnn(C)c4)c(N4CC(O)C4)n3)c2)cn1]
226
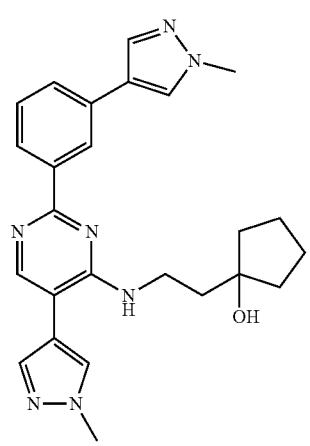 [SMILES: Cn1cc(-c2cccc(-c3ncc(-c4cnn(C)c4)c(NCCC4(O)CCCC4)n3)c2)cn1]
227
TABLE 1-continued
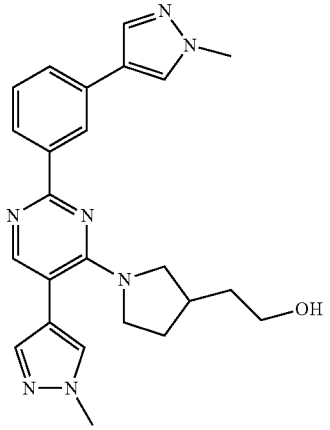 [SMILES: Cn1cc(-c2cccc(-c3ncc(-c4cnn(C)c4)c(N4CCC(CCO)C4)n3)c2)cn1]
228
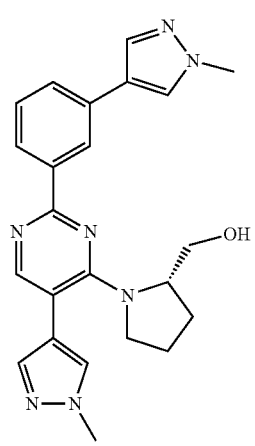 [SMILES: Cn1cc(-c2cccc(-c3ncc(-c4cnn(C)c4)c(N4CCC[C@H]4CO)n3)c2)cn1]
229
230

TABLE 1-continued
231 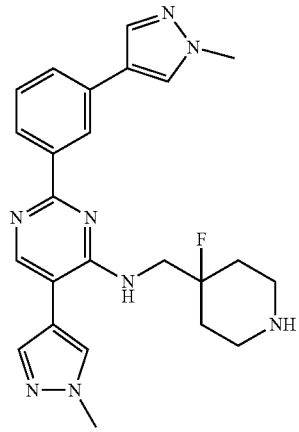 [SMILES: Cn1cc(-c2cccc(-c3ncc(-c4cnn(C)c4)c(NCC4(F)CCNCC4)n3)c2)cn1]
232 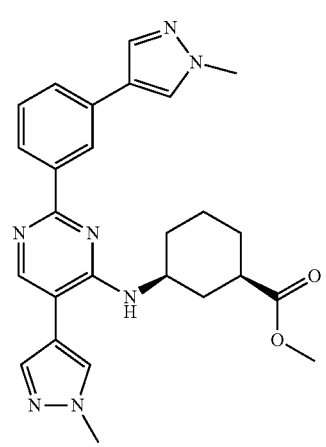
233 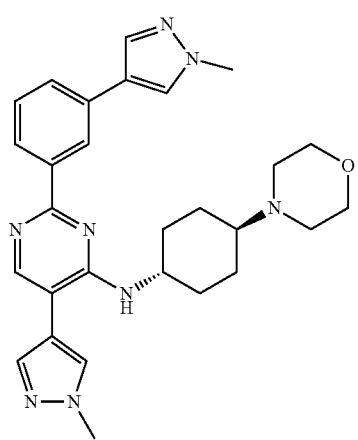 [SMILES: Cn1cc(-c2cccc(-c3ncc(-c4cnn(C)c4)c(N[C@H]4CC[C@H](N5CCOCC5)CC4)n3)c2)cn1]
TABLE 1-continued
234 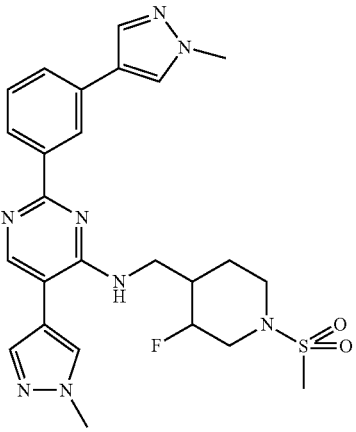 [SMILES: Cn1cc(-c2cccc(-c3ncc(-c4cnn(C)c4)c(NCC4CCN(S(C)(=O)=O)CC4F)n3)c2)cn1]
235 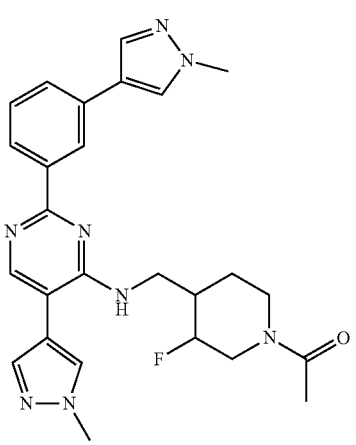
236 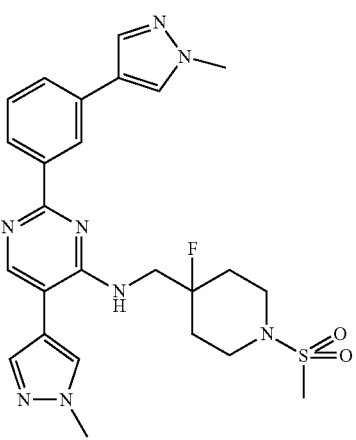 [SMILES: Cn1cc(-c2cccc(-c3ncc(-c4cnn(C)c4)c(NCC4(F)CCN(S(C)(=O)=O)CC4)n3)c2)cn1]

TABLE 1-continued
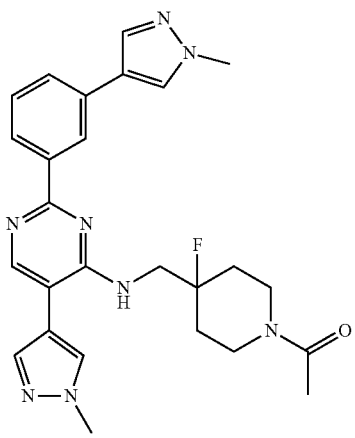 [SMILES: CC(=O)N1CCC(F)(CNc2nc(-c3cccc(-c4cnn(C)c4)c3)ncc2-c2cnn(C)c2)CC1]
237
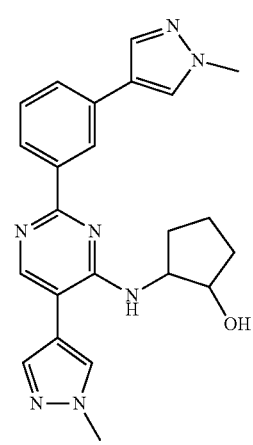 [SMILES: Cn1cc(-c2cccc(-c3ncc(-c4cnn(C)c4)c(NC4CCCC4O)n3)c2)cn1]
238
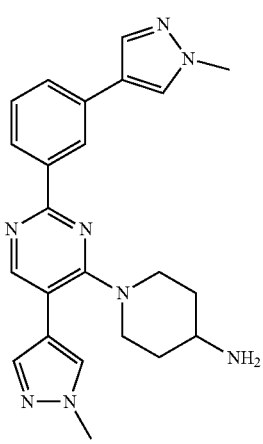 [SMILES: Cn1cc(-c2cccc(-c3ncc(-c4cnn(C)c4)c(N4CCC(N)CC4)n3)c2)cn1]
239
TABLE 1-continued
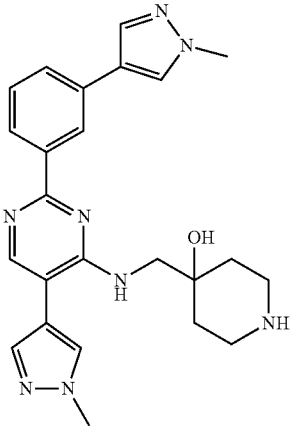 [SMILES: Cn1cc(-c2cccc(-c3ncc(-c4cnn(C)c4)c(NCC4(O)CCNCC4)n3)c2)cn1]
240
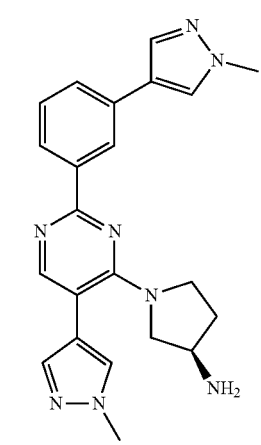
241
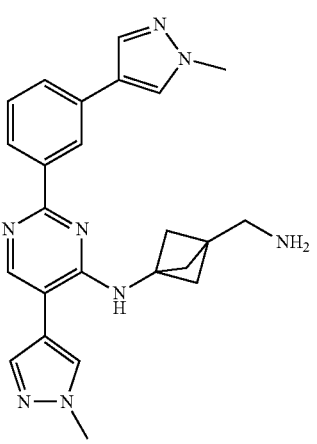 [SMILES: Cn1cc(-c2cccc(-c3ncc(-c4cnn(C)c4)c(NC45CC(CN)(C4)C5)n3)c2)cn1]
242

TABLE 1-continued
| | |
|---|---|
| 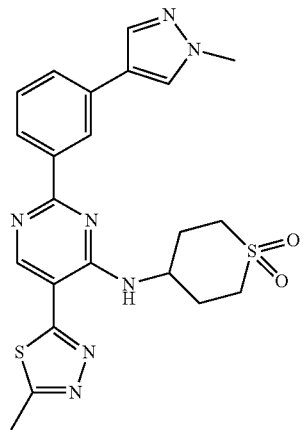 [SMILES: Cc1nnc(-c2cnc(-c3cccc(-c4cnn(C)c4)c3)nc2NC2CCS(=O)(=O)CC2)s1] 243 | 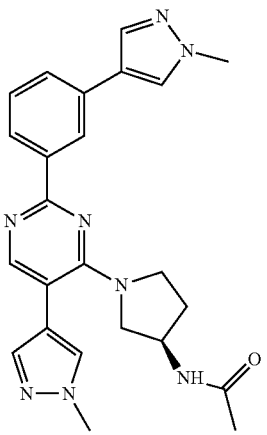 [SMILES: CC(=O)N[C@@H]1CCN(c2nc(-c3cccc(-c4cnn(C)c4)c3)ncc2-c2cnn(C)c2)C1] 246 |
| 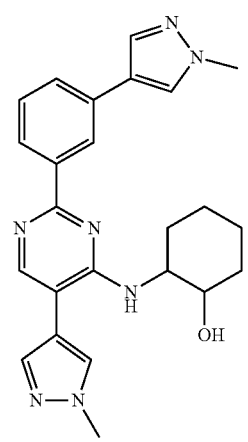 244 | 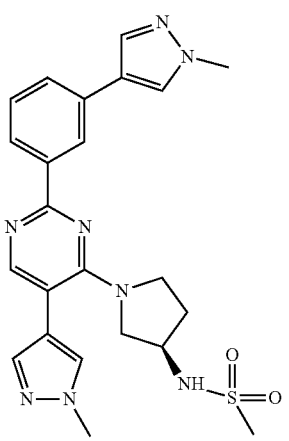 [SMILES: Cn1cc(-c2cccc(-c3ncc(-c4cnn(C)c4)c(N4CC[C@@H](NS(C)(=O)=O)C4)n3)c2)cn1] 247 |
| 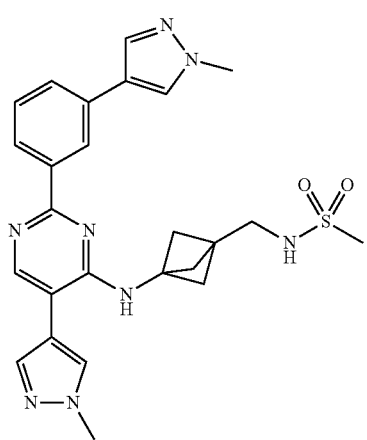 245 | 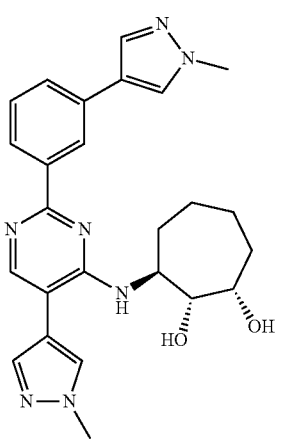 [SMILES: Cn1cc(-c2cccc(-c3ncc(-c4cnn(C)c4)c(N[C@H]4CCCC[C@H](O)[C@@H]4O)n3)c2)cn1] 248 |

TABLE 1-continued
249 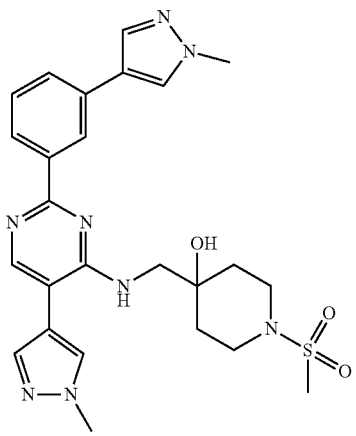
250 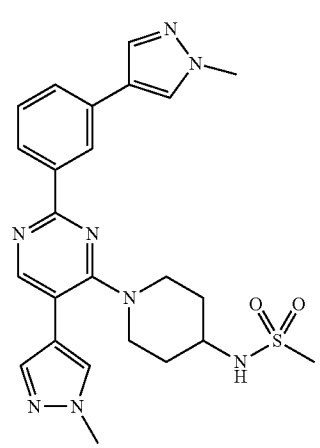 [SMILES: Cn1cc(-c2cccc(-c3ncc(-c4cnn(C)c4)c(N4CCC(NS(C)(=O)=O)CC4)n3)c2)cn1]
251 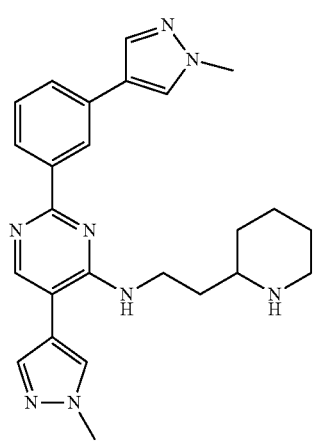
TABLE 1-continued
252 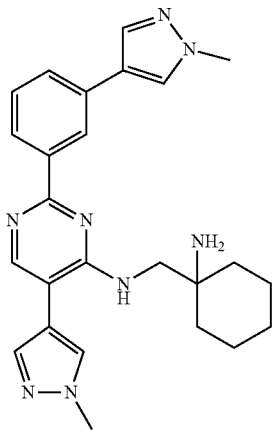 [SMILES: Cn1cc(-c2cccc(-c3ncc(-c4cnn(C)c4)c(NCC4(N)CCCCC4)n3)c2)cn1]
253 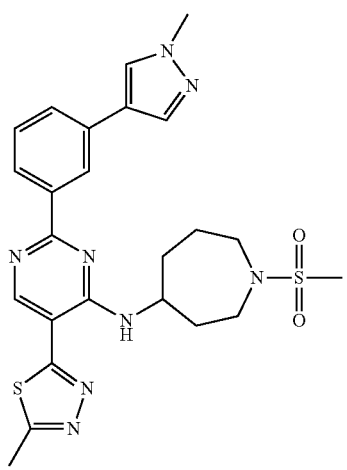
254 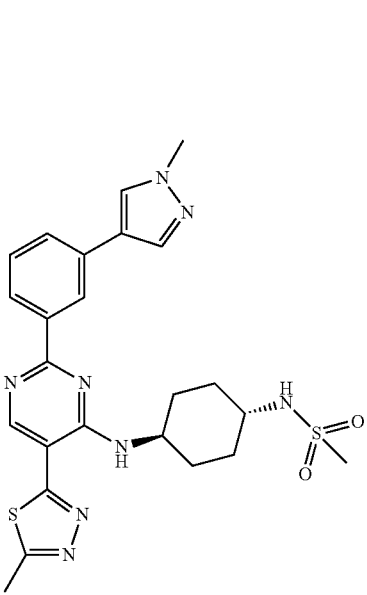 [SMILES: Cc1nnc(-c2cnc(-c3cccc(-c4cnn(C)c4)c3)nc2N[C@H]2CC[C@H](NS(C)(=O)=O)CC2)s1]

TABLE 1-continued
255 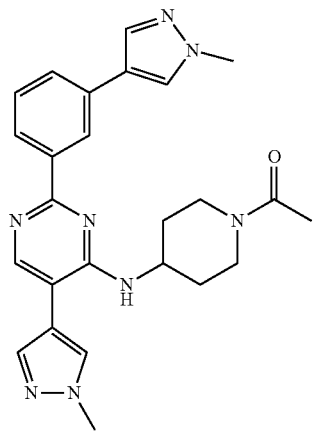 [SMILES: CC(=O)N1CCC(Nc2nc(-c3cccc(-c4cnn(C)c4)c3)ncc2-c2cnn(C)c2)CC1]
256 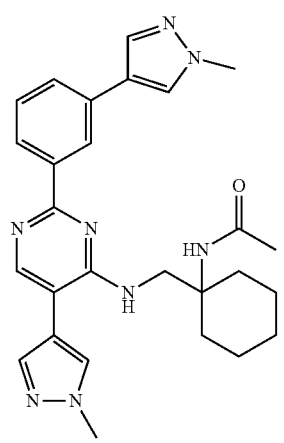 [SMILES: CC(=O)NC1(CNc2nc(-c3cccc(-c4cnn(C)c4)c3)ncc2-c2cnn(C)c2)CCCCC1]
257 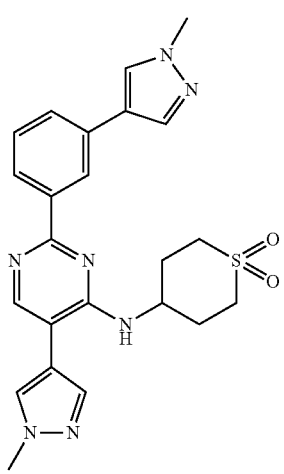 [SMILES: Cn1cc(-c2cccc(-c3ncc(-c4cnn(C)c4)c(NC4CCS(=O)(=O)CC4)n3)c2)cn1]
TABLE 1-continued
258 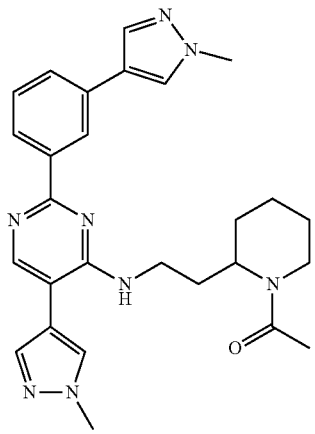 [SMILES: CC(=O)N1CCCCC1CCNc1nc(-c2cccc(-c3cnn(C)c3)c2)ncc1-c1cnn(C)c1]
259 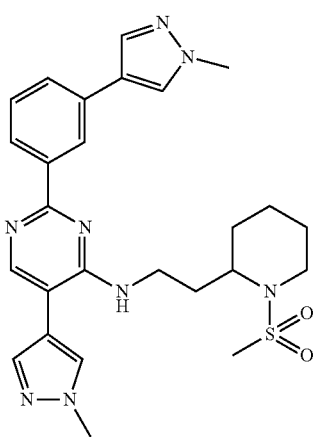 [SMILES: Cn1cc(-c2cccc(-c3ncc(-c4cnn(C)c4)c(NCCC4CCCCN4S(C)(=O)=O)n3)c2)cn1]
260 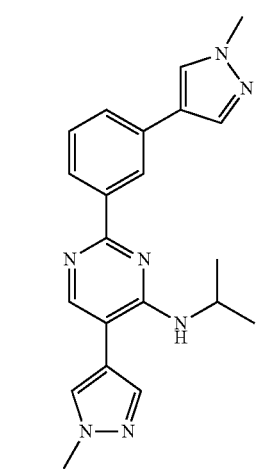 [SMILES: CC(C)Nc1nc(-c2cccc(-c3cnn(C)c3)c2)ncc1-c1cnn(C)c1]

TABLE 1-continued
261 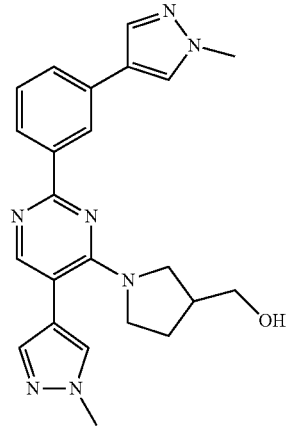
262 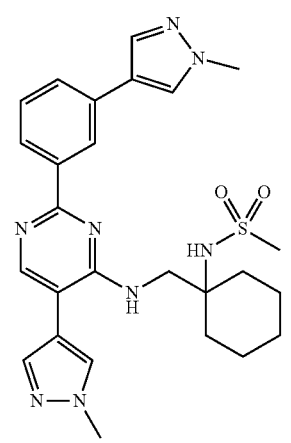 [SMILES: Cn1cc(-c2cccc(-c3ncc(-c4cnn(C)c4)c(NCC4(NS(C)(=O)=O)CCCCC4)n3)c2)cn1]
263 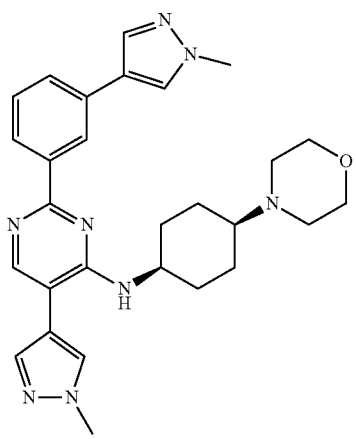 [SMILES: Cn1cc(-c2cccc(-c3ncc(-c4cnn(C)c4)c(N[C@H]4CC[C@@H](N5CCOCC5)CC4)n3)c2)cn1]
TABLE 1-continued
264 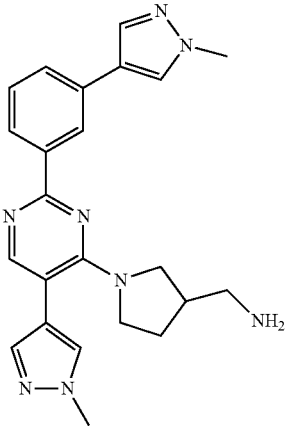 [SMILES: Cn1cc(-c2cccc(-c3ncc(-c4cnn(C)c4)c(N4CCC(CN)C4)n3)c2)cn1]
265 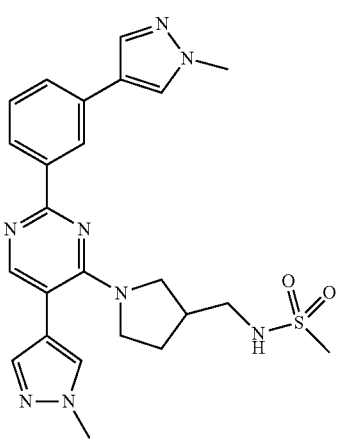 [SMILES: Cn1cc(-c2cccc(-c3ncc(-c4cnn(C)c4)c(N4CCC(CNS(C)(=O)=O)C4)n3)c2)cn1]
266 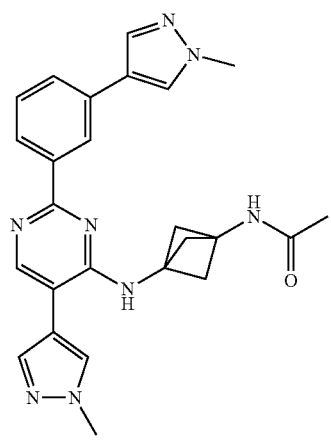 [SMILES: CC(=O)NC12CC(Nc3nc(-c4cccc(-c5cnn(C)c5)c4)ncc3-c3cnn(C)c3)(C1)C2]

TABLE 1-continued
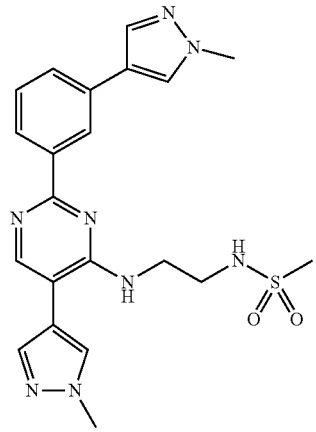 267
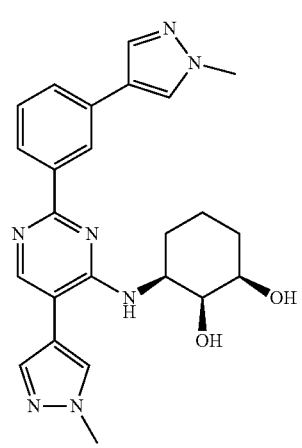 268
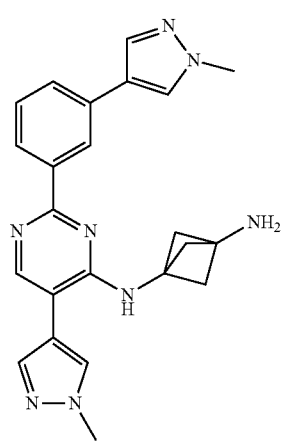 [SMILES: Cn1cc(-c2cccc(-c3ncc(-c4cnn(C)c4)c(NC45CC(N)(C4)C5)n3)c2)cn1] 269
TABLE 1-continued
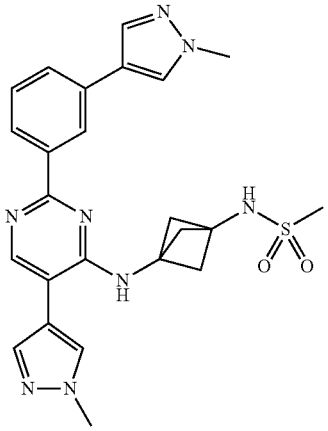 [SMILES: Cn1cc(-c2cccc(-c3ncc(-c4cnn(C)c4)c(NC45CC(NS(C)(=O)=O)(C4)C5)n3)c2)cn1] 270
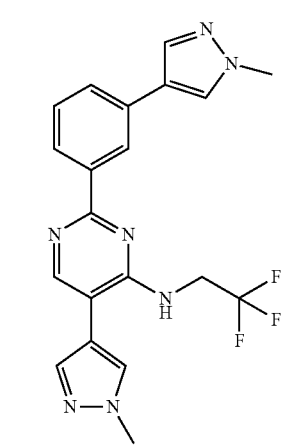 [SMILES: Cn1cc(-c2cccc(-c3ncc(-c4cnn(C)c4)c(NCC(F)(F)F)n3)c2)cn1] 271
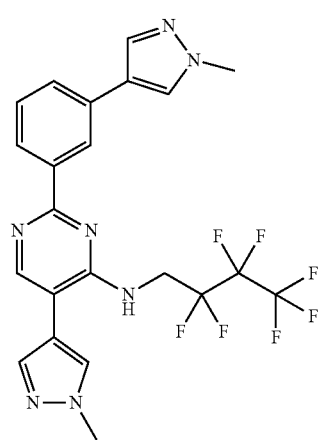 272

TABLE 1-continued
273 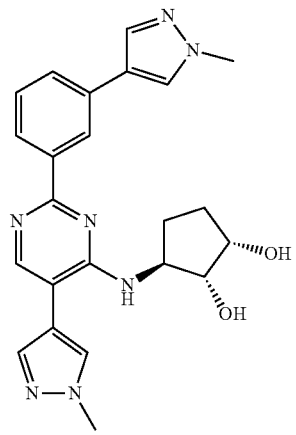 [SMILES: Cn1cc(-c2cccc(-c3ncc(-c4cnn(C)c4)c(N[C@H]4CC[C@H](O)[C@@H]4O)n3)c2)cn1]
274 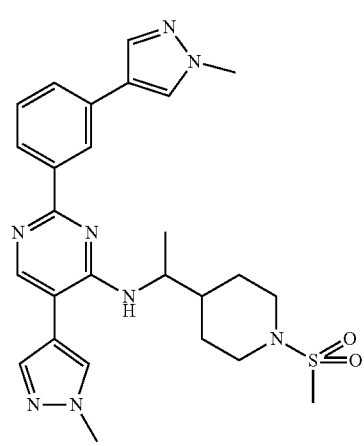 [SMILES: CC(Nc1nc(-c2cccc(-c3cnn(C)c3)c2)ncc1-c1cnn(C)c1)C1CCN(S(C)(=O)=O)CC1]
275 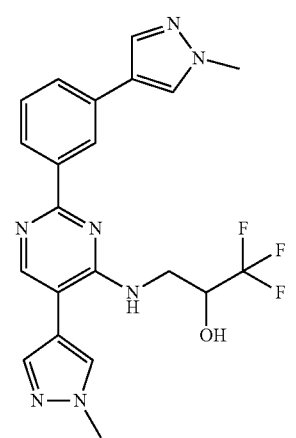
TABLE 1-continued
276 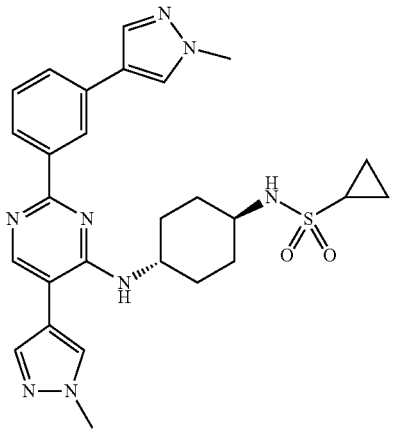 [SMILES: Cn1cc(-c2cccc(-c3ncc(-c4cnn(C)c4)c(N[C@H]4CC[C@H](NS(=O)(=O)C5CC5)CC4)n3)c2)cn1]
277 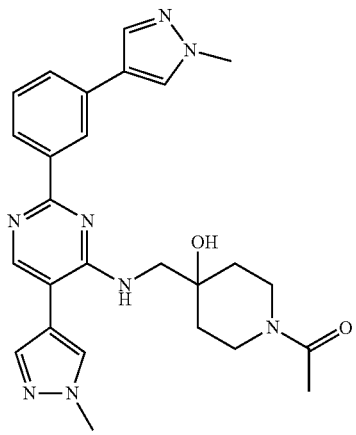 [SMILES: CC(=O)N1CCC(O)(CNc2nc(-c3cccc(-c4cnn(C)c4)c3)ncc2-c2cnn(C)c2)CC1]
278 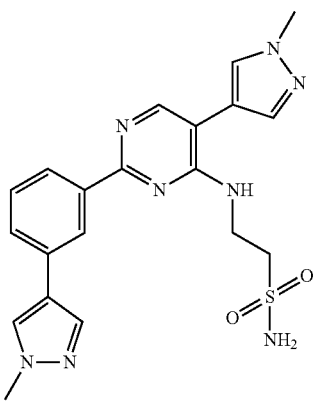 [SMILES: Cn1cc(-c2cccc(-c3ncc(-c4cnn(C)c4)c(NCCS(N)(=O)=O)n3)c2)cn1]

TABLE 1-continued
279
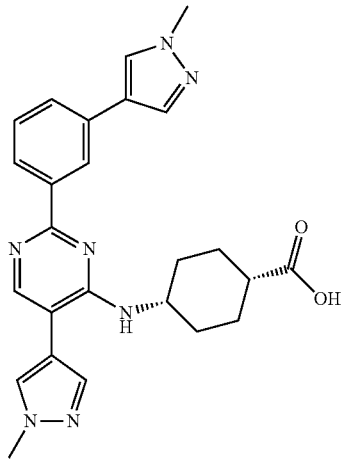 [SMILES: Cn1cc(-c2cccc(-c3ncc(-c4cnn(C)c4)c(N[C@H]4CC[C@@H](C(=O)O)CC4)n3)c2)cn1]
280
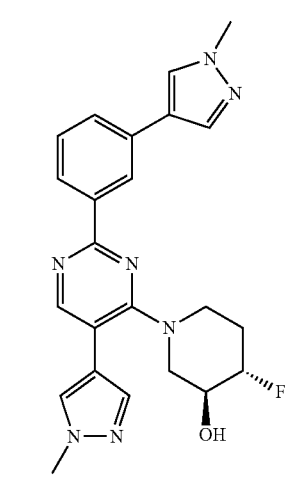 [SMILES: Cn1cc(-c2cccc(-c3ncc(-c4cnn(C)c4)c(N4CC[C@H](F)[C@@H](O)C4)n3)c2)cn1]
281
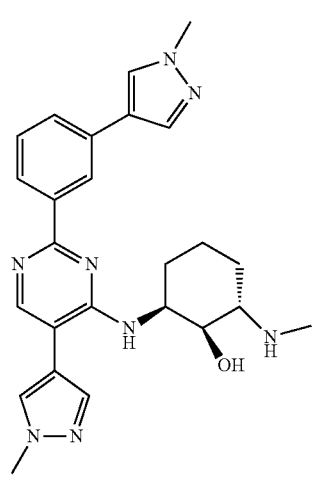
TABLE 1-continued
282
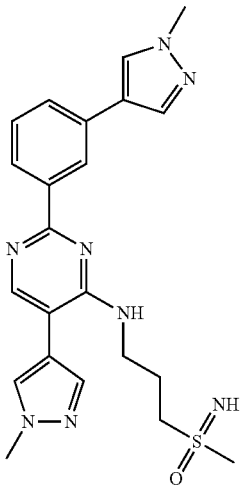
283
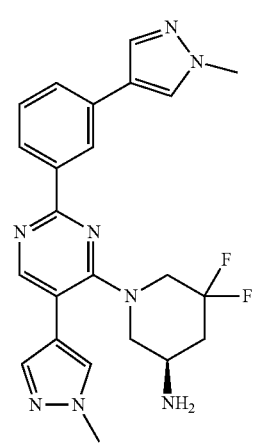 [SMILES: Cn1cc(-c2cccc(-c3ncc(-c4cnn(C)c4)c(N4C[C@H](N)CC(F)(F)C4)n3)c2)cn1]
284
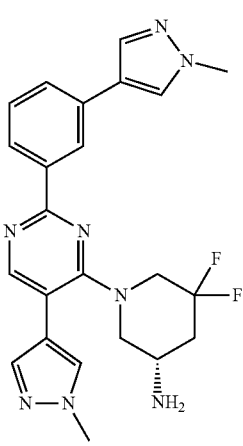

TABLE 1-continued
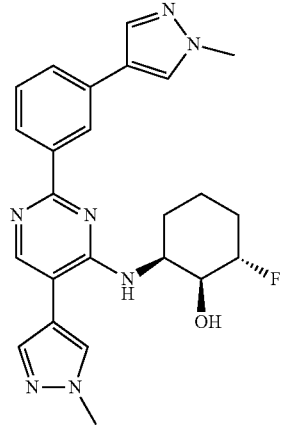 [SMILES: Cn1cc(-c2cccc(-c3ncc(-c4cnn(C)c4)c(N[C@H]4CCC[C@H](F)[C@H]4O)n3)c2)cn1]
285
286
287
TABLE 1-continued
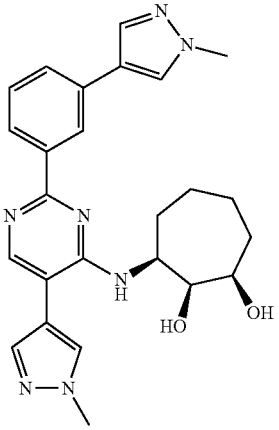
288
289
290

TABLE 1-continued

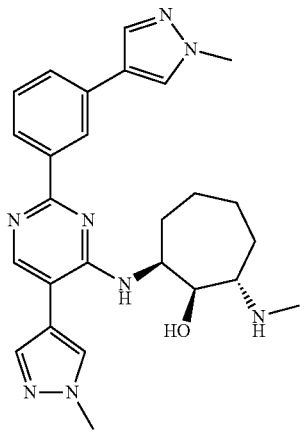 [SMILES: CN[C@H]1CCCC[C@H](Nc2nc(-c3cccc(-c4cnn(C)c4)c3)ncc2-c2cnn(C)c2)[C@@H]1O]

291

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

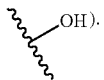

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit IRAK, or a mutant thereof, in a biological sample or in a patient. In certain embodiments, the amount of compound in compositions of this invention is such that is effective to measurably inhibit IRAK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from an IRAK related disorder, comprising administering to said subject an effective amount of a compound of formula I and related formulae.

The present invention preferably relates to a method, wherein the IRAK associated disorder is an autoimmune disorder or condition associated with an overactive immune response or cancer. The present invention furthermore relates to a method of treating a subject suffering from an immunoregulatory abnormality, comprising administering to said subject a compound of formula (I), and related formulae in an amount that is effective for treating said immunoregulatory abnormality.

The present invention preferably relates to a method wherein the immunoregulatory abnormality is an autoimmune or chronic inflammatory disease selected from the group consisting of: allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

The present invention furthermore relates to a method wherein the immunoregulatory abnormality is bone marrow or organ transplant rejection or graft-versus-host disease.

The present invention furthermore relates to a method wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, parkison diseases, trauma, and chronic bacterial infection.

In certain embodiments, disorders associated with IRAK are selected from Rheumatoid Arthritis, Psoriatic arthritis, Osteoarthritis, Systemic Lupus Erythematosus, Lupus nephritis, Ankylosing Spondylitis, Osteoporosis, Systemic sclerosis, Multiple Sclerosis, Psoriasis, Type I diabetes, Type II diabetes, Inflammatory Bowel Disease (Cronh's Disease and Ulcerative Colitis), Hyperimmunoglobulinemia D and periodic fever syndrome, Cryopyrin-associated periodic syndromes, Schnitzler's syndrome, Systemic juvenile idiopathic arthritis, Adult's onset Still's disease, Gout, Pseudogout, SAPHO syndrome, Castleman's disease, Sepsis, Stroke, Atherosclerosis, Celiac disease, DIRA (Deficiency of IL-1 Receptor Antagonist), Alzheimer's disease, Parkinson's disease, and Cancer.

In certain embodiments, the cancer is selected from carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g., epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

In certain embodiments, the cancer is brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogneous leukemia, myeloid cell leukemia, glioma, Kaposi's sarcoma, or any other type of solid or liquid tumors. In some embodiments, the cancer is metastatic cancer. In some embodiments, the cancer is colorectal cancer. In some embodiments, the cancer is colon cancer.

In various embodiments, compounds of formula (I), and related formulae exhibit a IC50 for the binding to IRAK of less than about 5 $\mu$M, preferably less than about 1 $\mu$M and even more preferably less than about 0.100 $\mu$M.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit IRAK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing IRAK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of IRAK activity if expedient.

The invention also relates to the use of compounds according to formula (I) and/or physiologically acceptable salts thereof for the prophylactic or therapeutic treatment and/or monitoring of diseases that are caused, mediated and/or propagated by IRAK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by IRAK activity. In certain embodiments, the invention provides the use of a compound according to formula I or physiologically acceptable salts thereof, for the production of a medicament for the prophylactic or therapeutic treatment of a IRAK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with IRAK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with IRAK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustinet[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malatei[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab, tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomabt[1,3], vintafolidet[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1]Prop. INN (Proposed International Nonproprietary Name); [2]Rec. INN (Recommended International Nonproprietary Names); [3]USAN (United States Adopted Name); [4]no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting IRAK activity in a biological sample comprising the step of contacting said biological sample with a compound of this invention, or a composition comprising said compound.

According to another embodiment, the invention relates to a method of inhibiting IRAK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of IRAK, including the evaluation of the many factors thought to influence, and be influenced by, the production of IRAK and the interaction of IRAK. The present compounds are also useful in the development of other compounds that interact with IRAK since the present compounds provide important structure-activity relationship (SAR) information that facilitate that development. Compounds of the present invention that bind to IRAK can be used as reagents for detecting IRAK in living cells, fixed cells, in biological fluids, in tissue homogenates, in purified, natural biological materials, etc. For example, by labeling such compounds, one can identify cells expressing IRAK. In addition, based on their ability to bind IRAK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing IRAK inside permeabilized cells. The compounds of the invention can also be utilized as commercial research reagents for various medical research and diagnostic uses. Such uses can include but are not limited to: use as a calibration standard for quantifying the activities of candidate IRAK inhibitors in a variety of functional assays; use as blocking reagents in random compound screening, i.e. in looking for new families of IRAK ligands, the compounds can be used to block recovery of the presently claimed IRAK compounds; use in the co-crystallization with IRAK enzyme, i.e. the compounds of the present invention will allow formation of crystals of the compound bound to IRAK, enabling the determination of enzyme/compound structure by x-ray crystallography; other research and diagnostic applications, wherein IRAK is preferably activated or such activation is conveniently calibrated against a known quantity of an IRAK inhibitor, etc.; use in assays as probes for determining the expression of IRAK in cells; and developing assays for detecting compounds which bind to the same site as the IRAK binding ligands.

The compounds of the invention can be applied either themselves and/or in combination with physical measurements for diagnostics of treatment effectiveness. Pharmaceutical compositions containing said compounds and the use of said compounds to treat IRAK-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of IRAK, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All reactions were conducted at room temperature unless otherwise noted. All compounds of the present invention were synthesiszed by processes developed by the inventors. $^1$H-NMR spectra were acquired on a Bruker Avance III 400 or a Bruker DPX-300 MHz. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), qt (quintuplet) or br (broad).

Mass spectra were obtained on Agilent 1200 Series mass spectrometers from Agilent Technologies, using either Atmospheric Chemical Ionization (APCI) or Electrospray Ionization (ESI). Column: XBridge C8, 3.5 µm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B or a LC/MS Waters ZMD (ESI).

HPLC data were obtained using Agilent 1100 series HPLC from Agilent technologies using a column (XBridge C8, 3.5 µm, 4.6×50 mm) and two mobile phases (mobile phase A: water+0.1% TFA; mobile phase B: ACN+0.1% TFA). The flow rate was 2 ml/min. The gradient method was: 0 min: 5% B; 8 min: 100% B; 8.1 min: 100% B; 8.5 min: 5% B; 10 min 5% B, unless otherwise indicated.

The microwave reactions were conducted using Biotage Initiator Microwave Synthesizer or a single mode microwave reactor Emrys™ Optimiser using standard protocols that are known in the art.

Compound numbers utilized in the Examples below correspond to compound numbers set forth supra.

The following abbreviations refer to the abbreviations used below:
Ac (acetyl), BINAP (2,2'-bis(disphenylphosphino)-1,1'-binaphthalene), dba (dibenzylidene acetone), Bu (Butyl), tBu (tert-Butyl), DCE (dichloroethane), DCM (Dichloromethane), δ (chemical shift), DIEA (di-isopropyl ethylamine), DMA (dimethyl acetamide), DMSO (Dimethyl Sulfoxide), DMF (N,N-Dimethylformamide), Dppf (1,1-bis (diphenyl phosphine ferrocene)), EtOAc (Ethyl acetate), EtOH (Ethanol), eq (equivalent), g (gram), cHex (Cyclohexane), HATU (N-[(Dimethylamino)(3H-[1,2,3]triazolo[4,5-b]pyridin-3-yloxy)methylene]-N-methylmethanaminiumhexafluoro phosphate), HPLC (High Performance Liquid Chromatography), h (hour), LDA (lithium diisopropyl amine), LiHMDS (lithium bis(trimethylsilyl)amide), MHz (Megahertz), MeOH (Methanol), min (minute), mL (milliliter), mmol (millimole), mM (millimolar), mp (melting point), MS (Mass Spectrometry), MW (microwave), NMR (Nuclear Magnetic Resonance), O/N (overnight), PBS (Phosphate Buffered Saline), RT (room temperature), TEA (Triethyl amine), TFA (Trifluoroacetic acid), THF (Tetrahydrofuran), TLC (Thin Layer Chromatography).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, N.Y., 1994 and, Theodora W. Greene and Peter G. M. Wuts in "Protective Groups in Organic Synthesis", Wiley Interscience, 3$^{rd}$ Edition 1999.

Scheme 1: Example of synthetic route for phenyl-pyridines

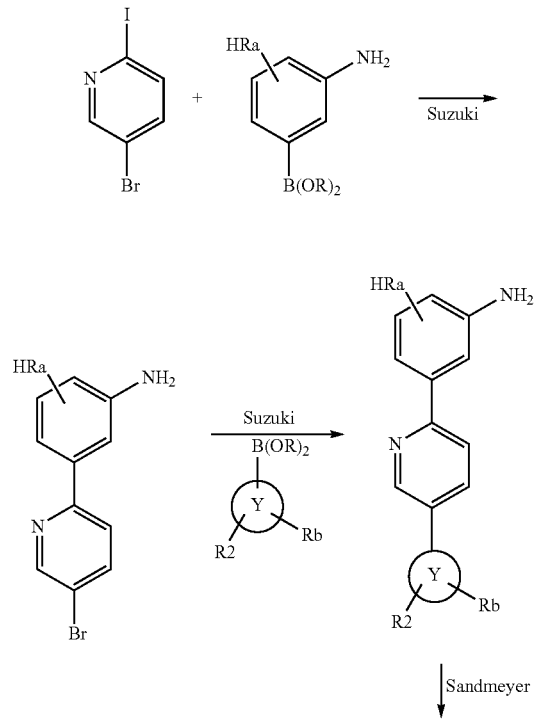

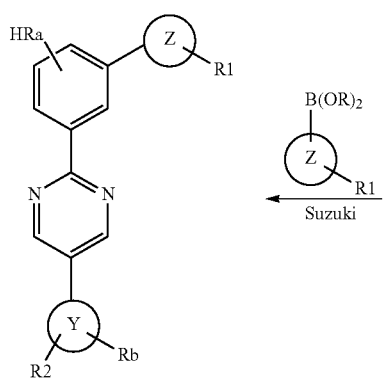
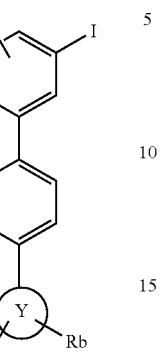
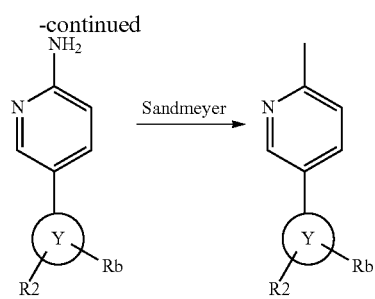
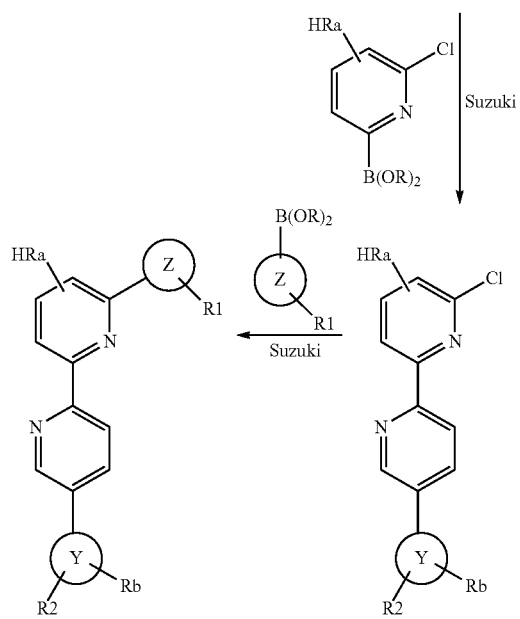
Scheme 2: Example of synthetic route for pyridinyl-pyridines
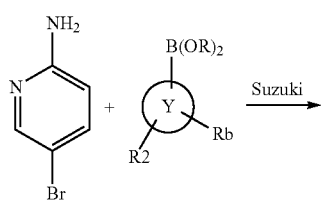
Scheme 3: Example of synthetic route for pyrazolyl-pyrimidines where A is O or NR
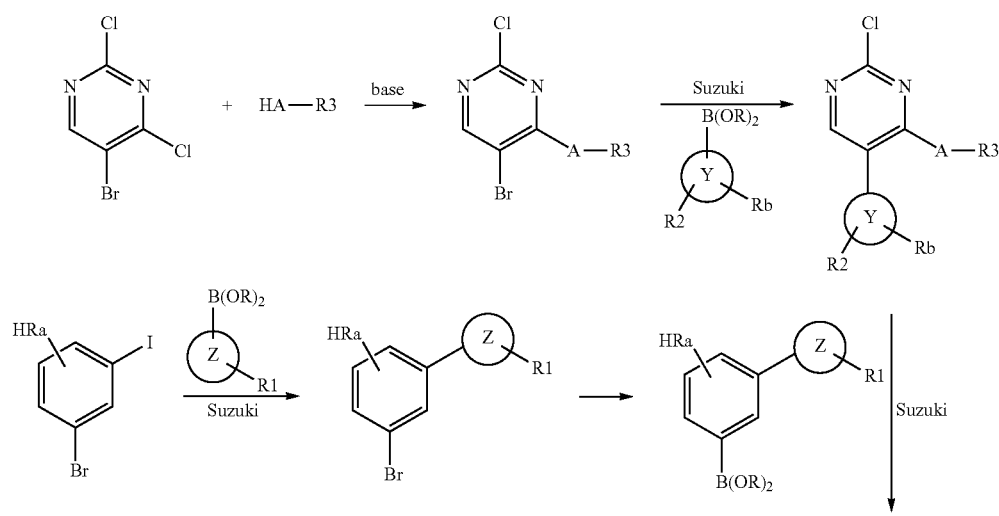

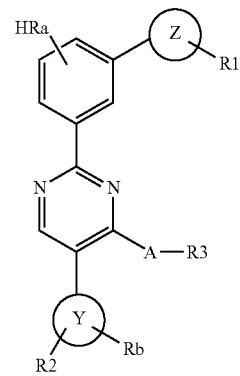
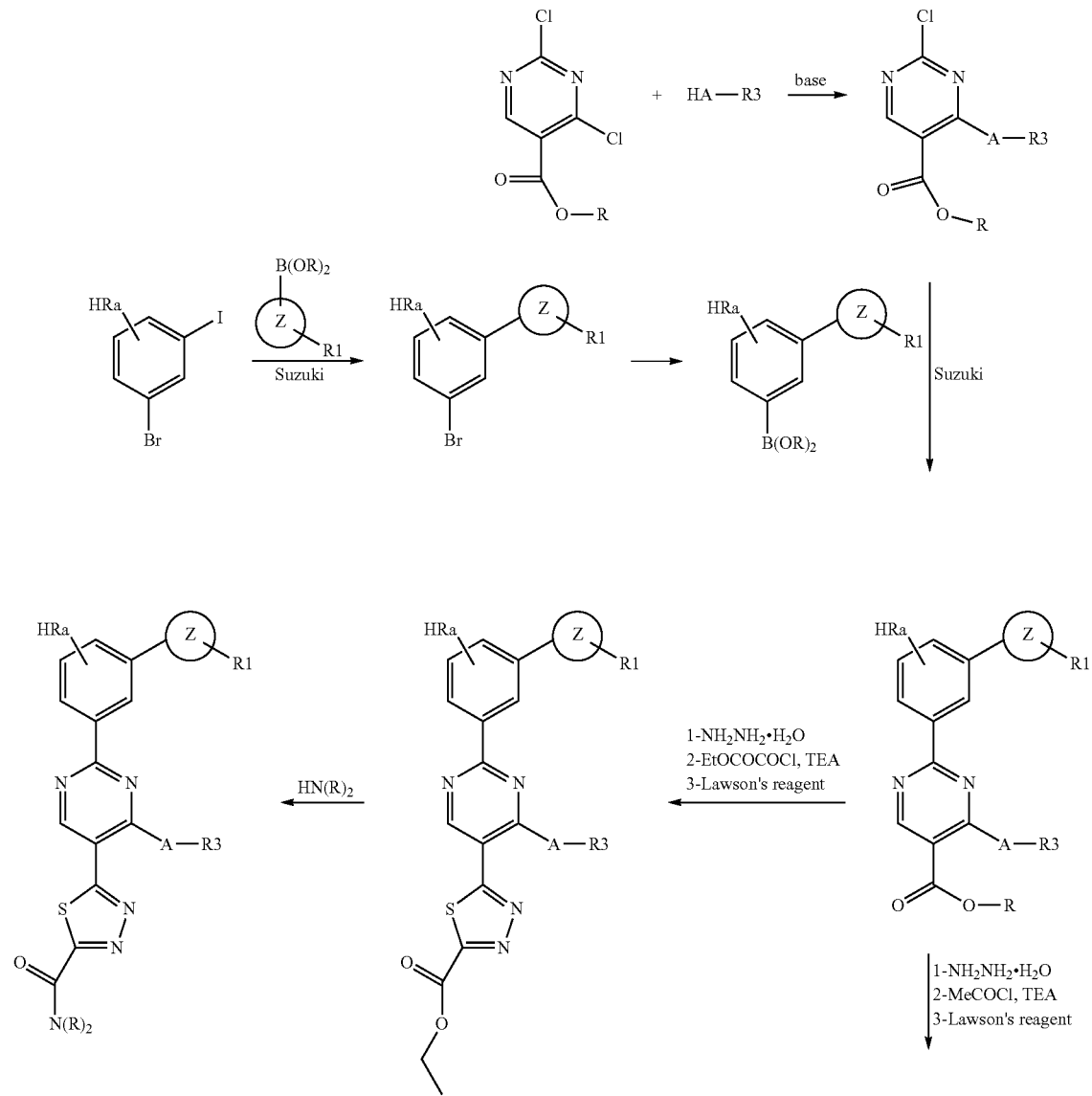
Scheme 4: Example of synthetic route for Thiadiazolyl-pyrimidines where A is O or NR

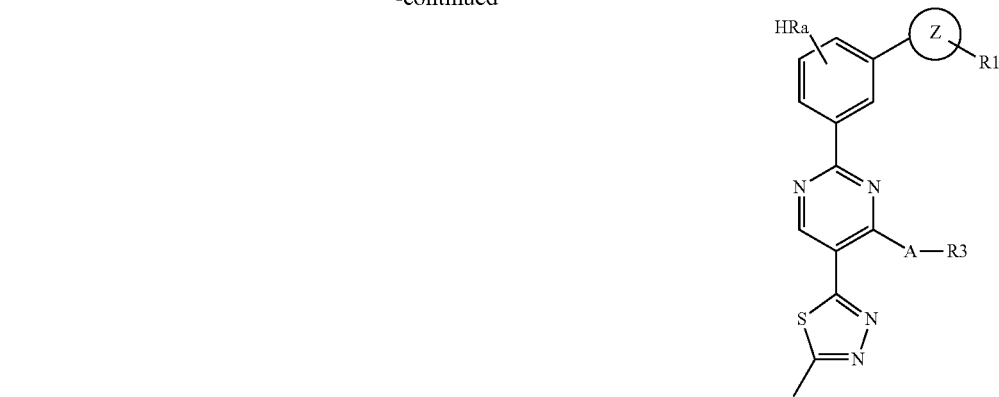

Intermediate 1: tert-butyl 4-{4-[6-(3-aminophenyl)pyridin-3-yl]-1H-pyrazol-1-yl}piperidine-1-carboxylate

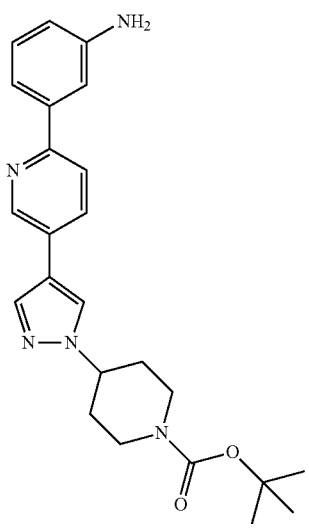 [SMILES: CC(C)(C)OC(=O)N1CCC(n2cc(-c3ccc(-c4cccc(N)c4)nc3)cn2)CC1]

A mixture of 5-bromo-2-iodopyridine (500 mg; 1.76 mmol; 1.00 eq.), 3-aminophenylboronic acid (241 mg; 1.76 mmol; 1.00 eq.), potassium carbonate (974 mg; 7.04 mmol; 4.00 eq.) and Pd(PPh$_3$)$_4$ (102 mg; 0.09 mmol; 0.05 eq.) in dioxane (7.50 mL) and water (3.75 mL) was heated in a sealed vial at 100° C. overnight. The reaction mixture was then diluted with EtOAc and washed with water. The organic layer was back-extracted with EtOAc and the combined organic layers were dried over MgSO$_4$, filtered and concentrated to give 3-(5-bromopyridin-2-yl)aniline (438 mg, 100%). 3-(5-bromopyridin-2-yl)aniline (435 mg; 1.75 mmol; 1.00 eq.), 4-[4-(4,4,5,5-Tetramethyl-[1,3,2]dioxaborolan-2-yl)-pyrazol-1-yl]-piperidine-1-carboxylic acid tert-butyl ester (659 mg; 1.75 mmol; 1.00 eq.), potassium carbonate (965 mg; 6.98 mmol; 4.00 eq.) and Pd(PPh$_3$)$_4$ (101 mg; 0.09 mmol; 0.05 eq.) were then suspended in dioxane (6.5 mL) and water (3.4 mL) in a sealed vial. The reaction mixture was heated in the MW at 120° C. for 30 minutes, then diluted with EtOAc and washed with water. The organic layer was back-extracted with EtOAc. The combined organic layers were dried over MgSO$_4$, filtered and concentrated. Purification by flash chromatography on silica (EtOAc:DCM, gradient from 50 to 100%) afforded the title compound as a beige solid (390 mg; 37%). 1H NMR (300 MHz, DMSO-d6): 8.87 (dd, J=2.0 Hz, 0.6 Hz, 1H), 8.42 (s, 1H), 8.02-7.98 (m, 2H), 7.79 (dd, J=8.4 Hz, 0.6 Hz, 1H), 7.34 (t, J=2.0 Hz, 1H), 7.19 (dt, J=7.8 Hz, 1.5 Hz, 1H), 7.11 (t, J=7.8 Hz, 1H), 6.62-6.58 (m, 1H), 5.18 (s, 2H), 4.43-4.34 (m, 1H), 4.07-3.99 (m, 2H), 2.93 (m, 2H), 2.07-2.03 (m, 2H), 1.88-1.74 (m, 2H), 1.43 (s, 9H).

Intermediate 2: tert-butyl 4-{4-[6-(3-iodophenyl)pyridin-3-yl]-1H-pyrazol-1-yl}piperidine-1-carboxylate

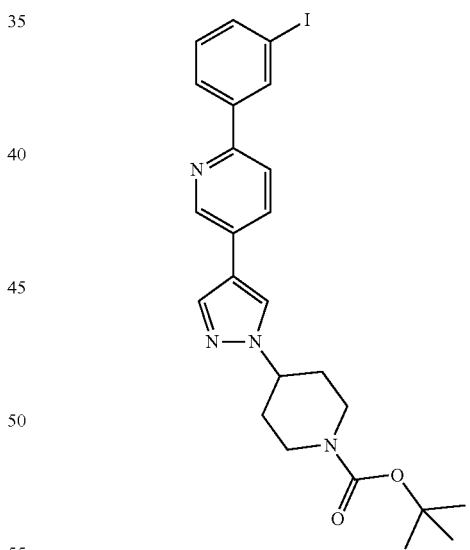

Isopentyl nitrite (stabilized, 375 µl; 2.79 mmol; 3.00 eq.) was added to a solution of tert-butyl 4-4-[6-(3-aminophenyl)pyridin-3-yl]-1H-pyrazol-1-ylpiperidine-1-carboxylate (390 mg; 0.93 mmol; 1.00 eq.), Copper(I) iodide (212 mg; 1.12 mmol; 1.20 eq.) and diiodomethane (377 µl; 4.65 mmol; 5.00 eq.) in dry THF (15.6 mL) and the reaction mixture was refluxed for 1 hour. The reaction mixture was then filtered through a celite pad and the filtrate was concentrated to dryness. Purification by flash chromatography on silica (EtOAc: Heptane, gradient from 20 to 100% of EtOAc) afforded the title compound (215 mg; 43.6%). 1H NMR (300 MHz, DMSO-d6): 8.94 (dd, J=2.0 Hz, 0.7 Hz, 1H), 8.47-8.45 (m, 2H), 8.13-7.95 (m, 4H), 7.79-7.76 (m, 2H), 7.29 (t, J=7.8 Hz, 1H), 4.45-4.35 (m, 1H), 4.08-4.00 (m, 2H), 2.94 (m, 2H), 2.04-2.03 (m, 2H), 1.88-1.74 (m, 2H), 1.43 (s, 9H). LC/MS: 531.5 (M+1).

Intermediate 3: 4-[4-(6-Amino-pyridin-3-yl)-pyrazol-1-yl]-piperidine-1-carboxylic Acid Tert-Butyl Ester

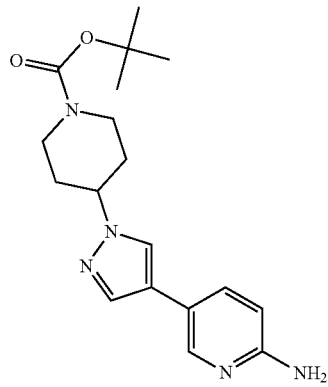 [SMILES: CC(C)(C)OC(=O)N1CCC(n2cc(-c3ccc(N)nc3)cn2)CC1]

A mixture of 5-Iodo-pyridin-2-ylamine (1.10 g; 5.00 mmol; 1.0 eq.), 4-[4-(4,4,5,5-Tetramethyl-[1,3,2]dioxaborolan-2-yl)-pyrazol-1-yl]-piperidine-1-carboxylic acid tert-butyl ester (2.07 g; 5.50 mmol; 1.10 eq.), Pd(PPh₃)₄ (289 mg; 0.25 mmol; 0.05 eq.) and potassium carbonate (2.07 g; 15.00 mmol; 3.00 eq.) in dioxane (38 mL) was heated in a sealed vial at 100° c. overnight. The reaction mixture was then diluted with EtOAc and washed with water. The organic layer was back-extracted with EtOAc. The combined organic layers were dried over MgSO₄, filtered and concentrated. The solid obtained was suspended in EtOAc, filtered and dried under vacuum to give the title compound as a beige solid (1 g, 70%). HPLC: (254 nm) 95%; Rt (min) 2.60; LC/MS: 344.3 (M+1).

Intermediate 4: 4-[4-(6-Iodo-pyridin-3-yl)-pyrazol-1-yl]-piperidine-1-carboxylic Acid Tert-Butyl Ester

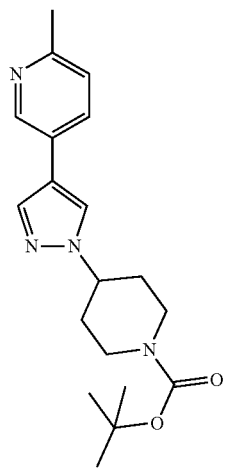 [SMILES: Cc1ccc(-c2cnn(C3CCN(C(=O)OC(C)(C)C)CC3)c2)cn1]

The title compound was obtained following procedure described for intermediate 2 from 4-[4-(6-Amino-pyridin-3-yl)-pyrazol-1-yl]-piperidine-1-carboxylic acid tert-butyl ester (1.21 g; 3.52 mmol; 1.00 éq.) as a brown gum (390 mg; 0.86 mmol). HPLC: (254 nm) 68%; Rt (min) 4.44. LC/MS: 455.4 (M+1).

Intermediate 5: 4-[4-(6'-Chloro-[2,2']bipyridinyl-5-yl)-pyrazol-1-yl]-piperidine-1-carboxylic Acid Tert-Butyl Ester

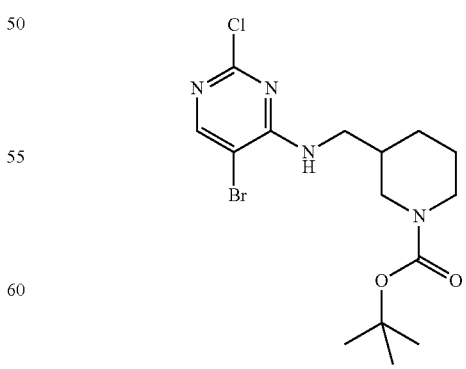

The title compound was obtained following procedure described for example 1, step 1 from 4-[4-(6-Iodo-pyridin-3-yl)-pyrazol-1-yl]-piperidine-1-carboxylic acid tert-butyl ester (150 mg; 0.33 mmol; 1.00 eq.) and 2-Chloro-6-(4,4,5,5-tetramethyl-[1,3,2]dioxaborolan-2-yl)-pyridine (87 mg; 0.36 mmol; 1.10 eq.) as a brown gum (180 mg, quantitative). LC/MS: 440.4 (M+1).

Intermediate 6: 3-[(5-Bromo-2-chloro-pyrimidin-4-ylamino)-methyl]-piperidine-1-carboxylic Acid Tert-Butyl Ester 5-Bromo-2,4-dichloro-pyrimidine (2.12 g; 9.33 mmol; 2.00 eq.) was added to a suspension of NaH (134 mg; 5.6 mmol; 1.20 eq.) in THF (16 mL) maintained at 0° C. The reaction mixture was stirred for 5 min before the addition of 3-Aminomethyl-piperidine-1-carboxylic acid tert-butyl ester (1.0 g; 4.67 mmol; 1.00 eq.). It was then stirred at 0° C. overnight, diluted with methanol, filtered through a celite pad and concentrated. Purification by flash chromatography on silica (EtOAc:Hexane, gradient from 0 to 100% then MeOH:DCM, gradient from 0 to 20%) afforded the title compound in the second eluting fraction as a white powder (587 mg, 31%). 1H NMR (400 MHz, Chloroform-d) δ 8.22 (s, 1H), 4.84 (brs, 1H), 4.37-4.12 (m, 2H), 3.25-3.09 (m, 2H), 3.03 (m, 1H), 2.99-2.86 (m, 1H), 1.90 (m, 2H), 1.81 (m, 1H), 1.67 (m, 1H), 1.46 (s, 9H), 1.32 (m, 1H). LC/MS: 405.0 (M+1).

Intermediate 7: 3-{[2-Chloro-5-(1-methyl-1H-pyrazol-4-yl)-pyrimidin-4-ylamino]-methyl}-piperidine-1-carboxylic Acid Tert-Butyl Ester

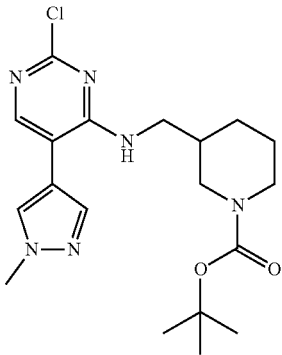 [SMILES: Cn1cc(-c2cnc(Cl)nc2NCC2CCCN(C(=O)OC(C)(C)C)C2)cn1]

A mixture of 3-[(5-Bromo-2-chloro-pyrimidin-4-ylamino)-methyl]-piperidine-1-carboxylic acid tert-butyl ester (252 mg; 0.62 mmol; 1.00 eq.), 1-Methyl-4-(4,4,5,5-tetramethyl-[1,3,2]dioxaborolan-2-yl)-1H-pyrazole (194 mg; 0.93 mmol; 1.50 eq.), $K_3PO_4$ (264 mg; 1.24 mmol; 2.00 eq.) and Pd(dppf)Cl$_2$ (23 mg; 0.03 mmol; 0.05 eq.) in water (0.2 mL) and 2-Methyltetrahydrofuran (5.6 mL) was degassed with Ar and heated in a sealed tube to 100° C. for 2 h. It was then filtered through a celite pad and concentrated under reduced pressure. Purification by flash chromatography on silica (EtOAc:Hexanes, gradient from 0 to 100%) afforded the title compound as a white solid (97 mg, 38%). LC/MS: 407.7 (M+1).

Intermediate 8: [1-(5-Bromo-2-chloro-pyrimidin-4-yl)-piperidin-3-ylmethyl]-carbamic Acid Tert-Butyl Ester

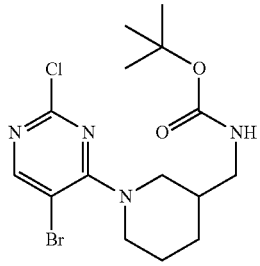 [SMILES: CC(C)(C)OC(=O)NCC1CCCN(c2nc(Cl)ncc2Br)C1]

The title compound was obtained following procedure described for intermediate 6 from 5-Bromo-2,4-dichloro-pyrimidine (3.3 mL; 23.33 mmol; 2.00 eq.) and piperidin-3-ylmethyl-carbamic acid tert-butyl ester (2.5 g; 11.7 mmol; 1.00 eq.) as a yellow solid (4 g, 80%). 1H NMR (400 MHz, Chloroform-d) δ 8.24 (s, 1H), 4.81 (s, 1H), 4.27 (t, J=13.7 Hz, 2H), 3.16 (m, 2H), 3.10-3.02 (m, 1H), 3.02-2.85 (m, 1H), 1.98-1.86 (m, 2H), 1.81 (m, 1H), 1.74-1.61 (m, 1H), 1.48 (s, 9H), 1.42-1.23 (m, 1H). LC/MS: 405.1 (M+1).

Intermediate 9: {1-[2-Chloro-5-(1-methyl-1H-pyrazol-4-yl)-pyrimidin-4-yl]-piperidin-3-ylmethyl}-carbamic Acid Tert-Butyl Ester

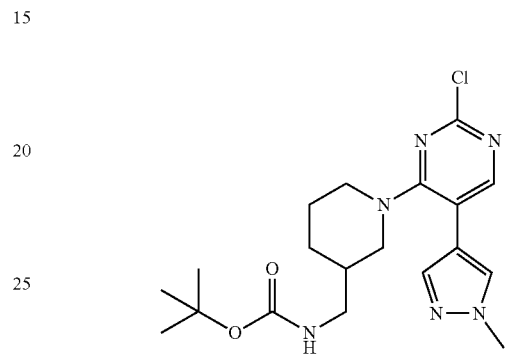

A mixture of [1-(5-Bromo-2-chloro-pyrimidin-4-yl)-piperidin-3-ylmethyl]-carbamic acid tert-butyl ester (750 mg; 1.85 mmol; 1.00 eq.), 1-Methyl-4-(4,4,5,5-tetramethyl-[1,3,2]dioxaborolan-2-yl)-1H-pyrazole (462 mg; 2.22 mmol; 1.20 eq.), potassium phosphate (785 mg; 3.70 mmol; 2.00 eq.) and Pd(dppf)Cl$_2$.DCM (135 mg; 0.18 mmol; 0.10 eq.) in water (0.60 mL), and 2-Methyltetrahydrofuran (5.6 mL) was degassed with Ar and heated in a sealed tube to 100° C. for 2 h. It was then filtered through a celite pad and concentrated under reduced pressure. Purification by flash chromatography on silica (EtOAc:Hexanes, gradient from 0 to 100%) afforded the title compound as a yellow foam (640 mg, 85%). $^1$H NMR (400 MHz, Chloroform-d) δ 7.94 (s, 1H), 7.55 (s, 1H), 7.49 (s, 1H), 4.85 (t, J=6.4 Hz, 1H), 3.96 (s, 3H), 3.87-3.73 (m, 1H), 3.73-3.58 (m, 1H), 3.04 (dt, J=12.8, 5.8 Hz, 1H), 2.87 (m, 3H), 1.86-1.68 (m, 2H), 1.68-1.54 (m, 1H), 1.43 (brs, 11H); LC/MS: 407.2 (M+1).

Intermediate 10: 4-[(5-Bromo-2-chloro-pyrimidin-4-ylamino)-methyl]-piperidine-1-carboxylic Acid Tert-Butyl Ester

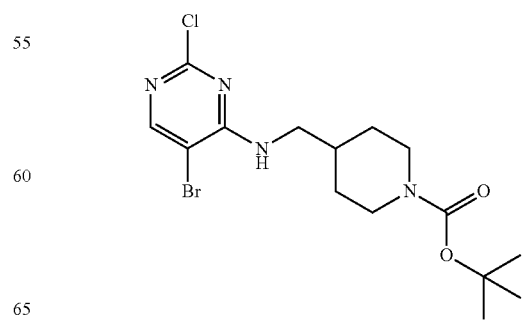

The title compound was obtained following procedure described for intermediate 6 from 5-Bromo-2,4-dichloro-pyrimidine (1.33 mL; 9.33 mmol; 2.00 eq.) and 4-Aminomethyl-piperidine-1-carboxylic acid tert-butyl ester (1 g; 4.67 mmol; 1.00 eq.) as a white solid (1.6 g, 83%). LC/MS: 405 (M+1).

Intermediate 11: 4-{[2-Chloro-5-(1-methyl-1H-pyrazol-4-yl)-pyrimidin-4-ylamino]-methyl}-piperidine-1-carboxylic Acid Tert-Butyl Ester

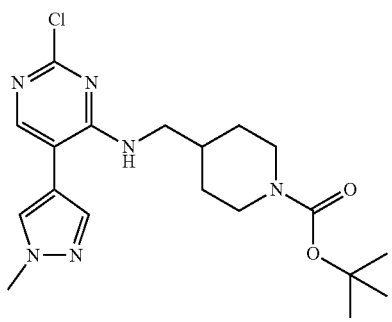 [SMILES: Cn1cc(-c2cnc(Cl)nc2NCC2CCN(C(=O)OC(C)(C)C)CC2)cn1]

The title compound was obtained following procedure described for intermediate 9 from 3-[(5-Bromo-2-chloro-pyrimidin-4-ylamino)-methyl]-piperidine-1-carboxylic acid tert-butyl ester (300 mg; 0.74 mmol; 1.00 eq.) and 1-Methyl-4-(4,4,5,5-tetramethyl-[1,3,2]dioxaborolan-2-yl)-1H-pyrazole (prepared as described in WO 2014008992; 231 mg; 1.11 mmol; 1.50 eq) as (125 mg, 42%). LS/MS: 407.2 (M+1).

Intermediate 12: 5-Bromo-2-chloro-4-(tetrahydro-pyran-2-ylmethoxy)-pyrimidine

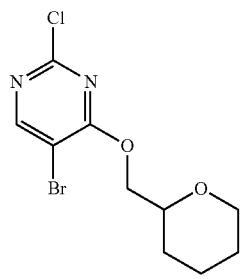 [SMILES: Clc1ncc(Br)c(OCC2CCCCO2)n1]

5-Bromo-2,4-dichloro-pyrimidine (4.16 mL; 29.3 mmol; 2.00 eq.) was added to a suspension of NaH (702 mg; 17.6 mmol; 1.20 eq.) in THF (37 mL) maintained at 0° C. The reaction mixture was stirred for 5 min before the addition of (tetrahydro-pyran-2-yl)-methanol (1.7 mL; 14.6 mmol; 1.00 eq.). It was then stirred at 0° C. overnight, diluted with methanol, filtered through a celite pad and concentrated. Purification by flash chromatography on silica (EtOAc: Hexane, 0 to 50%) afforded the title compound as a white solid (1.61 g, 34%). LC/MS: 307.0 (M+H).

Intermediate 13: 5-(1-Methyl-1H-pyrazol-3-yl)-2-[3-(1-methyl-1H-pyrazol-4-yl)-phenyl]-4-(tetrahydro-pyran-2-ylmethoxy)-pyrimidine

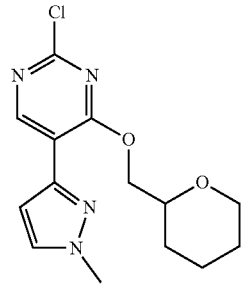 [SMILES: Cn1ccc(-c2cnc(Cl)nc2OCC2CCCCO2)n1]

A solution of 5-Bromo-2-chloro-4-(tetrahydro-pyran-2-ylmethoxy)-pyrimidine (400 mg; 1.30 mmol; 1.00 eq.), 1-Methyl-3-(4,4,5,5-tetramethyl-[1,3,2]dioxaborolan-2-yl)-1H-pyrazole (406 mg; 1.95 mmol; 1.50 eq.), $K_3PO_4$ (552 mg; 2.60 mmol; 2.00 eq.) and Pd(dppf)Cl2*DCM (95 mg; 0.13 mmol; 0.10 eq.) in water (0.30 mL) and 2-Methyltetrahydrofuran (3.00 mL; 29.95 mmol; 23.03 eq.) was degassed by bubbling 15 min with Ar(g), then heated to 100° C. for 30 min. It was then cooled to room temperature and filtered through a celite pad. The pad was rinsed with EtOAc and the filtrate was concentrated under reduced pressure. Purification by flash chromatography on silica (EtOAc: Hexane, gradient from 0 to 100% then MeOH/DCM, gradient from 10 to 20%) afforded the title compound as a light yellow solid (272 mg, 64.4%). LC/MS: 309.9 (M+1).

Intermediate 14: 5-Bromo-2-chloro-4-(3-methyl-oxetan-3-ylmethoxy)-pyrimidine

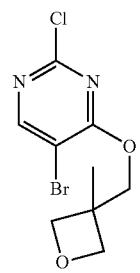

(3-Methyl-oxetan-3-yl)-methanol (2 g; 19.6 mmol; 1.00 eq.) was added dropwise over 15 min to a suspension of Sodium hydride (60% in oil, 0.98 g; 24.48 mmol; 1.25 eq.) and 5-Bromo-2,4-dichloro-pyrimidine (8.92 g; 39.2 mmol; 2.00 eq.) in THF (50 mL) maintained at 0° C. under nitrogen atmosphere. The solvent was then removed under reduced pressure and the crude residue was purified by flash column chromatography on silica (EtOAc: Hexane, gradient from 0 to 100% then MeOH: DCM gradient from 10 to 20%) to afford the title compound as a white solid (375 mg, 6.5%). 1H NMR (400 MHz, Chloroform-d) δ 8.47 (s, 1H), 4.63 (d, J=6.1 Hz, 2H), 4.55 (s, 2H), 4.47 (d, J=6.1 Hz, 2H), 1.46 (s, 3H).

Intermediate 15

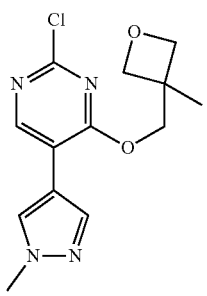

The title compound was prepared following procedure described for intermediate 13 from 5-Bromo-2-chloro-4-(3-methyl-oxetan-3-ylmethoxy)-pyrimidine (375 mg; 1.28 mmol; 1.00 eq.), 1-Methyl-4-(4,4,5,5-tetramethyl-[1,3,2]dioxaborolan-2-yl)-1H-pyrazole (399 mg; 1.92 mmol; 1.50 eq.) as a tan solid (165.1 mg, 44%). LC/MS: 407.72 (M+1).

Intermediate 16: 3-{[2-Chloro-5-(1-methyl-1H-pyrazol-3-yl)-pyrimidin-4-ylamino]-methyl}-piperidine-1-carboxylic Acid Tert-Butyl Ester

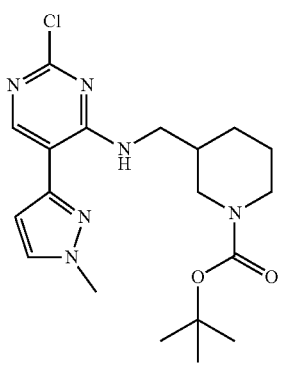 [SMILES: Cn1ccc(-c2cnc(Cl)nc2NCC2CCCN(C(=O)OC(C)(C)C)C2)n1]

The title compound was obtained following procedure described for intermediate 9 from 3-[(5-Bromo-2-chloro-pyrimidin-4-ylamino)-methyl]-piperidine-1-carboxylic acid tert-butyl ester (400 mg; 0.99 mmol; 1.00 eq.) and 1-Methyl-3-(4,4,5,5-tetramethyl-[1,3,2]dioxaborolan-2-yl)-1H-pyrazole (308 mg; 1.48 mmol; 1.50 eq.) as a brown solid (680 mg, quantitative). LC/MS: 407.2 (M+1).

Intermediate 17: 5-Bromo-2-chloro-4-(oxetan-3-ylmethoxy)-pyrimidine

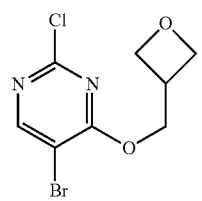 [SMILES: Clc1ncc(Br)c(OCC2COC2)n1]

The title compound was obtained following the procedure described for Intermediate 14 from 5-Bromo-2,4-dichloro-pyrimidine (1.62 mL; 11.35 mmol; 2.00 eq.) and oxetan-3-yl-methanol (500 mg; 5.68 mmol; 1.00 eq.) as a yellow oil (500 mg, 31.5%). 1H NMR (400 MHz, Chloroform-d) δ 8.42 (d, J=1.1 Hz, 1H), 4.84 (ddd, J=7.7, 6.3, 1.1 Hz, 2H), 4.67 (dd, J=6.7, 1.1 Hz, 2H), 4.62-4.42 (m, 2H), 3.48 (qt, J=5.8 Hz, 1H).

Intermediate 18: 2-Chloro-5-(1-methyl-1H-pyrazol-4-yl)-4-(oxetan-3-ylmethoxy)-pyrimidine

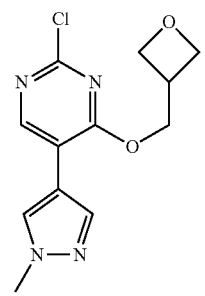 [SMILES: Cn1cc(-c2cnc(Cl)nc2OCC2COC2)cn1]

The title compound was obtained following the procedure described for intermediate 9 from 5-Bromo-2-chloro-4-(oxetan-3-ylmethoxy)-pyrimidine (500 mg; 1.79 mmol; 1.00 eq.) and 1-Methyl-4-(4,4,5,5-tetramethyl-[1,3,2]dioxaborolan-2-yl)-1H-pyrazole (558 mg; 2.68 mmol; 1.50 eq.) as a white solid (109 mg, 22%). LC/MS: 281.1 (M+1).

Intermediate 19: 4-{[2-Chloro-5-(1-methyl-1H-pyrazol-3-yl)-pyrimidin-4-ylamino]-methyl}-piperidine-1-carboxylic Acid Tert-Butyl Ester

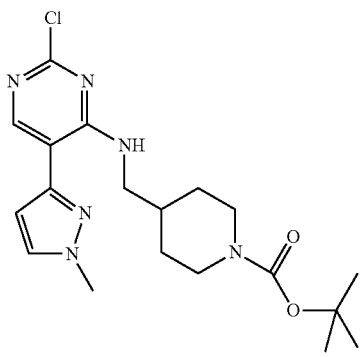 [SMILES: Cn1ccc(-c2cnc(Cl)nc2NCC2CCN(C(=O)OC(C)(C)C)CC2)n1]

The title compound was obtained following the procedure described for intermediate 9 from 4-[(5-Bromo-2-chloro-pyrimidin-4-ylamino)-methyl]-piperidine-1-carboxylic acid tert-butyl ester (800 mg; 1.97 mmol; 1.00 eq.), 1-Methyl-3-(4,4,5,5-tetramethyl-[1,3,2]dioxaborolan-2-yl)-1H-pyrazole (615 mg; 2.96 mmol; 1.50 eq.) as a brown solid (541 mg, 67%). LC/MS: 407.2 (M+1).

Intermediate 20: [2-Chloro-5-(1-methyl-1H-pyrazol-4-yl)-pyrimidin-4-yl]-(tetrahydro-pyran-4-ylmethyl)-amine

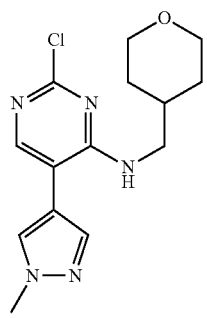 [SMILES: Cn1cc(-c2cnc(Cl)nc2NCC2CCOCC2)cn1]

The title compound was obtained following procedure described for intermediate 7 from (5-Bromo-2-chloro-pyrimidin-4-yl)-(tetrahydro-pyran-4-ylmethyl)-amine (335 mg; 1.09 mmol; 1.00 eq.) and 1-Methyl-4-(4,4,5,5-tetramethyl-[1,3,2]dioxaborolan-2-yl)-1H-pyrazole (341 mg; 1.64 mmol; 1.50 eq.) as a brown oil (206 mg, 49%). LC/MS: 308.2 (M+1).

Intermediate 21: (5-Bromo-2-chloro-pyrimidin-4-yl)-(1-methanesulfonyl-piperidin-4-yl)-amine

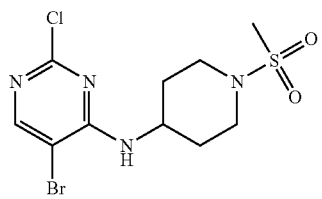 [SMILES: CS(=O)(=O)N1CCC(Nc2nc(Cl)ncc2Br)CC1]

A solution of 5-Bromo-2,4-dichloro-pyrimidine (1.72 mL; 13.46 mmol; 1.20 eq.), 1-Methanesulfonyl-piperidin-4-ylamine (2.0 g; 11.22 mmol; 1.00 eq.) and DIPEA (3.0 mL; 17.22 mmol; 1.54 eq.) in THF (34.00 mL) was stirred at RT for 90 min under nitrogen atmosphere. Solvent was removed under reduced pressure and the crude was purified by flash chromatography on silica (EtOAc: hexane, gradient from 60% to 100%) to give the title compound as a white solid (318 mg, 8%). LC/MS: 369.0 (M+1).

Intermediate 22: [2-Chloro-5-(1-methyl-1H-pyrazol-4-yl)-pyrimidin-4-yl]-(1-methanesulfonyl-piperidin-4-yl)-amine

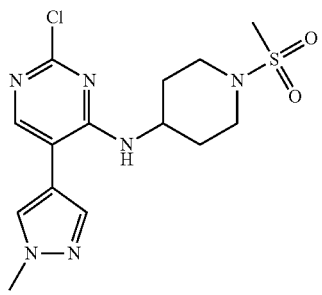 [SMILES: Cn1cc(-c2cnc(Cl)nc2NC2CCN(S(C)(=O)=O)CC2)cn1]

The title compound was obtained following the procedure described for intermediate 7 from (5-Bromo-2-chloro-pyrimidin-4-yl)-(1-methanesulfonyl-piperidin-4-yl)-amine (2165 mg; 5.86 mmol; 1.00 eq.) and 1-Methyl-4-(4,4,5,5-tetramethyl-[1,3,2]dioxaborolan-2-yl)-1H-pyrazole (1828 mg; 8.78 mmol; 1.50 eq.) as a beige solid (870 mg, 32%). LC/MS: 371.1 (M+1).

Intermediate 23: 2-Chloro-4-isopropylamino-pyrimidine-5-carboxylic Acid Ethyl Ester

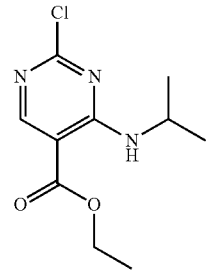 [SMILES: CCOC(=O)c1cnc(Cl)nc1NC(C)C]

A solution of 2,4-Dichloro-pyrimidine-5-carboxylic acid ethyl ester (8.00 g; 34.4 mmol; 1.00 eq.), Ethyl-diisopropylamine (12.10 mL; 68.77 mmol; 2.00 eq.) and Isopropylamine (2.09 g; 35.1 mmol; 1.02 eq.) in DCM (80 mL) was stirred for 3 h at RT. The reaction mixture was then washed with water and organic layer was dried over sodium sulfate, filtered and concentrated. Purification by flash chromatography on silica afforded the title compound as a colorless liquid (7.6 g; 30.28 mmol; 88.1%). 1H NMR (400 MHz, DMSO) δ 8.61 (s, 1H), 8.24 (d, J=7.6 Hz, 1H), 4.32-4.27 (m, 2H), 4.25-4.22 (m, 1H), 1.30 (t, J=7.0 Hz, 3H), 1.21 (d, J=6.5 Hz, 6H); HPLC: (254 nm) 96%; Rt 4.69 min; LC/MS: 244 (M+1).

Intermediate 24: 4-Isopropylamino-2-[3-(1-methyl-1H-pyrazol-4-yl)-phenyl]-pyrimidine-5-carboxylic Acid Ethyl Ester

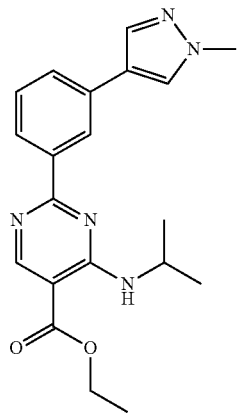 [SMILES: CCOC(=O)c1cnc(-c2cccc(-c3cnn(C)c3)c2)nc1NC(C)C]

Pd(dppf)$_2$Cl$_2$.CH$_2$Cl$_2$ was added to a degassed solution of 2-Chloro-4-isopropylamino-pyrimidine-5-carboxylic acid ethyl ester (7.0 g; 28.0 mmol; 1.00 eq.), potassium carbonate (7.98 g; 56.00 mmol; 2.00 eq.) and 1-Methyl-4-[3-(4,4,5,5-tetramethyl-[1,3,2]dioxaborolan-2-yl)-phenyl]-1H-pyrazole (11 g; 30.80 mmol; 1.10 eq.) in Dioxane-1,4 (140 mL) and Water (35 mL). The reaction mixture was stirred at 100 OC overnight. It was then filtered through a celite pad and concentrated under reduced pressure. The residue was diluted with Water (50 mL) and extracted with ethyl acetate (2×50 mL). Combined organic layers were dried over anhydrous Na$_2$SO$_4$, filtered and concentrated. Purification by flash chromatography on silica (EtOAc: PE, 50:50) afforded the title compound as a white solid (3.5 g, 29%). HPLC: (254 nm) 90%; Rt 3.88 min; LC/MS: 366.3 (M+1).

Intermediate 25: 4-Isopropylamino-2-[3-(1-methyl-1H-pyrazol-4-yl)-phenyl]-pyrimidine-5-carboxylic Acid Hydrazide

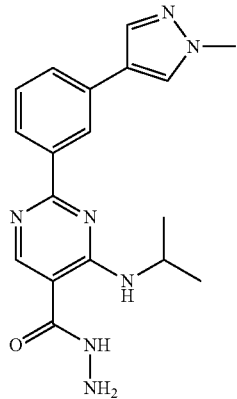 [SMILES: CC(C)Nc1nc(-c2cccc(-c3cnn(C)c3)c2)ncc1C(=O)NN]

Hydrazine monohydrate (0.17 mL; 3.47 mmol; 5.00 eq.) was added to a stirred solution of 4-Isopropylamino-2-[3-(1-methyl-1H-pyrazol-4-yl)-phenyl]-pyrimidine-5-carboxylic acid ethyl ester (300 mg; 0.69 mmol; 1.00 eq.) in Ethanol (6.00 mL). The reaction mixture was refluxed at 90° C. overnight. It was then cooled down to room temperature and concentrated under reduced pressure (half volume). The precipitated was filtered and washed with cold Ethanol to afford the title compound as a white solid (180 mg, 73%). 1H NMR (400 MHz, DMSO): 9.94 (s, 1H), 8.66 (s, 1H), 8.60 (d, J=7.4 Hz, 1H), 8.48 (s, 1H), 8.21 (s, 1H), 8.17 (d, J=7.9 Hz, 1H), 7.88 (s, 1H), 7.70 (d, J=7.8 Hz, 1H), 7.48 (t, J=7.8 Hz, 1H), 4.52 (brs, 2H), 4.47-4.39 (m, 1H), 3.88 (s, 3H), 1.28 (d, J=6.52 Hz, 6H). HPLC: (254 nm) 94%; Rt 2.9 min; LC/MS: 352.3 (M+1).

Intermediate 26: 5-{4-Isopropylamino-2-[3-(1-methyl-1H-pyrazol-4-yl)-phenyl]-pyrimidin-5-yl}-[1,3,4]thiadiazole-2-carboxylic Acid Ethyl Ester

Step 1: (N'-{4-Isopropylamino-2-[3-(1-methyl-1H-pyrazol-4-yl)-phenyl]-pyrimidine-5-carbonyl}-hydrazino)-oxo-acetic Acid Ethyl Ester

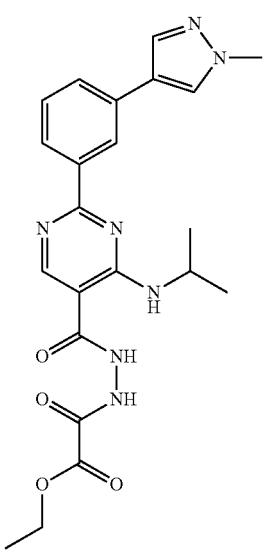 [SMILES: CCOC(=O)C(=O)NNC(=O)c1cnc(-c2cccc(-c3cnn(C)c3)c2)nc1NC(C)C]

Chloro-oxo-acetic acid ethyl ester (0.32 mL; 2.82 mmol; 1.05 eq.) was added drop wise to a solution of 4-Isopropylamino-2-[3-(1-methyl-1H-pyrazol-4-yl)-phenyl]-pyrimidine-5-carboxylic acid hydrazide (0.95 g; 2.68 mmol; 1.0 eq.) and TEA (1.05 mL; 8.05 mmol; 3.00 eq.) in DCM (28.50 mL) maintained at 0° C. The reaction mixture was allowed to warm to RT and stirred for 30 min. It was quenched with a saturated solution of NaHCO₃, then extracted with DCM. The combined organic layers were dried over Na₂SO₄, filtered and concentrated. Purification by flash chromatography on silica (DCM:MeOH) afforded the title compound as a yellow solid (1 g, 70%). HPLC: (254 nm) 92%; Rt 3.36 min; LC/MS: 452.2 (M+1).

Step 2: 5-{4-Isopropylamino-2-[3-(1-methyl-1H-pyrazol-4-yl)-phenyl]-pyrimidin-5-yl}-[1,3,4]thiadiazole-2-carboxylic Acid Ethyl Ester

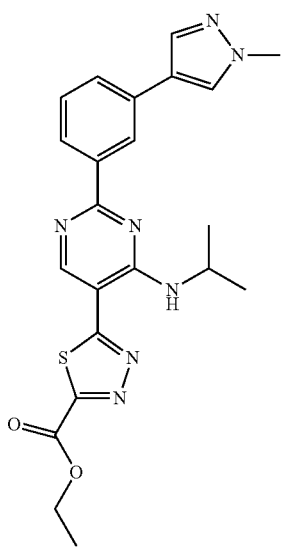 [SMILES: CCOC(=O)c1nnc(-c2cnc(-c3cccc(-c4cnn(C)c4)c3)nc2NC(C)C)s1]

A solution of (N'-{4-Isopropylamino-2-[3-(1-methyl-1H-pyrazol-4-yl)-phenyl]-pyrimidine-5-carbonyl}-hydrazino)-oxo-acetic acid ethyl ester (0.78 g; 1.62 mmol; 1.00 eq.) and 2,4-Bis-(4-methoxy-phenyl)-[1,3,2,4]dithiadiphosphetane 2,4-disulfide (1.49 g; 3.57 mmol; 2.20 eq.) in THF (39 mL) was heated at reflux for 3 h. The reaction mixture was then diluted with ethyl acetate and washed twice with 10% NaHCO₃ solution. The organic layer was dried over Na₂SO₄, filtered and concentrated. Purification by flash chromatography on silica (DCM:MeOH) afforded the title compound as a yellow solid (1 g, 82%). 1H NMR (400 MHz, DMSO-d6) δ: 8.99 (s, 1H), 8.85 (d, J=7.24 Hz, 1H), 8.55 (s, 1H), 8.31-8.21 (m, 2H), 7.90 (s, 1H), 7.75 (d, J=7.40 Hz, 1H), 7.52 (t, J=8.08 Hz, 1H), 5.75 (s, 2H), 4.65-4.60 (m, 1H), 4.49-4.44 (m, 2H), 3.89 (s, 3H), 3.80-3.60 (m, 1H), 1.39-1.35 (m, 9H). HPLC: (254 nm) 99%; Rt 4.33 min; LC/MS: 450.2 (M+H).

Intermediate 27: 4-(1-tert-Butoxycarbonyl-piperidin-3-ylamino)-2-chloro-pyrimidine-5-carboxylic Acid Ethyl Ester

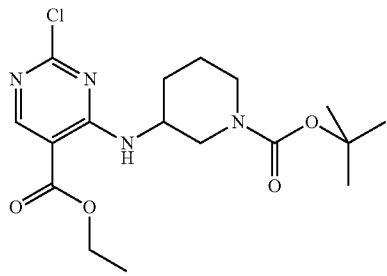 [SMILES: CCOC(=O)c1cnc(Cl)nc1NC1CCCN(C(=O)OC(C)(C)C)C1]

The title compound was obtained following the procedure described for Intermediate 23 from 2,4-Dichloro-pyrimidine-5-carboxylic acid ethyl ester (5.0 g; 21.49 mmol; 1.00 eq.) and 3-Amino-piperidine-1-carboxylic acid tert-butyl ester (4.43 g; 21.92 mmol; 1.02 eq.) as a yellow gum (8.50 g; 17.14 mmol; 79.7%). HPLC: (254 nm) 72%; Rt 5.27 min; LC/MS: 385 (M+1).

Intermediate 28: 3-{5-Hydrazinocarbonyl-2-[3-(1-methyl-1H-pyrazol-4-yl)-phenyl]-pyrimidin-4-ylamino}-piperidine-1-carboxylic Acid Tert-Butyl Ester

Step 1: 4-(1-tert-Butoxycarbonyl-piperidin-3-ylamino)-2-[3-(1-methyl-1H-pyrazol-4-yl)-phenyl]-pyrimidine-5-carboxylic Acid Ethyl Ester

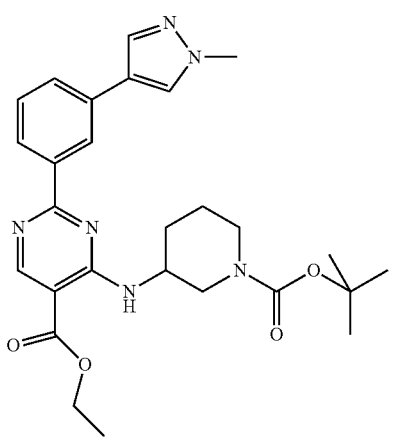 [SMILES: CCOC(=O)c1cnc(-c2cccc(-c3cnn(C)c3)c2)nc1NC1CCCN(C(=O)OC(C)(C)C)C1]

The title compound was obtained following the procedure described for intermediate 24 from 4-(1-tert-Butoxycarbonyl-piperidin-3-ylamino)-2-chloro-pyrimidine-5-carboxylic acid ethyl ester (8.0 g; 16.01 mmol; 1.00 eq.) and 1-Methyl-4-[3-(4,4,5,5-tetramethyl-[1,3,2]dioxaborolan-2-yl)-phenyl]-1H-pyrazole (6.29 g; 17.61 mmol; 1.10 eq.) as a gum (5.0 g, 59%). HPLC: (254 nm) 93%; Rt 4.51 min; LC/MS: 507.2 (M+1).

Step 2: 3-{5-Hydrazinocarbonyl-2-[3-(1-methyl-1H-pyrazol-4-yl)-phenyl]-pyrimidin-4-ylamino}-piperidine-1-carboxylic Acid Tert-Butyl Ester

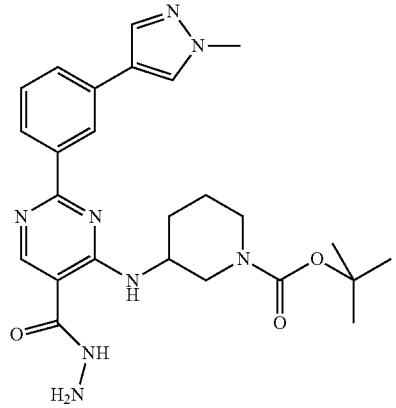 [SMILES: Cn1cc(-c2cccc(-c3ncc(C(=O)NN)c(NC4CCCN(C(=O)OC(C)(C)C)C4)n3)c2)cn1]

The title compound was obtained following procedure described in intermediate 25 from 4-(1-tert-Butoxycarbonyl-piperidin-3-ylamino)-2-[3-(1-methyl-1H-pyrazol-4-yl)-phenyl]-pyrimidine-5-carboxylic acid ethyl ester (3.0 g; 5.68 mmol; 1.00 eq.) as an off-white solid (2 g, 69%).

HPLC: (254 nm) 89%; Rt 3.53 min; LC/MS: 493.2 (M+H).

Intermediate 29: 3-{5-(5-Ethoxycarbonyl-[1,3,4]thiadiazol-2-yl)-2-[3-(1-methyl-H-pyrazol-4-yl)-phenyl]-pyrimidin-4-ylamino}-piperidine-1-carboxylic Acid Tert-Butyl Ester

Step 1: 3-{5-(N'-Ethoxyoxalyl-hydrazinocarbonyl)-2-[3-(1-methyl-1H-pyrazol-4-yl)-phenyl]-pyrimidin-4-ylamino}-piperidine-1-carboxylic Acid Tert-Butyl Ester

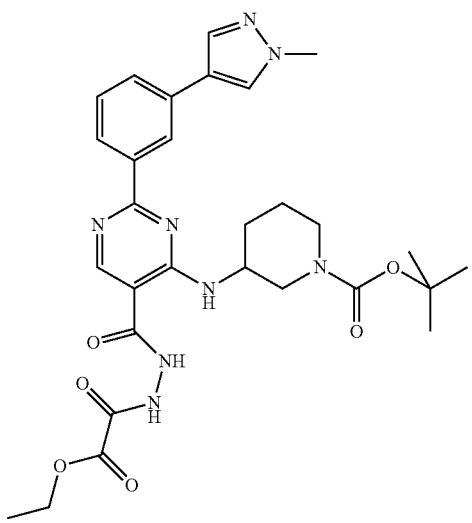 [SMILES: CCOC(=O)C(=O)NNC(=O)c1cnc(-c2cccc(-c3cnn(C)c3)c2)nc1NC1CCCN(C(=O)OC(C)(C)C)C1]

The title compound was obtained following the procedure described for intermediate 26, step 1 from 3-{5-Hydrazinocarbonyl-2-[3-(1-methyl-1H-pyrazol-4-yl)-phenyl]- pyrimidin-4-ylamino}-piperidine-1-carboxylic acid tert-butyl ester (500 mg; 0.98 mmol; 1.00 eq.) in DCM (10 mL) and Chloro-oxo-acetic acid ethyl ester (0.12 mL; 1.03 mmol; 1.05 eq.) as a yellow solid (420 mg, 66%). HLPC: (254 nm) 89%; Rt 3.94 min; LC/MS: 593.3 (M+H).

Step 2: 3-{5-(5-Ethoxycarbonyl-[1,3,4]thiadiazol-2-yl)-2-[3-(1-methyl-1H-pyrazol-4-yl)-phenyl]-pyrimidin-4-ylamino}-piperidine-1-carboxylic Acid Tert-Butyl Ester

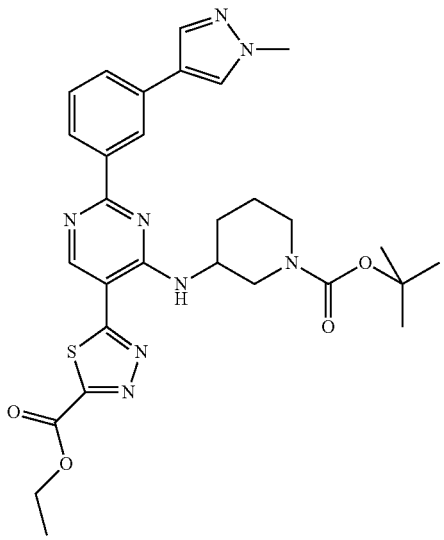 [SMILES: CCOC(=O)c1nnc(-c2cnc(-c3cccc(-c4cnn(C)c4)c3)nc2NC2CCCN(C(=O)OC(C)(C)C)C2)s1]

The title compound was obtained following the procedure described for intermediate 26, step 2 from 3-{5-(N'-Ethoxyoxalyl-hydrazinocarbonyl)-2-[3-(1-methyl-1H-pyrazol-4-yl)-phenyl]-pyrimidin-4-ylamino}-piperidine-1-carboxylic acid tert-butyl ester (300 mg; 0.47 mmol; 1.00 eq.) as a yellow solid (150 mg, 52%). HPLC: (254 nm) 88%; Rt 5.05 min; LC/MS: 591.2 (M+H).

Intermediate 30: 4-[(1-tert-Butoxycarbonyl-azetidin-3-ylmethyl)-amino]-2-chloro-pyrimidine-5-carboxylic Acid Ethyl Ester

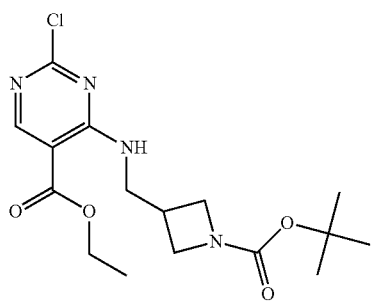 [SMILES: CCOC(=O)c1cnc(Cl)nc1NCC1CN(C(=O)OC(C)(C)C)C1]

The title compound was obtained following the procedure described for intermediate 23 from 2,4-Dichloro-pyrimidine-5-carboxylic acid ethyl ester (2.50 g; 10.74 mmol; 1.00 eq.) and 3-Aminomethyl-azetidine-1-carboxylic acid tert-butyl ester (2.06 g; 10.96 mmol; 1.02 eq.) as a colorless gum (2.0 g, 54%). HPLC: (254 nm) 98%; Rt 6.35 min; LC/MS: 369.0 (M+H).

Intermediate 31: 3-({5-Hydrazinocarbonyl-2-[3-(1-methyl-1H-pyrazol-4-yl)-phenyl]-pyrimidin-4-ylamino}-methyl)-azetidine-1-carboxylic Acid Tert-Butyl Ester Step 1: 4-[(1-tert-Butoxycarbonyl-azetidin-3-ylmethyl)-amino]-2-[3-(1-methyl-1H-pyrazol-4-yl)-phenyl]-pyrimidine-5-carboxylic Acid Ethyl Ester

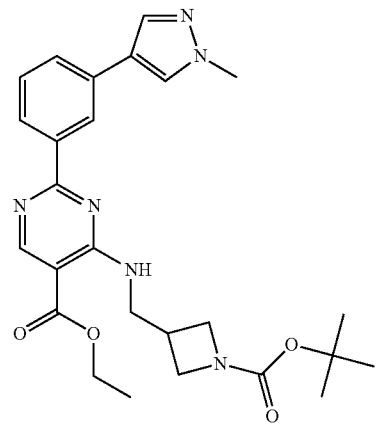 [SMILES: CCOC(=O)c1cnc(-c2cccc(-c3cnn(C)c3)c2)nc1NCC1CN(C(=O)OC(C)(C)C)C1]

The title compound was obtained following the procedure described for intermediate 24 from 4-[(1-tert-Butoxycarbonyl-azetidin-3-ylmethyl)-amino]-2-chloro-pyrimidine-5-carboxylic acid ethyl ester (2.20 g; 5.81 mmol; 1.00 eq.) and 1-Methyl-4-[3-(4,4,5,5-tetramethyl-[1,3,2]dioxaborolan-2-yl)-phenyl]-1H-pyrazole (2.28 g; 6.40 mmol; 1.10 eq.) as a white solid (2.0 g, 54%). 1H NMR (400 MHz, DMSO-d6) δ: 8.86 (s, 1H), 8.51-8.47 (m, 1H), 8.21-8.19 (m, 2H), 7.89 (d, J=0.44 Hz, 1H), 7.75-7.72 (m, 1H), 7.49 (t, J=7.76 Hz, 1H), 4.36-4.30 (m, 2H), 3.88 (s, 6H), 3.74-3.80 (m, 2H), 3.20-3.00 (m, 1H), 1.35-1.31 (m, 12H). HPLC (XBridge C8 (50×4.6 mm, 3.5 µm): (254 nm) 96%; Rt 4.0 min; LC/MS: 493.2 (M+H).

Step 2: 3-({5-Hydrazinocarbonyl-2-[3-(1-methyl-1H-pyrazol-4-yl)-phenyl]-pyrimidin-4-ylamino}-methyl)-azetidine-1-carboxylic Acid Tert-Butyl Ester

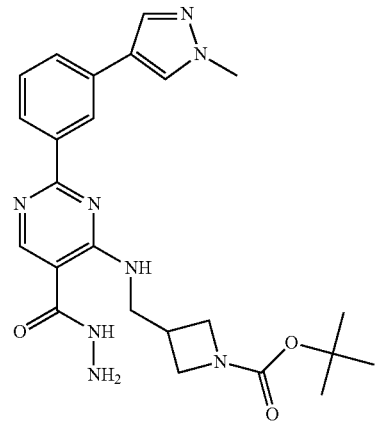 [SMILES: Cn1cc(-c2cccc(-c3ncc(C(=O)NN)c(NCC4CN(C(=O)OC(C)(C)C)C4)n3)c2)cn1]

The title compound was obtained following the procedure described for intermediate 25 from phenyl]-pyrimidine-5-carboxylic acid ethyl ester (1.10 g; 2.14 mmol; 1.00 eq.) as an off-white solid (900 mg, 82%). HPLC (254 nm) 90%; Rt 3.43 min; LC/MS: 479.2 (M+H).

Intermediate 32: 5-{4-[(1-tert-Butoxycarbonyl-azetidin-3-ylmethyl)-amino]-2-[3-(1-methyl-1H-pyrazol-4-yl)-phenyl]-pyrimidin-5-yl}-[1,3,4]thiadiazole-2-carboxylic Acid Methyl Ester Step 1: 3-({5-(N'-Methoxyoxalyl-hydrazinocarbonyl)-2-[3-(1-methyl-1H-pyrazol-4-yl)-phenyl]-pyrimidin-4-ylamino}-methyl)-azetidine-1-carboxylic Acid Tert-Butyl Ester

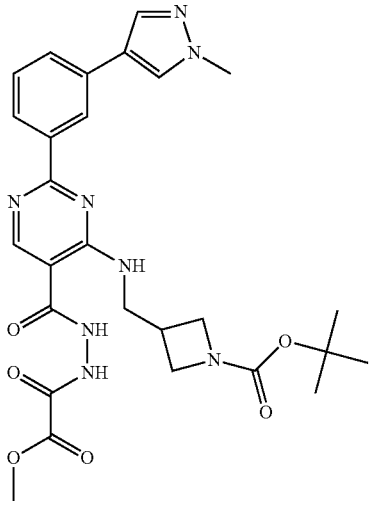 [SMILES: COC(=O)C(=O)NNC(=O)c1cnc(-c2cccc(-c3cnn(C)c3)c2)nc1NCC1CN(C(=O)OC(C)(C)C)C1]

The title compound was obtained following the procedure described for intermediate 26, step 1 from 3-({5-Hydrazinocarbonyl-2-[3-(1-methyl-1H-pyrazol-4-yl)-phenyl]-pyrimidin-4-ylamino}-methyl)-azetidine-1-carboxylic acid tert-butyl ester (400 mg; 0.78 mmol; 1.00 eq.) and Chloro-oxo-acetic acid methyl ester (0.08 mL; 0.82 mmol; 1.05 eq.) as a yellow solid (300 mg, 66%) HPLC: (254 nm) 94%; Rt 3.55 min; LC/MS: 565.3 (M+H).

Step 2: 5-{4-[(1-tert-Butoxycarbonyl-azetidin-3-ylmethyl)-amino]-2-[3-(1-methyl-1H-pyrazol-4-yl)-phenyl]-pyrimidin-5-yl}-[1,3,4]thiadiazole-2-carboxylic Acid Methyl Ester

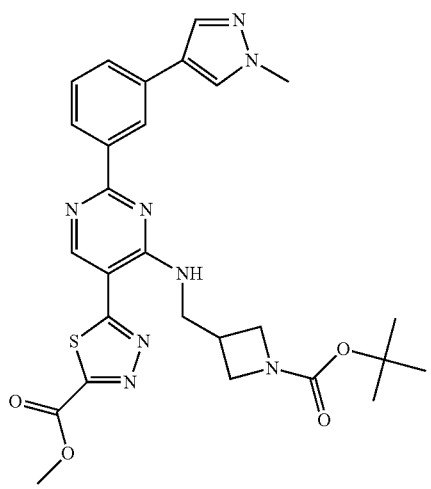 [SMILES: COC(=O)c1nnc(-c2cnc(-c3cccc(-c4cnn(C)c4)c3)nc2NCC2CN(C(=O)OC(C)(C)C)C2)s1]

The title compound was obtained following the procedure described for intermediate 26, step 2 from 3-({5-(N'-Methoxyoxalyl-hydrazinocarbonyl)-2-[3-(1-methyl-1H-pyrazol-4-yl)-phenyl]-pyrimidin-4-ylamino}-methyl)-azetidine-1-carboxylic acid tert-butyl ester (300 mg; 0.51 mmol; 1.00 eq.) as a yellow solid (150 mg; 52%). HPLC: (254 nm) 92%; Rt 4.44 min; LC/MS: 563.3 (M+H).

Intermediate 33: [5-(6-Chloro-4-isopropylamino-pyridin-3-yl)-[1,3,4]thiadiazol-2-yl]-((R)-3-hydroxy-pyrrolidin-1-yl)-methanone Step 1: 6-Chloro-4-isopropylamino-nicotinic Acid Hydrazide

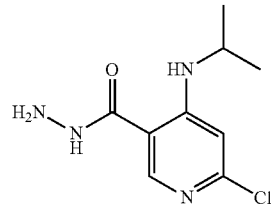

A solution of Hydrazine hydrate monohydrate (8.07 mL; 164 mmol) and 6-Chloro-4-isopropylamino-nicotinic acid ethyl ester (7.0 g; 27.4 mmol) in Ethanol (50 mL) was reflux at 80° C. for 3 hrs. The reaction mixture was then concentrated under reduced pressure and the crude was triturated with diethyl ether to afford the desired product as white solid (6 g, 79%). LC/MS: 229.00 (M+1).

Step 2: [N'-(6-Chloro-4-isopropylamino-pyridine-3-carbonyl)-hydrazino]-oxo-acetic Acid Methyl Ester

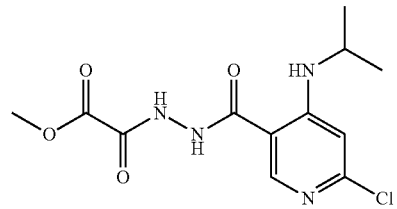 [SMILES: COC(=O)C(=O)NNC(=O)c1cnc(Cl)cc1NC(C)C]

The title compound was obtained following the procedure described for Intermediate 26, step 1 from 6-Chloro-4-isopropylamino-nicotinic acid hydrazide (5.5 g; 21.6 mmol) as a white solid (4 g, 50%). 1H NMR (400 MHz, DMSO-d6): δ 10.44 (s, 1H), 8.56 (s, 1H), 8.40 (s, 1H), 6.70 (s, 1H), 3.82 (s, 3H), 3.48-0.00 (m, 1H), 1.16-1.09 (m, 6H).

Step 3: 5-(6-Chloro-4-isopropylamino-pyridin-3-yl)-[1,3,4]thiadiazole-2-carboxylic Acid Methyl Ester

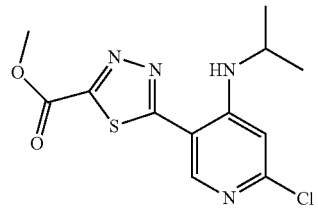 [SMILES: COC(=O)c1nnc(-c2cnc(Cl)cc2NC(C)C)s1]

The title compound was obtained following the procedure described for intermediate 26, step 2 from [N'-(6-Chloro-4-isopropylamino-pyridine-3-carbonyl)-hydrazino]-oxo-acetic acid methyl ester (4.0 g; 10.8 mmol) as an off white solid (3 g, 67%). LC/MS: 313.0 (M+1).

Step 4: [5-(6-Chloro-4-isopropylamino-pyridin-3-yl)-[1,3,4]thiadiazol-2-yl]-((R)-3-hydroxy-pyrrolidin-1-yl)-methanone

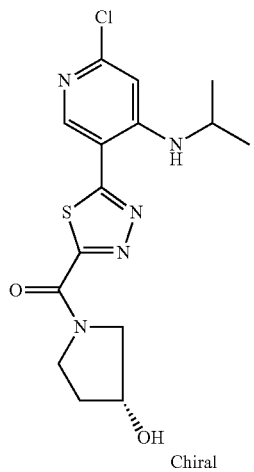 [SMILES: CC(C)Nc1cc(Cl)ncc1-c1nnc(C(=O)N2CC[C@@H](O)C2)s1]

Chiral

A solution of 5-(6-Chloro-4-isopropylamino-pyridin-3-yl)-[1,3,4]thiadiazole-2-carboxylic acid methyl ester (2.5 g; 7.2 mmol) and (R)-Pyrrolidin-3-ol (3.84 g; 43.16 mmol) in Methanol (25 mL) was heated in microwave at 80° C. for 1 hrs. Solvent was removed under reduced pressure and the crude was purified by flash chromatography on silica (PE, EtOAc) to afford the title compound as a pale yellow solid (1 g, 41%). 1H NMR (400 MHz, DMSO-d6) δ 8.76 (d, 1H), 8.55 (s, 1H), 6.95 (s, 1H), 5.08 (d, 1H), 4.39 (d, 1H), 4.19-3.93 (m, 3H), 3.68-3.53 (m, 2H), 1.99 (m, 2H), 1.27 (d, 6H).

Intermediate 33: 2-[2-Chloro-5-(1-methyl-1H-pyrazol-4-yl)-pyrimidin-4-ylamino]-acetamide

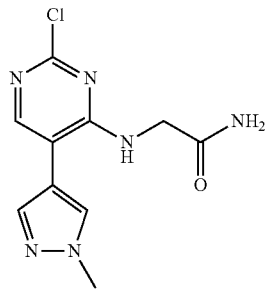 [SMILES: Cn1cc(-c2cnc(Cl)nc2NCC(N)=O)cn1]

A mixture of 2-(5-Bromo-2-chloro-pyrimidin-4-ylamino)-acetamide (Aurora Building Blocks; 200 mg; 0.75 mmol; 1.00 eq.), 1-Methyl-4-(4,4,5,5-tetramethyl-[1,3]dioxolan-2-yl)-1H-pyrazole (166 mg; 0.79 mmol; 1.05 eq.), Tetrakis(triphenylphosphine)palladium (4.35 mg; 0.002 mmol; 0.01 eq.), potassium carbonate (125 mg; 0.90 mmol; 1.20 eq.) in dioxane (6 mL) and water (0.6 mL) was stirred in a sealed vial at 90° C. overnight. The reaction mixture was then concentrated under reduced pressure and purified by flash chromatography on KPNH (EtOAc: MeOH gradient from 0:100 to 30:70) to give the title compound as a white solid (183 mg, 87%). LC/MS: 267.1 (M+H).

Intermediate 34: [2-Chloro-5-(1-methyl-1H-pyrazol-3-yl)-pyrimidin-4-yl]-cyclobutyl-amine

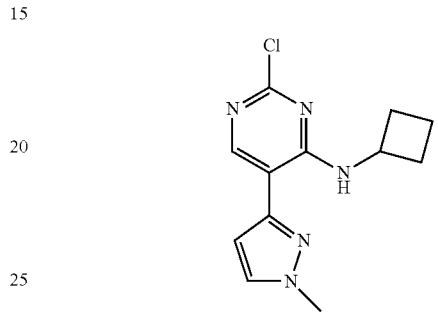

A mixture of (5-Bromo-2-chloro-pyrimidin-4-yl)-cyclobutyl-amine (Aurora Building Blocks, 200 mg; 0.76 mmol; 1.00 eq.), 1-Methyl-3-(4,4,5,5-tetramethyl-[1,3,2]dioxaborolan-2-yl)-1H-pyrazole (166 mg; 0.80 mmol; 1.05 eq.), Bis(triphenylphosphine)palladium (II) dichloride (2.81 mg; 0.002 mmol; 0.01 eq.) and potassium carbonate (126 mg; 0.91 mmol; 1.20 eq.) dioxane (6 mL) and Water (0.60 mL) was stirred at 90° C. overnight in a sealed vial. The reaction mixture was then concentrated under reduced pressure and purified by flash chromatography on silica (EtOAc: hexane, gradient from 10 to 50%) to give the title compound as a white solid (63 mg, 30%). LC/MS: 264.6 (M+H)

Intermediate 35: 6-(5-Bromo-2-chloro-pyrimidin-4-ylamino)-2-aza-spiro[3.3]heptane-2-carboxylic Acid Tert-Butyl Ester

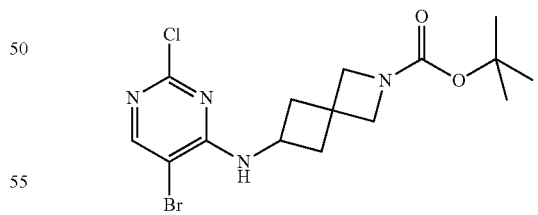

A mixture of 5-Bromo-2,4-dichloro-pyrimidine (650 mg; 2.85 mmol; 1.00 eq.), 6-Amino-2-aza-spiro[3.3]heptane-2-carboxylic acid tert-butyl ester (727 mg; 3.42 mmol; 1.20 eq.), Ethyl-diisopropyl-amine (1.49 mL; 8.56 mmol; 3.00 eq.) in NMP (5.0 mL) was stirred at 50° C. overnight. The mixture was then concentrated under reduced pressure and purified by flash chromatography on silica (EtOAc: Hexanes, gradient from 0 to 40%) to give the title compound as a white solid (1.2 g, 100%). LC/MS: 403 (M+H) 403.

Intermediate 36: 6-[2-Chloro-5-(1-methyl-1H-pyrazol-4-yl)-pyrimidin-4-ylamino]-2-aza-spiro[3.3]heptane-2-carboxylic Acid Tert-Butyl Ester

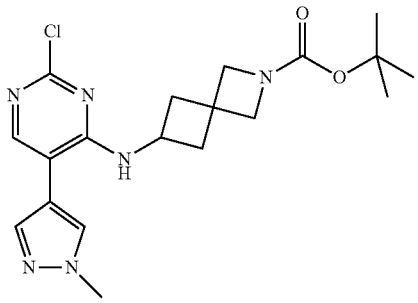 [SMILES: Cn1cc(-c2cnc(Cl)nc2NC2CC3(C2)CN(C(=O)OC(C)(C)C)C3)cn1]

A mixture of 6-(5-Bromo-2-chloro-pyrimidin-4-ylamino)-2-aza-spiro[3.3]heptane-2-carboxylic acid tert-butyl ester (200 mg; 0.50 mmol; 1.00 eq.), 1-Methyl-4-(4,4,5,5-tetramethyl-[1,3,2]dioxaborolan-2-yl)-1H-pyrazole (155 mg; 0.74 mmol; 1.50 eq.), Bis(triphenylphosphine)palladium (II) dichloride (1.83 mg; 0.002 mmol; 0.01 eq.) and potassium carbonate (82 mg; 0.59 mmol; 1.20 eq.) in dioxane (5 mL) and water (0.5 mL) was stirred at 100° C. overnight in a sealed vial. The mixture was then concentrated under reduced pressure and purified by flash chromatography on silica (EtOAc:Hexanes, gradient from 20 to 100% then MeOH: EtOAc, gradient from 0 to 20%) to give the title compound as a yellow solid (201 mg, 95%). LC/MS: 405.2 (M+H).

Intermediate 37: 4-[(5-Bromo-2-chloro-pyrimidin-4-ylamino)-methyl]-piperidine-1-carboxylic Acid Tert-Butyl Ester

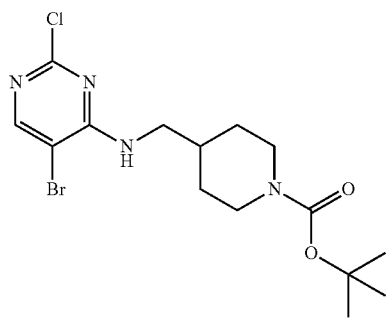 [SMILES: CC(C)(C)OC(=O)N1CCC(CNc2nc(Cl)ncc2Br)CC1]

4-Aminomethyl-piperidine-1-carboxylic acid tert-butyl ester (3.39 g; 15.80 mmol; 1.20 eq.) and 5-Bromo-2,4-dichloro-pyrimidine (3.00 g; 13.17 mmol; 1.00 eq.) were dissolved in THF (30 mL) and DIPEA (6.9 mL). The mixture was stirred under N2 at 50° C. for 2 h. The reaction mixture was then diluted with water (150 mL) and EtOAc (75 mL). The layers were separated and the aqueous layer was extracted with EtOAc (3×50 mL). The combined organic layers were washed with water and brine, dried over Na$_2$SO$_4$, filtered and concentrated to afford a colorless oil. Purification by flash chromatography on silica (EtOAc: Hexane, gradient from 10 to 30%) afforded the title compound as a white solid (4.0 g, 75%). $^1$H NMR (400 MHz, DMSO-d6) δ 8.24 (s, 1H), 7.75 (t, 1H), 3.92 (d, 2H), 3.27 (t, 2H), 2.79-2.59 (bs, 2H), 1.81 (m, 1H), 1.60 (dd, 2H), 1.40 (s, 9H), 1.02 (qd, 2H). LC/MS: 349 ((M-tBu)+H).

Intermediate 38: tert-butyl N-[(1S,2S,3S)-3-amino-2-hydroxycyclohexyl]-N-methylcarbamate (Relative Stereochemistry-Racemic)

Step 1: benzyl N-[(1S,2R,3S)-2-hydroxy-3-(methylamino)cyclohexyl]carbamate (Relative Stereochemistry-Racemic)

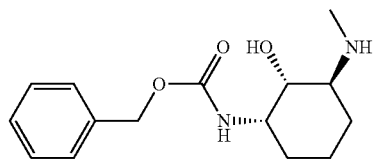 [SMILES: CN[C@H]1CCC[C@H](NC(=O)OCc2ccccc2)[C@@H]1O]

A solution of benzyl N-[(1S,2S,6R)-7-oxabicyclo[4.1.0]heptan-2-yl]carbamate (relative stereochemistrty, racemic, prepared as described in Org. Lett., 2003, p. 4955-49557, 730 mg, 2.66 mmol, 1.00 eq.) and methyl amine (850 mg, 26.82 mmol, 10.1 eq.,) in Methanol (10 mL) was stirred in a sealed tube for 16 h at 45° C. The resulting mixture was concentrated under vacuum and purified by flash chromatography on silica (methanol/DCM, 1:10) to afford the tittle compound as a light yellow oil (800 mg, 97%).

Step 2: benzyl N-[(1S,2S,3S)-3-{[(tert-butoxy)carbonyl](methyl)amino}-2-hydroxycyclohexyl]carbamate (Relative Stereochemistry-Racemic)

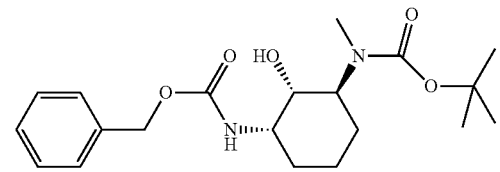 [SMILES: CN(C(=O)OC(C)(C)C)[C@H]1CCC[C@H](NC(=O)OCc2ccccc2)[C@@H]1O]

A solution of benzyl N-[(1S,2R,3S)-2-hydroxy-3-(methylamino)cyclohexyl]carbamate (Racemic, 800 mg, 2.59 mmol, 1.00 eq.), TEA (535 mg, 5.18 mmol, 2.00 eq.,), Boc2O (864 mg, 3.88 mmol, 1.50 eq.) in DCM (40 mL) was stirred for 2 h at 25° C. The resulting mixture was concentrated under vacuum and purified by flash chromatography on silica (methanol/DCM, 1:15) to afford the tittle compound a light yellow solid (1 g, 92%).

Step 3: tert-butyl N-[(1S,2S,3S)-3-amino-2-hydroxycyclohexyl]-N-methylcarbamate (Relative Stereochemistry-Racemic)

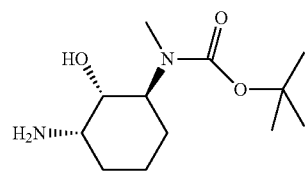 [SMILES: CN(C(=O)OC(C)(C)C)[C@H]1CCC[C@H](N)[C@@H]1O]

Pd/C (253 mg, 0.24 mmol, 0.10 eq.) was added to a solution of benzyl N-[(1S,2S,3S)-3-[[(tert-butoxy)carbonyl](methyl)amino]-2-hydroxycyclohexyl]carbamate (1 g, 2.38 mmol, 1.00 eq.) in MeOH (4 mL) maintained under nitrogen atmosphere. The mixture was then hydrogenated at room temperature for 16 hours using a hydrogen balloon. The solids were filtered out and the resulting mixture was concentrated under vacuum to afford the title compound as a light yellow solid (630 mg, 98%).

Intermediate 39: tert-butyl N-[(1S,2S,3S)-3-[(5-bromo-2-chloropyrimidin-4-yl)amino]-2-hydroxycyclohexyl]-N-methylcarbamate (Relative Stereochemistry-Racemic)

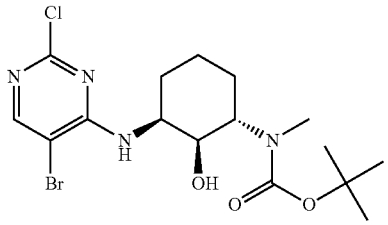 [SMILES: CN(C(=O)OC(C)(C)C)[C@H]1CCC[C@H](Nc2nc(Cl)ncc2Br)[C@@H]1O]

A solution of tert-butyl N-[(1S,2S,3S)-3-amino-2-hydroxycyclohexyl]-N-methylcarbamate (630 mg, 2.32 mmol, 1.00 eq.), 5-bromo-2,4-dichloropyrimidine (652 mg, 2.80 mmol, 1.21 eq.) and DIEA (612 mg, 4.64 mmol, 2.00 eq.) in THF (10 mL) was stirred at RT for 2 h. The resulting mixture was concentrated under vacuum and purified by flash chromatography on silica (EtOAc/PE, 1:2) to afford the title compound as a yellow solid (630 mg, 56%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 2.2 min, hold 1.0 min; 254 nm): (purity) 90%; [M+H]+ Cac. 435.1; found 435.1.

Intermediate 40: tert-butyl N-[(1S,2S,3S)-3-{[2-chloro-5-(1-methyl-1H-pyrazol-4-yl)pyrimidin-4-yl]amino}-2-hydroxycyclohexyl]-N-methylcarbamate (Relative Stereochemistry-Racemic)

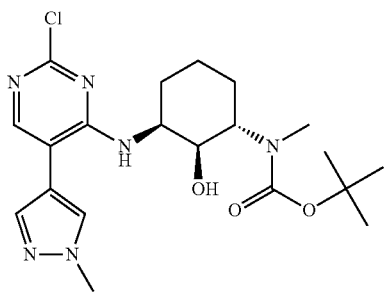 [SMILES: CN(C(=O)OC(C)(C)C)[C@H]1CCC[C@H](Nc2nc(Cl)ncc2-c2cnn(C)c2)[C@@H]1O]

A mixture of tert-butyl N-[(1S,2S,3S)-3-[(5-bromo-2-chloropyrimidin-4-yl)amino]-2-hydroxycyclohexyl]-N-methylcarbamate (630 mg, 1.30 mmol, 1.00 eq., 90%), 1-methyl-4-(tetramethyl-1,3,2-dioxaborolan-2-yl)-1H-pyrazole (415 mg, 1.95 mmol, 1.50 eq., 98%), Pd(dppf)Cl₂.CH₂Cl₂ (108 mg, 0.13 mmol, 0.10 eq., 98%) and K3PO4 (566 mg, 2.61 mmol, 2.01 eq.) in dioxane (10 mL) and water (2 mL) was degassed with nitrogen and heated at 100° C. for 2 h in a sealed tubed. The resulting mixture was concentrated under vacuum and purified by flash chromatography on silica (EtOAc/PE, 1:1) to afford the title compound as a yellow solid (420 mg, 66%).

Intermediate 41: tert-butyl N-[1-(5-bromo-2-chloropyrimidin-4-yl)-5,5-difluoropiperidin-3-yl]carbamate

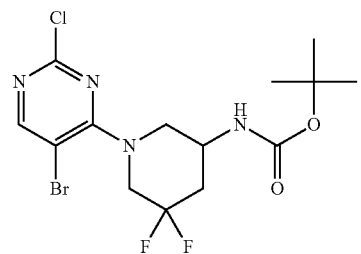 [SMILES: CC(C)(C)OC(=O)NC1CN(c2nc(Cl)ncc2Br)CC(F)(F)C1]

The title compound was obtained following the procedure described for intermediate 39 from tert-butyl N-(5,5-difluoropiperidin-3-yl)carbamate (500 mg, 2.01 mmol, 0.93 eq.) as a white solid (460 mg, 37%).

Intermediate 42: tert-butyl N-{1-[2-chloro-5-(1-methyl-1H-pyrazol-4-yl)pyrimidin-4-yl]-5,5-difluoropiperidin-3-yl}carbamate

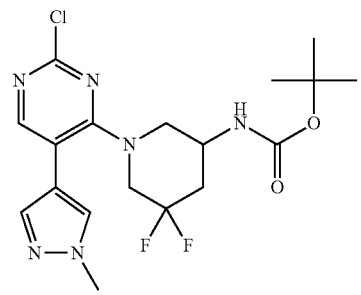 [SMILES: Cn1cc(-c2cnc(Cl)nc2N2CC(NC(=O)OC(C)(C)C)CC(F)(F)C2)cn1]

The title compound was obtained following the procedure described for intermediate 40 from tert-butyl N-[1-(5-bromo-2-chloropyrimidin-4-yl)-5,5-difluoropiperidin-3-yl]carbamate (460 mg, 0.81 mmol, 1.00 eq.) as a white solid (220 mg, 57%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 2.2 min, hold 1.0 min; 254 nm): (purity) 90%; [M+H]+ Cac. 428.2; found 428.2.

Intermediate 43: (1S,2S,6S)-2-amino-6-fluorocyclohexan-1-ol (Relative Stereochemistry, Racemic)

Step 1: Benzyl N-[(1S,2S,6R)-7-oxabicyclo[4.1.0]heptan-2-yl]carbamate (Relative Stereochemistry, Racemic)

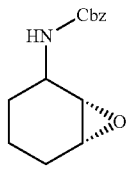

A solution of benzyl N-(cyclohex-2-en-1-yl)carbamate (400 mg, 1.56 mmol, 1.00 eq., 90%), sodium bicarbonate (267 mg, 3.11 mmol, 2.00 eq., 98%), and m-CPBA (549 mg, 3.12 mmol, 2.00 eq., 98%) in DCM (25 mL) was stirred for 3 h at 20° C. The reaction was then quenched by the addition of 15 mL of $Na_2SO_3$ and diluted with 30 mL of water. It was then extracted with DCM (3×15 mL). Combined organic layers were concentrated under vacuum and purified by flash chromatography on silica (EA/PE, 1:5) to give the title compound as a brown solid.

Step 2: benzyl N-[(1S,2S,3S)-3-fluoro-2-hydroxycyclohexyl]carbamate Carbamate (Relative Stereochemistry, Racemic)

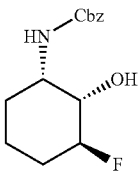

HF-pyridine (0.5 mL, 3.88 mmol, 1.52 eq., 70% purity) was added dropwise to a solution of DCM (10 mL) maintained under nitrogen atmosphere at 0° C. A solution of the of benzyl N-[7-oxabicyclo[4.1.0]heptan-2-yl]carbamate (700 mg, 2.55 mmol, 1.00 eq.) in dichloromethane (3 mL) was then added dropwise and the resulting mixture was stirred for 2 h at 0° C. The pH value of the solution was adjusted to 7 with saturated sodium bicarbonate (aq.). After dilution with 20 mL of $H_2O$, The resulting mixture was extracted with DCM (3×15 mL). Combined organic layers were washed with brine (20 mL), dried over anhydrous $Na_2SO_4$, filtered and concentrated. Purification by flash chromatography on silica (EA/PE, 1:15 to 1:4) afforded the title compound as a light yellow solid (700 mg, 93% yield).

Step 3: (1S,2S,6S)-2-amino-6-fluorocyclohexan-1-ol (Relative Stereochemistry, Racemic)

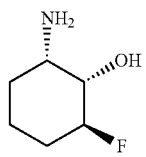

The title compound was obtained following the procedure described for example 38, step 3 from benzyl N-[(1S,2S,3S)-3-fluoro-2-hydroxycyclohexyl]carbamate (racemic, relative configuration, 700 mg, 2.36 mmol) as a white solid (300 mg, 86%).

Intermediate 44: (1S,2S,6S)-2-[(5-bromo-2-chloropyrimidin-4-yl)amino]-6-fluorocyclohexan-1-ol (Relative Stereochemistry, Racemic)

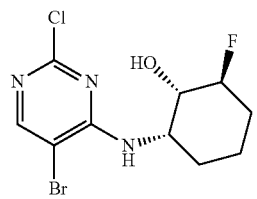

The title compound was obtained following the procedure described for example 39 from (1S,2S,6S)-2-amino-6-fluorocyclohexan-1-ol (Intermediate 43, 300 mg, 2.03 mmol, 1.00 eq.) as a yellow solid (500 mg, 68%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 2.2 min, hold 1.0 min; 254 nm): (purity) 90%; [M+H]+ Cac. 324.0; found 324.0.

Intermediate 45: (1S,2S,6S)-2-[[2-chloro-5-(1-methyl-1H-pyrazol-4-yl)pyrimidin-4-yl]amino]-6-fluorocyclohexan-1-ol (Relative Stereochemistry, Racemic)

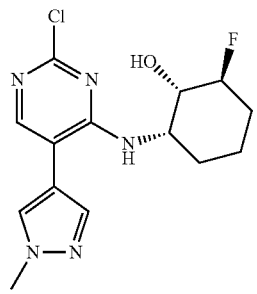 [SMILES: Cn1cc(-c2cnc(Cl)nc2N[C@H]2CCC[C@H](F)[C@H]2O)cn1]

The title compound was obtained following the procedure described for example 40 from (1S,2S,6S)-2-[(5-bromo-2-chloropyrimidin-4-yl)amino]-6-fluorocyclohexan-1-ol (Intermediate 44, racemic, 440 mg, 1.22 mmol, 1.00 eq.) a yellow solid (360 mg, 82%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 2.2 min, hold 1.0 min; 254 nm): [M+H]+ Cac. 326.0; found 326.0.

Intermediate 46: (1S,6R)-6-amino-2,2-difluorocyclohexan-1-ol

Step 1: 2,2-difluoro-6-{[(1R)-1-phenylethyl]amino}cyclohexan-1-ol

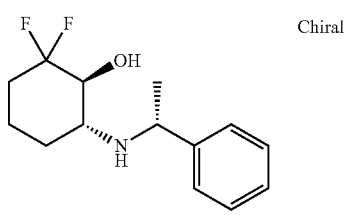 [SMILES: C[C@@H](N[C@@H]1CCCC(F)(F)[C@H]1O)c1ccccc1]

A solution of (1R)-1-phenylethan-1-amine (2.375 g, 18.62 mmol, 1.30 eq., 95%) in DCM (12 mL) was cooled to 0° C. and treated with trimethylaluminium (11 mL, 1.20 eq., 2M in toluene) under nitrogen atmosphere. It was stirred for 1 h before the addition of a solution of (1R,6R)-2,2-difluoro-7-oxabicyclo[4.1.0]heptane (racemic, relative stereochemistry, 2.260 g, 14.32 mmol, 1.00 eq.) in DCM (50 mL). The resulting solution was stirred for 2 days at RT. The reaction was then quenched by the addition of NH$_4$Cl aq. The aqueous layer was extracted with dichloromethane and the combined organic layers were washed with brine, dried over anhydrous sodium sulfate, filtrated and concentrated under vacuum. Purification by flash chromatography on silica (MTBE/petroleum ether, 1:10) afforded the title compound (first eluting isomer) as a white solid (1.36 g, 33%).

Step 2: (1S,6R)-6-amino-2,2-difluorocyclohexan-1-ol

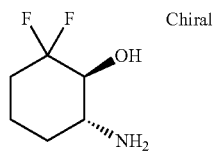

A solution of (1S,6R)-2,2-difluoro-6-[[(1R)-1-phenylethyl]amino]cyclohexan-1-ol (1.360 g, 4.79 mmol, 1.00 eq.) in MeOH (30 mL) was degassed with nitrogen before the addition of Palladium on carbon (1.701 g, 9.59 mmol, 2.00 eq., 60%). The reaction mixture was then placed under Hydrogen atmosphere (1 atm.) and stirred O/N at RT. The mixture was filtered through a celite pad and concentrated to afford the title compound as a white solid (765 mg, 95%). 1H NMR (300 MHz, Methanol-d4, ppm) 3.40-3.30 (m, 1H), 2.73 (m, 1H), 2.05 (m, 1H), 1.90-1.39 (m, 4H), 1.34-1.17 (m, 1H).

Intermediate 47: (1S,6R)-6-[(5-bromo-2-chloropyrimidin-4-yl)amino]-2,2-difluorocyclohexan-1-ol

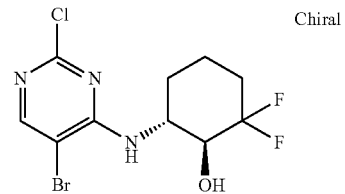 [SMILES: O[C@H]1[C@H](Nc2nc(Cl)ncc2Br)CCCC1(F)F]

The title compound was obtained following the procedure described for intermediate 39 from (1S,6R)-6-amino-2,2-difluorocyclohexan-1-ol (200 mg, 1.19 mmol, 1.00 eq.) as a yellow solid (451 mg, 87%).

Intermediate 48: (1S,6R)-6-{[2-chloro-5-(1-methyl-1H-pyrazol-4-yl)pyrimidin-4-yl]amino}-2,2-difluorocyclohexan-1-ol

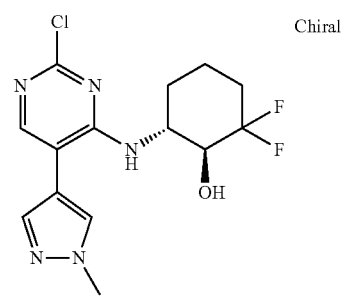 [SMILES: Cn1cc(-c2cnc(Cl)nc2N[C@@H]2CCCC(F)(F)[C@H]2O)cn1]

The title compound was obtained following the procedure described for intermediate 40 from (1S,6R)-6-[(5-bromo-2-chloropyrimidin-4-yl)amino]-2,2-difluorocyclohexan-1-ol (451 mg, 1.04 mmol, 1.00 eq.) as a yellow solid (208 mg, 58%).

Intermediate 49: (3aS,4S,8aR)-2,2-dimethyl-octahydrocyclohepta[d][1,3]dioxol-4-amine Hydrochloride (Racemic—Relative Stereochemistry)

Step 1: 2,2,2-trichloro-N-[(1S,2S,3R)-2,3-dihydroxycycloheptyl]acetamide (Racemic—Relative Stereochemistry)

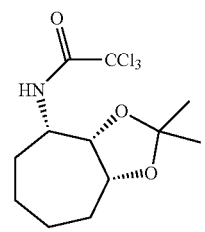

A solution of 2,2,2-trichloro-N-[(1S,2S,3R)-2,3-dihydroxycycloheptyl]acetamide (racemic—relative stereochemistry, prepared as described in JOC, 2002, p 7946-7956, 10 mg, 0.03 mmol, 1.00 eq.), 2,2-dimethoxypropane (7 mg, 0.06 mmol, 2.06 eq.) and TsOH (0.5 mg, 0.09 eq.) in Acetone (1 mL) was stirred at RT for 16 h. The reaction mixture was then concentrated under reduced pressure and the residue was redissolved in DCM. The organic layer was washed with sat. NaHCO₃, brine, dried over anhydrous magnesium sulfate, filtered and concentrated to afford the title compound which was used directly in the next step.

Step 2: (3aS,4S,8aR)-2,2-dimethyl-octahydrocyclohepta[d][1,3]dioxol-4-amine Hydrochloride (Racemic—Relative Stereochemistry)

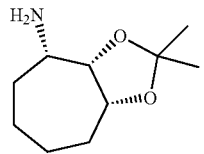

NaBH₄ (71 mg, 1.78 mmol, 5.04 eq.) was added portionwise to a solution of N-[(3aS,4S,8aR)-2,2-dimethyl-octahydrocyclohepta[d][1,3]dioxol-4-yl]-2,2,2-trichloroacetamide (racemic, 130 mg, 0.35 mmol, 1.00 eq.) in ethanol (10 mL) maintained at 0° C. The resulting solution was then stirred for 16 h at 40° C. The reaction was quenched by the addition of a solution of hydrogen chloride (1M). The mixture was finally concentrated under reduced pressure to afford the title compound as a white solid (140 mg).

Intermediate 50: N-[(3aS,4S,8aR)-2,2-dimethyl-octahydrocyclohepta[d][1,3]dioxol-4-yl]-5-bromo-2-chloropyrimidin-4-amine (Racemic—Relative Stereochemistry)

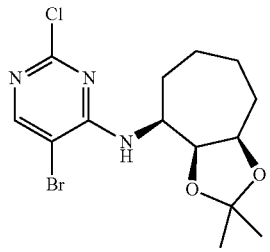 [SMILES: CC1(C)O[C@H]2[C@@H](Nc3nc(Cl)ncc3Br)CCCC[C@H]2O1]

The title compound was obtained following the procedure described for intermediate 39 from (3aS,4S,8aR)-2,2-dimethyl-octahydrocyclohepta[d][1,3]dioxol-4-amine hydrochloride (racemic, 185 mg, 0.90 mmol, 0.79 eq.) as an off-white solid (210 mg, 44%). 1H NMR (300 MHz, Chloroform-d) 8.11 (s, 1H), 6.01 (d, J=8.2 Hz, 1H), 4.49 (t, J=7.3 Hz, 1H), 4.34 (d, J=8.3 Hz, 1H), 4.23 (t, J=9.1 Hz, 1H), 2.22-1.90 (m, 2H), 1.73 (dd, J=11.4, 5.8 Hz, 3H), 1.54 (s, 6H), 1.37 (s, 3H).

Intermediate 51: N-[(3aS,4S,8aR)-2,2-dimethyl-octahydrocyclohepta[d][1,3]dioxol-4-yl]-2-chloro-5-(1-methyl-1H-pyrazol-4-yl)pyrimidin-4-amine (Racemic—Relative Stereochemistry)

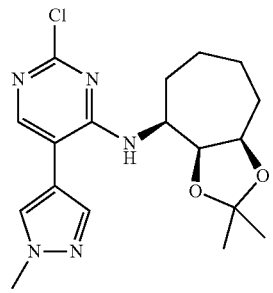

The title compound was obtained following the procedure described for intermediate 40 from N-[(3aS,4S,8aR)-2,2-dimethyl-octahydrocyclohepta[d][1,3]dioxol-4-yl]-5-bromo-2-chloropyrimidin-4-amine (racemic, 240 mg, 0.57 mmol, 1.00 eq.), as an yellow oil (185 mg, 77%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 2.2 min, hold 1.0 min; 254 nm): (purity) 87.3%; [M+H]+ Cac. 378.2; found 378.2.

Intermediate 52: (1S,2S,3S)-3-amino-2-(methoxymethoxy)cyclohexyl Acetate (Racemic—Relative Stereochemistry)

Step 1: (1S,2S,3S)-3-{[(benzyloxy)carbonyl]amino}-2-hydroxycyclohexyl Acetate (Racemic—Relative Stereochemistry)

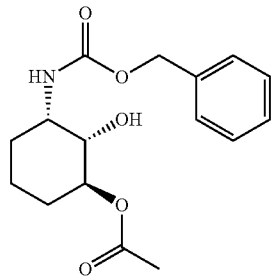 [SMILES: CC(=O)O[C@H]1CCC[C@H](NC(=O)OCc2ccccc2)[C@@H]1O]

A mixture of benzyl N-[(1S,2S,6R)-7-oxabicyclo[4.1.0]heptan-2-yl]carbamate (obtained as described in Org. Lett., 2003, p 4955-4957, 350 mg, 1.27 mmol, 1.00 eq., NaOAc (214 mg, 2.56 mmol, 2.01 eq.) and acetic acid (5 mL) was stirred for 30 min at 100° C. The reaction mixture was then cooled to RT and diluted with 60 mL of water. The pH was adjusted to 7 by addition of a solution of sodium bicarbonate. And the resulting solution was extracted with DCM (3x). The combined organic layers were washed with brine, dried over sodium sulfate, filtered and concentrated under vacuum to afford the title compound as an off-white solid (300 mg, 69%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 2.2 min, hold 1.0 min; 254 nm): [M+Na]+23 Cac. 330.0; found 330.0.

Step 2: (1S,2S,3S)-3-{[(benzyloxy)carbonyl]
amino}-2-(methoxymethoxy)cyclohexyl Acetate
(Racemic—Relative Stereochemistry)

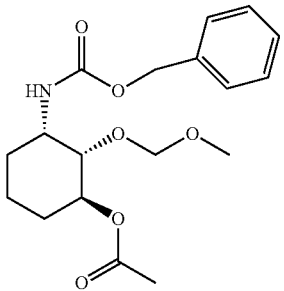 [SMILES: COCO[C@H]1[C@@H](NC(=O)OCc2ccccc2)CCC[C@@H]1OC(C)=O]

A solution of (1S,2S,3S)-3-[[(benzyloxy)carbonyl]amino]-2-hydroxycyclohexyl acetate (250 mg, 0.73 mmol, 1.00 eq.), DIEA (194 mg, 1.47 mmol, 2.01 eq.) and chloro(methoxy)methane (91 mg, 1.11 mmol, 1.51 eq.) in DMF (15 mL) was stirred for 3 h at 70° C. under nitrogen atmosphere. The reaction was then quenched by the addition of a sat. $Na_2CO_3$ solution. It was then extracted with DCM (3×). Combined organic layers were washed with brine, dried over magnesium sulfate, filtered and concentrated. Purification by flash chromatography on silica (EtOAc/PE, 1:6) afforded the title compound as a yellow solid (270 mg, 94%). LC/MS: [M+H]+ Cac. 352.1; found 352.1.

Step 3:
(1S,2S,3S)-3-amino-2-(methoxymethoxy)cyclohexyl
Acetate (Racemic—Relative Stereochemistry)

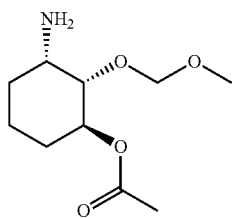

The title compound was obtained following the procedure described for intermediate 43, step 2 from (1S,2S,3S)-3-[[(benzyloxy)carbonyl]amino]-2-(methoxymethoxy)cyclohexyl acetate (250 mg, 0.64 mmol, 1.00 eq.) as a colorless oil (150 mg, 97%). LC/MS: [M+H]+ Calc. 218.2; found 218.2.

Intermediate 53: (1S,2S,3S)-3-[(5-bromo-2-chloropyrimidin-4-yl)amino]-2-(methoxymethoxy)cyclohexyl Acetate (Relative Stereochemistry, Racemic)

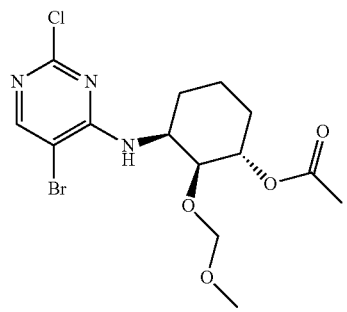 [SMILES: COCO[C@H]1[C@@H](Nc2nc(Cl)ncc2Br)CCC[C@@H]1OC(C)=O]

The title compound was obtained following the procedure described for example 39 from (1S,2S,3S)-3-amino-2-(methoxymethoxy)cyclohexyl Acetate (Intermediate 52, racemic, 370 mg, 1.53 mmol, 1.00 eq.), as a yellow solid (560 mg, 80%). MS: m/z=408.1 [M+H]+.

Intermediate 54: (1S,2S,3S)-3-[[2-chloro-5-(1-methyl-1H-pyrazol-4-yl)pyrimidin-4-yl]amino]-2-(methoxymethoxy)cyclohexyl Acetate ((Relative Stereochemistry, Racemic)

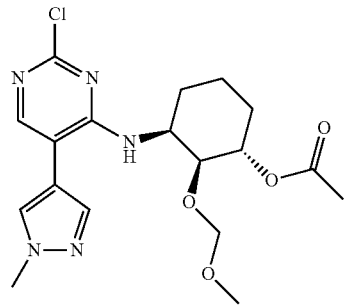 [SMILES: COCO[C@H]1[C@@H](Nc2nc(Cl)ncc2-c2cnn(C)c2)CCC[C@@H]1OC(C)=O]

The title compound was obtained following the procedure described for example 40 from (1S,2S,3S)-3-[(5-bromo-2-chloropyrimidin-4-yl)amino]-2-(methoxymethoxy)cyclohexyl acetate (Intermediate 53, racemic, 560 mg, 1.23 mmol, 1.00 eq.) as a yellow solid (330 mg, 59%).

Intermediate 55: 5-bromo-2-chloro-N-(cyclohept-2-en-1-yl)pyrimidin-4-amine

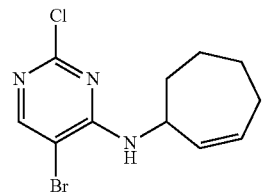 [SMILES: Clc1ncc(Br)c(NC2C=CCCCC2)n1]

The title compound was obtained following the procedure described for intermediate 39 from cyclohept-2-en-1-amine (650 mg, 2.92 mmol, 1.02 eq.) as a yellow oil (460 mg, 48%). LC/MS: [M+H]+ Calc. 302.0; found 302.0.

Intermediate 56: 2-chloro-N-(cyclohept-2-en-1-yl)-5-(1-methyl-1H-pyrazol-4-yl)pyrimidin-4-amine

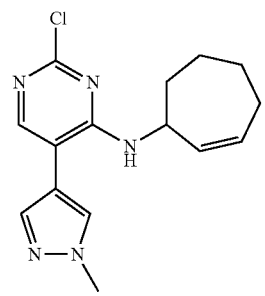 [SMILES: Cn1cc(-c2cnc(Cl)nc2NC2C=CCCCC2)cn1]

The title compound was obtained following the procedure described for intermediate 40 from 5-bromo-2-chloro-N-(cyclohept-2-en-1-yl)pyrimidin-4-amine (intermediate 55, 450 mg, 1.34 mmol, 1.00 eq.) as a yellow oil (100 mg, 22%). LC/MS: [M+H]+ Calc. 304.1; found 304.0.

Example 1: 2-[3-(1-Methyl-1H-pyrazol-4-yl)-phenyl]-5-(1-piperidin-4-yl-1H-pyrazol-4-yl)-pyridine Hydrochloride Step 1: tert-butyl 4-(4-{6-[3-(1-methyl-1H-pyrazol-4-yl)phenyl]pyridin-3-yl}-1H-pyrazol-1-yl)piperidine-1-carboxylate

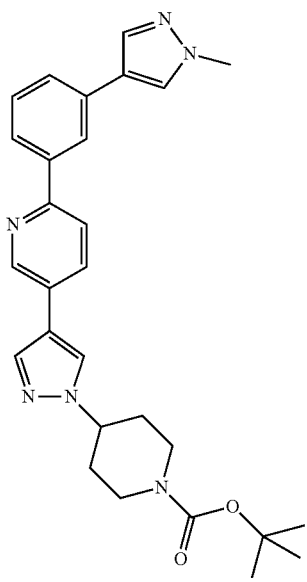 [SMILES: Cn1cc(-c2cccc(-c3ccc(-c4cnn(C5CCN(C(=O)OC(C)(C)C)CC5)c4)cn3)c2)cn1]

A mixture of tert-butyl 4-4-[6-(3-iodophenyl)pyridin-3-yl]-1H-pyrazol-1-ylpiperidine-1-carboxylate (215 mg; 0.41 mmol; 1.00 eq.), 1-methyl-4-(4,4,5,5-tetramethyl-1,3,2-dioxaborolan-2-yl)-1H-pyrazole (84 mg; 0.41 mmol; 1.00 eq.), Pd(PPh$_3$)$_4$ (23 mg; 0.02 mmol; 0.05 eq.) and potassium carbonate (168 mg; 1.22 mmol; 3.0 eq.) in dioxane (3.2 mL) and water (1.61 mL) was heated in a sealed tube in MW at 120° C. for 30 minutes. The reaction mixture was then diluted with EtOAc and washed with water. The organic layer was back-extracted with EtOAc and the combined organic layers were dried over MgSO4, filtered and concentrated. Purification by flash chromatography on silica (EtOAct: Heptanes, gradient from 50 to 100%) afforded the title compound as a yellow gum (110 mg; 56%). 1H NMR (300 MHz, DMSO-d6) δ 8.94 (dd, J=2.0 Hz, 1.0 Hz, 1H), 8.46 (s, 1H), 8.26-8.05 (m, 2H), 8.07-8.05 (m, 3H), 7.96 (d, J=1.0 Hz, 1H), 7.93 (ddd, J=7.9 Hz, 2.0 Hz, 1.0 Hz, 1H), 7.61 (ddd, J=7.9 Hz, 2.0 Hz, 1.0 Hz, 1H), 7.46 (t, J=7.9 Hz, 1H), 4.46-4.35 (m, 1H), 4.09 (m, 2H), 3.89 (s, 3H), 2.94 (m, 2H), 2.09-2.04 (m, 2H), 1.89-1.75 (m, 2H), 1.43 (s, 9H). LC/MS: 485.6 (M+1).

Step 2: 2-[3-(1-Methyl-1H-pyrazol-4-yl)-phenyl]-5-(1-piperidin-4-yl-1H-pyrazol-4-yl)-pyridine Hydrochloride

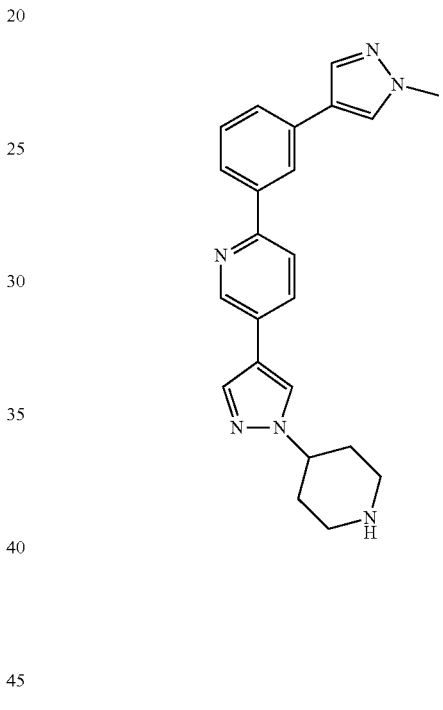

A solution of tert-butyl 4-(4-6-[3-(1-methyl-1H-pyrazol-4-yl)phenyl]pyridin-3-yl-1H-pyrazol-1-yl)piperidine-1-carboxylate (110 mg; 0.23 mmol; 1.00 eq.) and hydrogen chloride (0.85 mL of a 4N solution in dioxane; 3.40 mmol; 15 eq.) in DCM (1.1 mL) and MeOH (1.10 mL) was stirred at RT for 1 hour. The reaction mixture was filtered off and the resulting solid was washed with DCM. Purification by autopreparative LC/MS afforded the title compound as a yellow powder (65 mg; 67%). 1H NMR (300 MHz, DMSO-d6) δ 9.35-9.26 (m, 1H), 9.13-9.06 (m, 1H), 9.05 (d, J=2.0 Hz, 1H), 8.63 (s, 1H), 8.45 (d, J=9.1 Hz, 1H), 8.36 (t, J=2.0 Hz, 1H), 8.32-8.29 (m, 2H), 8.26 (s, 1H), 8.03 (d, J=1.0 Hz, 1H), 7.96-7.92 (m, 1H), 7.73 (dt, J=7.8 Hz, 1.0 Hz, 1H), 7.55 (t, J=7.8 Hz, 1H), 4.61-4.51 (m, 1H), 3.90 (s, 3H), 3.42-3.38 (m, 2H), 3.16-3.06 (m, 2H), 2.29-2.14 (m, 4H); HPLC: (254 nm) 100%; Rt (min) 2.02. LC/MS: 385.5 (M+1).

183

Example 2: 6'-(1-Methyl-1H-pyrazol-4-yl)-5-(1-piperidin-4-yl-1H-pyrazol-4-yl)-[2,2']bipyridinyl

Step 1: 4-{4-[6'-(1-Methyl-1H-pyrazol-4-yl)-[2,2']bipyridinyl-5-yl]-pyrazol-1-yl}-piperidine-1-carboxylic Acid Tert-Butyl Ester

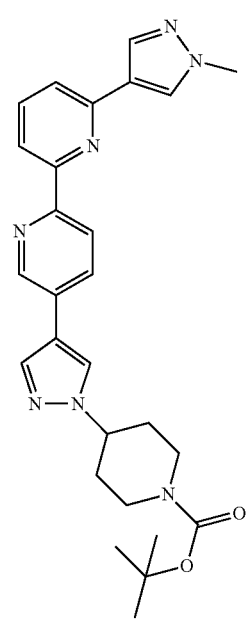 [SMILES: Cn1cc(-c2cccc(-c3ccc(-c4cnn(C5CCN(C(=O)OC(C)(C)C)CC5)c4)cn3)n2)cn1]

A mixture of 4-[4-(6'-Chloro-[2,2']bipyridinyl-5-yl)-pyrazol-1-yl]-piperidine-1-carboxylic acid tert-butyl ester (130 mg; 0.30 mmol; 1.0 eq.), Pd(PPh$_3$)$_2$Cl$_2$ (21 mg; 0.03 mmol; 0.10 eq.), PPh$_3$ (15.5 mg; 0.06 mmol; 0.20 eq.), cesium fluoride (134.7 mg; 0.89 mmol; 3.00 eq.) and 1-Methyl-4-(4,4,5,5-tetramethyl-[1,3,2]dioxaborolan-2-yl)-1H-pyrazole (92 mg; 0.44 mmol; 1.50 eq.) in 1,2-Dimethoxy-ethane (2.2 mL) was heated in a sealed vial at 100° C. overnight. The mixture was then filtered through a celite pad. Aqueous phase was extracted with DCM and combined organic phases were washed with water, dried over MgSO$_4$, filtered and concentrated. Purification by flash chromatography on silica (EtOAc: Heptanes, 80:20) afforded the title compound (104 mg, 72%). LC/MS: 486.3 (M+1).

184

Step 2: 6'-(1-Methyl-1H-pyrazol-4-yl)-5-(1-piperidin-4-yl-1H-pyrazol-4-yl)-[2,2']bipyridinyl

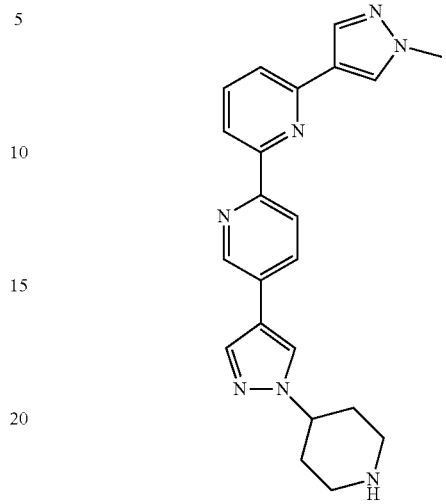

The title compound was obtained following procedure described for example 1, step 2 from 4-{4-[6'-(1-Methyl-1H-pyrazol-4-yl)-[2,2']bipyridinyl-5-yl]-pyrazol-1-yl}-piperidine-1-carboxylic acid tert-butyl ester (100 mg; 0.21 mmol; 1.00 eq.) as a beige solid (10 mg, 13%). 1H NMR (300 MHz, DMSO-d6) δ 8.97 (d, J=1.7 Hz, 1H), 8.52 (d, J=8.0 Hz, 1H), 8.46-8.43 (m, 2H), 8.32 (bs, 1H), 8.17-8.10 (m, 4H), 7.89 (t, J=8.0 Hz, 1H), 7.67 (dd, J=8.0 Hz, 1.0 Hz, 1H), 4.41-4.28 (m, 1H), 3.92 (s, 3H), 3.23-3.19 (m, 2H), 2.86-2.73 (m, 2H), 2.13-1.89 (m, 4H). HPLC: (254 nm) 98%; Rt (min) 1.61. LC/MS: 386.4 (M+1).

Example 3: 3-({5-(1-Methyl-1H-pyrazol-4-yl)-2-[3-(1-methyl-1H-pyrazol-4-yl)-phenyl]-pyrimidin-4-ylamino}-methyl)-piperidine-1-carboxylic Acid Tert-Butyl Ester

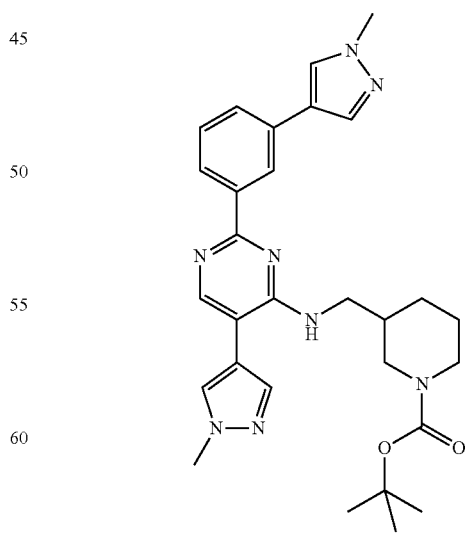

A mixture of 3-{[2-Chloro-5-(1-methyl-1H-pyrazol-4-yl)-pyrimidin-4-ylamino]-methyl}-piperidine-1-carboxylic acid tert-butyl ester (94 mg; 0.23 mmol; 1.00 eq.), Pd(PPh₃)Cl₂ (3.2 mg; 0.01 mmol; 0.02 eq.), potassium carbonate (0.15 mL of a 2 M aq. solution), 1-Methyl-4-[3-(4,4,5,5-tetramethyl-[1,3,2]dioxaborolan-2-yl)-phenyl]-1H-pyrazole (prepared as described in WO 2014008992; 79 mg; 0.28 mmol; 1.20 eq.) in degassed dioxane (1.1 mL) was heated in a sealed vial in MW at 150° C. for 20 min. It was then filtered through a celite pad and concentrated under reduced pressure. Purification by flash chromatography on silica (EtOAc:Hexanes, gradient from 0 to 100% then MeOH:DCM, gradient from 0 to 20%) to afford the title compound as a yellow foam (48 mg, 34%). 1H NMR (400 MHz, Chloroform-d) δ 8.53 (s, 1H), 8.33 (s, 1H), 8.27 (d, J=7.8 Hz, 1H), 7.86 (s, 1H), 7.75 (s, 1H), 7.71 (s, 1H), 7.64-7.53 (app m, 2H), 7.47 (d, J=7.6 Hz, 1H), 4.56 (s, 1H), 4.00 (s, 3H), 3.97 (s, 3H), 3.86 (d, J=12.3 Hz, 1H), 3.04 (t, J=6.5 Hz, 2H), 2.94-2.80 (t, 1H), 2.72 (t, J=11.5 Hz, 1H), 1.95-1.76 (app m, 3H), 1.71 (d, J=12.9 Hz, 1H), 1.64-1.50 (m, 1H), 1.44 (s, 9H), 1.23 (td, J=13.9, 13.4, 8.0 Hz, 1H); HPLC: (254 nm) 95.8%; RT (min) 3.629; LC/MS: 429.4 (M+1).

Example 4: {5-(1-Methyl-1H-pyrazol-4-yl)-2-[3-(1-methyl-1H-pyrazol-4-yl)-phenyl]-pyrimidin-4-yl}-piperidin-3-ylmethyl-amine Hydrochloride

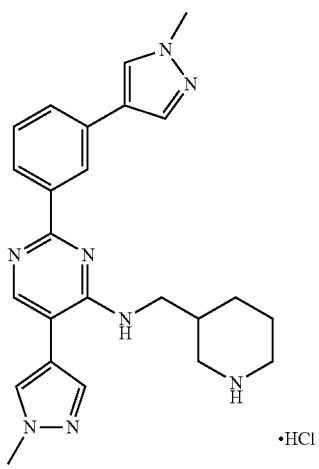 [SMILES: Cn1cc(-c2cccc(-c3ncc(-c4cnn(C)c4)c(NCC4CCCNC4)n3)c2)cn1 ; Cl]

A solution of 3-({5-(1-Methyl-1H-pyrazol-4-yl)-2-[3-(1-methyl-1H-pyrazol-4-yl)-phenyl]-pyrimidin-4-ylamino}-methyl)-piperidine-1-carboxylic acid tert-butyl ester (34 mg; 0.06 mmol; 1.0 eq.) and hydrogen chloride (1.0 mL of a 2M solution in Et₂O; 0.2 mmol; 3.3 eq.) in methanol (3.00 mL) was stirred at RT for 30 min. The reaction mixture was co-evaporated with 5×10 mL Et₂O and dried under reduced pressure to give the title compound as a white solid (26 mg, 81%). 1H NMR (400 MHz, Methanol-d4) δ 8.61 (s, 1H), 8.56 (s, 1H), 8.50 (s, 1H), 8.23 (s, 1H), 8.21 (s, 1H), 8.09 (s, 1H), 8.01 (d, J=7.7 Hz, 1H), 7.85 (s, 1H), 7.74 (t, J=7.7 Hz, 1H), 4.74 (m, 1H), 4.28 (brs, 1H), 4.15 (s, 3H), 4.05 (s, 3H), 3.21 (d, J=10.5 Hz, 2H), 3.07-2.83 (m, 2H), 2.19 (brs, 1H), 2.05 (d, J=12.6 Hz, 1H), 1.84 (d, J=13.2 Hz, 1H), 1.68 (m, 1H), 1.50 (m, 1H). HPLC: (254 nm) 100%; RT (min) 2.29. LCMS: 429.2 (M+1).

Example 5: (1-{5-(1-Methyl-1H-pyrazol-4-yl)-2-[3-(1-methyl-1H-pyrazol-4-yl)-phenyl]-pyrimidin-4-yl}-piperidin-3-ylmethyl)-carbamic Acid Tert-Butyl Ester

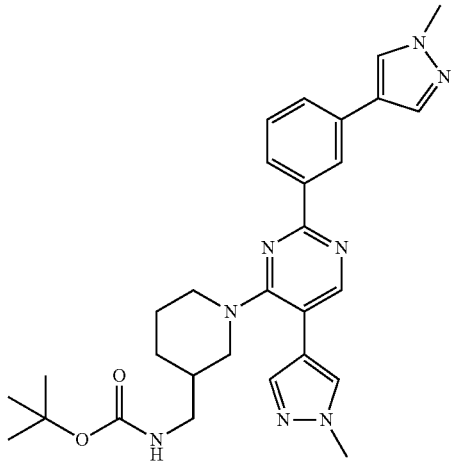 [SMILES: Cn1cc(-c2cccc(-c3ncc(-c4cnn(C)c4)c(N4CCCC(CNC(=O)OC(C)(C)C)C4)n3)c2)cn1]

A mixture of {1-[2-Chloro-5-(1-methyl-1H-pyrazol-4-yl)-pyrimidin-4-yl]-piperidin-3-ylmethyl}-carbamic acid tert-butyl ester (285 mg; 0.70 mmol; 1.00 eq.), Pd(PPh₃)Cl₂ (98 mg; 0.14 mmol; 0.20 eq.), 1-Methyl-4-[3-(4,4,5,5-tetramethyl-[1,3,2]dioxaborolan-2-yl)-phenyl]-1H-pyrazole (prepared as described in WO 2014008992; 238 mg, 0.84 mmol, 1.2 eq.) and potassium carbonate (0.2 mL of a 2M solution in water) in degassed dioxane (3.3 mL) was heated in a sealed vial in 150° C. for 80 min. It was then filtered through a celite pad and concentrated under reduced pressure. Purification by flash chromatography on silica (EtOAc:Hexanes, gradient from 0:100% then MeOH:DCM gradient from 0 to 20%), followed by a second purification by Preparative HPLC afforded the title compound as a white solid. 1H NMR (400 MHz, Chloroform-d) δ 8.54 (s, 1H), 8.35 (s, 1H), 8.29 (d, J=7.8 Hz, 1H), 7.88 (s, 1H), 7.77 (s, 1H), 7.72 (d, J=3.3 Hz, 1H), 7.62 (s, 1H), 7.57 (d, J=2.5 Hz, 1H), 7.49 (d, J=7.5 Hz, 1H), 4.56 (brs, 1H), 4.02 (s, 3H), 3.99 (s, 3H), 3.94 (d, J=3.0 Hz, 2H), 3.06 (t, J=6.5 Hz, 2H), 2.94-2.85 (t, 2H), 2.74 (t, J=11.7 Hz, 1H), 2.35 (t, J=7.3 Hz, 1H), 1.87 (d, J=11.5 Hz, 2H), 1.46 (s, 9H), 1.00 (t, J=7.6 Hz, 1H). HPLC: (254 nm) 97.9%; RT (min) 3.48; LC/MS: 529.3 (M+1).

Example 6: C-(1-{5-(1-Methyl-1H-pyrazol-4-yl)-2-[3-(1-methyl-1H-pyrazol-4-yl)-phenyl]-pyrimidin-4-yl}-piperidin-3-yl)-methylamine Hydrochoride

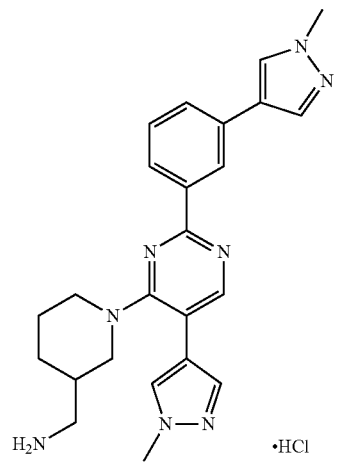 [SMILES: Cn1cc(-c2cccc(-c3ncc(-c4cnn(C)c4)c(N4CCCC(CN)C4)n3)c2)cn1 ; Cl]

The title compound was obtained following the procedure described for example 4 from (1-{5-(1-Methyl-1H-pyrazol-4-yl)-2-[3-(1-methyl-1H-pyrazol-4-yl)-phenyl]-pyrimidin-4-yl}-piperidin-3-ylmethyl)-carbamic acid tert-butyl ester (78 mg; 0.15 mmol; 1.00 eq.) as a yellow powder (30 mg, 30%). 1H NMR (400 MHz, Methanol-d4) δ 8.38 (s, 1H), 8.21 (s, 1H), 8.17 (s, 1H), 8.10 (d, J=7.9 Hz, 1H), 8.05 (s, 1H), 8.00 (s, 1H), 7.95 (d, J=7.8 Hz, 1H), 7.76 (s, 1H), 7.68 (t, J=7.8 Hz, 1H), 4.73 (brs, 1H), 4.25 (brs, 1H), 4.15 (s, 3H), 4.05 (s, 3H), 3.23 (m, 2H), 3.08-2.84 (m, 2H), 2.21 (m, 1H), 2.05 (brs, 1H), 1.84 (brs, 1H), 1.68 (brs, 1H), 1.51 (brs, 1H), 1.32 (m, 1H). HPLC: (254 nm) 94.6%; RT (min) 2.231; LC/MS: 429.3 (M+1). HPLC: (254 nm) 94.6%; RT (min) 2.23; LC/MS: 429.3 (M+1).

Example 7: {5-(1-Methyl-1H-pyrazol-4-yl)-2-[3-(1-methyl-1H-pyrazol-4-yl)-phenyl]-pyrimidin-4-yl}-piperidin-4-ylmethyl-amine Step 1: 4-({5-(1-Methyl-1H-pyrazol-4-yl)-2-[3-(1-methyl-1H-pyrazol-4-yl)-phenyl]-pyrimidin-4-ylamino}-methyl)-piperidine-1-carboxylic Acid Tert-Butyl Ester

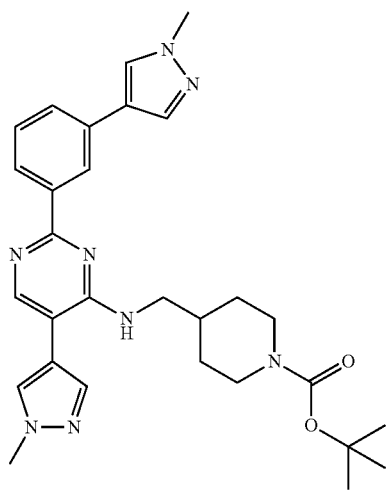 [SMILES: Cn1cc(-c2cccc(-c3ncc(-c4cnn(C)c4)c(NCC4CCN(C(=O)OC(C)(C)C)CC4)n3)c2)cn1]

The title compound was obtained following the procedure described for example 3 from 4-{[2-Chloro-5-(1-methyl-1H-pyrazol-4-yl)-pyrimidin-4-ylamino]-methyl}-piperidine-1-carboxylic acid tert-butyl ester (125 mg; 0.31 mmol; 1.00 eq.) and 1-Methyl-4-[3-(4,4,5,5-tetramethyl-[1,3,2]dioxaborolan-2-yl)-phenyl]-1H-pyrazole (105 mg; 0.37 mmol; 1.20 eq.) as a yellow foam (87 mg, 48%). LC/MS: 529.4 (M+1).

Step 2: {5-(1-Methyl-1H-pyrazol-4-yl)-2-[3-(1-methyl-1H-pyrazol-4-yl)-phenyl]-pyrimidin-4-yl}-piperidin-4-ylmethyl-amine Hydrochloride

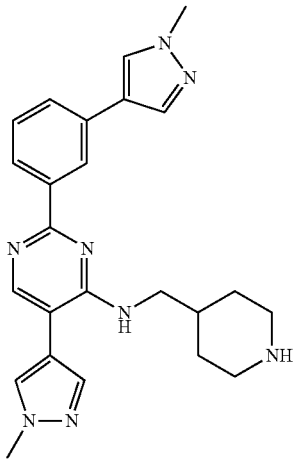 [SMILES: Cn1cc(-c2cccc(-c3ncc(-c4cnn(C)c4)c(NCC4CCNCC4)n3)c2)cn1]

A solution of 4-({5-(1-Methyl-1H-pyrazol-4-yl)-2-[3-(1-methyl-1H-pyrazol-4-yl)-phenyl]-pyrimidin-4-ylamino}-methyl)-piperidine-1-carboxylic acid tert-butyl ester (84 mg; 0.16 mmol; 1.00 eq.) and hydrogen chloride (3.0 mL of a 2M solution in Et$_2$O; 0.16 mmol; 1.00 eq.) in MeOH (3.00 mL) was stirred at RT for 30 min. The reaction mixture was co-evaporated with 5×10 mL Et$_2$O and dried under reduced pressure to give the title compound as a yellow oil (68 mg, quantitative). 1H NMR (400 MHz, Methanol-d4) δ 8.48 (s, 1H), 8.40 (s, 1H), 8.26 (s, 1H), 8.17 (s, 1H), 8.13 (d, J=7.9 Hz, 1H), 8.04 (s, 1H), 7.95 (d, J=7.8 Hz, 1H), 7.78 (s, 1H), 7.68 (d, J=7.8 Hz, 1H), 4.77-4.54 (m, 1H), 4.06 (s, 3H), 4.01 (s, 3H), 3.21 (t, J=12.6 Hz, 2H), 2.91 (d, J=6.9 Hz, 2H), 2.19-2.00 (m, 1H), 2.00-1.84 (m, 2H), 1.57-1.37 (m, 2H); HPLC: (254 nm) 98.3%; RT (min) 2.21; LC/MS: 429.3 (M+1).

Example 8: 5-(1-Methyl-1H-pyrazol-3-yl)-2-[3-(1-methyl-1H-pyrazol-4-yl)-phenyl]-4-(tetrahydropyran-2-ylmethoxy)-pyrimidine

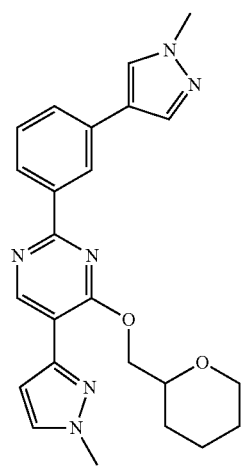 [SMILES: Cn1cc(-c2cccc(-c3ncc(-c4ccn(C)n4)c(OCC4CCCCO4)n3)c2)cn1]

The title compound was obtained following the procedure described for example 3 from 2-Chloro-5-(1-methyl-1H-pyrazol-3-yl)-4-(tetrahydro-pyran-2-ylmethoxy)-pyrimidine (209 mg; 0.68 mmol; 1.00 eq.) and 1-Methyl-4-[3-(4,4,5,5-tetramethyl-[1,3,2]dioxaborolan-2-yl)-phenyl]-1H-pyrazole (prepared as described in WO 2014008992; 231 mg; 0.81 mmol; 1.20 eq.) as a beige powder (38 mg, 12%). 1H NMR (400 MHz, Chloroform-d) δ 9.23 (s, 1H), 8.58 (d, J=1.9 Hz, 1H), 8.33 (dt, J=7.7, 1.4 Hz, 1H), 7.88 (s, 1H), 7.75 (s, 1H), 7.59 (dt, J=7.7, 1.5 Hz, 1H), 7.49 (t, J=7.8 Hz, 1H), 7.45 (s, 1H), 6.94 (d, J=2.2 Hz, 1H), 4.64 (d, J=5.2 Hz, 2H), 4.00 (s, 3H), 3.99 (s, 3H), 3.88 (m, 1H), 3.61-3.47 (m, 2H), 1.87-1.76 (m, 2H), 1.64-1.52 (m, 4H); UPLC: (254 nm) 93%; RT (min) 3.9; LC/MS: 431.2 (M+1).

Example 9: 4-(3-Methyl-oxetan-3-ylmethoxy)-5-(1-methyl-1H-pyrazol-4-yl)-2-[3-(1-methyl-1H-pyrazol-4-yl)-phenyl]-pyrimidine

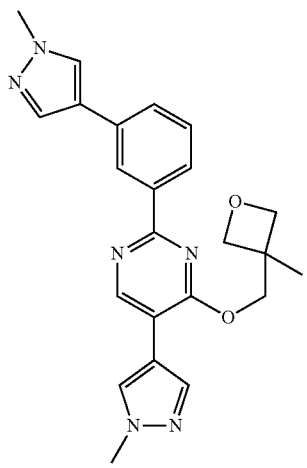 [SMILES: Cn1cc(-c2cccc(-c3ncc(-c4cnn(C)c4)c(OCC4(C)COC4)n3)c2)cn1]

The title compound was obtained following the procedure described for example 3 from 2-Chloro-4-(3-methyl-oxetan-3-ylmethoxy)-5-(1-methyl-1H-pyrazol-4-yl)-pyrimidine (151 mg; 0.51 mmol; 1.00 eq.), and 1-Methyl-4-[3-(4,4,5,5-tetramethyl-[1,3,2]dioxaborolan-2-yl)-phenyl]-1H-pyrazole (prepared as described in WO 2014008992; 175 mg; 0.62 mmol; 1.20 eq.) as a white solid (165 mg, 44%). 1H NMR (400 MHz, Methanol-d4) δ 8.87 (s, 1H), 8.55 (d, J=1.9 Hz, 1H), 8.31 (s, 1H), 8.25 (d, J=7.8 Hz, 1H), 8.09 (s, 1H), 8.03 (s, 1H), 7.90 (s, 1H), 7.67 (d, J=7.7 Hz, 1H), 7.48 (t, J=7.7 Hz, 1H), 4.83 (d, J=6.1 Hz, 2H), 4.70 (s, 2H), 4.59 (d, J=6.0 Hz, 2H), 3.96 (s, 3H), 3.95 (s, 3H), 1.51 (s, 3H); UPLC: (254 nm) 100%; RT (min) 3.27; LC/MS: 417.2 (M+1).

Example 10: {5-(1-Methyl-1H-pyrazol-3-yl)-2-[3-(1-methyl-1H-pyrazol-4-yl)-phenyl]-pyrimidin-4-yl}-piperidin-3-ylmethyl-amine Step 1: 3-({5-(1-Methyl-1H-pyrazol-3-yl)-2-[3-(1-methyl-1H-pyrazol-4-yl)-phenyl]-pyrimidin-4-ylamino}-methyl)-piperidine-1-carboxylic Acid Tert-Butyl Ester

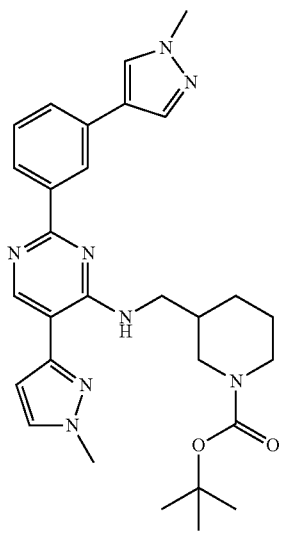 [SMILES: Cn1cc(-c2cccc(-c3ncc(-c4ccn(C)n4)c(NCC4CCCN(C(=O)OC(C)(C)C)C4)n3)c2)cn1]

The title compound was obtained following procedure described for example 3 from 3-{[2-Chloro-5-(1-methyl-1H-pyrazol-3-yl)-pyrimidin-4-ylamino]-methyl}-piperidine-1-carboxylic acid tert-butyl ester (261 mg; 0.64 mmol; 1.00 eq.) and 1-Methyl-4-[3-(4,4,5,5-tetramethyl-[1,3,2]dioxaborolan-2-yl)-phenyl]-1H-pyrazole (219 mg; 0.77 mmol; 1.20 eq.) as beige solid (19 mg, 55%). LC/MS: 529.4 (M+1).

Step 2: {5-(1-Methyl-1H-pyrazol-3-yl)-2-[3-(1-methyl-1H-pyrazol-4-yl)-phenyl]-pyrimidin-4-yl}-piperidin-3-ylmethyl-amine hydrochloride

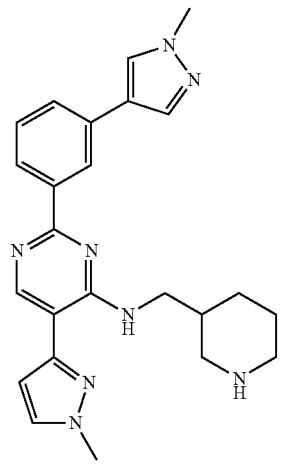 [SMILES: Cn1cc(-c2cccc(-c3ncc(-c4ccn(C)n4)c(NCC4CCCNC4)n3)c2)cn1]

The title compound was obtained following procedure described for example 4 from 3-({5-(1-Methyl-1H-pyrazol-3-yl)-2-[3-(1-methyl-1H-pyrazol-4-yl)-phenyl]-pyrimidin-4-ylamino}-methyl)-piperidine-1-carboxylic acid tert-butyl ester (15 mg; 0.03 mmol; 1.00 eq.) as a white solid (10 mg, 80%). 1H NMR (400 MHz, Methanol-d4) δ 8.71 (s, 1H), 8.47-8.40 (m, 1H), 8.18 (s, 1H), 8.13 (d, J=7.7 Hz, 1H), 8.01 (s, 1H), 7.95 (d, J=7.8 Hz, 1H), 7.87-7.81 (m, 1H), 7.69 (t, J=7.8 Hz, 1H), 7.08-6.99 (m, 1H), 4.08 (s, 3H), 4.05 (s, 3H), 3.61-3.48 (d, 2H), 2.96 (q, J=13.5, 12.4 Hz, 2H), 2.42 (brs, 2H), 2.08 (dd, J=25.8, 14.3 Hz, 2H), 1.84 (t, J=13.1 Hz, 2H), 1.64-1.42 (m, 2H), 1.20 (s, 1H); HPLC: (254 nm) 100%; RT (min) 2.462. LC/MS: calc.: 429.2 (M+1).

Example 11: 5-(1-Methyl-1H-pyrazol-4-yl)-2-[3-(1-methyl-1H-pyrazol-4-yl)-phenyl]-4-(oxetan-3-yl-methoxy)-pyrimidine

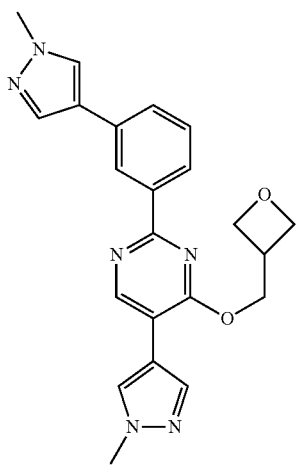 [SMILES: Cn1cc(-c2cccc(-c3ncc(-c4cnn(C)c4)c(OCC4COC4)n3)c2)cn1]

The title compound was obtained following the procedure described for example 3 from 2-Chloro-5-(1-methyl-1H-pyrazol-4-yl)-4-(oxetan-3-ylmethoxy)-pyrimidine (55 mg; 0.20 mmol; 1.00 eq.) and 1-Methyl-4-[3-(4,4,5,5-tetramethyl-[1,3,2]dioxaborolan-2-yl)-phenyl]-1H-pyrazole (67 mg; 0.24 mmol; 1.20 eq.) as a white solid (13 mg, 16%). 1H NMR (400 MHz, Chloroform-d) δ 8.83 (s, 1H), 8.56 (d, J=1.8 Hz, 1H), 8.30 (d, J=7.8 Hz, 1H), 8.07 (s, 1H), 7.98 (s, 1H), 7.88 (s, 1H), 7.75 (s, 1H), 7.60 (d, J=7.7 Hz, 1H), 7.50 (t, J=7.7 Hz, 1H), 5.06-4.96 (m, 2H), 4.88 (d, J=5.6 Hz, 2H), 4.75 (t, J=6.0 Hz, 2H), 3.99 (s, 6H), 3.59 (qt, J=5.5 Hz, 1H); UPLC (H2O TFA 0.1%-ACN TFA 0.1%; Gradient 8 min TFA): (254 nm) 80%; RT (min) 2.97; LC/MS: 403.2 (M+1).

Example 12: {5-(1-Methyl-1H-pyrazol-3-yl)-2-[3-(1-methyl-1H-pyrazol-4-yl)-phenyl]-pyrimidin-4-yl}-piperidin-4-ylmethyl-amine Step 1: 4-({5-(1-Methyl-1H-pyrazol-3-yl)-2-[3-(1-methyl-1H-pyrazol-4-yl)-phenyl]-pyrimidin-4-ylamino}-methyl)-piperidine-1-carboxylic Acid Tert-Butyl Ester

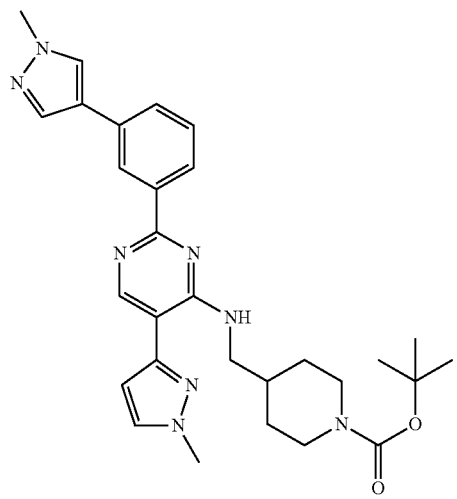 [SMILES: Cn1cc(-c2cccc(-c3ncc(-c4ccn(C)n4)c(NCC4CCN(C(=O)OC(C)(C)C)CC4)n3)c2)cn1]

The title compound was obtained following procedure described for example 3 from 4-{[2-Chloro-5-(1-methyl-1H-pyrazol-3-yl)-pyrimidin-4-ylamino]-methyl}-piperidine-1-carboxylic acid tert-butyl ester (541 mg; 1.33 mmol; 1.00 eq.) and 1-Methyl-4-[3-(4,4,5,5-tetramethyl-[1,3,2]dioxaborolan-2-yl)-phenyl]-1H-pyrazole (453 mg; 1.60 mmol; 1.20 eq.) as a beige solid (53 mg, 7%). LC/MS: 529.3 (M+1).

Step 2: {5-(1-Methyl-1H-pyrazol-3-yl)-2-[3-(1-methyl-1H-pyrazol-4-yl)-phenyl]-pyrimidin-4-yl}-piperidin-4-ylmethyl-amine

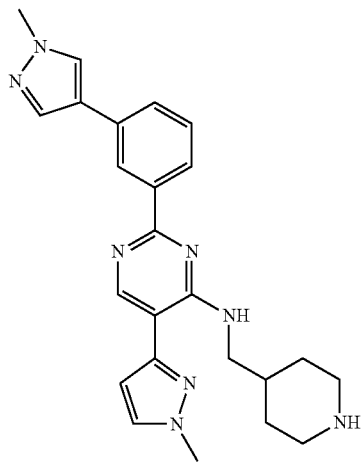 [SMILES: Cn1cc(-c2cccc(-c3ncc(-c4ccn(C)n4)c(NCC4CCNCC4)n3)c2)cn1]

The title compound was obtained following procedure described for example 4 from 4-({5-(1-Methyl-1H-pyrazol- 3-yl)-2-[3-(1-methyl-1H-pyrazol-4-yl)-phenyl]-pyrimidin-4-ylamino}-methyl)-piperidine-1-carboxylic acid tert-butyl ester (52 mg; 0.10 mmol; 1.00 eq) as a beige solid (40 mg, 94%). 1H NMR (400 MHz, Methanol-d4) δ 8.69 (d, J=0.9 Hz, 1H), 8.41 (d, J=2.2 Hz, 1H), 8.16 (s, 1H), 8.11 (d, J=8.3 Hz, 1H), 8.00 (s, 1H), 7.95 (d, J=7.8 Hz, 1H), 7.85 (d, J=2.4 Hz, 1H), 7.68 (t, J=7.8 Hz, 1H), 7.04 (d, J=2.4 Hz, 1H), 4.08 (s, 3H), 4.00 (d, J=3.2 Hz, 3H), 3.52-3.44 (m, 2H), 3.12-3.00 (m, 2H), 2.35-2.21 (m, 1H), 2.14 (d, J=14.4 Hz, 2H), 1.75-1.54 (m, 2H), 1.20 (t, J=7.0 Hz, 2H); UPLC: (254 nm) 100%; RT (min) 1.9; LC/MS: 429.3 (M+1).

Example 13: {5-(1-Methyl-1H-pyrazol-4-yl)-2-[3-(1-methyl-1H-pyrazol-4-yl)-phenyl]-pyrimidin-4-yl}-(tetrahydro-pyran-4-ylmethyl)-amine

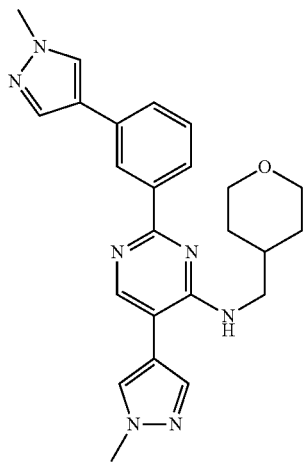 [SMILES: Cn1cc(-c2cccc(-c3ncc(-c4cnn(C)c4)c(NCC4CCOCC4)n3)c2)cn1]

The title compound was obtained following procedure described for example 3 from [2-Chloro-5-(1-methyl-1H-pyrazol-4-yl)-pyrimidin-4-yl]-(tetrahydro-pyran-4-ylmethyl)-amine (206 mg; 0.67 mmol; 1.00 eq.) and 1-Methyl-4-[3-(4,4,5,5-tetramethyl-[1,3,2]dioxaborolan-2-yl)-phenyl]-1H-pyrazole (228 mg; 0.80 mmol; 1.20 eq.) as a beige solid (93 mg, 32%). 1H NMR (400 MHz, Chloroform-d) δ 8.54-8.49 (m, 1H), 8.25 (m, 2H), 7.88 (s, 1H), 7.75 (s, 1H), 7.68 (s, 1H), 7.63-7.59 (m, 1H), 7.49 (t, J=7.7 Hz, 1H), 5.39 (t, J=6.1 Hz, 1H), 5.12 (brs, 2H), 4.03 (s, 3H), 3.99 (s, 3H), 3.58 (t, J=6.4 Hz, 2H), 3.42 (t, J=11.8 Hz, 2H), 2.00 (m, 1H), 1.77-1.65 (m, 2H), 1.46 (m, 2H); UPLC (H2O TFA 0.1%-ACN TFA 0.1%; Gradient 8 min TFA): (254 nm) 100%; RT (min) 2.39; LC/MS: 430.2 (M+1).

Example 14: (1-Methanesulfonyl-piperidin-4-yl)-{5-(1-methyl-1H-pyrazol-4-yl)-2-[3-(1-methyl-1H-pyrazol-4-yl)-phenyl]-pyrimidin-4-yl}-amine

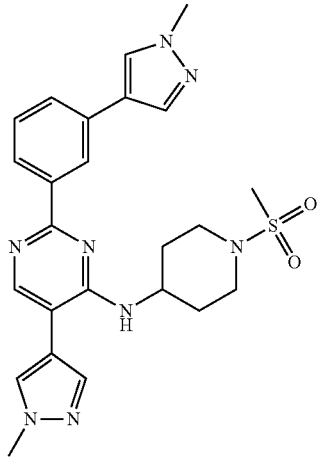 [SMILES: Cn1cc(-c2cccc(-c3ncc(-c4cnn(C)c4)c(NC4CCN(S(C)(=O)=O)CC4)n3)c2)cn1]

The title compound was obtained following the procedure described for example 3 from [2-Chloro-5-(1-methyl-1H-pyrazol-4-yl)-pyrimidin-4-yl]-(1-methanesulfonyl-piperidin-4-yl)-amine (870 mg; 2.35 mmol; 1.00 eq) and 1-Methyl-4-[3-(4,4,5,5-tetramethyl-[1,3,2]dioxaborolan-2-yl)-phenyl]-1H-pyrazole (780 mg; 2.82 mmol; 1.20 eq.) as a white solid (600 mg, 52%). 1H NMR (400 MHz, Chloroform-d) δ 8.51 (brs, 1H), 8.26 (d, J=1.2 Hz, 1H), 8.21 (dd, J=7.8, 1.5 Hz, 1H), 7.88 (s, 1H), 7.74 (s, 1H), 7.67 (s, 1H), 7.60 (dd, J=7.8, 1.6 Hz, 1H), 7.56 (s, 1H), 7.49 (t, J=7.7 Hz, 1H), 5.09 (d, J=7.2 Hz, 1H), 4.36 (m, 1H), 4.04 (s, 3H), 4.00 (s, 3H), 3.88 (d, J=11.9, 2H), 3.06-2.91 (m, 2H), 2.87 (s, 3H), 2.29 (m, 2H), 1.67 (m, 2H); UPLC (H2O TFA 0.1%-ACN TFA 0.1%; Gradient 8 min TFA): (254 nm) 100%; RT (min) 2.17; LC/MS: 493.2 (M+1).

Example 15: Isopropyl-[2-[3-(1-methyl-1H-pyrazol-4-yl)-phenyl]-5-(5-methyl-[1,3,4]thiadiazol-2-yl)-pyrimidin-4-yl]-amine Step 1: 4-Isopropylamino-2-[3-(1-methyl-1H-pyrazol-4-yl)-phenyl]-pyrimidine-5-carboxylic Acid N'-acetyl-hydrazide

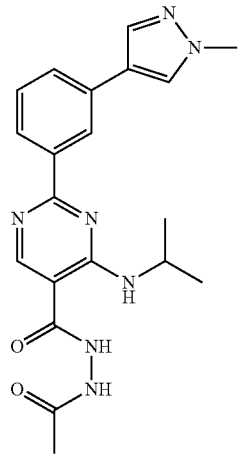 [SMILES: CC(=O)NNC(=O)c1cnc(-c2cccc(-c3cnn(C)c3)c2)nc1NC(C)C]

Acetyl chloride (0.04 mL; 0.53 mmol; 1.05 eq.) was added dropwise to a solution of 4-Isopropylamino-2-[3-(1-methyl-1H-pyrazol-4-yl)-phenyl]-pyrimidine-5-carboxylic acid hydrazide (180 mg; 0.50 mmol; 1.00 eq.) and TEA (0.2 mL, 1.51 mmol; 3.00 eq.) in DCM (4.5 mL) maintained at 0° C. The reaction mixture was warmed up to room temperature and stirred for 30 min. It was then quenched with a saturated NaHCO₃ solution and extracted with DCM. The organic layer was dried over Na₂SO₄, filtered and concentrated. Purification by flash chromatography on silica (DCM: MeOH) afforded the title compound as a yellow gum (160 mg, 74%). 1H NMR (400 MHz, DMSO-d6) δ: 10.44 (s, 1H), 9.88 (s, 1H), 8.79 (s, 1H), 8.50-8.49 (m, 2H), 8.22 (s, 1H), 8.19 (d, J=7.9 Hz, 1H), 7.89 (s, 1H), 7.72 (d, J=8.2 Hz, 1H), 7.49 (t, J=7.8 Hz, 1H), 4.50-4.42 (m, 1H), 3.88 (s, 3H), 1.93 (s, 3H), 1.28 (d, J=6.52 Hz, 6H). HPLC (254 nm) 90%; Rt 2.88 min; LC/MS: 394.2 (M+H).

Step 2: Isopropyl-[2-[3-(1-methyl-1H-pyrazol-4-yl)-phenyl]-5-(5-methyl-[1,3,4]thiadiazol-2-yl)-pyrimidin-4-yl]-amine

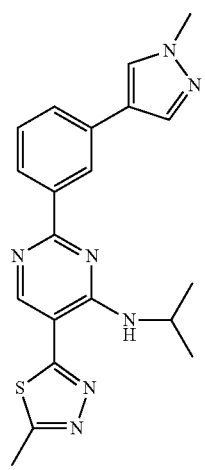 [SMILES: Cc1nnc(-c2cnc(-c3cccc(-c4cnn(C)c4)c3)nc2NC(C)C)s1]

A solution of 2,4-Bis-(4-methoxy-phenyl)-[1,3,2,4]dithiadiphosphetane 2,4-disulfide (311 mg; 0.75 mmol; 2.00 eq.) and 4-Isopropylamino-2-[3-(1-methyl-1H-pyrazol-4-yl)-phenyl]-pyrimidine-5-carboxylic acid N'-acetyl-hydrazide (160 mg; 0.37 mmol; 1.00 eq.) in THF (8.0 mL) was heated to reflux for 2 h. It was then diluted with ethyl acetate and washed with a 10% NaHCO₃ solution. The organic layer was separated, dried over Na₂SO₄, filtered and concentrated. Purification by flash column chromatography on silica (DCM/MeOH) afforded the title compound as a yellow solid (80 mg, 52%). 1H NMR (400 MHz, DMSO-d6) δ: 8.85 (d, J=7.2 Hz, 1H), 8.80 (s, 1H), 8.53 (s, 1H), 8.23 (s, 1H), 8.20 (s, 1H), 7.89 (s, 1H), 7.72 (d, J=7.7 Hz, 1H), 7.51 (t, J=7.8 Hz, 1H), 4.62-4.57 (m, 1H), 3.89 (s, 3H), 2.80 (s, 3H), 1.37 (d, J=6.48 Hz, 6H). HPLC: (254 nm) 94%; Rt 3.58 min. LC/MS: 392.3 (M+H).

Example 16: ((R)-3-Hydroxy-pyrrolidin-1-yl)-(5-{4-isopropylamino-2-[3-(1-methyl-1H-pyrazol-4-yl)-phenyl]-pyrimidin-5-yl}-[1,3,4]thiadiazol-2-yl)-methanone

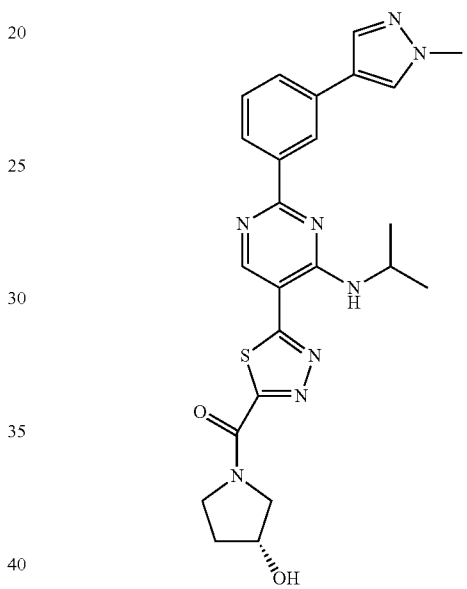

Bis(trimethyl aluminium)-1,4-diaza bicyclo(2.2.2)octane adduct (78 mg; 0.30 mmol; 1.00 eq.) at 0° C. followed by (R)-Pyrrolidin-3-ol (32 mg; 0.36 mmol; 1.20 eq.) were added to a solution of 5-{4-Isopropylamino-2-[3-(1-methyl-1H-pyrazol-4-yl)-phenyl]-pyrimidin-5-yl}-[1,3,4]thiadiazole-2-carboxylic acid ethyl ester (150 mg; 0.30 mmol; 1.00 eq.) in THF (3.00 mL). The reaction mixture was heated to reflux for 8 h in a sealed tube. It was then cooled down to RT, diluted with ethyl acetate and washed with a 1.5 N HCl solution. The organic layer was separated, dried over Na₂SO₄, filtered and concentrated. Purification by flash chromatography on silica (DCM/MeOH) afforded the title compound as a yellow solid (80 mg, 51%). 1H NMR (400 MHz, DMSO-d6) δ: 8.96 (s, 1H), 8.88 (d, J=7.20 Hz, 1H), 8.55 (t, J=1.52 Hz, 1H), 8.23 (t, J=7.04 Hz, 2H), 7.90 (d, J=0.56 Hz, 1H), 7.74 (d, J=7.84 Hz, 1H), 7.52 (t, J=7.72 Hz, 1H), 5.10 (d, J=3.48 Hz, 1H), 4.66-4.61 (m, 1H), 4.38 (d, J=24.84 Hz, 1H), 4.21 (d, J=8.92 Hz, 2H), 3.89 (s, 3H), 3.72-3.51 (m, 2H), 2.05-1.86 (m, 2H), 1.40-1.22 (m, 6H). HPLC: (254 nm) 95%; Rt 3.53 min. LC/MS: 491.2 (M+H).

Example 17: [2-[3-(1-Methyl-1H-pyrazol-4-yl)-phenyl]-5-(5-methyl-[1,3,4]thiadiazol-2-yl)-pyrimidin-4-yl]-piperidin-3-yl-amine Hydrochloride Step 1: 3-{5-(N'-Acetyl-hydrazinocarbonyl)-2-[3-(1-methyl-1H-pyrazol-4-yl)-phenyl]-pyrimidin-4-ylamino}-piperidine-1-carboxylic Acid Tert-Butyl Ester

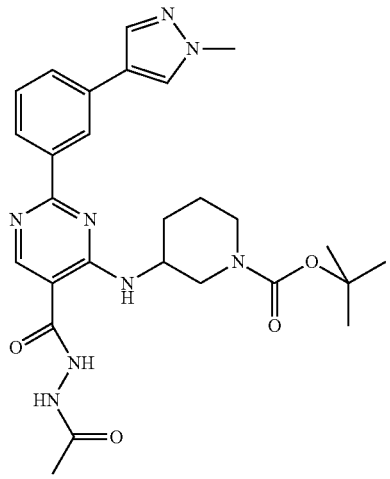 [SMILES: CC(=O)NNC(=O)c1cnc(-c2cccc(-c3cnn(C)c3)c2)nc1NC1CCCN(C(=O)OC(C)(C)C)C1]

The title compound was obtained following the procedure described for example 15, step 1 from 3-{5-Hydrazinocarbonyl-2-[3-(1-methyl-1H-pyrazol-4-yl)-phenyl]-pyrimidin-4-ylamino}-piperidine-1-carboxylic acid tert-butyl ester (600 mg; 1.18 mmol; 1.00 eq.) as a yellow solid (500 mg, 70%). HPLC (Column: XBridge C8, 3.5 µm, 4.6×50 mm): (254 nm) 81%; Rt 3.5 min; LC/MS: 535.2 (M+H).

Step 2: 3-[2-[3-(1-Methyl-1H-pyrazol-4-yl)-phenyl]-5-(5-methyl-[1,3,4]thiadiazol-2-yl)-pyrimidin-4-ylamino]-piperidine-1-carboxylic Acid Tert-Butyl Ester

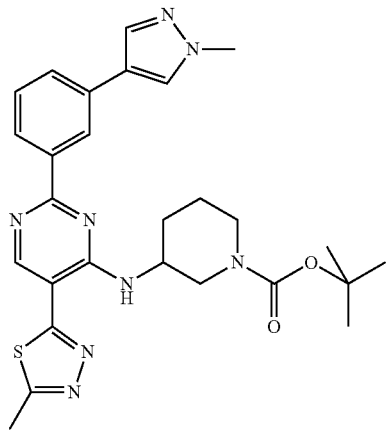 [SMILES: Cc1nnc(-c2cnc(-c3cccc(-c4cnn(C)c4)c3)nc2NC2CCCN(C(=O)OC(C)(C)C)C2)s1]

The title compound was obtained following the procedure described for example 15, step 2 from 3-{5-(N'-Acetyl-hydrazinocarbonyl)-2-[3-(1-methyl-1H-pyrazol-4-yl)-phenyl]-pyrimidin-4-ylamino}-piperidine-1-carboxylic acid tert-butyl ester (500 mg; 0.83 mmol; 1.00 eq.) as a yellow solid (350 mg; 71.2%). HPLC: (254 nm) 74%; Rt 4.21 min; LC/MS: 533.3 (M+H).

Step 3: [2-[3-(1-Methyl-1H-pyrazol-4-yl)-phenyl]-5-(5-methyl-[1,3,4]thiadiazol-2-yl)-pyrimidin-4-yl]-piperidin-3-yl-amine Hydrochloride

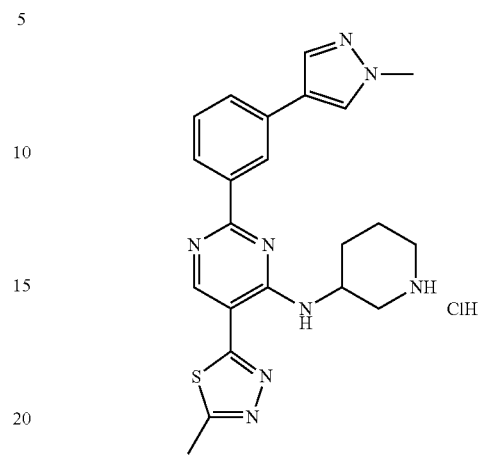

A solution of 3-[2-[3-(1-Methyl-1H-pyrazol-4-yl)-phenyl]-5-(5-methyl-[1,3,4]thiadiazol-2-yl)-pyrimidin-4-ylamino]-piperidine-1-carboxylic acid tert-butyl ester (100 mg; 0.14 mmol; 1.00 eq.) and hydrogen chloride (1 mL of a 4M solution in dioxane) in dioxane (0.5 mL) was stirred at RT for 4 h. The reaction mixture was then concentrated under reduced pressure and the precipitate was filtered off, washed with diethyl ether (20 mL) and dried to afford the title compound as white solid (20 mg, 29%). 1H NMR (400 MHz, DMSO-d6) δ: 9.06 (d, J=7.12 Hz, 1H), 8.83 (s, 1H), 8.54 (t, J=1.56 Hz, 1H), 8.26 (d, J=7.92 Hz, 1H), 8.22 (s, 1H), 7.91 (s, 1H), 7.74-7.72 (m, 1H), 7.51 (t, J=7.72 Hz, 1H), 4.60-4.50 (m, 1H), 3.89 (s, 3H), 2.99-2.93 (m, 1H), 2.90-2.82 (m, 1H), 2.81-2.80 (m, 4H), 2.30-2.00 (m, 1H), 1.82-1.73 (m, 3H). HPLC: (254 nm) 91%; Rt 2.6 min. LC/MS: 433.3 (M+H).

Example 18: 5-[2-[3-(1-Methyl-1H-pyrazol-4-yl)-phenyl]-4-(piperidin-3-ylamino)-pyrimidin-5-yl]-[1,3,4]thiadiazole-2-carboxylic Acid Methyl Ester Hydrochloride

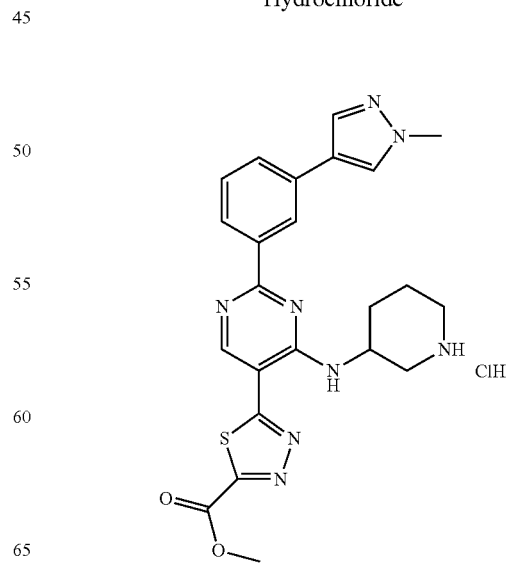

A solution of 3-{5-(5-Methoxycarbonyl-[1,3,4]thiadiazol-2-yl)-2-[3-(1-methyl-1H-pyrazol-4-yl)-phenyl]-pyrimidin-4-ylamino}-piperidine-1-carboxylic acid tert-butyl ester (100 mg; 0.17 mmol; 1.00 eq.) and hydrogen chloride (2 mL of a 4M solution in dioxane) in dioxane (5 mL) was stirred at RT for 4 h. The reaction mixture was then concentrated under reduced pressure and purified by Preparative HPLC to afford the title compound as a yellow solid (45 mg, 51%). 1H NMR (400 MHz, DMSO-d6) δ: 9.08 (s, 1H), 8.91 (d, J=7.20 Hz, 1H), 8.7-8.8 (brs, 2H), 8.57 (s, 1H), 8.31 (d, J=7.88 Hz, 1H), 8.24 (s, 1H), 7.94 (s, 1H), 7.77 (d, J=7.96 Hz, 1H), 7.54 (t, J=7.72 Hz, 1H), 4.71 (s, 1H), 4.01 (s, 3H), 3.90 (s, 3H), 3.32-3.29 (m, 1H), 3.18-3.16 (m, 1H), 2.98-2.95 (m, 1H), 2.17-2.15 (m, 1H), 2.01-1.98 (m, 1H), 1.89-1.84 (m, 2H). HPLC: (254 nm) 98%; Rt 3.01 min; LC/MS: 477.2 (M+H).

Example 19: 5-{4-[(Azetidin-3-ylmethyl)-amino]-2-[3-(1-methyl-1H-pyrazol-4-yl)-phenyl]-pyrimidin-5-yl}-[1,3,4]thiadiazole-2-carboxylic Acid Methyl Ester Trifluoroacetate

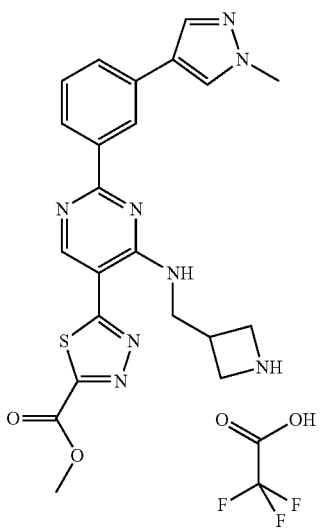

Trifluoroacetic acid (1.00 mL) was added to a solution of 5-{4-[(1-tert-Butoxycarbonyl-azetidin-3-ylmethyl)-amino]-2-[3-(1-methyl-1H-pyrazol-4-yl)-phenyl]-pyrimidin-5-yl}-[1,3,4]thiadiazole-2-carboxylic acid methyl ester (100 mg; 0.17 mmol; 1.00 eq.) in DCM (5 mL) maintained at 0° C. The reaction mixture was then allowed to warm to RT and stirred for 2 h. It was then concentrated under reduced pressure and purified by preparative HPLC to afford the title compound as a yellow solid (20 mg; 20%). 1H NMR (400 MHz, DMSO-d6) δ 9.09 (t, J=5.84 Hz, 1H), 9.03 (s, 1H), 8.54 (s, 2H), 8.43 (s, 1H), 8.27 (d, J=8.00 Hz, 1H), 8.23 (s, 1H), 7.93 (s, 1H), 7.76 (d, J=8.12 Hz, 1H), 7.53 (t, J=7.76 Hz, 1H), 4.03-3.94 (m, 9H), 3.90 (s, 3H), 3.36-3.29 (m, 1H). HPLC: (254 nm) 93%; Rt 2.76 min. LC/MS: 463.3 (M+H).

Example 20: ((R)-3-Hydroxy-pyrrolidin-1-yl)-{5-[2-[3-(1-methyl-1H-pyrazol-4-yl)-phenyl]-4-(piperidin-3-ylamino)-pyrimidin-5-yl]-[1,3,4]thiadiazol-2-yl}-methanone Hydrochloride Step 1: 3-{5-[5-((R)-3-Hydroxy-pyrrolidine-1-carbonyl)-[1,3,4]thiadiazol-2-yl]-2-[3-(1-methyl-1H-pyrazol-4-yl)-phenyl]-pyrimidin-4-ylamino}-piperidine-1-carboxylic Acid Tert-Butyl Ester Chiral

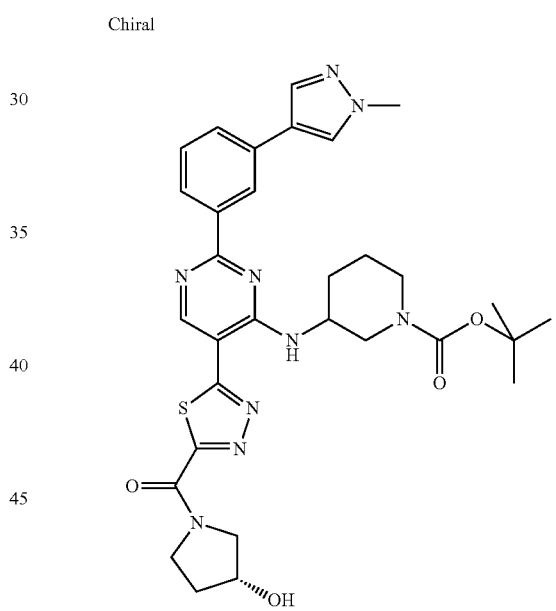

The title compound was obtained following the procedure described for example 16, step 1 from 3-{5-(5-Ethoxycarbonyl-[1,3,4]thiadiazol-2-yl)-2-[3-(1-methyl-1H-pyrazol-4-yl)-phenyl]-pyrimidin-4-ylamino}-piperidine-1-carboxylic acid tert-butyl ester (150 mg; 0.24 mmol; 1.00 eq.) and (R)-Pyrrolidin-3-ol (32.22 mg; 0.36 mmol; 1.50 eq.) as a yellow solid (100 mg, 63%). HPLC: (254 nm) 94%; Rt 4.07 min; LC/MS: 632.2 (M+H).

Step 2: ((R)-3-Hydroxy-pyrrolidin-1-yl)-{5-[2-[3-(1-methyl-1H-pyrazol-4-yl)-phenyl]-4-(piperidin-3-ylamino)-pyrimidin-5-yl]-[1,3,4]thiadiazol-2-yl}-methanone Hydrochloride

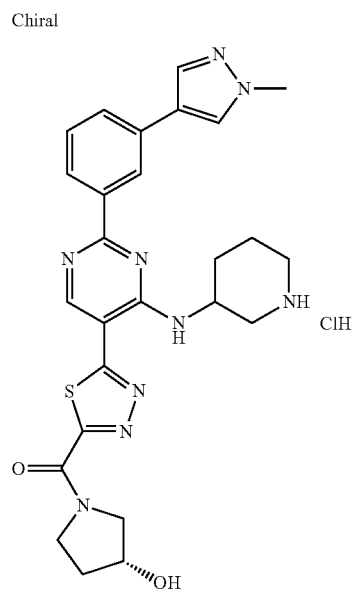 [SMILES: Cn1cc(-c2cccc(-c3ncc(-c4nnc(C(=O)N5CC[C@@H](O)C5)s4)c(NC4CCCNC4)n3)c2)cn1 ; Cl]

The title compound was obtained following the procedure described for example 18, step 1 from 3-{5-[5-((R)-3-Hydroxy-pyrrolidine-1-carbonyl)-[1,3,4]thiadiazol-2-yl]-2-[3-(1-methyl-1H-pyrazol-4-yl)-phenyl]-pyrimidin-4-ylamino}-piperidine-1-carboxylic acid tert-butyl ester (100 mg; 0.15 mmol; 1.00 eq.) as a yellow solid (20 mg, 23%). 1H NMR (400 MHz, DMSO-d6) δ 9.04 (s, 1H), 8.96 (d, J=7.24 Hz, 1H), 8.75 (s, 2H), 8.56 (s, 1H), 8.31 (d, J=7.84 Hz, 1H), 8.24 (s, 1H), 7.94 (s, 1H), 7.76 (d, J=8.12 Hz, 1H), 7.54 (t, J=7.80 Hz, 1H), 4.72 (s, 1H), 4.42-4.36 (m, 1H), 4.22-4.17 (m, 1H), 4.01-3.99 (m, 2H), 3.90 (s, 3H), 3.61-3.60 (m, 2H), 3.32-3.29 (m, 1H), 3.19-3.17 (m, 1H), 2.97 (s, 1H), 2.17-2.16 (m, 1H), 1.98-1.96 (m, 2H), 1.88-1.84 (m, 2H). HPLC (XBridge C8 (50×4.6) mm, 3.5 μm; A: 10 mM NH4HCO3 in H2O, B:ACN;): (254 nm) 98%; Rt 4.55 min. LC/MS: 532.1 (M+H).

Example 21: ((R)-3-Hydroxy-pyrrolidin-1-yl)-(5-{4-isopropylamino-6-[3-(1-methyl-1H-pyrazol-4-yl)-phenyl]-pyridin-3-yl}-[1,3,4]thiadiazol-2-yl)-methanone

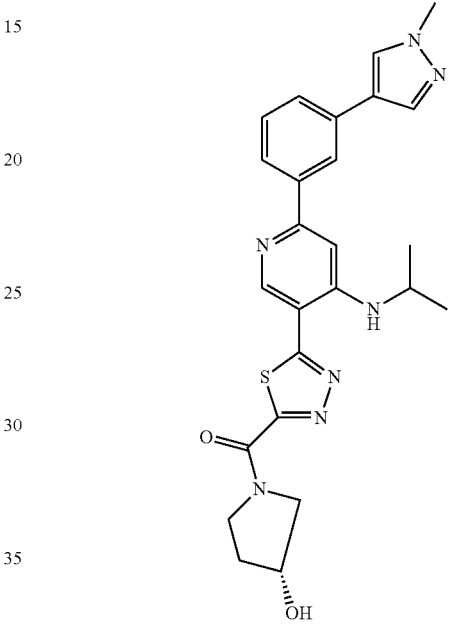

A mixture of 1-Methyl-4-[3-(4,4,5,5-tetramethyl-[1,3,2]dioxaborolan-2-yl)-phenyl]-1H-pyrazole (250 mg; 0.88 mmol; 1.00 eq.), [5-(6-Chloro-4-isopropylamino-pyridin-3-yl)-[1,3,4]thiadiazol-2-yl]-((R)-3-hydroxy-pyrrolidin-1-yl)-methanone (324 mg; 0.88 mmol; 1.00 eq.), K2CO3 (365 mg; 2.64 mmol; 3.00 eq.) and trans-Dichlorobis(tricyclohexylphosphine)palladium(II) (6.49 mg; 0.01 mmol; 0.01 eq.) in dioxane (4 mL) and in water (0.4 mL) was degassed and heated at 100° C. for 0.5 hour. Upon completion, the reaction was filtered and organic layer was concentrated and purified by flash chromatography on silica with a gradient of 10-100% ethyl acetate in hexanes, affording the title compound as a beige solid (115 mg, 27%). 1H NMR (400 MHz, DMSO-d6) δ 8.81 (s, 1H), 8.67 (d, 1H), 8.28-8.21 (m, 2H), 7.99-7.92 (m, 2H), 7.65 (d, 1H), 7.48 (t, 1H), 7.36 (s, 1H), 3.94-3.87 (m, 3H), 5.75 (s, 1H), 5.07 (d, 1H), 4.39 (d, 1H), 4.24 (m, 2H), 4.09-3.97 (m, 2H), 3.73-3.50 (m, 2H), 1.34 (d, 6H). HPLC: (254 nm) 96.6%; Rt (min) 3.09. LC/MS: 490.2.

Example 22: ((R)-3-Hydroxy-pyrrolidin-1-yl)-{5-[4-isopropylamino-6'-(1-methyl-1H-pyrazol-4-yl)-[2,2']bipyridinyl-5-yl]-[1,3,4]thiadiazol-2-yl}-methanone

Step 1: [5-(6'-Chloro-4-isopropylamino-[2,2']bipyridinyl-5-yl)-[1,3,4]thiadiazol-2-yl]-((R)-3-hydroxy-pyrrolidin-1-yl)-methanone

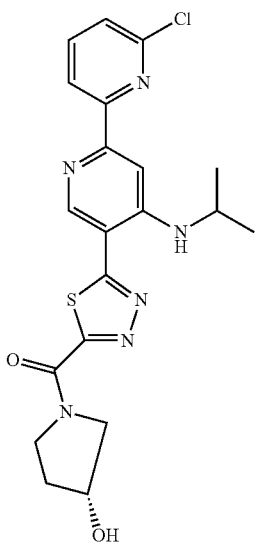

A mixture of 2-Chloro-6-(4,4,5,5-tetramethyl-[1,3,2]dioxaborolan-2-yl)-pyridine (332.71 mg; 1.39 mmol; 1.00 eq.), [5-(6-Chloro-4-isopropylamino-pyridin-3-yl)-[1,3,4]thiadiazol-2-yl]-((R)-3-hydroxy-pyrrolidin-1-yl)-methanone (511.00 mg; 1.39 mmol; 1.00 eq.), a solution of $K_2CO_3$ (575.94 mg; 4.17 mmol; 3.00 eq.) in water (0.4 mL) and trans-Dichlorobis(tricyclohexylphosphine)palladium(II) (10.25 mg; 0.01 mmol; 0.01 eq.) in dioxane (4 mL) was degassed few minutes and heated at 100° C. for 0.5 hour. Upon completion, the reaction was filtered and organic layer was concentrated and purified by flash chromatography on silica with a gradient of 10-100% ethyl acetate in hexanes, affording the title compound (175 mg; 15.8%) as a beige solid.

Step 2: ((R)-3-Hydroxy-pyrrolidin-1-yl)-{5-[4-isopropylamino-6'-(1-methyl-1H-pyrazol-4-yl)-[2,2']bipyridinyl-5-yl]-[1,3,4]thiadiazol-2-yl}-methanone

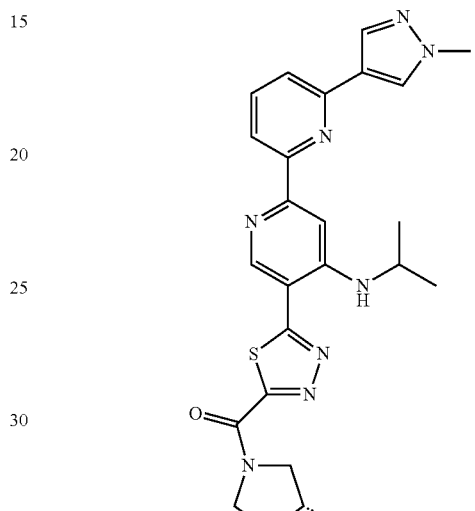

[5-(6'-Chloro-4-isopropylamino-[2,2']bipyridinyl-5-yl)-[1,3,4]thiadiazol-2-yl]-((R)-3-hydroxy-pyrrolidin-1-yl)-methanone (85 mg; 0.11 mmol; 1.00 eq.) was dissolved in DMF (4.00 mL; 51.44 mmol; 481.41 eq.). Then 1-Methyl-4-(4,4,5,5-tetramethyl-[1,3,2]dioxaborolan-2-yl)-1H-pyrazole (33.35 mg; 0.16 mmol; 1.50 eq.) was added in one portion followed by a solution of $NaHCO_3$ (10.77 mg; 0.13 mmol; 1.20 eq.) in water (0.40 mL; 22.20 mmol; 207.74 eq.). The reaction was degassed with nitrogen gas and Bis(triphenylphosphine)palladium(II) chloride (0.38 mg; 0.00 mmol; 0.01 eq.) was added. Reaction mixture was stirred at 80° C. overnight. The reaction mixture was cooled down to RT and diluted with 200 mL water and extracted with ethyl acetate (3×80 mL). The combined organic phase was washed with water (2×75 mL) and brine (1×75 mL); dried over $Na_2SO_4$, filtered and concentrated to a golden oil which was purified by preparative HPLC to give the title compound as a fluffy yellow solid (32.1 mg, 61.2%). 1H NMR (400 MHz, DMSO-d6) δ 12.73 (s, 1H), 8.84 (s, 2H), 8.42 (s, 3H), 8.26-8.19 (m, 3H), 8.16 (d, 4H), 8.00 (s, 3H), 7.98-7.90 (m, 3H), 7.75 (d, 3H), 5.09 (s, 3H), 4.43 (s, 2H), 4.38 (s, 2H), 4.22 (d, 6H), 4.06 (t, 5H), 3.99-3.92 (m, 9H), 3.75-3.51 (m, 6H), 1.99 (dd, 5H), 1.47-1.36 (m, 17H). HPLC: (254 nm) 100%; Rt (min) 2.25. LC/MS: 491.4.

Example 23: 2-[3-(1-Methyl-1H-pyrazol-4-yl)-phenyl]-5-[1-(tetrahydro-pyran-4-yl)-1H-pyrazol-4-yl]-4-trifluoromethyl-pyridine Step 1: 5-Chloro-2-[3-(1-methyl-1H-pyrazol-4-yl)-phenyl]-4-trifluoromethyl-pyridine

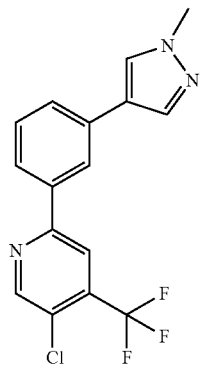 [SMILES: Cn1cc(-c2cccc(-c3cc(C(F)(F)F)c(Cl)cn3)c2)cn1]

A mixture of 2-Bromo-5-chloro-4-trifluoromethyl-pyridine (0.23 mL; 1.92 mmol; 1.00 eq.), 1-Methyl-4-[3-(4,4,5,5-tetramethyl-[1,3,2]dioxaborolan-2-yl)-phenyl]-1H-pyrazole (573 mg; 2.02 mmol; 1.05 eq.), Tetrakis(triphenylphosphine)palladium (11 mg; 0.01 mmol; 0.01 eq.) and potassium carbonate (0.32 g; 2.30 mmol; 1.20 eq.) in dioxane (10.00 mL) and water (1 mL) was stirred in a sealed tube at 90° C. overnight. It was then concentrated under reduced pressure and purified by flash chromatography on silica (EtOAc: Hexane, gradient from 10 to 50%) to give the title compound as a yellow solid (285 mg, 42%); LC/MS: 338.1 (M+1).

Step 2: 2-[3-(1-Methyl-1H-pyrazol-4-yl)-phenyl]-5-[1-(tetrahydro-pyran-4-yl)-1H-pyrazol-4-yl]-4-trifluoromethyl-pyridine

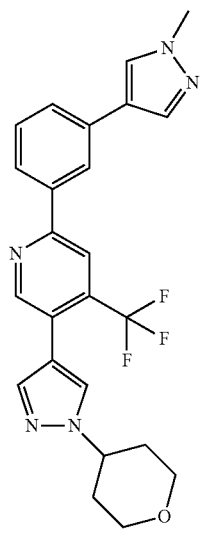 [SMILES: Cn1cc(-c2cccc(-c3cc(C(F)(F)F)c(-c4cnn(C5CCOCC5)c4)cn3)c2)cn1]

A mixture of 5-Chloro-2-[3-(1-methyl-1H-pyrazol-4-yl)-phenyl]-4-trifluoromethyl-pyridine (40 mg; 0.12 mmol; 1.00 eq.), 1-(Tetrahydro-pyran-4-yl)-4-(4,4,5,5-tetramethyl-[1,3,2]dioxaborolan-2-yl)-1H-pyrazole (35 mg; 0.12 mmol; 1.05 eq.), Tetrakis(triphenylphosphine)palladium (0.68 mg; 0.0006 mmol; 0.01 eq.) and potassium carbonate (0.02 g; 0.14 mmol; 1.20 eq.) in Dioxane (1 mL) and Water (0.1 mL) was stirred in a sealed vial at 150° C. overnight. It was then concentrated under reduced pressure and purified by flash chromatography on silica (Hexane: EtOAc, gradient from 80:20 to 100:0 then EtOAc: MeOH, 100 to 80%) then by preparative HPLC to give the title compound as a white solid (35 mg, 62%). 1H NMR (400 MHz, DMSO-d6) δ 8.94 (s, 1H), 8.32 (d, J=15.7 Hz, 3H), 8.20 (s, 1H), 8.06-7.99 (m, 2H), 7.79 (s, 1H), 7.70 (d, J=7.5 Hz, 1H), 7.53 (t, J=7.8 Hz, 1H), 4.53 (td, J=10.2, 5.1 Hz, 1H), 4.00 (dt, J=13.6, 2.7 Hz, 2H), 3.91 (d, J=1.4 Hz, 3H), 3.50 (td, J=11.2, 3.8 Hz, 2H), 2.04 (dtd, J=12.0, 6.7, 5.2, 2.2 Hz, 4H); HPLC: 99.8% (254 nm); Rt (min) 4.45; LC/MS: 454.2 (M+1).

Example 24: 4-Methyl-2-[3-(1-methyl-1H-pyrazol-4-yl)-phenyl]-5-[1-(tetrahydro-pyran-4-yl)-1H-pyrazol-4-yl]-pyridine Step 1: 2-Chloro-4-methyl-5-[1-(tetrahydro-pyran-4-yl)-1H-pyrazol-4-yl]-pyridine

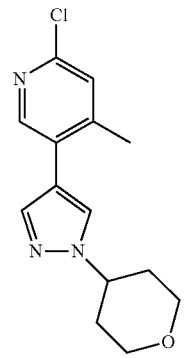 [SMILES: Cc1cc(Cl)ncc1-c1cnn(C2CCOCC2)c1]

A mixture of 5-Bromo-2-chloro-4-methyl-pyridine (200 mg; 0.97 mmol; 1.00 eq.), 1-(Tetrahydro-pyran-4-yl)-4-(4,4,5,5-tetramethyl-[1,3,2]dioxaborolan-2-yl)-1H-pyrazole (283 mg; 1.02 mmol; 1.05 eq.), [1,1'-bis(diphenylphosphino)ferrocene]dichloropalladium(II), complex with dichloromethane (1:1) (158 mg; 0.19 mmol; 0.20 eq.), cesium carbonate (947 mg; 2.91 mmol; 3.00 eq.) s in dioxane (5.00 mL) and water (0.50 mL) was stirred in a sealed vial at 90° C. overnight. It was then concentrated under reduced pressure and purified by flash chromatography on silica (Hexane: EtOAc, gradient from 80 to 20%) to afford the title compound as a yellow solid (170 mg, 63%). LC/MS: 278.1 (M+1).

Step 2: 4-Methyl-2-[3-(1-methyl-1H-pyrazol-4-yl)-phenyl]-5-[1-(tetrahydro-pyran-4-yl)-1H-pyrazol-4-yl]-pyridine

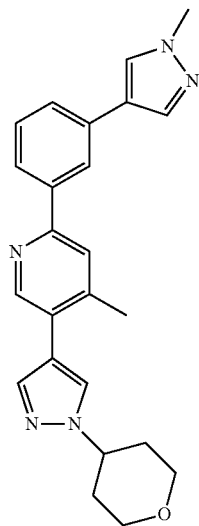 [SMILES: Cc1cc(-c2cccc(-c3cnn(C)c3)c2)ncc1-c1cnn(C2CCOCC2)c1]

A mixture of 2-Chloro-4-methyl-5-[1-(tetrahydro-pyran-4-yl)-1H-pyrazol-4-yl]-pyridine (50 mg; 0.18 mmol; 1.00 eq.), 1-Methyl-4-[3-(4,4,5,5-tetramethyl-[1,3,2]dioxaborolan-2-yl)-phenyl]-1H-pyrazole (54 mg; 0.19 mmol; 1.05 eq.), [1,1'-bis(diphenylphosphino)ferrocene]dichloropalladium(II), complex with dichloromethane (1:1) (0.74 mg; 0.0006 mmol; 0.01 eq.), cesium carbonate (90 mg; 0.27 mmol; 1.50 eq.) in Dioxane (2 mL) and Water (0.20 mL) was stirred in a sealed vial at 120° C. overnight. It was then concentrated under reduced pressure and purified by flash chromatography on KPNH (Hexane:EtOAc, gradient 70 to 20%) then by preparative HPLC to give to title compound as a white solid (15 mg, 21%). 1H NMR (400 MHz, DMSO-d6) δ 8.69 (s, 1H), 8.30-8.21 (m, 4H), 7.99-7.86 (m, 5H), 7.61 (d, J=7.4 Hz, 2H), 7.47 (t, J=7.7 Hz, 1H), 4.49 (p, J=8.4, 7.6 Hz, 1H), 4.04-3.97 (m, 3H), 3.90 (d, J=1.3 Hz, 3H), 3.55-3.46 (m, 3H), 2.04 (td, J=10.6, 9.2, 3.7 Hz, 5H); HPLC: 91% (254 nm); LC/MS: 400.2 (M+1).

Example 25 and 26: 2-{5-(1-Methyl-1H-pyrazol-4-yl)-2-[3-(1-methyl-1H-pyrazol-4-yl)-phenyl]-pyrimidin-4-ylamino}-acetamide formate and {5-(1-Methyl-1H-pyrazol-4-yl)-2-[3-(1-methyl-1H-pyrazol-4-yl)-phenyl]-pyrimidin-4-ylamino}-acetic Acid Formate

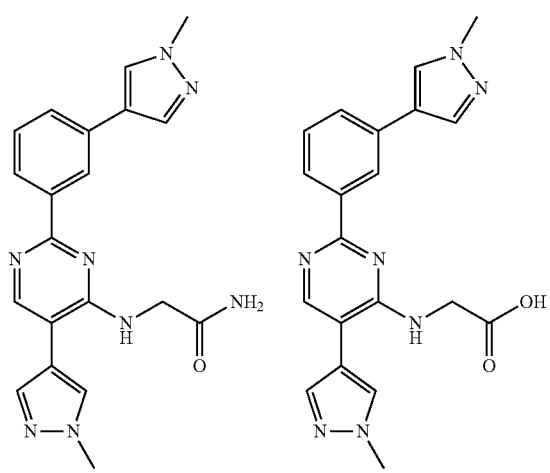 [SMILES: Cn1cc(-c2cccc(-c3ncc(-c4cnn(C)c4)c(NCC(N)=O)n3)c2)cn1 ; Cn1cc(-c2cccc(-c3ncc(-c4cnn(C)c4)c(NCC(=O)O)n3)c2)cn1]

A mixture of 2-[2-Chloro-5-(1-methyl-1H-pyrazol-4-yl)-pyrimidin-4-ylamino]-acetamide (50 mg; 0.19 mmol; 1.00 eq.), 1-Methyl-4-[3-(4,4,5,5-tetramethyl-[1,3,2]dioxaborolan-2-yl)-phenyl]-1H-pyrazole (80 mg; 0.28 mmol; 1.50 eq.), [1,1'-bis(diphenylphosphino)ferrocene]dichloropalladium(II).CH$_2$Cl$_2$ (15 mg; 0.02 mmol; 0.10 eq.) and cesium carbonate (91.6 mg; 0.28 mmol; 1.50 eq.) in dioxane (2 mL) and water (0.20 mL) was stirred at 120° C. overnight. The reaction mixture was then concentrated under reduced pressure and purified by flash chromatography on KPNH (EtOAc: MeOH gradient from 0 to 100%) to give the title compounds as a mixture. The two compounds were separated by preparative HPLC:

First eluting fraction (example 25, 2-{5-(1-Methyl-1H-pyrazol-4-yl)-2-[3-(1-methyl-1H-pyrazol-4-yl)-phenyl]-pyrimidin-4-ylamino}-acetamide formate): white solid (9 mg, 11%): 1H NMR (400 MHz, DMSO-d6) δ 8.55 (d, J=1.9 Hz, 1H), 8.42 (s, OH), 8.28 (s, 1H), 8.23-8.15 (m, 2H), 8.11 (s, 1H), 7.94 (s, 1H), 7.81 (s, 1H), 7.66 (d, J=7.8 Hz, 1H), 7.53 (s, 1H), 7.45 (t, J=7.7 Hz, 1H), 7.12 (s, 1H), 6.93 (t, J=5.4 Hz, 1H), 6.63 (s, 1H), 4.03-3.88 (m, 8H); HPLC: 98.8% (254 nm); LC/MS: 389.2 (M+H).

Second eluting fraction (example 26, 5-(1-Methyl-1H-pyrazol-4-yl)-2-[3-(1-methyl-1H-pyrazol-4-yl)-phenyl]-pyrimidin-4-ylamino}-acetic formate): white solid (12 mg, 14.7%): 1H NMR (400 MHz, DMSO-d6) δ 8.51 (s, 1H), 8.30 (s, 1H), 8.20-8.14 (m, 2H), 8.07 (s, 1H), 7.91 (s, 1H), 7.78 (s, 1H), 7.66 (d, J=8.0 Hz, 1H), 7.45 (t, J=7.7 Hz, 1H), 7.08 (t, J=5.5 Hz, 1H), 6.52 (s, OH), 4.08 (s, 2H), 3.92 (d, J=15.5 Hz, 4H); HPLC: 98.6% (254 nm); LC/MS: 390.2 (M+1)

Example 27: Cyclobutyl-{5-(1-methyl-1H-pyrazol-3-yl)-2-[3-(1-methyl-1H-pyrazol-4-yl)-phenyl]-pyrimidin-4-yl}-amine

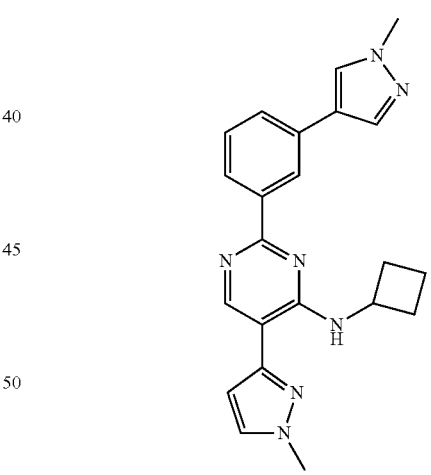

A mixture of [2-Chloro-5-(1-methyl-1H-pyrazol-3-yl)-pyrimidin-4-yl]-cyclobutyl-amine (60 mg; 0.23 mmol; 1.00 eq.), 1-Methyl-4-[3-(4,4,5,5-tetramethyl-[1,3,2]dioxaborolan-2-yl)-phenyl]-1H-pyrazole (97 mg; 0.34 mmol; 1.50 eq.), [1,1'-bis(diphenylphosphino)ferrocene]dichloropalladium(II).CH$_2$Cl$_2$ (18 mg; 0.02 mmol; 0.10 eq.) and cesium carbonate (111 mg; 0.34 mmol; 1.50 eq.) in dioxane (2.00 mL) and water (0.20 mL) was stirred at 120° C. overnight in a sealed vial. The reaction mixture was then concentrated under reduced pressure and purified by flash chromatography on KPNH (EtOAc: hexane, gradient from 40 to 70%) followed by a second purification by preparative HPLC to give the title compounds as a white solid (17 mg, 17%). 1H NMR (400 MHz, DMSO-d6) δ 9.21 (s, 1H), 8.78 (s, 1H), 8.53 (t, J=1.8 Hz, 1H), 8.27-8.12 (m, 2H), 7.98-7.87 (m, 2H), 7.74 (dt, J=7.7, 1.4 Hz, 1H), 7.54 (t, J=7.7 Hz, 1H), 7.04 (d, J=2.4 Hz, 1H), 4.81 (h, J=8.0 Hz, 1H), 3.96 (d, J=34.9 Hz, 6H), 2.18-2.05 (m, 2H), 1.96-1.81 (m, 2H); HPLC: 98.0% (254 nm); LC/MS: 386.2 (M+H).

Example 28: 2-Aminomethyl-2-(2-{5-(1-methyl-1H-pyrazol-4-yl)-2-[3-(1-methyl-1H-pyrazol-4-yl)-phenyl]-pyrimidin-4-ylamino}-ethyl)-propane-1,3-diol Step 1: 6-{5-(1-Methyl-1H-pyrazol-4-yl)-2-[3-(1-methyl-1H-pyrazol-4-yl)-phenyl]-pyrimidin-4-ylamino}-2-aza-spiro[3.3]heptane-2-carboxylic Acid Tert-Butyl Ester

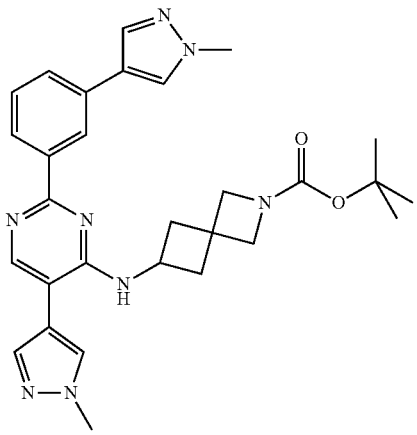 [SMILES: Cn1cc(-c2cccc(-c3ncc(-c4cnn(C)c4)c(NC4CC5(C4)CN(C(=O)OC(C)(C)C)C5)n3)c2)cn1]

A mixture of 6-[2-Chloro-5-(1-methyl-1H-pyrazol-4-yl)-pyrimidin-4-ylamino]-2-aza-spiro[3.3]heptane-2-carboxylic acid tert-butyl ester (190 mg; 0.47 mmol; 1.00 eq.), 1-Methyl-4-[3-(4,4,5,5-tetramethyl-[1,3,2]dioxaborolan-2-yl)-phenyl]-1H-pyrazole (160 mg; 0.56 mmol; 1.20 eq.), [1,1'-bis(diphenylphosphino)ferrocene]dichloropalladium (II).CH$_2$Cl$_2$ (38 mg; 0.05 mmol; 0.10 eq.), cesium carbonate (229 mg; 0.70 mmol; 1.50 eq.) in dioxane (3.00 mL) and water (0.30 mL) was stirred at 120° C. overnight in a sealed tube. The mixture was then concentrated under reduced pressure and purified by flash chromatography on silica (MeOH: EtOAc, gradient from 0:100 to 20:80) to give the title compound as a yellow solid (156 mg, 63%). LC/MS: 527.3 (M+H).

Step 2: 2-Aminomethyl-2-(2-{5-(1-methyl-1H-pyrazol-4-yl)-2-[3-(1-methyl-1H-pyrazol-4-yl)-phenyl]-pyrimidin-4-ylamino}-ethyl)-propane-1,3-diol

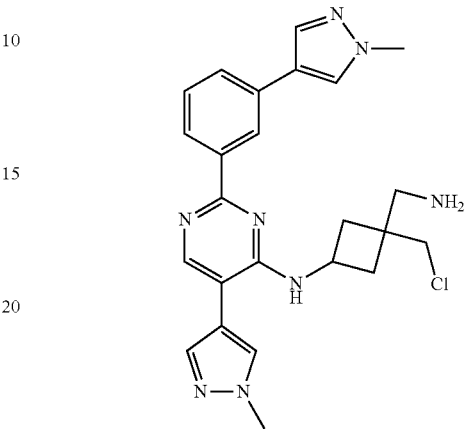

Hydrogen chloride (0.71 mL of a 2 M solution in Et2O; 1.42 mmol; 5.00 eq.) was added to a solution of 6-{5-(1-Methyl-1H-pyrazol-4-yl)-2-[3-(1-methyl-1H-pyrazol-4-yl)-phenyl]-pyrimidin-4-ylamino}-2-aza-spiro[3.3]heptane-2-carboxylic acid tert-butyl ester (150 mg; 0.28 mmol; 1.00 eq.) in methanol (3.00 mL). The reaction mixture was then stirred at rt overnight.

LCMS analysis of the reaction mixture indicated that the reaction was complete but major product appeared to be a ring-opening by-product. Reaction mixture was concentrated under reduced pressure and purified by preparative HPLC to afford the title compound as a white solid (13 mg, 10%). 1H NMR (400 MHz, DMSO-d6) δ 8.53 (d, J=1.9 Hz, 1H), 8.25-8.15 (m, 3H), 8.06 (s, 1H), 7.90 (s, 1H), 7.76 (s, 1H), 7.66 (d, J=7.7 Hz, 1H), 7.47 (t, J=7.6 Hz, 1H), 6.77 (d, J=6.3 Hz, 1H), 4.73 (m, 1H), 3.99-3.86 (m, 7H), 2.67 (s, 2H), 2.35-2.27 (m, 2H), 2.05-1.96 (m, 2H); HPLC: 97.0% (254 nm); LC/MS: 463.3 (M+H).

Compounds below were prepared following similar routes and protocols:

| Structure | Example | Analyticals |
|---|---|---|
| (structure shown) | 29 | white solid. HPLC(Column): (254 nm) 98%. LC/MS(Column): (M + H) 372.2. 1H NMR (400 MHz, DMSO-d6) δ 9.14 (s, 1H), 8.78 (s, 1H), 8.61 (t, J = 1.8 Hz, 1H), 8.25 (d, J = 8.2 Hz, 2H), 7.99-7.87 (m, 2H), 7.77 (dt, J = 7.7, 1.4 Hz, 1H), 7.55 (t, J = 7.8 Hz, 1H), 7.04 (d, J = 2.4 Hz, 1H), 3.94 (d, J = 23.6 Hz, 6H), 3.26 (tq, J = 7.5, 3.9 Hz, 1H), 0.98 (td, J = 7.0, 4.9 Hz, 2H), 0.75-0.68 (m, 2H). |

| Structure | Example | Analyticals |
|---|---|---|
| 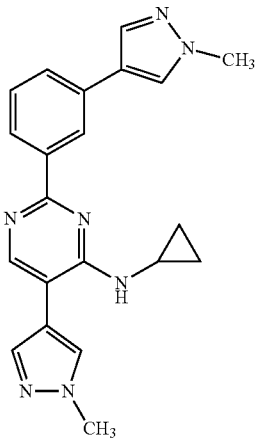 [SMILES: Cn1cc(-c2cccc(-c3ncc(-c4cnn(C)c4)c(NC4CC4)n3)c2)cn1] | 30 | white solid. HPLC(Column): (254 nm) 97%. LC/MS(Column): (M + H) 372.2. 1H NMR (400 MHz, DMSO-d6) δ 8.56 (t, J = 1.8 Hz, 1H), 8.28-8.17 (m, 3H), 8.01 (s, 1H), 7.88 (s, 1H), 7.74-7.64 (m, 2H), 7.47 (t, J = 7.7 Hz, 1H), 6.66 (d, J = 3.2 Hz, 1H), 3.90 (s, 5H), 3.01 (tq, J = 7.2, 3.7 Hz, 1H), 0.82 (td, J = 7.0, 4.7 Hz, 2H), 0.69-0.63 (m, 2H). |
| 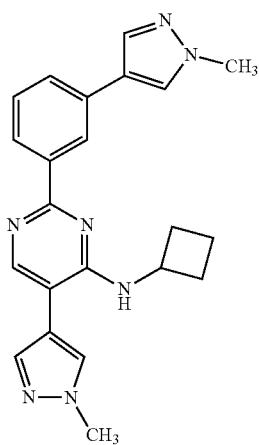 [SMILES: Cn1cc(-c2cccc(-c3ncc(-c4cnn(C)c4)c(NC4CCC4)n3)c2)cn1] | 31 | white solid. HPLC(Column): (254 nm) 99%. LC/MS(Column): (M + H) 386.2. 1H NMR (400 MHz, DMSO-d6) δ 8.49 (t, J = 1.8 Hz, 1H), 8.23-8.16 (m, 3H), 8.06 (s, 1H), 7.88 (s, 1H), 7.74 (s, 1H), 7.66 (dt, J = 7.6, 1.5 Hz, 1H), 7.48 (t, J = 7.7 Hz, 1H), 6.63 (d, J = 6.8 Hz, 1H), 4.72 (h, J = 8.0 Hz, 1H), 3.92 (d, J = 10.2 Hz, 6H), 2.36 (ddt, J = 14.6, 10.5, 5.2 Hz, 2H), 2.16 (pd, J = 9.5, 5.4 Hz, 2H), 1.83-1.71 (m, 2H). |
| 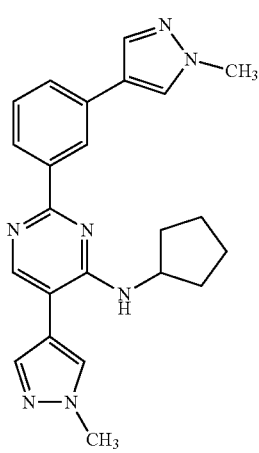 | 32 | white solid. HPLC(Column): (254 nm) 99%. LC/MS(Column): (M + H) 400.2. 1H NMR (400 MHz, DMSO-d6) δ 8.50 (t, J = 1.8 Hz, 1H), 8.23-8.17 (m, 3H), 8.04 (s, 1H), 7.87 (d, J = 0.8 Hz, 1H), 7.74 (d, J = 0.8 Hz, 1H), 7.66 (dt, J = 7.7, 1.5 Hz, 1H), 7.48 (t, J = 7.7 Hz, 1H), 6.20 (d, J = 6.8 Hz, 1H), 4.56 (h, J = 7.0 Hz, 1H), 3.91 (d, J = 9.6 Hz, 6H), 2.09 (dt, J = 7.7, 4.5 Hz, 2H), 1.76-1.59 (m, 7H). |

| Structure | Example | Analyticals |
|---|---|---|
| 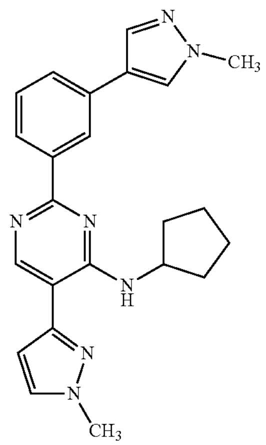 [SMILES: Cn1cc(-c2cccc(-c3ncc(-c4ccn(C)n4)c(NC4CCCC4)n3)c2)cn1] | 33 | white solid. HPLC(Column): (254 nm) 99%. LC/MS(Column): (M + H) 400.3. 1H NMR (400 MHz, DMSO-d6) δ 8.73 (d, J = 30.3 Hz, 2H), 8.54 (t, J = 1.7 Hz, 1H), 8.26-8.17 (m, 2H), 7.88 (dd, J = 4.5, 1.6 Hz, 2H), 7.67 (dt, J = 7.7, 1.5 Hz, 1H), 7.49 (t, J = 7.7 Hz, 1H), 6.95 (d, J = 2.4 Hz, 1H), 4.63 (h, J = 6.5 Hz, 1H), 3.93 (d, J = 19.6 Hz, 6H), 2.24-2.12 (m, 2H), 1.84-1.57 (m, 4H). |
| 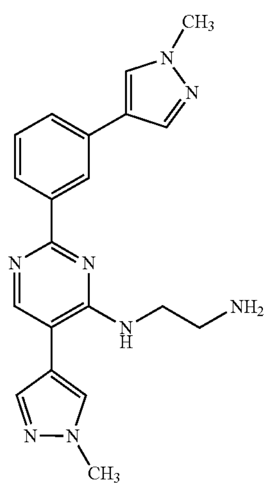 [SMILES: Cn1cc(-c2cccc(-c3ncc(-c4cnn(C)c4)c(NCCN)n3)c2)cn1] | 34 | yellow solid. HPLC(Column): (254 nm) 98%. LC/MS(Column): (M + H) 375.3. 1H NMR (400 MHz, DMSO-d6) δ 8.66 (t, J = 1.8 Hz, 1H), 8.43-8.03 (m, 9H), 7.88 (d, J = 16.6 Hz, 2H), 7.60 (t, J = 7.8 Hz, 1H), 3.94 (d, J = 13.7 Hz, 7H), 3.18 (h, J = 6.3 Hz, 2H). |
| 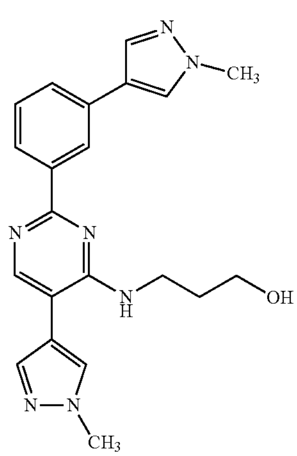 | 35 | white solid. HPLC(Column): (254 nm) 100%. LC/MS(Column): (M + H) 390.2. 1H NMR (400 MHz, DMSO-d6) δ 8.53 (s, 1H), 8.20 (t, J = 6.4 Hz, 3H), 8.04 (s, 1H), 7.89 (s, 1H), 7.79-7.62 (m, 2H), 7.47 (t, J = 7.7 Hz, 1H), 6.75 (t, J = 5.6 Hz, 1H), 4.66 (d, J = 4.7 Hz, 1H), 3.91 (d, J = 8.9 Hz, 6H), 3.60 (dq, J = 21.8, 5.8, 5.2 Hz, 4H), 1.84 (p, J = 6.5 Hz, 2H). |

| Structure | Example | Analyticals |
|---|---|---|
| 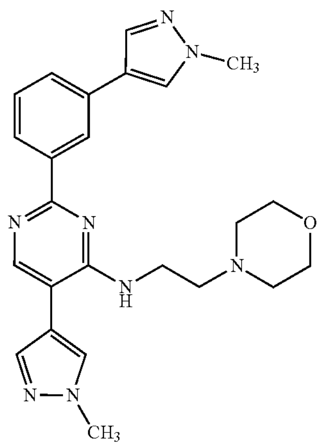 [SMILES: Cn1cc(-c2cccc(-c3ncc(-c4cnn(C)c4)c(NCCN4CCOCC4)n3)c2)cn1] | 36 | white solid. HPLC(Column): (254 nm) 100%. LC/MS(Column): (M + H) 445.3. 1H NMR (400 MHz, DMSO-d6) δ 8.51 (d, J = 1.7 Hz, 1H), 8.26-8.15 (m, 3H), 8.05 (s, 1H), 7.88 (s, 1H), 7.76 (s, 1H), 7.66 (dd, J = 7.7, 1.6 Hz, 1H), 7.47 (td, J = 7.7, 1.2 Hz, 1H), 6.63 (t, J = 5.4 Hz, 1H), 3.92 (dd, J = 13.9, 1.2 Hz, 6H), 3.67 (q, J = 6.4 Hz, 2H), 3.62-3.55 (m, 4H), 2.60 (t, J = 6.8 Hz, 2H), 2.48 (d, J = 4.7 Hz, 3H). |
| 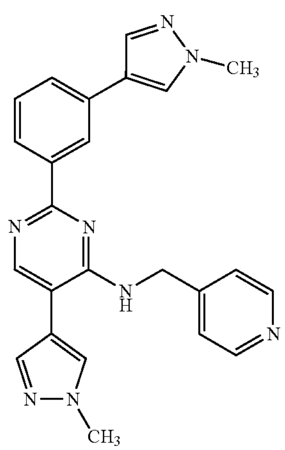 [SMILES: Cn1cc(-c2cccc(-c3ncc(-c4cnn(C)c4)c(NCc4ccncc4)n3)c2)cn1] | 37 | off-white solid. HPLC(Column): (254 nm) 100%. LC/MS(Column): (M + H) 423.2. 1H NMR (400 MHz, DMSO-d6) δ 8.54-8.44 (m, 2H), 8.27 (dd, J = 7.0, 1.4 Hz, 2H), 8.13 (s, 1H), 8.07 (s, 1H), 8.01 (dd, J = 7.8, 1.5 Hz, 1H), 7.85-7.77 (m, 2H), 7.64-7.58 (m, 1H), 7.48-7.36 (m, 4H), 4.73 (d, J = 5.7 Hz, 2H), 3.93 (dd, J = 17.4, 1.2 Hz, 6H). |
| 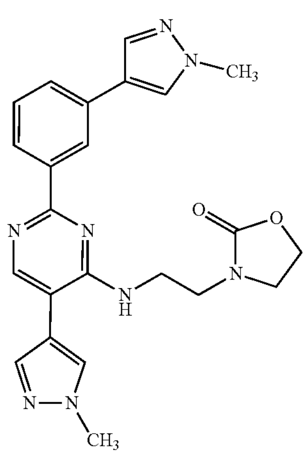 [SMILES: Cn1cc(-c2cccc(-c3ncc(-c4cnn(C)c4)c(NCCN4CCOC4=O)n3)c2)cn1] | 38 | white solid. HPLC(Column): (254 nm) 100%. LC/MS(Column): (M + H) 445.2. 1H NMR (400 MHz, DMSO-d6) δ 8.52 (d, J = 1.6 Hz, 1H), 8.27-8.19 (m, 3H), 8.01 (s, 1H), 7.92 (s, 1H), 7.73 (s, 1H), 7.69-7.64 (m, 1H), 7.46 (td, J = 7.8, 1.2 Hz, 1H), 6.82 (t, J = 5.9 Hz, 1H), 4.17 (dd, J = 8.9, 6.9 Hz, 2H), 3.91 (dd, J = 11.4, 1.3 Hz, 6H), 3.70 (ddd, J = 23.0, 10.5, 6.8 Hz, 4H), 3.49 (t, J = 6.2 Hz, 2H). |

-continued

| Structure | Example | Analyticals |
|---|---|---|
| 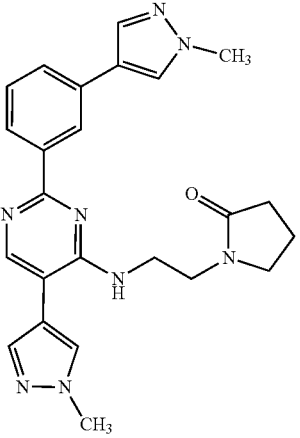 | 39 | white solid. HPLC(Column): (254 nm) 100%. LC/MS(Column): (M + H) 443.2. 1H NMR (400 MHz, DMSO-d6) δ 8.54 (d, J = 1.7 Hz, 1H), 8.29 (s, 1H), 8.26-8.19 (m, 2H), 8.02 (s, 1H), 7.93 (s, 1H), 7.73 (s, 1H), 7.69-7.64 (m, 1H), 7.49-7.43 (m, 1H), 6.76 (t, J = 5.9 Hz, 1H), 3.91 (dd, J = 9.1, 1.3 Hz, 6H), 3.71 (q, J = 6.1 Hz, 2H), 3.48 (dt, J = 13.4, 6.6 Hz, 4H), 2.15 (t, J = 8.0 Hz, 2H), 1.82 (p, J = 7.7 Hz, 2H). |
| 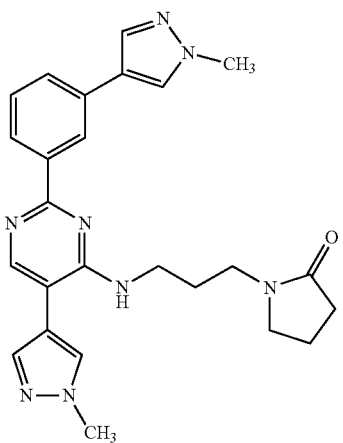 | 40 | white solid. HPLC(Column): (254 nm) 100%. LC/MS(Column): (M + H) 457.3. 1H NMR (400 MHz, DMSO-d6) δ 8.52-8.46 (m, 1H), 8.26-8.15 (m, 3H), 8.09 (s, 1H), 7.89 (s, 1H), 7.77 (s, 1H), 7.69-7.63 (m, 1H), 7.47 (t, J = 7.8 Hz, 1H), 6.72 (t, J = 5.9 Hz, 1H), 3.91 (dd, J = 8.4, 1.2 Hz, 6H), 3.52 (q, J = 6.5 Hz, 2H), 3.37 (t, J = 7.0 Hz, 2H), 2.23 (t, J = 8.0 Hz, 2H), 1.88 (dp, J = 20.8, 7.2 Hz, 4H). |
| 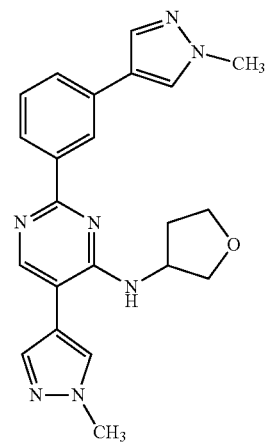 [SMILES: Cn1cc(-c2cccc(-c3ncc(-c4cnn(C)c4)c(NC4CCOC4)n3)c2)cn1] | 41 | white solid. HPLC(Column): (254 nm) 100%. LC/MS(Column): (M + H) 402.2. 1H NMR (400 MHz, DMSO-d6) δ 8.50 (q, J = 1.5 Hz, 1H), 8.26 (d, J = 1.1 Hz, 1H), 8.19 (d, J = 8.3 Hz, 2H), 8.06 (s, 1H), 7.89 (s, 1H), 7.76 (s, 1H), 7.67 (dd, J = 7.7, 1.6 Hz, 1H), 7.52-7.45 (m, 1H), 6.47 (d, J = 6.0 Hz, 1H), 4.77 (h, J = 5.6 Hz, 1H), 4.11-4.04 (m, 1H), 3.91 (dd, J = 9.0, 1.1 Hz, 7H), 3.78 (td, J = 8.3, 6.6 Hz, 1H), 3.69 (dd, J = 8.8, 4.7 Hz, 1H), 2.29 (ddd, J = 15.1, 13.5, 7.5 Hz, 1H), 2.11-2.01 (m, 1H). |

-continued

| Structure | Example | Analyticals |
|---|---|---|
| 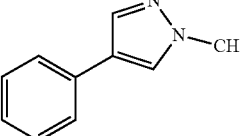 | 42 | white solid. HPLC(Column): (254 nm) 100%; (NMR looks 100%.). LC/MS(Column): (M + H) 436.2. 1H NMR (400 MHz, DMSO-d6) δ 8.50 (d, J = 1.7 Hz, 1H), 8.23-8.16 (m, 3H), 8.02 (s, 1H), 7.88 (s, 1H), 7.73 (s, 1H), 7.69-7.64 (m, 1H), 7.47 (t, J = 7.7 Hz, 1H), 6.89 (t, J = 6.0 Hz, 1H), 3.91 (dd, J = 12.9, 1.2 Hz, 6H), 3.70 (t, J = 6.2 Hz, 2H), 2.74-2.57 (m, 3H). |
| 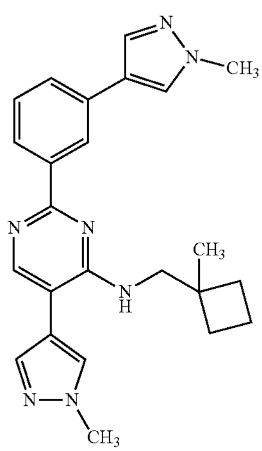 [SMILES: Cn1cc(-c2cccc(-c3ncc(-c4cnn(C)c4)c(NCC4(C)CCC4)n3)c2)cn1] | 43 | white solid. HPLC(Column): (254 nm) 100%. LC/MS(Column): (M + H) 414.3. 1H NMR (400 MHz, DMSO-d6) δ 8.55-8.48 (m, 1H), 8.25-8.14 (m, 3H), 8.03 (s, 1H), 7.86 (s, 1H), 7.74 (s, 1H), 7.65 (dd, J = 7.6, 1.6 Hz, 1H), 7.47 (td, J = 7.7, 1.2 Hz, 1H), 6.57 (t, J = 6.3 Hz, 1H), 3.92 (dd, J = 14.4, 1.2 Hz, 6H), 3.64 (d, J = 6.1 Hz, 2H), 2.06 (dt, J = 9.8, 7.6 Hz, 2H), 1.87 (p, J = 7.5 Hz, 2H), 1.65 (q, J = 8.3, 7.8 Hz, 2H), 1.18 (d, J = 1.2 Hz, 3H). |
| 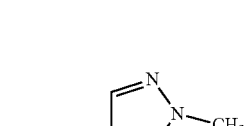 | 44 | white solid. HPLC(Column): (254 nm) 100%. LC/MS(Column): (M + H) 429.2. 1H NMR (400 MHz, DMSO-d6) δ 8.49 (d, J = 1.8 Hz, 1H), 8.26-8.14 (m, 3H), 8.08 (s, 1H), 7.87 (s, 1H), 7.78 (s, 1H), 7.69-7.62 (m, 1H), 7.47 (t, J = 7.7 Hz, 1H), 5.91 (d, J = 7.0 Hz, 1H), 4.20 (qd, J = 8.5, 7.8, 4.5 Hz, 1H), 3.92 (d, J = 17.0 Hz, 6H), 2.91 (p, J = 4.8 Hz, 1H), 1.89 (dtd, J = 13.2, 9.8, 9.2, 3.8 Hz, 2H), 1.76-1.60 (m, 4H), 1.45 (dp, J = 15.2, 6.2, 5.2 Hz, 2H). |

-continued

| Structure | Example | Analyticals |
|---|---|---|
| 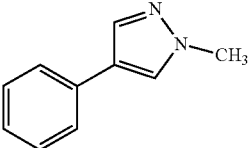 | 45 | white solid. HPLC(Column): (254 nm) 100%. LC/MS(Column): (M + H) 434.2. 1H NMR (400 MHz, DMSO-d6) δ 8.53 (s, 1H), 8.37-8.32 (m, 1H), 8.25-8.18 (m, 2H), 7.96-7.89 (m, 2H), 7.69 (d, J = 7.7 Hz, 1H), 7.62-7.57 (m, 1H), 7.53-7.46 (m, 1H), 4.71 (td, J = 23.2, 8.3 Hz, 4H), 4.34 (d, J = 21.9 Hz, 2H), 3.96-3.86 (m, 6H), 2.91-2.82 (m, 3H). |
| 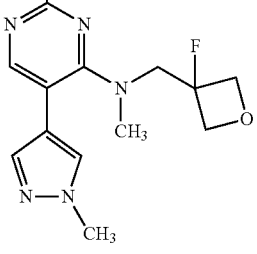 | 46 | white solid. HPLC(Column): (254 nm) 95%. LC/MS(Column): (M + H) 402.2. 1H NMR (400 MHz, DMSO-d6) δ 8.50 (s, 1H), 8.26-8.14 (m, 3H), 8.09-8.03 (m, 1H), 7.91-7.85 (m, 1H), 7.78-7.72 (m, 1H), 7.66 (d, J = 7.6 Hz, 1H), 7.48 (ddd, J = 9.1, 5.3, 2.1 Hz, 1H), 6.60 (dd, J = 6.1, 2.3 Hz, 1H), 5.04 (s, 1H), 4.74 (q, J = 6.9 Hz, 1H), 4.39-4.29 (m, 1H), 3.98-3.84 (m, 5H), 2.45-2.36 (m, 2H), 2.29 (td, J = 9.4, 8.9, 3.8 Hz, 2H). |
| 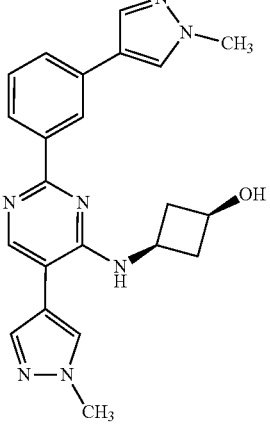 | 47 | white solid. HPLC(Column): (254 nm) 98%. LC/MS(Column): (M + H) 402.2. 1H NMR (400 MHz, DMSO-d6) δ 8.50 (d, J = 1.8 Hz, 1H), 8.25-8.15 (m, 3H), 8.05 (s, 1H), 7.89 (s, 1H), 7.74 (s, 1H), 7.69-7.62 (m, 1H), 7.47 (t, J = 7.7 Hz, 1H), 6.55 (d, J = 6.5 Hz, 1H), 5.06 (s, 1H), 4.17 (h, J = 7.9 Hz, 1H), 3.91 (d, J = 9.7 Hz, 7H), 2.76-2.66 (m, 2H), 2.07-1.96 (m, 2H). |

| Structure | Example | Analyticals |
|---|---|---|
| (structure 48) | 48 | white solid. HPLC(Column): (254 nm) 96%. LC/MS(Column): (M + H) 422.2. 1H NMR (400 MHz, DMSO-d6) δ 8.53-8.45 (m, 1H), 8.28 (d, J = 1.3 Hz, 1H), 8.19 (d, J = 10.7 Hz, 2H), 8.06 (s, 1H), 7.88 (s, 1H), 7.76 (s, 1H), 7.70-7.64 (m, 1H), 7.49 (t, J = 7.7 Hz, 1H), 7.02 (d, J = 6.1 Hz, 1H), 4.55 (hept, J = 7.3 Hz, 1H), 3.92 (dd, J = 13.0, 1.3 Hz, 5H), 3.10-2.81 (m, 4H). |
| (structure 49) | 49 | white solid. HPLC(Column): (254 nm) 100%. LC/MS(Column): (M + H) 464.2. 1H NMR (400 MHz, DMSO-d6) δ 8.50 (s, 1H), 8.28-8.16 (m, 3H), 8.07-8.01 (m, 1H), 7.94-7.89 (m, 1H), 7.77-7.72 (m, 1H), 7.67 (d, J = 7.8 Hz, 1H), 7.48 (ddd, J = 7.9, 4.7, 1.7 Hz, 1H), 6.99-6.92 (m, 1H), 4.69 (hept, J = 8.4, 7.7 Hz, 1H), 3.96-3.81 (m, 7H), 2.96-2.87 (m, 3H), 2.72 (q, J = 8.8 Hz, 2H), 2.49-2.42 (m, 2H). |
| (structure 50) | 50 | white solid. HPLC(Column): (254 nm) 100%. LC/MS(Column): (M + H) 404.2. 1H NMR (400 MHz, DMSO-d6) δ 8.49 (d, J = 1.6 Hz, 1H), 8.27-8.15 (m, 3H), 8.06 (d, J = 3.5 Hz, 1H), 7.89 (d, J = 9.4 Hz, 1H), 7.76 (d, J = 7.3 Hz, 1H), 7.70-7.63 (m, 1H), 7.48 (q, J = 7.2 Hz, 1H), 6.82 (t, J = 5.6 Hz, 1H), 5.42-5.35 (m, 0H), 5.25 (td, J = 6.1, 3.1 Hz, 0H), 5.06 (p, J = 6.8 Hz, 0H), 4.96-4.82 (m, 1H), 4.28 (q, J = 8.0 Hz, 0H), 3.96-3.87 (m, 6H), 2.85 (pd, J = 6.8, 3.3 Hz, 1H), 2.61 (dddd, J = 17.3, 12.9, 9.1, 4.9 Hz, 2H), 2.49-2.36 (m, 1H). |

| Structure | Example | Analyticals |
|---|---|---|
| 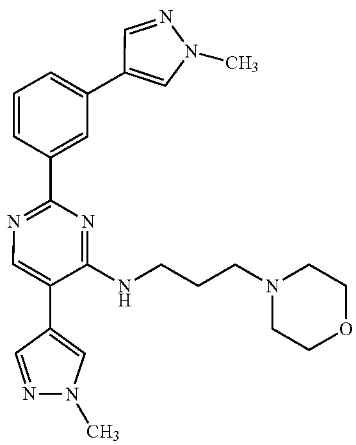 [SMILES: Cn1cc(-c2cccc(-c3ncc(-c4cnn(C)c4)c(NCCCN4CCOCC4)n3)c2)cn1] | 51 | white solid. HPLC(Column): (254 nm) 99%. LC/MS(Column): (M + H) 459.3. 1H NMR (400 MHz, DMSO-d6) δ 8.49 (t, J = 1.7 Hz, 1H), 8.24-8.13 (m, 3H), 8.04 (s, 1H), 7.88 (s, 1H), 7.74 (s, 1H), 7.70-7.62 (m, 1H), 7.47 (t, J = 7.7 Hz, 1H), 6.77 (t, J = 5.6 Hz, 1H), 3.91 (d, J = 9.3 Hz, 6H), 3.64-3.46 (m, 6H), 2.37 (dt, J = 20.1, 5.7 Hz, 6H), 1.81 (h, J = 6.9 Hz, 2H). |
| 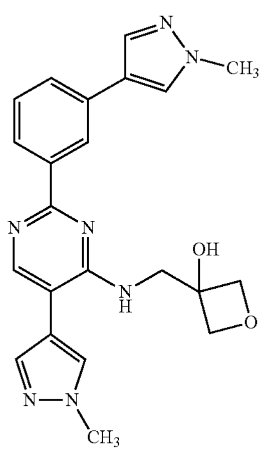 [SMILES: Cn1cc(-c2cccc(-c3ncc(-c4cnn(C)c4)c(NCC4(O)COC4)n3)c2)cn1] | 52 | white solid. HPLC(Column): (254 nm) 97%. LC/MS(Column): (M + H) 418.2. 1H NMR (400 MHz, DMSO-d6) δ 8.53 (d, J = 1.8 Hz, 1H), 8.28-8.15 (m, 3H), 8.07 (s, 1H), 7.91 (s, 1H), 7.77 (s, 1H), 7.72-7.64 (m, 1H), 7.48 (t, J = 7.7 Hz, 1H), 6.63 (t, J = 6.0 Hz, 1H), 6.08 (s, 1H), 4.60 (d, J = 6.1 Hz, 2H), 4.47 (d, J = 6.2 Hz, 2H), 4.01-3.85 (m, 8H). |
| 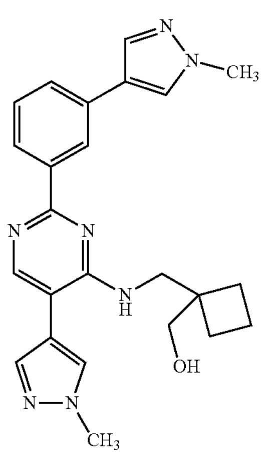 [SMILES: Cn1cc(-c2cccc(-c3ncc(-c4cnn(C)c4)c(NCC4(CO)CCC4)n3)c2)cn1] | 53 | white solid. HPLC(Column): (254 nm) 100%. LC/MS(Column): (M + H) 430.3. 1H NMR (400 MHz, DMSO-d6) δ 8.52 (d, J = 1.7 Hz, 1H), 8.26-8.16 (m, 3H), 8.01 (s, 1H), 7.89 (s, 1H), 7.74 (s, 1H), 7.69-7.63 (m, 1H), 7.48 (t, J = 7.7 Hz, 1H), 6.76 (t, J = 5.6 Hz, 1H), 5.02 (s, 1H), 3.91 (d, J = 9.2 Hz, 7H), 3.75 (d, J = 5.5 Hz, 2H), 3.52 (s, 2H), 1.96-1.76 (m, 6H). |

| Structure | Example | Analyticals |
|---|---|---|
| 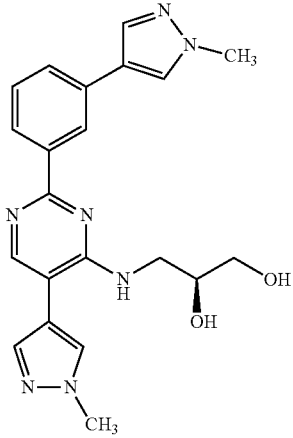 [SMILES: Cn1cc(-c2cccc(-c3ncc(-c4cnn(C)c4)c(NC[C@H](O)CO)n3)c2)cn1] | 54 | white solid. HPLC(Column): (254 nm) 96.1%. LC/MS(Column): (M + H) 406.1H NMR (400 MHz, DMSO-d6) δ 8.53 (d, J = 1.7 Hz, 1H), 8.25-8.16 (m, 3H), 8.06 (s, 1H), 7.91 (s, 1H), 7.76 (s, 1H), 7.70-7.63 (m, 1H), 7.47 (t, J = 7.7 Hz, 1H), 6.53 (t, J = 5.3 Hz, 1H), 4.97-4.89 (m, 1H), 4.79-4.71 (m, 1H), 3.97-3.76 (m, 7H), 3.45 (h, J = 5.4 Hz, 3H). |
| 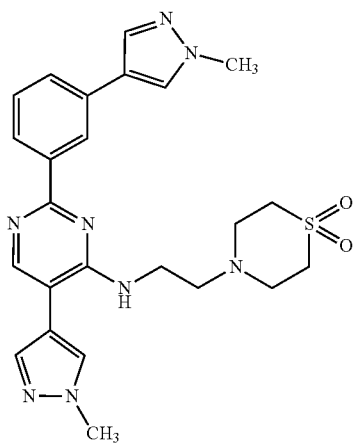 [SMILES: Cn1cc(-c2cccc(-c3ncc(-c4cnn(C)c4)c(NCCN4CCS(=O)(=O)CC4)n3)c2)cn1] | 55 | off-white solid. HPLC(Column): (254 nm) 97%. LC/MS(Column): (M + H) 493.2. 1H NMR (400 MHz, DMSO-d6) δ 8.50 (d, J = 1.7 Hz, 1H), 8.25-8.15 (m, 3H), 8.05 (s, 1H), 7.89 (s, 1H), 7.76 (s, 1H), 7.69-7.63 (m, 1H), 7.48 (t, J = 7.7 Hz, 1H), 6.69-6.60 (m, 1H), 3.92 (d, J = 12.1 Hz, 6H), 3.67 (q, J = 6.4 Hz, 2H), 3.04 (d, J = 2.8 Hz, 8H), 2.80 (t, J = 6.7 Hz, 2H). |
| 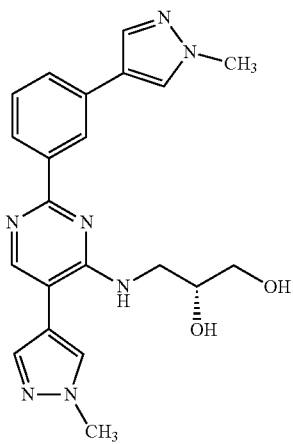 [SMILES: Cn1cc(-c2cccc(-c3ncc(-c4cnn(C)c4)c(NC[C@@H](O)CO)n3)c2)cn1] | 56 | white solid. HPLC(Column): (254 nm) 91%. LC/MS(Column): (M + H) 406.9. 1H NMR (400 MHz, DMSO-d6) δ 8.53 (d, J = 2.3 Hz, 1H), 8.26-8.16 (m, 3H), 8.09-8.03 (m, 1H), 7.93-7.88 (m, 1H), 7.79-7.73 (m, 1H), 7.66 (d, J = 7.7 Hz, 1H), 7.50-7.42 (m, 1H), 7.27 (s, 1H), 6.80-6.45 (m, 2H), 4.96-4.89 (m, 1H), 4.79-4.71 (m, 1H), 3.98-3.76 (m, 8H), 3.45 (q, J = 7.2 Hz, 3H). |

| Structure | Example | Analyticals |
|---|---|---|
| 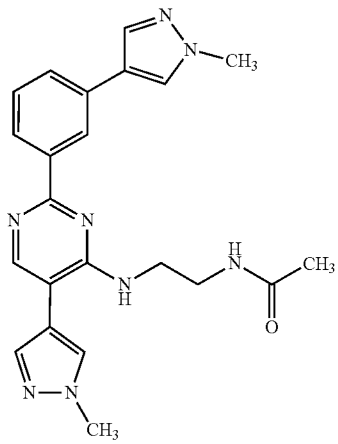 [SMILES: CC(=O)NCCNc1nc(-c2cccc(-c3cnn(C)c3)c2)ncc1-c1cnn(C)c1] | 57 | white solid. HPLC(Column): (254 nm) 97%. LC/MS(Column): (M + H) 417.85. 1H NMR (400 MHz, DMSO-d6) δ 8.54 (s, 1H), 8.36-8.29 (m, 1H), 8.25-8.18 (m, 2H), 8.08-8.00 (m, 2H), 7.97-7.91 (m, 1H), 7.78-7.73 (m, 1H), 7.66 (d, J = 7.8 Hz, 1H), 7.45 (ddd, J = 9.0, 5.4, 2.2 Hz, 1H), 6.74 (d, J = 6.1 Hz, 1H), 3.95-3.86 (m, 6H), 3.62 (dt, J = 6.7, 3.7 Hz, 2H), 3.41-3.35 (m, 2H), 1.84-1.78 (m, 3H). |
| 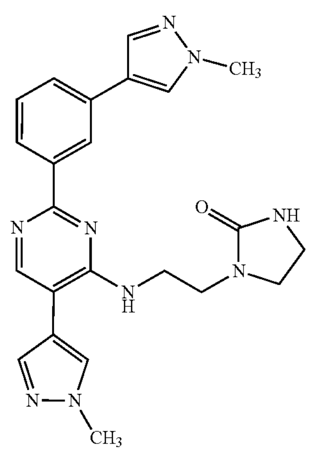 [SMILES: Cn1cc(-c2cccc(-c3ncc(-c4cnn(C)c4)c(NCCN4CCNC4=O)n3)c2)cn1] | 58 | yellow solid. HPLC(Column): (254 nm) 82%. LC/MS(Column): (M + H) 444.9. 1H NMR (400 MHz, DMSO-d6) δ 8.53 (d, J = 2.3 Hz, 1H), 8.29-8.18 (m, 3H), 8.06-8.01 (m, 1H), 7.92-7.88 (m, 1H), 7.77-7.71 (m, 1H), 7.66 (d, J = 8.0 Hz, 1H), 7.46 (ddd, J = 9.4, 5.5, 1.8 Hz, 1H), 6.71 (q, J = 5.0, 4.4 Hz, 1H), 6.29 (s, 1H), 3.94-3.86 (m, 6H), 3.71-3.62 (m, 2H), 3.51-3.44 (m, 2H), 3.41-3.35 (m, 2H), 3.22-3.15 (m, 2H). |
| 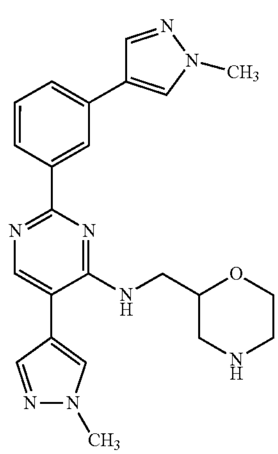 [SMILES: Cn1cc(-c2cccc(-c3ncc(-c4cnn(C)c4)c(NCC4CNCCO4)n3)c2)cn1] | 59 | off-white solid. HPLC(Column): (254 nm) 95%. LC/MS(Column): (M + H) 431.85. 1H NMR (400 MHz, DMSO-d6) δ 8.51 (s, 1H), 8.25-8.13 (m, 3H), 8.06-8.00 (m, 1H), 7.90-7.85 (m, 1H), 7.76-7.70 (m, 1H), 7.66 (d, J = 7.8 Hz, 1H), 7.48 (ddd, J = 9.3, 5.4, 1.7 Hz, 1H), 6.61 (d, J = 6.2 Hz, 1H), 3.95-3.84 (m, 6H), 3.79-3.68 (m, 2H), 3.66-3.57 (m, 1H), 3.47 (ddd, J = 24.3, 11.9, 6.9 Hz, 2H), 2.88 (d, J = 12.2 Hz, 1H), 2.64 (d, J = 9.5 Hz, 2H), 2.47-2.41 (m, 1H). |

-continued

| Structure | Example | Analyticals |
|---|---|---|
| (structure) | 60 | light brown solid. HPLC(Column): (254 nm) 94%. LC/MS(Column): (M + H) 429.3. |
| (structure) | 61 | light brown solid. HPLC(Column): (254 nm) 96%. LC/MS(Column): (M + H) 429.3. |
| (structure) | 62 | white solid. HPLC(Column): (254 nm) 96%. LC/MS(Column): (M + H) 402.3. 1H NMR (400 MHz, DMSO-d6) δ 8.48 (s, 1H), 8.23-8.15 (m, 3H), 8.05 (s, 1H), 7.88 (s, 1H), 7.74 (s, 1H), 7.65 (d, J = 7.7 Hz, 1H), 7.47 (t, J = 7.7 Hz, 1H), 6.46 (d, J = 6.8 Hz, 1H), 4.26 (h, J = 8.1 Hz, 1H), 3.91 (d, J = 11.8 Hz, 6H), 3.11 (q, J = 7.9 Hz, 1H), 2.69 (q, J = 8.4 Hz, 2H), 1.82-1.73 (m, 2H). |

-continued

| Structure | Example | Analyticals |
|---|---|---|
| 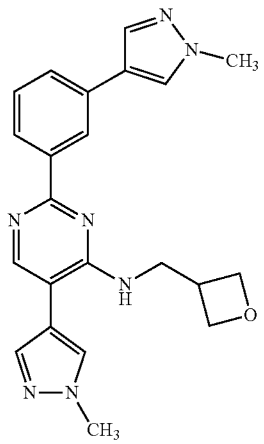 [SMILES: Cn1cc(-c2cccc(-c3ncc(-c4cnn(C)c4)c(NCC4COC4)n3)c2)cn1] | 63 | brown solid. HPLC(Column): (254 nm) 98%. LC/MS(Column): (M + H) 403.3. 1H NMR (400 MHz, DMSO-d6) δ 8.50 (d, J = 1.9 Hz, 1H), 8.24-8.14 (m, 3H), 8.02 (s, 1H), 7.88 (d, J = 1.6 Hz, 1H), 7.73 (d, J = 1.5 Hz, 1H), 7.66 (d, J = 7.7 Hz, 1H), 7.47 (td, J = 7.8, 1.6 Hz, 1H), 6.93-6.85 (m, 1H), 4.68 (td, J = 6.7, 5.7, 1.6 Hz, 2H), 4.47 (td, J = 5.9, 1.6 Hz, 2H), 3.95-3.81 (m, 8H), 3.42-3.35 (m, 1H). |
| 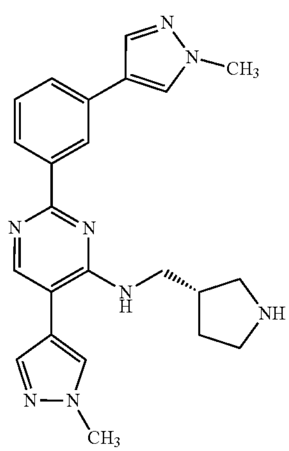 [SMILES: Cn1cc(-c2cccc(-c3ncc(-c4cnn(C)c4)c(NC[C@H]4CCNC4)n3)c2)cn1] | 64 | brown solid. HPLC(Column): (254 nm) 94%. LC/MS(Column): (M + H) 415.3. |
| 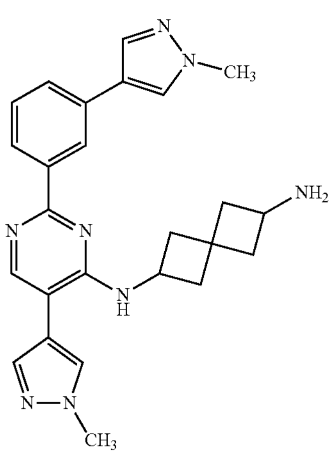 [SMILES: Cn1cc(-c2cccc(-c3ncc(-c4cnn(C)c4)c(NC4CC5(CC(N)C5)C4)n3)c2)cn1] | 65 | white solid. HPLC(Column): (254 nm) 95%. LC/MS(Column): (M + H) 441.3. |

| Structure | Example | Analyticals |
|---|---|---|
| 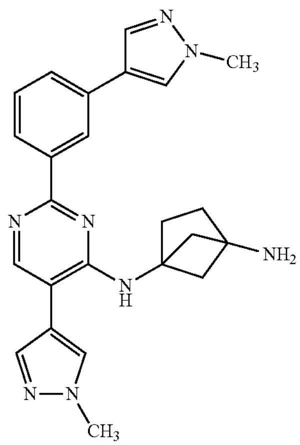 [SMILES: Cn1cc(-c2cccc(-c3ncc(-c4cnn(C)c4)c(NC45CCC(N)(C4)C5)n3)c2)cn1] | 66 | off-white solid. HPLC(Column): (254 nm) 97%. LC/MS(Column): (M + H) 427.3. 1H NMR (400 MHz, DMSO-d6) δ 8.53 (s, 1H), 8.24-8.12 (m, 3H), 8.02 (d, J = 2.2 Hz, 1H), 7.86 (d, J = 2.2 Hz, 1H), 7.75-7.62 (m, 2H), 7.50 (dt, J = 9.9, 5.0 Hz, 1H), 7.29 (s, 1H), 6.71 (d, J = 13.7 Hz, 2H), 3.91 (t, J = 3.2 Hz, 6H), 2.06 (t, J = 6.2 Hz, 2H), 1.94-1.86 (m, 2H), 1.74-1.60 (m, 4H). |
| 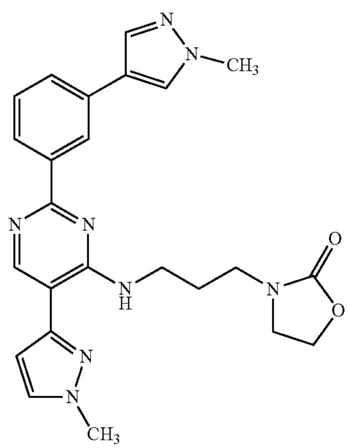 [SMILES: Cn1cc(-c2cccc(-c3ncc(-c4ccn(C)n4)c(NCCCN4CCOC4=O)n3)c2)cn1] | 67 | white solid. HPLC(Column): (254 nm) 99%. LC/MS(Column): (M + H) 459.3. 1H NMR (400 MHz, DMSO-d6) δ 8.81-8.67 (m, 2H), 8.53 (d, J = 2.2 Hz, 1H), 8.26-8.17 (m, 2H), 7.93-7.85 (m, 2H), 7.68 (d, J = 7.7 Hz, 1H), 7.52-7.45 (m, 1H), 6.95 (d, J = 2.4 Hz, 1H), 4.27-4.18 (m, 2H), 3.99-3.87 (m, 6H), 3.78-3.69 (m, 2H), 3.62-3.54 (m, 2H), 1.99-1.90 (m, 2H). |
| 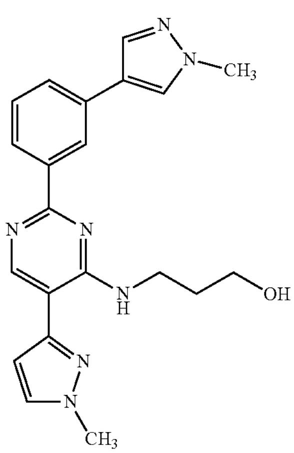 [SMILES: Cn1cc(-c2cccc(-c3ncc(-c4ccn(C)n4)c(NCCCO)n3)c2)cn1] | 68 | white solid. HPLC(Column): (254 nm) 98%. LC/MS(Column): (M + H) 390.2. 1H NMR (400 MHz, DMSO-d6) δ 8.78-8.64 (m, 2H), 8.55 (d, J = 1.9 Hz, 1H), 8.22 (d, J = 6.8 Hz, 2H), 7.93-7.84 (m, 2H), 7.67 (d, J = 7.7 Hz, 1H), 7.52-7.44 (m, 1H), 6.94 (d, J = 2.4 Hz, 1H), 4.70-4.63 (m, 1H), 3.98-3.88 (m, 6H), 3.82-3.72 (m, 2H), 3.65-3.58 (m, 2H), 1.92-1.83 (m, 2H). |

| Structure | Example | Analyticals |
|---|---|---|
| 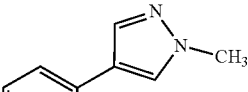 | 69 | off-white solid. HPLC(Column): (254 nm) 100%. LC/MS(Column): (M + H) 445.3. 1H NMR (400 MHz, DMSO-d6) δ 8.86 (d, J = 5.4 Hz, 1H), 8.76 (d, J = 2.1 Hz, 1H), 8.54 (d, J = 2.0 Hz, 1H), 8.27-8.18 (m, 2H), 7.93-7.85 (m, 2H), 7.67 (d, J = 7.7 Hz, 1H), 7.48 (td, J = 7.9, 2.4 Hz, 1H), 6.94 (d, J = 2.4 Hz, 1H), 4.01-3.96 (m, 3H), 3.92-3.88 (m, 3H), 3.86-3.79 (m, 2H), 3.66 (t, J = 4.1 Hz, 4H), 2.70-2.63 (m, 2H). |
| 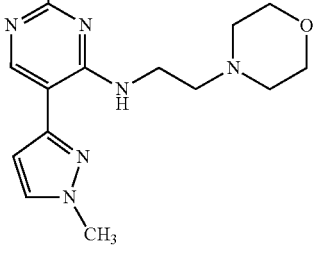 | 70 | white solid. HPLC(Column): (254 nm) 99%. LC/MS(Column): (M + H) 443.3. |
| 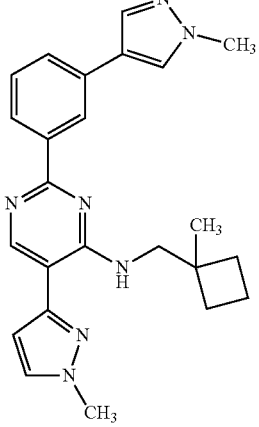 | 71 | white solid. HPLC(Column): (254 nm) 99%. LC/MS(Column): (M + H) 414.3. |

-continued

| Structure | Example | Analyticals |
|---|---|---|
| 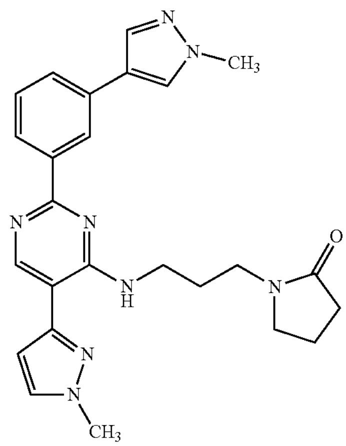 [SMILES: Cn1cc(-c2cccc(-c3ncc(-c4ccn(C)n4)c(NCCCN4CCCC4=O)n3)c2)cn1] | 72 | white solid. HPLC(Column): (254 nm) 100%. LC/MS(Column): (M + H) 457.3. |
| 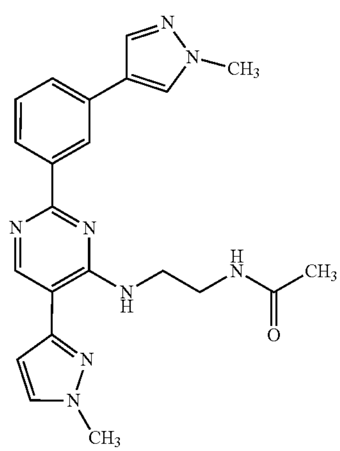 [SMILES: CC(=O)NCCNc1nc(-c2cccc(-c3cnn(C)c3)c2)ncc1-c1ccn(C)n1] | 73 | white solid. HPLC(Column): (254 nm) 99%. LC/MS(Column): (M + H) 417.3. |
| 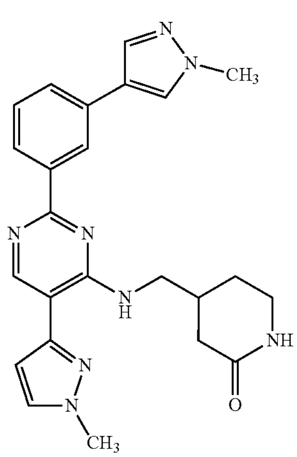 [SMILES: Cn1cc(-c2cccc(-c3ncc(-c4ccn(C)n4)c(NCC4CCNC(=O)C4)n3)c2)cn1] | 74 | pink solid. HPLC(Column): (254 nm) 100%. LC/MS(Column): (M + H) 443.3. |

| Structure | Example | Analyticals |
|---|---|---|
| 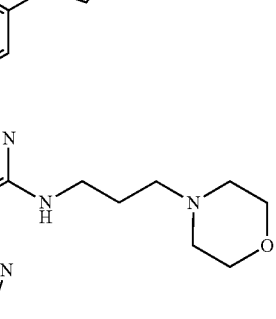 | 75 | gray solid. HPLC(Column): (254 nm) 89%.<br>LC/MS(Column): (M + H) 459.3. |
| 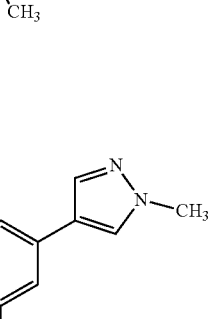 | 76 | brown solid. HPLC(Column): (254 nm) 97%.<br>LC/MS(Column): (M + H) 443.3. |
| 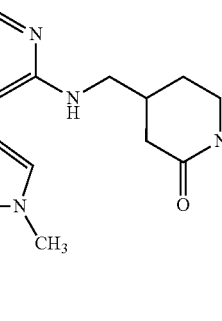 | 77 | white solid. HPLC(Column): (254 nm) 97%.<br>LC/MS(Column): (M + H) 427.3. |

| Structure | Example | Analyticals |
|---|---|---|
| 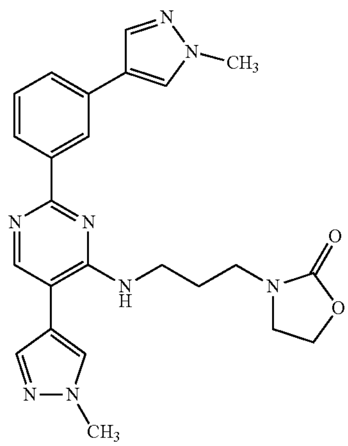 [SMILES: Cn1cc(-c2cccc(-c3ncc(-c4cnn(C)c4)c(NCCCN4CCOC4=O)n3)c2)cn1] | 78 | white solid. HPLC(Column): (254 nm) 99%. LC/MS(Column): (M + H) 459.3. 1H NMR (400 MHz, DMSO-d6) δ 8.44-8.39 (m, 1H), 8.16-8.08 (m, 3H), 7.98 (d, J = 0.9 Hz, 1H), 7.82 (d, J = 0.9 Hz, 1H), 7.68 (d, J = 0.9 Hz, 1H), 7.58 (ddd, J = 7.7, 1.9, 1.2 Hz, 1H), 7.42-7.37 (m, 1H), 6.64 (t, J = 5.8 Hz, 1H), 4.19-4.13 (m, 2H), 3.83 (d, J = 8.8 Hz, 6H), 3.53-3.46 (m, 4H), 3.22 (t, J = 7.0 Hz, 2H), 1.83 (p, J = 7.0 Hz, 2H). |
| 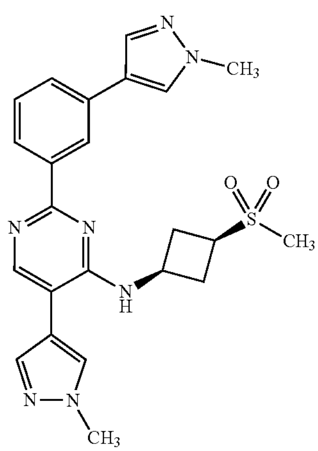 [SMILES: Cn1cc(-c2cccc(-c3ncc(-c4cnn(C)c4)c(N[C@H]4C[C@@H](S(C)(=O)=O)C4)n3)c2)cn1] | 79 | white solid. HPLC(Column): (254 nm) 99%. LC/MS(Column): (M + H) 464.3. |
| 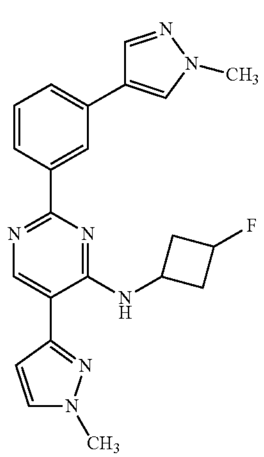 [SMILES: Cn1cc(-c2cccc(-c3ncc(-c4ccn(C)n4)c(NC4CC(F)C4)n3)c2)cn1] | 80 | white solid. HPLC(Column): (254 nm) 98%. LC/MS(Column): (M + H) 404.2. |

| Structure | Example | Analyticals |
|---|---|---|
| (structure) | 81 | white solid. HPLC(Column): (254 nm) 99%.<br>LC/MS(Column): (M + H) 436.3. |
| (structure) | 82 | white solid. HPLC(Column): (254 nm) 99%.<br>LC/MS(Column): (M + H) 402.2. |
| (structure) | 83 | white solid. HPLC: (254 nm) 91%.<br>LC/MS: (M + H) 406.2. |

| Structure | Example | Analyticals |
|---|---|---|
| 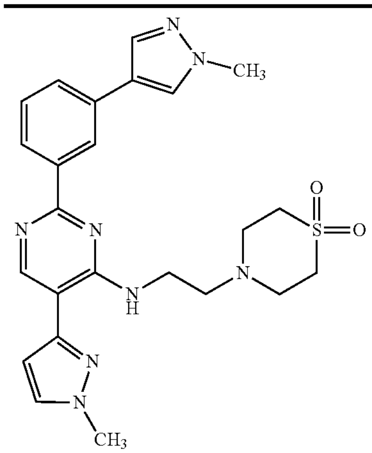 | 84 | white solid. HPLC: (254 nm) 97.5%. LC/MS: (M + H) 493. |
| 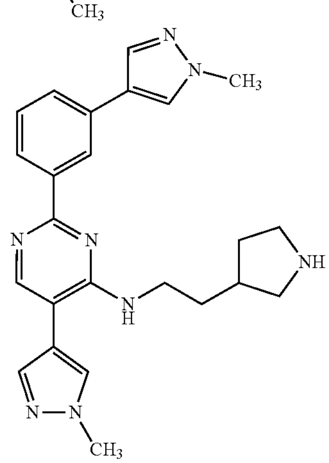 | 85 | white solid. HPLC: (254 nm) 90%. LC/MS: (M + H) 429.3. |

Example 86: 1-Methyl-8-(4-{2-[3-(1-methyl-1H-pyrazol-4-yl)-phenyl]-4-[(piperidin-4-ylmethyl)-amino]-pyrimidin-5-yl}-pyrazol-1-yl)-1-aza-spiro[4.5]decan-2-one Hydrochloride Step 1: 4-({2-Chloro-5-[1-(1-methyl-2-oxo-1-aza-spiro[4.5]dec-8-yl)-1H-pyrazol-4-yl]-pyrimidin-4-ylamino}-methyl)-piperidine-1-carboxylic Acid Tert-Butyl Ester

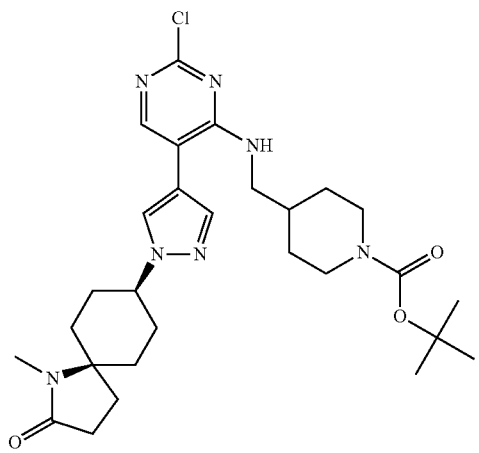 [SMILES: CN1C(=O)CC[C@]12CC[C@H](n1cc(-c3cnc(Cl)nc3NCC3CCN(C(=O)OC(C)(C)C)CC3)cn1)CC2]

A mixture of 8-(4-Bromo-pyrazol-1-yl)-1-methyl-1-aza-spiro[4.5]decan-2-one (410 mg; 1.31 mmol; 1.00 eq.), 4,4,5,5,4',4',5',5'-Octamethyl-[2,2']bi[[1,3,2]dioxaborolanyl] (366 mg; 1.44 mmol; 1.10 eq.), Potassium acetate (193 mg; 1.97 mmol; 1.50 eq.) and PdCl$_2$(PPh$_3$)$_2$ (9 mg; 0.01 mmol; 0.01 eq.) in Dioxane (7.50 mL) was stirred at 100° C. under N2 atmosphere for 22 h. The reaction mixture was cooled to room temperature and treated with 0.5× the amounts of reagents added originally (except for bromide sm) and stirred at 100° C. for 29 h. It was cooled to room temperature and 4-[(5-Bromo-2-chloro-pyrimidin-4-ylamino)-methyl]-piperidine-1-carboxylic acid tert-butyl ester (586 mg; 1.44 mmol; 1.10 eq.) in dioxane (2 mL), and K$_2$CO$_3$ (544 mg; 3.94 mmol; 3.00 eq.) in water (2.50 mL) were added. Nitrogen was bubbled through the solution for 5 min, PdCl$_2$(PPh$_3$)$_2$ (9 mg; 0.01 mmol; 0.01 eq.) was added and the mixture was stirred at 90° C. overnight. It was cooled to room temperature and diluted with EtOAc (10 mL) and water (2 mL). The aqueous layer was removed and the organic layer was filtered and concentrated. Purification by flash chromatography on silica (EtOAc:Hexane, gradient from 20 to 70% then MeOH:DCM, 10:90) afforded the title compound as a golden foam (390 mg, 32%). LC/MS: 559 (M+H).

Step 2: methyl-1H-pyrazol-4-yl)-phenyl]-pyrimidin-4-ylamino}-methyl)-piperidine-1-carboxylic Acid Tert-Butyl Ester

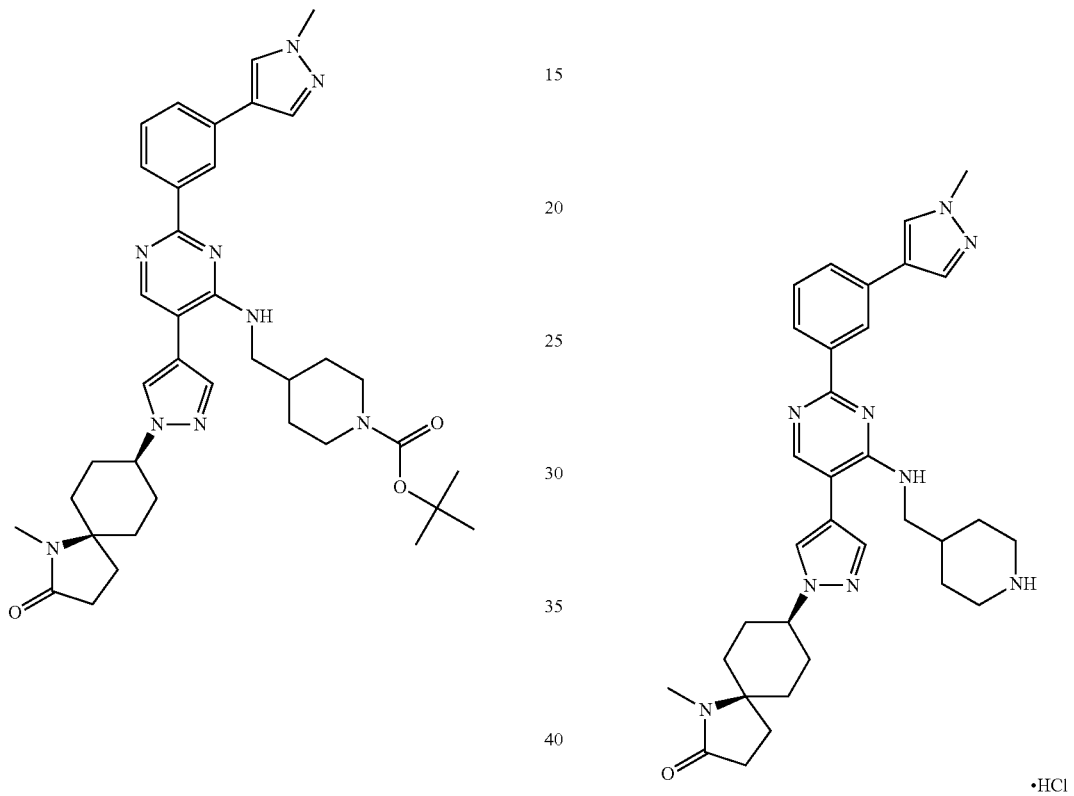

A mixture of 4-({2-Chloro-5-[1-(1-methyl-2-oxo-1-aza-spiro[4.5]dec-8-yl)-1H-pyrazol-4-yl]-pyrimidin-4-ylamino}-methyl)-piperidine-1-carboxylic acid tert-butyl ester (390 mg; 0.42 mmol; 1.00 eq.), 1-Methyl-4-[3-(4,4,5,5-tetramethyl-[1,3,2]dioxaborolan-2-yl)-phenyl]-1H-pyrazole (179 mg; 0.63 mmol; 1.50 eq.), and [1,1'-bis(diphenylphosphino)ferrocene]dichloropalladium(II).CH$_2$Cl$_2$ (34 mg; 0.04 mmol; 0.10 eq.) and cesium carbonate (629 µl; 1.26 mmol; 3.00 eq.) in dioxane (6.0 mL) was stirred at 100° C. under nitrogen atmosphere overnight. The reaction mixture was then cooled to room temperature and diluted with EtOAc (10 mL) and water (3 mL). The organic layer was separated, filtered through celite and concentrated under reduced pressure. Purification by flash chromatography (EtOAc, 100% then MeOH:DCM, gradient from 0 to 10%) afforded the title compound as a golden oil (229 mg, 80%). $^1$H NMR (400 MHz, DMSO-d6) δ 8.50 (s, 1H), 8.23 (s, 1H), 8.18 (d, 2H), 8.12 (s, 1H), 7.86 (s, 1H), 7.78 (s, 1H), 7.65 (d, 1H), 7.47 (t, 1H), 6.76 (t, 1H), 4.27 (m, 1H), 4.02-3.91 (m, 2H), 3.90 (s, 3H), 3.47 (t, 2H), 2.71 (m, 1H), 2.68 (s, 3H), 2.28 (t, 2H), 2.14 (d, 2H), 2.10-1.86 (m, 6H), 1.73 (d, 2H), 1.55 (d, 2H), 1.39 (s, 9H), 1.13 (qd, 2H). LC/MS: 680 (M+1).

Step 3: 1-Methyl-8-(4-{2-[3-(-methyl-1H-pyrazol-4-yl)-phenyl]-4-[(piperidin-4-ylmethy)-amino]-pyrimidin-5-yl}-pyrazol-1-yl)-1-aza-spiro[4.5]decan-2-one Hydrochloride Hydrogen chloride (0.71 mL of a 2 M solution in Et$_2$O; 1.42 mmol; 5.00 eq.) was added to a solution of 4-({5-[1-(1-Methyl-2-oxo-1-aza-spiro[4.5]dec-8-yl)-1H-pyrazol-4-yl]-2-[3-(1-methyl-1H-pyrazol-4-yl)-phenyl]-pyrimidin-4-ylamino}-methyl)-piperidine-1-carboxylic acid tert-butyl ester (225 mg; 0.33 mmol; 1.00 eq.) in MeOH (3 mL). Reaction mixture was stirred 2 h at room temperature. It was then diluted in Et20 and filtered. The solid was dried under high vacuum to yield the title compound a white solid (180 mg, 79%). $^1$H NMR (400 MHz, DMSO-d6) δ 8.93 (brs, 2H), 8.68 (s, 1H), 8.64 (m, 1H), 8.37 (s, 1H), 8.33 (s, 1H), 8.23 (s, 1H), 8.17 (d, 1H), 8.06 (s, 1H), 7.91 (d, 2H), 7.65 (t, 1H), 4.32 (m, 1H), 3.64 (t, 2H), 3.28 (d, 2H), 2.93-2.77 (m, 2H), 2.68 (s, 3H), 2.28 (t, 2H), 2.20-1.91 (m, 9H), 1.91-1.80 (d, 2H), 1.57 (m, 4H). LC/MS: 580 (M+1).

Example 87: 1-Methyl-8-(4-{4-[(1-methyl-piperidin-4-ylmethyl)-amino]-2-[3-(1-methyl-1H-pyrazol-4-yl)-phenyl]-pyrimidin-5-yl}-pyrazol-1-yl)-1-azaspiro[4.5]decan-2-one

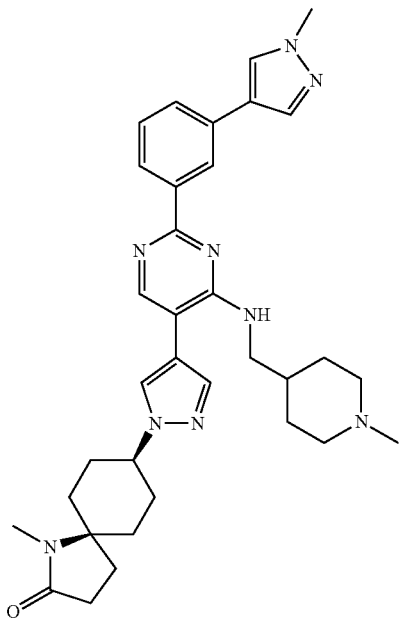

Iodomethane (stabilised with silver, 5 μl; 79.81 μmol; 1.10 eq.) was added dropwise to a solution of 1-Methyl-8-(4-{2-[3-(1-methyl-1H-pyrazol-4-yl)-phenyl]-4-[(piperidin-4-ylmethyl)-amino]-pyrimidin-5-yl}-pyrazol-1-yl)-1-azaspiro[4.5]decan-2-one hydrochloride (3) (50 mg; 0.07 mmol; 1.00 eq.) and TEA (40 μl; 0.29 mmol; 4.00 eq.) in N,N-Dimethylformamide (3.0 mL). The clear solution was stirred overnight at RT concentrated under reduced pressure and purified by prep HPLC (C-18 (10 um), 30×150 mm, 0.1% NH4OH modified mobile phases (A=water, B=ACN), Method 25 to 75% ACN over 25 min at 60 mL/min) to afford the title compound as a white solid (8 mg, 17%). $^1$H NMR (500 MHz, DMSO-d6) δ 8.49 (t, 1H), 8.21 (s, 1H), 8.16 (d, 2H), 8.10 (s, 1H), 7.84 (s, 1H), 7.76 (s, 1H), 7.66-7.61 (m, 1H), 7.46 (t, 1H), 6.73 (t, 1H), 4.31-4.19 (m, 1H), 3.88 (s, 3H), 3.44 (t, 2H), 2.75 (d, 2H), 2.66 (s, 3H), 2.26 (t, 2H), 2.11 (s, 5H), 2.05-1.88 (m, 6H), 1.85-1.72 (m, 3H), 1.68 (d, 2H), 1.52 (d, 2H), 1.27 (m, 2H); LC/MS: 594 (M+1).

Compounds below were prepared following similar routes and protocols:

| Structure | Example | Analyticals |
|---|---|---|
| 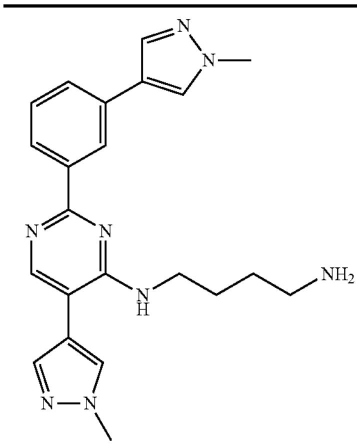 | 88 | brown solid. HPLC: (254 nm) 80%. LC/MS: (M + H) 403.8. |
| 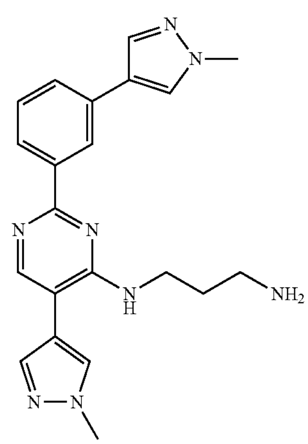 [SMILES: Cn1cc(-c2cccc(-c3ncc(-c4cnn(C)c4)c(NCCCN)n3)c2)cn1] | 89 | Brown solid. HPLC: (254 nm) 91%. LC/MS: (M + H) 389.8. |

-continued
| Structure | Example | Analyticals |
|---|---|---|
| 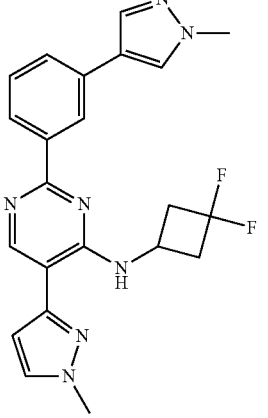 | 90 | white solid. HPLC(Column): (254 nm) 100%. LC/MS(Column): (M + H) 422.7. |
| 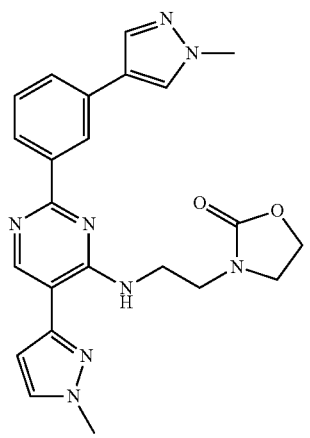 [SMILES: Cn1cc(-c2cccc(-c3ncc(-c4ccn(C)n4)c(NCCN4CCOC4=O)n3)c2)cn1] | 91 | white solid. HPLC(Column): (254 nm) 99%. LC/MS(Column): (M + H) 445.7. |
| 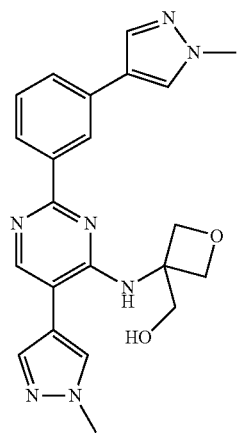 [SMILES: Cn1cc(-c2cccc(-c3ncc(-c4cnn(C)c4)c(NC4(CO)COC4)n3)c2)cn1] | 92 | yellow solid. HPLC(Column): (254 nm) 98%. LC/MS(Column): (M + H) 418.8. |

| Structure | Example | Analyticals |
|---|---|---|
| 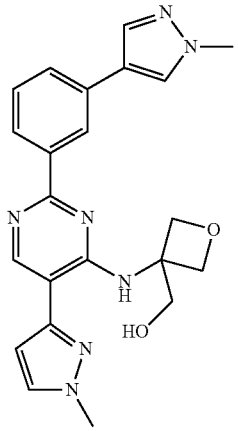 [SMILES: Cn1cc(-c2cccc(-c3ncc(-c4ccn(C)n4)c(NC4(CO)COC4)n3)c2)cn1] | 93 | off-white solid. HPLC(Column): (254 nm) 97%. LC/MS(Column): (M + H) 417.75. |
| 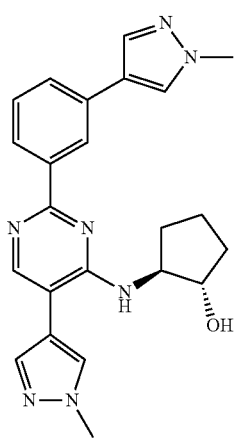 [SMILES: Cn1cc(-c2cccc(-c3ncc(-c4cnn(C)c4)c(N[C@H]4CCC[C@@H]4O)n3)c2)cn1] | 94 | white solid. Racemic. Trans isomer. HPLC(Column): (254 nm) 99%. LC/MS(Column): (M + H) 416.8. |
| 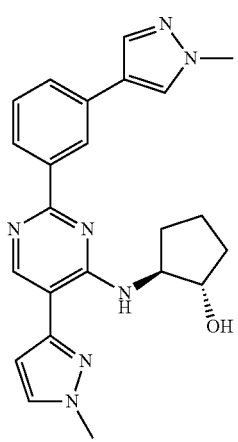 [SMILES: Cn1cc(-c2cccc(-c3ncc(-c4ccn(C)n4)c(N[C@H]4CCC[C@@H]4O)n3)c2)cn1] | 95 | white solid. Racemic-trans isomer. HPLC(Column): (254 nm) 98%. LC/MS(Column): (M + H) 416.75. |

-continued

| Structure | Example | Analyticals |
|---|---|---|
| 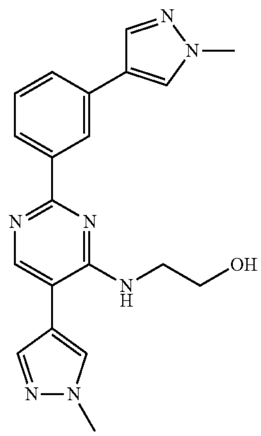 [SMILES: Cn1cc(-c2cccc(-c3ncc(-c4cnn(C)c4)c(NCCO)n3)c2)cn1] | 96 | HPLC(Column): (254 nm) 99%. LC/MS(Column): (M + H) 376.75. |
| 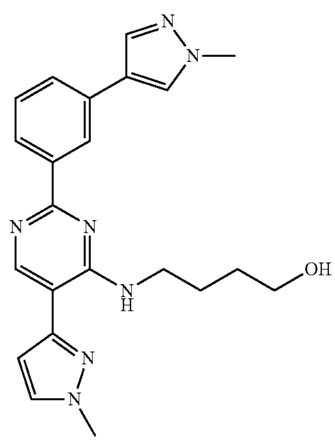 [SMILES: Cn1cc(-c2cccc(-c3ncc(-c4ccn(C)n4)c(NCCCCO)n3)c2)cn1] | 97 | white solid. HPLC(Column): (254 nm) 99%. LC/MS(Column): (M + H) 404.75. |
| 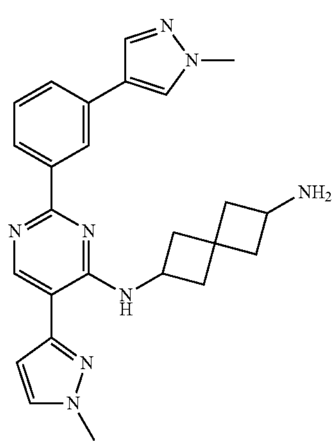 [SMILES: Cn1cc(-c2cccc(-c3ncc(-c4ccn(C)n4)c(NC4CC5(CC(N)C5)C4)n3)c2)cn1] | 98 | white solid. HPLC(Column): (254 nm) 95%. LC/MS(Column): (M + H) 440.75. |

-continued

| Structure | Example | Analyticals |
|---|---|---|
| 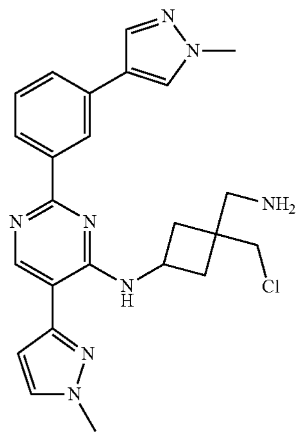 [SMILES: Cn1cc(-c2cccc(-c3ncc(-c4ccn(C)n4)c(NC4CC(CN)(CCl)C4)n3)c2)cn1] | 99 | white solid. HPLC(Column): (254 nm) 98%. LC/MS(Column): (M + H) 464.75. |
| 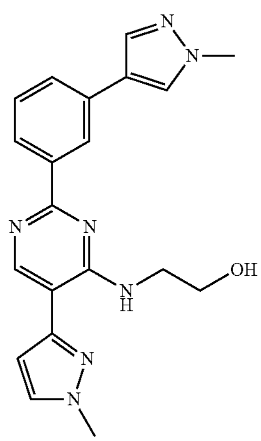 | 100 | white solid. HPLC(Column): (254 nm) 99%. LC/MS(Column): (M + H) 376.25. |
| 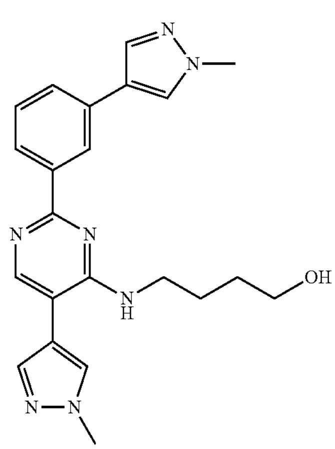 [SMILES: Cn1cc(-c2cccc(-c3ncc(-c4cnn(C)c4)c(NCCCCO)n3)c2)cn1] | 101 | yellow solid. HPLC(Column): (254 nm) 95%. LC/MS(Column): (M + H) 404.3. |

-continued
| Structure | Example | Analyticals |
|---|---|---|
| 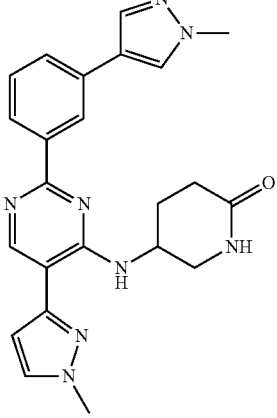 | 102 | hite solid. HPLC(Column): (254 nm) 92%. LC/MS(Column): (M + H) 429.3. |
| 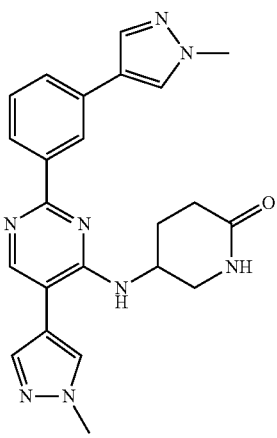 [SMILES: Cn1cc(-c2cccc(-c3ncc(-c4cnn(C)c4)c(NC4CCC(=O)NC4)n3)c2)cn1] | 103 | HPLC(Column): (254 nm) 99%. LC/MS(Column): (M + H) 429.3. |
| 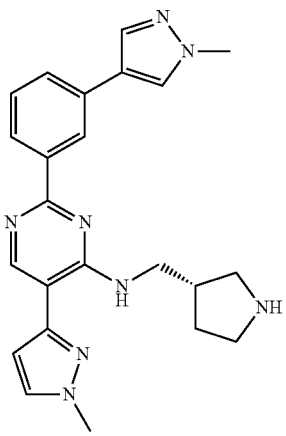 [SMILES: Cn1cc(-c2cccc(-c3ncc(-c4ccn(C)n4)c(NC[C@H]4CCNC4)n3)c2)cn1] | 104 | off-white solid. HPLC(Column): (254 nm) 94%. LC/MS(Column): (M + H) 415.3. |

-continued

| Structure | Example | Analyticals |
|---|---|---|
| 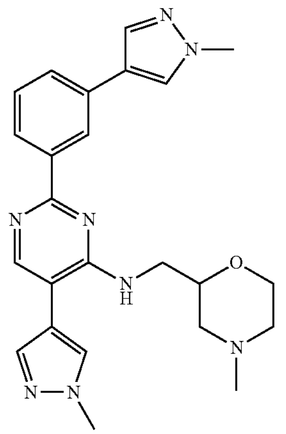 [SMILES: CN1CCOC(CNc2nc(-c3cccc(-c4cnn(C)c4)c3)ncc2-c2cnn(C)c2)C1] | 105 | brown solid. HPLC: (254 nm) 98.7%. LC/MS(Column): (M + H) 445.3. |
| 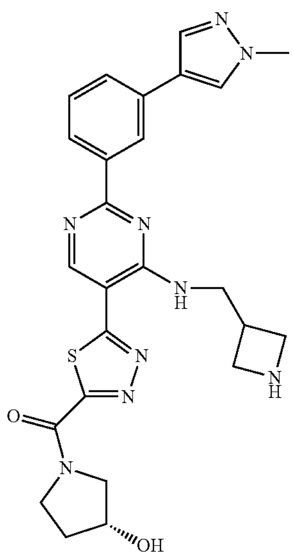 [SMILES: Cn1cc(-c2cccc(-c3ncc(-c4nnc(C(=O)N5CC[C@@H](O)C5)s4)c(NCC4CNC4)n3)c2)cn1] | 106 | Pale yellow solid. HPLC(Xbridge): (percent area) 93.8%. LC/MS(Column): (M + H)518.2. 1H NMR (400 MHz, MeOD): 8.90 (s, 1H), 8.59 (s, 1H), 8.29 (d, J = 7.84 Hz, 1H), 8.07 (s, 1H), 7.92 (s, 1H), 7.75 (d, J = 9.48 Hz, 1H), 7.53 (t, J = 7.76 Hz, 1H), 4.57-4.53 (m, 1H), 4.36 (s, 1H), 4.22-4.11 (m, 7H), 3.97 (s, 3H), 3.86-3.83 (m, 2H), 3.75-3.74 (m, 1H), 3.65-3.53 (m, 1H), 3.32-3.31 (m, 1H), 2.14-2.11 (m, 3H). |
| 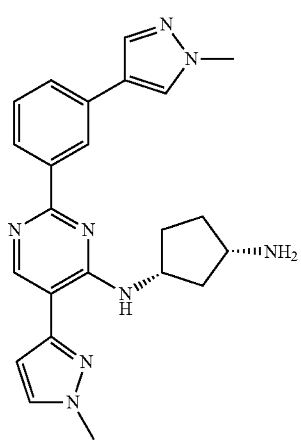 [SMILES: Cn1cc(-c2cccc(-c3ncc(-c4ccn(C)n4)c(N[C@@H]4CC[C@H](N)C4)n3)c2)cn1] | 107 | white solid. Racemic-Cis isomer. . HPLC(Column): (254 nm) 96%. LC/MS(Column): (M + H) 415.3 |

-continued
| Structure | Example | Analyticals |
|---|---|---|
| 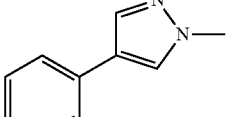 | 108 | white solid. Racemic. Cis isomer. HPLC(Column): (254 nm) 93.4%. LC/MS(Column): (M + H) 415.3. |
| 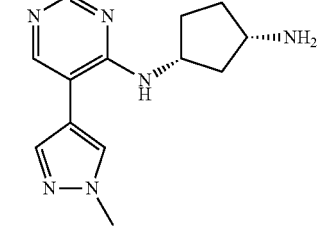 | 109 | white solid. HPLC(Column): (254 nm) 100%. LC/MS(Column): (M + H) 431.3. |
| 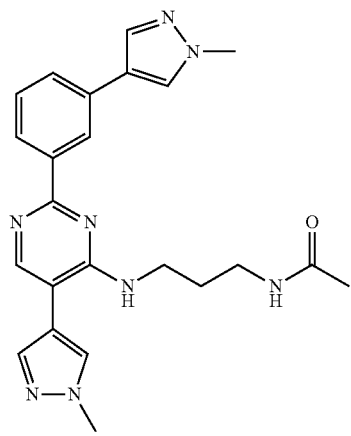 | 110 | white solid. HPLC(Column): (254 nm) 96%. LC/MS(Column): (M + H) 459.5 |

-continued

| Structure | Example | Analyticals |
|---|---|---|
| 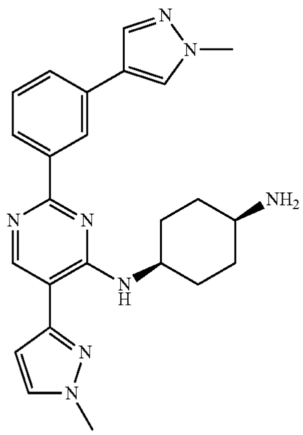 [SMILES: Cn1cc(-c2cccc(-c3ncc(-c4ccn(C)n4)c(N[C@H]4CC[C@@H](N)CC4)n3)c2)cn1] | 111 | white solid. Cis isomer. HPLC(Column): (254 nm) 100%. LC/MS(Column): (M + H) 429.3. |
| 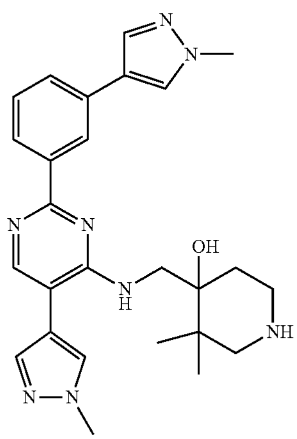 [SMILES: Cn1cc(-c2cccc(-c3ncc(-c4cnn(C)c4)c(NCC4(O)CCNCC4(C)C)n3)c2)cn1] | 112 | white solid. HPLC(Column): (percent area) 100%. LC/MS(Column): (M + H) 473.4. |
| 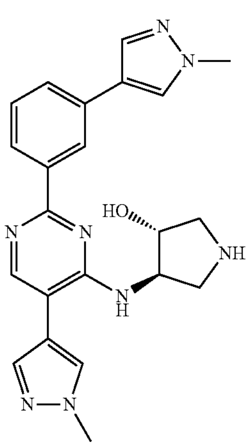 [SMILES: Cn1cc(-c2cccc(-c3ncc(-c4cnn(C)c4)c(N[C@@H]4CNC[C@H]4O)n3)c2)cn1] | 113 | white solid. Racemic. Cis isomer. HPLC(Column): (254 nm) 100%. LC/MS(Column): (M + H) 417.3. |

-continued

| Structure | Example | Analyticals |
|---|---|---|
| (structure) | 114 | white solid. HPLC(Column): (254 nm) 98%. LC/MS(Column): (M + H) 473.35. |
| (structure) | 115 | white solid. HPLC(Column): (254 nm) 100%. LC/MS(Column): (M + H) 431.3. |
| (structure) | 116 | white solid. Racemic. Cis isomer. HPLC(Column): (254 nm) 97%. LC/MS(Column): (M + H) 445.3. |

-continued
| Structure | Example | Analyticals |
|---|---|---|
| 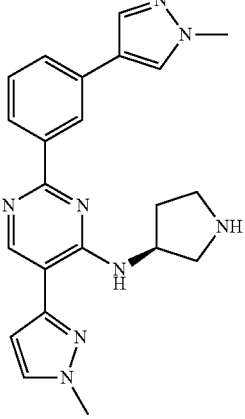 | 117 | white solid. HPLC(Column): (254 nm) 92%. LC/MS(Column): (M + H) 401.3. |
| 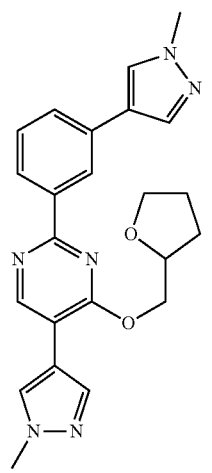 [SMILES: Cn1cc(-c2cccc(-c3ncc(-c4cnn(C)c4)c(OCC4CCCO4)n3)c2)cn1] | 118 | Brown solid. HPLC(Column UPLC): 91%. LC/MS(Column): (M + H) 417.4 |
| 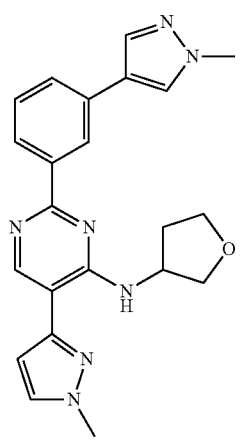 [SMILES: Cn1cc(-c2cccc(-c3ncc(-c4ccn(C)n4)c(NC4CCOC4)n3)c2)cn1] | 119 | white solid. HPLC(Column): (254 nm) 99%. LC/MS(Column): (M + H) 402.3. |

-continued

| Structure | Example | Analyticals |
|---|---|---|
| 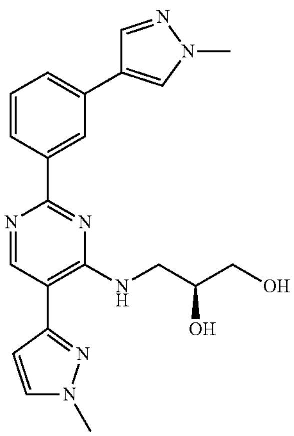 [SMILES: Cn1cc(-c2cccc(-c3ncc(-c4ccn(C)n4)c(NC[C@H](O)CO)n3)c2)cn1] | 120 | white solid. HPLC(Column): (254 nm) 97%.<br>LC/MS(Column): (M + H) 406.3. |
| 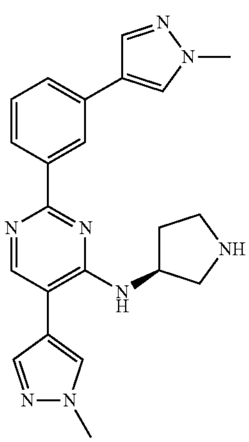 [SMILES: Cn1cc(-c2cccc(-c3ncc(-c4cnn(C)c4)c(N[C@H]4CCNC4)n3)c2)cn1] | 121 | white solid. HPLC(Column): (254 nm) 91%.<br>LC/MS(Column): (M + H) 401.3. |
| 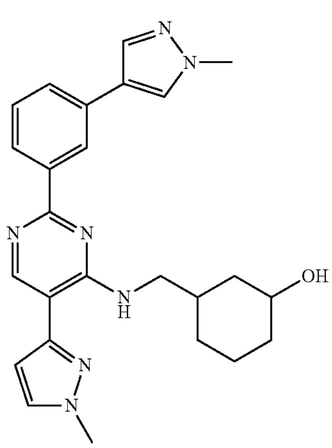 [SMILES: Cn1cc(-c2cccc(-c3ncc(-c4ccn(C)n4)c(NCC4CCCC(O)C4)n3)c2)cn1] | 122 | off-white solid. HPLC(Column): (254 nm) 100%.<br>LC/MS(Column): (M + H) 444.3. |

-continued

| Structure | Example | Analyticals |
|---|---|---|
| 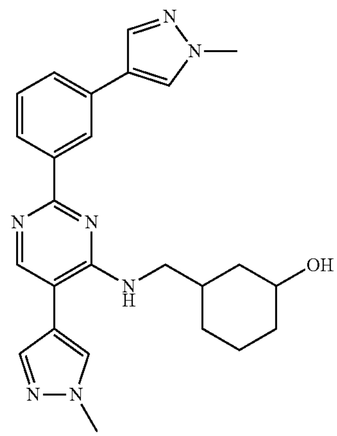 [SMILES: Cn1cc(-c2cccc(-c3ncc(-c4cnn(C)c4)c(NCC4CCCC(O)C4)n3)c2)cn1] | 123 | off-white solid. HPLC(Column): (254 nm) 100%. LC/MS(Column): (M + H) 444.3. |
| 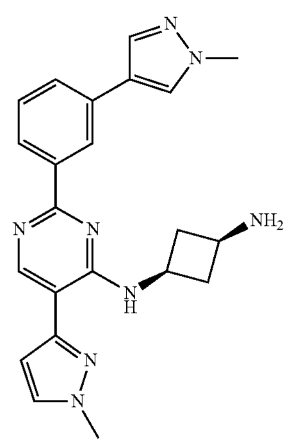 [SMILES: Cn1cc(-c2cccc(-c3ncc(-c4ccn(C)n4)c(N[C@H]4C[C@@H](N)C4)n3)c2)cn1] | 124 | white solid. HPLC(Column): (254 nm) 96%. LC/MS(Column): (M + H) 401.3. |
| 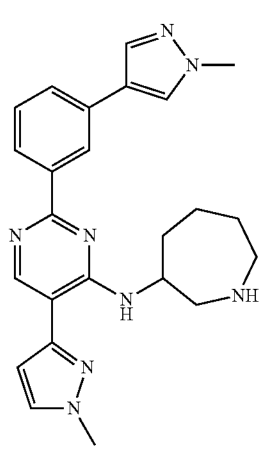 [SMILES: Cn1cc(-c2cccc(-c3ncc(-c4ccn(C)n4)c(NC4CCCCNC4)n3)c2)cn1] | 125 | white solid. HPLC(Column): (254 nm) 98%. LC/MS(Column): (M + H) 429.3. |

| Structure | Example | Analyticals |
|---|---|---|
| 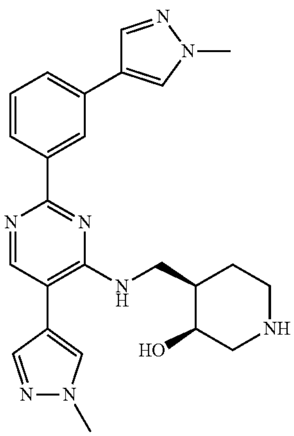 [SMILES: Cn1cc(-c2cccc(-c3ncc(-c4cnn(C)c4)c(NC[C@H]4CCNC[C@H]4O)n3)c2)cn1] | 126 | white solid. Racemic. Cis isomer. HPLC(Column): (254 nm) 99%. LC/MS(Column): (M + H) 445.3. |
| 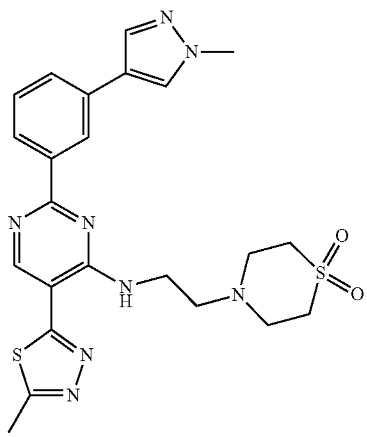 [SMILES: Cc1nnc(-c2cnc(-c3cccc(-c4cnn(C)c4)c3)nc2NCCN2CCS(=O)(=O)CC2)s1] | 127 | Off white Solid. HPLC(Xbridge): (254 nm) 94.1%. LC/MS(Column): (M + H) 511.0. 400 MHz, DMSO-d6: 9.34-9.32 (m, 1H), 8.80 (s, 1H), 8.54 (s, 1H), 8.25-8.21 (m, 1H), 7.90 (s, 1H), 7.72 (d, J = 7.68 Hz, 1H), 7.51 (t, J = 7.72 Hz, 1H), 3.89 (s, 3H), 3.87-3.87 (m, 2H), 3.32 (m, 4H), 3.12-3.06 (m, 4H), 2.86 (t, J = 6.16 Hz, 2H), 2.50-2.49 (m, 3H), 2.45 (s, 1H) |
| 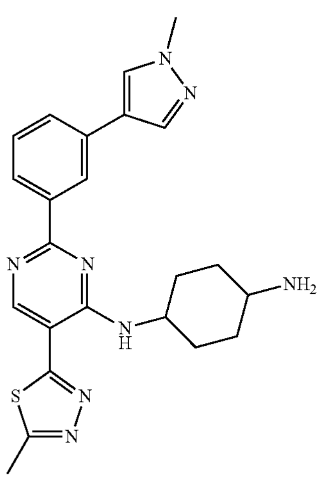 [SMILES: Cc1nnc(-c2cnc(-c3cccc(-c4cnn(C)c4)c3)nc2NC2CCC(N)CC2)s1] | 128 | Off white solid. HPLC(Xbridge): (254 nm) 93.1%. LC/MS(Column): (M + H) 447.0. 1H NMR (400 MHz, DMSO-d6): 8.92 (d, J = 6.80 Hz, 1H), 8.83 (s, 1H), 8.54 (s, 1H), 8.22-8.21 (m, 2H), 7.88 (s, 1H), 7.74 (d, J = 7.96 Hz, 1H), 7.53 (t, J = 7.80 Hz, 1H), 3.90 (s, 3H), 2.80 (s, 3H), 2.07 (d, J = 10.08 Hz, 2H), 1.71-0.00 (m, 1H), 1.63-1.51 (m, 4H), 1.36-0.00 (m, 4H), 1.16-1.14 (m, 1H) |

| Structure | Example | Analyticals |
|---|---|---|
| 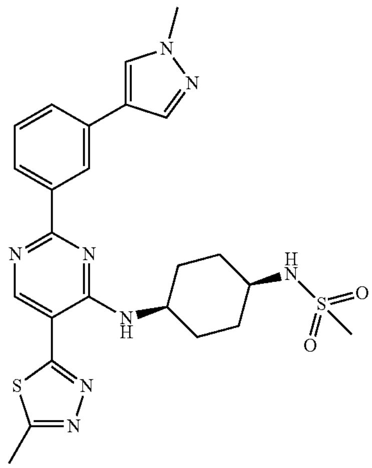 [SMILES: Cc1nnc(-c2cnc(-c3cccc(-c4cnn(C)c4)c3)nc2N[C@H]2CC[C@@H](NS(C)(=O)=O)CC2)s1] | 129 | Off white solid. HPLC(Column): (Xbrdge) 98.8%. LC/MS(Column): (M + H) 525.2. 1H-NMR (400 MHz, DMSO-d6): 9.14 (d, J = 7.20 Hz, 1H), 8.83 (s, 1H), 8.54 (s, 1H), 8.21-8.24 (m, 2H), 7.90 (s, 1H), 7.73 (d, J = 7.60 Hz, 1H), 7.52 (t, J = 8.00 Hz, 1H), 7.22 (d, J = 6.80 Hz, 1H), 4.45-4.48 (m, 1H), 3.91 (s, 3H), 3.34-3.35 (m, 1H), 2.95 (s, 3H), 2.82 (s, 3H). |
| 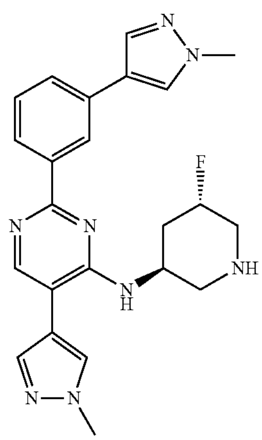 [SMILES: Cn1cc(-c2cccc(-c3ncc(-c4cnn(C)c4)c(N[C@@H]4CNC[C@@H](F)C4)n3)c2)cn1] | 130 | white solid. HPLC(Column): (254 nm) 97%. LC/MS(Column): (M + H) 433.3. |
| 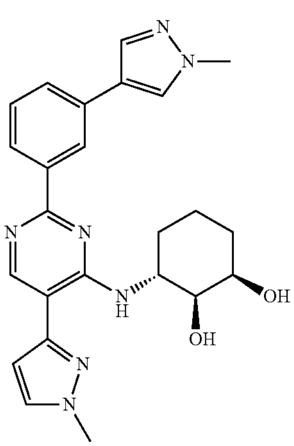 [SMILES: Cn1cc(-c2cccc(-c3ncc(-c4ccn(C)n4)c(N[C@@H]4CCC[C@@H](O)[C@H]4O)n3)c2)cn1] | 131 | brown solid. Racemic. HPLC(Column): (254 nm) 95%. LC/MS(Column): (M + H) 446.3. |

| Structure | Example | Analyticals |
|---|---|---|
| 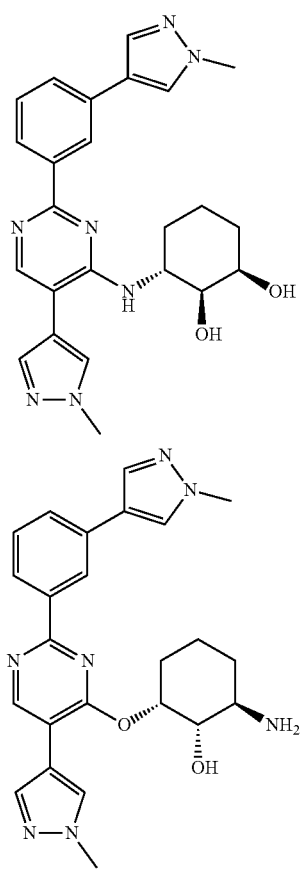 | 132 | brown solid. Racemic. HPLC(Column): (254 nm) 93%. LC/MS(Column): (M + H) 446.3. |

Example 133 and 134: (1R,2S,3R)-3-{5-(1-Methyl-1H-pyrazol-4-yl)-2-[3-(1-methyl-1H-pyrazol-4-yl)-phenyl]-pyrimidin-4-ylamino}-cyclohexane-1,2-diol and (1S,2R,6R)-2-Amino-6-{5-(1-methyl-1H-pyrazol-4-yl)-2-[3-(1-methyl-1H-pyrazol-4-yl)-phenyl]-pyrimidin-4-yloxy}-cyclohexanol (Racemics—Relative Configuration)

A suspension of a racemic mixture of (1S,2R,3S) and (1R,2S,3R)-3-[2-Chloro-5-(1-methyl-1H-pyrazol-4-yl)-pyrimidin-4-ylamino]-cyclohexane-1,2-diol (390 mg; 1.20 mmol; 1.00 eq.), 1-Methyl-4-[3-(4,4,5,5-tetramethyl-[1,3,2]dioxaborolan-2-yl)-phenyl]-1H-pyrazole (411 mg; 1.45 mmol; 1.20 eq.), [1,1'-bis(diphenylphosphino)ferrocene]dichloropalladium(II).CH$_2$Cl$_2$ (98 mg; 0.12 mmol; 0.10 eq.) and cesium carbonate (589 mg; 1.81 mmol; 1.50 eq.) in dioxane (4 mL) and water (0.4 mL) was stirred at 120° C. overnight in a sealed tubed. The reaction mixture was then cooled to RT, filtered through a celite pad, concentrated and purified by prep-HPLC (23-25% CH$_3$CN in 0.1% NH$_4$OH in H$_2$O) to give the title compound (175 mg, 36%), as a racemic mixture of (1S,2R,3R) and (1R,2S,3R)-3-{5-(1-Methyl-1H-pyrazol-4-yl)-2-[3-(1-methyl-1H-pyrazol-4-yl)-phenyl]-pyrimidin-4-ylamino}-cyclohexane-1,2-diol (175.00 mg; 0.39 mmol) as a white solid. 1H NMR (400 MHz, DMSO-d6) δ 8.53 (s, 1H), 8.23-8.15 (m, 3H), 8.07 (s, 1H), 7.86 (s, 1H), 7.78 (s, 1H), 7.66 (d, J=7.7 Hz, 1H), 7.48 (t, J=8.5 Hz, 1H), 6.06 (d, J=6.8 Hz, 1H), 4.59 (d, J=6.4 Hz, 1H), 4.52-4.48 (m, 1H), 4.40 (m, 1H), 3.93 (s, 3H), 3.90 (s, 3H), 3.63-3.56 (m, 1H), 2.21-2.11 (m, 1H), 1.77 (m, 2H), 1.48-1.26 (m, 3H). LC/MS446.2 (M+H).

A second fraction containing a racemic mixture of (1S, 2R,3R) and (1S,2R,6R)-2-Amino-6-{5-(1-methyl-1H-pyrazol-4-yl)-2-[3-(1-methyl-1H-pyrazol-4-yl)-phenyl]-pyrimidin-4-yloxy}-cyclohexanol (O-alkylation side-product) was isolated as a white solid (24 mg). 1H NMR (400 MHz, DMSO-d6) 8.49 (s, 1H), 8.25 (s, 1H), 8.20-8.14 (m, 2H), 8.07 (s, 1H), 7.87 (s, 1H), 7.80 (s, 1H), 7.65 (d, J=7.7 Hz, 1H), 7.50-7.44 (m, 1H), 6.69 (s, 1H), 5.07-4.84 (m, 2H), 4.40 (s, 1H), 3.95 (s, 3H), 3.88 (s, 3H), 3.74 (m, 2H), 1.64 (m, 4H), 1.52 (s, 1H), 1.31 (s, 1H). LC/MS: 446.3 (M+H).

Compounds below were prepared following similar routes and protocols:

| Structure | Example | Analyticals |
|---|---|---|
| 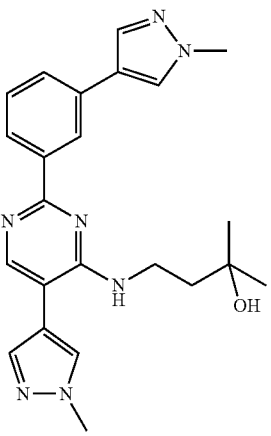 [SMILES: Cn1cc(-c2cccc(-c3ncc(-c4cnn(C)c4)c(NCCC(C)(C)O)n3)c2)cn1] | 135 | white solid. HPLC(Column): (254 nm) 99%. LC/MS(Column): (M + H) 418.3. |
| 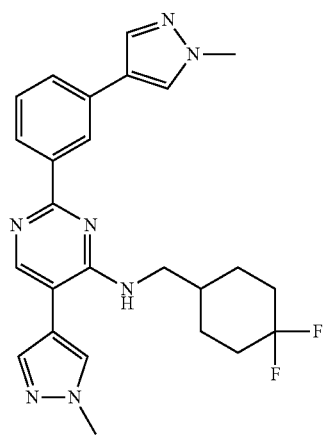 [SMILES: Cn1cc(-c2cccc(-c3ncc(-c4cnn(C)c4)c(NCC4CCC(F)(F)CC4)n3)c2)cn1] | 136 | white solid. HPLC(Column): (254 nm) 100%. LC/MS(Column): (M + H) 464.3. |
| 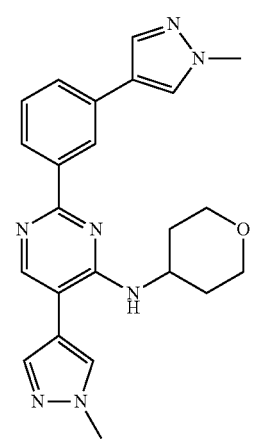 | 137 | white solid. HPLC(Column): (254 nm) 96%. LC/MS(Column): (M + H) 416.3. |

-continued
| Structure | Example | Analyticals |
|---|---|---|
| 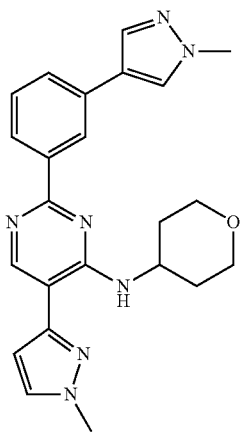 | 138 | white solid. HPLC(Column): (254 nm) 95%. LC/MS(Column): (M + H) 416.3. |
| 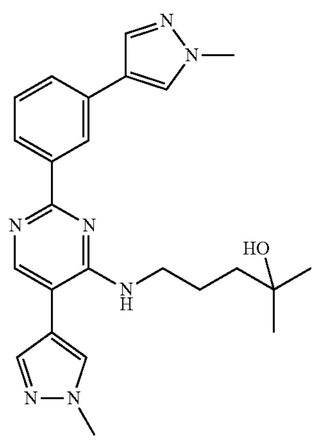 [SMILES: Cn1cc(-c2cccc(-c3ncc(-c4cnn(C)c4)c(NCCCC(C)(C)O)n3)c2)cn1] | 139 | white solid. HPLC(Column): (254 nm) 99%. LC/MS(Column): (M + H) 432.3. |
| 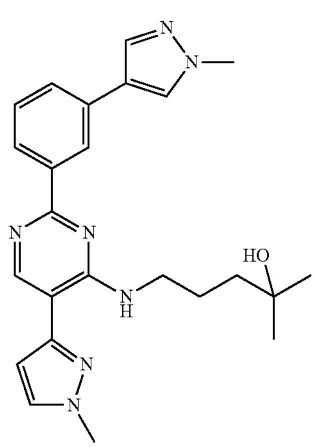 [SMILES: Cn1cc(-c2cccc(-c3ncc(-c4ccn(C)n4)c(NCCCC(C)(C)O)n3)c2)cn1] | 140 | white solid HPLC(Column): (254 nm) 100%. LC/MS(Column): (M + H) 432.3. |

| Structure | Example | Analyticals |
|---|---|---|
| 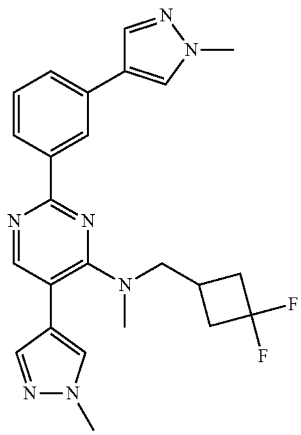 [SMILES: CN(CC1CC(F)(F)C1)c1nc(-c2cccc(-c3cnn(C)c3)c2)ncc1-c1cnn(C)c1] | 141 | white solid. HPLC(Column): (254 nm) 95%. LC/MS(Column): (M + H) 450.3. |
| 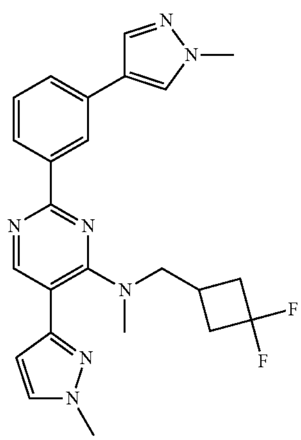 [SMILES: CN(CC1CC(F)(F)C1)c1nc(-c2cccc(-c3cnn(C)c3)c2)ncc1-c1ccn(C)n1] | 142 | white solid. HPLC(Column): (254 nm) 99%. LC/MS(Column): (M + H) 450.3. |
| 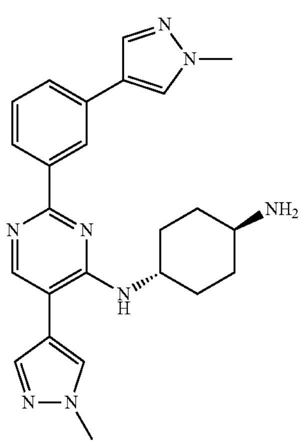 [SMILES: Cn1cc(-c2cccc(-c3ncc(-c4cnn(C)c4)c(N[C@H]4CC[C@H](N)CC4)n3)c2)cn1] | 143 | white solid. HPLC(Column): (254 nm) 93%. LC/MS(Column): (M + H) 429.3. |

-continued

| Structure | Example | Analyticals |
|---|---|---|
| 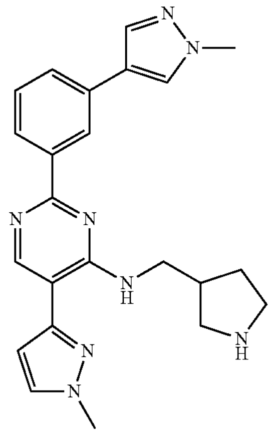 [SMILES: Cn1cc(-c2cccc(-c3ncc(-c4ccn(C)n4)c(NCC4CCNC4)n3)c2)cn1] | 144 | white solid. HPLC(Column): (254 nm) 91%. LC/MS(Column): (M + H) 415.3. |
| 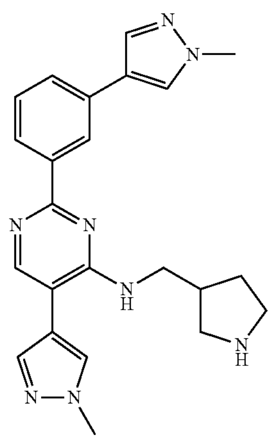 [SMILES: Cn1cc(-c2cccc(-c3ncc(-c4cnn(C)c4)c(NCC4CCNC4)n3)c2)cn1] | 145 | white solid. HPLC(Column): (254 nm) 100%. LC/MS(Column): (M + H) 415.3. |
| 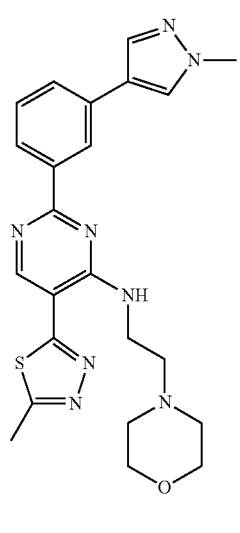 | 146 | Off white solid. HPLC(X-Bridge): (254 nm) 98.8%. LC/MS(Column): (M + H) 463.3. 1H NMR (DMSO-d6, 400 MHz): ppm 9.29 (s, 1H), 8.78 (s, 1H), 8.54 (s, 1H), 8.25-8.21 (m, 2H), 7.92-7.90 (m, 1H), 7.81-7.71 (m, 1H), 7.51 (d, J = 7.6 Hz, 1H), 4.16 (s, 1H), 3.89-3.80 (m, 5H), 3.62-3.59 (m, 4H), 3.58-3.48 (m, 1H), 3.31-3.21 (m, 1H), 2.81 (s, 3H), 2.66-2.49 (m, 3H). |

-continued

| Structure | Example | Analyticals |
|---|---|---|
| 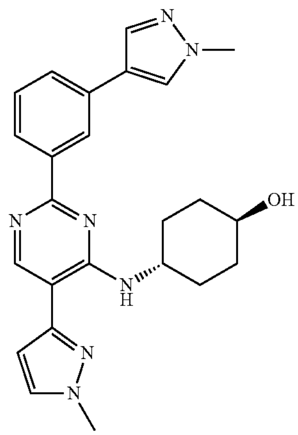 [SMILES: Cn1cc(-c2cccc(-c3ncc(-c4ccn(C)n4)c(N[C@H]4CC[C@H](O)CC4)n3)c2)cn1] | 147 | white solid. Off white solid. HPLC(Column): (254 nm) 98%. LC/MS(Column): (M + H) 430.4. |
| 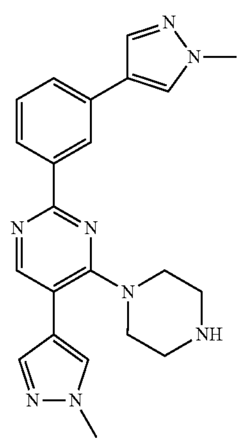 [SMILES: Cn1cc(-c2cccc(-c3ncc(-c4cnn(C)c4)c(N4CCNCC4)n3)c2)cn1] | 148 | white solid. HPLC(Column): (254 nm) 97%. LC/MS(Column): (M + H) 401.2. |
| 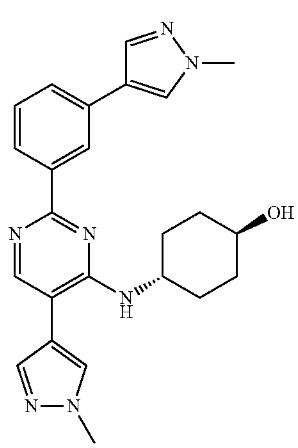 [SMILES: Cn1cc(-c2cccc(-c3ncc(-c4cnn(C)c4)c(N[C@H]4CC[C@H](O)CC4)n3)c2)cn1] | 149 | white solid. Trans isomer. HPLC: (254 nm) 90%. LC/MS(Column): (M + H) 430.1. 1H NMR (400 MHz, DMSO-d6) d 8.51 (s, 1H), 8.19 (ddd, J = 13.7, 6.8, 4.1 Hz, 3H), 8.03 (d, J = 2.4 Hz, 1H), 7.88-7.84 (m, 1H), 7.76-7.71 (m, 1H), 7.66 (d, J = 7.7 Hz, 1H), 7.51-7.46 (m, 1H), 6.08 (d, J = 7.8 Hz, 1H), 4.58 (t, J = 3.1 Hz, 1H), 4.10 (d, J = 9.9 Hz, 1H), 3.94-3.89 (m, 6H), 3.45 (s, 1H), 2.02 (d, J = 12.4 Hz, 2H), 1.91 (d, J = 12.1 Hz, 2H), 1.42 (dq, J = 41.7, 12.5 Hz, 4H). |

-continued

| Structure | Example | Analyticals |
|---|---|---|
| 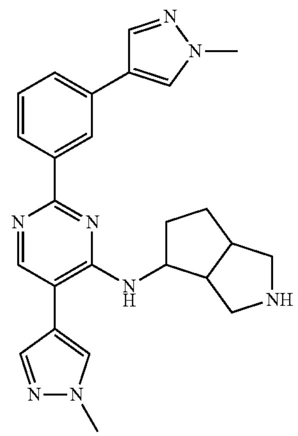 [SMILES: Cn1cc(-c2cccc(-c3ncc(-c4cnn(C)c4)c(NC4CCC5CNCC54)n3)c2)cn1] | 150 | white solid. HPLC(Column): (254 nm) 98%. LC/MS(Column): (M + H) 441.3. |
| 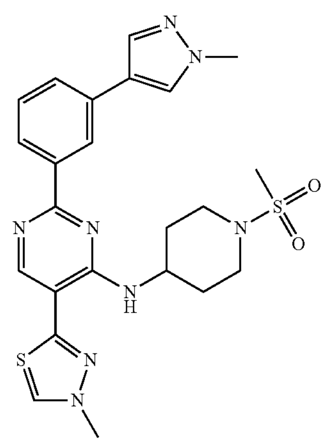 | 151 | Pale yellow solid. HPLC(Xbridge): (254 nm) 91.3%. LC/MS(Column): (M + H) 511.2. |
| 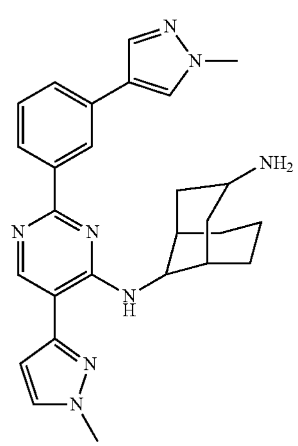 [SMILES: Cn1cc(-c2cccc(-c3ncc(-c4ccn(C)n4)c(NC4C5CCCC4CC(N)C5)n3)c2)cn1] | 152 | white solid. HPLC(Column): (254 nm) 83%. LC/MS(Column): (M + H) 469.3. |

-continued
| Structure | Example | Analyticals |
|---|---|---|
| 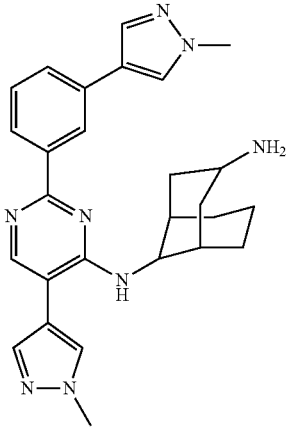 [SMILES: Cn1cc(-c2cccc(-c3ncc(-c4cnn(C)c4)c(NC4C5CCCC4CC(N)C5)n3)c2)cn1] | 153 | white solid. HPLC(Column): (254 nm) 99%. LC/MS(Column): (M + H) 469.3. |
| 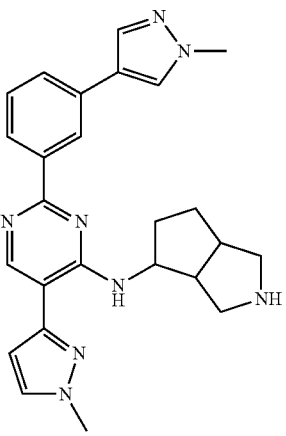 [SMILES: Cn1cc(-c2cccc(-c3ncc(-c4ccn(C)n4)c(NC4CCC5CNCC54)n3)c2)cn1] | 154 | white solid. HPLC(Column): (254 nm) 95%. LC/MS(Column): (M + H) 441.3. |
| 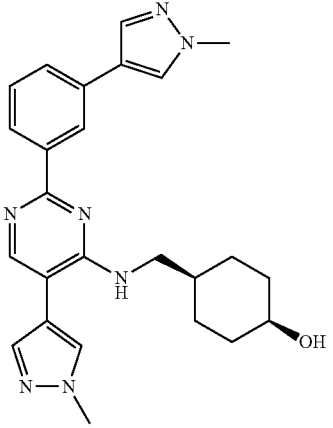 [SMILES: Cn1cc(-c2cccc(-c3ncc(-c4cnn(C)c4)c(NC[C@H]4CC[C@@H](O)CC4)n3)c2)cn1] | 155 | white solid. Trans isomer. HPLC(Column): (254 nm) 95%. LC/MS(Column): (M + H) 444.3. |

-continued

| Structure | Example | Analyticals |
|---|---|---|
| 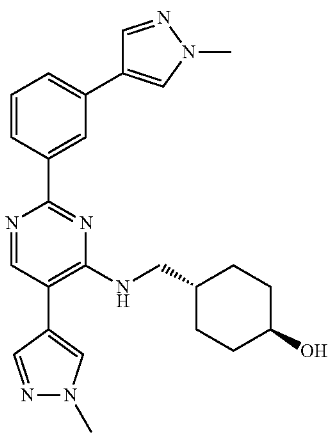 [SMILES: Cn1cc(-c2cccc(-c3ncc(-c4cnn(C)c4)c(NC[C@H]4CC[C@H](O)CC4)n3)c2)cn1] | 156 | white solid. Cis isomer. HPLC(Column): (254 nm) 99%. LC/MS(Column): (M + H) 444.3. Cis-isomer |
| 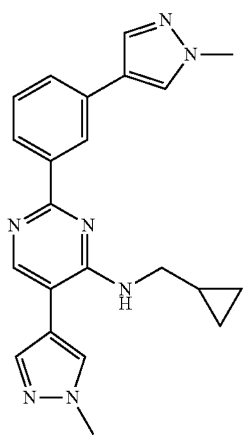 [SMILES: Cn1cc(-c2cccc(-c3ncc(-c4cnn(C)c4)c(NCC4CC4)n3)c2)cn1] | 157 | white solid. HPLC(Column): (254 nm) 99%. LC/MS(Column): (M + H) 386.2. |
| 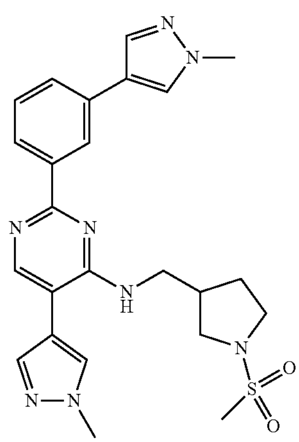 [SMILES: Cn1cc(-c2cccc(-c3ncc(-c4cnn(C)c4)c(NCC4CCN(S(C)(=O)=O)C4)n3)c2)cn1] | 158 | white solid. HPLC(Column): (254 nm) 93%. LC/MS(Column): (M + H) 493.2. |

-continued

| Structure | Example | Analyticals |
|---|---|---|
| 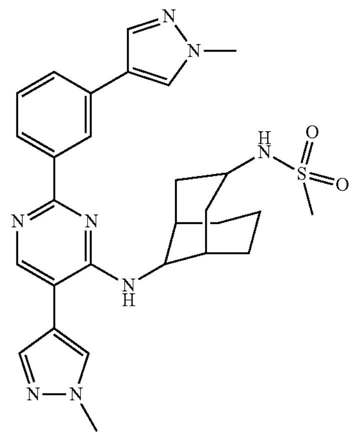 [SMILES: Cn1cc(-c2cccc(-c3ncc(-c4cnn(C)c4)c(NC4C5CCCC4CC(NS(C)(=O)=O)C5)n3)c2)cn1] | 159 | white solid. HPLC(Column): (254 nm) 95%. LC/MS(Column): (M + H) 547.3. |
| 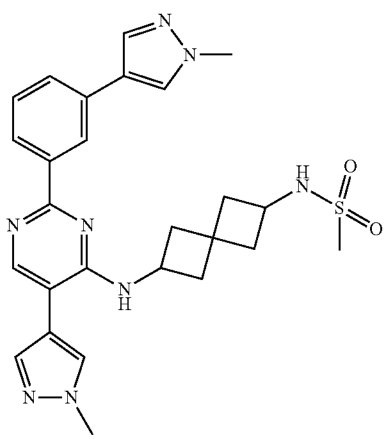 [SMILES: Cn1cc(-c2cccc(-c3ncc(-c4cnn(C)c4)c(NC4CC5(C4)CC(NS(C)(=O)=O)C5)n3)c2)cn1] | 160 | white solid. HPLC(Column): (254 nm) 97%. LC/MS(Column): (M + H) 519.3. |
| 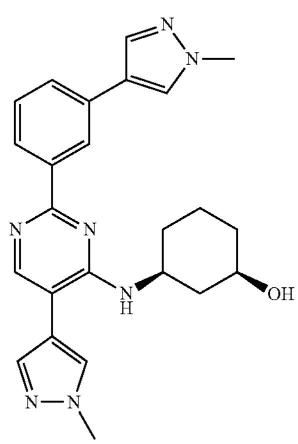 [SMILES: Cn1cc(-c2cccc(-c3ncc(-c4cnn(C)c4)c(N[C@H]4CCC[C@@H](O)C4)n3)c2)cn1] | 161 | white solid. Racemic. Cis isome. HPLC(Column): (254 nm) 94%. LC/MS(Column): (M + H) 430.3. |

| Structure | Example | Analyticals |
|---|---|---|
| 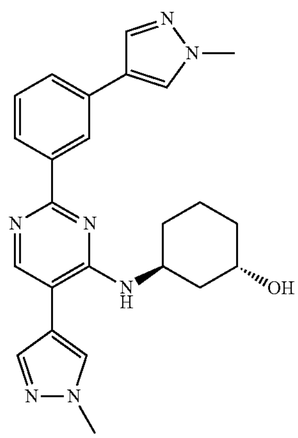 [SMILES: Cn1cc(-c2cccc(-c3ncc(-c4cnn(C)c4)c(N[C@H]4CCC[C@H](O)C4)n3)c2)cn1] | 162 | white solid. Racemic. Trans isomer.<br>HPLC(Column): (254 nm) 90%.<br>LC/MS(Column): (M + H) 430.3. |
| 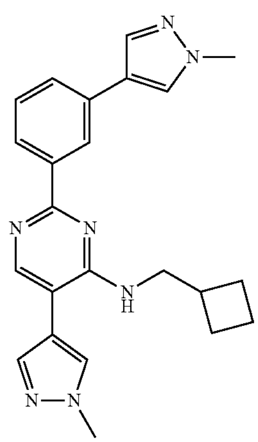 [SMILES: Cn1cc(-c2cccc(-c3ncc(-c4cnn(C)c4)c(NCC4CCC4)n3)c2)cn1] | 163 | white solid. HPLC(Column): (254 nm) 97%.<br>LC/MS(Column): (M + H) 400.2. |
| 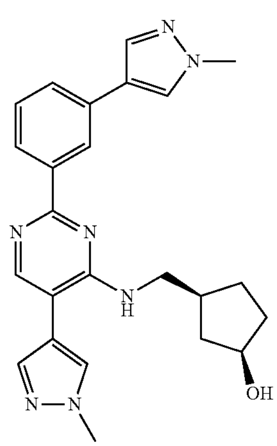 [SMILES: Cn1cc(-c2cccc(-c3ncc(-c4cnn(C)c4)c(NC[C@H]4CC[C@@H](O)C4)n3)c2)cn1] | 164 | white solid. Racemic. Cis Isomer.<br>HPLC(Column): (254 nm) 99%.<br>LC/MS(Column): (M + H) 430.3. |

| Structure | Example | Analyticals |
|---|---|---|
| 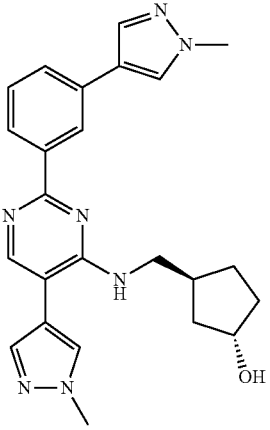 [SMILES: Cn1cc(-c2cccc(-c3ncc(-c4cnn(C)c4)c(NC[C@H]4CC[C@H](O)C4)n3)c2)cn1] | 165 | white solid. Racemic. Trans isomer. HPLC(Column): (254 nm) 99%. LC/MS(Column): (M + H) 430.3. |
| 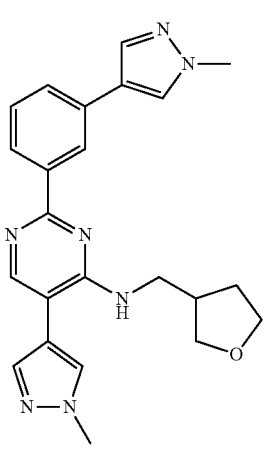 [SMILES: Cn1cc(-c2cccc(-c3ncc(-c4cnn(C)c4)c(NCC4CCOC4)n3)c2)cn1] | 166 | white solid. Racemic. HPLC(Column): (254 nm) 93%. LC/MS(Column): (M + H) 416.2. |
| 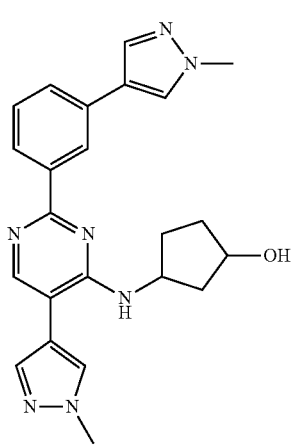 [SMILES: Cn1cc(-c2cccc(-c3ncc(-c4cnn(C)c4)c(NC4CCC(O)C4)n3)c2)cn1] | 167 | Racemic-HPLC(Column): (254 nm) 100%. LC/MS(Column): (M + H) 416.2. |

-continued
| Structure | Example | Analyticals |
|---|---|---|
| 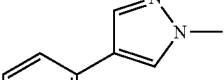 | 168 | white solid. HPLC(Column): (254 nm) 96%. LC/MS(Column): (M + H) 519.3. |
| 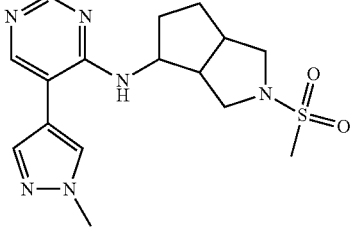 | 169 | white solid. HPLC(Column): (254 nm) 96%. LC/MS(Column): (M + H) 519.3. |
| 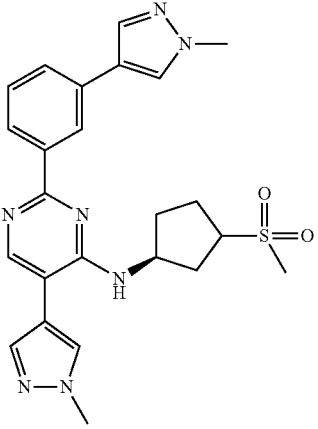 [SMILES: Cn1cc(-c2cccc(-c3ncc(-c4cnn(C)c4)c(N[C@H]4CCC(S(C)(=O)=O)C4)n3)c2)cn1] | 170 | white solid. HPLC(Column): (254 nm) 98%. LC/MS(Column): (M + H) 479.2. |

| Structure | Example | Analyticals |
|---|---|---|
| 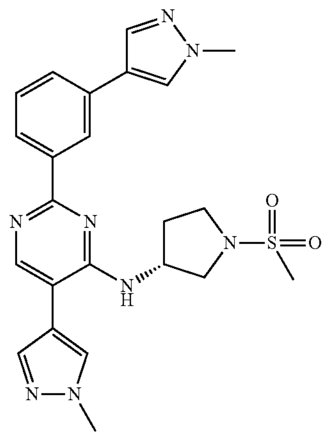 [SMILES: Cn1cc(-c2cccc(-c3ncc(-c4cnn(C)c4)c(N[C@@H]4CCN(S(C)(=O)=O)C4)n3)c2)cn1] | 171 | white solid. HPLC(Column): (254 nm) 95%. LC/MS(Column): (M + H) 479.2. |
| 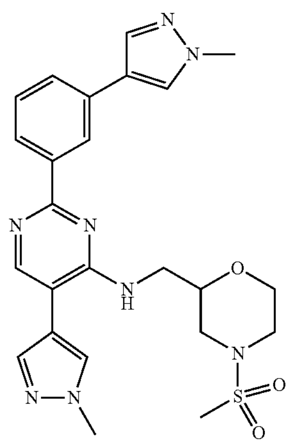 [SMILES: Cn1cc(-c2cccc(-c3ncc(-c4cnn(C)c4)c(NCC4CN(S(C)(=O)=O)CCO4)n3)c2)cn1] | 172 | white solid. HPLC(Column): (254 nm) 95%. LC/MS(Column): (M + H) 509.25. |
| 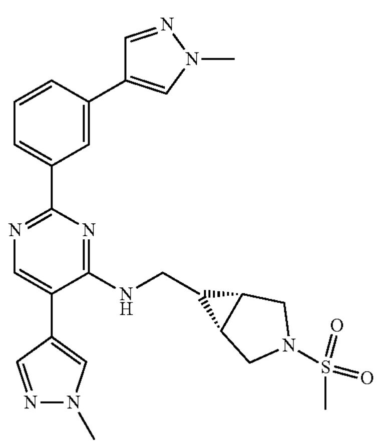 | 173 | white solid. HPLC(Column): (254 nm) 96%. LC/MS(Column): (M + H) 505.3. |

| Structure | Example | Analyticals |
|---|---|---|
| 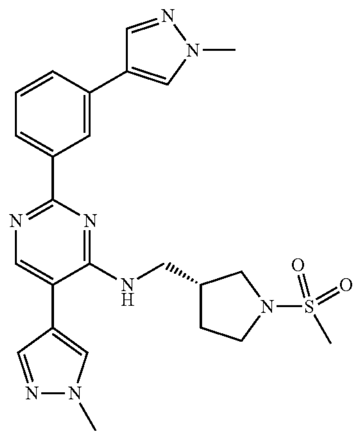 [SMILES: Cn1cc(-c2cccc(-c3ncc(-c4cnn(C)c4)c(NC[C@H]4CCN(S(C)(=O)=O)C4)n3)c2)cn1] | 174 | white solid. HPLC(Column): (254 nm) 91%. LC/MS(Column): (M + H) 493.25. |
| 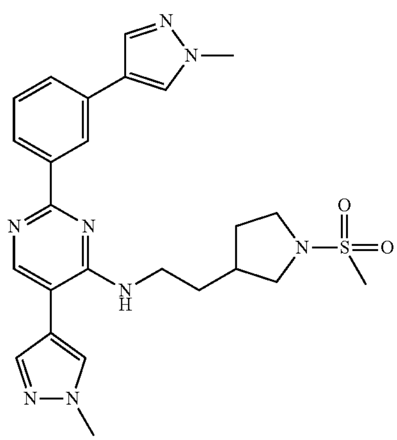 [SMILES: Cn1cc(-c2cccc(-c3ncc(-c4cnn(C)c4)c(NCCC4CCN(S(C)(=O)=O)C4)n3)c2)cn1] | 175 | white solid. HPLC(Column): (254 nm) 94%. LC/MS(Column): (M + H) 507.3. |
| 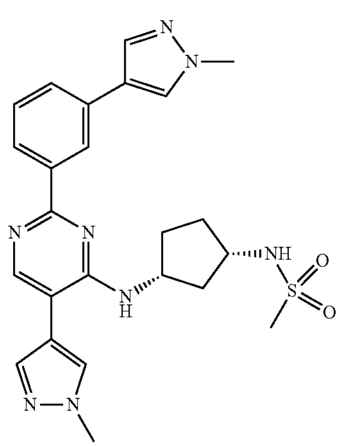 [SMILES: Cn1cc(-c2cccc(-c3ncc(-c4cnn(C)c4)c(N[C@@H]4CC[C@H](NS(C)(=O)=O)C4)n3)c2)cn1] | 176 | white solid. Racemic. Cis isomer. HPLC(Column): (254 nm) 94%. LC/MS(Column): (M + H) 493.25. |

-continued
| Structure | Example | Analyticals |
|---|---|---|
| 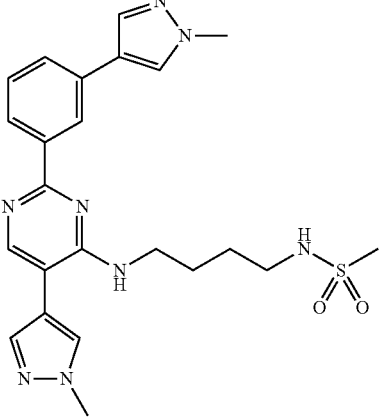 | 177 | white solid. HPLC(Column): (254 nm) 96%.<br>LC/MS(Column): (M + H) 481.3. |
| 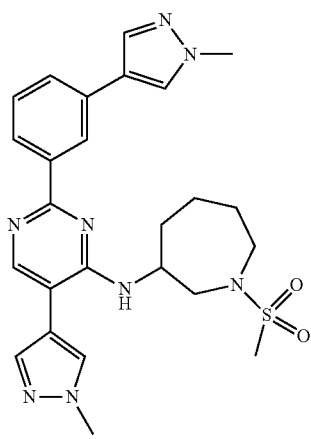 [SMILES: Cn1cc(-c2cccc(-c3ncc(-c4cnn(C)c4)c(NC4CCCCN(S(C)(=O)=O)C4)n3)c2)cn1] | 178 | white solid. HPLC(Column): (254 nm) 94%.<br>LC/MS(Column): (M + H) 507.35. |
| 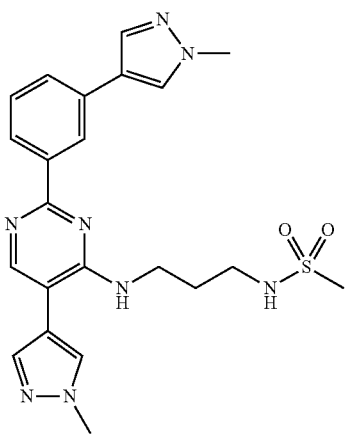 [SMILES: Cn1cc(-c2cccc(-c3ncc(-c4cnn(C)c4)c(NCCCNS(C)(=O)=O)n3)c2)cn1] | 179 | white solid. HPLC(Column): (254 nm) 97%.<br>LC/MS(Column): (M + H) 467.3. |

-continued

| Structure | Example | Analyticals |
|---|---|---|
| 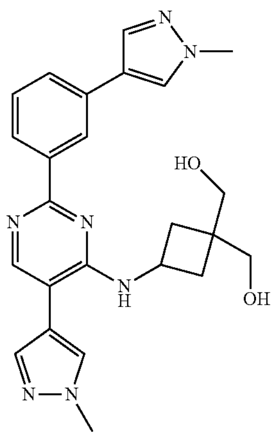 [SMILES: Cn1cc(-c2cccc(-c3ncc(-c4cnn(C)c4)c(NC4CC(CO)(CO)C4)n3)c2)cn1] | 180 | yellow solid. HPLC(Column): (254 nm) 89%. LC/MS(Column): (M + H) 446.4. |
| 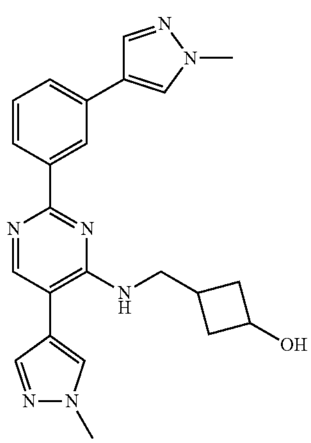 [SMILES: Cn1cc(-c2cccc(-c3ncc(-c4cnn(C)c4)c(NCC4CC(O)C4)n3)c2)cn1] | 181 | white solid. HPLC(Column): (254 nm) 98%. LC/MS(Column): (M + H) 416.2. |
| 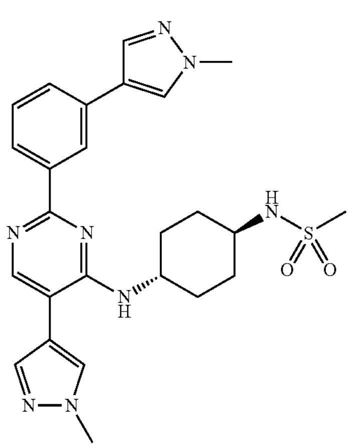 [SMILES: Cn1cc(-c2cccc(-c3ncc(-c4cnn(C)c4)c(N[C@H]4CC[C@H](NS(C)(=O)=O)CC4)n3)c2)cn1] | 182 | white solid. Trans isomer. HPLC(Column): (254 nm) 96%. LC/MS(Column): (M + H) 507.3. |

-continued

| Structure | Example | Analyticals |
|---|---|---|
| 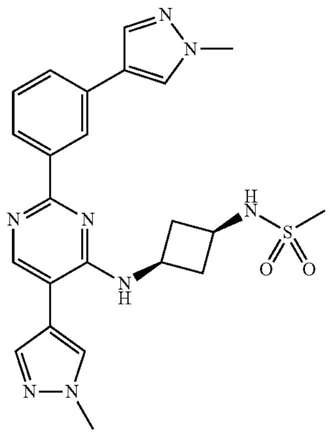 [SMILES: Cn1cc(-c2cccc(-c3ncc(-c4cnn(C)c4)c(N[C@H]4C[C@@H](NS(C)(=O)=O)C4)n3)c2)cn1] | 183 | white solid. Cis-isomer. HPLC(Column): (254 nm) 95%. LC/MS(Column): (M + H) 479.2. |
| 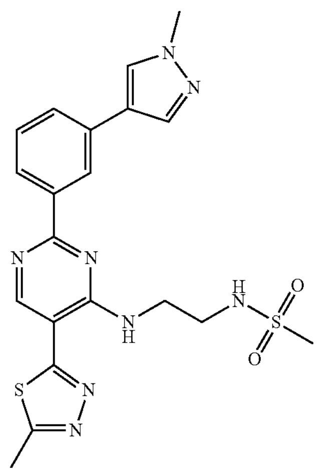 | 184 | Off White Solid. HPLC (Xbridge): (254 nm) 93.4%. LC/MS(Column): (M + H) 471.0. 1H NMR (DMSO-d6, 400 MHz): 9.07 (t, J = 5.9 Hz, 1H), 8.81 (s, 1H), 8.55-8.55 (m, 1H), 8.26 (d, J = 7.9 Hz, 1H), 8.23 (s, 1H), 7.93 (s, 1H), 7.73 (d, J = 8.1 Hz, 1H), 7.50 (t, J = 7.8 Hz, 1H), 7.33 (t, J = 5.8 Hz, 1H), 3.89 (s, 4H), 2.91 (s, 3H), 2.81 (s, 3H), 2.49 (s, 3H). |
| 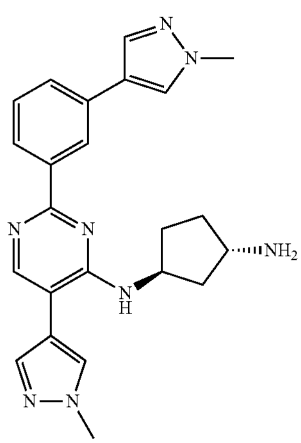 [SMILES: Cn1cc(-c2cccc(-c3ncc(-c4cnn(C)c4)c(N[C@H]4CC[C@H](N)C4)n3)c2)cn1] | 185 | white solid. HPLC(Column): (254 nm) 97%. LC/MS(Column): (M + H) 415.25. 1H NMR (400 MHz, DMSO-d6) d 8.52 (d, J = 6.7 Hz, 1H), 8.21 (d, J = 2.0 Hz, 3H), 8.04 (s, 1H), 7.89 (s, 1H), 7.74 (s, 1H), 7.66 (d, J = 7.6 Hz, 1H), 7.47 (t, J = 7.7 Hz, 1H), 6.21 (d, J = 6.9 Hz, 1H), 4.74 (m, 1H), 3.94 (s, 3H), 3.85 (s, 3H), 3.44 (m 1H), 2.23 (m, 1H), 1.88 (m, 3H), 1.47 (m, 2H). |

-continued

| Structure | Example | Analyticals |
|---|---|---|
| 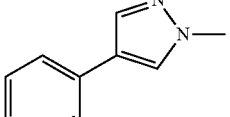 | 186 | white solid. HPLC(Column): (254 nm) 97%. LC/MS(Column): (M + H) 455.3. 1H NMR (400 MHz, DMSO-d6) d 8.51 (s, 1H), 8.17 (dd, J = 15.6, 9.5 Hz, 3H), 8.07 (s, 1H), 7.85 (s, 1H), 7.75 (s, 1H), 7.67 (d, J = 7.7 Hz, 1H), 7.51 (t, J = 7.7 Hz, 1H), 5.38 (s, 1H), 3.92 (s, 3H), 3.88 (s, 3H), 2.19 (m, 6H), 1.63 (m, 6H), 1.31 (s, 2H). |
| 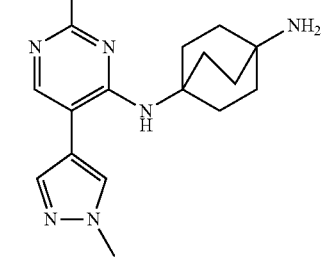 | 187 | white solid. HPLC(Column): (254 nm) 97%. LC/MS(Column): (M + H) 533.3. 1H NMR (400 MHz, DMSO-d6) d 8.50 (s, 1H), 8.24-8.04 (m, 4H), 7.87 (s, 1H), 7.76 (s, 1H), 7.68 (d, J = 7.7 Hz, 1H), 7.51 (t, J = 7.7 Hz, 1H), 6.94 (s, 1H), 5.44 (s, 1H), 3.92 (s, 6H), 2.97 (s, 3H), 2.29-2.17 (m, 6H), 2.07-1.93 (m, 6H). |
| 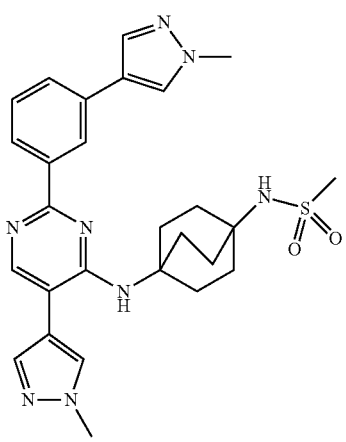 | 188 | white solid. HPLC(Column): (254 nm) 100%. LC/MS(Column): (M + H) 415.3. 1H NMR (400 MHz, DMSO-d6) d 8.51 (d, J = 10.8 Hz, 1H), 8.19 (m, 3H), 8.06 (d, J = 9.3 Hz, 1H), 7.88 (s, 1H), 7.75 (d, J = 4.5 Hz, 1H), 7.66 (d, J = 7.7 Hz, 1H), 7.48 (t, J = 7.7 Hz, 1H), 6.60 (dd, J = 17.6, 6.7 Hz, 1H), 4.68 (m, 0.3H), 4.55 (m, 0.7H), 3.93 (s, 3H), 3.88 (s, 3H), 3.00 (m, 0.3H), 2.74 (m, 0.7H), 2.58 (d, J = 6.5 Hz, 1H), 2.47-2.40 (m, 1H), 2.28-1.99 (m, 2.7H), 1.78 (m, 1.3H). |

-continued

| Structure | Example | Analyticals |
|---|---|---|
| 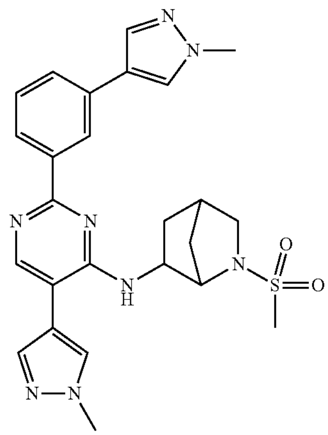 [SMILES: Cn1cc(-c2cccc(-c3ncc(-c4cnn(C)c4)c(NC4CC5CC4N(S(C)(=O)=O)C5)n3)c2)cn1] | 189 | white solid. HPLC(Column): (254 nm) 99%. LC/MS(Column): (M + H) 505.3. 1H NMR (400 MHz, DMSO-d6) d 8.50 (s, 1H), 8.33 (s, 1H), 8.20 (d, J = 8.8 Hz, 2H), 8.10 (s, 1H), 7.90 (s, 1H), 7.83 (s, 1H), 7.66 (d, J = 7.6 Hz, 1H), 7.47 (t, J = 7.7 Hz, 1H), 6.24 (d, J = 7.7 Hz, 1H), 4.66 (ddt, J = 10.7, 6.7, 3.3 Hz, 1H), 4.22 (s, 1H), 3.90 (s, 6H), 3.10 (d, J = 8.6 Hz, 1H), 2.97 (s, 3H), 2.65 (s, 1H), 2.35-2.27 (m, 1H), 2.09 (d, J = 5.5 Hz, 1H), 1.82 (d, J = 10.6 Hz, 1H), 1.72 (d, J = 10.8 Hz, 1H), 1.19 (dt, J = 13.4, 3.2 Hz, 1H). |
| 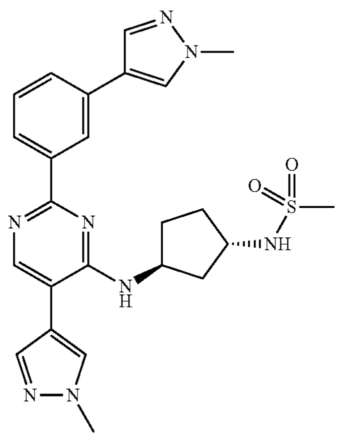 [SMILES: Cn1cc(-c2cccc(-c3ncc(-c4cnn(C)c4)c(N[C@H]4CC[C@H](NS(C)(=O)=O)C4)n3)c2)cn1] | 190 | white solid. HPLC(Column): (254 nm) 96%. LC/MS(Column): (M + H) 493.25. 1H NMR (400 MHz, DMSO-d6) d 8.51 (s, 1H), 8.21 (m, 3H), 8.04 (s, 1H), 7.89 (s, 1H), 7.75 (s, 1H), 7.67 (d, J = 7.6 Hz, 1H), 7.47 (t, J = 7.7 Hz, 1H), 7.19 (s, 1H), 6.39 (d, J = 6.9 Hz, 1H), 4.73 (m, 1H), 3.92 (s, 3H), 3.85 (s, 3H), 3.84 (m, 1H)), 2.91 (s, 3H), 2.23 (m, 1H), 2.04 (m, 3H), 1.61 (m, 2H). |
| 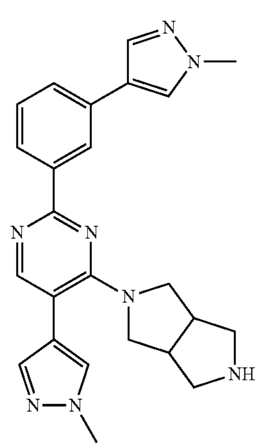 [SMILES: Cn1cc(-c2cccc(-c3ncc(-c4cnn(C)c4)c(N4CC5CNCC5C4)n3)c2)cn1] | 191 | off white solid. HPLC(Column): (254 nm) 97%. LC/MS(Column): (M + H) 427.3. 1H NMR (400 MHz, DMSO-d6) d 8.49 (d, J = 1.8 Hz, 1H), 8.23-8.14 (m, 3H), 7.89 (d, J = 10.1 Hz, 2H), 7.67 (dt, J = 7.7, 1.4 Hz, 1H), 7.56 (s, 1H), 7.47 (t, J = 7.7 Hz, 1H), 3.90 (d, J = 3.1 Hz, 6H), 3.61 (m 7m, 2H), 3.24 (m, 2H), 2.88 (m, 2H), 2.71 (m, 2H), 2.59 (m, 2H). |

-continued

| Structure | Example | Analyticals |
|---|---|---|
| 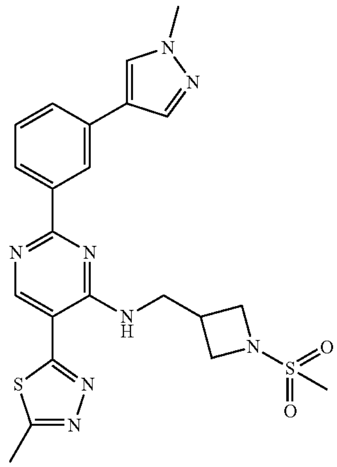 | 192 | white solid. HPLC(Column): (254 nm) 95.3%. LC/MS(Column): (M + H) 497.0. 1H-NMR (400 MHz, DMSO-d6): 9.12 (t, J = 5.60 Hz, 1H), 8.82 (s, 1H), 8.55 (s, 1H), 8.26 (d, J = 8.00 Hz, 1H), 8.22 (s, 1H), 7.92 (s, 1H), 7.75 (d, J = 7.20 Hz, 1H), 7.52 (t, J = 7.60 Hz, 1H), 4.04 (t, J = 6.40 Hz, 2H), 3.97 (t, J = 8.40 Hz, 2H), 3.90 (s, 3H), 3.81 (t, J = 6.00 Hz, 2H), 3.07-3.12 (m, 1H), 2.98 (s, 3H). |
| 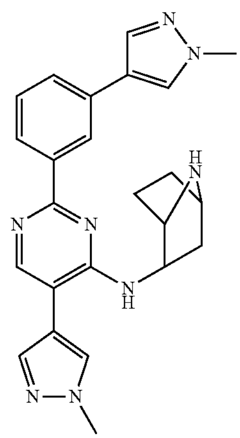 [SMILES: Cn1cc(-c2cccc(-c3ncc(-c4cnn(C)c4)c(NC4CC5CCC4N5)n3)c2)cn1] | 193 | white solid. HPLC(Column): (254 nm) 100%. LC/MS(Column): (M + H) 427.3. |
| 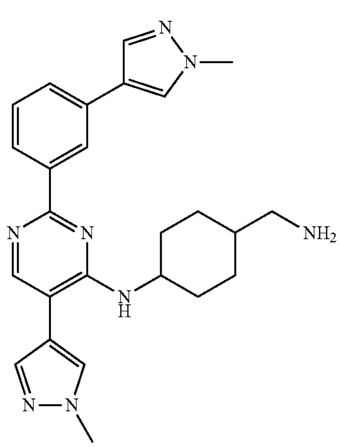 [SMILES: Cn1cc(-c2cccc(-c3ncc(-c4cnn(C)c4)c(NC4CCC(CN)CC4)n3)c2)cn1] | 194 | white solid. HPLC(Column): (254 nm) 97%. LC/MS(Column): (M + H) 443.3. 1H NMR (400 MHz, DMSO-d6) d 8.49 (s, 1H), 8.25-8.13 (m, 3H), 8.05 (d, J = 4.6 Hz, 1H), 7.87 (s, 1H), 7.76 (s, 1H), 7.65 (d, J = 7.6 Hz, 1H), 7.47 (t, J = 7.7 Hz, 1H), 5.95 (m, 1H), 4.34-4.22 (m, 1H), 3.93 (s, 3H), 3.90 (s, 3H), 2.96 (t, J = 6.2 Hz, 1H), 1.86-1.34 (m, 10H) |

Example 195 and 196: Cis and Trans N-(3-{5-(1-Methyl-1H-pyrazol-4-yl)-2-[3-(1-methyl-1H-pyrazol-4-yl)-phenyl]-pyrimidin-4-ylamino}-cyclobutyl-methyl)-methanesulfonamide

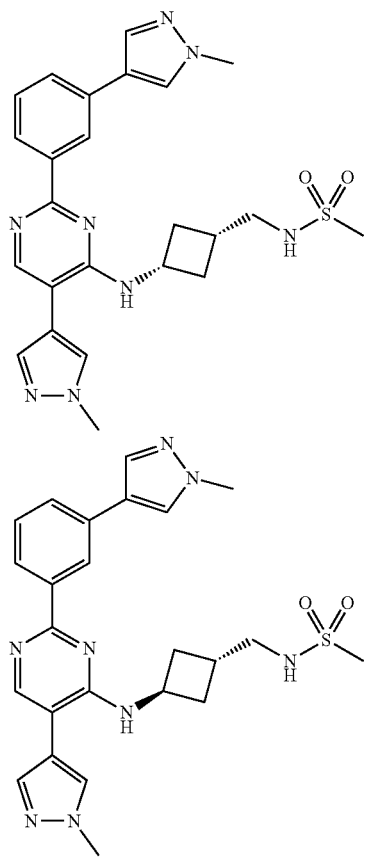

Methanesulfonyl chloride (0.07 ml; 0.93 mmol; 1.20 eq.) was added to a solution of (3-Aminomethyl-cyclobutyl)-{5-(1-methyl-1H-pyrazol-4-yl)-2-[3-(1-methyl-1H-pyrazol-4-yl)-phenyl]-pyrimidin-4-yl}-amine hydrochloride (350 mg; 0.78 mmol; 1.00 eq.) and TEA (0.22 mL; 1.55 mmol; 2.00 eq.) in DMF (3 mL). The reaction mixture was stirred at room temperature overnight. It was then concentrated under reduced pressure and purified by preparative HPLC (25-28% CH$_3$CN in 0.1% NH$_4$OH in H$_2$O) to give the tittle compounds as cis and trans isomers: First eluting isomer: Yellow solid (17 mg). 1H NMR (400 MHz, DMSO-d6) δ 8.50 (d, J=1.9 Hz, 1H), 8.25-8.16 (m, 3H), 8.07 (s, 1H), 7.90 (s, 1H), 7.76 (s, 1H), 7.67 (d, J=7.7 Hz, 1H), 7.47 (t, J=7.7 Hz, 1H), 7.17-7.06 (m, 1H), 6.66 (d, J=6.5 Hz, 1H), 4.77 (m, 1H), 3.93 (s, 3H), 3.91 (s, 3H), 3.17 (t, J=6.7 Hz, 2H), 2.95 (s, 3H), 2.29 (m, 5H). LC/MS: 493.3 (M+H). Second eluting isomer: white solid (17 mg). $^1$H NMR (400 MHz, DMSO-d$_6$) δ 8.49 (d, J=1.9 Hz, 1H), 8.25-8.16 (m, 3H), 8.05 (s, 1H), 7.89 (s, 1H), 7.75 (s, 1H), 7.66 (d, J=7.7 Hz, 1H), 7.48 (t, J=7.7 Hz, 1H), 6.98 (brs, 1H), 6.63 (d, J=6.9 Hz, 1H), 4.61 (m, 1H), 3.93 (s, 3H), 3.90 (s, 3H), 3.02 (d, J=6.9 Hz, 2H), 2.89 (s, 3H), 2.31-2.14 (m, 1H), 1.90-1.79 (m, 2H). LC/MS: 493.3 (M+H).

Compounds below were prepared following similar routes and protocols:

| Structure | Example | Analyticals |
|---|---|---|
| 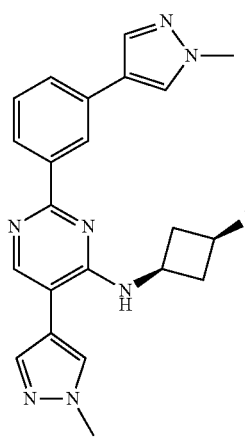 | 197 | white solid. Trans isomer. HPLC: (254 nm) 99%. LC/MS(Column): (M + H) 401.3. 1H NMR (400 MHz, DMSO-d6) d 8.51 (s, 1H), 8.25-8.15 (m, 3H), 8.06 (s, 1H), 7.89 (s, 1H), 7.76 (s, 1H), 7.66 (d, J = 7.7 Hz, 1H), 7.47 (t, J = 7.7 Hz, 1H), 6.55 (m, 1H), 4.77 (m, 1H), 3.92 (s, 3H), 3.90 (s, 3H), 3.55 (s, 1H), 2.35 (m, 2H), 2.19-2.06 (m, 2H) |

| Structure | Example | Analyticals |
|---|---|---|
| 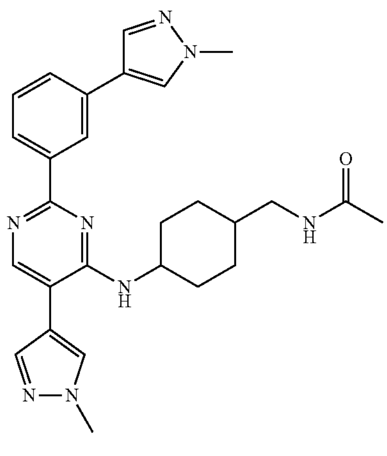 [SMILES: CC(=O)NCC1CCC(Nc2nc(-c3cccc(-c4cnn(C)c4)c3)ncc2-c2cnn(C)c2)CC1] | 198 | white solid. HPLC: (254 nm) 100%. LC/MS(Column): (M + H) 485.4. 1H NMR (400 MHz, DMSO-d6) d 8.49 (s, 1H), 8.25-8.13 (m, 3H), 8.06 (s, 1H), 7.88-7.75 (m, 3H), 7.66 (d, J = 7.7 Hz, 1H), 7.47 (t, J = 7.7 Hz, 1H), 6.01 (d, J = 7.0 Hz, 1H), 4.32-4.23 (m, 1H), 3.92 (s, 3H), 3.90 (s, 3H), 3.07 (t, J = 6.4 Hz, 2H), 1.82 (s, 3H), 1.74-1.55 (m, 7H), 1.41 (m, 2H) |
| 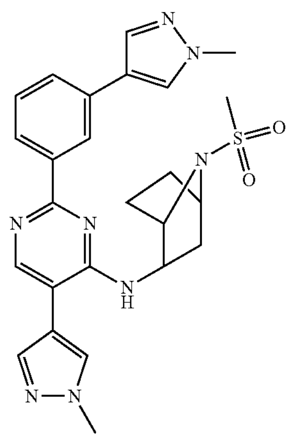 [SMILES: Cn1cc(-c2cccc(-c3ncc(-c4cnn(C)c4)c(NC4CC5CCC4N5S(C)(=O)=O)n3)c2)cn1] | 199 | white solid. HPLC(Column): (254 nm) 99%. LC/MS(Column): (M + H) 505.3. 1H NMR (400 MHz, DMSO-d6) d 8.53 (d, J = 1.8 Hz, 1H), 8.27-8.18 (m, 3H), 8.05 (s, 1H), 7.94 (s, 1H), 7.76 (s, 1H), 7.69 (d, J = 7.7 Hz, 1H), 7.46 (t, J = 7.8 Hz, 1H), 6.68 (d, J = 5.0 Hz, 1H), 4.77 (t, J = 4.5 Hz, 1H), 4.52 (dd, J = 11.1, 5.2 Hz, 1H), 4.22 (t, J = 4.7 Hz, 1H), 3.92 (s, 3H), 3.90 (s, 3H), 3.16 (s,, 3H), 2.32 (m, 1H), 1.85 (m, 2H), 1.75-1.61 (m, 3H) |
| 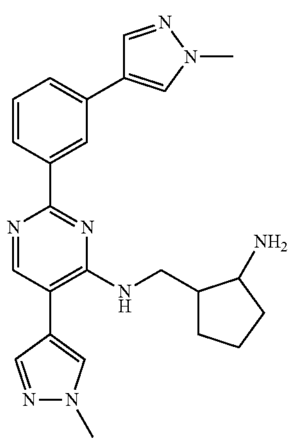 [SMILES: Cn1cc(-c2cccc(-c3ncc(-c4cnn(C)c4)c(NCC4CCCC4N)n3)c2)cn1] | 200 | white solid. HPLC(Column): (254 nm) 100%. LC/MS(Column): (M + H) 429.3 |

| Structure | Example | Analyticals |
|---|---|---|
| 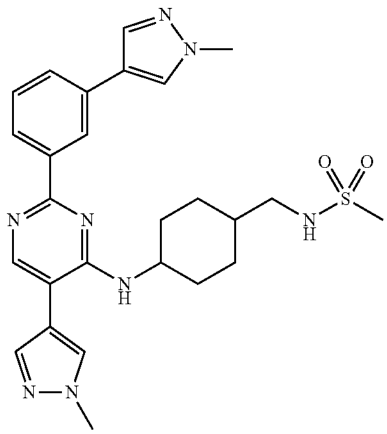 [SMILES: Cn1cc(-c2cccc(-c3ncc(-c4cnn(C)c4)c(NC4CCC(CNS(C)(=O)=O)CC4)n3)c2)cn1] | 201 | white solid. HPLC(Column): (254 nm) 100%. LC/MS(Column): (M + H) 521.3. 1H NMR (400 MHz, DMSO-d6) d 8.49 (d, J = 1.8 Hz, 1H), 8.25-8.14 (m, 3H), 8.06 (s, 1H), 7.87 (s, 1H), 7.77 (s, 1H), 7.66 (d, J = 7.8 Hz, 1H), 7.47 (t, J = 7.7 Hz, 1H), 6.99 (s, 1H), 6.01 (d, J = 6.9 Hz, 1H), 4.33-4.23 (m, 1H), 3.92 (s, 3H), 3.90 (s, 3H), 2.99-2.88 (m, 5H), 1.84-1.59 (m, 7H), 1.48 (m, 2H) |
| 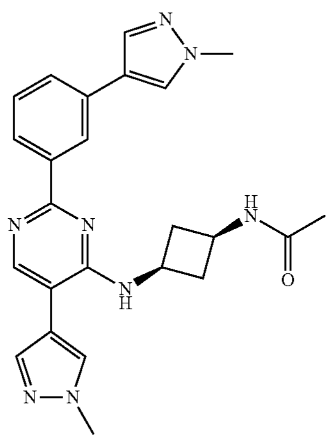 [SMILES: CC(=O)N[C@H]1C[C@@H](Nc2nc(-c3cccc(-c4cnn(C)c4)c3)ncc2-c2cnn(C)c2)C1] | 202 | yellow solid. HPLC(Column): (254 nm) 100%. LC/MS(Column): (M + H) 443.3. 1H NMR (400 MHz, DMSO-d6) d 8.51 (d, J = 1.8 Hz, 1H), 8.33 (d, J = 7.0 Hz, 1H), 8.25-8.16 (m, 3H), 8.07 (s, 1H), 7.89 (s, 1H), 7.76 (s, 1H), 7.67 (d, J = 7.7 Hz, 1H), 7.48 (t, J = 7.7 Hz, 1H), 6.75 (d, J = 6.0 Hz, 1H), 4.78 (m, 1H), 4.25 (m, 1H), 3.92 (s, 3H), 3.90 (s, 3H), 2.47 (d, J = 7.4 Hz, 2H), 2.33 (m, 2H), 1.86 (s, 3H). |
| 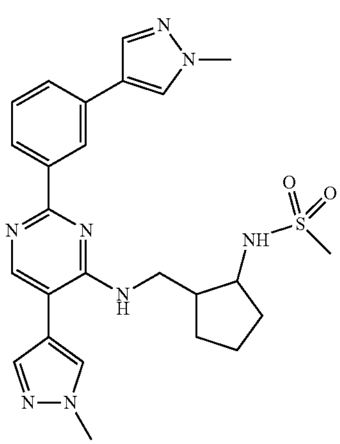 [SMILES: Cn1cc(-c2cccc(-c3ncc(-c4cnn(C)c4)c(NCC4CCCC4NS(C)(=O)=O)n3)c2)cn1] | 203 | white solid. HPLC(Column): (254 nm) 100%. LC/MS(Column): (M + H) 507.3. 1H NMR (400 MHz, DMSO-d6) d 8.55-8.47 (m, 1H), 8.20 (m, 3H), 8.04 (s, 1H), 7.91-7.85 (m, 1H), 7.74 (s, 1H), 7.66 (d, J = 7.7 Hz, 1H), 7.47 (t, J = 7.8 Hz, 1H), 7.13 (t, J = 9.3 Hz, 1H), 6.65 (t, 6.0 Hz, 0.5H), 6.55 (t, J = 6 Hz, 0.5H), 3.94 (s, 3H), 3.90 (s, 3H), 3.86-3.63 (m, 2H), 3.51 (m, 2H), 2.97-2.83 (m, 3H), 2.31 (m, 1H), 2.05-1.36 (m, 6H). |

| Structure | Example | Analyticals |
|---|---|---|
| 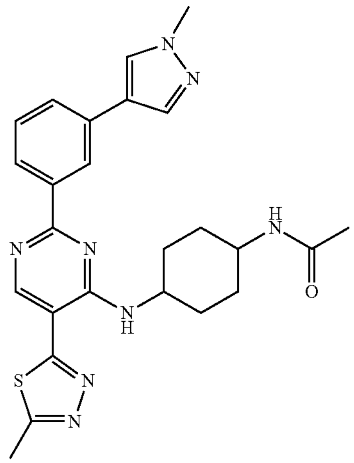 [SMILES: CC(=O)NC1CCC(Nc2nc(-c3cccc(-c4cnn(C)c4)c3)ncc2-c2nnc(C)s2)CC1] | 205 | Off white solid. HPLC(Column): (254 nm) 96.1%. LC/MS(Column): (M + H) 489.2. 1H-NMR (400 MHz, DMSO-d6): 9.27 (d, J = 6.80 Hz, 1H), 8.83 (s, 1H), 8.54 (s, 1H), 8.23 (s, 1H), 8.21 (s, 1H), 7.94 (d, J = 7.20 Hz, 1H), 7.90 (s, 1H), 7.75 (d, J = 7.60 Hz, 1H), 7.53 (t, J = 7.60 Hz, 1H), 4.56-4.56 (m, 1H), 3.91 (s, 3H), 3.80-3.82 (m, 1H), 2.83 (s, 3H), 1.91-1.95 (m, 4H), 1.83 (s, 3H), 1.74 (m, 2H), 1.60 (m, 2H). |

Examples 206 and 207: N-[(Cis)-2-({5-(1-Methyl-1H-pyrazol-4-yl)-2-[3-(1-methyl-1H-pyrazol-4-yl)-phenyl]-pyrimidin-4-ylamino}-methyl)-cyclopentyl]-acetamide and N-[(Trans)-2-({5-(1-Methyl-1H-pyrazol-4-yl)-2-[3-(1-methyl-1H-pyrazol-4-yl)-phenyl]-pyrimidin-4-ylamino}-methyl)-cyclopentyl]-acetamide

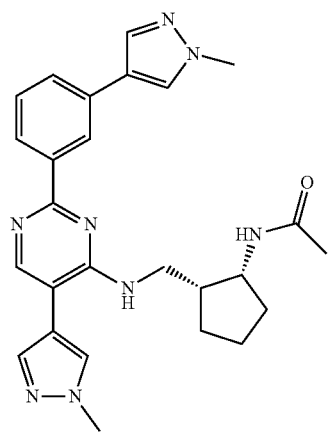

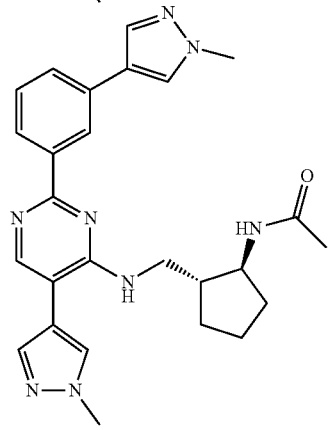

Acetyl chloride (0.01 ml; 0.13 mmol; 1.20 eq.) was added to a solution of (2-Amino-cyclopentylmethyl)-{5-(1-methyl-1H-pyrazol-4-yl)-2-[3-(1-methyl-1H-pyrazol-4-yl)-phenyl]-pyrimidin-4-yl}-amine hydrochloride (50 mg; 0.11 mmol; 1.00 eq.) and TEA (0.03 ml; 0.22 mmol; 2.00 eq.) in DMF (2 mL). The reaction mixture was stirred at RT overnight. It was then concentrated under reduced pressure and purified by preparative HPLC (25-28% CH$_3$CN in 0.1% NH$_4$OH in H$_2$O) to give the title compounds as cis and trans isomers: First eluting isomer: Yellow solid (15 mg). 1H NMR (400 MHz, DMSO-d6) δ 8.50 (s, 1H), 8.20 (m, 3H), 8.08 (s, 1H), 7.90 (m, 2H), 7.76 (s, 1H), 7.65 (m, 1H), 7.46 (t, J=7.7 Hz, 1H), 6.73 (t, J=5.6 Hz, 1H), 3.92 (s, 3H), 3.87 (s, 3H), 3.86 (m, 1H), 3.69 (m, 1H), 3.43 (m, 1H), 2.11 (mz, 1H), 1.89 (m, 4H), 1.85 (s, 3H), 1.62 (m 2H), 1.44 (m, 2H). LC/MS: 471.2 (M+H). Second eluting isomer: Yellow solid (11 mg). 1H NMR (400 MHz, DMSO-d6) δ 8.51 (s, 1H), 8.20 (m, 3H), 8.11 (s, 1H), 7.89 (s, 1H), 7.81 (m, 2H), 7.66 (d, J=7.6 Hz, 1H), 7.46 (t, J=7.7 Hz, 1H), 6.75 (m, 1H), 4.22 (m, 1H), 3.92 (s, 3H), 3.90 (s, 3H), 3.86 (m, 1H), 3.11 (m, 1H), 2.27 (m, 1H), 1.87 (s, 3H), 1.81-1.71 (m, 3H), 1.60-1.49 (m, 2H), 1.41 (m, 1H). LC/MS: 471.2 (M+H).

Example 208: (1S,2R,3S)-3-{5-(1-Methyl-1H-pyrazol-4-yl)-2-[3-(1-methyl-1H-pyrazol-4-yl)-phenyl]-pyrimidin-4-ylamino}-cyclohexane-1,2-diol Step 1: ((3aR,4S,7aS)-2,2-Dimethyl-hexahydro-benzo[1,3]dioxol-4-yl)-{5-(1-methyl-1H-pyrazol-4-yl)-2-[3-(1-methyl-1H-pyrazol-4-yl)-phenyl]-pyrimidin-4-yl}-amine

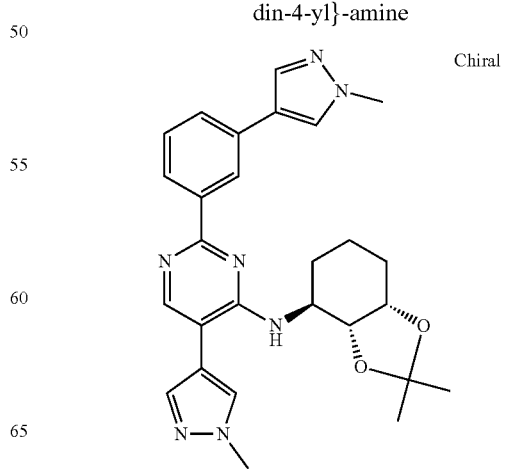

The title compound was obtained following the procedure described for example 28 from 2-[(3aR,4S,7aS)-2,2-dimethylhexahydro-1,3-benzodioxol-4-yl]-1H-isoindole-1,3(2H)-dione (prepared as described in WO 2010017051). LC/MS: 486.3 (M+H).

Step 2: (1S,2R,3S)-3-{5-(1-Methyl-1H-pyrazol-4-yl)-2-[3-(1-methyl-1H-pyrazol-4-yl)-phenyl]-pyrimidin-4-ylamino}-cyclohexane-1,2-diol

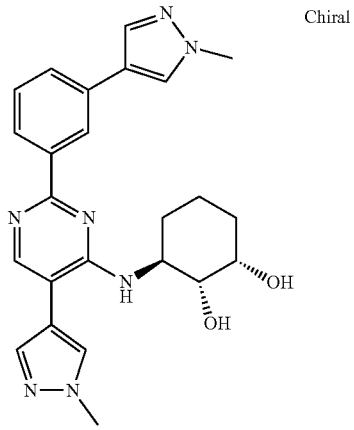 [SMILES: Cn1cc(-c2cccc(-c3ncc(-c4cnn(C)c4)c(N[C@H]4CCC[C@H](O)[C@@H]4O)n3)c2)cn1]

Hydrogen chloride (1.24 ml; 2.47 mmol; 5.00 eq.) (2.0 M solution in Et2O) was added to a solution of ((3aR,4S,7aS)-2,2-Dimethyl-hexahydro-benzo[1,3]dioxol-4-yl)-{5-(1-methyl-1H-pyrazol-4-yl)-2-[3-(1-methyl-1H-pyrazol-4-yl)-phenyl]-pyrimidin-4-yl}-amine (240 mg; 0.49 mmol; 1.00 eq.) in methanol (3.0 mL). The reaction mixture was stirred at rt overnight. It was then concentrated under reduced pressure and purified using prep-HPLC (20-24% CH$_3$CN in 0.1% NH$_4$OH in H$_2$O) to give the title compound as a white solid (180 mg; 82%). 1H NMR (400 MHz, DMSO-d6) δ 8.53 (s, 1H), 8.24-8.14 (m, 3H), 8.07 (s, 1H), 7.86 (s, 1H), 7.78 (s, 1H), 7.66 (d, J=7.7 Hz, 1H), 7.48 (t, J=7.8 Hz, 1H), 6.06 (d, J=6.9 Hz, 1H), 4.73-4.35 (m, 3H), 3.92 (m, 7H), 3.59 (d, J=9.7 Hz, 1H), 2.20-2.11 (m, 1H), 1.77 (m, 2H), 1.37 (m, 3H). LC/MS: 446.2 (M+H).

Compounds below were prepared following similar routes and protocols:

| Structure | Example | Analyticals |
|---|---|---|
| 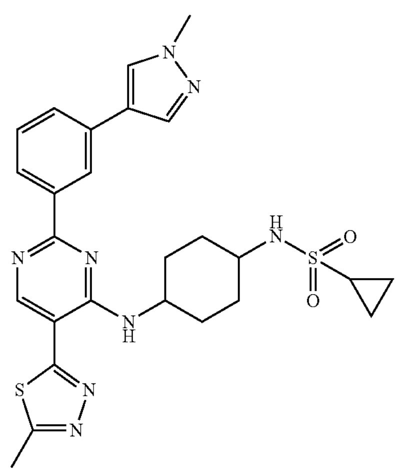 [SMILES: Cc1nnc(-c2cnc(-c3cccc(-c4cnn(C)c4)c3)nc2NC2CCC(NS(=O)(=O)C3CC3)CC2)s1] | 209 | Off white solid. Pure trans isomer. HPLC(Column): (254 nm) 94.9%. LC/MS: (M + H) 551.0. 1H-NMR (400 MHz, CDCl3): 8.96 (d, J = 7.60 Hz, 1H), 8.65 (s, 1H), 8.59 (t, J = 1.60 Hz, 1H), 8.30 (d, J = 5.20 Hz, 1H), 7.89 (s, 1H), 7.74 (s, 1H), 7.62 (d, J = 1.60 Hz, 1H), 7.51 (t, J = 7.60 Hz, 1H), 4.35-4.39 (m, 1H), 4.17 (d, J = 7.60 Hz, 1H), 4.00 (s, 3H), 3.48-3.49 (m, 1H), 2.86 (s, 3H), 2.49-2.49 (m, 1H), 2.34 (m, 2H), 2.28 (m, 2H), 1.58 (m, 3H), 1.24 (m, 2H), 1.05 (m, 2H). |

-continued

| Structure | Example | Analyticals |
|---|---|---|
| 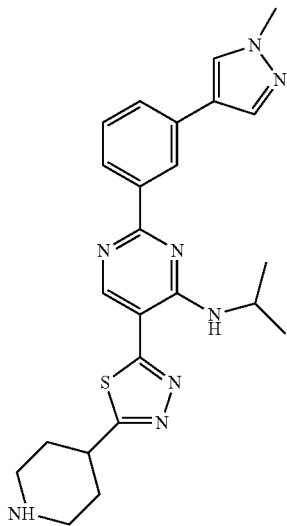 [SMILES: CC(C)Nc1nc(-c2cccc(-c3cnn(C)c3)c2)ncc1-c1nnc(C2CCNCC2)s1] | 210 | Off white solid. HPLC(Column): (254 nm): 93.4%. LC/MS: (M + H) 461.2. 1H-NMR (400 MHz, DMSO-d6): 8.89 (s, 1H), 8.86 (s, 1H), 8.55-8.56 (m, 3H), 8.25 (d, J = 8.00 Hz, 1H), 8.22 (s, 1H), 7.90 (s, 1H), 7.75 (d, J = 7.60 Hz, 1H), 7.53 (t, J = 7.60 Hz, 1H), 4.62-4.65 (m, 1H), 3.91 (s, 3H), 3.62-3.70 (m, 1H), 3.40 (m, 2H), 3.10 (t, J = 11.20 Hz, 2H), 2.29 (d, J = 11.60 Hz, 1H), 1.98-2.01 (m, 2H), 1.37 (m, 6H). |

Examples 211 and 212: Cis and Trans N-(3-{5-(1-Methyl-1H-pyrazol-4-yl)-2-[3-(1-methyl-1H-pyrazol-4-yl)-phenyl]-pyrimidin-4-ylamino}-cyclobutyl-methyl)-acetamide

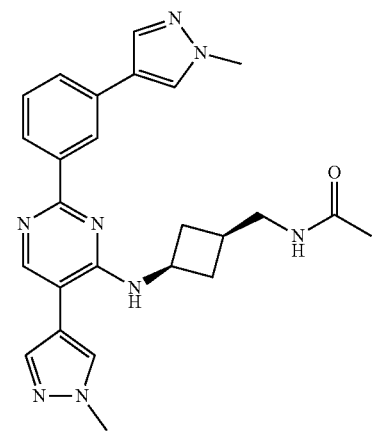

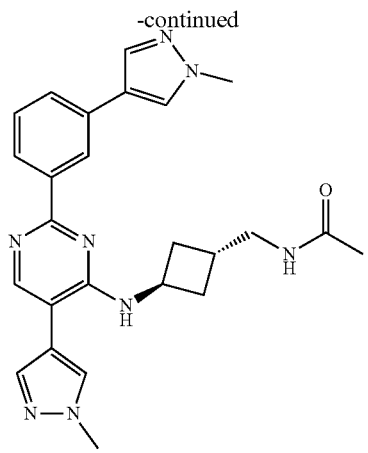

The title compounds were obtained following the procedure described for examples 208 and 209, from (3-Aminomethyl-cyclobutyl)-{5-(1H-pyrazol-4-yl)-2-[3-(1-methyl-1H-pyrazol-4-yl)-phenyl]-pyrimidin-4-yl}-amine hydrochloride (mixture of the two isomers). First eluting isomer: White solid (47 mg). 1H NMR (400 MHz, DMSO-d6) δ 8.50 (s, 1H), 8.24-8.15 (m, 3H), 8.06 (s, 1H), 7.90 (m, 1H), 7.85 (s, 1H), 7.75 (s, 1H), 7.67 (d, J=7.7 Hz, 1H), 7.47 (td, J=7.8, 2.0 Hz, 1H), 6.64 (d, J=6.6 Hz, 1H), 4.79 (m, 1H), 3.93 (s, 3H), 3.90 (s, 3H), 3.28 (t, J=7.3 Hz, 2H), 2.33-2.14 (m, 5H), 1.85 (s, 3H). LC/MS: 457.3 (M+H). Second eluting isomer: White solid (25 mg). 1H NMR (400 MHz, DMSO-d6) δ 8.50 (s, 1H), 8.18-8.22 (m, 3H), 8.05 (2, 1H), 7.89 (s, 1H), 7.80 (m, 1H), 7.75 (s, 1H), 7.66 (d, J=4 Hz, 1H, 7.48 (t, J=8 Hz, 1H), 6.60 (d, J=8 Hz, 1H), 4.55 (m, 1H), 3.93 (s, 3H), 3.90 (s, 3H), 3.13 (m, 2H), 2.45 (m, 2H), 2.17 (m, 1H), 1.85 (m, 1H), 1.77 (s, 3H). LC/MS: 457.3 (M+H).

Compounds below were prepared following similar routes and protocols:

| Structure | Example | Analyticals |
|---|---|---|
| 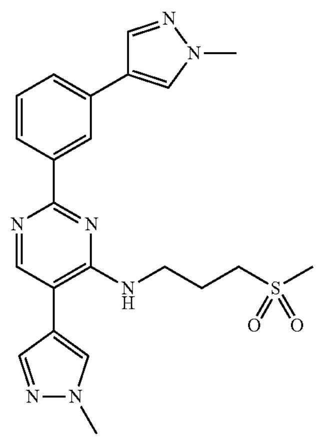 [SMILES: Cn1cc(-c2cccc(-c3ncc(-c4cnn(C)c4)c(NCCCS(C)(=O)=O)n3)c2)cn1] | 213 | white solid. HPLC: (254 nm) 97%. LC/MS: (M + H) 452.2. 1H NMR (400 MHz, DMSO-d6) d 8.50 (d, J = 2.1 Hz, 1H), 8.25-8.17 (m, 3H), 8.08-8.02 (m, 1H), 7.90 (s, 1H), 7.76 (d, J = 1.7 Hz, 1H), 7.66 (d, J = 7.7 Hz, 1H), 7.50-7.43 (m, 1H), 6.82 (d, J = 6.0 Hz, 1H), 3.93 (s, 3H), 3.89 (s, 3H), 3.67 (m, 2H), 3.24 (t, J = 7.9 Hz, 2H), 3.07 (s, 3H), 2.13 (m, 2H). |
| 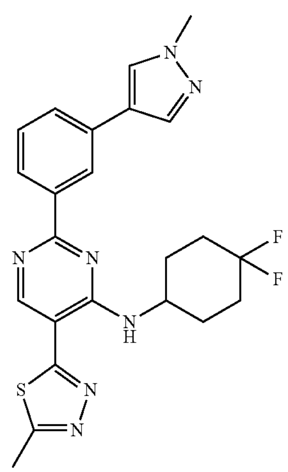 [SMILES: Cc1nnc(-c2cnc(-c3cccc(-c4cnn(C)c4)c3)nc2NC2CCC(F)(F)CC2)s1] | 214 | Yellow solid. HPLC: (254 nm) 92.6%. LC/MS: (M + H) 468.0. 1H-NMR (400 MHz, DMSO-d6): 9.01 (d, J = 7.20 Hz, 1H), 8.84 (s, 1H), 8.57 (t, J = 1.60 Hz, 1H), 8.27 (d, J = 7.60 Hz, 1H), 8.22 (s, 1H), 7.92 (s, 1H), 7.74 (d, J = 800 Hz, 1H), 7.53 (t, J = 7.60 Hz, 1H), 4.51-4.53 (m, 1H), 3.91 (s, 3H), 2.82 (s, 3H), 2.11-2.22 (m, 6H), 1.76-1.79 (m, 2H). |
| 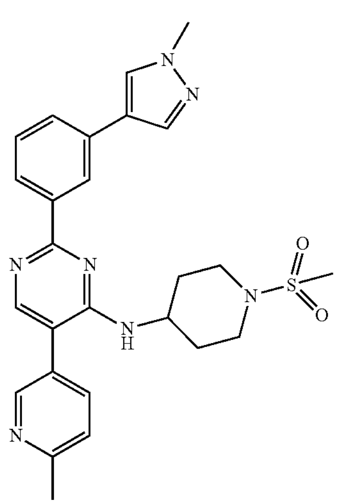 [SMILES: Cc1ccc(-c2cnc(-c3cccc(-c4cnn(C)c4)c3)nc2NC2CCN(S(C)(=O)=O)CC2)cn1] | 215 | White solid. HPLC: (254 nm) 95.6%. LC/MS: (M + H) 504.2. 1H NMR (400 MHz, DMSO-d6): ppm 8.56-8.51 (m, 2H), 8.21-8.19 (m, 2H), 8.13 (s, 1H), 7.90 (s, 1H), 7.81-7.78 (m, 1H), 7.70-7.68 (m, 1H), 7.50-7.46 (m, 1H), 7.40-7.38 (m, 1H), 6.77 (d, J = 8.0 Hz, 1H), 4.33-4.29 (m, 1H), 3.89 (s, 3H), 3.63-3.60 (m, 2H), 2.98-2.91 (m, 5H), 2.55 (s, 3H), 2.04-2.01 (m, 2H), 1.72-1.63 (m, 2H). |

-continued

| Structure | Example | Analyticals |
|---|---|---|
| 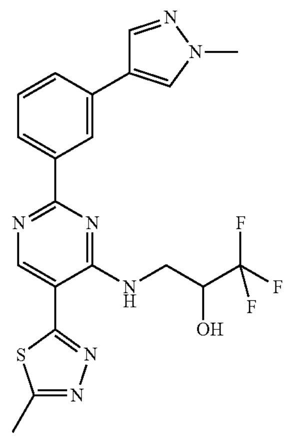 [SMILES: Cc1nnc(-c2cnc(-c3cccc(-c4cnn(C)c4)c3)nc2NCC(O)C(F)(F)F)s1] | 216 | Pale Yellow Solid. HPLC: (254 nm) 95.7%. LC/MS: (M + H) 462.0. |
| 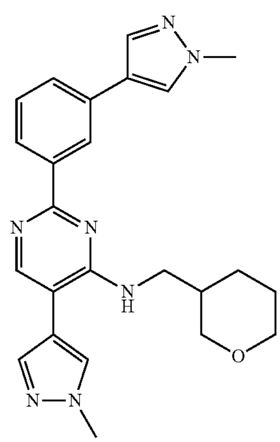 [SMILES: Cn1cc(-c2cccc(-c3ncc(-c4cnn(C)c4)c(NCC4CCCOC4)n3)c2)cn1] | 217 | white solid. HPLC(Column): (254 nm) 95%. LC/MS(Column): (M + H) 430.3. 1H NMR (400 MHz, DMSO-d6) d 8.51 (s, 1H), 8.23-8.13 (m, 3H), 8.02 (s, 1H), 7.87 (s, 1H), 7.72 (s, 1H), 7.66 (d, J = 7.7 Hz, 1H), 7.48 (t, J = 7.7 Hz, 1H), 7.40 (m, 1H), 6.76 (t, J = 5.9 Hz, 1H), 3.95-3.81 (m, 7H), 3.73 (d, J = 11.2 Hz, 1H), 3.47-3.35 (m, 3H), 3.23 (t, J = 10.2 Hz, 1H), 2.12-2.02 (m, 1H), 1.90-1.82 (m, 1H), 1.68-1.60 (m, 1H), 1.54-1.28 (m, 2H). |
| 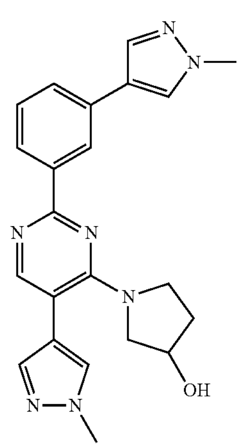 [SMILES: Cn1cc(-c2cccc(-c3ncc(-c4cnn(C)c4)c(N4CCC(O)C4)n3)c2)cn1] | 218 | white solid. HPLC(Column): (254 nm) 90.5%. LC/MS(Column): (M + H) 402.2. 1H NMR (400 MHz, DMSO-d6) d 8.53-8.47 (m, 1H), 8.22-8.11 (m, 3H), 7.86 (d, J = 22.3 Hz, 2H), 7.66 (d, J = 7.6 Hz, 1H), 7.53-7.44 (m, 2H), 4.90 (s, 1H), 4.28 (d, J = 4.8 Hz, 1H), 3.90 (d, J = 1.8 Hz, 6H), 3.58 (q, J = 9.4, 8.7 Hz, 1H), 3.52-3.42 (m, 2H), 3.16 (d, J = 11.8 Hz, 1H), 1.96-1.78 (m, 2H). |

-continued

| Structure | Example | Analyticals |
|---|---|---|
| 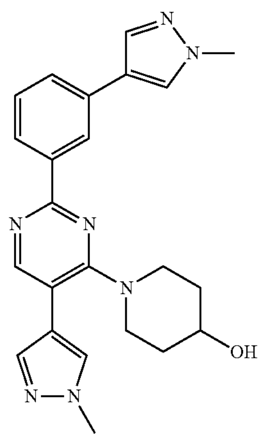 [SMILES: Cn1cc(-c2cccc(-c3ncc(-c4cnn(C)c4)c(N4CCC(O)CC4)n3)c2)cn1] | 219 | hite solid. HPLC(Column): (254 nm) 99%. LC/MS(Column): (M + H) 416.25. 1H NMR (400 MHz, DMSO-d6) d 8.46 (d, J = 24.2 Hz, 2H), 8.23-8.15 (m, 2H), 8.06 (s, 1H), 7.89 (s, 1H), 7.78 (s, 1H), 7.67 (d, J = 7.7 Hz, 1H), 7.48 (t, J = 7.8 Hz, 1H), 4.71 (s, 1H), 3.91 (d, J = 6.6 Hz, 6H), 3.80-3.67 (m, 3H), 3.06 (t, J = 11.5 Hz, 2H), 1.87-1.75 (m, 2H), 1.47 (m, 2H). |
| 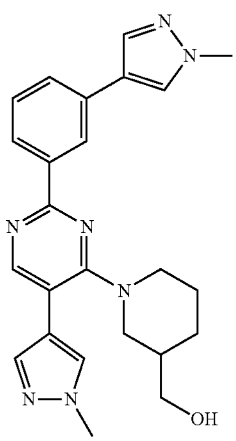 [SMILES: Cn1cc(-c2cccc(-c3ncc(-c4cnn(C)c4)c(N4CCCC(CO)C4)n3)c2)cn1] | 220 | white solid. HPLC(Column): (254 nm) 96%. LC/MS(Column): (M + H) 430.3. |
| 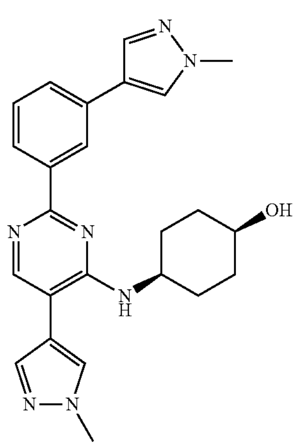 [SMILES: Cn1cc(-c2cccc(-c3ncc(-c4cnn(C)c4)c(N[C@H]4CC[C@@H](O)CC4)n3)c2)cn1] | 221 | white solid. HPLC(Column): (254 nm) 98%. LC/MS(Column): (M + H) 430.3. 1H NMR (400 MHz, DMSO-d6) d 8.50 (d, J = 2.0 Hz, 1H), 8.24-8.14 (m, 3H), 8.07 (d, J = 1.8 Hz, 1H), 7.86 (d, J = 1.9 Hz, 1H), 7.75 (d, J = 1.8 Hz, 1H), 7.65 (d, J = 7.7 Hz, 1H), 7.47 (td, J = 7.8, 1.9 Hz, 1H), 5.98 (d, J = 7.0 Hz, 1H), 4.45-4.38 (m, 1H), 4.17 (d, J = 10.6 Hz, 1H), 3.91 (m, 6H), 3.82-3.76 (m, 1H), 1.87 (m, 2H), 1.77-1.60 (m, 6H). |

| Structure | Example | Analyticals |
|---|---|---|
| 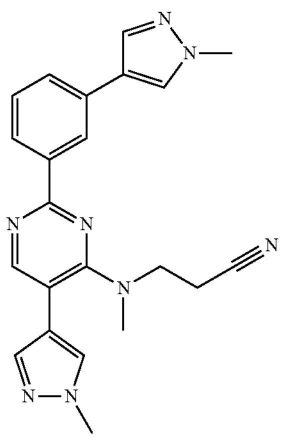 [SMILES: CN(CCC#N)c1nc(-c2cccc(-c3cnn(C)c3)c2)ncc1-c1cnn(C)c1] | 222 | white solid. HPLC: (254 nm) 93%. LC/MS: (M + H) 399.3.. 1H NMR (400 MHz, DMSO-d6) d 8.50 (s, 1H), 8.34 (s, 1H), 8.23-8.17 (m, 2H), 7.93 (d, J = 14.0 Hz, 2H), 7.71-7.64 (m, 2H), 7.49 (t, J = 7.9 Hz, 1H), 3.90 (d, J = 8.0 Hz, 8H), 2.94 (t, J = 6.8 Hz, 2H), 2.86 (s, 3H). |
| 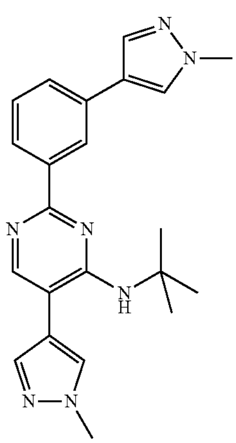 [SMILES: Cn1cc(-c2cccc(-c3ncc(-c4cnn(C)c4)c(NC(C)(C)C)n3)c2)cn1] | 223 | white solid. HPLC(Column): (254 nm) 99%. LC/MS(Column): (M + H) 388.3. 1H NMR (400 MHz, DMSO-d6) d 8.50 (s, 1H), 8.22-8.06 (m, 4H), 7.85 (s, 1H), 7.78 (s, 1H), 7.66 (d, J = 7.6 Hz, 1H), 7.49 (t, J = 7.7 Hz, 1H), 5.57 (s, 1H), 3.91 (d, J = 9.6 Hz, 6H), 1.56 (s, 9H). |
| 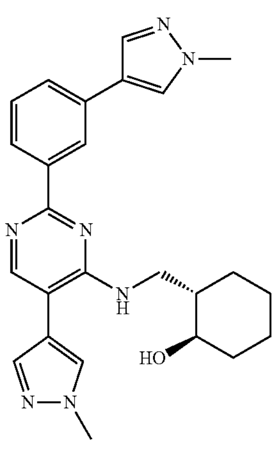 [SMILES: Cn1cc(-c2cccc(-c3ncc(-c4cnn(C)c4)c(NC[C@@H]4CCCC[C@H]4O)n3)c2)cn1] | 224 | hite solid. HPLC(Column): (254 nm) 99%. LC/MS(Column): (M + H) 444.3. 1H NMR (400 MHz, DMSO-d6) d 8.55 (s, 1H), 8.26-8.15 (m, 3H), 8.02 (d, J = 1.9 Hz, 1H), 7.91 (d, J = 1.9 Hz, 1H), 7.74 (d, J = 1.9 Hz, 1H), 7.65 (d, J = 7.7 Hz, 1H), 7.46 (td, J = 7.8, 2.0 Hz, 1H), 6.92 (t, J = 5.4 Hz, 1H), 5.09 (s, 1H), 3.912 (2, 3H), 3.89 (s, 3H), 3.61 (m, 2H), 3.26 (dd, J = 10.7, 4.8 Hz, 1H), 1.91-1.75 (m, 2H), 1.69-1.57 (m, 3H), 1.26-1.02 (m, 4H). |

| Structure | Example | Analyticals |
|---|---|---|
| 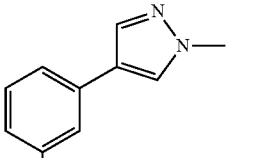 | 225 | white solid. HPLC(Column): (254 nm) 88%. LC/MS(Column): (M + H) 444.2. 1H NMR (400 MHz, DMSO-d6) d 8.50 (s, 1H), 8.17 (m, 3H), 8.02 (s, 1H), 7.87 (s, 1H), 7.73 (s, 1H), 7.65 (d, J = 7.7 Hz, 1H), 7.47 (t, J = 7.7 Hz, 1H), 6.78-6.70 (m, 1H), 4.57 (s, 1H), 3.92 (2, 3H), 3.89 (s, 3H), 3.86 (s, 1H), 3.52 (t, J = 6.3 Hz, 2H), 1.93-1.83 (m, 1H), 1.74-1.32 (m, 7H), 1.28-1.17 (m, 1H). |
| 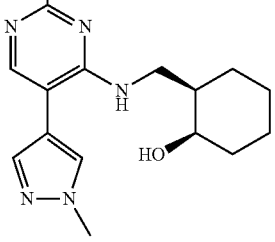 | 226 | off-white solid. HPLC(Column): (254 nm) 93%. LC/MS(Column): (M + H) 388.1. 1H NMR (400 MHz, DMSO-d6) d 8.49 (s, 1H), 8.22-8.16 (m, 3H), 7.90-7.86 (m, 2H), 7.67 (d, J = 7.7 Hz, 1H), 7.58 (d, J = 1.6 Hz, 1H), 7.50-7.45 (m, 1H), 5.60 (s, 1H), 4.46 (m, 1H), 4.15 (t, J = 8.2 Hz, 2H), 3.93 (s, 3), 3.86 (s, 3H), 3.70 (dd, J = 9.8, 4.3 Hz, 2H). |
| 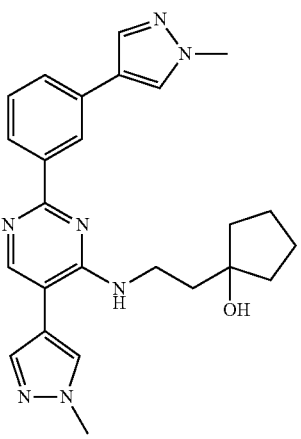 [SMILES: Cn1cc(-c2cccc(-c3ncc(-c4cnn(C)c4)c(NCCC4(O)CCCC4)n3)c2)cn1] | 227 | off-white solid. HPLC(Column): (254 nm) 99%. LC/MS(Column): (M + H) 444.2. 1H NMR (400 MHz, DMSO-d6) d 8.53 (s, 1H), 8.23-8.16 (m, 3H), 8.03 (s, 1H), 7.88 (s, 1H), 7.75 (s, 1H), 7.65 (d, J = 7.6 Hz, 1H), 7.45 (dd, J = 8.5, 6.8 Hz, 1H), 6.86 (t, J = 5.5 Hz, 1H), 4.44 (s, 1H), 3.91 (2, 3H), 3.88 (s, 3H), 3.70 (m, 2H), 1.88 (m, 2H), 1.69 (m, 4H), 1.56 (m, 4H). |

| Structure | Example | Analyticals |
|---|---|---|
| 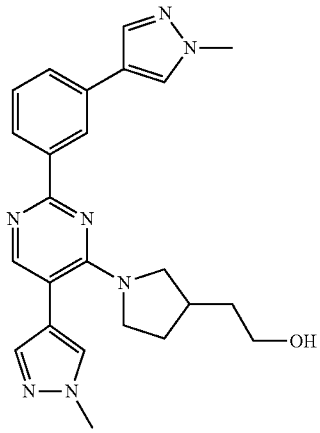 [SMILES: Cn1cc(-c2cccc(-c3ncc(-c4cnn(C)c4)c(N4CCC(CCO)C4)n3)c2)cn1] | 228 | off-white solid. HPLC: (254 nm) 97.7%. LC/MS: (M + H) 430.2. 1H NMR (400 MHz, DMSO-d6) 8.50 (s, 1H), 8.19 (d, J = 8.2 Hz, 2H), 8.12 (d, J = 1.9 Hz, 1H), 7.89 (d, J = 1.6 Hz, 1H), 7.83 (d, J = 1.7 Hz, 1H), 7.66 (d, J = 7.6 Hz, 1H), 7.52 (d, J = 1.7 Hz, 1H), 7.47 (td, J = 7.8, 1.8 Hz, 1H), 4.45 (s, 1H), 3.91 (s, 3H), 3.89 (2, 3H), 3.58-3.52 (m, 1H), 3.41 (dt, J = 21.5, 7.9 Hz, 4H), 3.04 (t, J = 9.8 Hz, 1H), 2.20 (m, 1H), 2.00 (m, 1H), 1.55-1.43 (m, 3H). |
| 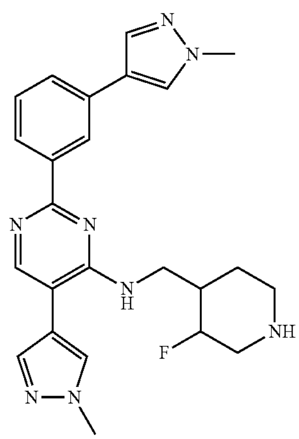 [SMILES: Cn1cc(-c2cccc(-c3ncc(-c4cnn(C)c4)c(NCC4CCNCC4F)n3)c2)cn1] | 229 | hite solid. HPLC(Column): (254 nm) 98%. LC/MS(Column): (M + H) 447.2. 1H NMR (400 MHz, DMSO-d6): 8.50 (s, 1H), 8.23-8.14 (m, 3H), 8.03 (s, 1H), 7.86 (s, 1H), 7.73 (s, 1H), 7.65 (d, J = 7.7 Hz, 1H), 7.47 (t, J = 7.8 Hz, 1H), 6.77 (t, J = 5.8 Hz, 1H), 4.68 (d, J = 48 Hz, 1), 3.92 (2, 3H), 3.89 (s, 3H), 3.63 (dt, J = 13.4, 6.5 Hz, 1H), 3.47 (dt, J = 12.8, 6.2 Hz, 1H), 3.10 (t, J = 12.9 Hz, 1H), 2.95 (d, J = 13.0 Hz, 1H), 2.71-2.56 (m, 1H), 2.44 (d, J = 12.3 Hz, 1H), 2.24-2.06 (m, 1H), 1.91 (s, 1H), 1.54-1.39 (m, 2H). |
| 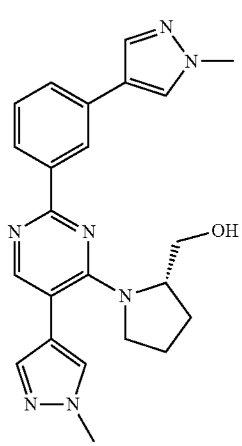 [SMILES: Cn1cc(-c2cccc(-c3ncc(-c4cnn(C)c4)c(N4CCC[C@H]4CO)n3)c2)cn1] | 230 | hite solid. HPLC(Column): (254 nm) 97%. LC/MS(Column): (M + H) 416.2. 1H NMR (400 MHz, DMSO-d6) 8.52 (s, 1H), 8.22-8.15 (m, 3H), 7.90 (s, 1H), 7.84 (d, J = 1.5 Hz, 1H), 7.67 (d, J = 7.7 Hz, 1H), 7.55 (s, 1H), 7.47 (t, J = 7.7 Hz, 1H), 4.75 (s, 1H), 4.53 (m, 1H), 3.90 (s, 3H), 3.88 (s, 3H), 3.79-3.73 (m, 1H), 3.57 (dd, J = 10.6, 6.6 Hz, 1H), 3.20-3.13 (m, 1H), 2.97 (m, 1H), 1.91 (m, 3H), 1.72-1.60 (m, 1H). |

| Structure | Example | Analyticals |
|---|---|---|
| 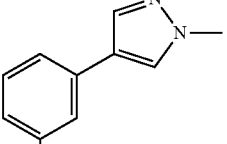 | 231 | off-white solid. HPLC(Column): (254 nm) 98%. LC/MS(Column): (M + H) 447.2. 1H NMR (400 MHz, DMSO-d6) 8.51 (s, 1H), 8.26-8.16 (m, 3H), 8.05 (s, 1H), 7.89 (s, 1H), 7.75 (d, J = 1.6 Hz, 1H), 7.66 (d, J = 7.7 Hz, 1H), 7.48 (dd, J = 8.5, 6.9 Hz, 1H), 6.59-6.50 (m, 1H), 3.93 (s, 3H), 3.88 (s, 3H), 3.84 (m, 2H), 2.83-2.65 (m, 4H), 1.77-1.58 (m, 4H). |
| 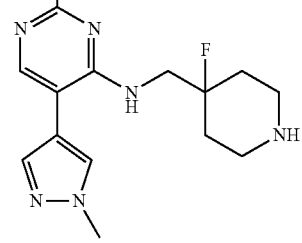 | 232 | white solid. HPLC(Column): (254 nm) 98%. LC/MS(Column): (M + H) 472.2. 1H NMR (400 MHz, DMSO-d6) 8.50 (s, 1H), 8.24-8.14 (m, 3H), 8.05 (s, 1H), 7.88 (s, 1H), 7.74 (s, 1H), 7.66 (d, J = 7.7 Hz, 1H), 7.47 (t, J = 8.0 Hz, 1H), 6.23 (d, J = 7.6 Hz, 1H), 4.26-4.16 (m, 1H), 3.91 (s, 3H), 3.89 (s, 3H), 3.60 (s, 3H), 2.62 (m, 1H), 2.28 (m, 1H), 2.04-1.81 (m, 3H), 1.61-1.22 (m, 5H). |
| 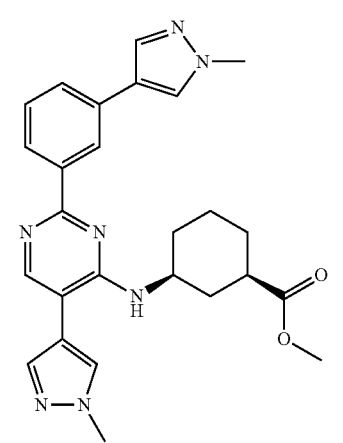 | 233 | brown solid. HPLC(Column): (254 nm) 93%. LC/MS(Column): (M + H) 499.2. |

| Structure | Example | Analyticals |
|---|---|---|
| 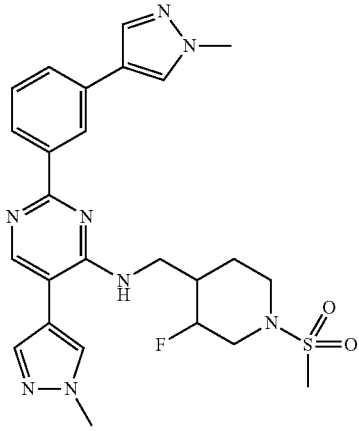 [SMILES: Cn1cc(-c2cccc(-c3ncc(-c4cnn(C)c4)c(NCC4CCN(S(C)(=O)=O)CC4F)n3)c2)cn1] | 234 | white solid. HPLC(Column): (254 nm) 97%. LC/MS(Column): (M + H) 525.2. |
| 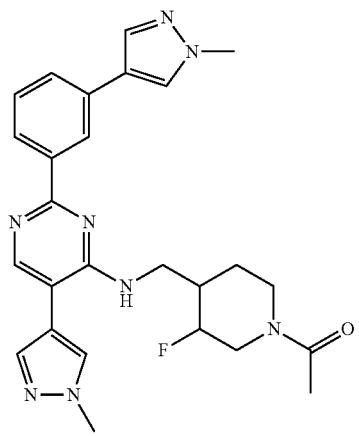 [SMILES: CC(=O)N1CCC(CNc2nc(-c3cccc(-c4cnn(C)c4)c3)ncc2-c2cnn(C)c2)C(F)C1] | 235 | white solid. HPLC(Column): (254 nm) 96%. LC/MS(Column): (M + H) 489.2. |
| 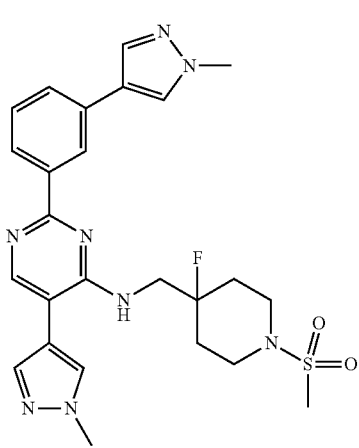 [SMILES: Cn1cc(-c2cccc(-c3ncc(-c4cnn(C)c4)c(NCC4(F)CCN(S(C)(=O)=O)CC4)n3)c2)cn1] | 236 | white solid. HPLC(Column): (254 nm) 98%. LC/MS(Column): (M + H) 525.2. 1H NMR (400 MHz, DMSO-d6) 8.50 (s, 1H), 8.27-8.16 (m, 3H), 8.05 (d, J = 1.7 Hz, 1H), 7.89 (d, J = 1.7 Hz, 1H), 7.76 (d, J = 1.8 Hz, 1H), 7.67 (d, J = 7.7 Hz, 1H), 7.51-7.45 (m, 1H), 6.68 (t, J = 6.4 Hz, 1H), 3.96-3.85 (m, 8H), 3.50 (m, 2H), 2.98-2.85 (m, 5H), 2.00-1.80 (m, 4H). |

| Structure | Example | Analyticals |
|---|---|---|
| 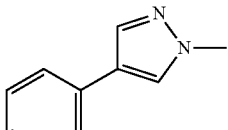 | 237 | white solid. HPLC(Column): (254 nm) 96%. LC/MS(Column): (M + H) 489.2. |
| 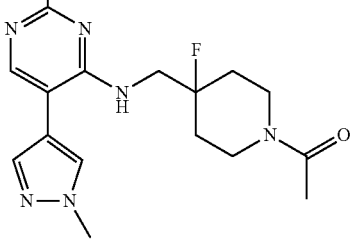 | 238 | white solid. HPLC(Column): (254 nm) 100%. LC/MS(Column): (M + H) 416.2. 1H NMR (400 MHz, DMSO-d6) 8.54 (d, J = 1.8 Hz, 1H), 8.24-8.16 (m, 3H), 8.06 (s, 1H), 7.89 (s, 1H), 7.76 (d, J = 1.6 Hz, 1H), 7.66 (d, J = 7.7 Hz, 1H), 7.47 (t, J = 7.6 Hz, 1H), 6.21 (d, J = 6.6 Hz, 1H), 4.87 (s, 1H), 4.29 (m, 1H), 4.13 (m, 1H), 3.91 (s, 3H), 3.89 (s, 3H), 2.25 (m, 1H), 1.90 (m, 1H), 1.70 (m, 2H), 1.56 (m, 2H). |
| 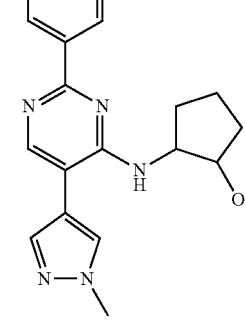 | 239 | white solid. HPLC(Column): (254 nm) 98%. LC/MS(Column): (M + H) 415.2. 1H NMR (400 MHz, DMSO-d6) 8.49 (s, 1H), 8.43 (d, J = 1.5 Hz, 1H), 8.19 (m, 2H), 8.05 (s, 1H), 7.89 (s, 1H), 7.77 (s, 1H), 7.67 (d, J = 7.7 Hz, 1H), 7.48 (t, J = 7.8 Hz, 1H), 3.91 (m, 8H), 2.90 (m, 2H), 2.82-2.73 (m, 1H), 1.75 (d, J = 12.0 Hz, 2H), 1.32 (m, 2H). |

-continued

| Structure | Example | Analyticals |
|---|---|---|
| 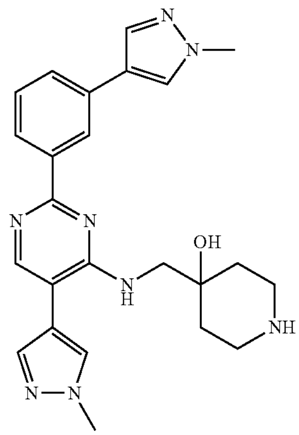 [SMILES: Cn1cc(-c2cccc(-c3ncc(-c4cnn(C)c4)c(NCC4(O)CCNCC4)n3)c2)cn1] | 240 | white solid. HPLC(Column): (254 nm) 95%. LC/MS(Column): (M + H) 445.2. 1H NMR (400 MHz, DMSO-d6) 8.51 (s, 1H), 8.19 (m, 3H), 8.07 (s, 1H), 7.89 (s, 1H), 7.77 (s, 1H), 7.66 (d, J = 7.7 Hz, 1H), 7.48 (t, J = 7.7 Hz, 1H), 6.28 (t, J = 6.0 Hz, 1H), 4.70 (s, 1H), 3.92 (s, 3H), 3.89 (s, 3H), 3.63 (d, J = 5.7 Hz, 2H), 2.85-2.60 (m, 4H), 1.54-1.39 (m, 4H). |
| 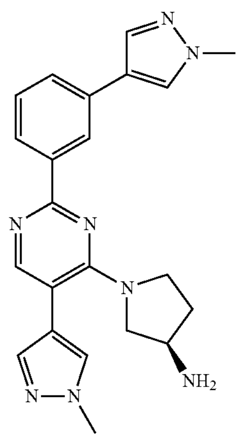 [SMILES: Cn1cc(-c2cccc(-c3ncc(-c4cnn(C)c4)c(N4CC[C@@H](N)C4)n3)c2)cn1] | 241 | white solid. HPLC(Column): (254 nm) 99%. LC/MS(Column): (M + H) 401.15. |
| 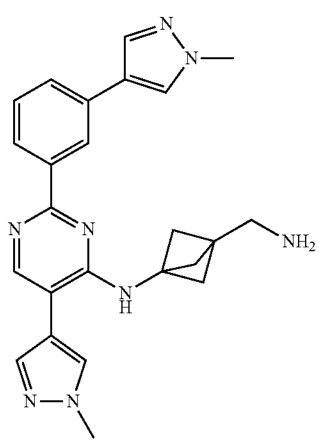 [SMILES: Cn1cc(-c2cccc(-c3ncc(-c4cnn(C)c4)c(NC45CC(CN)(C4)C5)n3)c2)cn1] | 242 | white solid. HPLC(Column): (254 nm) 98%. LC/MS(Column): (M + H) 427.2. 1H NMR (400 MHz, DMSO-d6) 8.56 (d, J = 15.5 Hz, 1H), 8.25-8.12 (m, 3H), 8.00 (s, 1H), 7.87 (s, 1H), 7.68 (m, 2H), 7.49 (t, J = 7.7 Hz, 1H), 7.05 (s, 1H), 3.95-3.86 (m, 6H), 2.77 (s, 2H), 2.11 (s, 6H). |

| Structure | Example | Analyticals |
|---|---|---|
| 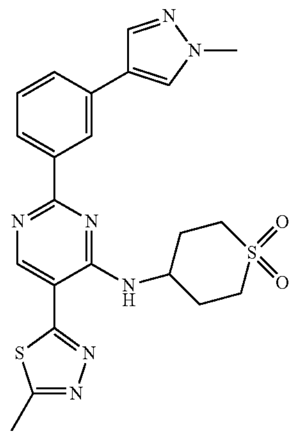 [SMILES: Cc1nnc(-c2cnc(-c3cccc(-c4cnn(C)c4)c3)nc2NC2CCS(=O)(=O)CC2)s1] | 243 | Off white solid. HPLC: (254 nm) 94.6%. LC/MS: (M + H) 482.2. 1H-NMR (400 MHz, DMSO-d6): 8.99 (d, J = 7.20 Hz, 1H), 8.85 (s, 1H), 8.58 (s, 1H), 8.31 (d, J = 8.00 Hz, 1H), 8.23 (s, 1H), 7.96 (s, 1H), 7.75 (d, J = 7.60 Hz, 1H), 7.53 (t, J = 7.60 Hz, 1H), 4.68-4.69 (m, 1H), 3.91 (s, 3H), 3.51-3.57 (m, 2H), 3.17-3.21 (m, 2H), 2.82 (s, 3H), 2.50-2.50 (m, 2H). |
| 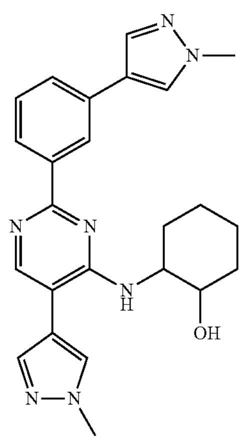 [SMILES: Cn1cc(-c2cccc(-c3ncc(-c4cnn(C)c4)c(NC4CCCCC4O)n3)c2)cn1] | 244 | white solid. HPLC(Column): (254 nm) 98%. LC/MS(Column): (M + H) 430.2. 1H NMR (400 MHz, DMSO-d6) 8.51 (s, 1H), 8.24-8.14 (m, 3H), 8.09 (s, 1H), 7.86 (s, 1H), 7.79 (s, 1H), 7.66 (d, J = 7.7 Hz, 1H), 7.49 (t, J = 7.9 Hz, 1H), 6.11 (d, J = 6.5 Hz, 1H), 4.86-4.78 (m, 1H), 3.92 (m, 7H), 3.64-3.52 (m, 1H), 2.30-2.20 (m, 1H), 2.00-1.91 (m, 1H), 1.77-1.67 (m, 2H), 1.44-1.23 (m, 4H). |
| 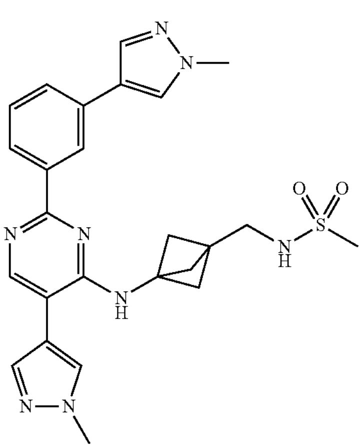 [SMILES: Cn1cc(-c2cccc(-c3ncc(-c4cnn(C)c4)c(NC45CC(CNS(C)(=O)=O)(C4)C5)n3)c2)cn1] | 245 | white solid. HPLC(Column): (254 nm) 86%. LC/MS(Column): (M + H) 505.2. 1H NMR (400 MHz, DMSO-d6) 8.52 (s, 1H), 8.24-8.14 (m, 3H), 8.01 (d, J = 2.2 Hz, 1H), 7.88 (d, J = 2.2 Hz, 1H), 7.71-7.67 (m, 2H), 7.53-7.48 (m, 1H), 7.08 (t, J = 6.3 Hz, 1H), 3.91 (s, 3H), 3.89 (s, 3H), 3.25-3.22 (m, 2H), 2.95-2.89 (m, 3H), 2.17 (d, J = 2.1 Hz, 6H). |

| Structure | Example | Analyticals |
|---|---|---|
| 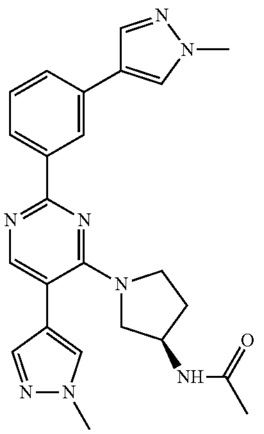 [SMILES: CC(=O)N[C@@H]1CCN(c2nc(-c3cccc(-c4cnn(C)c4)c3)ncc2-c2cnn(C)c2)C1] | 246 | white solid. HPLC(Column): (254 nm) 97%. LC/MS(Column): (M + H) 443.2. 1H NMR (400 MHz, DMSO-d6) 8.51 (s, 1H), 8.23-8.14 (m, 3H), 8.07 (d, J = 6.8 Hz, 1H), 7.90 (d, J = 1.9 Hz, 1H), 7.85 (d, J = 1.9 Hz, 1H), 7.67 (d, J = 7.7 Hz, 1H), 7.55 (s, 1H), 7.48 (t, J = 8.1 Hz, 1H), 4.24 (m, 1H), 3.91 (s, 3H), 3.89 (2, 3H), 3.51 (m, 3H), 3.23-3.17 (m, 1H), 2.03 (m, 1H), 1.80 (s, 3H), 1.77 (s, 1H). |
| 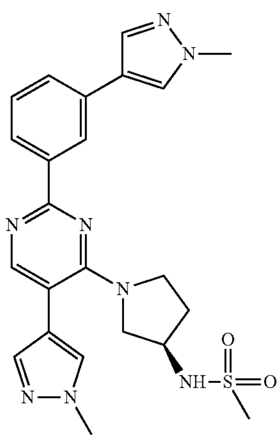 [SMILES: Cn1cc(-c2cccc(-c3ncc(-c4cnn(C)c4)c(N4CC[C@@H](NS(C)(=O)=O)C4)n3)c2)cn1] | 247 | white solid. HPLC(Column): (254 nm) 97%. LC/MS(Column): (M + H) 479.1. 1H NMR (400 MHz, DMSO-d6) 8.51 (s, 1H), 8.23-8.16 (m, 3H), 7.88 (dd, J = 15.1, 2.1 Hz, 2H), 7.67 (d, J = 7.8 Hz, 1H), 7.55 (d, J = 2.1 Hz, 1H), 7.48 (td, J = 7.8, 2.0 Hz, 1H), 7.37 (s, 1H), 3.90 (m, 7H), 3.62 (m, 1H), 3.54 (m, 1H), 3.43 (m, 1H), 2.95 (s, 3H), 2.17-2.09 (m, 1H), 1.89 (m, 1H). |
| 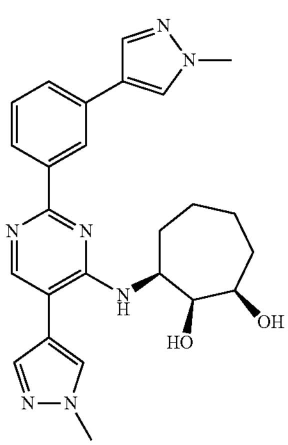 [SMILES: Cn1cc(-c2cccc(-c3ncc(-c4cnn(C)c4)c(N[C@H]4CCCC[C@@H](O)[C@H]4O)n3)c2)cn1] | 248 | white solid. HPLC(Column): (254 nm) 98%. LC/MS(Column): (M + H) 460.2. |

-continued

| Structure | Example | Analyticals |
|---|---|---|
| 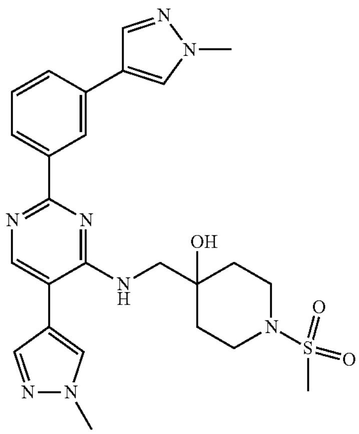 [SMILES: Cn1cc(-c2cccc(-c3ncc(-c4cnn(C)c4)c(NCC4(O)CCN(S(C)(=O)=O)CC4)n3)c2)cn1] | 249 | white solid. HPLC(Column): (254 nm) 95%. LC/MS(Column): (M + H) 523.2 |
| 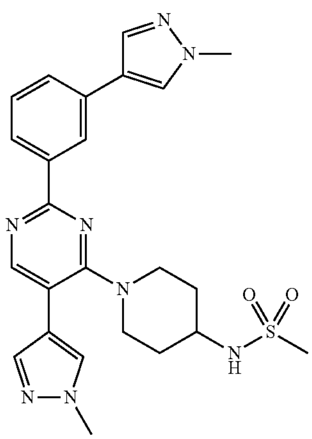 [SMILES: Cn1cc(-c2cccc(-c3ncc(-c4cnn(C)c4)c(N4CCC(NS(C)(=O)=O)CC4)n3)c2)cn1] | 250 | white solid. HPLC(Column): (254 nm) 89%. LC/MS: (M + H) 493.2. 1H NMR (400 MHz, DMSO-d6) 8.52-8.44 (m, 2H), 8.24-8.16 (m, 2H), 8.09-8.04 (m, 1H), 7.91 (d, J = 2.0 Hz, 1H), 7.81-7.75 (m, 1H), 7.68 (d, J = 7.7 Hz, 1H), 7.53-7.46 (m, 1H), 3.95-3.86 (m, 8H), 3.42 (m, 7.9 Hz, 1H), 3.05-2.91 (m, 5H), 1.91 (m, 2H), 1.55 (m, 2H). |
| 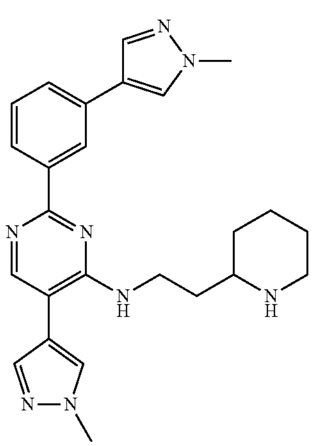 [SMILES: Cn1cc(-c2cccc(-c3ncc(-c4cnn(C)c4)c(NCCC4CCCCN4)n3)c2)cn1] | 251 | white solid. HPLC(Column): (254 nm) 94%. LC/MS(Column): (M + H) 443.2. |

| Structure | Example | Analyticals |
|---|---|---|
| 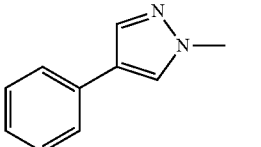 | 252 | white solid. HPLC: (254 nm) 97%. LC/MS: (M + H) 443.2. 1H NMR (400 MHz, DMSO-d6) 8.52 (s, 1H), 8.20 (m, 3H), 8.08 (d, J = 2.0 Hz, 1H), 7.90-7.85 (m, 1H), 7.81-7.76 (m, 1H), 7.66 (d, J = 7.7 Hz, 1H), 7.48 (tt, J = 7.6, 1.5 Hz, 1H), 6.48 (d, J = 5.7 Hz, 1H), 3.96 (s, 3H), 3.87 (s, 3H), 3.55-3.47 (m, 2H), 1.62-1.28 (m, 12H). |
| 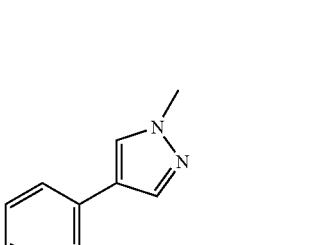 | 253 | Off white solid. HPLC: (254 nm) 98.1%. LC/MS: (M + H) 525.3. 1H-NMR (400 MHz, DMSO-d6): 9.06 (d, J = 7.20 Hz, 1H), 8.83 (s, 1H), 8.55 (s, 1H), 8.26 (d, J = 7.60 Hz, 1H), 8.20 (s, 1H), 7.92 (s, 1H), 7.75 (d, J = 8.00 Hz, 1H), 7.53 (t, J = 7.60 Hz, 1H), 4.56-4.56 (m, 1H), 3.91 (s, 3H), 3.47-3.48 (m, 3H), 3.36-3.46 (m, 1H), 2.96 (s, 3H), 2.82 (s, 3H), 2.27-2.28 (m, 1H), 2.10-2.12 (m, 1H), 1.89-1.91 (m, 4H). |
| 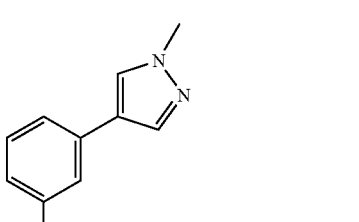 | 254 | Off white solid. HPLC: (254 nm) 96.7%. LC/MS: (M + H) 525.0. 1H-NMR (400 MHz, Acetone): 9.10 (d, J = 7.60 Hz, 1H), 8.76 (s, 1H), 8.70 (t, J = 1.60 Hz, 1H), 8.34 (d, J = 5.20 Hz, 1H), 8.07 (s, 1H), 7.88 (s, 1H), 7.74 (d, J = 5.20 Hz, 1H), 7.51 (t, J = 8.00 Hz, 1H), 4.38-4.39 (m, 1H), 3.98 (s, 3H), 3.80 (s, 1H), 3.45-3.46 (m, 1H), 3.10 (m, 1H), 3.00 (s, 3H), 2.38 (m, 2H), 2.24 (m, 2H), 2.08 (s, 3H), 1.63-1.74 (m, 4H). |

| Structure | Example | Analyticals |
|---|---|---|
| 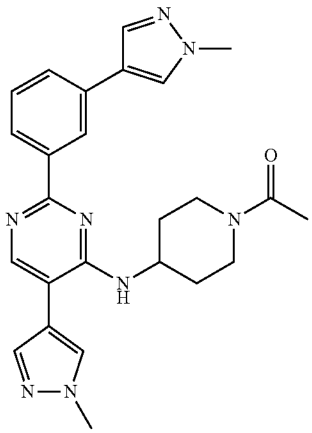 [SMILES: CC(=O)N1CCC(Nc2nc(-c3cccc(-c4cnn(C)c4)c3)ncc2-c2cnn(C)c2)CC1] | 255 | white solid. HPLC(Column): (254 nm) 94%. LC/MS(Column): (M + H) 457.2. 1H NMR (400 MHz, DMSO-d6) d 8.50 (s, 1H), 8.26-8.15 (m, 3H), 8.05 (s, 1H), 7.89 (s, 1H), 7.75 (s, 1H), 7.66 (d, J = 7.7 Hz, 1H), 7.47 (t, J = 7.9 Hz, 1H), 6.27 (dd, J = 20.1, 7.5 Hz, 1H), 4.39 (m, 2H), 3.91 (m, 7H), 3.25 (m 1H), 2.84 (m, 1H), 2.12-1.84 (m, 5H), 1.71-1.47 (m, 2H). |
| 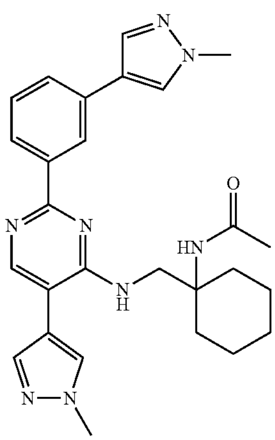 [SMILES: CC(=O)NC1(CNc2nc(-c3cccc(-c4cnn(C)c4)c3)ncc2-c2cnn(C)c2)CCCCC1] | 256 | yellow solid. HPLC(Column): (254 nm) 91%. LC/MS(Column): (M + H) 485.2. 1H NMR (400 MHz, DMSO-d6) d 8.59 (s, 1H), 8.32 (s, 1H), 8.21 (q, J = 3.5 Hz, 2H), 8.06 (s, 1H), 7.96 (s, 1H), 7.78 (s, 1H), 7.66 (d, J = 7.7 Hz, 1H), 7.48-7.38 (m, 2H), 6.64 (d, J = 6.4 Hz, 1H), 3.91 (m, 8H), 2.17-2.09 (m, 2H), 1.82 (s, 3H), 1.57-1.39 (m, 7H), 1.26 (m, 1H). |
| 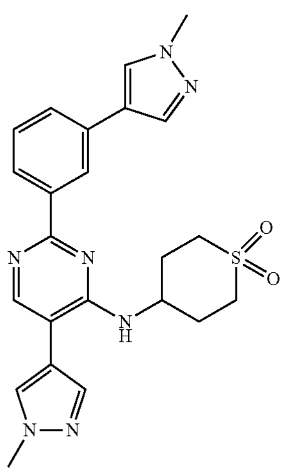 [SMILES: Cn1cc(-c2cccc(-c3ncc(-c4cnn(C)c4)c(NC4CCS(=O)(=O)CC4)n3)c2)cn1] | 257 | White solid. HPLC: (254 nm) 99.5%. LC/MS: (M + H) 464.2. 1H NMR (400 MHz, DMSO-d6): 8.51 (s, 1H), 8.26-8.22 (m, 3H), 8.07 (s, 1H), 7.94 (s, 1H), 7.76 (s, 1H), 7.67 (d, J = 7.6 Hz, 1H), 7.47 (t, J = 8.0 Hz, 1H), 6.55 (d, J = 7.6 Hz, 1H), 4.55-4.54 (m, 1H), 3.92 (s, 3H), 3.90 (s, 3H), 3.50-3.42 (m, 2H), 3.17-3.14 (m, 2H), 2.26-2.23 (m, 4H). |

| Structure | Example | Analyticals |
|---|---|---|
| 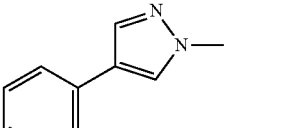 | 258 | light brown solid. HPLC(Column): (254 nm) 86%. LC/MS(Column): (M + H) 485.2. |
| 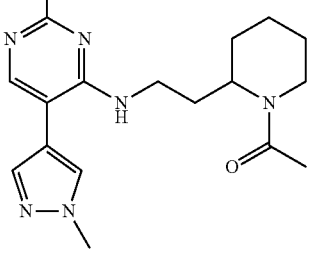 | 259 | white solid. HPLC(Column): (254 nm) 92%. LC/MS(Column): (M + H) 521.1. 1H NMR (400 MHz, DMSO-d6) d 8.50 (s, 1H), 8.25-8.16 (m, 3H), 8.07-8.02 (m, 1H), 7.92-7.86 (m, 1H), 7.78-7.71 (m, 1H), 7.66 (d, J = 7.7 Hz, 1H), 7.46 (ddd, J = 9.2, 5.2, 1.8 Hz, 1H), 6.64 (d, J = 6.1 Hz, 1H), 4.06-3.97 (m, 1H), 3.95 (s, 3H), 3.86 (s, 3H), 3.75-3.56 (m, 2H), 3.45 (m, 1H), 3.11-2.92 (m, 4H), 2.14-2.03 (m, 1H), 1.86 (m, 1H), 1.73-1.38 (m, 6H). |
| 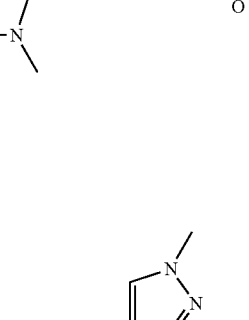 | 260 | light yellow solid. HPLC(Column): (254 nm) 97.7%. |

-continued

| Structure | Example | Analyticals |
|---|---|---|
| 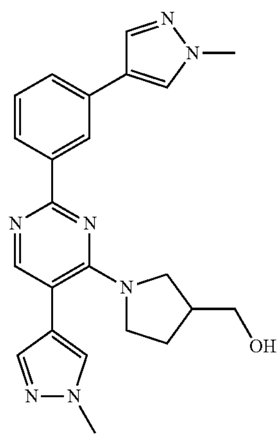 [SMILES: Cn1cc(-c2cccc(-c3ncc(-c4cnn(C)c4)c(N4CCC(CO)C4)n3)c2)cn1] | 261 | white solid. HPLC: (254 nm) 99%. LC/MS: (M + H) 416.2. 1H NMR (400 MHz, DMSO-d6) 8.49 (s, 1H), 8.19 (d, J = 8.5 Hz, 2H), 8.13 (d, J = 1.8 Hz, 1H), 7.89 (d, J = 1.7 Hz, 1H), 7.84 (s, 1H), 7.66 (d, J = 7.7 Hz, 1H), 7.53 (d, J = 1.8 Hz, 1H), 7.47 (t, J = 7.7 Hz, 1H), 4.66 (s, 1H), 3.90 (s, 3H), 3.89 (s, 3H), 3.54-3.20 (m, 6H), 2.28 (m, 1H), 1.92 (m, 1H), 1.65 (m, 1H). |
| 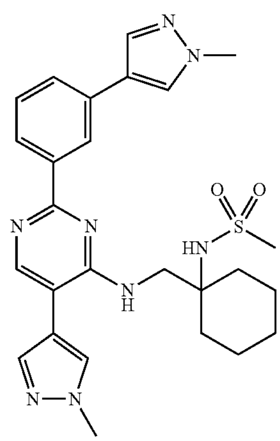 [SMILES: Cn1cc(-c2cccc(-c3ncc(-c4cnn(C)c4)c(NCC4(NS(C)(=O)=O)CCCCC4)n3)c2)cn1] | 262 | white solid. HPLC: (254 nm) 94%. LC/MS: (M + H) 521.1. 1H NMR (400 MHz, DMSO-d6) d 8.54 (s, 1H), 8.28-8.24 (m, 1H), 8.20 (m, 2H), 8.11 (d, J = 2.0 Hz, 1H), 7.91-7.87 (m, 1H), 7.80 (d, J = 2.0 Hz, 1H), 7.66 (d, J = 7.7 Hz, 1H), 7.50-7.44 (m, 1H), 6.95 (s, 1H), 6.30 (t, J = 6.3 Hz, 1H), 3.97-3.88 (m, 8H), 3.06-3.02 (m, 3H), 1.86 (t, J = 8.4 Hz, 2H), 1.59 (m, 6H), 1.47-1.34 (m, 2H). |
| 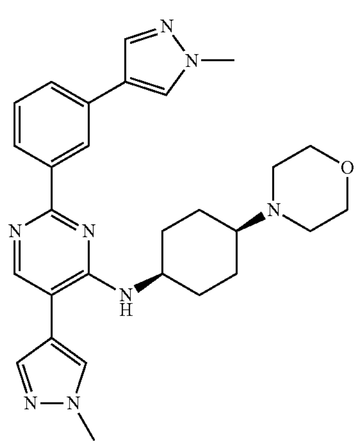 [SMILES: Cn1cc(-c2cccc(-c3ncc(-c4cnn(C)c4)c(N[C@H]4CC[C@@H](N5CCOCC5)CC4)n3)c2)cn1] | 263 | brown solid HPLC(Column): (254 nm) 96%. LC/MS(Column): (M + H) 499.2. |

-continued

| Structure | Example | Analyticals |
|---|---|---|
| 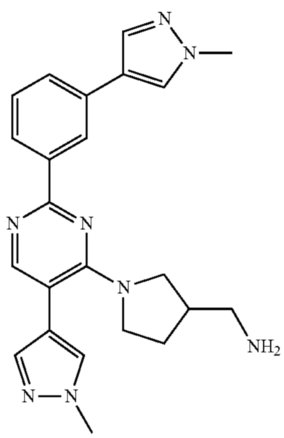 [SMILES: Cn1cc(-c2cccc(-c3ncc(-c4cnn(C)c4)c(N4CCC(CN)C4)n3)c2)cn1] | 264 | white solid. HPLC(Column): (254 nm) 95%.<br>LC/MS(Column): (M + H) 415.2. |
| 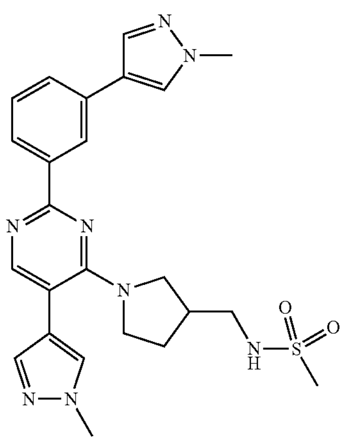 [SMILES: Cn1cc(-c2cccc(-c3ncc(-c4cnn(C)c4)c(N4CCC(CNS(C)(=O)=O)C4)n3)c2)cn1] | 265 | white solid. HPLC(Column): (254 nm) 95%.<br>LC/MS(Column): (M + H) 493.1. 1H NMR (400 MHz, DMSO-d6) 8.51 (s, 1H), 8.24-8.10 (m, 3H), 7.90 (s, 1H), 7.83 (s, 1H), 7.67 (d, J = 7.8 Hz, 1H), 7.55-7.43 (m, 2H), 7.15 (s, 1H), 3.90 (brs, 6H), 3.55 (m, 1H), 3.39 m, 2H), 3.23 (m, 1H), 2.99 (m, 2H), 2.89 (d, J = 2.2 Hz, 3H), 2.33 (m, 1H), 1.97 (m, 1H), 1.65 (m, 1H). |
| 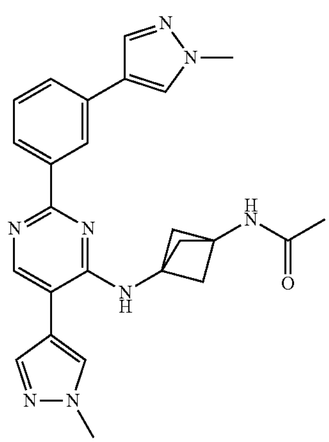 [SMILES: CC(=O)NC12CC(Nc3nc(-c4cccc(-c5cnn(C)c5)c4)ncc3-c3cnn(C)c3)(C1)C2] | 266 | white solid. HPLC(Column): (254 nm) 91%.<br>LC/MS(Column): (M + H) 455.2. 1H NMR (400 MHz, DMSO-d6) 8.58 (d, J = 11.9 Hz, 2H), 8.35 (s, 1H), 8.25-8.15 (m, 2H), 8.00 (s, 1H), 7.93 (s, 1H), 7.70 (d, J = 8.4 Hz, 2H), 7.48 (t, J = 7.9 Hz, 1H), 7.16 (s, 1H), 3.99 (s, 3H), 3.87 (s, 3H), 2.49-2.37 (m, 6H), 1.85 (d, J = 2.1 Hz, 3H). |

-continued

| Structure | Example | Analyticals |
|---|---|---|
| 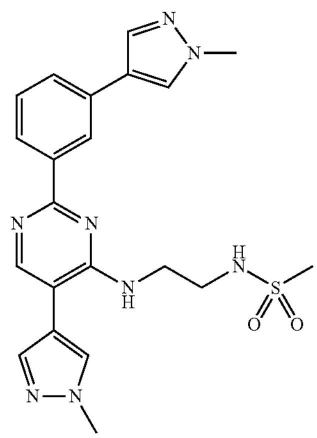 [SMILES: Cn1cc(-c2cccc(-c3ncc(-c4cnn(C)c4)c(NCCNS(C)(=O)=O)n3)c2)cn1] | 267 | off-white solid. HPLC(Column): (254 nm) 99%. LC/MS(Column): (M + H) 453.1. 1H NMR (400 MHz, DMSO-d6) 8.51 (s, 1H), 8.26-8.17 (m, 3H), 8.06 (s, 1H), 7.94-7.88 (m, 1H), 7.79-7.73 (m, 1H), 7.66 (d, J = 7.7 Hz, 1H), 3.29-3.23 (m, 2H), 7.49-7.43 (m, 1H), 7.24 (s, 1H), 6.74 (d, J = 6.1 Hz, 1H), 3.94-3.86 (m, 6H), 3.68 (m, 2H), 2.92-2.88 (m, 3H). |
| 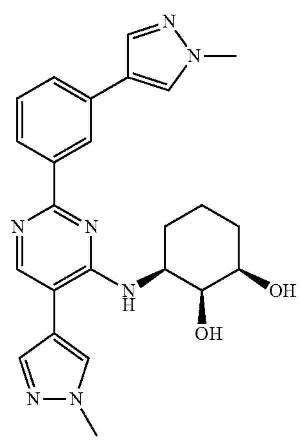 [SMILES: Cn1cc(-c2cccc(-c3ncc(-c4cnn(C)c4)c(N[C@H]4CCC[C@@H](O)[C@H]4O)n3)c2)cn1] | 268 | white solid HPLC(Column): (254 nm) 86%. LC/MS(Column): (M + H) 446.1. |
| 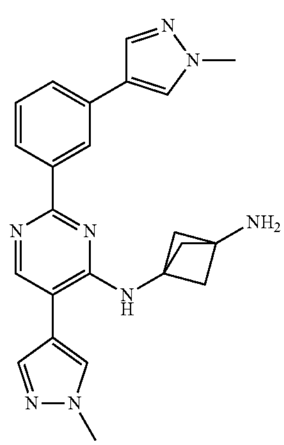 [SMILES: Cn1cc(-c2cccc(-c3ncc(-c4cnn(C)c4)c(NC45CC(N)(C4)C5)n3)c2)cn1] | 269 | white solid. HPLC(Column): (254 nm) 81%. LC/MS(Column): (M + H) 413.1. |

-continued

| Structure | Example | Analyticals |
|---|---|---|
| 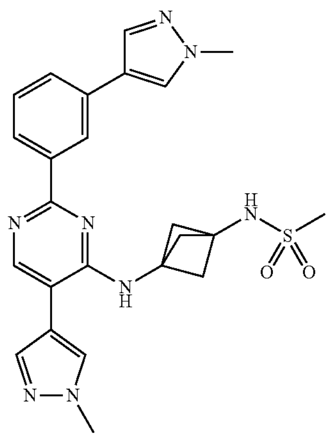 [SMILES: Cn1cc(-c2cccc(-c3ncc(-c4cnn(C)c4)c(NC45CC(NS(C)(=O)=O)(C4)C5)n3)c2)cn1] | 270 | white solid. HPLC(Column): (254 nm) 87%. LC/MS(Column): (M + H) 491.1. |
| 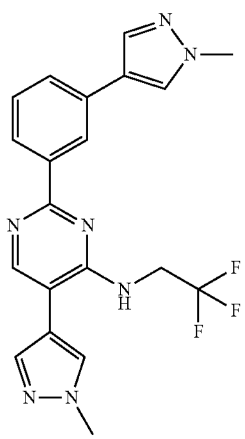 [SMILES: Cn1cc(-c2cccc(-c3ncc(-c4cnn(C)c4)c(NCC(F)(F)F)n3)c2)cn1] | 271 | white solid. HPLC(Column): (254 nm) 100%. LC/MS(Column): (M + H) 414.1. 1H NMR (400 MHz, DMSO-d6) 8.52 (d, J = 2.1 Hz, 1H), 8.38-8.31 (m, 1H), 8.23-8.16 (m, 2H), 8.06-8.01 (m, 1H), 7.91-7.84 (m, 1H), 7.79-7.72 (m, 1H), 7.68 (d, J = 7.8 Hz, 1H), 7.49 (m, 1H), 7.21-7.11 (m, 1H), 4.44-4.31 (m, 2H), 3.94 (s, 3H), 3.90 (s, 3H). |
| 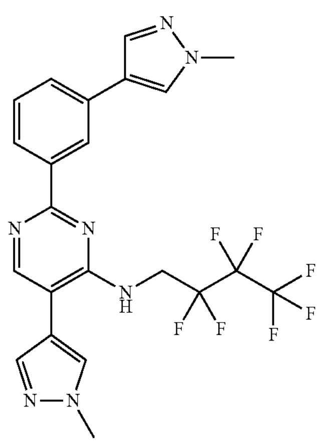 [SMILES: Cn1cc(-c2cccc(-c3ncc(-c4cnn(C)c4)c(NCC(F)(F)C(F)(F)C(F)(F)F)n3)c2)cn1] | 272 | white solid. HPLC(Column): (254 nm) 100%. LC/MS(Column): (M + H) 514. |

-continued

| Structure | Example | Analyticals |
|---|---|---|
| 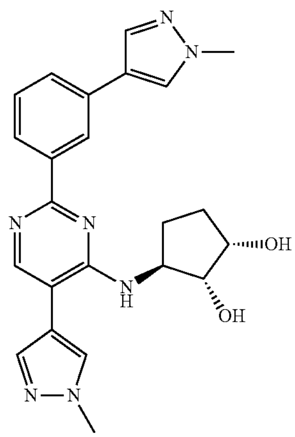 [SMILES: Cn1cc(-c2cccc(-c3ncc(-c4cnn(C)c4)c(N[C@H]4CC[C@H](O)[C@@H]4O)n3)c2)cn1] | 273 | white solid. HPLC(Column): (254 nm) 98%. LC/MS(Column): (M + H) 432.1. |
| 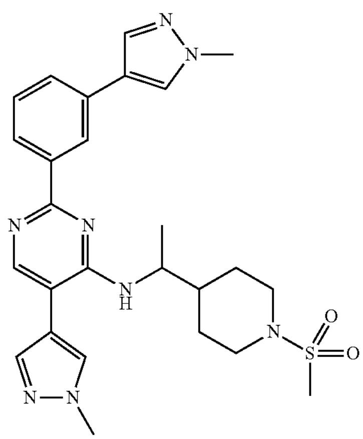 [SMILES: CC(Nc1nc(-c2cccc(-c3cnn(C)c3)c2)ncc1-c1cnn(C)c1)C1CCN(S(C)(=O)=O)CC1] | 274 | white solid. HPLC(Column): (254 nm) 96%. LC/MS(Column): (M + H) 521.1. 1H NMR (400 MHz, DMSO-d6) 8.48 (s, 1H), 8.18 (m, 3H), 8.02 (d, J = 2.0 Hz, 1H), 7.90-7.84 (m, 1H), 7.75-7.70 (m, 1H), 7.66 (d, J = 7.8 Hz, 1H), 7.48 (m, 1H), 6.20-6.14 (m, 1H), 4.41 (m, 1H), 3.94 (s, 3H), 3.90 (s, 3H), 3.61 (t, J = 11.0 Hz, 2H), 2.83 (s, 3H), 2.69-2.59 (m, 2H), 1.83 (m, 3H), 1.41-1.22 (m, 5H). |
| 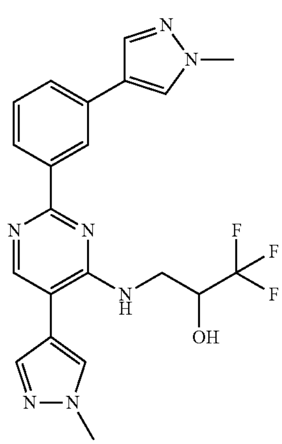 [SMILES: Cn1cc(-c2cccc(-c3ncc(-c4cnn(C)c4)c(NCC(O)C(F)(F)F)n3)c2)cn1] | 275 | white solid. HPLC(Column): (254 nm) 96%. LC/MS(Column): (M + H) 444.1. 1H NMR (400 MHz, DMSO-d6) 8.51 (s, 1H), 8.32-8.26 (m, 1H), 8.18 (m, 2H), 8.07 (s, 1H), 7.88 (s, 1H), 7.72 (s, 1H), 7.67 (m, 1H), 7.51-7.44 (m, 1H), 6.82 (brs, 1H), 6.49 (brs, 1H), 4.52-4.42 (m, 1H), 4.02 (m, 1H), 3.94 (s, 3H), 3.90 (s, 3H), 3.55 (m, 1H). |

| Structure | Example | Analyticals |
|---|---|---|
| 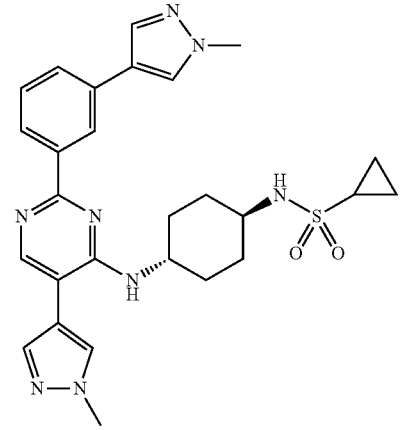 [SMILES: Cn1cc(-c2cccc(-c3ncc(-c4cnn(C)c4)c(N[C@H]4CC[C@H](NS(=O)(=O)C5CC5)CC4)n3)c2)cn1] | 276 | yellow solid. HPLC(Column): (254 nm) 99%. LC/MS(Column): (M + H) 533.1. 1H NMR (400 MHz, DMSO-d6) 8.50 (s, 1H), 8.25-8.13 (m, 3H), 8.03 (s, 1H), 7.86 (s, 1H), 7.76-7.72 (m, 1H), 7.66 (d, J = 7.8 Hz, 1H), 7.49 (m, 1H), 7.11 (d, J = 7.9 Hz, 1H), 6.17-6.10 (m, 1H), 4.09 (d, J = 8.6 Hz, 1H), 3.93 (s, 3H), 3.90 (s, 3H), 3.16 (m, 1H), 2.62-2.55 (m, 1H), 2.04 (m, 4H), 1.50 (m, 4H), 1.01-0.87 (m, 4H). |
| 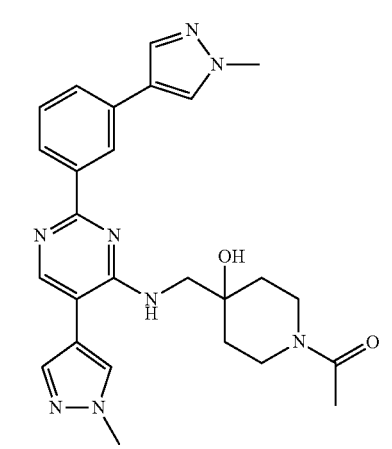 | 277 | white solid. HPLC(Column): (254 nm) 95%. LC/MS(Column): (M + H) 487.2. 1H NMR (400 MHz, DMSO-d6) 8.50 (s, 1H), 8.30-8.02 (m, 4H), 7.89 (s, 1H), 7.78 (s, 1H), 7.67 (d, J = 7.6 Hz, 1H), 7.48 (t, J = 7.8 Hz, 1H), 6.42 (m, 1H), 5.01 (s, 1H), 4.14-3.82 (m, 7H), 3.73-3.56 (m, 3H), 3.01 (t, J = 11.2 Hz, 1H), 1.97 (s, 3H), 1.64-1.43 (m, 4H). |
| 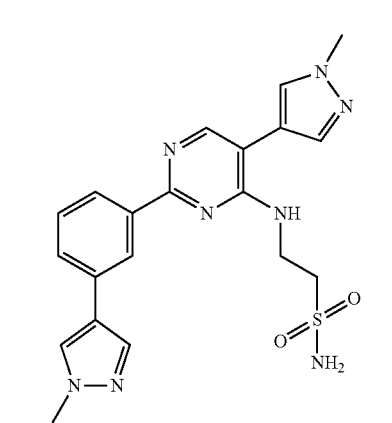 [SMILES: Cn1cc(-c2cccc(-c3ncc(-c4cnn(C)c4)c(NCCS(N)(=O)=O)n3)c2)cn1] | 278 | white solid. HPLC(Column): (254 nm) 99.2%. LC/MS(Column): (M + H) 439.3. 1H NMR (400 MHz, DMSO-d6): 8.56 (s, 1H), 8.27 (s, 1H), 8.24-8.21 (m, 2H), 8.06 (s, 1H), 7.94 (s, 1H), 7.77 (s, 1H), 7.68 (d, J = 8.0 Hz, 1H), 7.46 (t, J = 7.6 Hz, 1H), 7.04 (s, 2H), 6.91 (t, J = 6.0 Hz, 1H), 3.99-3.94 (m, 2H), 3.92 (s, 3H), 3.89 (s, 3H), 3.40 (t, J = 7.60 Hz, 2H). |

-continued

| Structure | Example | Analyticals |
|---|---|---|
| 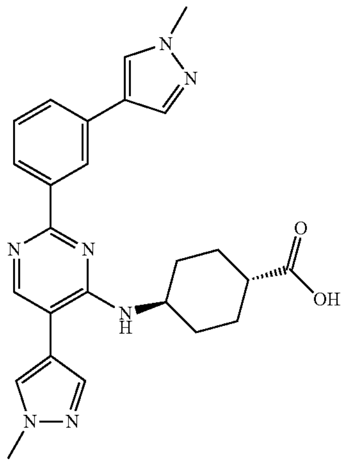 [SMILES: Cn1cc(-c2cccc(-c3ncc(-c4cnn(C)c4)c(N[C@H]4CC[C@H](C(=O)O)CC4)n3)c2)cn1] | 279 | Off white solid. HPLC(Column): (254 nm) 98.4%. LC/MS(Column): (M + H) 458.0. 400 MHz, DMSO-d6): 8.49 (s, 1H), 8.20 (d, J = 4.8 Hz, 2H), 8.16 (d, J = 8.0 Hz, 1H), 8.10 (s, 1H), 7.87 (s, 1H), 7.74 (s, 1H), 7.66 (d, J = 7.6 Hz, 1H), 7.48 (t, J = 7.6 Hz, 1H), 5.79 (d, J = 6.8 Hz, 1H), 4.21-4.19 (m, 1H), 3.93-3.90 (m, 6H), 2.00 (s, 1H), 1.87-1.85 (m, 2H), 1.75-1.71 (m, 4H), 1.58-1.53 (m, 2H). |
| 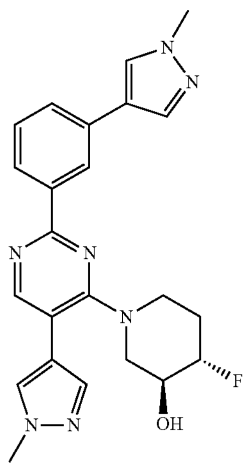 [SMILES: Cn1cc(-c2cccc(-c3ncc(-c4cnn(C)c4)c(N4CC[C@H](F)[C@@H](O)C4)n3)c2)cn1] | 280 | HPLC(Column): (254 nm) 99%. LC/MS(Column): (M + H) 434.4. |
| 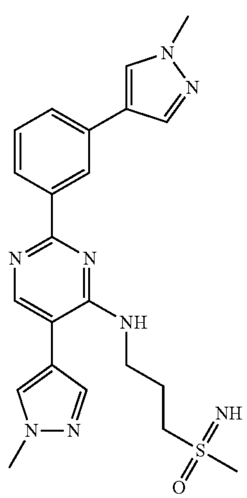 | 282 | White solid. HPLC(Column): (254 nm) 97.8%. LC/MS(Column): (M + H) 451.2. 1H NMR (400 MHz, DMSO-d6): 8.49 (t, J = 1.6 Hz, 1H), 8.24-8.18 (m, 3H), 8.06 (s, 1H), 7.91 (s, 1H), 7.75 (s, 1H), 7.67-7.65 (m, 1H), 7.46 (t, J = 8.0 Hz, 1H), 6.75 (t, J = 127.6 Hz, 1H), 3.93 (s, 3H), 3.90 (s, 3H), 3.69-3.64 (m, 3H), 3.29 (s, 1H), 3.16 (t, J = 6.80 Hz, 2H), 2.91 (s, 3H), 2.70 (s, 1H), 2.20-2.11 (m, 3H), 1.93-1.89 (m, 1H). |

Example 281: (1R,2S,6S)-2-Methylamino-6-{5-(1-methyl-1-pyrazol-4-yl)-2-[3-(1-methyl-1H-pyrazol-4-yl)-phenyl]-pyrimidin-4-ylamino}-cyclohexanol (Racemic—Relative Configuration)

Step 1: tert-butyl N-[(1S,2S,3S)-2-hydroxy-3-{[5-(1-methyl-H-pyrazol-4-yl)-2-[3-(1-methyl-1H-pyrazol-4-yl)phenyl]pyrimidin-4-yl]amino}cyclohexyl]-N-methylcarbamate (Racemic Relative Configuration)

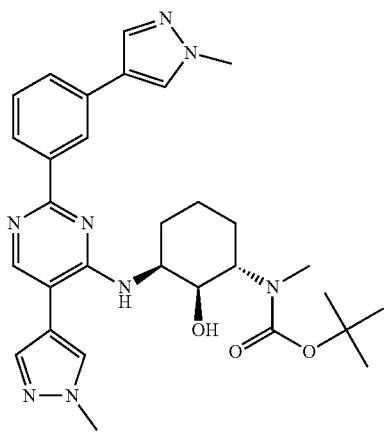 [SMILES: CN(C(=O)OC(C)(C)C)[C@H]1CCC[C@H](Nc2nc(-c3cccc(-c4cnn(C)c4)c3)ncc2-c2cnn(C)c2)[C@@H]1O]

A mixture of tert-butyl N-[(1S,2S,3S)-3-[[2-chloro-5-(1-methyl-1H-pyrazol-4-yl)pyrimidin-4-yl]amino]-2-hydroxycyclohexyl]-N-methylcarbamate (Intermediate 40, racemic, relative configuration, 420 mg, 0.87 mmol, 1.00 equiv, 90%), 1-methyl-4-[3-(tetramethyl-1,3,2-dioxaborolan-2-yl)phenyl]-1H-pyrazole (440 mg, 1.30 mmol, 1.50 equiv, 84%), Pd(PPh3)2Cl2 (62 mg, 0.09 mmol, 0.10 equiv, 98%) and potassium carbonate (245 mg, 1.74 mmol, 2.01 equiv, 98%) in dioxane (10 mL) and water (1 mL) was degassed with nitrogen and heated in MW at 150° C. for 30 min. The resulting mixture was concentrated under vacuum and purified by flash chromatography on silica (MeOH/DCM, 1:5) to afford the title compound as a yellow solid (390 mg, 73%). LC/MS (Column: Shim-pack XR-ODS, 3.0*50 mm, 2.2 um; Mobile Phase A: Water/0.05% TFA, Mobile Phase B: ACN/0.05% TFA; Flow rate: 1.0 mL/min; Gradient: 5% B to 100% B in 3.6 min, hold 1.0 min; 254 nm): (purity) 90%; [M+H]+ Cac. 559.3; found 559.3.

Step 2: (1R,2S,6S)-2-{[5-(1-methyl-1H-pyrazol-4-yl)-2-[3-(1-methyl-1H-pyrazol-4-yl)phenyl]pyrimidin-4-yl]amino}-6-(methylamino)cyclohexan-1-o (Racemic Relative Configuration)

A solution of tert-butyl N-[(1S,2S,3S)-2-hydroxy-3-[[5-(1-methyl-1H-pyrazol-4-yl)-2-[3-(1-methyl-1H-pyrazol-4-yl)phenyl]pyrimidin-4-yl]amino]cyclohexyl]-N-methylcarbamate (50 mg, 0.08 mmol, 1.00 equiv, 90%) and conc.HCl (0.5 mL, 6.01 mmol, 74 eq., 36.5%) in MeOH (2 mL) was stirred for 2 h at 25° C. The pH value of the solution was adjusted to 7 with sodium bicarbonate and the resulting mixture was concentrated under vacuum. The residue was dissolved in 10 mL of DCM, the solids were filtered out and the resulting mixture was concentrated under vacuum. Purification of the crude (25 mg) by HPLC afforded the title compound as yellow solid (5 mg, 15%). m.p.: 88-92° C. LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 98%; [M+H]+ Cac. 459.3; found 459.3. 1H NMR (300 MHz, DMSO-d6, ppm) δ 8.52 (t, J=1.7 Hz, 1H), 8.24-8.12 (m, 3H), 8.06 (s, 1H), 7.89 (s, 1H), 7.75 (s, 1H), 7.71-7.60 (m, 1H), 7.47 (t, J=7.7 Hz, 1H), 5.84 (d, J=7.7 Hz, 1H), 5.07 (d, J=4.4 Hz, 1H), 4.55 (s, 1H), 3.93 (s, 3H), 3.89 (s, 3H), 3.75 (q, J=3.9 Hz, 1H), 2.60 (d, J=3.8 Hz, 1H), 2.33 (s, 3H), 1.69 (m, 5H), 1.41 (m, 2H).

Example 283 and 284: (R)-5,5-Difluoro-1-{5-(1-methyl-1H-pyrazol-4-yl)-2-[3-(1-methyl-1H-pyrazol-4-yl)-phenyl]-pyrimidin-4-yl}-piperidin-3-ylamine and (S)-5,5-Difluoro-1-{5-(1-methyl-1H-pyrazol-4-yl)-2-[3-(1-methyl-1H-pyrazol-4-yl)-phenyl]-pyrimidin-4-yl}-piperidin-3-ylamine Step 1: tert-butyl N-{5,5-difluoro-1-[5-(1-methyl-1H-pyrazol-4-yl)-2-[3-(1-methyl-1H-pyrazol-4-yl)phenyl]pyrimidin-4-yl]piperidin-3-yl}carbamate

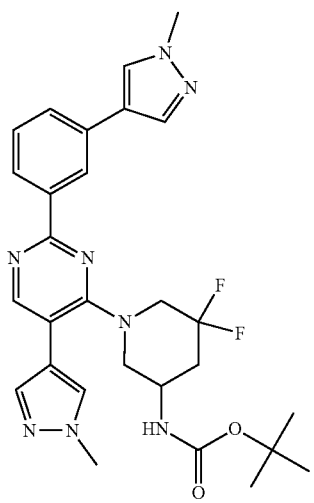 [SMILES: Cn1cc(-c2cccc(-c3ncc(-c4cnn(C)c4)c(N4CC(NC(=O)OC(C)(C)C)CC(F)(F)C4)n3)c2)cn1]

The title compound was obtained following the procedure described for example 281, step 1 from tert-butyl N-[1-[2-chloro-5-(1-methyl-1H-pyrazol-4-yl)pyrimidin-4-yl]-5,5-difluoropiperidin-3-yl]carbamate (Intermediate 42, 220 mg, 0.46 mmol, 1.00 eq.) as a white solid (135 mg, 44%). LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 83.7%; [M+H]+ Cac. 551.4; found 551.4.

Step 2: (3R) and (3S)-5,5-difluoro-1-[5-(1-methyl-H-pyrazol-4-yl)-2-[3-(1-methyl-1H-pyrazol-4-yl)phenyl]pyrimidin-4-yl]piperidin-3-amine

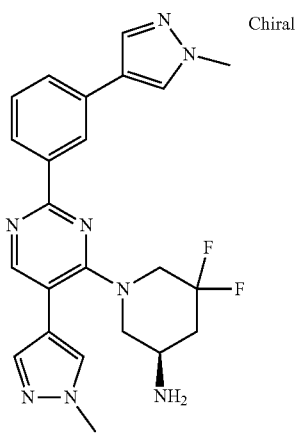

Trifluoroacetic acid (1 mL, 13.46 mmol, 70.85 equiv) was added dropwise to a solution of tert-butyl N-[5,5-difluoro-1-[5-(1-methyl-1H-pyrazol-4-yl)-2-[3-(1-methyl-1H-pyrazol-4-yl)phenyl]pyrimidin-4-yl]piperidin-3-yl]carbamate (125 mg, 0.19 mmol, 1.00 eq.) in dichloromethane (4 mL) maintained at 0° C. The resulting solution was stirred for 2 h at 25° C. It was then concentrated under vacuum and purified by Prep-HPLC (XBridge C18) to afford the title compound as a racemic mixture (30 mg). The two enantiomers were then separated by chiral prep-HPLC (Lux 5u Cellulose-4, AXIA Packed, 100.0% MeOH, 0.1% DEA).

First eluting enantiomer: white solid (14.4 mg, 16%). M.p.: 70-73° C. LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 97.5%; [M+H]+ Cac. 451.3; found 451.3. 1H NMR (400 MHz, DMSO, ppm): 8.49 (m, 2H), 8.21-8.18 (m, 2H), 8.03 (s, 1H), 7.90 (s, 1H), 7.73 (s, 1H), 7.68-7.66 (m, 1H), 7.49-7.45 (m, 1H), 4.10-4.08 (m, 1H), 3.94-3.85 (m, 7H), 3.35 (s, 1H), 3.30-3.17 (m, 1H), 2.69-2.63 (m, 1H), 2.49-2.47 (m, 1H), 2.31 (m, 1H), 1.83-1.72 (m, 1H).

Second elution enantiomer: white solid (15 mg, 17%). LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 97.8%; [M+H]+ Cac. 451.3; found 451.3.

Example 285 and 286: (1S,2S,6S)-2-Fluoro-6-{5-(1-methyl-1H-pyrazol-4-yl)-2-[3-(1-methyl-1H-pyrazol-4-yl)-phenyl]-pyrimidin-4-ylamino}-cyclohexanol and (1R,2R,6R)-2-Fluoro-6-{5-(1-methyl-1H-pyrazol-4-yl)-2-[3-(1-methyl-1H-pyrazol-4-yl)-phenyl]-pyrimidin-4-ylamino}-cyclohexanol

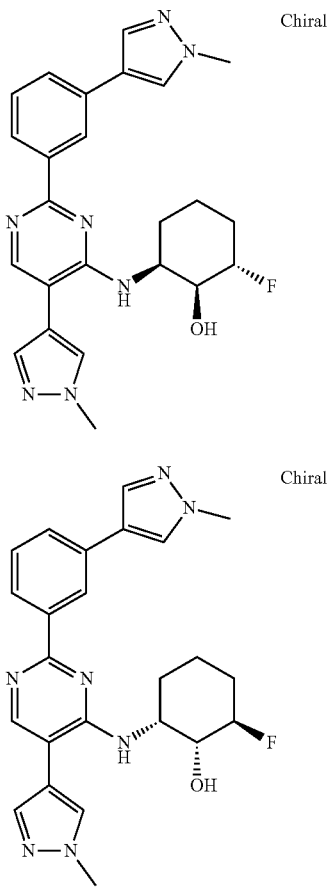

The racemic mixture of the title compounds was obtained following the procedure described for example 287 from (1S,2S,6S)-2-[[2-chloro-5-(1-methyl-1H-pyrazol-4-yl)pyrimidin-4-yl]amino]-6-fluorocyclohexan-1-ol (Intermediate 45, relative stereochemistry, racemic, 360 mg, 0.99 mmol, 1.00 eq.) Purification was performed by prep-HPLC [SHIMADZU: Column: XBridge BEH130 Prep C18 OBD Column, 19×150 mm, 5 μm, 13 nm; Mobile phase: water (10 mmol/L NH$_4$HCO$_3$) and ethanol (55% to 67% in 12 min); Detector: UV 254 nm] and the title compound was obtained as a white solid (200 mg, 43%). m.p: 176-180° C. HPLC (UV 254 nm): 94.57% purity. MS: m/z=448.2 [M+H]; $^1$H NMR (300 MHz, DMSO-d6, ppm): δ 8.51 (s, 1H), 8.26 (s, 1H), 8.17-8.14 (m, 2H), 8.07 (s, 1H), 7.86 (s, 1H), 7.77 (s, 1H), 7.67-7.65 (m, 1H), 7.50-7.44 (m, 1H), 5.91 (d, J=7.8 Hz, 1H), 5.55 (d, J=4.8 Hz, 1H), 4.87-4.65 (m, 1H), 4.52-4.42 (m, 1H), 4.07-4.02 (m, 1H), 3.93 (s, 3H), 3.88 (s, 3H), 1.85-1.55 (m, 6H).

This racemic mixture was resolved by chiral-prep-HPLC [Column: Repaired Chiral ADH, 21.2×250 mm, 5 μm; Mobile phase: hexane and ethanol (hold 30% ethanol in 25 min); Detector: UV 254/220 nm].

First eluting enantiomer: (1S,2S,6S)-2-fluoro-6-[[5-(1-methyl-1H-pyrazol-4-yl)-2-[3-(1-methyl-1H-pyrazol-4-yl)phenyl]pyrimidin-4-yl]amino]cyclohexan-1-ol (assumed stereochemistry): white solid (40 mg). m.p: 144-148° C. HPLC (UV 254 nm): 98.26% purity. Chiral purity: e.e. %>99.99%.

Second eluting enantiomer: (1R,2R,6R)-2-fluoro-6-[[5-(1-methyl-1H-pyrazol-4-yl)-2-[3-(1-methyl-1H-pyrazol-4-yl)phenyl]pyrimidin-4-yl]amino]cyclohexan-1-ol (assumed stereochemistry): white solid, 40 mg (9%). M.p: 200-202° C. HPLC (UV 254 nm): 99.25% purity. Chiral purity: e.e. %>99.99%.

Example 287: (1S,6R)-2,2-Difluoro-6-{5-(1-methyl-1H-pyrazol-4-yl)-2-[3-(1-methyl-1H-pyrazol-4-yl)-phenyl]-pyrimidin-4-ylamino}-cyclohexanol

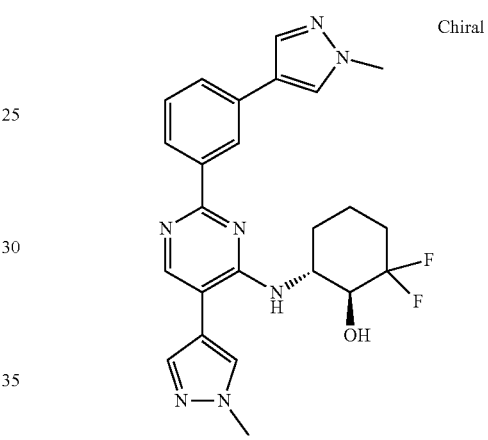

A mixture of (1S,6R)-6-[[2-chloro-5-(1-methyl-1H-pyrazol-4-yl)pyrimidin-4-yl]amino]-2,2-difluorocyclohexan-1-ol (Intermediate 46, 50 mg, 0.12 mmol, 1.00 eq.), 1-methyl-4-[3-(tetramethyl-1,3,2-dioxaborolan-2-yl)phenyl]-1H-pyrazole (53 mg, 0.18 mmol, 1.45 eq.), Pd(PCy$_3$)$_2$Cl$_2$ (11 mg, 0.01 mmol, 0.12 eq.) and K$_3$PO$_4$ (62 mg, 0.28 mmol, 2.27 eq) in dioxane (2 mL) and water (0.5 mL) was heated for 3 h at 100° C. under nitrogen atmosphere in a sealed tube. The resulting mixture was then concentrated under vacuum. The residue was diluted with DCM. The aqueous phase was separated and extracted twice with DCM. Combined organic phases were washed with brine, dried over magnesium sulfate, filtered and concentrated. Purification by Prep-HPLC (XBridge BEH130 Prep C18 OBD Column) afforded the title compound as a white solid (35 mg, 61%). LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 99.9%; [M+H]+ Cac. 466.3; found 466.3. 1H NMR (300 MHz, DMSO-d6, ppm) 8.48 (s, 1H), 8.23 (s, 1H), 8.17 (s, 1H), 8.13 (d, J=8.1 Hz, 1H), 8.05 (s, 1H), 7.84 (s, 1H), 7.78 (s, 1H), 7.65 (d, J=7.5 Hz, 1H), 7.48 (t, J=7.7 Hz, 1H), 6.36 (d, J=7.6 Hz, 1H), 5.62 (d, J=6.4 Hz, 1H), 4.31 (m, 1H), 3.92 (s, 3H), 3.89 (s, 3H), 2.13 (m, 2H), 1.75 (m, 2H), 1.53 (m, 2H).

Example 288 and 289: (1R,2S,3S)-3-{5-(1-Methyl-1H-pyrazol-4-yl)-2-[3-(1-methyl-1H-pyrazol-4-yl)-phenyl]-pyrimidin-4-ylamino}-cycloheptane-1,2-diol and (1S,2R,3R)-3-{5-(1-Methyl-1H-pyrazol-4-yl)-2-[3-(1-methyl-1H-pyrazol-4-yl)-phenyl]-pyrimidin-4-ylamino}-cycloheptane-1,2-diol Step 1: N-[(3aS,4S,8aR)-2,2-dimethyl-octahydrocyclohepta[d][1,3]dioxol-4-yl]-2-chloro-5-(1-methyl-1H-pyrazol-4-yl)pyrimidin-4-amine (Racemic—Relative Stereochemistry)

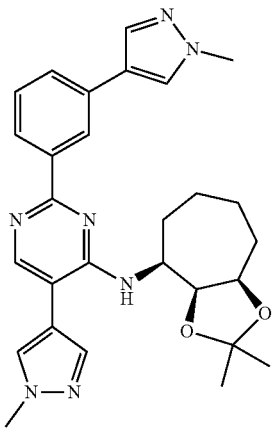

The title compound was obtained following the procedure described for example 287 from N-[(3aS,4S,8aR)-2,2-dimethyl-octahydrocyclohepta[d][1,3]dioxol-4-yl]-2-chloro-5-(1-methyl-1H-pyrazol-4-yl)pyrimidin-4-amine (Intermediate 51, 180 mg, 0.43 mmol, 1.00 eq.) as an yellow oil (220 mg, 92%). LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 90.0%; [M+H]+ Cac. 500.3; found 500.0.

Step 2: (1R,2S,3S)-3-{5-(1-Methyl-1H-pyrazol-4-yl)-2-[3-(1-methyl-1H-pyrazol-4-yl)-phenyl]-pyrimidin-4-ylamino}-cycloheptane-1,2-diol and (1S,2R,3R)-3-{5-(1-Methyl-1H-pyrazol-4-yl)-2-[3-(1-methyl-1H-pyrazol-4-yl)-phenyl]-pyrimidin-4-ylamino}-cycloheptane-1,2-diol

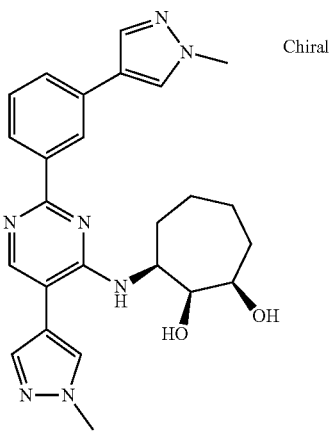

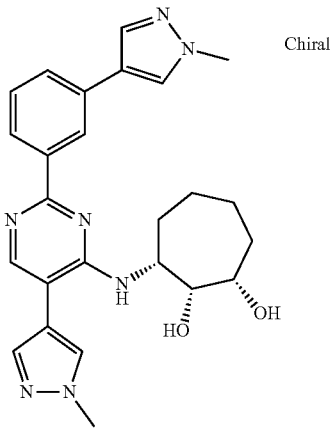

A solution of conc. HCl (0.75 mL, 24.68 mmol, 62 eq.) in MeOH (1 mL) was added dropwise to a solution of N-[(3aS,4S,8aR)-2,2-dimethyl-octahydrocyclohepta[d][1,3]dioxol-4-yl]-5-(1-methyl-1H-pyrazol-4-yl)-2-[3-(1-methyl-1H-pyrazol-4-yl)phenyl]pyrimidin-4-amine (220 mg, 0.40 mmol, 1.00 eq.) in MeOH (2 mL) maintained at 0° C. The resulting solution was stirred for 16 h at RT. The pH value of the solution was adjusted to 8 by addition of ammonia. The reaction mixture was concentrated under vacuum and purified by flash chromatography (H₂O:MeOH, 1:1) to afford the title compound as a racemic mixture (130 mg). The two enantiomers were separated by Chiral-Prep-HPLC (Chiralpak IC, MeOH).

First eluting isomer: 50 mg (31%). m.p.: 176-178° C. LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 99.1%; [M+H]+ Cac. 460.2; found 460.0. 1H NMR (300 MHz, Chloroform-d) 8.50 (s, 1H), 8.20 (d, J=8.0 Hz, 2H), 7.86 (s, 1H), 7.75 (s, 1H), 7.68 (s, 1H), 7.56 (d, J=10.6 Hz, 2H), 7.45 (t, J=7.7 Hz, 1H), 6.00 (d, J=7.4 Hz, 1H), 4.62-4.42 (m, 1H), 4.12 (d, J=2.8 Hz, 1H), 4.10-4.01 (m, 1H), 3.97 (d, J=8.0 Hz, 5H), 2.21-2.01 (m, 1H), 1.93 (q, J=9.8, 9.1 Hz, 1H), 1.86-1.76 (m, 3H), 1.69 (d, J=6.3 Hz, 3H), 1.63-1.45 (m, 2H).

Second eluting isomer: 59 mg (31%). m.p.: 176-178° C. LC/MS (Column: Shim-pack XR-ODS, 2.0*50 mm, 1.6 um; Mobile Phase A: Water/0.05% TFA, Mobile Phase B: ACN/0.05% TFA; Flow rate: 0.7 mL/min; Gradient: 5% B to 100% B in 2.1 min, hold 0.5 min; 220 nm): (purity) 98.6%; [M+H]+ Cac. 460.2; found 460.0.

Example 290: (1S,2R,6S)-2-Fluoro-6-{5-(1-methyl-1H-pyrazol-4-yl)-2-[3-(1-methyl-1H-pyrazol-4-yl)-phenyl]-pyrimidin-4-ylamino}-cyclohexanol (Racemic—Relative Configuration)

Step 1: (1S,2S,3S)-2-(methoxymethoxy)-3-[[5-(1-methyl-1H-pyrazol-4-yl)-2-[3-(1-methyl-1H-pyrazol-4-yl)phenyl]pyrimidin-4-yl]amino]cyclohexyl Acetate (Racemic—Relative Stereochemistry)

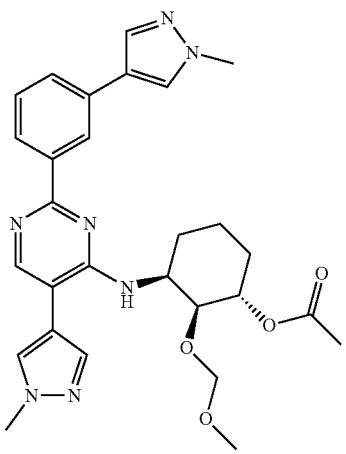 [SMILES: COCO[C@H]1[C@@H](Nc2nc(-c3cccc(-c4cnn(C)c4)c3)ncc2-c2cnn(C)c2)CCC[C@@H]1OC(C)=O]

The title compound was obtained following the procedure described for example 287 from (1S,2S,3S)-3-[[2-chloro-5-(1-methyl-1H-pyrazol-4-yl)pyrimidin-4-yl]amino]-2-(methoxymethoxy)cyclohexyl acetate (Intermediate 54, racemic, 330 mg, 0.72 mmol, 1.00 eq.) as a yellow solid (480 mg, 100%). MS: m/z=532.5 [M+H]+.

Step 2: (1S,2S,3S)-2-(methoxymethoxy)-3-[[5-(1-methyl-1H-pyrazol-4-yl)-2-[3-(1-methyl-1H-pyrazol-4-yl)phenyl]pyrimidin-4-yl]amino]cyclohexan-1-ol (Racemic—Relative Stereochemistry)

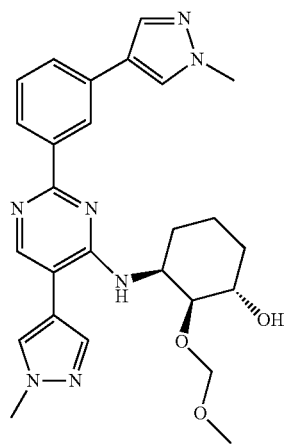 [SMILES: COCO[C@H]1[C@@H](Nc2nc(-c3cccc(-c4cnn(C)c4)c3)ncc2-c2cnn(C)c2)CCC[C@@H]1O]

A solution of (1S,2S,3S)-2-(methoxymethoxy)-3-[[5-(1-methyl-1H-pyrazol-4-yl)-2-[3-(1-methyl-1H-pyrazol-4-yl)phenyl]pyrimidin-4-yl]amino]cyclohexyl acetate (racemic, 480 mg, 0.81 mmol, 1.00 eq.) and sodium hydroxide (100 mg, 2.45 mmol, 3.02 eq.) in THF (10 mL) and water (2 mL) was stirred for 2 h at 25° C. It was then concentrated under reduced pressure and diluted with water (20 mL). The resulting mixture was extracted with DCM (3×10 mL). Combined organic layers were washed with brine, dried over anhydrous Na$_2$SO$_4$, filtered and concentrated under vacuum. Purification by flash chromatography on silica (MeOH/DCM, 1:100 to 1:25) afforded the title compound as a brown solid (340 mg, 77%). MS: m/z=490.4 [M+H]+.

Step 3: N-[(1S,2S,3R)-3-fluoro-2-(methoxymethoxy)cyclohexyl]-5-(1-methyl-H-pyrazol-4-yl)-2-[3-(1-methyl-1H-pyrazol-4-yl)phenyl]pyrimidin-4-amine (Racemic—Relative Stereochemistry)

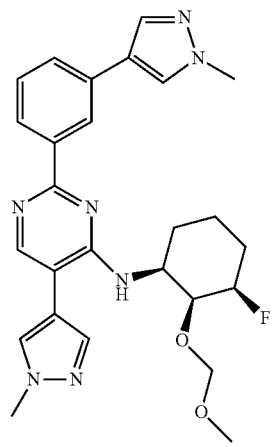 [SMILES: COCO[C@@H]1[C@H](F)CCC[C@@H]1Nc1nc(-c2cccc(-c3cnn(C)c3)c2)ncc1-c1cnn(C)c1]

A solution of (1S,2S,3S)-2-(methoxymethoxy)-3-[[5-(1-methyl-1H-pyrazol-4-yl)-2-[3-(1-methyl-1H-pyrazol-4-yl)phenyl]pyrimidin-4-yl]amino]cyclohexan-1-ol (racemic, 340 mg, 0.56 mmol, 1.00 eq., 80% purity) in dichloromethane (1 mL) was added dropwise to a solution of XtalFluor-E (195 mg, 0.83 mmol, 1.50 equiv, 98% purity) in DCM (10 mL) maintained at 0° C. under nitrogen atmosphere. TEA. 3HF (147 mg, 0.89 mmol, 1.61 equiv, 98% purity) was then added dropwise to the resulting mixture at 0° C. The reaction mixture was warmed to RT and stirred for another 1 h. It was then quenched by the addition of 20 mL of H$_2$O and extracted with DCM (3×10 mL). Combined organic layers were washed with brine (1 mL), dried over anhydrous sodium sulfate, filtered and concentrated. Purification by flash chromatography on silica (MeOH/DCM, 1:100 to 1:20) afforded the title compound as a yellow solid (144 mg, 47%). MS: m/z=492.4 [M+H]+.

391

Step 4: (1S,2R,6S)-2-fluoro-6-[[5-(1-methyl-1H-pyrazol-4-yl)-2-[3-(1-methyl-1H-pyrazol-4-yl)phenyl]pyrimidin-4-yl]amino]cyclohexan-1-ol (Racemic—Relative Stereochemistry)

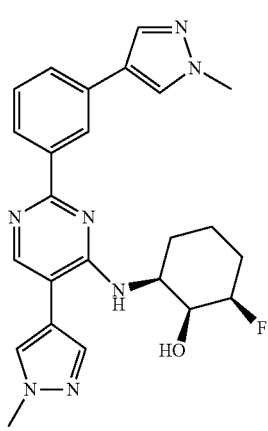 [SMILES: Cn1cc(-c2cccc(-c3ncc(-c4cnn(C)c4)c(N[C@H]4CCC[C@@H](F)[C@H]4O)n3)c2)cn1]

A saturated solution of HCl (g) in dioxane (2 mL) was added to a solution of N-[(1S,2S,3R)-3-fluoro-2-(methoxymethoxy)cyclohexyl]-5-(1-methyl-1H-pyrazol-4-yl)-2-[3-(1-methyl-1H-pyrazol-4-yl)phenyl]pyrimidin-4-amine (racemic, 139 mg, 0.28 mmol, 1.00 eq.) in dioxane (2 mL). The reaction mixture was stirred for 2 h at 25° C. The pH value of the solution was adjusted to 7 with saturated sodium bicarbonate (aq.) and the resulting mixture was concentrated under vacuum. The residue was diluted with 10 mL of DCM. The solids were filtered out. The filtrate was concentrated under vacuum and the crude product (100 mg) was purified by prep-HPLC [SHIMADZU: Column: XBridge BEH130 Prep C18 OBD Column, 19×150 mm, 5 µm, 13 nm; Mobile phase: waters (10 mmol/L $NH_4HCO_3$) and ACN (35% to 41% in 10 min); Detector: UV 254 nm] to afford the title compound as a white solid (73 mg, 56%). m.p.: 116-120° C. HPLC (UV 254 nm): 97.85% purity. MS: m/z=448.3 [M+H]+. 1H NMR (300 MHz, DMSO-d6, ppm): δ 8.51 (s, 1H), 8.26 (s, 1H), 8.17-8.14 (m, 2H), 8.07 (s, 1H), 7.86 (s, 1H), 7.77 (s, 1H), 7.69-7.63 (m, 1H), 7.50-7.43 (m, 1H), 5.90 (d, J=7.7 Hz, 1H), 5.54 (d, J=4.8 Hz, 1H), 4.87-4.67 (m, 1H), 4.52-4.42 (m, 1H), 4.06-4.02 (m, 1H), 3.93 (s, 3H), 3.88 (s, 3H), 1.82-1.56 (m, 6H).

392

Example 291: (1R,2S,7S)-2-Methylamino-7-{5-(1-pyrazol-4-yl)-2-[3-(1-methyl-1H-pyrazol-4-yl)-phenyl]-pyrimidin-4-ylamino}-cycloheptanol (Racemic—Relative Configuration)

Step 1: N-(cyclohept-2-en-1-yl)-5-(1-methyl-1H-pyrazol-4-yl)-2-[3-(1-methyl-1H-pyrazol-4-yl)phenyl]pyrimidin-4-amine

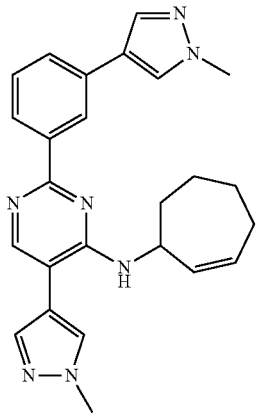 [SMILES: Cn1cc(-c2cccc(-c3ncc(-c4cnn(C)c4)c(NC4C=CCCCC4)n3)c2)cn1]

The title compound was obtained following the procedure described for example 287 from 2-chloro-N-(cyclohept-2-en-1-yl)-5-(1-methyl-1H-pyrazol-4-yl)pyrimidin-4-amine (Intermediate 56, 12 mg, 0.04 mmol, 1.00 eq.) as a yellow oil (10 mg, 59%). LC/MS: [M+H]+ Cac. 426.2; found 426.0.

Step 2: 5-(1-methyl-1H-pyrazol-4-yl)-2-[3-(1-methyl-1H-pyrazol-4-yl)phenyl]-N-[(1S,7R)-8-oxabicyclo[5.1.0]octan-2-yl]pyrimidin-4-amine (Racemic—Relative Stereochemistry)

mCPBA (156 mg, 0.86 mmol, 3.12 eq.) was added portion wise to a solution of N-(cyclohept-2-en-1-yl)-5-(1-methyl-1H-pyrazol-4-yl)-2-[3-(1-methyl-1H-pyrazol-4-yl)phenyl]pyrimidin-4-amine (130 mg, 0.27 mmol, 1.00 eq.) maintained at 0° C. and under nitrogen atmosphere in DCM (8 mL). Sodium bicarbonate (78 mg, 0.88 mmol, 3.21 eq.) was added and the resulting solution was stirred for 6 h at 20° C. After dilution with DCM, the mixture was then washed with sodium carbonate aq. and brine. Organic layer was dried over anhydrous sodium sulfate, filtrated and concentrated. Purification by flash chromatography on silica (DCM: MeOH, 20:1) afforded the title compound as an yellow oil (70 mg, 46%). LC/MS: [M+H]+ Cac. 442.2; found 442.0

Step 3: (1R,2S,7S)-2-[[5-(1-methyl-1H-pyrazol-4-yl)-2-[3-(1-methyl-1H-pyrazol-4-yl)phenyl]pyrimidin-4-yl]amino]-7-(methylamino)cycloheptan-1-ol (Racemic—Relative Stereochemistry)

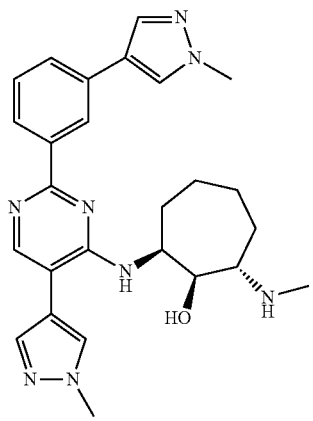 [SMILES: CN[C@H]1CCCC[C@H](Nc2nc(-c3cccc(-c4cnn(C)c4)c3)ncc2-c2cnn(C)c2)[C@@H]1O]

A solution of $CH_3NH_2$ (310 mg, 9.98 mmol) in MeOH (5 mL) was added over 5-(1-methyl-1H-pyrazol-4-yl)-2-[3-(1-methyl-1H-pyrazol-4-yl)phenyl]-N-[(1S,2S,7R)-8-oxabicyclo[5.1.0]octan-2-yl]pyrimidin-4-amine (racemic, 65 mg, 0.13 mmol, 1.00 equiv, 85% purity). The resulting reaction mixture was stirred for 36 h at 80° C. It was then concentrated under vacuum and the crude product (50 mg) was purified by prep-HPLC [SHIMADZU: Column: XBridge BEH130 Prep C18 OBD Column, 19×150 mm, 5 µm, 13 nm; Mobile phase: waters (10 mmol/L $NH_4HCO_3$) and ACN (27% to 34% in 8 min); Detector: UV 254 nm] to afford the title compound (10 mg, 16% yield) as an off-white solid. m.p. 120-122° C. HPLC (UV 254 nm): 96.53% purity. MS: m/z=473.2 [M+H]$^+$; 1H NMR (400 MHz, Chloroform-d, ppm): δ 8.46 (s, 1H), 8.21-8.17 (m, 2H), 7.85 (s, 1H), 7.73 (s, 1H), 7.66 (s, 1H), 7.61 (s, 1H), 7.58-7.53 (m, 1H), 7.48-7.42 (m, 1H), 5.93 (d, J=6.8 Hz, 1H), 4.53 (brs., 1H), 4.13-4.09 (m, 1H), 3.94 (s, 3H), 3.00-2.92 (m, 1H), 2.63 (s, 3H), 2.01-1.92 (m, 2H), 1.85-1.74 (m, 5H), 1.51-1.40 (m, 1H).

Example 292: Enzymatic Assays

IRAK1 Enzymatic Assay

IRAK1 is a human purified recombinant enzyme (His-TEV-IRAK1 (194-712)). In this assay, IRAK-1 hydrolyses ATP and autophosphorylates. Measurement of IRAK-1 inhibition was performed in streptavidin coated 384well FlashPlate (PerkinElmer #SMP410A).

His-TEV-IRAK-1 (15 ng/well), ATP (1 µM, [33P]ATP 0.25 µCi/well) and compounds in DMSO (range of concentrations from 20 M to 1 nM) or controls (2% DMSO) were incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Triton-X-100 0.01%. Kinase reaction was stopped by addition of EDTA. Supernatant was discarded, plates were washed three times with 150 mM NaCl and radioactivity was then measured in a Microbeta Trilux reader.

IRAK4 Enzymatic Assay

IRAK4 is a human purified recombinant enzyme (His-TEV-IRAK1 (194-712)). IRAK4 hydrolyses ATP, autophosphorylates and phosphorylates a Serine/Threonine generic peptidic substrate (STK: 61ST1BLC from CisBio International based in Bagnols/Cèze FR).

Measurement of IRAK-4 inhibition was performed in streptavidin coated 384well FlashPlate (PerkinElmer #SMP410A). His-TEV-IRAK4 (20 ng/well), ATP (2 µM, [$^{33}$P]ATP 0.25 Ci/well), STK1-biotin peptide (300 nM) and compounds in DMSO (range of concentrations from 20 M to 1 nM) or controls (2% DMSO) were incubated for 3 hours at 30° C. in assay buffer: Hepes pH7.0 50 mM, Fatty acid-free BSA 0.1%, Dithiothreitol DTT 2 mM, MgCl2 10 mM, EGTA 0.5 mM, Tween-20 0.01%, MnCl2 5 mM.

Kinase reaction was stopped by addition of EDTA. Supernatant was discarded, plates were washed three times with 150 mM NaCl and radioactivity was then measured in a Microbeta Trilux reader.

TLR7 Induced IL-6 in Human PBMC's

Human PBMC assay was used as one of the functional assay a to monitor the activity of of IRAK1 and IRAK4 small molecule inhibitors on TLR7 induced IL-6 secretion in human mononuclear cells (PBMC's). Human PBMCs were prepared from buffy coats (whole blood enriched with leukocytes and platelets) obtained from healthy volunteers used either fresh or frozen are plated in assay media (RPMI+ 2% P/S/L-glu+10% HI-FBS) and pre-treated with compounds in DMSO/media (range of concentrations from 25 uM to 0.4 nM) or controls (0.25% DMSO) for 30 minutes at 37° C. in assay media. Following pre-treatment with IRAK1 and IRAK4 inhibitors, PBMC's were stimulated with TLR7 specific ligand (2 uM) overnight (16-18 hrs) at 37° C. After incubation supernatant was transferred to 384 well PE AlphaPlate-384 (6005350) and IL-6 is quantified using Perkin Elmer IL-6 Alpha LISA kit (AL223C). Plates were read on an Envision® plate reader with Alpha Technology®.

Results are given in the following table.

| Compound | IRAK1 IC50 | IRAK4 IC50 | TLR7 induced IL-6 secretion in hPBMC's (IC50) |
| --- | --- | --- | --- |
| 1 | * | *** | ** |
| 2 | ** | *** | NT |
| 3 | ** | * | NT |
| 4 | ** | ** | NT |
| 5 | ** | * | NT |
| 6 | * | ** | NT |
| 7 | *** | *** | ** |
| 8 | * | ** | NT |
| 9 | ** | *** | ** |
| 10 | *** | *** | ** |
| 11 | * | *** | ** |
| 12 | * | * | NT |
| 13 | *** | *** | ** |
| 14 | **** | **** | NT |
| 15 | *** | **** | *** |
| 16 | *** | **** | *** |
| 17 | * | **** | *** |
| 18 | * | **** | *** |
| 19 | * | *** | ** |
| 20 | *** | ** | *** |
| 21 | ** | **** | ** |
| 22 | *** | **** | *** |
| 23 | * | ** | NT |
| 24 | * | ** | NT |
| 25 | * | ** | NT |
| 26 | * | * | NT |
| 27 | ** | *** | NT |
| 28 | **** | **** | *** |

| Compound | IRAK1 IC50 | IRAK4 IC50 | TLR7 induced IL-6 secretion in hPBMC's (IC50) |
|---|---|---|---|
| 29 | ** | *** | NT |
| 30 | *** | *** | NT |
| 31 | *** | *** | NT |
| 32 | *** | **** | ** |
| 33 | ** | ** | NT |
| 34 | * | ** | NT |
| 35 | *** | *** | ** |
| 36 | ** | *** | *** |
| 37 | ** | *** | ** |
| 38 | ** | *** | * |
| 39 | * | ** | NT |
| 40 | * | ** | NT |
| 41 | *** | *** | ** |
| 42 | *** | *** | *** |
| 43 | *** | *** | ** |
| 44 | *** | **** | *** |
| 45 | ** | *** | ** |
| 46 | *** | *** | * |
| 47 | ** | *** | * |
| 48 | *** | *** | * |
| 49 | *** | *** | * |
| 50 | *** | *** | ** |
| 51 | * | ** | NT |
| 52 | *** | **** | ** |
| 53 | *** | **** | ** |
| 54 | *** | *** | ** |
| 55 | *** | **** | ** |
| 56 | * | **** | ** |
| 57 | *** | *** | * |
| 58 | ** | ** | NT |
| 59 | * | *** | NT |
| 60 | ** | *** | ** |
| 61 | * | *** | NT |
| 62 | ** | *** | ** |
| 63 | *** | **** | ** |
| 64 | ** | *** | NT |
| 65 | *** | **** | *** |
| 66 | **** | **** | *** |
| 67 | * | *** | NT |
| 68 | ** | *** | NT |
| 69 | * | *** | NT |
| 70 | *** | ** | NT |
| 71 | * | * | NT |
| 72 | * | ** | NT |
| 73 | ** | ** | NT |
| 74 | ** | *** | NT |
| 75 | * | * | NT |
| 76 | ** | *** | * |
| 77 | * | *** | ** |
| 78 | ** | *** | NT |
| 79 | *** | *** | NT |
| 80 | * | *** | NT |
| 81 | ** | *** | * |
| 82 | ** | *** | NT |
| 83 | ** | *** | *** |
| 84 | ** | *** | * |
| 85 | * | *** | ** |
| 86 | ** | **** | * |
| 87 | ** | **** | ** |
| 88 | * | *** | NT |
| 89 | * | ** | NT |
| 90 | * | * | NT |
| 91 | * | * | NT |
| 92 | * | * | NT |
| 93 | *** | **** | *** |
| 94 | *** | **** | ** |
| 95 | * | **** | NT |
| 96 | ** | **** | NT |
| 97 | *** | **** | ** |
| 98 | ** | *** | NT |
| 99 | *** | **** | *** |
| 100 | ** | *** | NT |
| 101 | ** | **** | *** |
| 102 | ** | *** | NT |
| 103 | ** | **** | NT |
| 104 | ** | *** | NT |
| 105 | * | *** | NT |
| 106 | * | **** | NT |
| 107 | *** | *** | *** |
| 108 | *** | **** | *** |
| 109 | * | *** | NT |
| 110 | * | ** | NT |
| 111 | *** | **** | NT |
| 112 | ** | *** | ** |
| 113 | *** | **** | ** |
| 114 | ** | *** | NT |
| 115 | * | *** | *** |
| 116 | * | *** | NT |
| 117 | * | *** | NT |
| 118 | ** | **** | ** |
| 119 | ** | *** | * |
| 120 | *** | *** | NT |
| 121 | * | *** | NT |
| 122 | * | *** | NT |
| 123 | *** | **** | *** |
| 124 | * | *** | NT |
| 125 | * | *** | *** |
| 126 | * | *** | NT |
| 127 | * | **** | *** |
| 128 | *** | **** | *** |
| 129 | *** | **** | *** |
| 130 | ** | *** | NT |
| 131 | ** | **** | ** |
| 132 | *** | **** | *** |
| 133 | *** | **** | *** |
| 134 | **** | **** | **** |
| 135 | *** | **** | *** |
| 136 | *** | **** | ** |
| 137 | *** | **** | *** |
| 138 | ** | **** | ** |
| 139 | *** | *** | NT |
| 140 | ** | *** | NT |
| 141 | ** | *** | ** |
| 142 | * | ** | NT |
| 143 | *** | **** | *** |
| 144 | * | *** | NT |
| 145 | * | *** | NT |
| 146 | * | **** | ** |
| 147 | * | **** | NT |
| 148 | * | *** | NT |
| 149 | *** | **** | *** |
| 150 | * | *** | NT |
| 151 | *** | **** | *** |
| 152 | *** | **** | *** |
| 153 | *** | **** | NT |
| 154 | * | *** | NT |
| 155 | * | **** | NT |
| 156 | *** | **** | *** |
| 157 | *** | **** | NT |
| 158 | *** | **** | NT |
| 159 | * | **** | NT |
| 160 | *** | **** | NT |
| 161 | **** | **** | *** |
| 162 | *** | **** | *** |
| 163 | *** | **** | NT |
| 164 | ** | **** | NT |
| 165 | *** | **** | NT |
| 166 | *** | **** | NT |
| 167 | ** | **** | ** |
| 168 | * | **** | NT |
| 169 | *** | **** | * |
| 170 | *** | **** | ** |
| 171 | **** | **** | ** |
| 172 | *** | **** | NT |
| 173 | * | *** | NT |
| 174 | *** | **** | NT |
| 175 | *** | *** | NT |
| 176 | ** | **** | NT |
| 177 | *** | **** | NT |
| 178 | *** | *** | NT |

| Compound | IRAK1 IC50 | IRAK4 IC50 | TLR7 induced IL-6 secretion in hPBMC's (IC50) |
|---|---|---|---|
| 179 | *** | **** | ** |
| 180 | *** | **** | NT |
| 181 | *** | **** | ** |
| 182 | **** | **** | *** |
| 183 | *** | **** | ** |
| 184 | *** | **** | *** |
| 185 | ** | **** | ** |
| 186 | **** | **** | *** |
| 187 | **** | **** | *** |
| 188 | **** | **** | ** |
| 189 | * | * | NT |
| 190 | **** | **** | ** |
| 191 | * | *** | NT |
| 192 | ** | **** | NT |
| 193 | * | *** | NT |
| 194 | *** | **** | *** |
| 195 | **** | **** | ** |
| 196 | *** | *** | ** |
| 197 | * | *** | NT |
| 198 | ** | **** | NT |
| 199 | *** | **** | *** |
| 200 | ** | *** | NT |
| 201 | ** | **** | NT |
| 202 | ** | *** | NT |
| 203 | ** | *** | NT |
| 204 | *** | **** | *** |
| 205 | *** | **** | NT |
| 206 | * | *** | NT |
| 207 | | | NT |
| 208 | *** | **** | *** |
| 209 | **** | **** | *** |
| 210 | *** | **** | *** |
| 211 | *** | *** | ** |
| 212 | * | *** | NT |
| 213 | **** | **** | *** |
| 214 | * | **** | ** |
| 215 | *** | **** | *** |
| 216 | *** | **** | *** |
| 217 | *** | **** | ** |
| 218 | ** | *** | NT |
| 219 | *** | **** | ** |
| 220 | *** | **** | NT |
| 221 | *** | **** | *** |
| 222 | *** | *** | NT |
| 223 | *** | **** | NT |
| 224 | ** | **** | NT |
| 225 | *** | **** | *** |
| 226 | * | *** | NT |
| 227 | *** | **** | NT |
| 228 | * | ** | NT |
| 229 | * | *** | NT |
| 230 | * | ** | NT |
| 231 | * | ** | NT |
| 232 | *** | **** | NT |
| 233 | *** | **** | *** |
| 234 | ** | **** | NT |
| 235 | ** | *** | NT |
| 236 | ** | *** | NT |
| 237 | ** | *** | NT |
| 238 | *** | **** | *** |
| 239 | *** | *** | *** |
| 240 | * | *** | NT |
| 241 | ** | *** | NT |
| 242 | *** | **** | *** |
| 243 | ** | **** | *** |
| 244 | *** | **** | *** |
| 245 | **** | **** | *** |
| 246 | * | ** | NT |
| 247 | ** | *** | NT |
| 248 | *** | **** | *** |
| 249 | ** | *** | NT |
| 250 | ** | *** | NT |
| 251 | * | ** | NT |
| 252 | *** | **** | NT |
| 253 | **** | **** | *** |
| 254 | **** | **** | **** |
| 255 | *** | *** | NT |
| 256 | ** | **** | ** |
| 257 | *** | **** | ** |
| 258 | * | *** | NT |
| 259 | * | *** | NT |
| 260 | *** | *** | ** |
| 261 | ** | *** | NT |
| 262 | *** | **** | ** |
| 263 | * | ** | NT |
| 264 | * | ** | NT |
| 265 | *** | **** | * |
| 266 | **** | **** | *** |
| 267 | *** | **** | *** |
| 268 | **** | **** | **** |
| 269 | *** | **** | *** |
| 270 | **** | **** | **** |
| 271 | *** | **** | ** |
| 272 | *** | **** | ** |
| 273 | *** | **** | *** |
| 274 | * | *** | NT |
| 275 | *** | **** | *** |
| 276 | **** | **** | *** |
| 277 | * | *** | NT |
| 278 | **** | **** | *** |
| 279 | * | *** | * |
| 280 | *** | **** | ** |
| 281 | * | **** | ** |
| 282 | ** | *** | * |
| 283 | ** | ** | ** |
| 284 | ** | **** | *** |
| 285 | *** | **** | *** |
| 286 | *** | **** | *** |
| 287 | *** | **** | ** |
| 288 | **** | **** | **** |
| 289 | * | **** | *** |
| 290 | | | NT |
| 291 | | | NT |

\* $IC_{50} > 5$ μM
\*\* $IC_{50}$ ranges from 1 μM-5 μM
\*\*\* $IC_{50}$ ranges from 0.1 μM-1.0 μM
\*\*\*\* $IC_{50} < 0.1$ μM
NT Not Tested Example 293: Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4 \cdot 2H_2O$, 28.48 g of $Na_2HPO_4 \cdot 12 H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I,

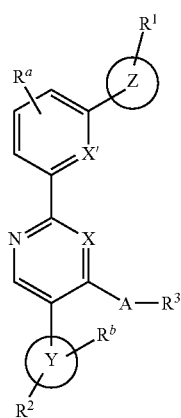

I or a pharmaceutically acceptable salt thereof, wherein:
X is CR or N;
A is O, S, SO$_2$, SO, —NRC(O), —NRSO$_2$, or N(R); or A is absent;
R$^3$ is H, C$_{1-6}$ aliphatic, C$_{3-10}$ aryl, a 3-8 membered saturated or partially unsaturated carbocyclic ring, or a 3-7 membered heterocylic ring having 1-4 heteroatoms independently selected from nitrogen, oxygen, or sulfur; each of which is optionally substituted; or R$^3$ is halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$; or when A is —NRC(O), —NRSO$_2$, or N(R); then R and R$^3$, together with the atoms to which each is attached, may form a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
X' is CR or N;
Ring Z is a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
R$^1$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
R$^a$ is absent, —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
Ring Y is an optionally substituted pyridyl, pyrazole or thiadiazole;
R$^2$ is —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
R$^b$ is absent, —R, halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$;
each R is independently hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
wherein when X is N and A is absent, then R$^3$ is not H.
2. The compound of claim 1, wherein X is CH.
3. The compound of claim 1, wherein X is N.
4. The compound of claim 1, wherein A is O or N(R), or A is absent.
5. The compound of claim 1, wherein R$^3$ is H, C$_{1-6}$ aliphatic, C$_{3-10}$ aryl, a 3-8 membered saturated or partially unsaturated carbocyclic ring, or a 3-7 membered heterocylic ring having 1-4 heteroatoms independently selected from nitrogen, oxygen, or sulfur; each of which is optionally substituted; or R$^3$ is -haloalkyl, —C(O)R, —CO$_2$R, or —C(O)N(R)$_2$.
6. The compound of claim 5, wherein R$^3$ is C$_{1-6}$ aliphatic, C$_{3-10}$ aryl, a 3-8 membered saturated or partially unsaturated carbocyclic ring, or a 3-7 membered heterocylic ring having 1-4 heteroatoms independently selected from nitrogen, oxygen, or sulfur; each of which is optionally substituted.

7. The compound of claim 1, wherein A-R³ is —H, —CH₃, —CF₃,
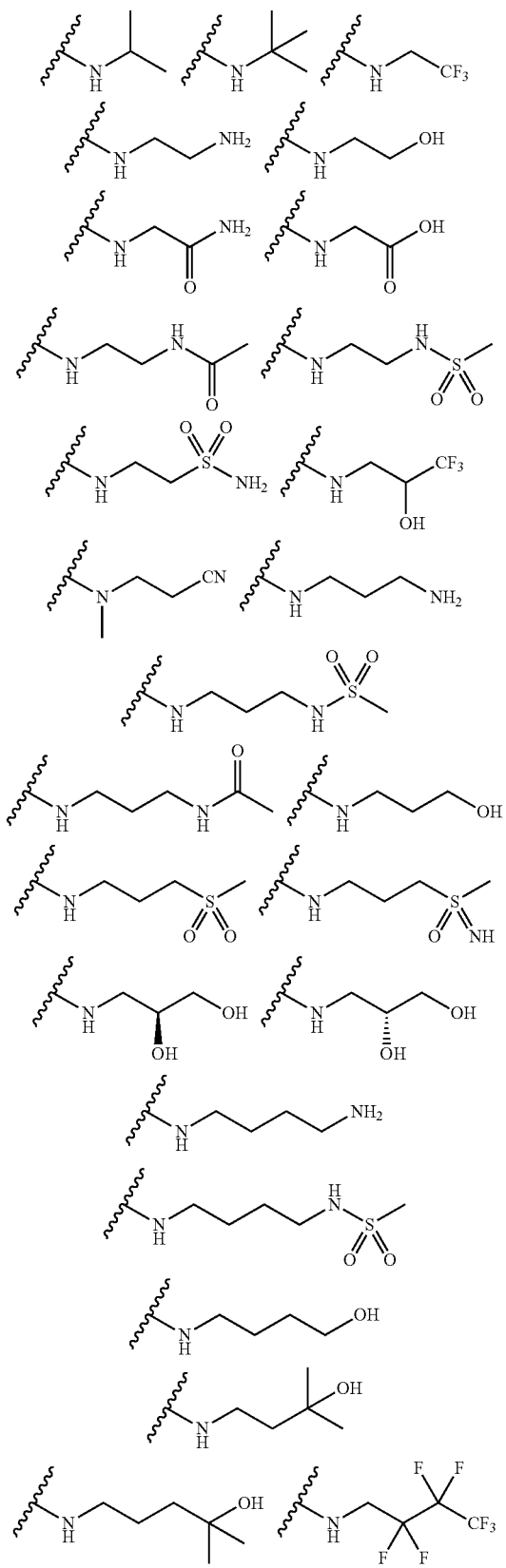

403
-continued
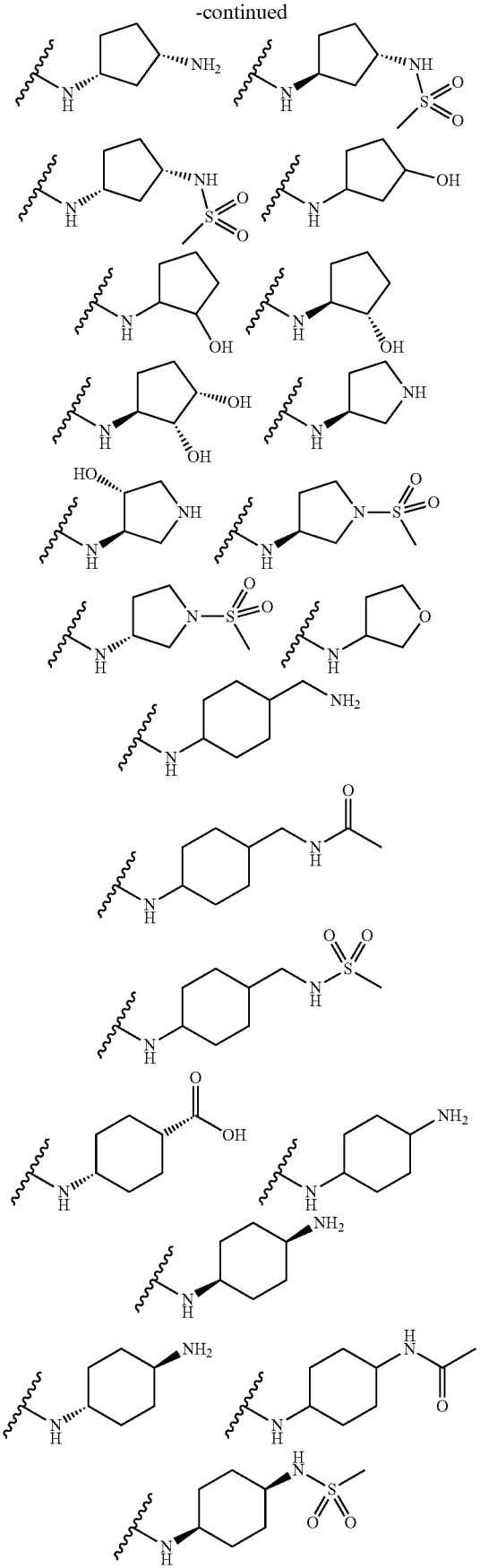
404
-continued
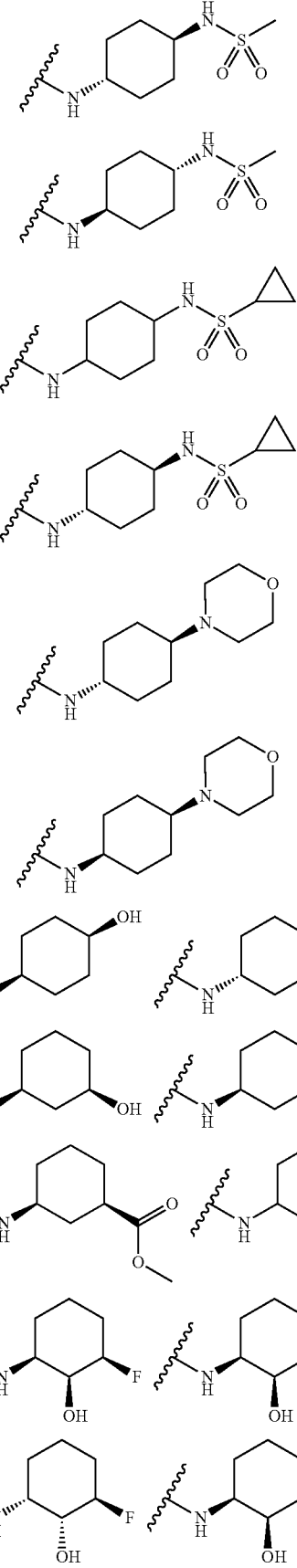

405
-continued
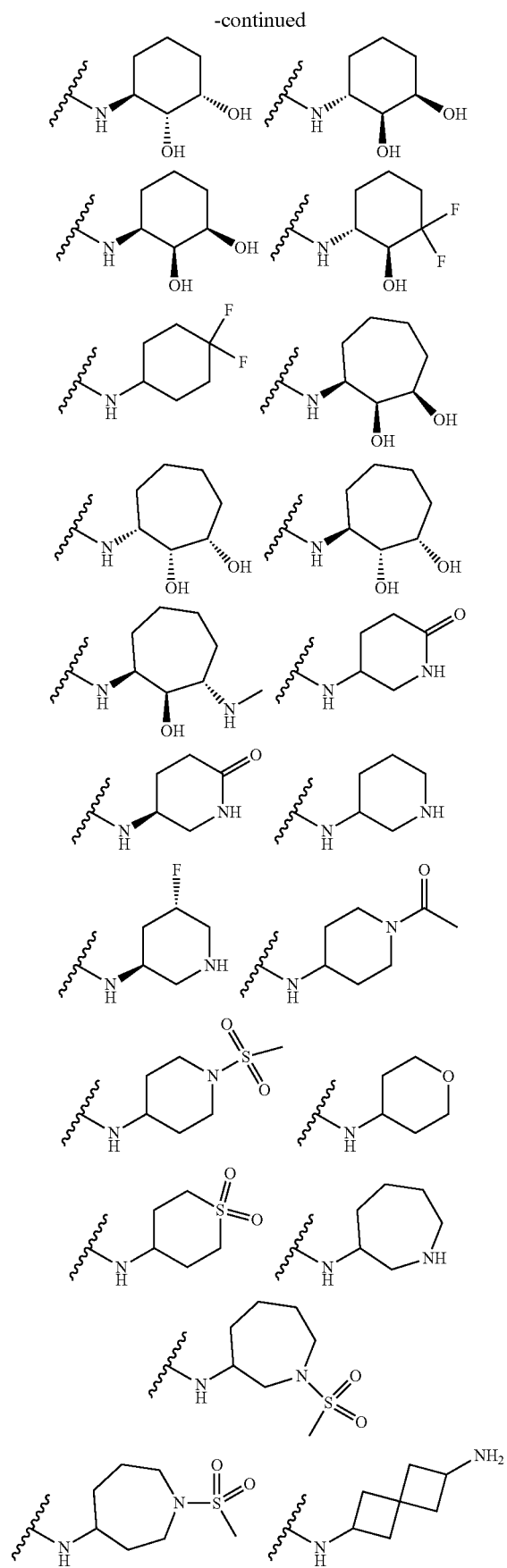
406
-continued
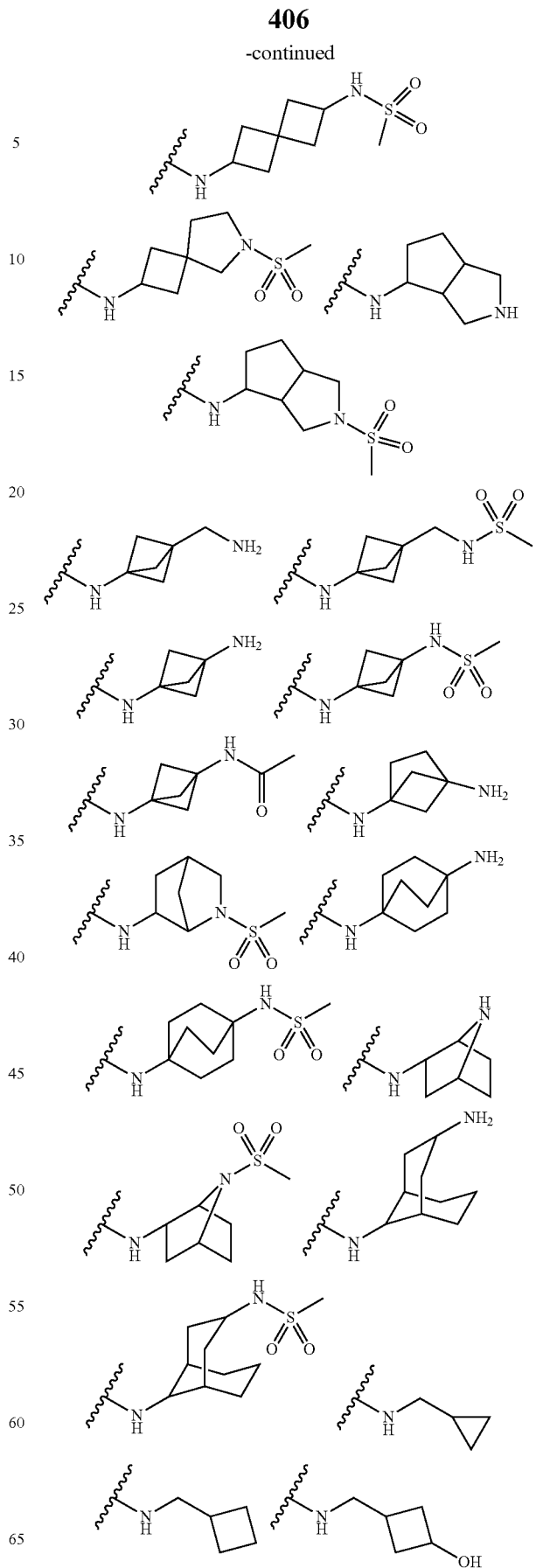

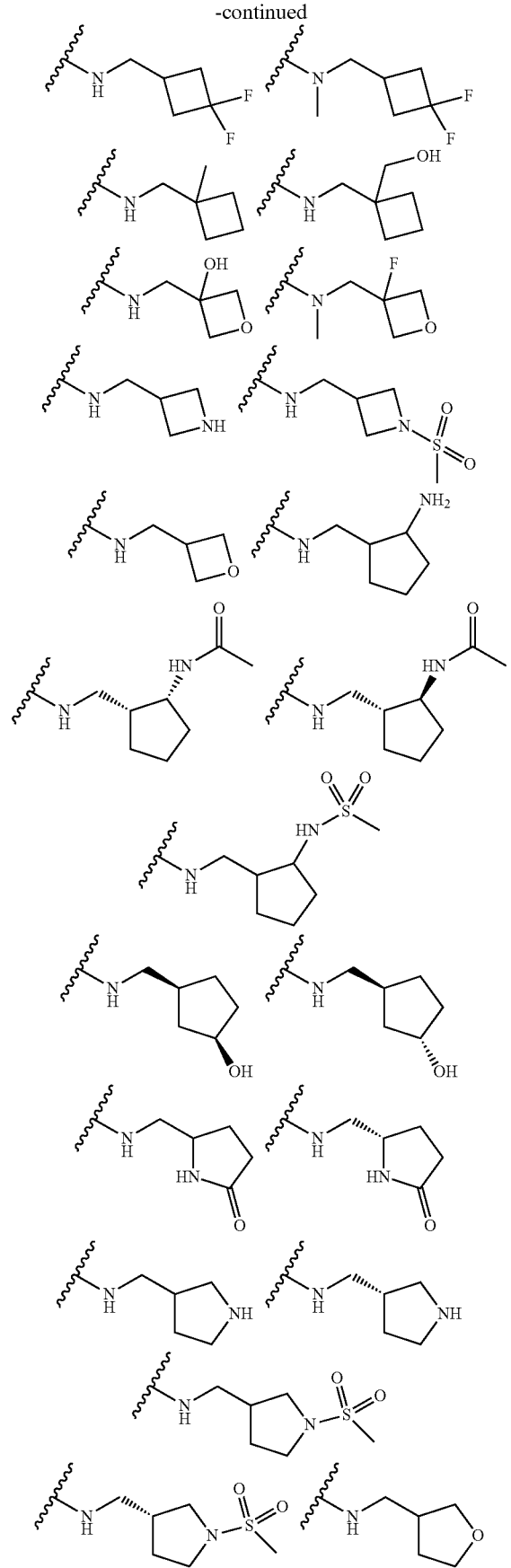
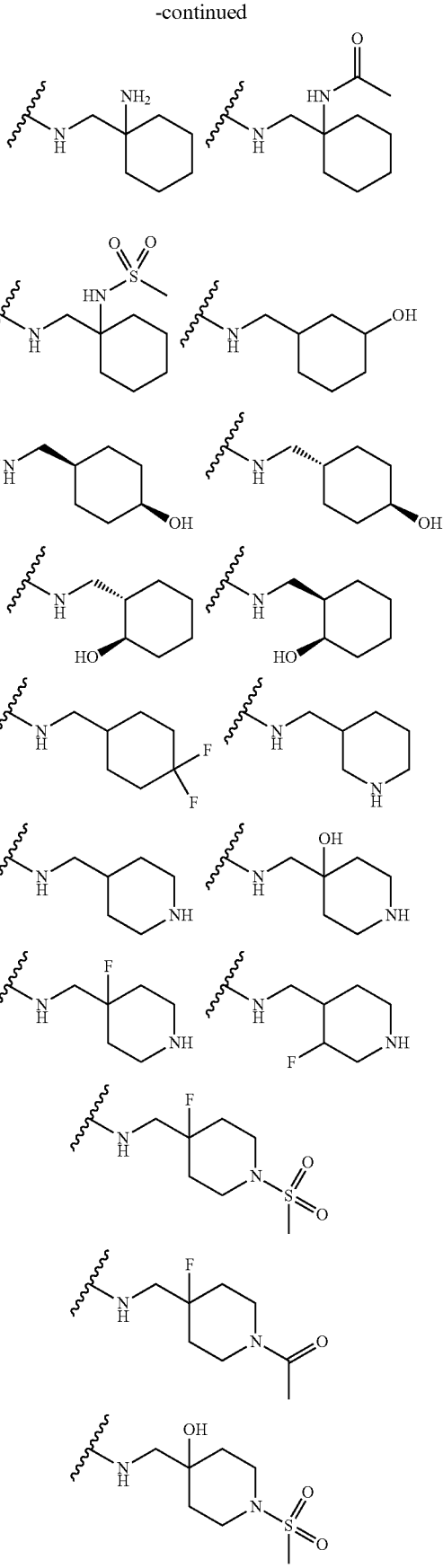

409
-continued
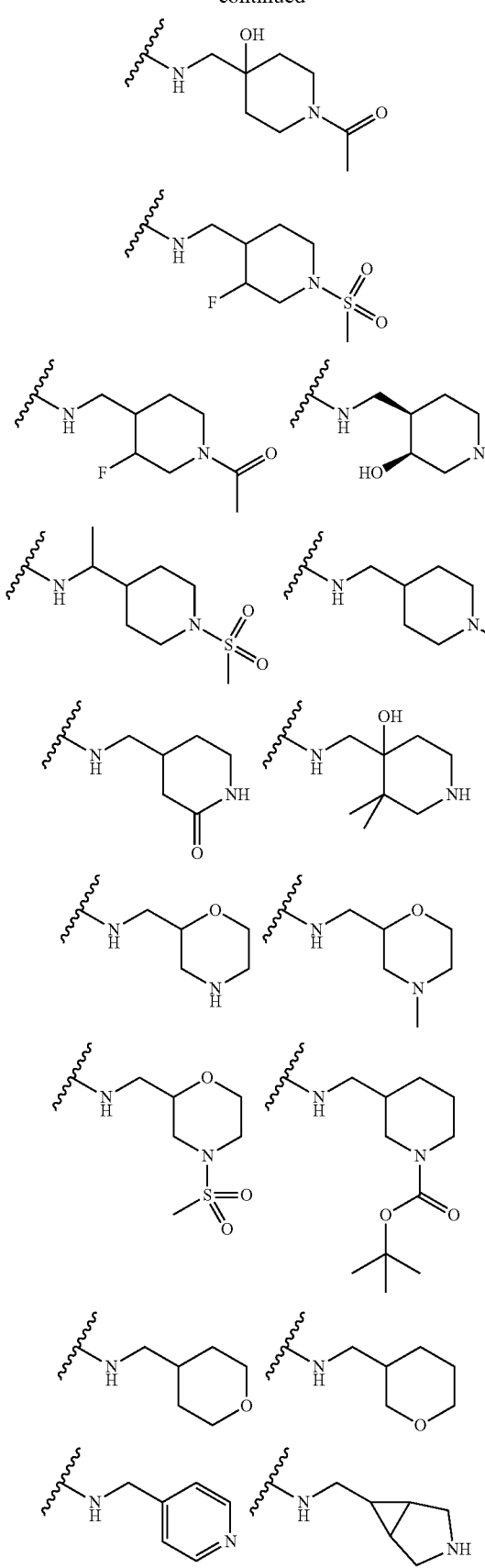
410
-continued
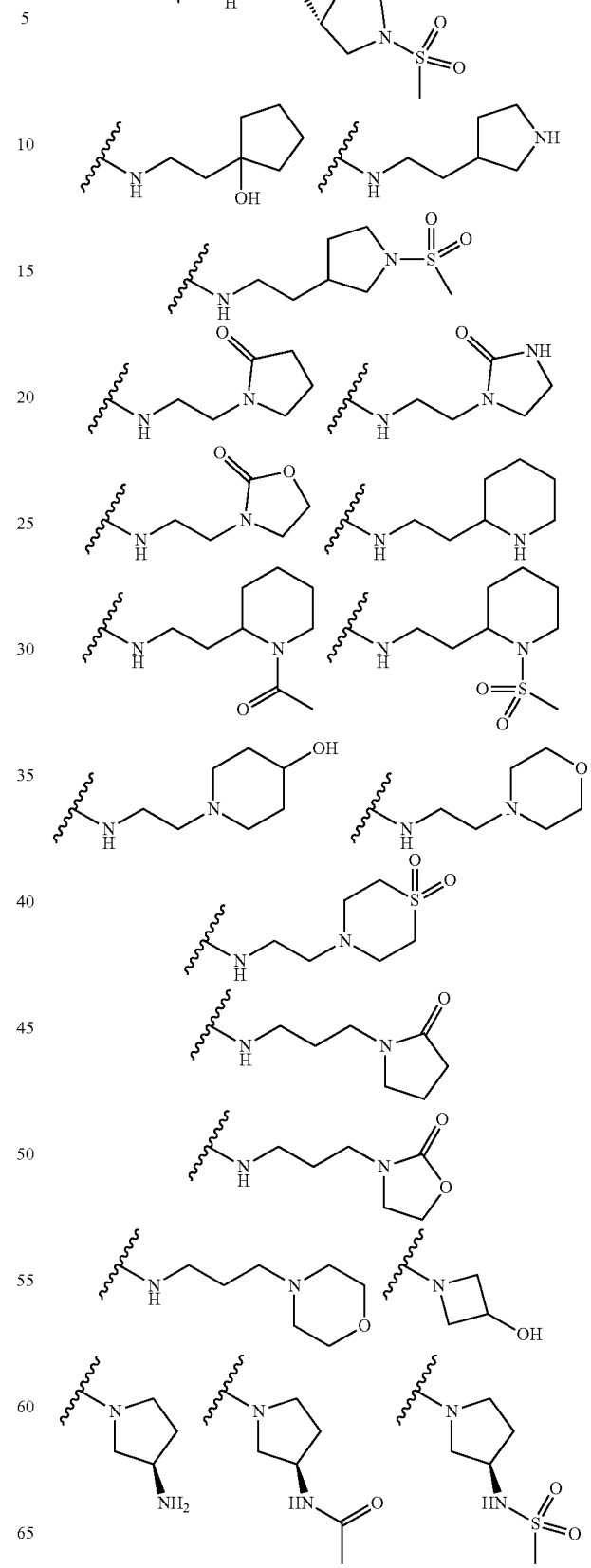

411
-continued
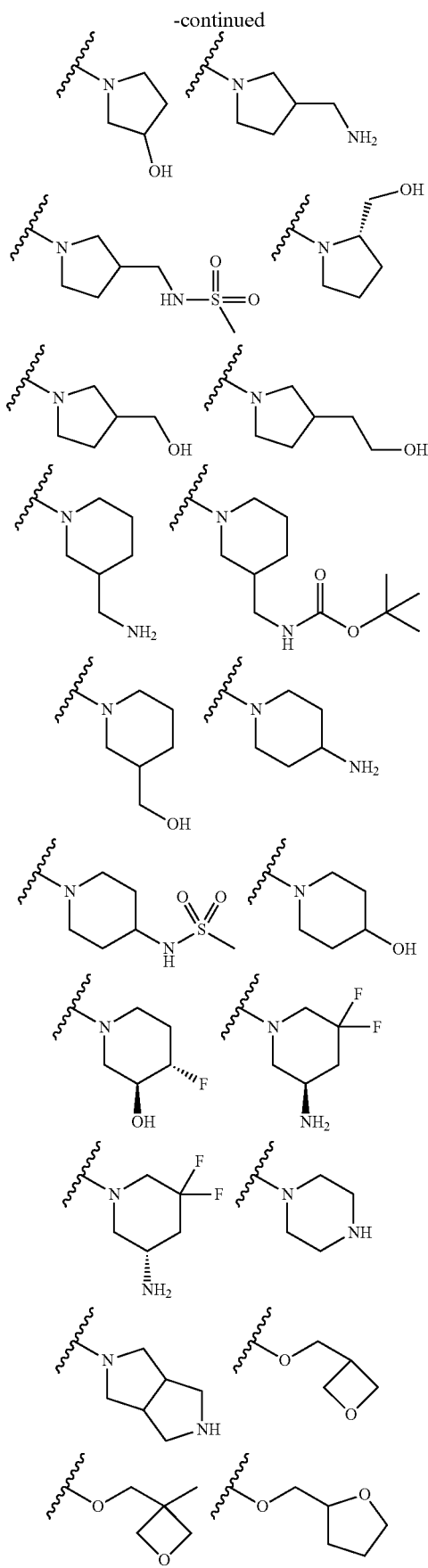
412
-continued
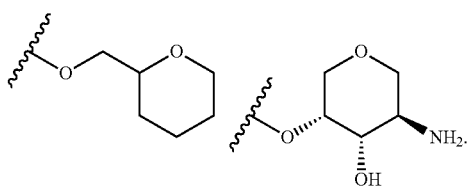
8. The compound of claim 1, wherein Ring Z is:
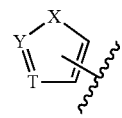
wherein X is O, S or $NR^1$; Y is C or N; and T is C or N.
9. The compound of claim 8, wherein Ring Z is
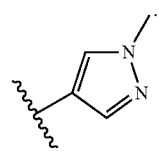 [SMILES: *c1cnn(C)c1]
10. The compound of claim 1, wherein Ring Y is
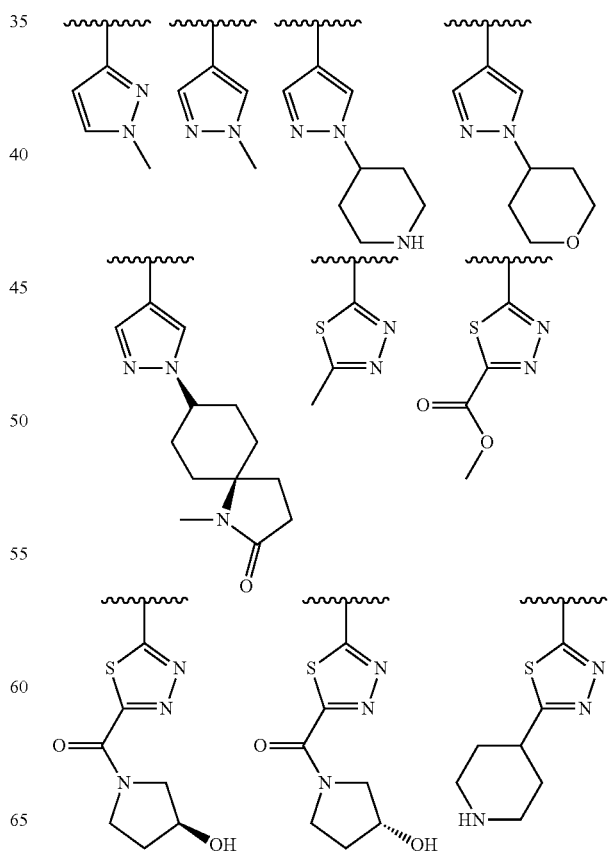

-continued
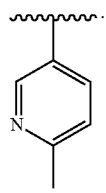
11. The compound of claim 1, of formula I-b,
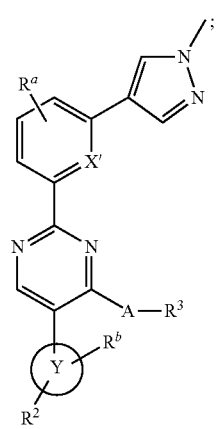
or a pharmaceutically acceptable salt thereof.
12. The compound of claim 1, of formula I-c,
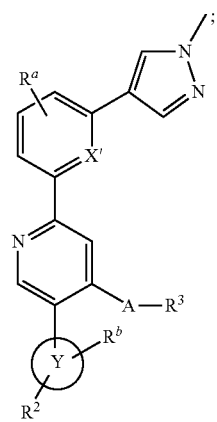
or a pharmaceutically acceptable salt thereof.
13. The compound of claim 1, selected from:
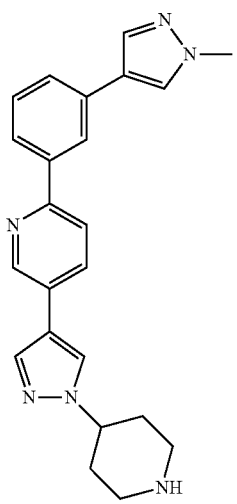
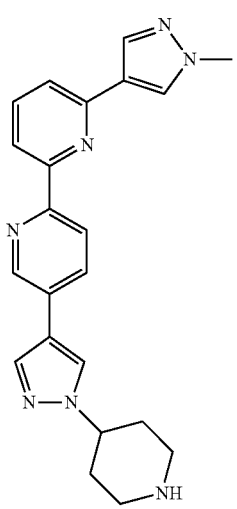
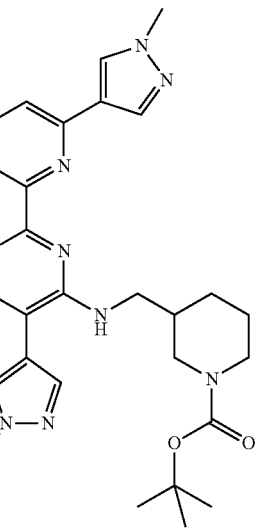

4
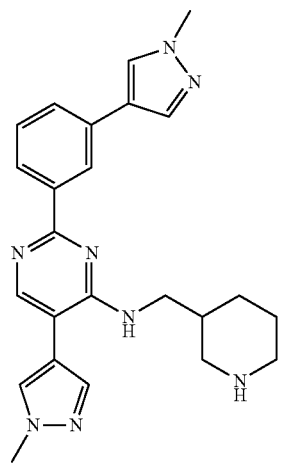
5
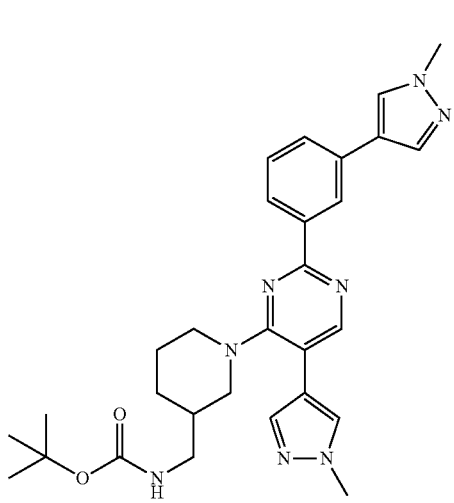
6
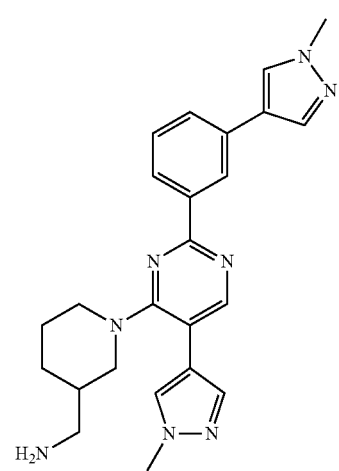
7
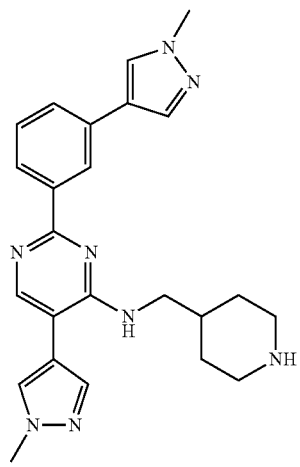
8
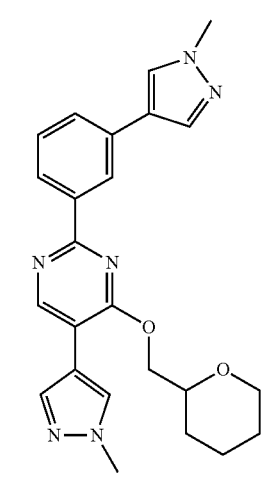
9
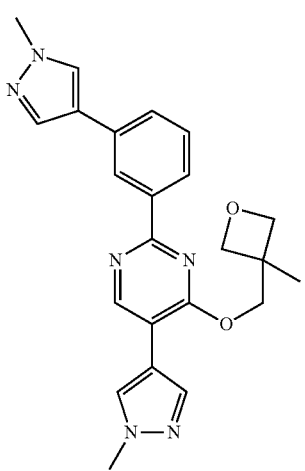

| 10 | 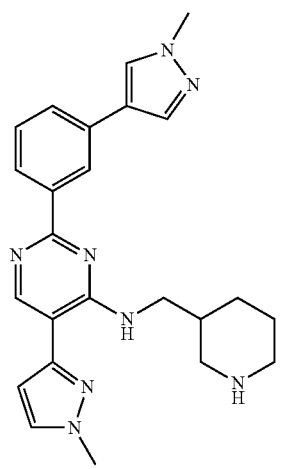 | 13 | 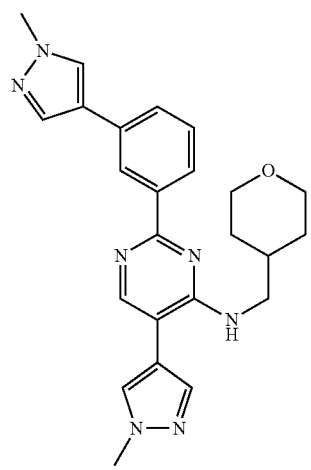 |
| 11 | 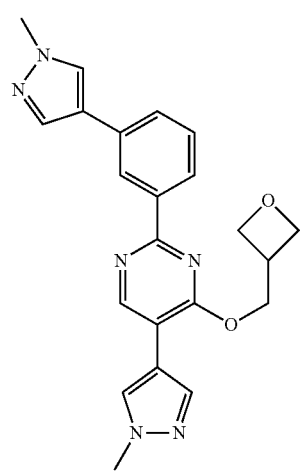 | 14 | 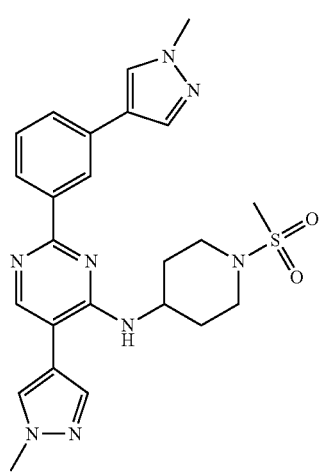 |
| 12 | 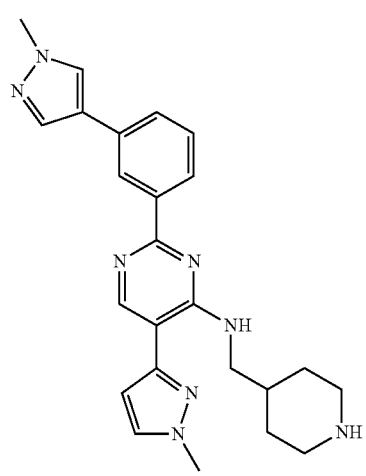 | 15 | 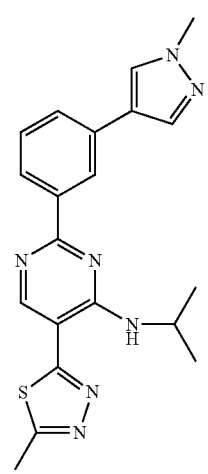 |

419
-continued
16
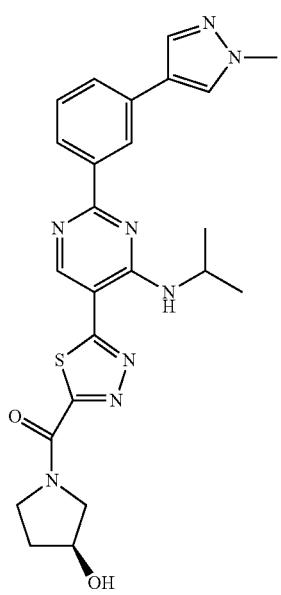
17
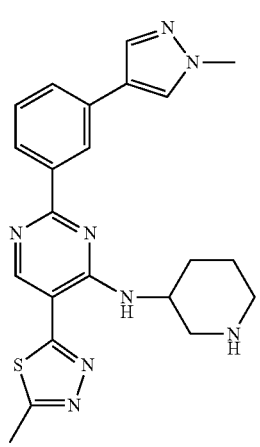
18
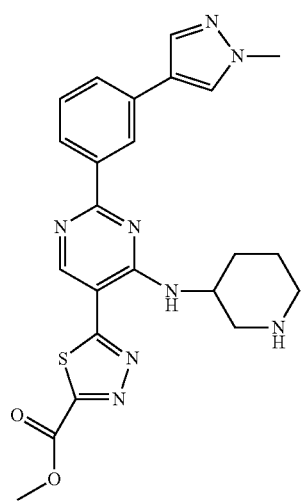
420
-continued
5
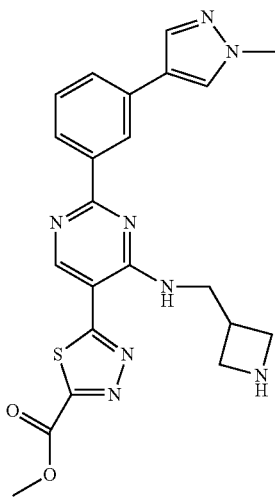
19
20
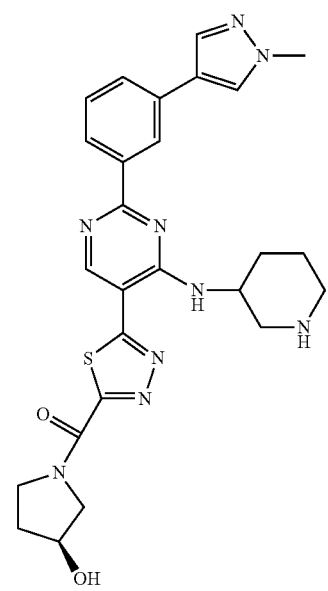

421
-continued
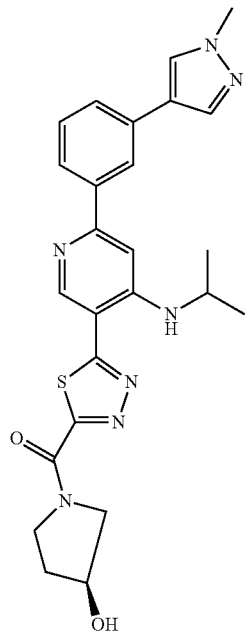
21
422
-continued
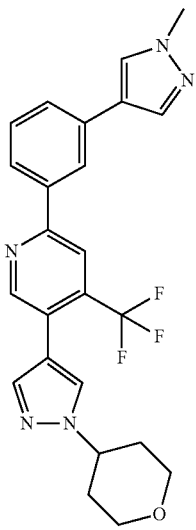
23
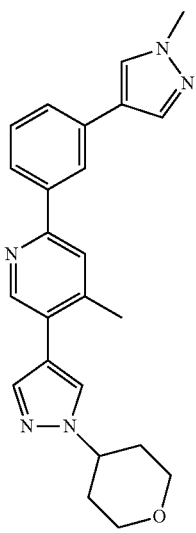
24
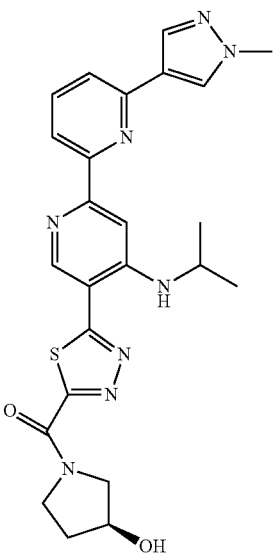
22
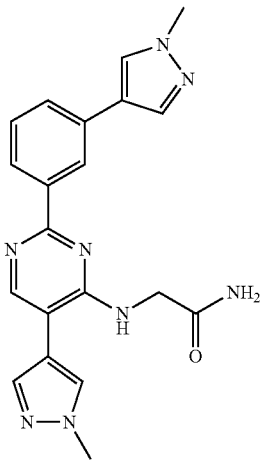
25

| 26 | 29 |
|---|---|
| 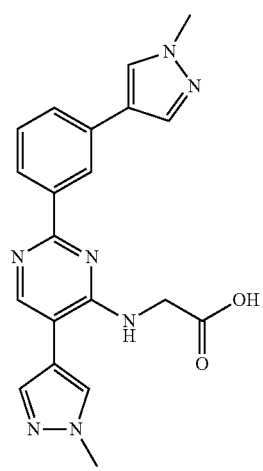 | 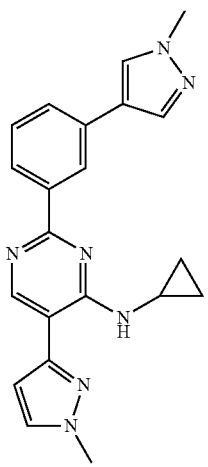 |
| 27 | 30 |
|---|---|
| 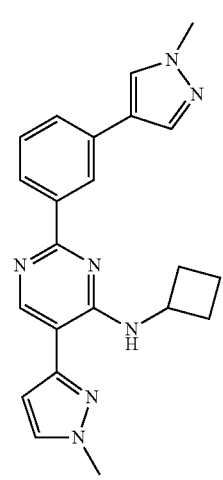 | 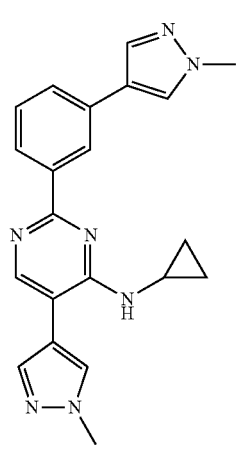 |
| 28 | 31 |
|---|---|
| 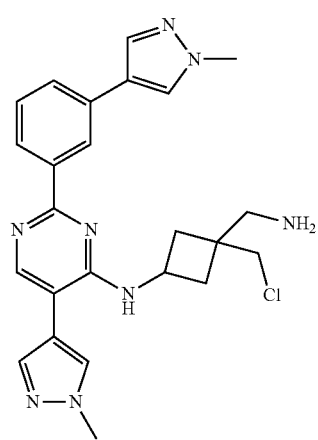 | 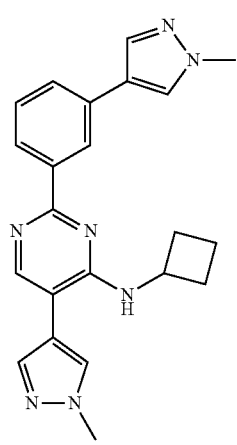 |

-continued
32
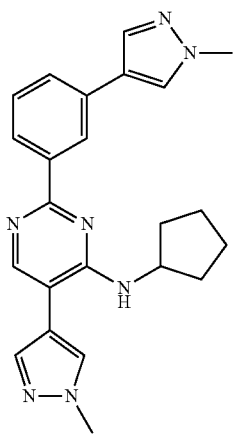
33
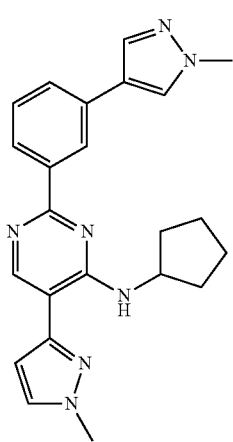
34
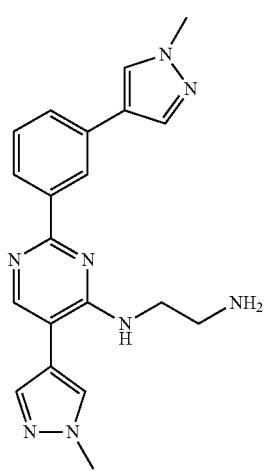
-continued
35
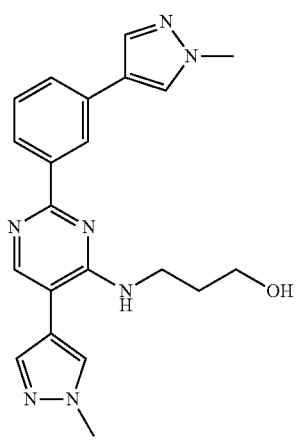
36
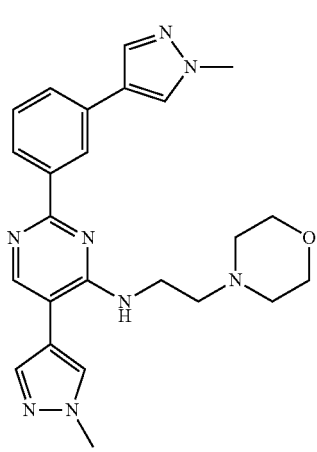
37
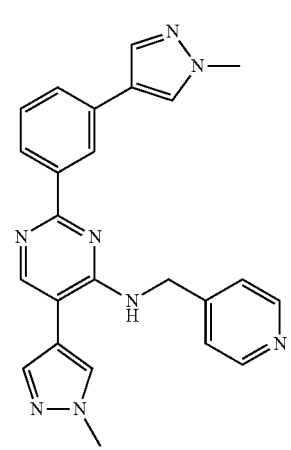

| 38 | 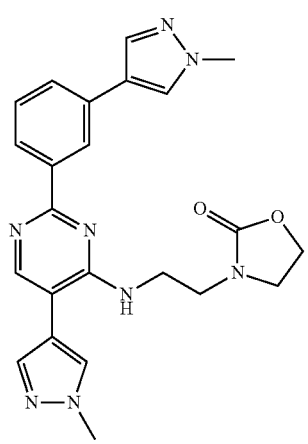 |
|---|---|
| 39 | 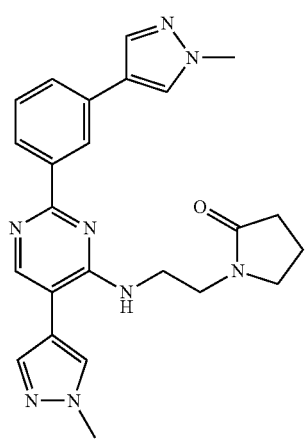 |
| 40 | 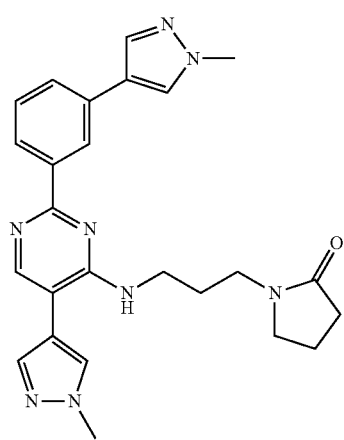 |
| 41 | 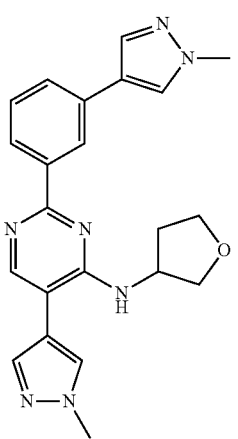 |
|---|---|
| 42 | 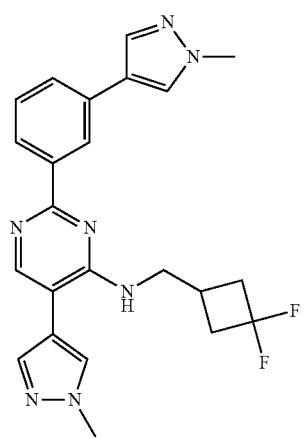 |
| 43 | 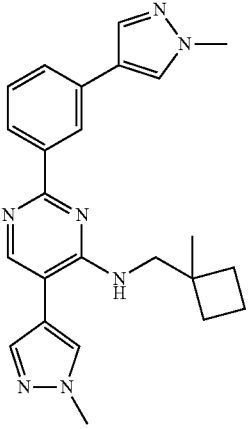 |

-continued
44
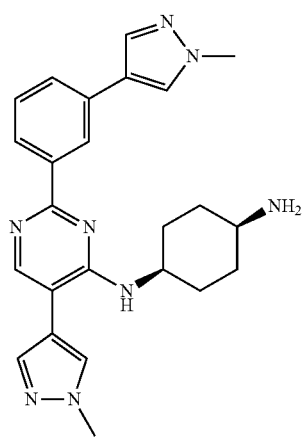
45
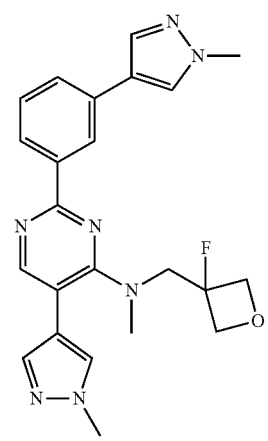
46
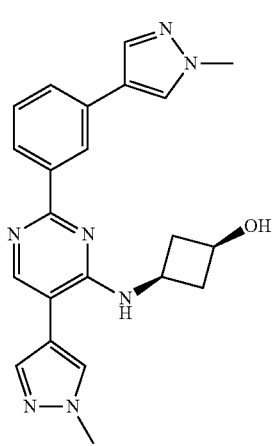
-continued
47
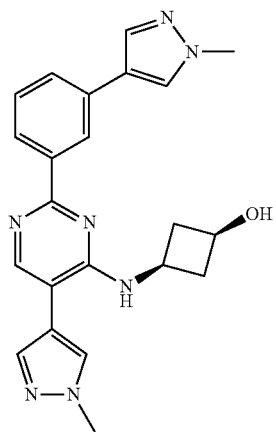
48
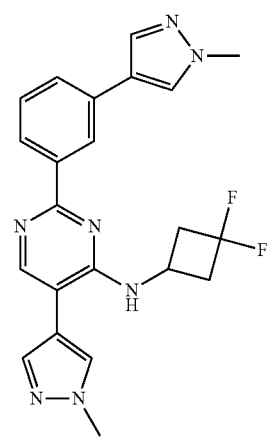
49
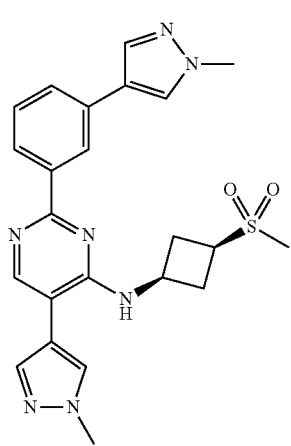

431
-continued
| | |
|---|---|
| 50 | 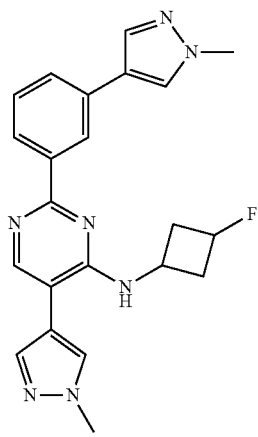 |
| | 53 |
432
-continued
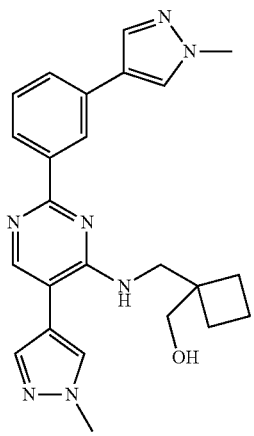
51
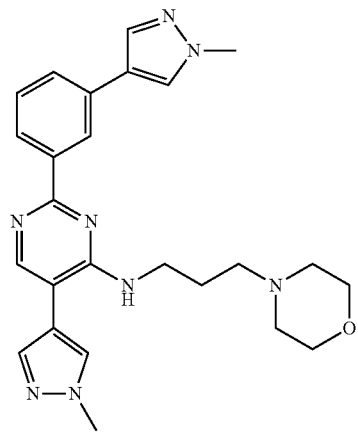
54
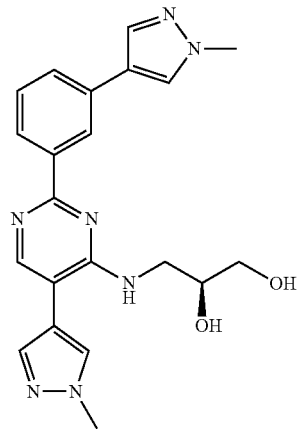
52
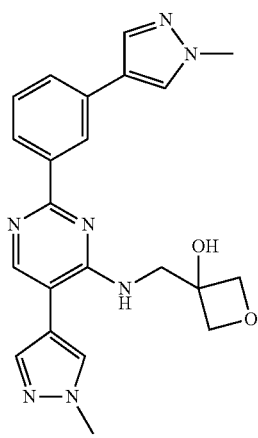
55
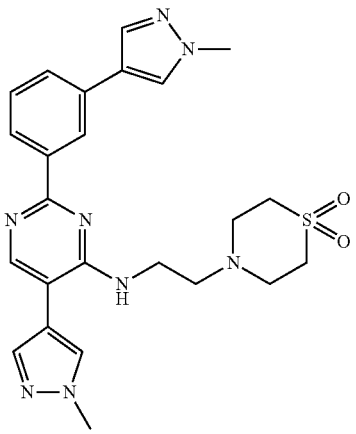

-continued
56
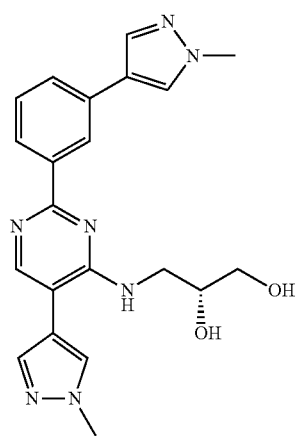
57
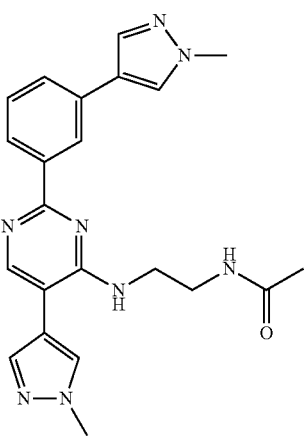
58
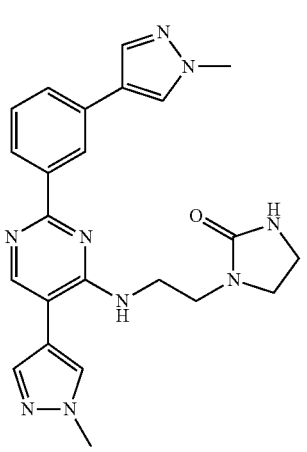
-continued
59
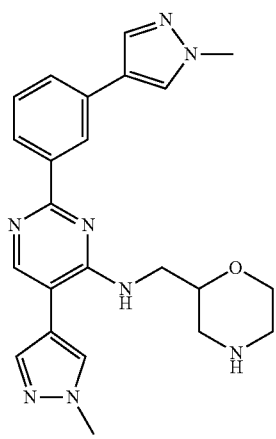
60
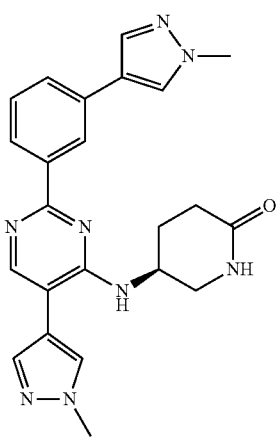
61
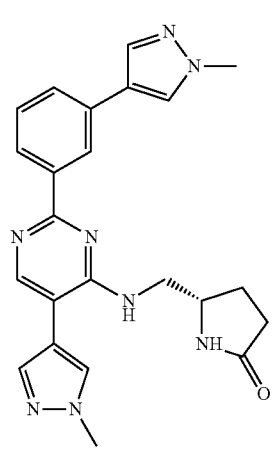

435
-continued
62
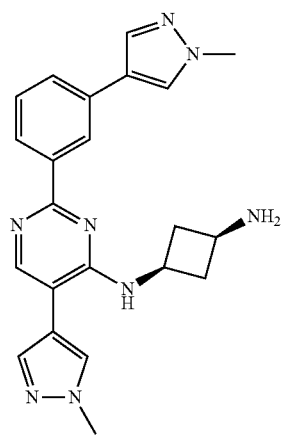
63
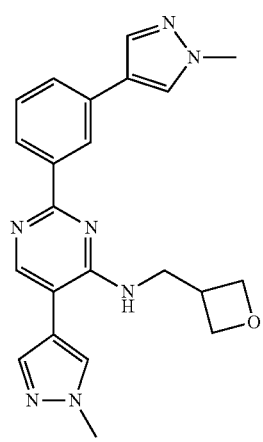
64
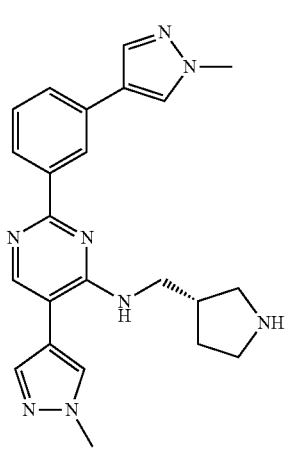
436
-continued
65
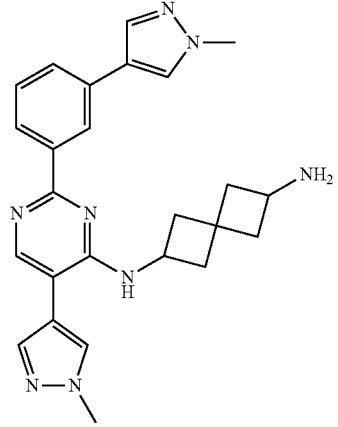
66
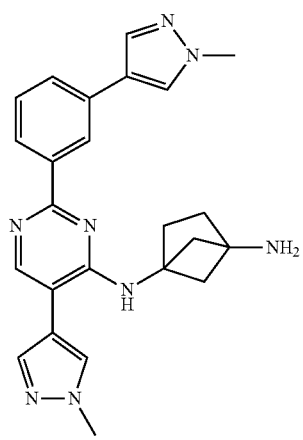
67
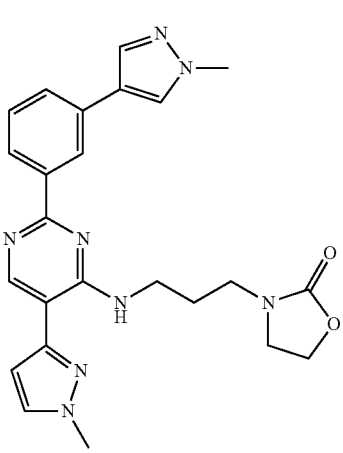

| 437 -continued | 438 -continued |
|---|---|
| 68 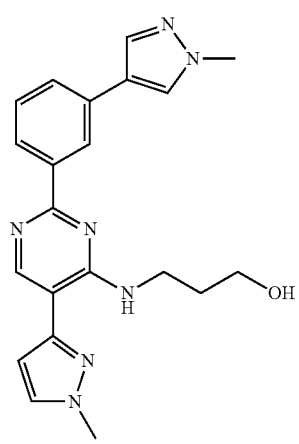 | 71 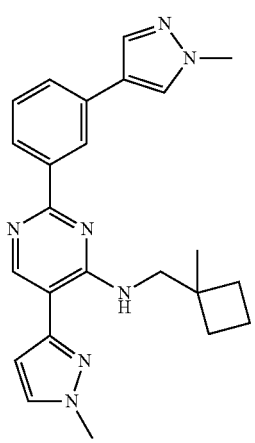 |
| 69 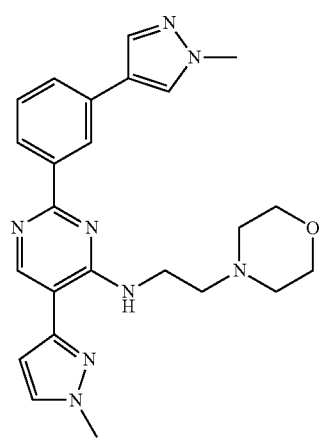 | 72 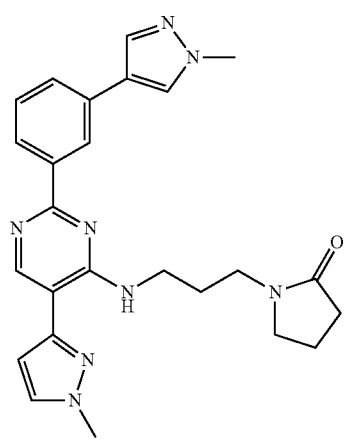 |
| 70 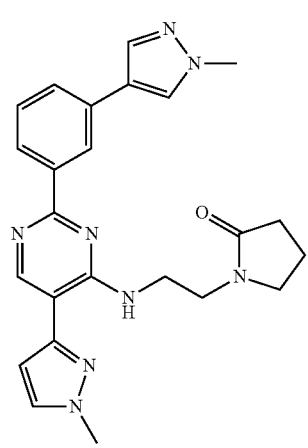 | 73 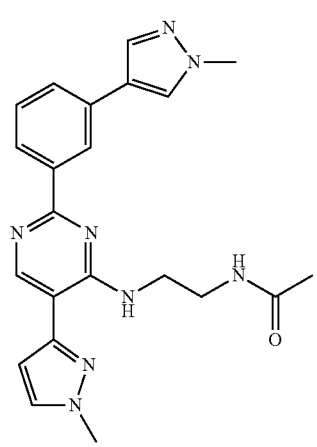 |

439 -continued
74
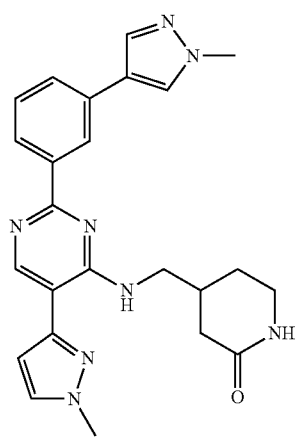
75
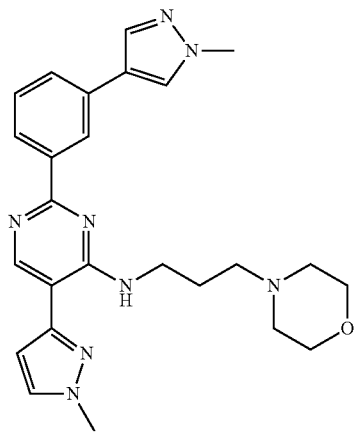
76
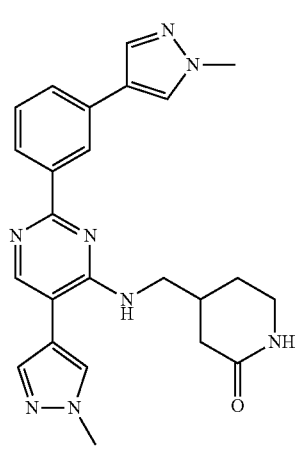
440 -continued
77
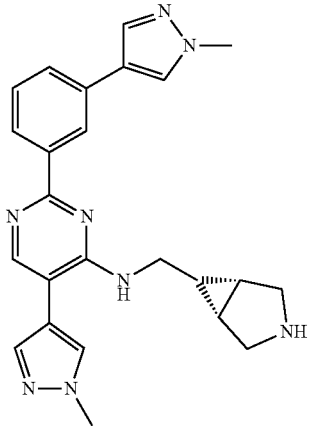
78
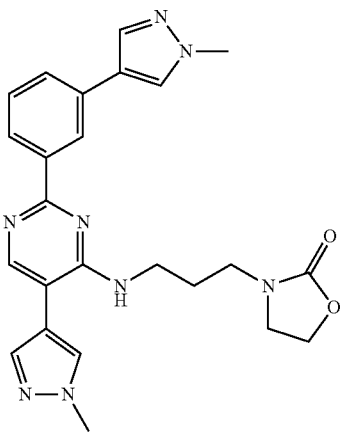
79
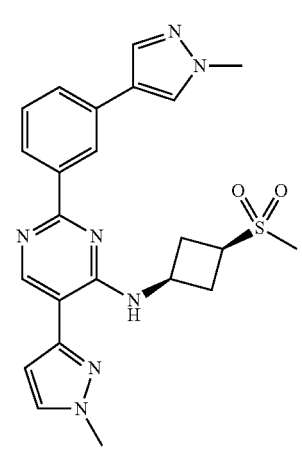

-continued
80
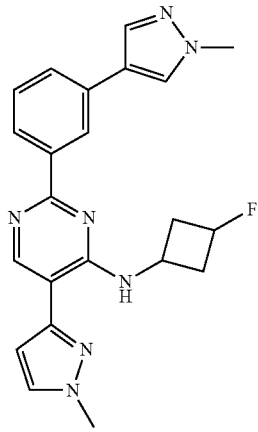
81
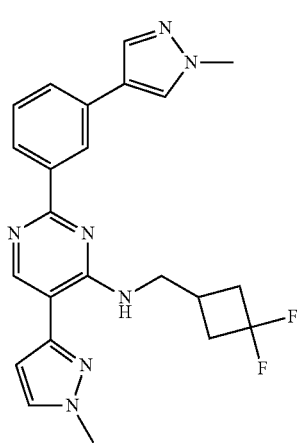
82
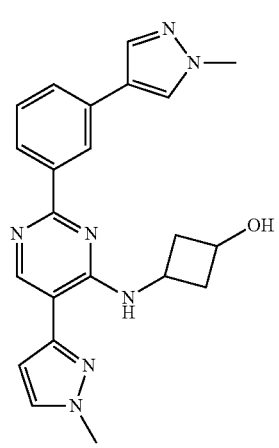
-continued
83
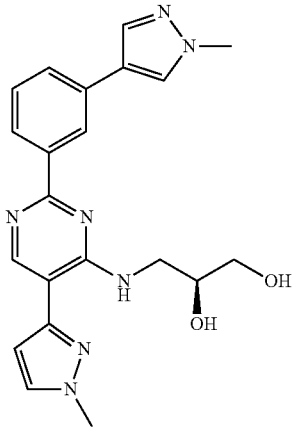
84
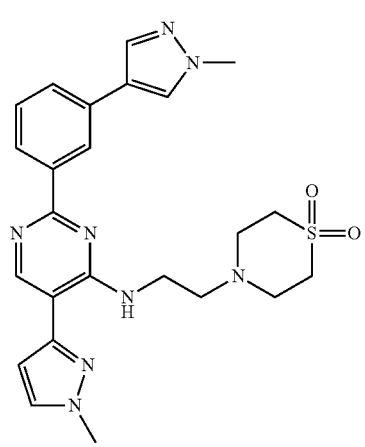
85
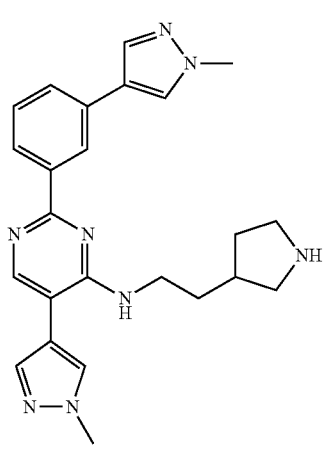

86
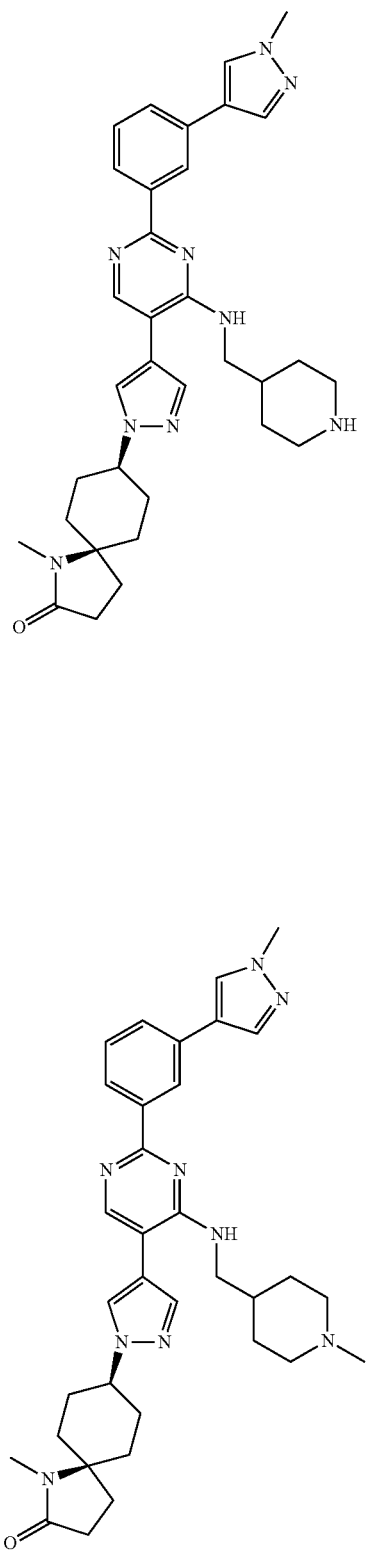
87
88
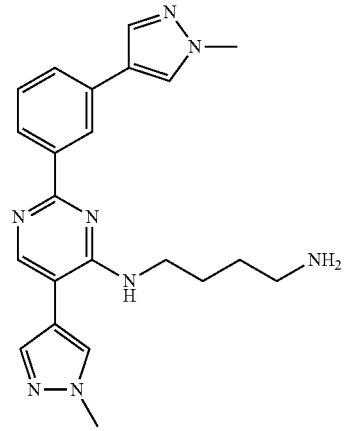
89
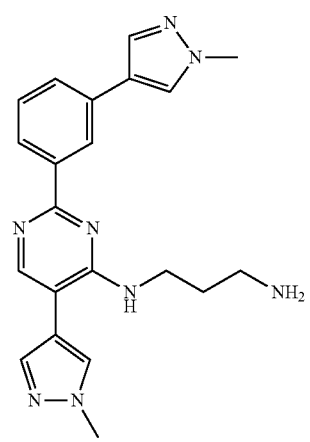
90
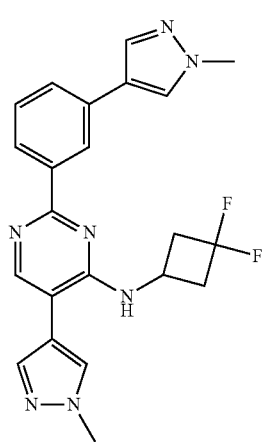

445
-continued
91
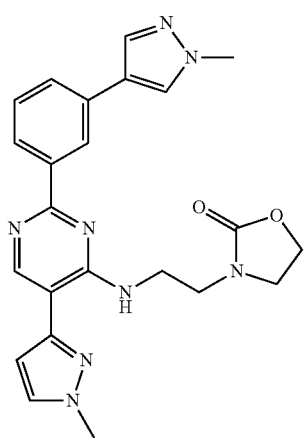
92
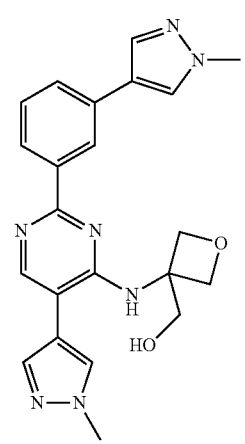
93
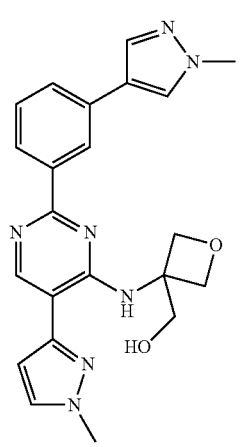
446
-continued
94
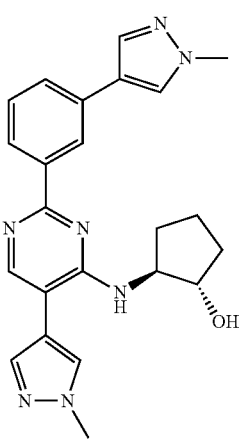
95
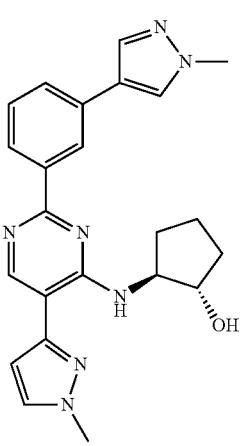
96
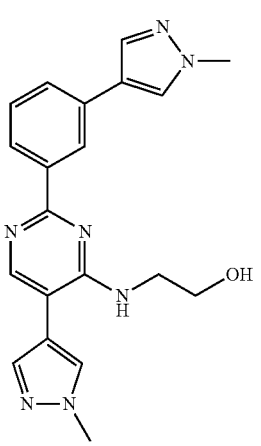

-continued
| | |
|---|---|
| 97 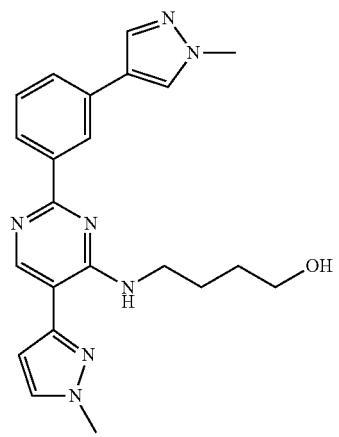 | 100 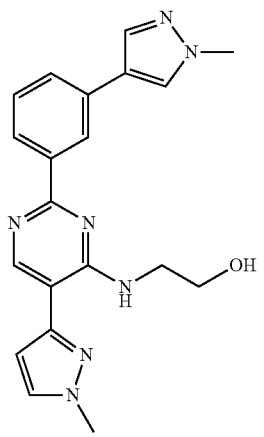 |
| 98 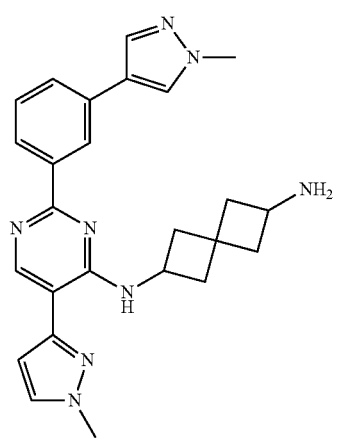 | 101 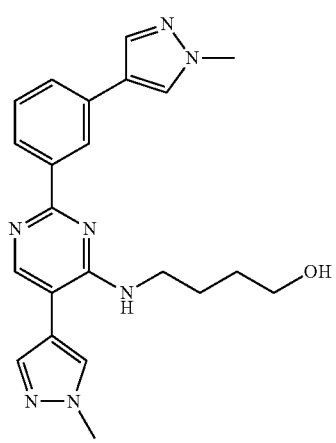 |
| 99 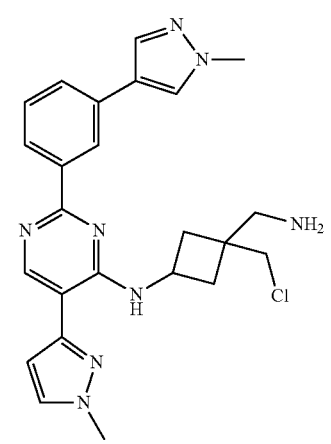 | 102 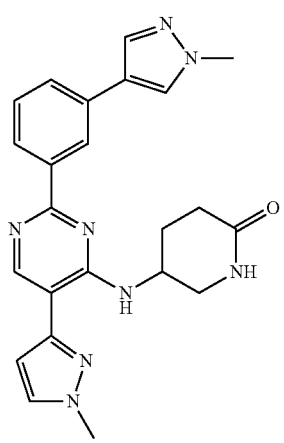 |

103 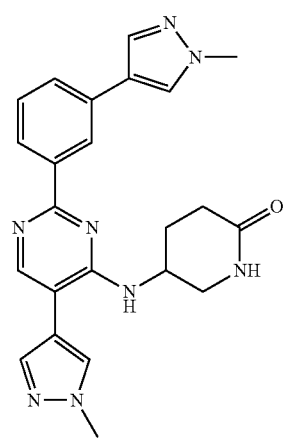
104 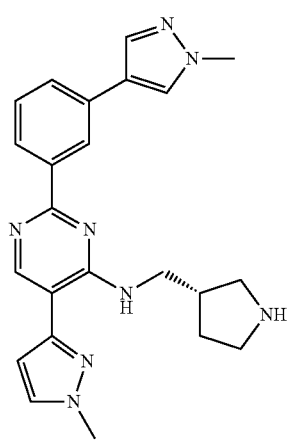
105 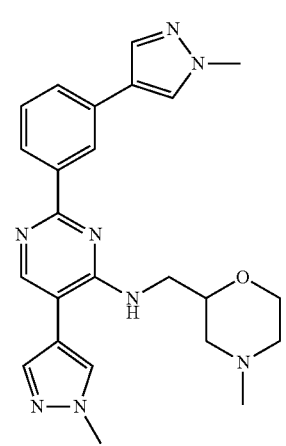
106 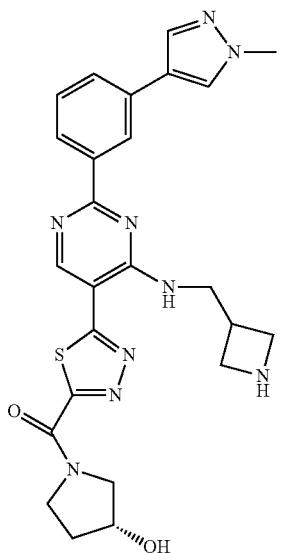
107 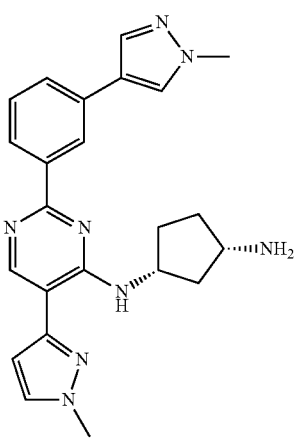
108 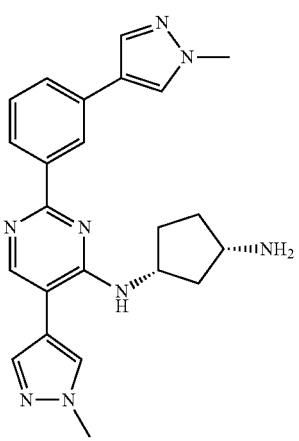

451
-continued
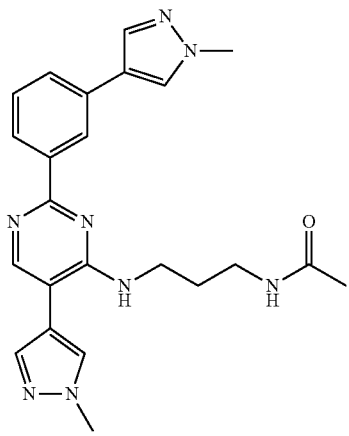
109
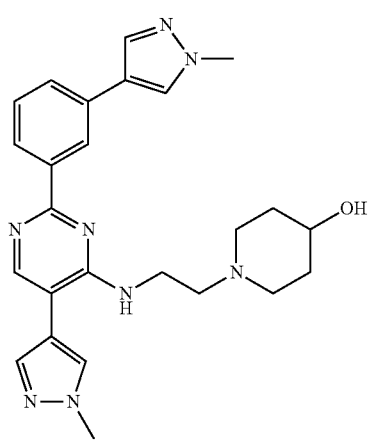
110
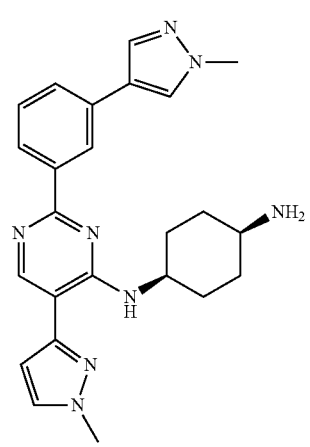
111
452
-continued
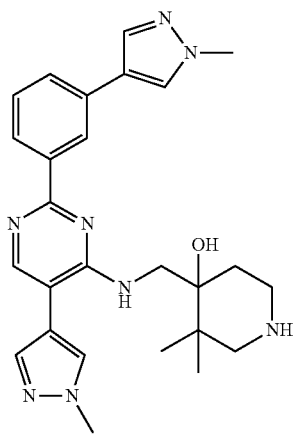
112
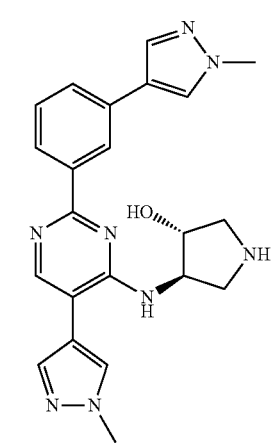
113
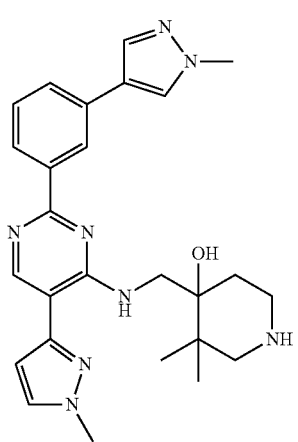
114

| 453 -continued | | 454 -continued | |
|---|---|---|---|
| 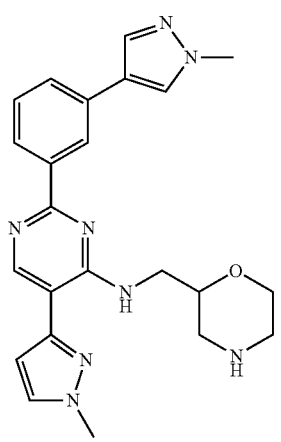 | 115 | 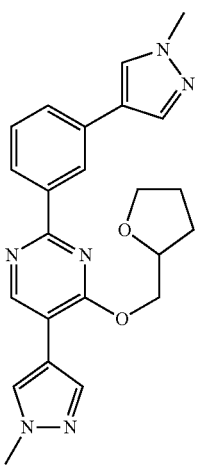 | 118 |
| 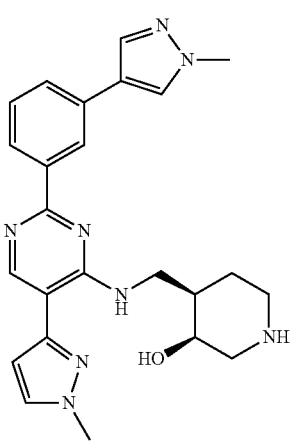 | 116 | 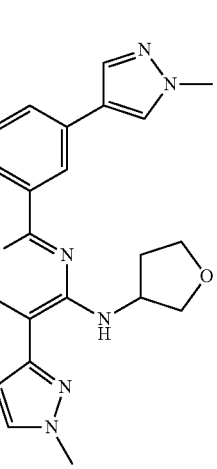 | 119 |
| 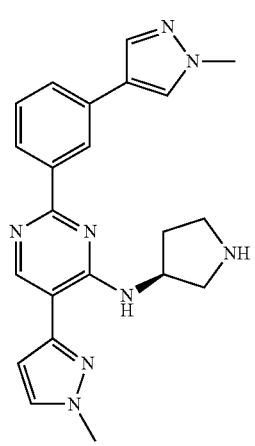 | 117 | 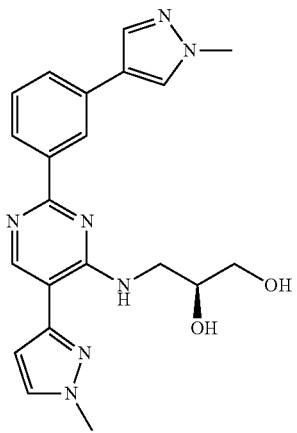 | 120 |

| 121 | 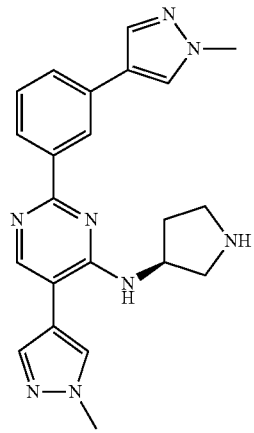 | 124 | 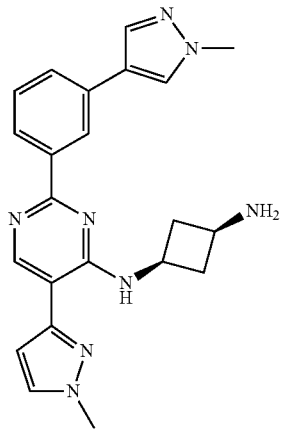 |
| 122 | 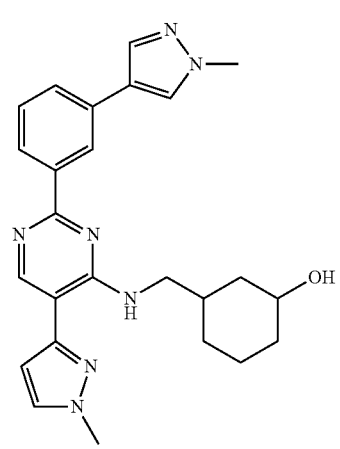 | 125 | 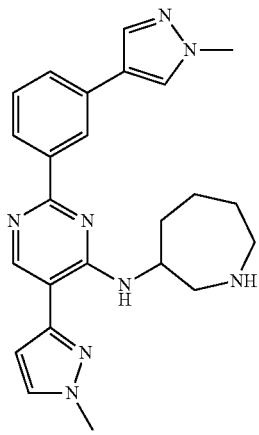 |
| 123 | 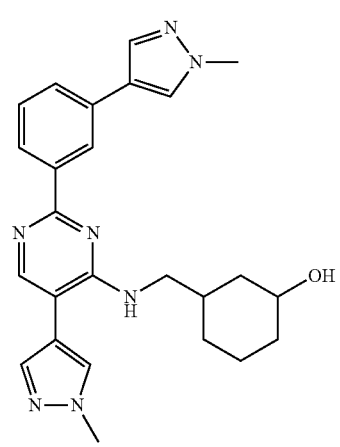 | 126 | 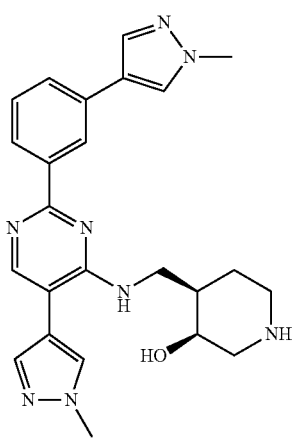 |

127
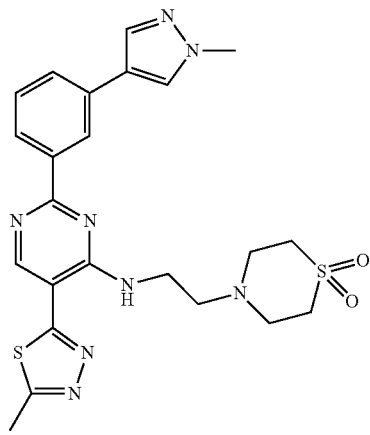
128
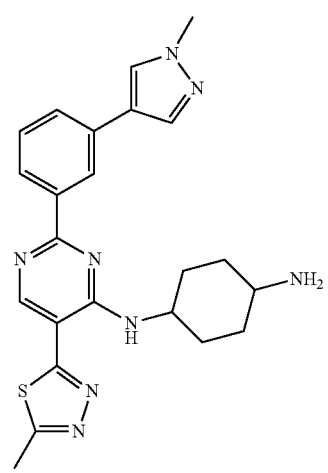
129
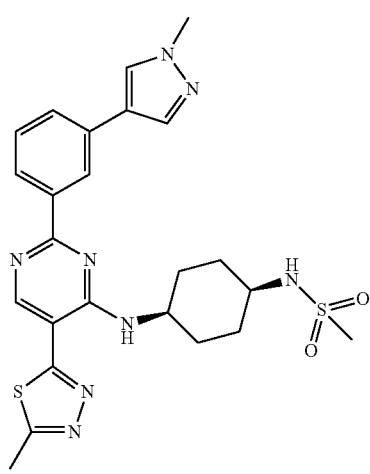
130
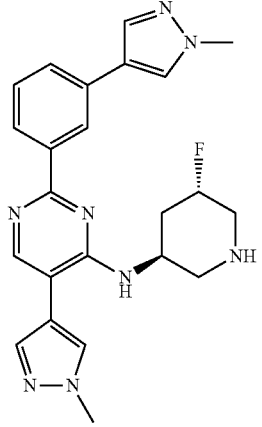
131
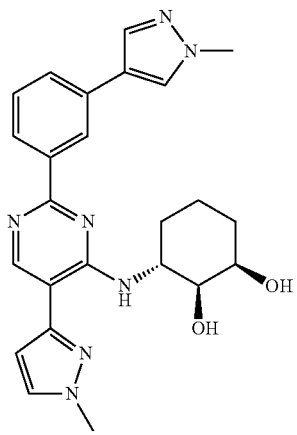
132
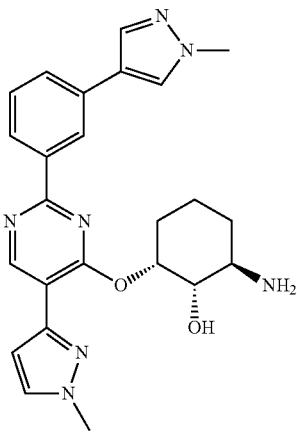

133 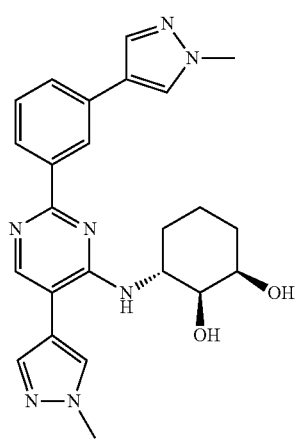
134 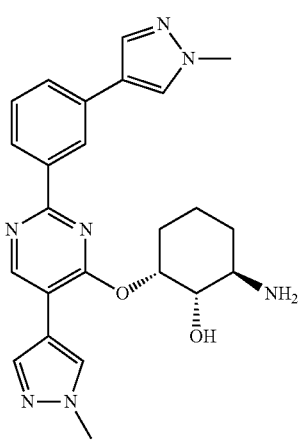
135 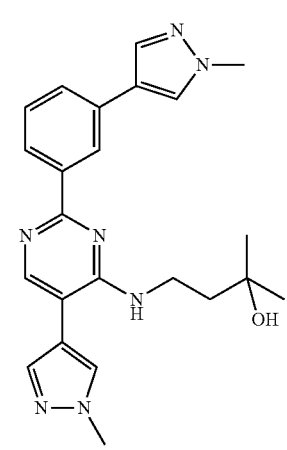
136 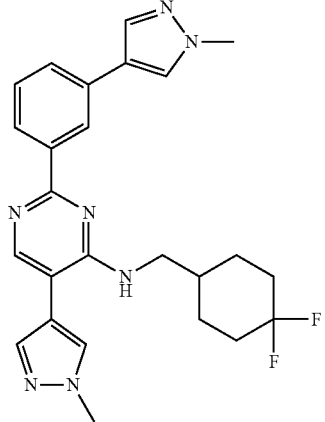
137 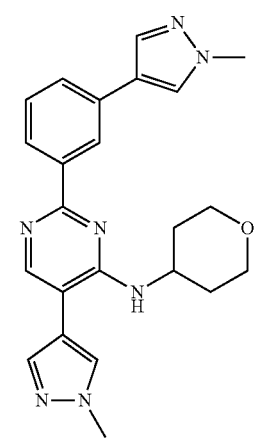
138 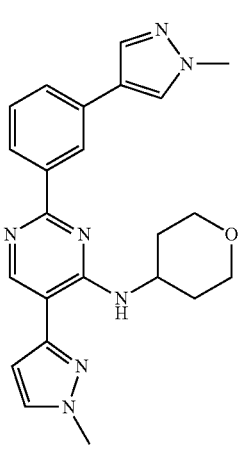

| 139 | 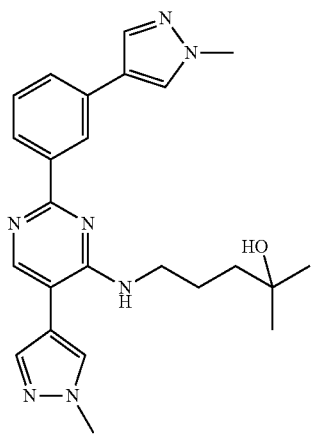 | 142 | 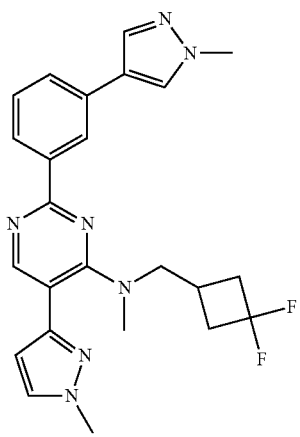 |
| 140 | 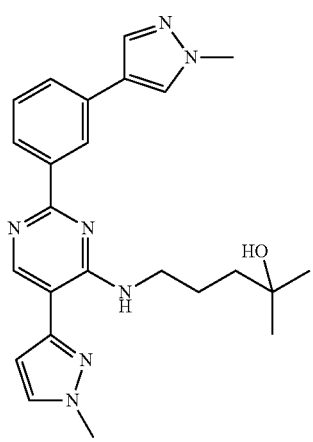 | 143 | 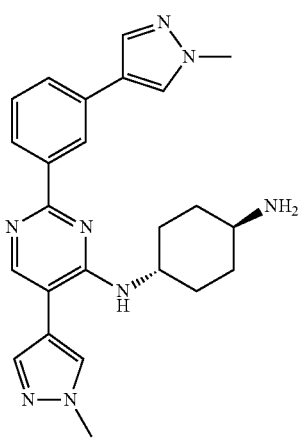 |
| 141 | 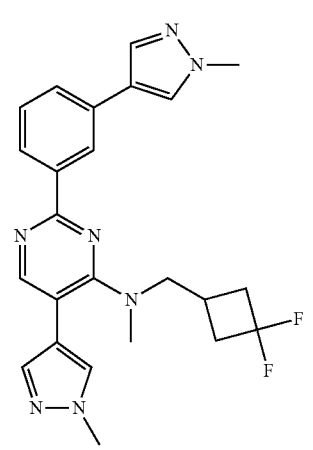 | 144 | 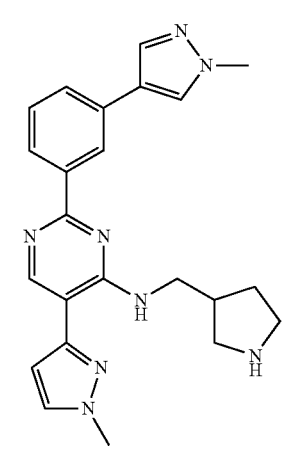 |

463 -continued
145 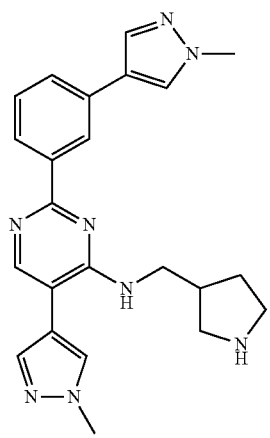
146 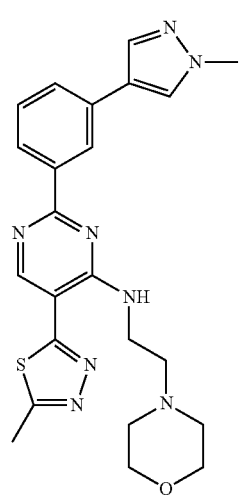
147 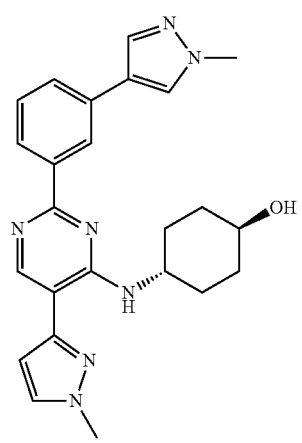
464 -continued
148 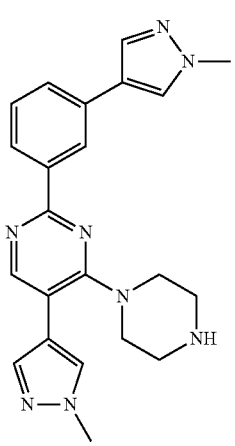
149 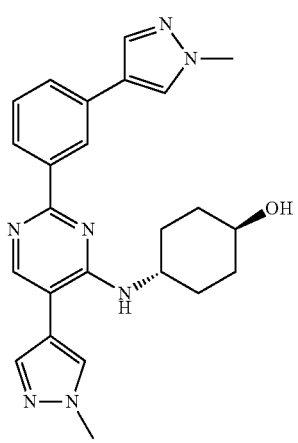
150 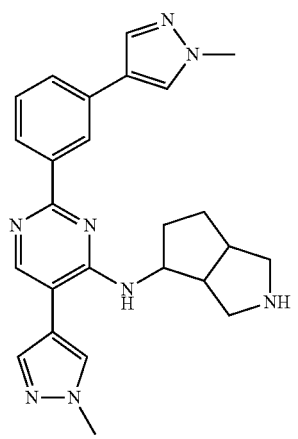

151 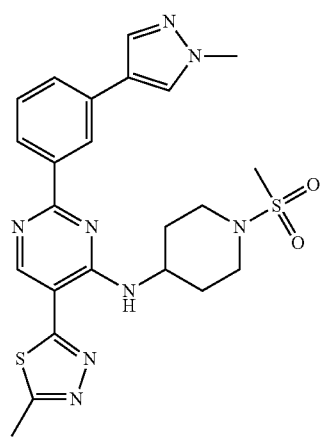
154 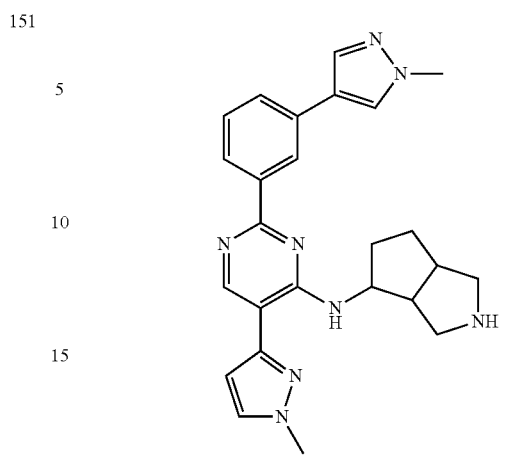
152 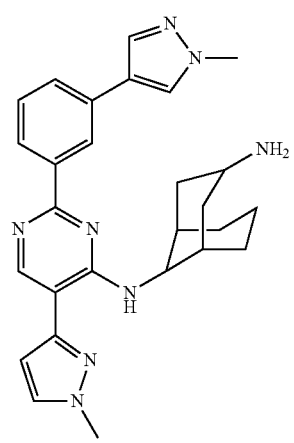
155 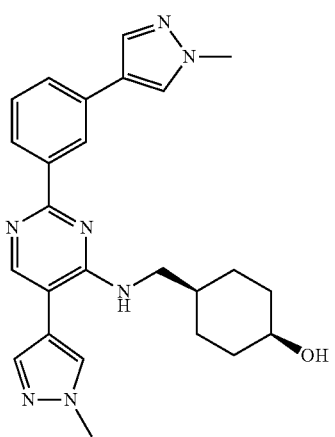
153 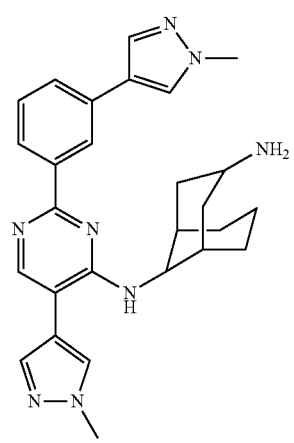
156 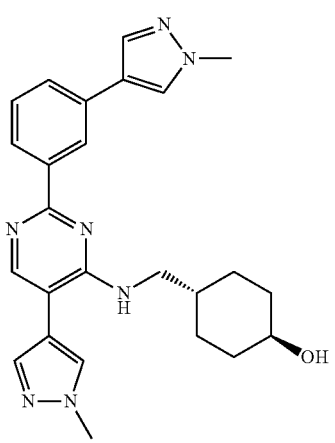

467
-continued
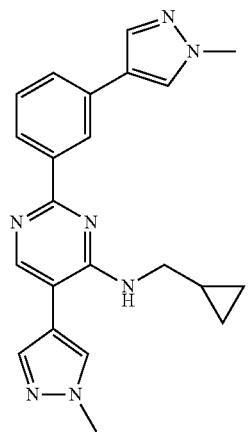
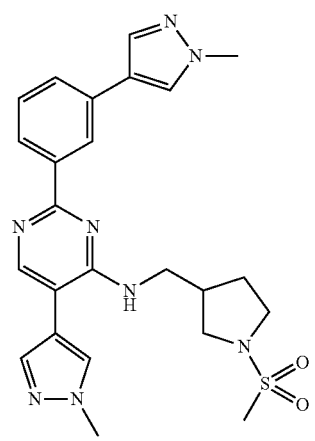
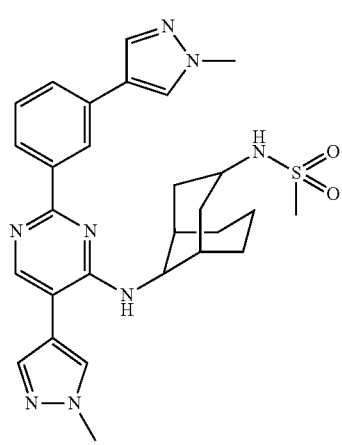
468
-continued
157
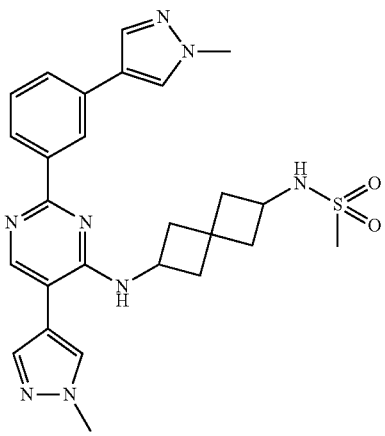
158
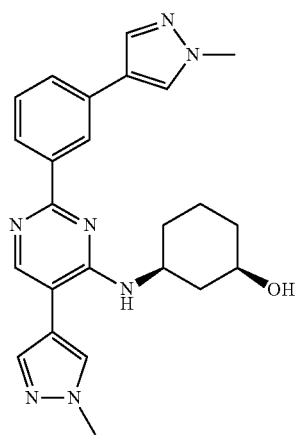
159
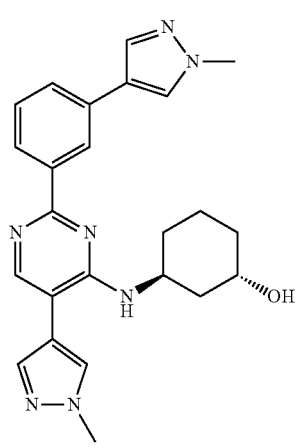
160
161
162

469
-continued
163
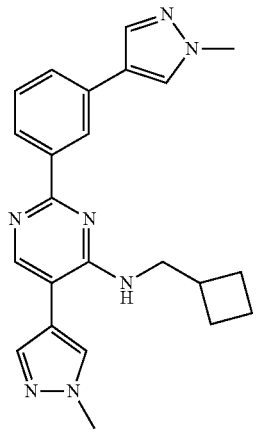
164
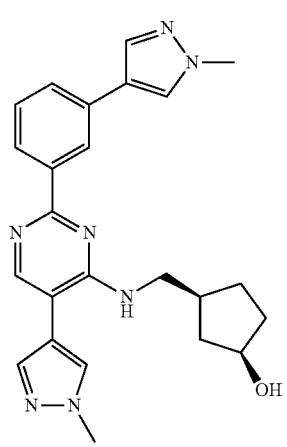
165
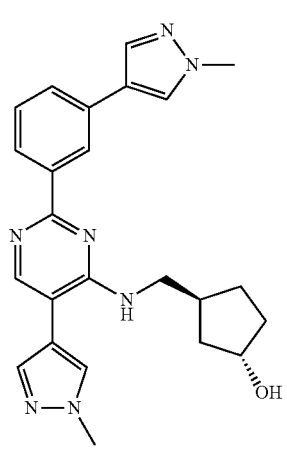
470
-continued
166
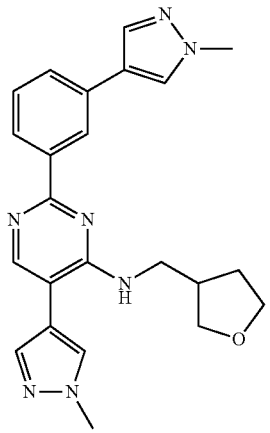
167
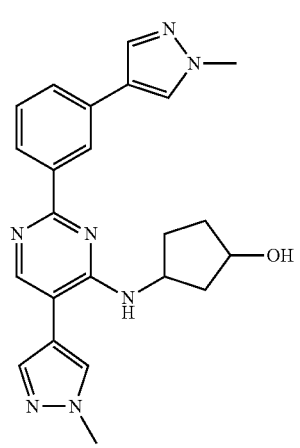
168
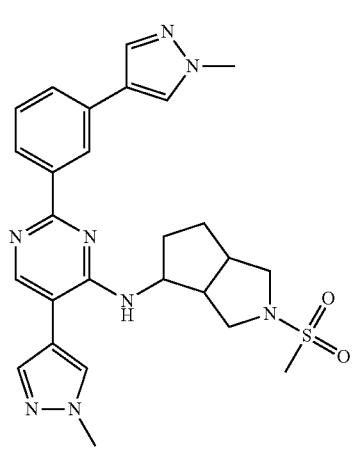

471
-continued
169
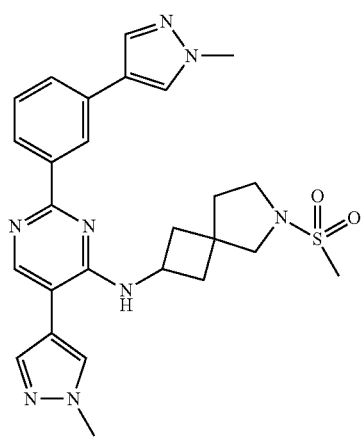
170
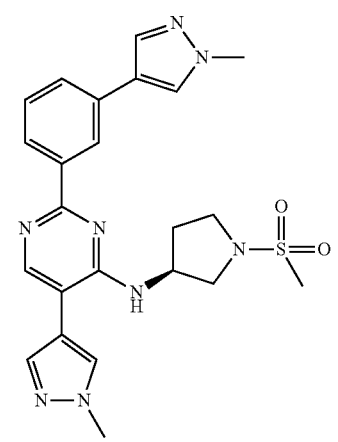
171
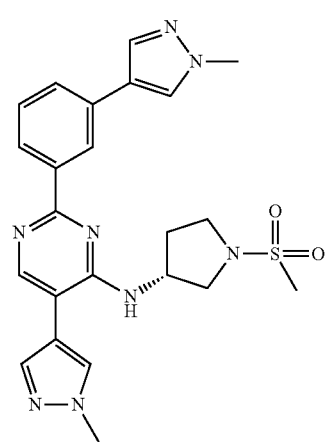
472
-continued
172
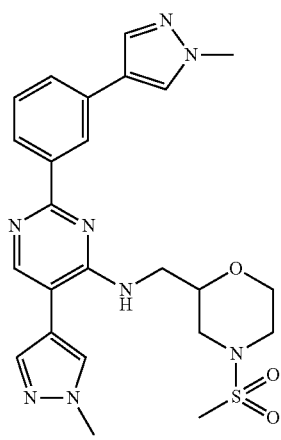
173
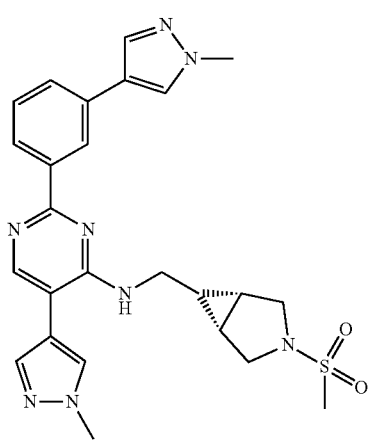
174
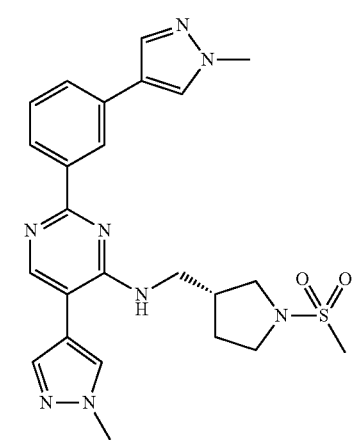

473
-continued
175
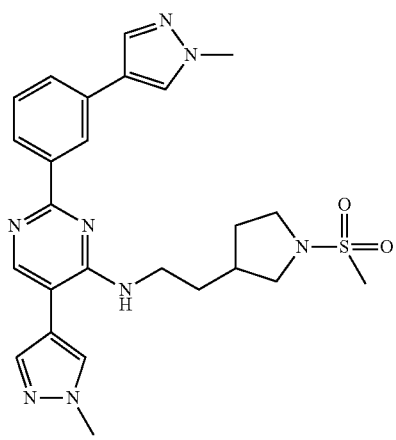
176
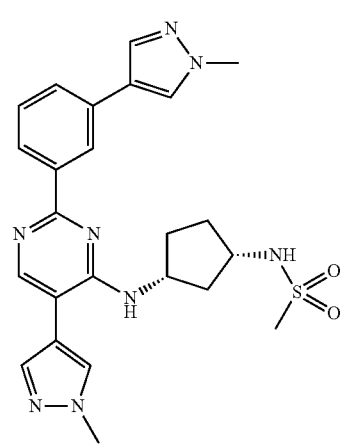
177
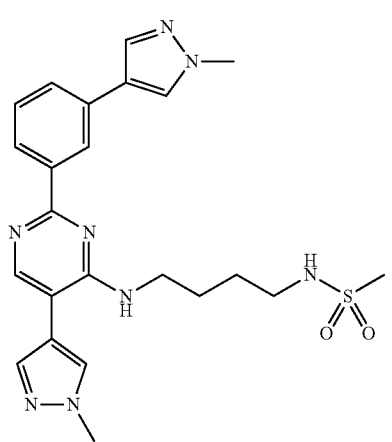
474
-continued
178
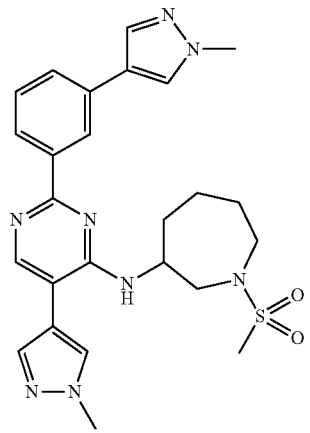
179
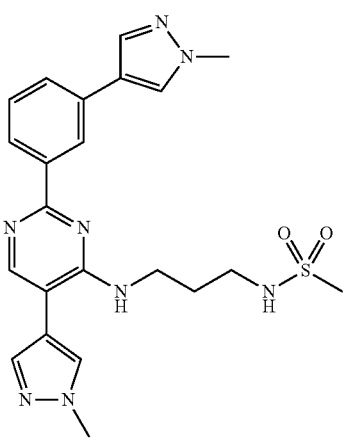
180
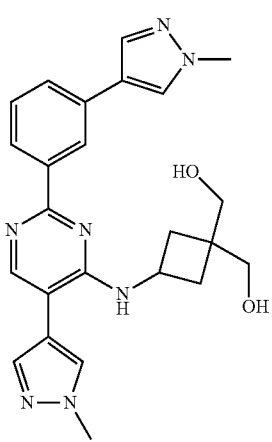

475
-continued
181
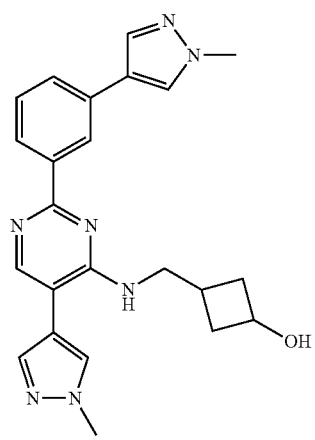
182
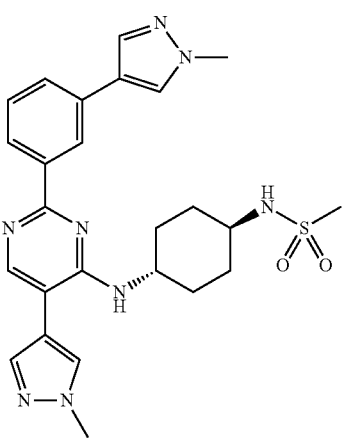
183
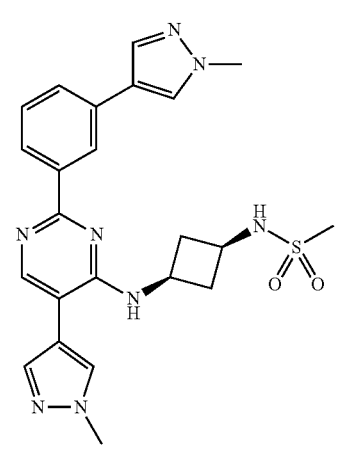
476
-continued
184
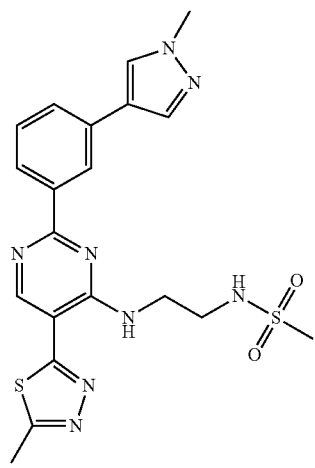
185
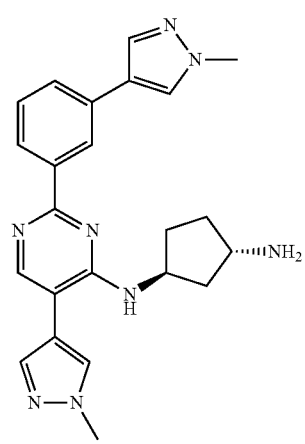
186
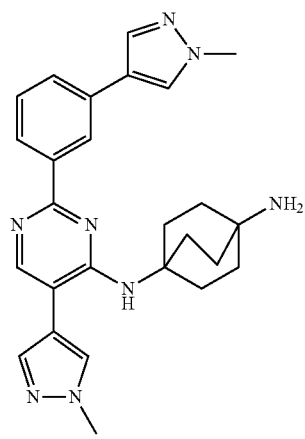

477
-continued
187
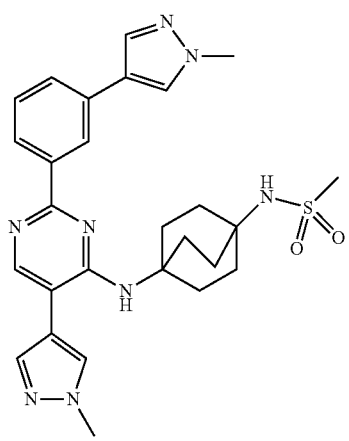
188
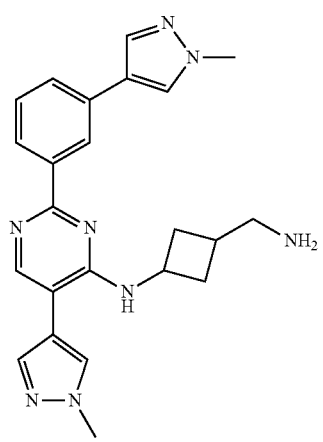
189
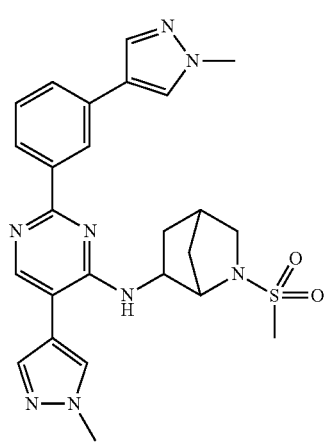
478
-continued
190
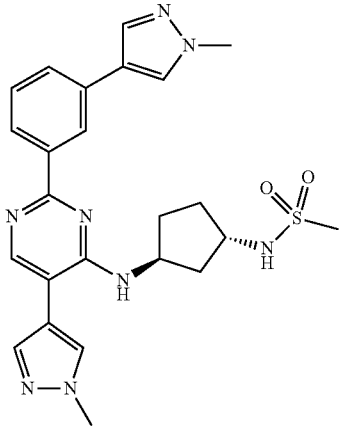
191
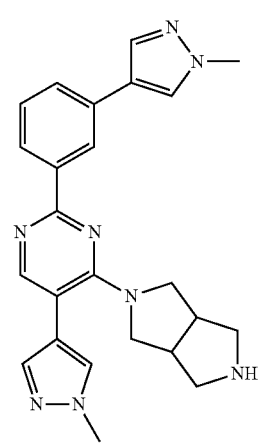
192
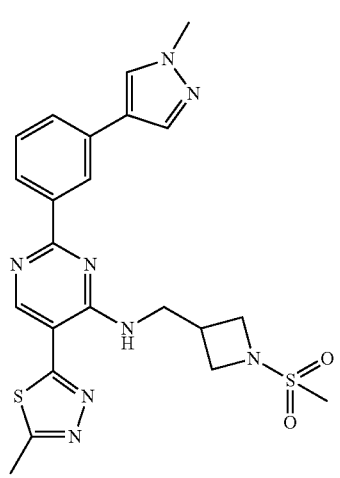

479
-continued
193
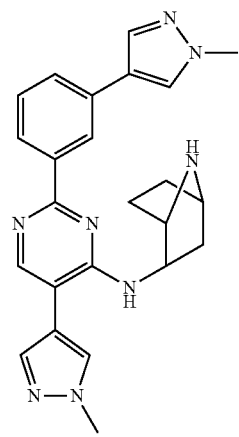
194
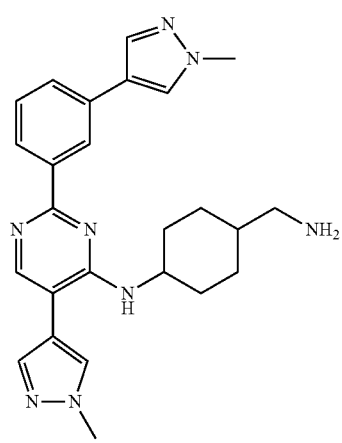
195
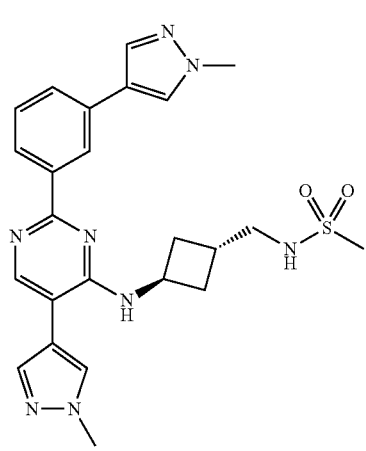
480
-continued
196
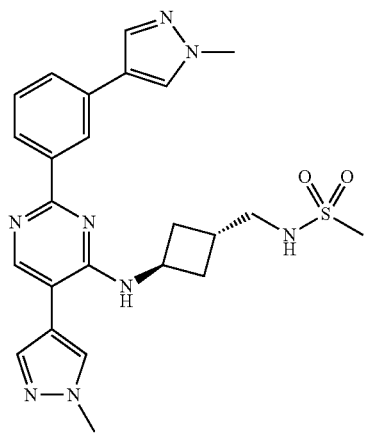
197
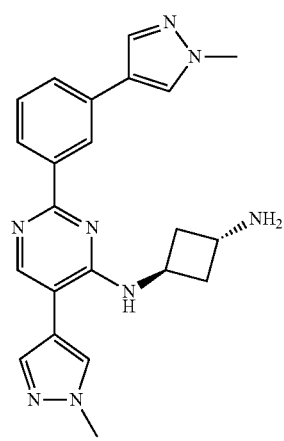
198
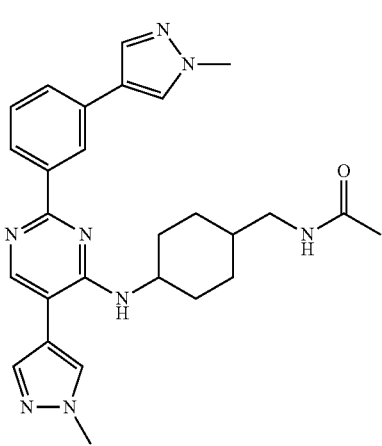

481
-continued
199
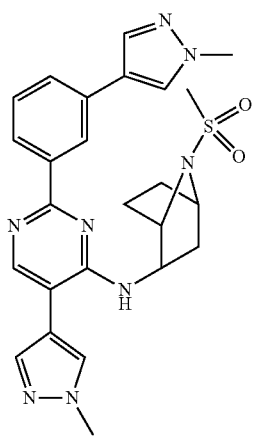
200
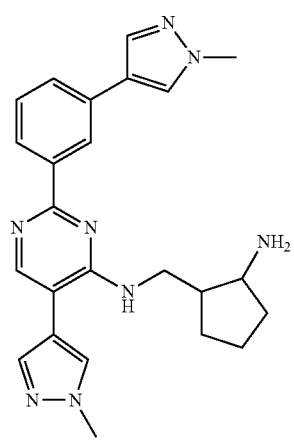
201
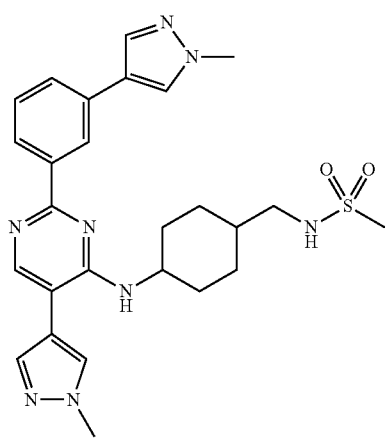
482
-continued
202
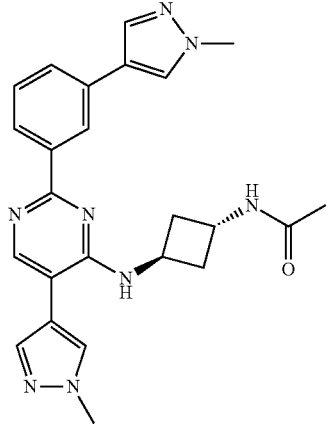
203
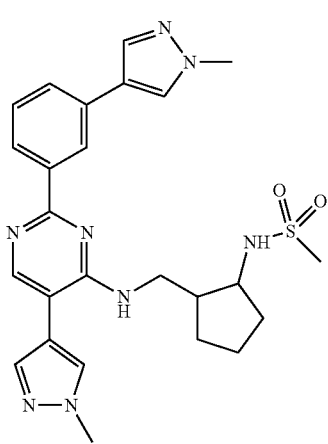
205
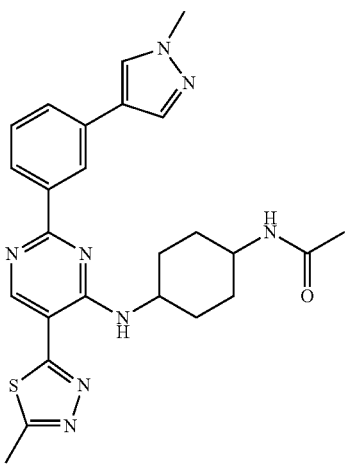

483
-continued
206
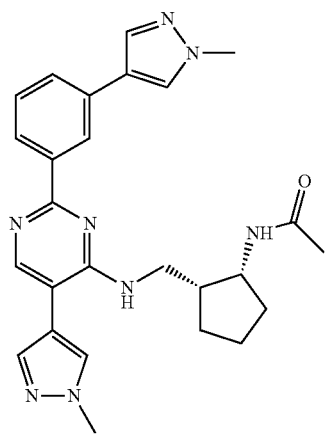
207
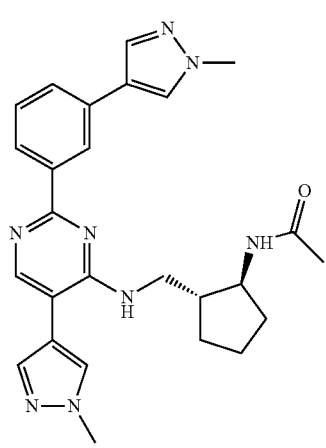
208
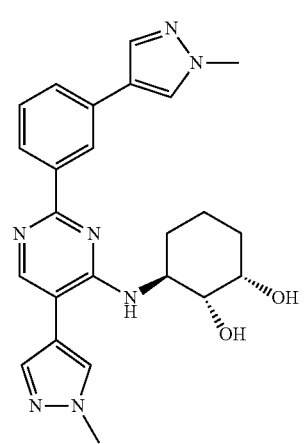
484
-continued
209
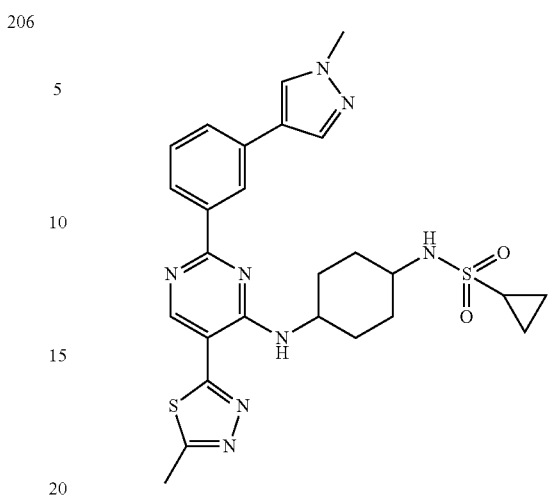
210
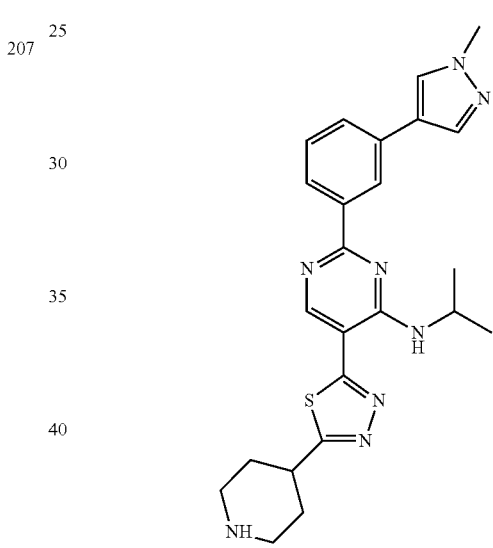
211
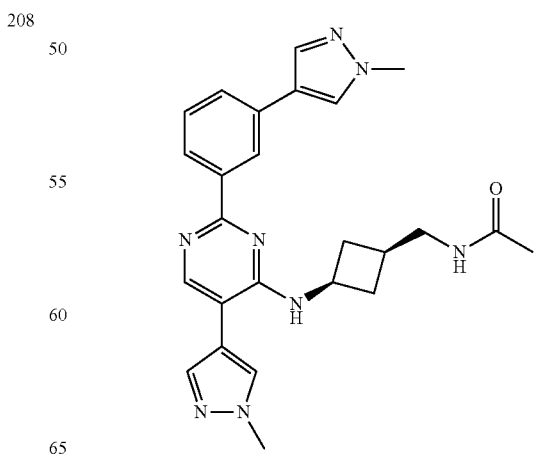

485
212 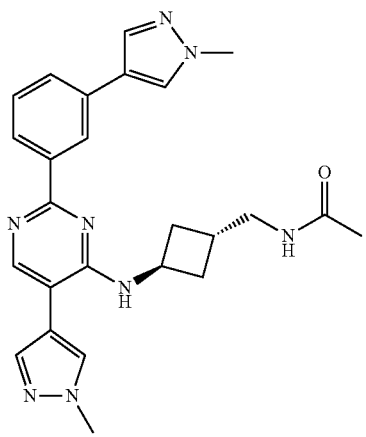
213 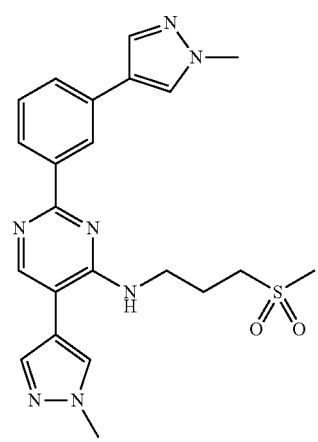
214 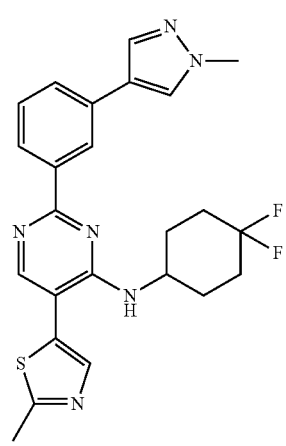
486
215 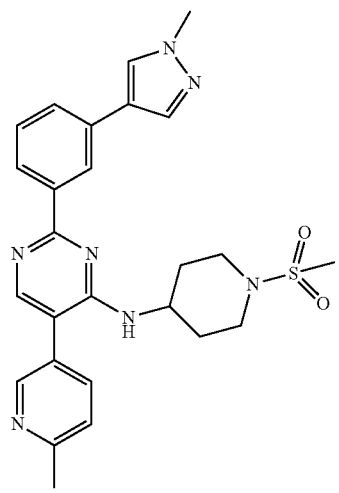
216 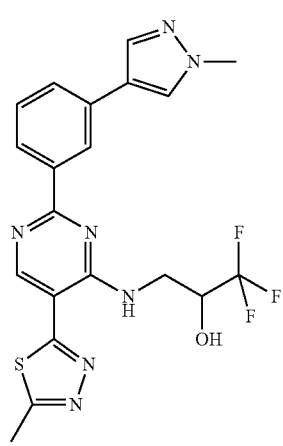
217 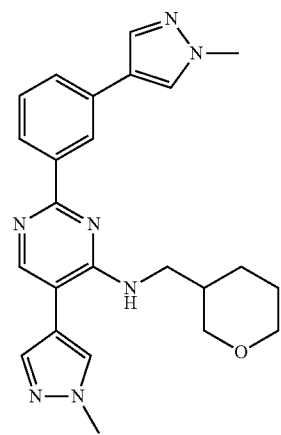

487
-continued
488
-continued
218 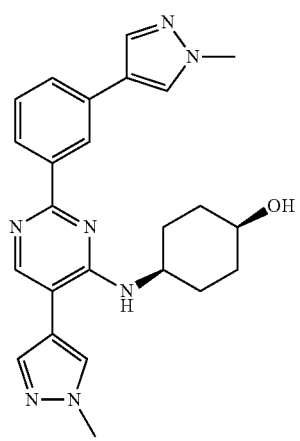
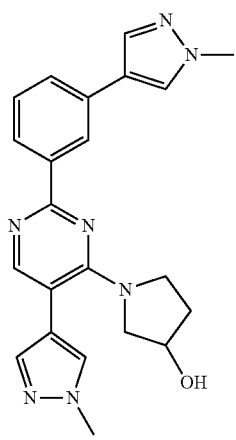
219 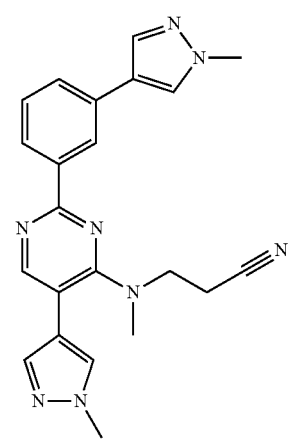
221
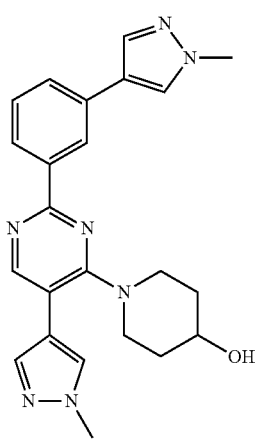
222
220 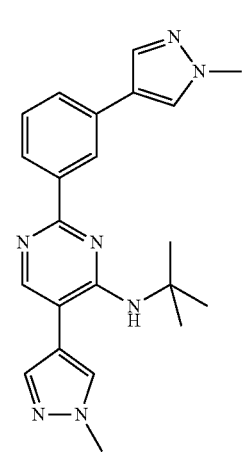
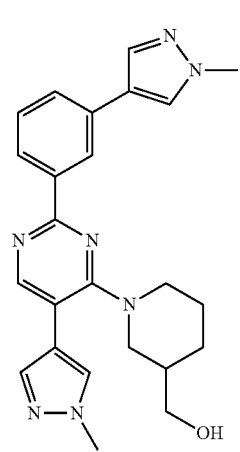
223

| | |
|---|---|
| 224 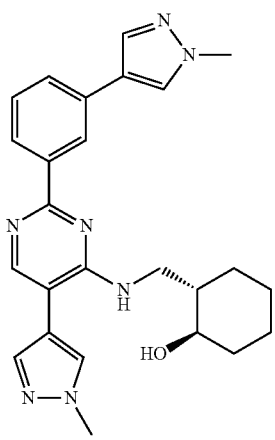 | 227 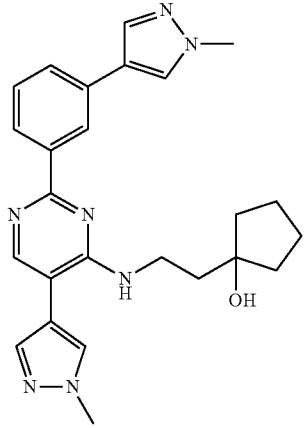 |
| 225 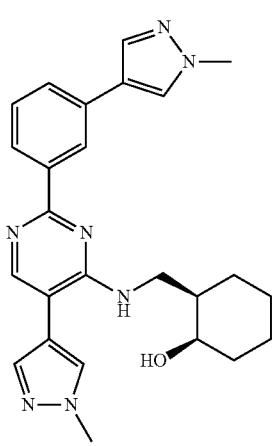 | 228 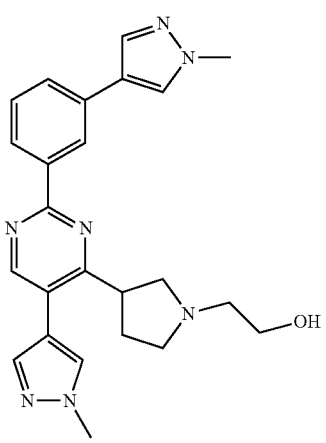 |
| 226 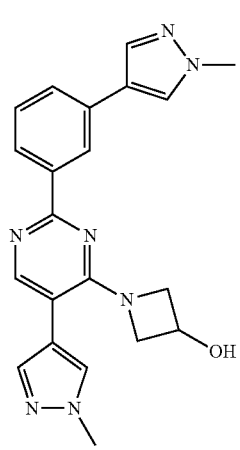 | 229 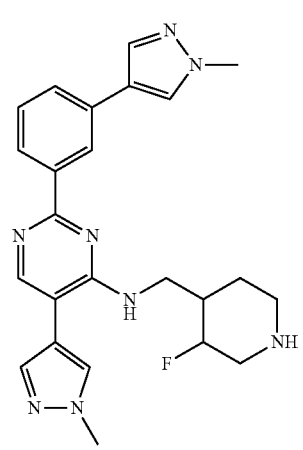 |

491
-continued
230
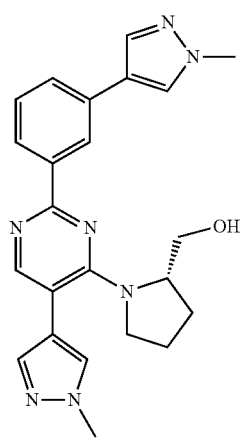
231
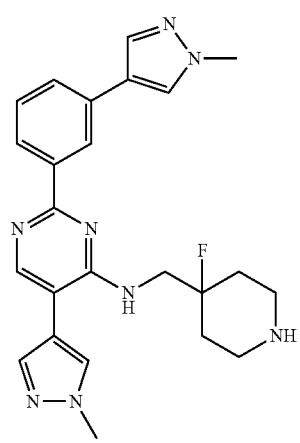
232
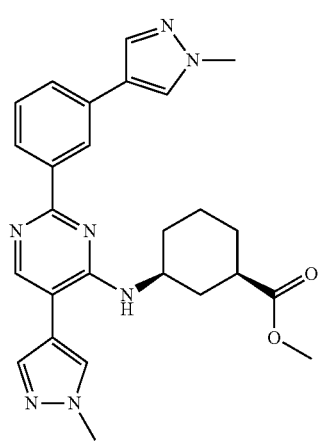
492
-continued
233
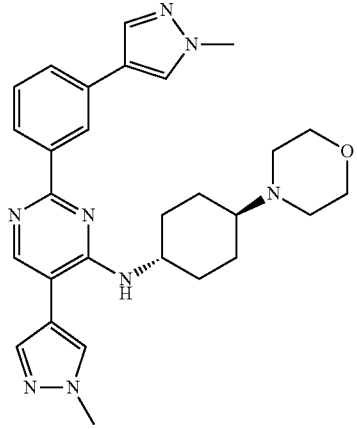
234
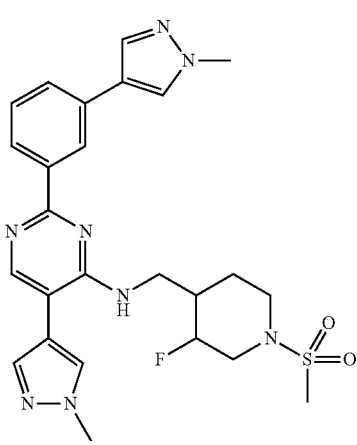
235
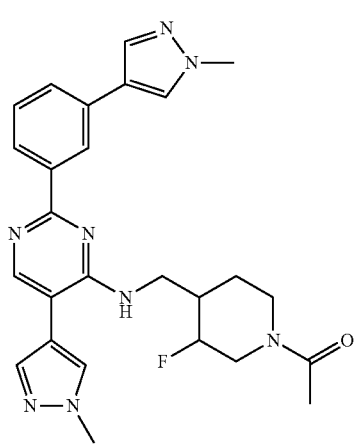

236 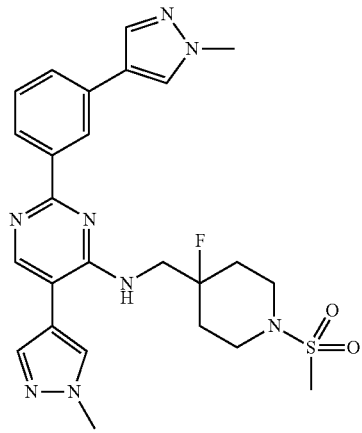
237 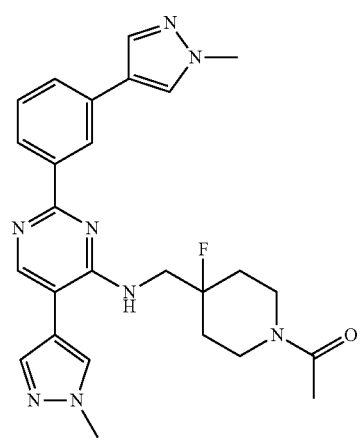
238 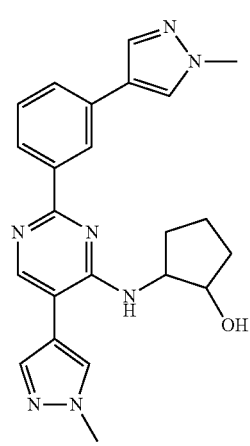
239 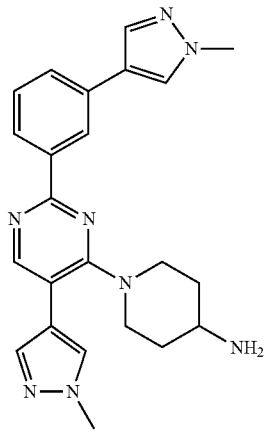
240 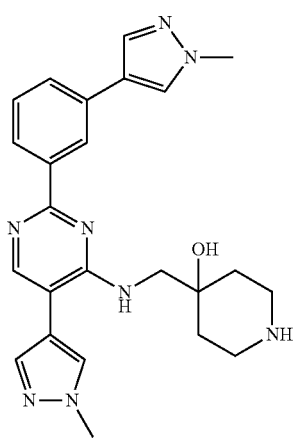
241 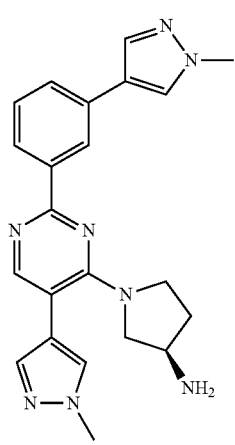

242 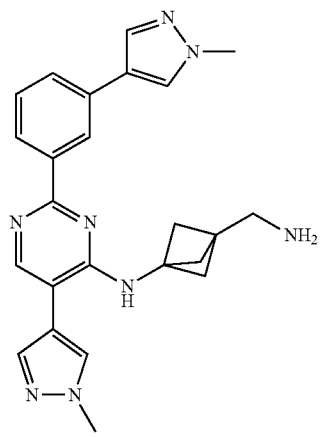
245 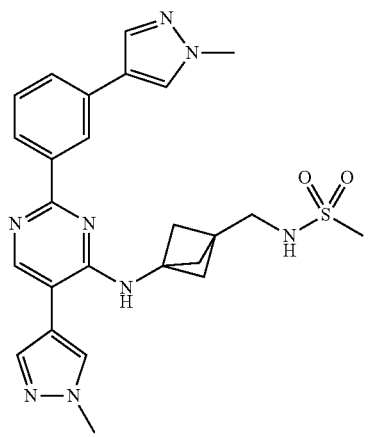
243 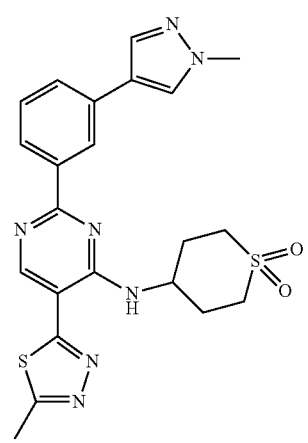
246 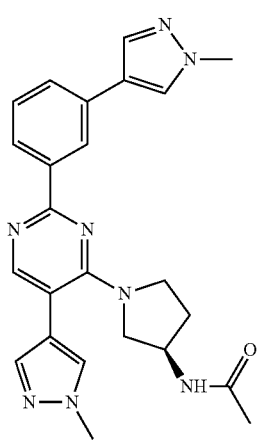
244 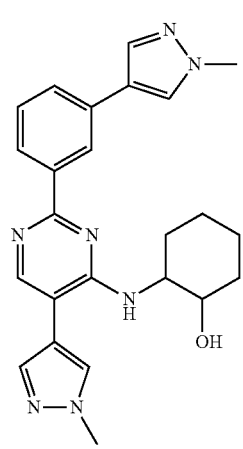
247 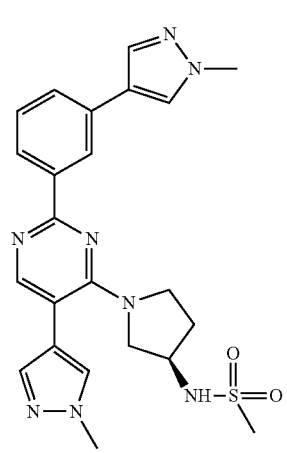

497
248
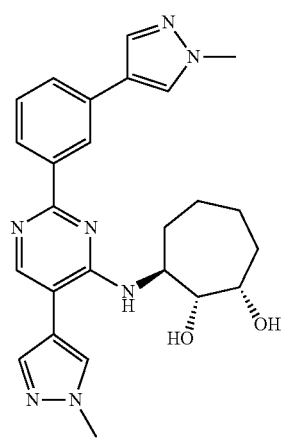
249
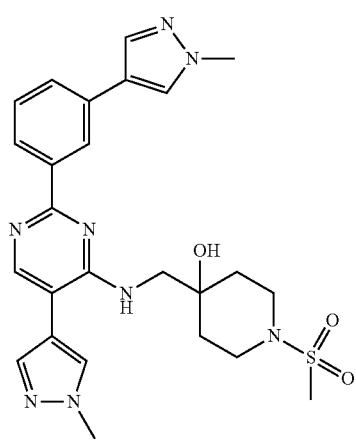
250
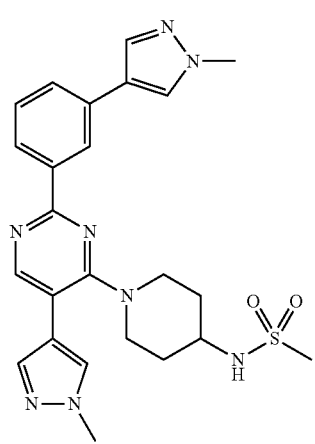
498
251
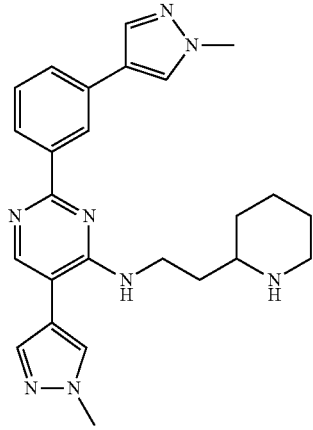
252
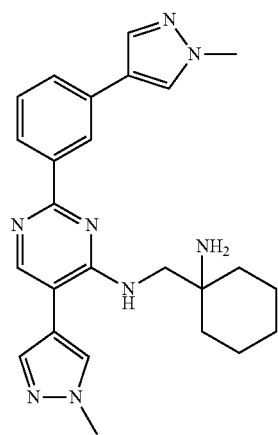
253
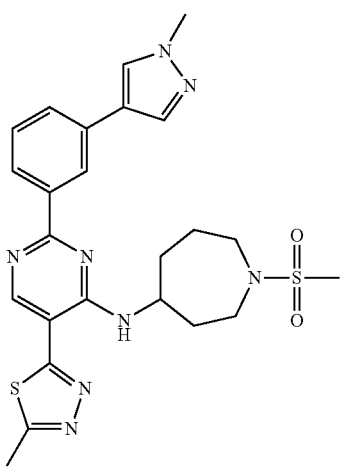

| 254 | 257 |
|---|---|
| 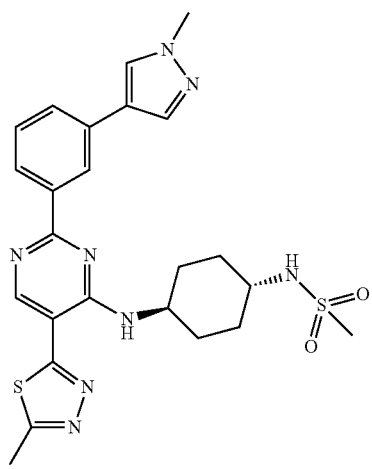 | 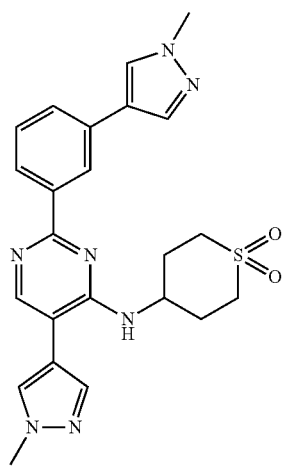 |
| 255 | 258 |
| 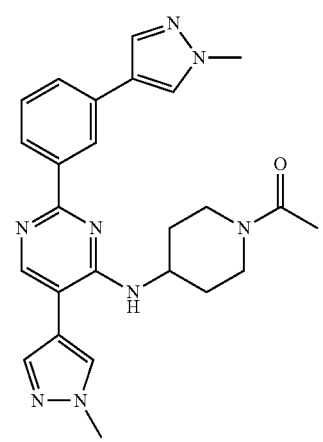 | 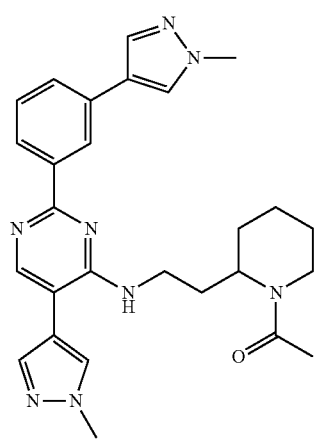 |
| 256 | 259 |
| 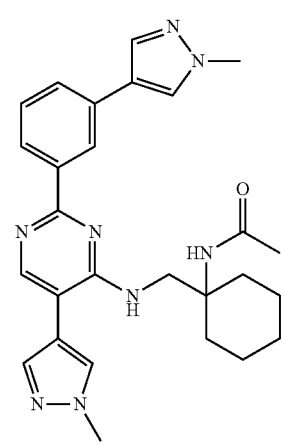 | 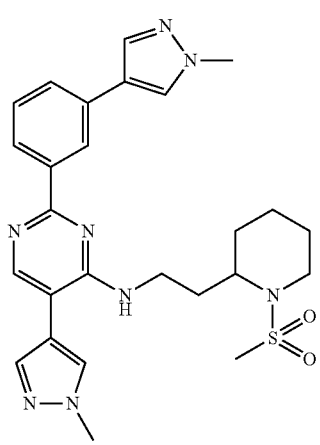 |

260
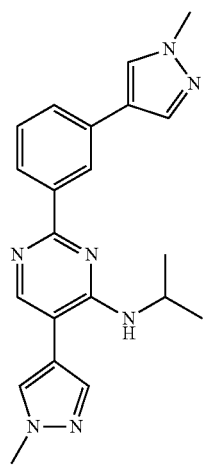
261
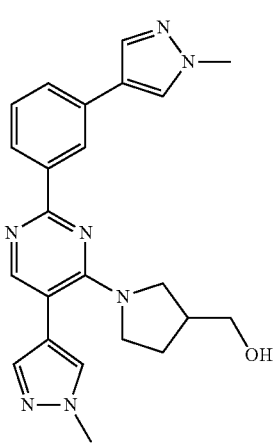
262
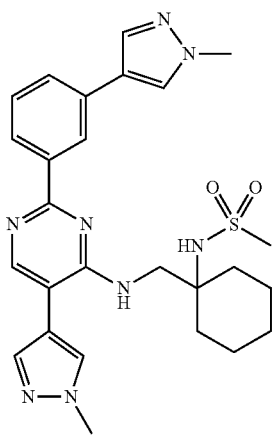
263
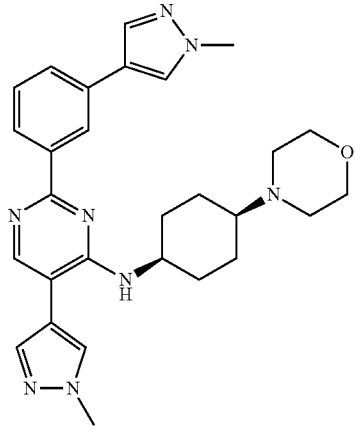
264
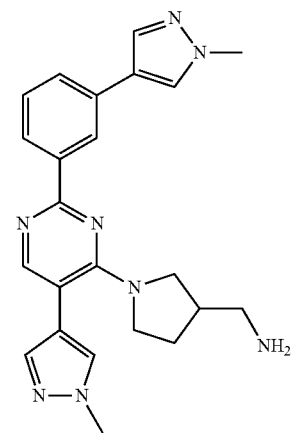
265
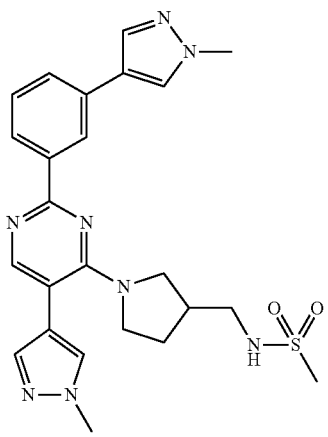

266
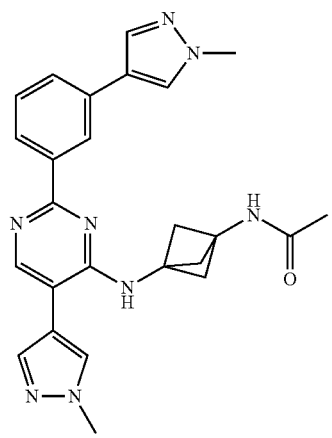
267
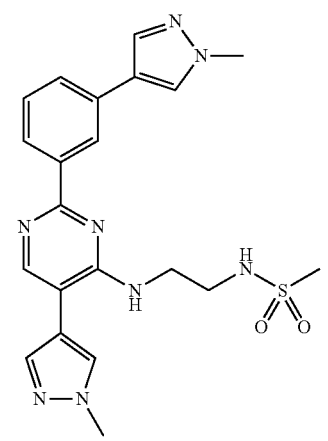
268
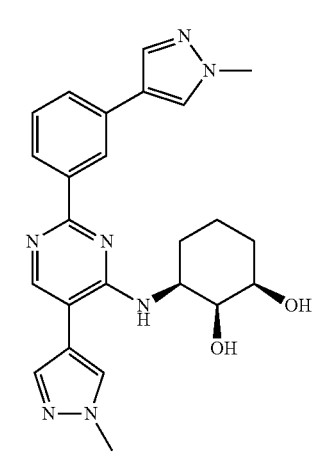
269
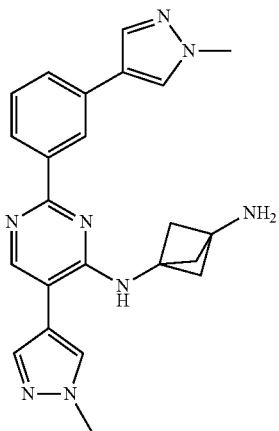
270
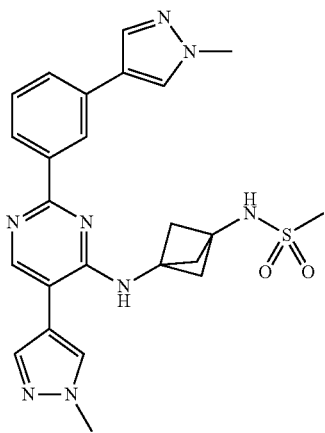
271
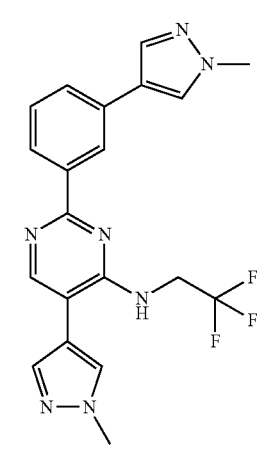

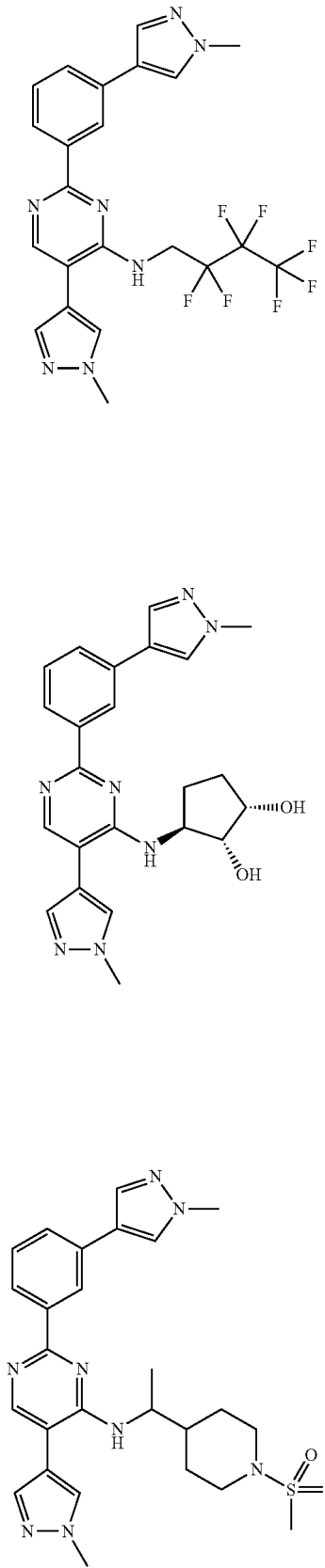
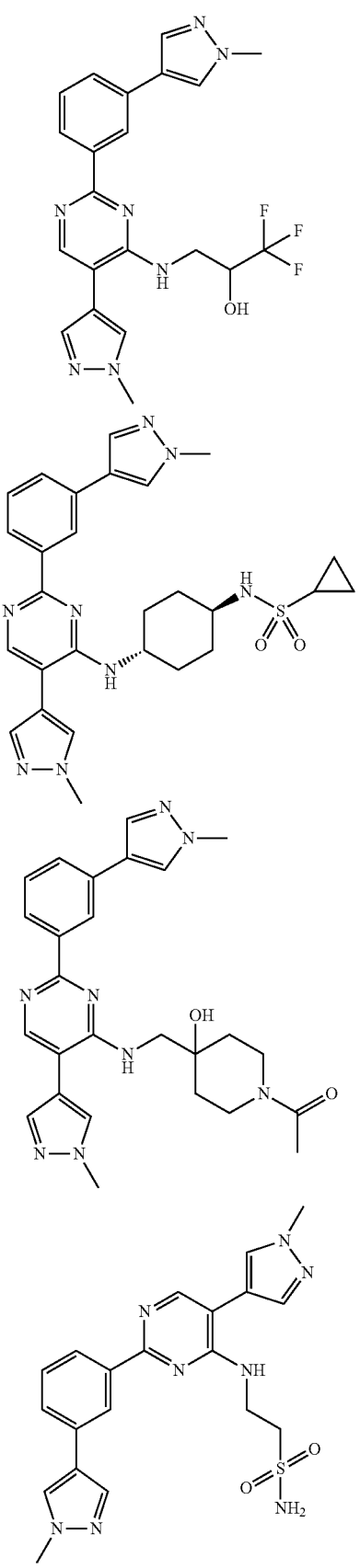

279
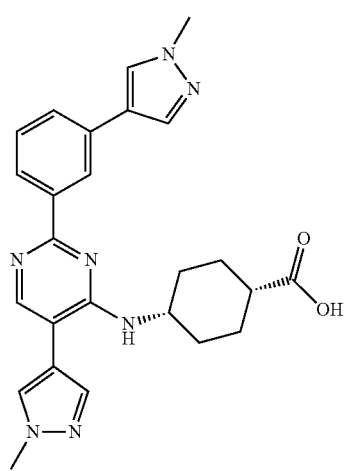
282
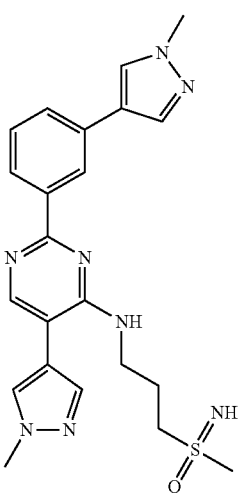
280
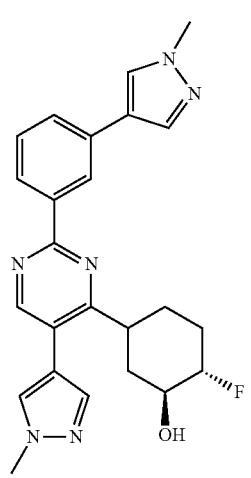
283
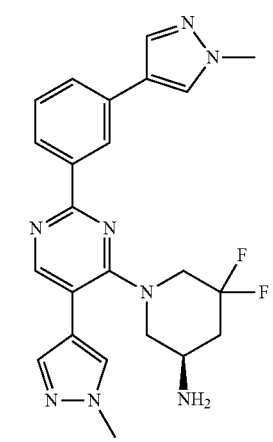
281
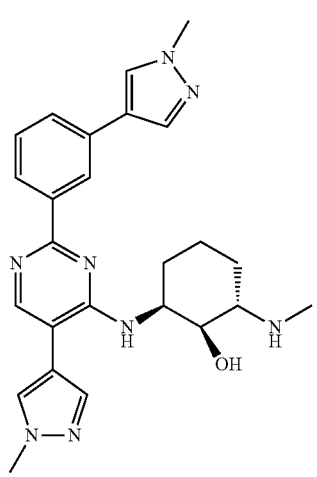
284
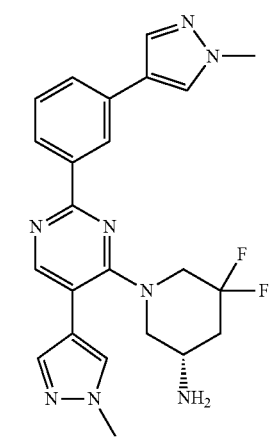

509
-continued
285
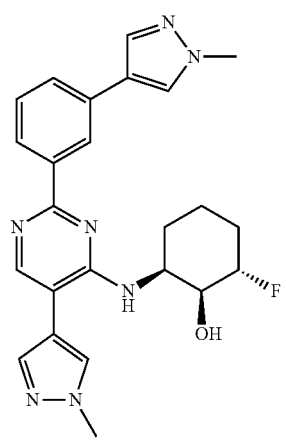
286
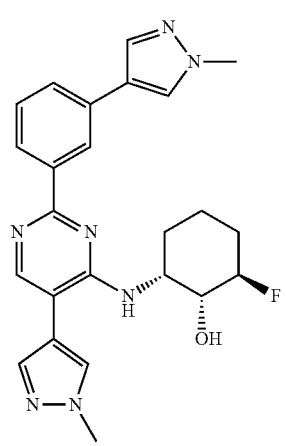
287
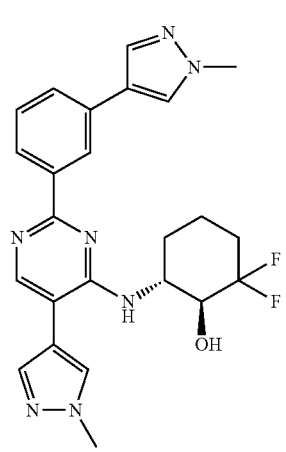
510
-continued
288
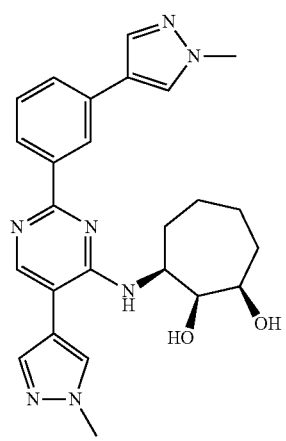
289
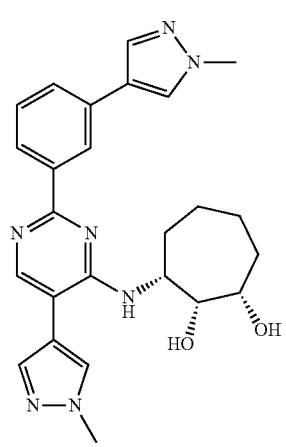
290
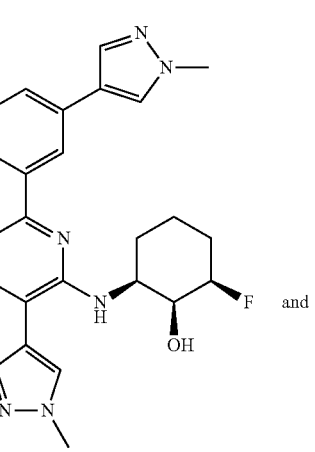
and

291

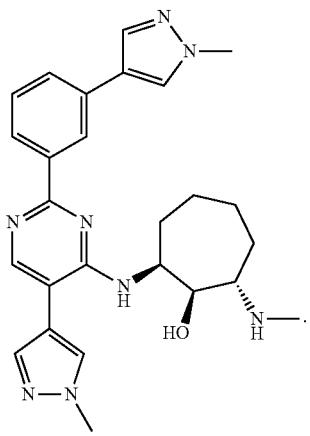

14. A pharmaceutical composition comprising a compound of claim 1, and a pharmaceutically acceptable adjuvant, carrier, or vehicle.

15. A method for treating a disorder is selected from Rheumatoid Arthritis, Systemic Lupus Erythematosus, Lupus nephritis, Multiple Sclerosis, Alzheimer's disease, Parkinson's disease, and Cancer, in a patient in need thereof, comprising the step of administering to said patient a compound of claim 1.

16. A method for treating cancer in a subject, comprising the step of administering to said subject a compound of claim 1 or a physiologically acceptable salt thereof.

17. A process for manufacturing a compound of formula I according to claim 1, comprising the steps of:

reacting a compound of formula (A):

A

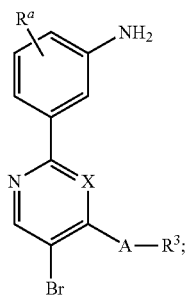

with

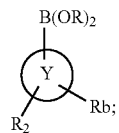

wherein X, Y, A, R, $R^a$, $R^b$, $R^2$ and $R^3$ are as defined in claim 1;

to provide a compound of formula (B):

B

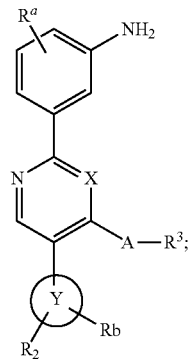

and reacting the compound of formula (B) with

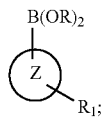

wherein Z and $R^1$ are as defined in claim 1;

to provide a compound of formula I of claim 1.

* * * * *